US012220421B2

(12) United States Patent
Abel-Santos et al.

(10) Patent No.: US 12,220,421 B2
(45) Date of Patent: Feb. 11, 2025

(54) **INHIBITORS OF *C. dIFFICILE* SPORE GERMINATION**

(71) Applicants: Ernesto Abel-Santos, Las Vegas, NV (US); Steven Firestine, Livonia, MI (US); Shiv Sharma, Canton, MI (US); Angel Schilke, Saline, MI (US); Christopher Yip, Emeryville, CA (US); Jacqueline Phan, Las Vegas, NV (US)

(72) Inventors: Ernesto Abel-Santos, Las Vegas, NV (US); Steven Firestine, Livonia, MI (US); Shiv Sharma, Canton, MI (US); Angel Schilke, Saline, MI (US); Christopher Yip, Emeryville, CA (US); Jacqueline Phan, Las Vegas, NV (US)

(73) Assignees: THE BOARDS OF REGENTS OF THE NEVADA SYSTEM OF HIGHER EDUCATION ON BEHALF OF THE UNIVERSITY OF NEVADA, LAS, Las Vegas, NV (US); THE BOARD OF GOVERNORS OF WAYNE STATE UNIVERSITY, Detroit, MI (US)

( * ) Notice: Subject to any disclaimer, the term of this patent is extended or adjusted under 35 U.S.C. 154(b) by 0 days.

(21) Appl. No.: 17/941,611

(22) Filed: Sep. 9, 2022

(65) Prior Publication Data
US 2023/0130602 A1    Apr. 27, 2023

Related U.S. Application Data

(60) Provisional application No. 63/319,079, filed on Mar. 11, 2022, provisional application No. 63/242,343, filed on Sep. 9, 2021.

(51) Int. Cl.
*A61K 31/575*    (2006.01)
*A61K 9/16*    (2006.01)
(Continued)

(52) U.S. Cl.
CPC .............. *A61K 31/575* (2013.01); *A61K 9/16* (2013.01); *A61K 47/06* (2013.01); *A61K 47/551* (2017.08); *A61P 31/04* (2018.01)

(58) Field of Classification Search
CPC ........ A61K 31/575; A61K 9/16; A61K 47/06; A61K 47/551; A61K 31/395;
(Continued)

(56) References Cited

U.S. PATENT DOCUMENTS 5,824,698 A    10/1998    Hasler et al.
6,326,364 B1    12/2001    Lin et al.
(Continued)

FOREIGN PATENT DOCUMENTS

CS         275631        3/1992
WO    WO-2002/060879 A2    8/2002
(Continued)

OTHER PUBLICATIONS

Xiong et al. "Site-Selective Electrooxidation of Methylarenes to Aromatic Acetals." Nature Communications, vol. 11, No. 1, Jun. 2020, p. 2706 (Year: 2020).*
(Continued)

*Primary Examiner* — Clinton A Brooks
*Assistant Examiner* — Kyle Nottingham
(74) *Attorney, Agent, or Firm* — Ballard Spahr LLP

(57) ABSTRACT

Provided herein are compounds, compositions, and methods useful for reducing, preventing, and/or inhibiting germination of *C. difficile* spores, including methods for inhibiting *C. difficile* germination to prevent or treating *C. difficile*-associated diseases and disorders such as, for example, severe diarrhea and colitis in a subject. This abstract is intended as a scanning tool for purposes of searching in the particular art and is not intended to be limiting of the present invention.

18 Claims, 1 Drawing Sheet

(51) Int. Cl.
  *A61K 47/06* (2006.01)
  *A61K 47/55* (2017.01)
  *A61P 31/04* (2006.01)
(58) Field of Classification Search
  CPC ............... A61K 31/4164; A61K 31/43; A61K 31/5383; A61K 31/7048; A61K 45/06; A61P 31/04; C07J 43/003
  See application file for complete search history.

(56) References Cited

U.S. PATENT DOCUMENTS

| | | | |
|---|---|---|---|
| 8,124,623 | B2 | 2/2012 | Hubschwerlen et al. |
| 8,389,516 | B2 | 3/2013 | Haydon et al. |
| 8,618,100 | B2 | 12/2013 | Guillemont et al. |
| 9,079,935 | B2 | 7/2015 | Abel-Santos et al. |
| 9,862,744 | B2 | 1/2018 | Abel-Santos et al. |
| 10,945,996 | B2 | 3/2021 | Abel-Santos et al. |
| 2007/0112048 | A1 | 5/2007 | Bavari et al. |
| 2008/0254010 | A1 | 10/2008 | Sasser et al. |
| 2010/0168203 | A1 | 7/2010 | Levin et al. |
| 2011/0086797 | A1 | 4/2011 | Dworkin |
| 2011/0183360 | A1 | 7/2011 | Rajagopal et al. |
| 2011/0229583 | A1 | 9/2011 | Tran et al. |
| 2011/0280847 | A1 | 11/2011 | Sorg et al. |
| 2012/0020950 | A1 | 1/2012 | Davis et al. |
| 2014/0045808 | A1* | 2/2014 | Abel-Santos ........... C07J 31/006 514/169 |
| 2016/0175223 | A1* | 6/2016 | Dayan ..................... A61K 8/63 514/182 |
| 2018/0000793 | A1* | 1/2018 | Abel-Santos ........... A61P 31/04 |
| 2018/0311259 | A1 | 11/2018 | Stappenbeck et al. |
| 2023/0174505 | A1* | 6/2023 | Farber ................. C07D 235/12 514/297 |

FOREIGN PATENT DOCUMENTS

| | | |
|---|---|---|
| WO | WO-2003/105846 A1 | 12/2003 |
| WO | WO-2004/041209 A2 | 5/2004 |
| WO | WO-2006/076009 A2 | 7/2006 |
| WO | WO-2007/056330 A1 | 5/2007 |
| WO | WO-2007/148093 A1 | 12/2007 |
| WO | WO-2010/062369 A2 | 6/2010 |
| WO | WO-2016/127102 A2 | 8/2016 |

OTHER PUBLICATIONS

Xiong et al. "Site-Selective Electrooxidation of Methylarenes to Aromatic Acetals." Nature Communications, vol. 11, No. 1, Jun. 2020. Supplementary Information. (Year: 2020).*
Garai et al. (2020) "Application of Fluorine- and Nitrogen-Walk Approaches: Defining the Structural and Functional Diversity of 2-Phenylindole Class of CB1 Receptor Positive Allosteric Modulators," *J Med Chem* 63(2): 542-568.
Leverrier et al. (2015) "Structure-activity relationship of hybrids of Cinchona alkaloids and bile acids with in vitro antiplasmodial and antitrypanosomal activities," *European Journal of Medicinal Chemistry* 100: 10-17.
PubChem-SID-104587389, Modify Date: Feb. 22, 2011.
Abel-Santos, E. et al., 2007. Differential nucleoside recognition during Bacillus cereus 569 (ATCC I0876) spore germination. New J. Chem. 31 (5):748-755.).
Archimandritis, et al., Clostridium difficile colitis associated with a 'triple' regimen, containing clarithromycin and metronidazole, to eradicate Helicobacter pylori, J. Int. Med., 1998, 243(3), 251-253.
Bandyopadhyay, P., et al., 2001. Ion conductors derived from cholic acid and spermine: Importance of facial hydrophilicity on Na+ transport and membrane selectivity. J. Am. Chem. Soc. 123(31):7691-7696.
Bertolini et al., A New Rational Hypothesis for the Pharmacophore of the Active Metabolite of Leflunomide, a Potent Immunosuppressive Drug, J. Med. Chem., 1997, 40, 2011-2016.

Bowser TE, et al., Novel anti-infection agents: small molecule inhibitors of bacterial tanscription factors, Bioorg. Med. Chem. Lett., 2007, 17, 5652-5655.
Buhling et al., Influence of anti-Helicobacter triple-therapy with metronidazole,omeprazole and clarithromycin on intestinal microflora, Aliment. Pharm. Ther., 2001, 15(9), 1445-1452.
Cieslak, et al., Clinical and Epidemiologic Principles of Anthrax, CDC Emerg. Infect. Dis., 1999, 5(4), 552-555.
Database Registry [online] Chemical Abstracts Service, Columbus, OH, US; Nov. 16, 1984 (Nov. 16, 1984), Chemical Abstracts Service Registry No. 145-42-6.
Dayal, B., et al., 1995. Microwave-induced rapid synthesis of sarcosine conjugated bile acids. Bioorg. Med. Chem. Lett. 5(12):1301-1306.
Dodatko, T., M. et al., 2010. Dissecting interactions between nucleosides and germination receptors in Bacillus cereus 569 spores. Microbiology. 156(4):1244-1255.
Foster, S. J. et al., 1990. Pulling the trigger: The mechanism ofbacterial spore germination. Mol. Microbial. 4(1):137-141.
Gargiulo, D., et al. 1989. Synthesis of mosesin-4, a naturally occurring steroid saponin with shark repellent activity, and its analog 7-ß-galactosyl ethyl cholate. Tetrahedron. 45(17):5423-5432.
Gisbert et al. (2005) Systematic review and meta-analysis: proton pump inhibitor vs. ranitidine bismuth citrate plus two antibiotics in Helicobacter pylorieradication.Helicobacter., 2005, 10(3), 157-171.
Grant No. CHE0957400 awarded by the National Science Foundation (Jul. 23, 2009).
Harsch et al. (2001) Pseudomembranous colitis after eradication of Helicobacterpylori infection with a triple therapy.Med. Sci. Monit., 2001, 7(4), 751-754.
Howerton et al., "Mapping Interactions between Germinants and Clostridium difficile Spores," Journal of Bacteriology, Jan. 2011, p. 274-282.
Iida, T. et al., 1982. Potential bile acid metabolites. 6. Stereoisomeric 3,7-dihydroxy-5ß-cholanic acids. J. Org. Chem 47(15):2966-2972.
Infectious Disease Society of America, 2004, Bad Bugs, No Drugs (35 pages).
Janssen et al. (2001) A systematic comparison of triple therapies for treatment of Helicobacter pylori infection with proton pump inhibitor/ ranitidine bismuth citrate plus clarithromycin and either amoxicillin or a nitroimidazole, Aliment. Pharmacal. Ther., 2001, 15(5), 613-624.
Indu, B., et al., 1993. Methanol-formic acid esterification equilibrium in sulfuric acid solutions: Influence of sodium salts. Ind. Eng. Chem. Res. 32( 5):981-985.
Nawaz et al. (1998) Clostridium difficile colitis associated with treatment of Helicobacter pylori infection. Am. J. Gastroenterol., 1998, 93(7), 1175-1176.
Preston, R. A. et al., 1988. Functional relationships between L- and D-alanine, inosine and NH4CI during germination of spores of Bacillus cereus. T. J. Gen. Microbial. 134(1I):3001-3010.
Ramirez, N. et al., 2010. Requirements for germination of Clostridium sordellii spores in vitro. J. Bacteriol. 192(2):418-425.
Rodbard, D. et al., 1978. Kinetics of two-site immunoradiometric ('sandwich') assays. I. Mathematical models for simulation, optimization, and curve fitting. Mol. Immunol. 15(2):71-76.
Rodbard, D.et al., 1977. Automated computer analysis for enzyme multiplied immunological techniques. Clin. Chem. 23(1):112-115.
Sidoova et al., CS 275631 B6 (Mar. 18, 1992) (CAS SciFinder abstract, database CAPLUS Acc No. 1994:270377).
Sorg, J. A. et al., 2008. Bile salts and glycine as cogerminants for Clostridium difficile spores. J. Bacterial. 190(7):2505-2512.
Spellberg et al. (2004) Trends in antimicrobial drug development: implications for the future.Clin. Infect. Dis., 2004, 38, 1279-1286.
Tserng, K. Y., et al., 1977. An improved procedure for the synthesis of glycine and taurine conjugates of bile acids. J. Lipid Res. 18(3):404-407.
Bhattacharjee et al., Reexamining the Germination Phenotypes of Several Clostridium difficile Strains Suggests Another Role for the CspC Germinant Receptor. J Bacteriol 2015, 198, 777-86.
Chen et al. , "A mouse model of Clostridium difficile-associated disease", (2008) Gastroenterology 135(6): 1984-1992.

(56) References Cited

OTHER PUBLICATIONS

Czepiel et al., Clostridium difficile infection: review. Eur J Clin Microbiol Infect Dis 2019, 38, 1211-1221.
Doll et al., Prevention of *Clostridioides difficile* in hospitals: A position paper of the International Society for Infectious Diseases. *Int J Infect Dis* 2021, 102, 188-195.
Durre, P., Physiology and Sporulation in Clostridium. In *The Bacterial Spore: From Molecules to Systems*, Eichenberger, P.; Driks, A., Eds. American Society for Microbiology: Washington D.C., 2016; vol. IV, pp. 315-329.
Francis et al., Bile acid recognition by the Clostridium difficile germinant receptor, CspC, is important for establishing infection. PLoS Pathog 2013, 9, e1003356.
Howerton et al., A new strategy for the prevention of Clostridium difficile infection, (2013) Journal of Infectious Diseases 207(10): 1498-1504.
Howerton et al., Effect of the Synthetic Bile Salt Analog CamSA on the Hamster Model of Clostridium difficile Infection. Antimicrob Agents Chemother 2018, 62, e02251-17.
Howerton et al., Fate of ingested Clostridium difficile spores in mice. PLoS One 2013, 8, e72620.
Howerton, A. Anti-Germinants as a New Strategy to Prevent Clostridium difficile Infections. University of Nevada, Las Vegas, Las Vegas, 2012.
Ida, Y. et al., "Synthesis of quinolinomorphinan derivatives as highly selective δ opioid receptor ligands", . Bioorg. Med. Chem., 2012, 20, 5810-5831.
Kevorkian and Shen, Revisiting the Role of Csp Family Proteins in Regulating Clostridium difficile Spore Germination. J Bacteriol 2017, 199, e00266-17.
Lawler et al., A Revised Understanding of Clostridioides difficile Spore Germination. Trends Microbiol 2020, 28, 744-752.
Palmieri et al., Inhibitory Effect of Ursodeoxycholic Acid on Clostridium difficile Germination is Insufficient to Prevent Colitis: A Study in Hamsters and Humans. Front Microbiol 2018, 9, 2849.
PDB codes: 2QO5, 1TW4, 3EM0, 3EL7, 2FT9, 5L8O, 2QO6, 2QO4, 4QE6, 6HL1.
Phan et al., An Aniline-Substituted Bile Salt Analog Protects both Mice and Hamsters from Multiple Clostridioides difficile Strains, (2022) *Antimicrobial Agents and Chemotherapy* 66(1):e01435-01421.
Ramirez et al., Kinetic evidence for the presence of putative germination receptors in Clostridium difficile spores. J Bacteriol 2010, 192, 4215-22.
Rohlfing et al., The CspC pseudoprotease regulates germination of Clostridioides difficile spores in response to multiple environmental signals. PLoS Genet 2019, 15, e1008224.
Setlow et al., Germination of Spores of the Orders Bacillales and Clostridiales. Annu Rev Microbiol 2017, 71, 459-477.
Sharma et al., The Design, Synthesis, and Characterizations of Spore Germination Inhibitors Effective against an Epidemic Strain of Clostridium difficile. J Med Chem 2018, 61, 6759-6778.
Shen et al., Sporulation and Germination in Clostridial Pathogens. Microbiol Spectr 2019, 7, GPP3-0017-2018.
Sorg and Sonenshein, Chenodeoxycholate is an inhibitor of Clostridium difficile spore germination. J Bacteriol 2009, 191, 1115-7.
Sorg and Sonenshein, Inhibiting the initiation of Clostridium difficile spore germination using analogs of chenodeoxycholic acid, a bile acid. J Bacteriol 2010, 192, 4983-90.
Stoltz et al., Synthesis and Biological Evaluation of Bile Acid Analogues Inhibitory to Clostridium difficile Spore Germination. J Med Chem 2017, 60, 3451-3471.
Weingarden et al., Ursodeoxycholic Acid Inhibits Clostridium difficile Spore Germination and Vegetative Growth, and Prevents the Recurrence of Ileal Pouchitis Associated With the Infection. *J Clin Gastroenterol* 2016, 50, 624-30.
Winston and Theriot, Diversification of host bile acids by members of the gut microbiota. Gut Microbes 2020, 11, 158-171.
Winston et al., Ursodeoxycholic Acid (UDCA) Mitigates the Host Inflammatory Response during *Clostridioides difficile* Infection by Altering Gut Bile Acids. *Infect Immun* 2020, 88, e00045-20.
Yip et al., Pharmacokinetics of CamSA, a potential prophylactic compound against Clostridioides difficile infections. Biochem Pharmacol 2021, 183, 114314.
U.S. Appl. No. 63/242,343, filed Sep. 9, 2021, Ernesto Abel-Santos (Board of Regents, University of Nevada, Las Vegas).
U.S. Appl. No. 63/319,079, filed Mar. 11, 2022, Ernesto Abel-Santos (Board of Regents, University of Nevada, Las Vegas).
U.S. Appl. No. 62/113,184, filed Feb. 6, 2015, Ernesto Abel-Santos (Board of Regents, University of Nevada, Las Vegas).
U.S. Appl. No. 15/545,645 (2018/0000793), filed Jul. 21, 2017 (Jan. 4, 2018), Ernesto Abel-Santos (Board of Regents, University of Nevada, Las Vegas).
U.S. Appl. No. 16/236,919 (U.S. Pat. No. 10,945,996), filed Dec. 31, 2018 (Mar. 16, 2021), Ernesto Abel-Santos (Board of Regents, University of Nevada, Las Vegas).
U.S. Appl. No. 17/168,155 (US2021/0228550), filed Feb. 4, 2021 (Jul. 29, 2021), Ernesto Abel-Santos (Board of Regents, University of Nevada, Las Vegas).
U.S. Appl. No. 61/682,505, filed Aug. 13, 2021, Ernesto Abel-Santos (Board of Regents, University of Nevada, Las Vegas).
U.S. Appl. No. 13/962,658 (US 2012/0045808), filed Aug. 8, 2013 (Feb. 13, 2014), Ernesto Abel-Santos (Board of Regents, University of Nevada, Las Vegas).
U.S. Appl. No. 14/798,276 (US2016/0009753, U.S. Pat. No. 9,862,744), filed Jul. 13, 2015 (Jan. 14, 2016), Ernesto Abel-Santos (Board of Regents, University of Nevada, Las Vegas).
U.S. Appl. No. 16/738,434 (reissue of '744), filed Jan. 9, 2020, Ernesto Abel-Santos (Board of Regents, University of Nevada, Las Vegas).
PCT, PCT/US2022/043053, Sep. 9, 2022, Ernesto Abel-Santos (Board of Regents, University of Nevada, Las Vegas).
PCT, PCT/US2016/016848 (WO 2016/127102), Feb. 5, 2016 (Aug. 11, 2016), Ernesto Abel-Santos (Board of Regents, University of Nevada, Las Vegas).

\* cited by examiner

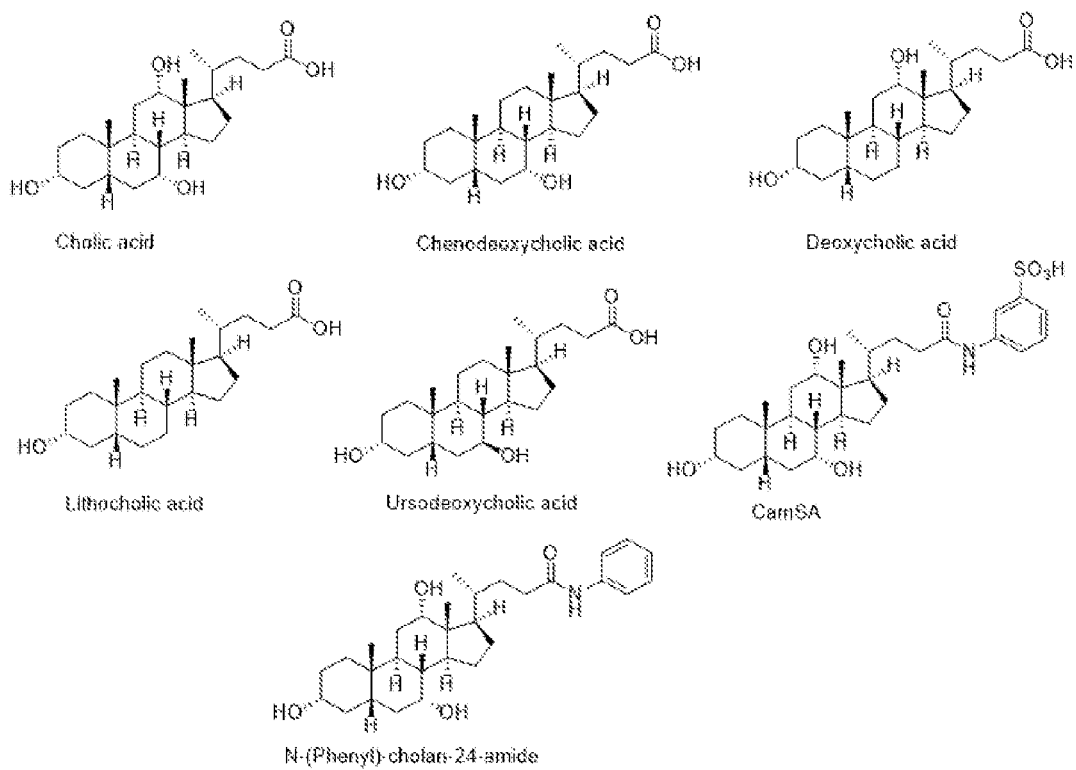

INHIBITORS OF *C. dIFFICILE* SPORE GERMINATION

CROSS-REFERENCE TO RELATED APPLICATIONS

This Application claims the benefit of U.S. Application No. 63/242,343, filed on Sep. 9, 2021, and U.S. Application No. 63/319,079, filed Mar. 11, 2022, the contents of which are incorporated herein by reference in their entirety.

STATEMENT REGARDING FEDERALLY SPONSORED RESEARCH

This invention was made with government support under Grant no. 1R01AI109139-01A1, awarded by the National Institutes of Health (NIH). The government has certain rights in the invention.

BACKGROUND

*Clostridioides* (*Clostridium difficile*) is a common Gram-positive, spore-forming bacterium that can cause severe and even deadly infections in the colon (Ryan, K. J., *Clostridium, Bacteroides*, and Other Anaerobes. In *Sherris Medical Microbiology, 7e*, McGraw-Hill Education: New York, NY, 2017 Chapter 29, sectionid=176086328; Czepiel et al., *Clostridium difficile* infection: review. *Eur J Clin Microbiol Infect Dis* 2019, 38, 1211-1221). Once the infection has been established in the gut, *C. difficile* produces toxins including the enterotoxin and cytotoxin, TcdA and TcdB respectively, resulting in diarrhea and severe damage to the intestinal lining of the gut (Di Bella et al., *Clostridium difficile* Toxins A and B: Insights into Pathogenic Properties and Extraintestinal Effects. *Toxins (Basel)* 2016, 8, E134). A 2019 CDC report indicated that in 2017, over 223,900 Americans contracted *C. difficile* resulting in 12,800 deaths and $1 billion in healthcare costs (Antibiotic Resistance Threats in the United States. CDC, Ed. CDC: Atlanta, GA, 2019). People 65 years or older are more susceptible and make up 80% of *C. difficile* infections deaths (Czepiel et al., *Clostridium difficile* infection: review. *Eur J Clin Microbiol Infect Dis* 2019, 38, 1211-1221). Immunocompromised individuals and patients using broad-spectrum antibiotics are also at risk from *C. difficile*. The CDC has listed *C. difficile* as one of the top five urgent threats to public health in its 2019 report (Antibiotic Resistance Threats in the United States. CDC, Ed. CDC: Atlanta, GA, 2019).

*C. difficile* is spread by an oral-fecal route of transmission (Czepiel et al., *Clostridium difficile* infection: review. *Eur J Clin Microbiol Infect Dis* 2019, 38, 1211-1221). The vegetative bacteria themselves are unable to accomplish this transition since they are susceptible to the relatively high oxygen content of air and the highly acidic conditions of the stomach. Instead, *C. difficile* is spread by spores that are heat-resistant, aerobically stable, acid- and radiation-resistant, and most importantly are not affected by antiseptic cleaners (Czepiel et al., *Clostridium difficile* infection: review. *Eur J Clin Microbiol Infect Dis* 2019, 38, 1211-1221; Durre, P., Physiology and Sporulation in *Clostridium*. In *The Bacterial Spore: From Molecules to Systems*, Eichenberger, P.; Driks, A., Eds. American Society for Microbiology: Washington D.C., 2016; Vol. IV, pp 315-329; Setlow et al., Germination of Spores of the Orders Bacillales and Clostridiales. *Annu Rev Microbiol* 2017, 71, 459-477). Spores are dormant and are viable for months on surfaces. Outbreaks are most common in hospitals and healthcare facilities as the spore is not killed with standard cleaning procedures (Doll et al., Prevention of *Clostridioides difficile* in hospitals: A position paper of the International Society for Infectious Diseases. *Int J Infect Dis* 2021, 102, 188-195).[7] Given the role of spores in the transmission of *C. difficile*, it is hypothesized that eradicating spores or preventing their germination could prevent the development of *C. difficile* infections.

Spore germination is regulated in vivo by bile acids, glycine, and other nutrients present within the gut (Durre, P., Physiology and Sporulation in *Clostridium*. In *The Bacterial Spore: From Molecules to Systems*, Eichenberger, P.; Driks, A., Eds. American Society for Microbiology: Washington D.C., 2016; Vol. IV, pp 315-329; Setlow et al., Germination of Spores of the Orders Bacillales and Clostridiales. *Annu Rev Microbiol* 2017, 71, 459-477; Lawler et al., A Revised Understanding of *Clostridioides difficile* Spore Germination. *Trends Microbiol* 2020, 28, 744-752; Shen et al., Sporulation and Germination in Clostridial Pathogens. *Microbiol Spectr* 2019, 7, GPP3-0017-2018; Howerton et al., Mapping interactions between germinants and *Clostridium difficile* spores. *J Bacteriol* 2011, 193, 274-82; Sorg and Sonenshein, Bile salts and glycine as cogerminants for *Clostridium difficile* spores. *J Bacteriol* 2008, 190, 2505-12). Several studies have shown that taurocholate, cholate, and deoxycholate activate germination, albeit with different potencies (Howerton et al., Mapping interactions between germinants and *Clostridium difficile* spores. *J Bacteriol* 2011, 193, 274-82; Sorg and Sonenshein, Bile salts and glycine as cogerminants for *Clostridium difficile* spores. *J Bacteriol* 2008, 190, 2505-12; Ramirez et al., Kinetic evidence for the presence of putative germination receptors in *Clostridium difficile* spores. *J Bacteriol* 2010, 192, 4215-22; Sorg and Sonenshein, Chenodeoxycholate is an inhibitor of *Clostridium difficile* spore germination. *J Bacteriol* 2009, 191, 1115-7; Sorg and Sonenshein, Inhibiting the initiation of *Clostridium difficile* spore germination using analogs of chenodeoxycholic acid, a bile acid. *J Bacteriol* 2010, 192, 4983-90). In contrast, the bile acid chenodeoxycholate inhibits spore germination (Sorg and Sonenshein, A. L., Chenodeoxycholate is an inhibitor of *Clostridium difficile* spore germination. *J Bacteriol* 2009, 191, 1115-7; Sorg and Sonenshein, Inhibiting the initiation of *Clostridium difficile* spore germination using analogs of chenodeoxycholic acid, a bile acid. *J Bacteriol* 2010, 192, 4983-90).

Taurocholate produced by the liver is quickly reabsorbed after entering the distal ileum via enterohepatic circulation (Howerton et al., Mapping interactions between germinants and *Clostridium difficile* spores. *J Bacteriol* 2011, 193, 274-82; Sorg and Sonenshein, Bile salts and glycine as cogerminants for *Clostridium difficile* spores. *J Bacteriol* 2008, 190, 2505-12; Ramirez et al., Kinetic evidence for the presence of putative germination receptors in *Clostridium difficile* spores. *J Bacteriol* 2010, 192, 4215-22; Sorg et al., Chenodeoxycholate is an inhibitor of *Clostridium difficile* spore germination. *J Bacteriol* 2009, 191, 1115-7; Sorg and Sonenshein, Inhibiting the initiation of *Clostridium difficile* spore germination using analogs of chenodeoxycholic acid, a bile acid. *J Bacteriol* 2010, 192, 4983-90). The taurocholate remaining in the gut is metabolized by the intestinal microbiome to generate cholic acid and taurine (Winston and Theriot, Diversification of host bile acids by members of the gut microbiota. *Gut Microbes* 2020, 11, 158-171). Cholic acid is further metabolized to chenodeoxycholate. Thus, under normal conditions, the concentration of taurocholate in the intestines is low and the concentration of chenodeoxycholate is high, resulting in inhibition of spore germination (Setlow et al., Germination of Spores of the Orders Bacillales and Clostridiales. *Annu Rev Microbiol* 2017, 71, 459-477; Lawler et al., A Revised Understanding of *Clostridioides difficile* Spore Germination. *Trends Microbiol* 2020, 28, 744-752; Shen et al., Sporulation and Germination in Clostridial Pathogens. *Microbiol Spectr* 2019, 7, GPP3-0017-2018; Sorg and Sonenshein, Bile salts and glycine as cogerminants for *Clostridium difficile* spores. *J Bacteriol* 2008, 190, 2505-12; Sorg and Sonenshein, Chenodeoxycholate is an inhibitor of *Clostridium difficile* spore germination. *J Bacteriol* 2009, 191, 1115-7). Upon treatment with antibiotics, the gut microbial population is depleted and altered, leading to an increase in the concentration of taurocholate and a decrease in chenodeoxycholate levels, thus promoting germination (Setlow et al., Germination of Spores of the Orders Bacillales and Clostridiales. *Annu Rev Microbiol* 2017, 71, 459-477; Lawler et al., A Revised Understanding of *Clostridioides difficile* Spore Germination. *Trends Microbiol* 2020, 28, 744-752; Shen et al., Sporulation and Germination in Clostridial Pathogens. *Microbiol Spectr* 2019, 7, GPP3-0017-2018). The connection between the gut microbiome, bile salt composition, and antibiotic use explains why patients on antibiotics have an increased risk of acquiring *C. difficile* (Czepiel et al., *Clostridium difficile* infection: review. *Eur J Clin Microbiol Infect Dis* 2019, 38, 1211-1221; Doll et al., Prevention of *Clostridioides difficile* in hospitals: A position paper of the International Society for Infectious Diseases. *Int J Infect Dis* 2021, 102, 188-195).

Given the role of bile salts in germination, it is not surprising that these agents have been examined as inhibitors of germination. Studies have found that the natural bile salt, chenodeoxycholate (FIG. 1) inhibits germination with a $K_i$ of 378 µM (Sorg and Sonenshein, Inhibiting the initiation of *Clostridium difficile* spore germination using analogs of chenodeoxycholic acid, a bile acid. *J Bacteriol* 2010, 192, 4983-90). Other natural compounds such as ursodeoxycholic acid and lithocholate have a $K_i$ of 213 µM and 104 µM respectively (Sorg and Sonenshein, Inhibiting the initiation of *Clostridium difficile* spore germination using analogs of chenodeoxycholic acid, a bile acid. *J Bacteriol* 2010, 192, 4983-90). Ursodeoxycholic acid has been used to treat a single patient with *C. difficile* ileal pouchitis and has been reported to reduce *C. difficile* recurrence in humans (Weingarden et al., Ursodeoxycholic Acid Inhibits *Clostridium difficile* Spore Germination and Vegetative Growth, and Prevents the Recurrence of Ileal Pouchitis Associated With the Infection. *J Clin Gastroenterol* 2016, 50, 624-30; Winston et al., Ursodeoxycholic Acid (UDCA) Mitigates the Host Inflammatory Response during *Clostridioides difficile* Infection by Altering Gut Bile *Acids. Infect Immun* 2020, 88, e00045-20). However, another study has suggested that ursodeoxycholic acid may not be useful in preventing *C. difficile* infections in humans (Palmieri et al., Inhibitory Effect of Ursodeoxycholic Acid on *Clostridium difficile* Germination Is Insufficient to Prevent Colitis: A Study in Hamsters and Humans. *Front Microbiol* 2018, 9, 2849). Analogs of ursodeoxycholate have also been prepared and these inhibited germination with $K_i$'s in the 5-100 µM range (Stoltz et al., Synthesis and Biological Evaluation of Bile Acid Analogues Inhibitory to *Clostridium difficile* Spore Germination. *J Med Chem* 2017, 60, 3451-3471).

Analogs of cholic acid have also been explored as antigerminants. CamSA (FIG. 1) is a potent inhibitor of spore germination ($K_i$ 50 µM) that has been shown to actively stop *C. difficile* germination in both the hamster and mouse models and hence prevent infection (Howerton et al., Mapping interactions between germinants and *Clostridium difficile* spores. *J Bacteriol* 2011, 193, 274-82; Howerton et al., A new strategy for the prevention of *Clostridium difficile* infection. *J Infect Dis* 2013, 207, 1498-504; Howerton et al., Fate of ingested *Clostridium difficile* spores in mice. *PLoS One* 2013, 8, e72620; Howerton et al., Effect of the Synthetic Bile Salt Analog CamSA on the Hamster Model of *Clostridium difficile* Infection. *Antimicrob Agents Chemother* 2018, 62, e02251-17; Yip et al., Pharmacokinetics of CamSA, a potential prophylactic compound against *Clostridioides difficile* infections. *Biochem Pharmacol* 2021, 183, 114314). Unfortunately, CamSA showed no inhibitory or prophylactic activity against the hypervirulent R20291 strain. The inability of CamSA to work on a hypervirulent strain, coupled with an increased prevalence of these strains in clinical settings, has necessitated continued exploration of cholic acid analogs.

Accordingly, there remains a need for compounds and compositions useful in inhibiting germination of *C. difficile* spores, as well as for preventing and/or treating diseases caused by infection of *C. difficile*. These needs and others are met by the present invention.

SUMMARY

In accordance with the purpose(s) of the invention, as embodied and broadly described herein, the invention, in one aspect, relates to compounds that can prevent germination of *C. difficile* spores and materials and methods for reducing or preventing *C. difficile* spore germination, as well as materials and methods for reducing, preventing, or treating adverse effects associated with exposure to germinated *C. difficile* such as, for example, severe diarrhea and colitis.

Thus, disclosed are compound having a structure represented by a formula:

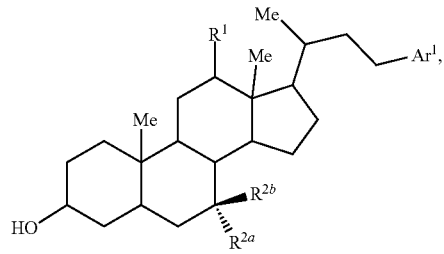

wherein each of $R^1$, $R^{2a}$, and $R^{2b}$ is independently selected from hydrogen and —OH; and wherein $Ar^1$ is a bicyclic heteroaryl having a structure represented by a formula selected from:

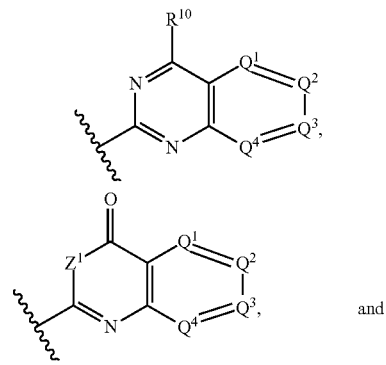

and

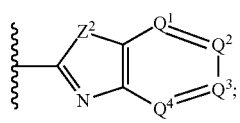

wherein $Z^1$ is selected from —O— and —NR$^{18}$—; wherein $R^{18}$, when present, is selected from hydrogen and C1-C4 alkyl; wherein $Z^2$ is selected from —O—, —S—, and —NR$^{19}$—; wherein $R^{19}$, when present, is selected from hydrogen and C1-C4 alkyl; wherein each of $Q^1$, $Q^2$, $Q^3$, and $Q^4$ is independently selected from —N= and —CR$^{20}$=; wherein each occurrence of $R^{20}$ is independently selected from hydrogen, halogen, C1-C4 alkyl, C1-C4 alkoxy, and phenyl; and wherein $R^{10}$ is selected from hydrogen, halogen, C1-C4 alkyl, C1-C4 alkoxy, C1-C4 haloalkyl, C1-C4 thioalkyl, and phenyl substituted with 0, 1, 2, or 3 groups independently selected from halogen, —CN, —NiH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; provided that when $Ar^1$ is:

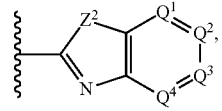

then: (a) at least one of $Q^1$, $Q^2$, $Q^3$, and $Q^4$ is —N= and at least one of $Q^1$, $Q^2$, $Q^3$, and $Q^4$ is —CR$^{20}$=, wherein $R^{20}$ is not hydrogen; or (b) at least two of $Q^1$, $Q^2$, $Q^3$, and $Q^4$ is —CR$^{20}$=, wherein at least two occurrences of $R^{20}$ are not hydrogen, or a pharmaceutically acceptable salt thereof.

Also disclosed are compounds selected from:

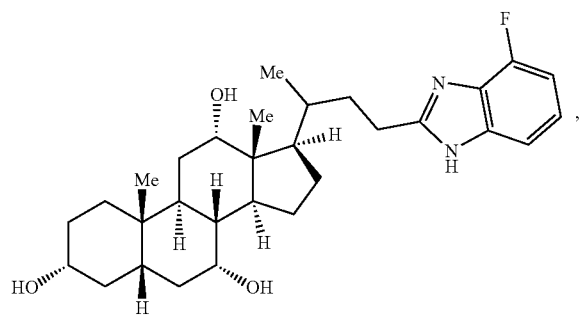

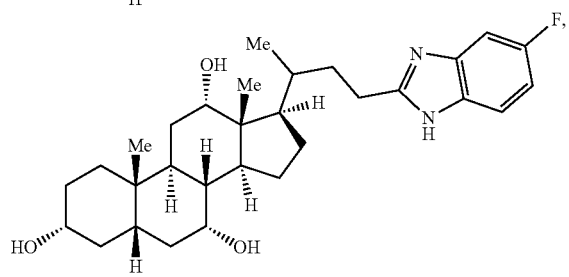

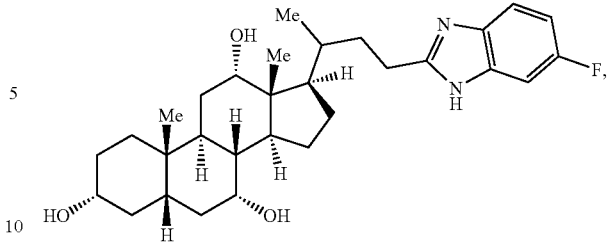

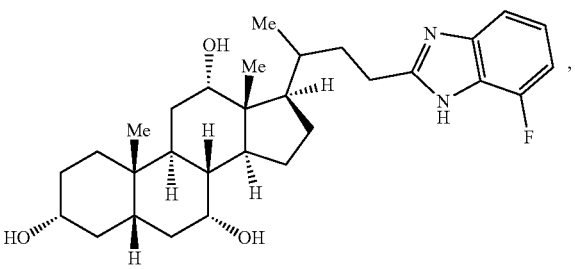

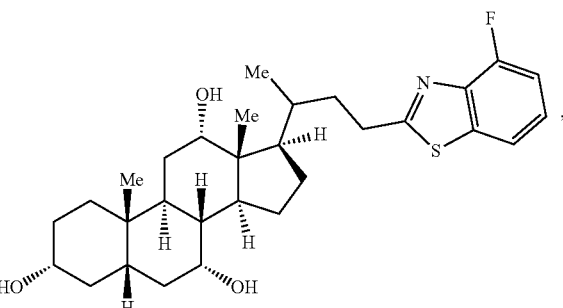

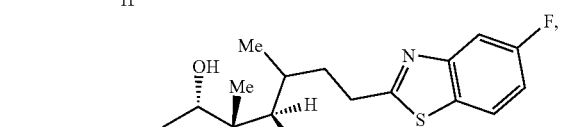

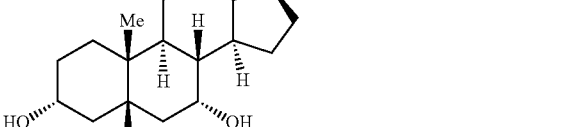

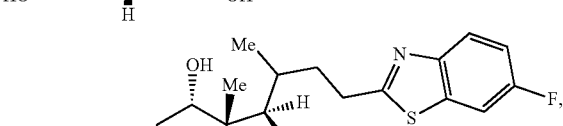

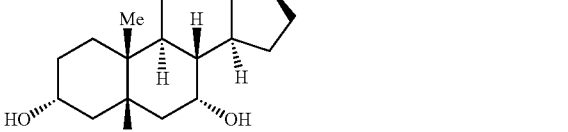

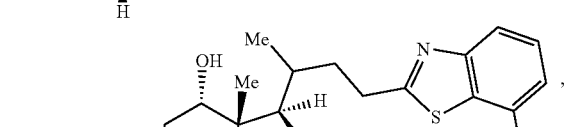

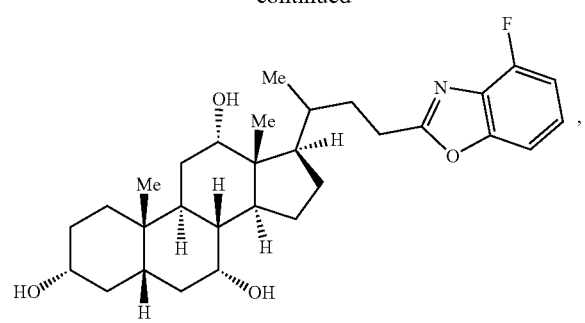
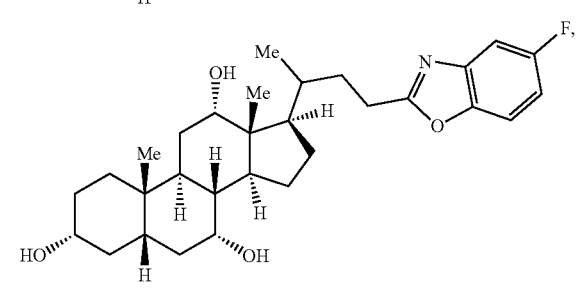
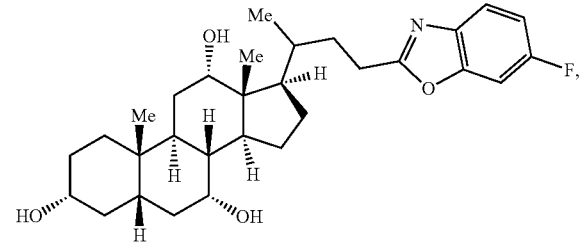
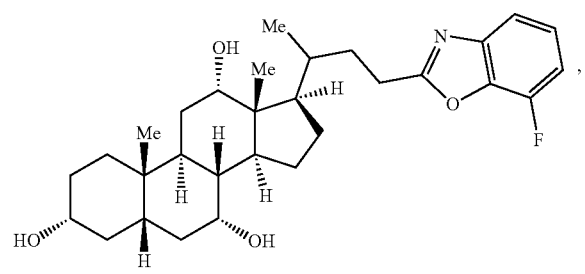
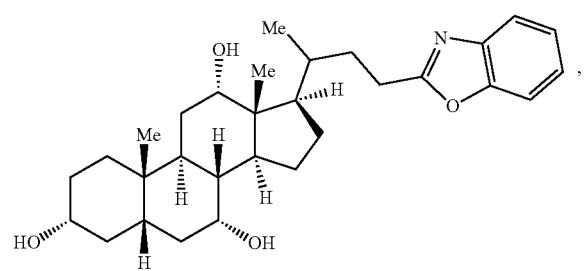
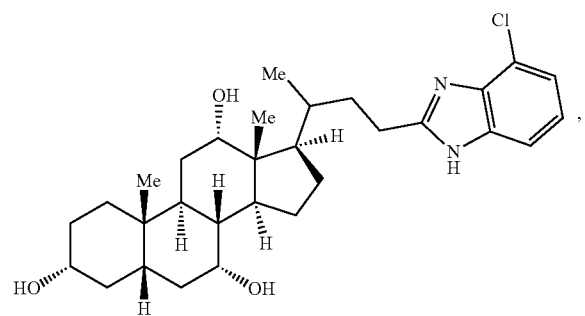
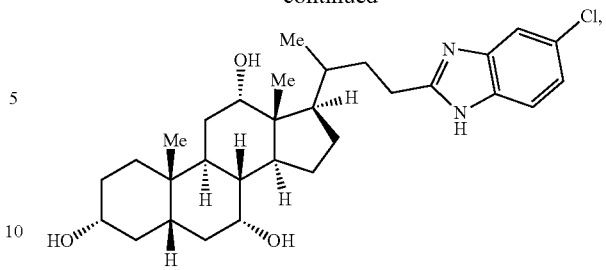

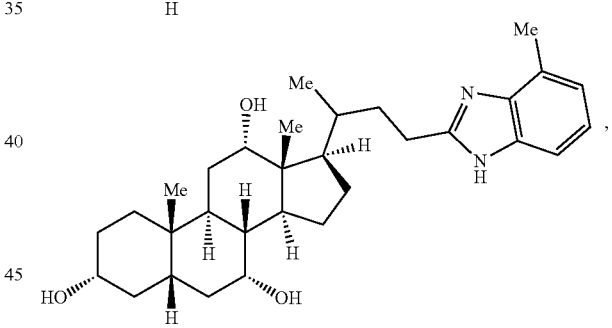
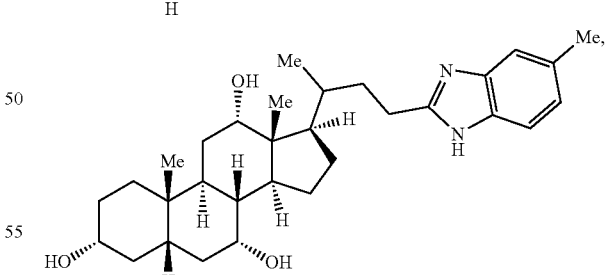
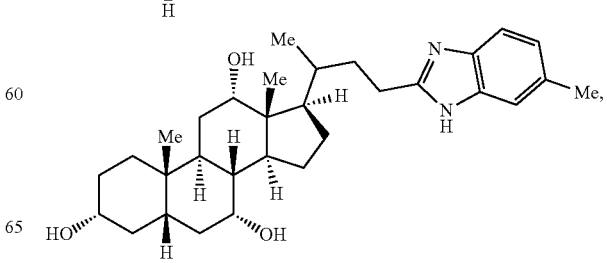

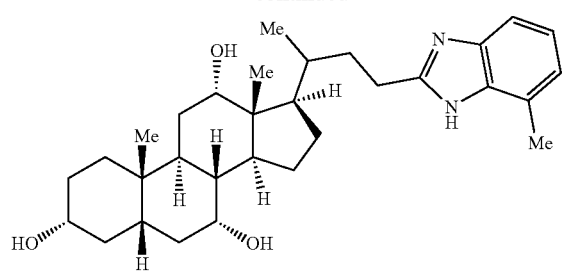
,
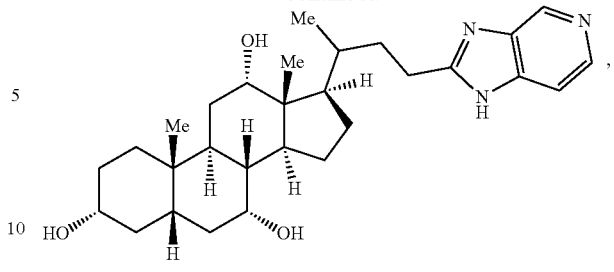
,
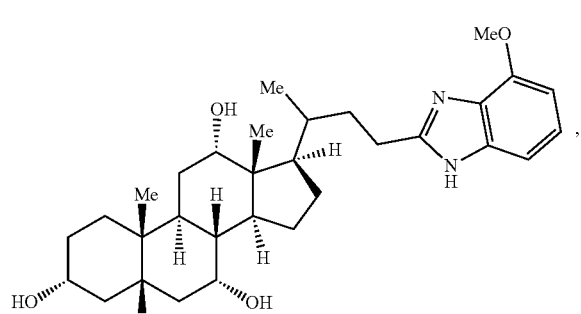
,
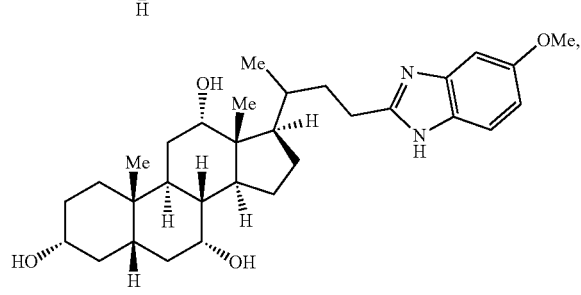
,
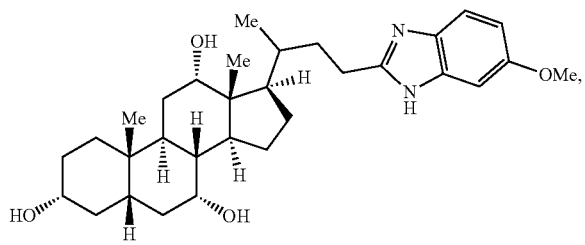
,
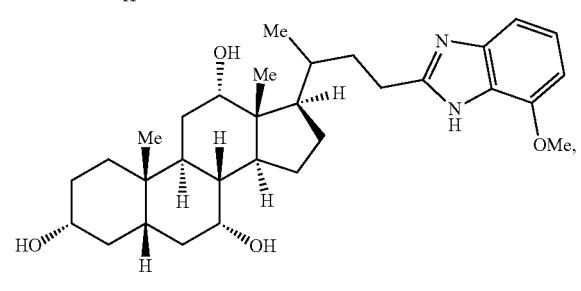
,
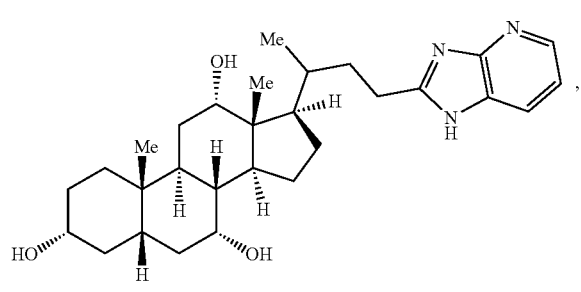
,
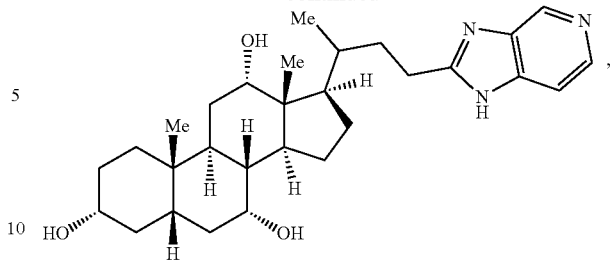

-continued
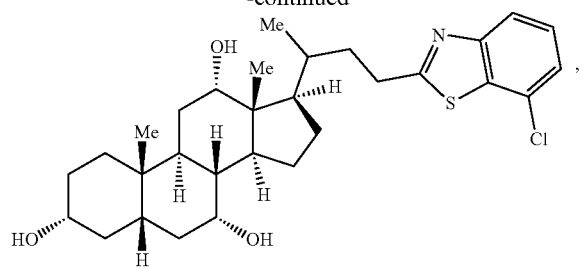
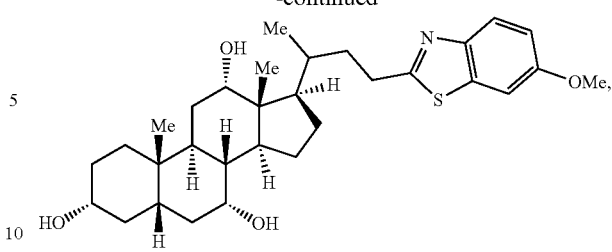
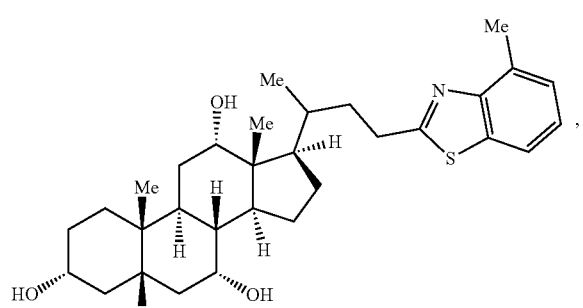
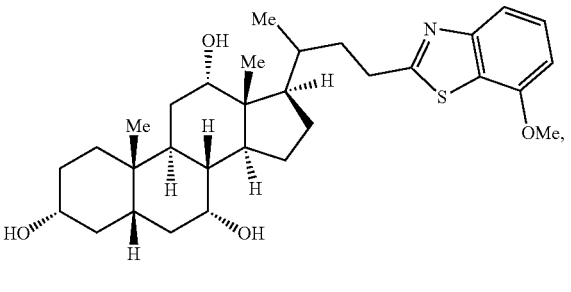
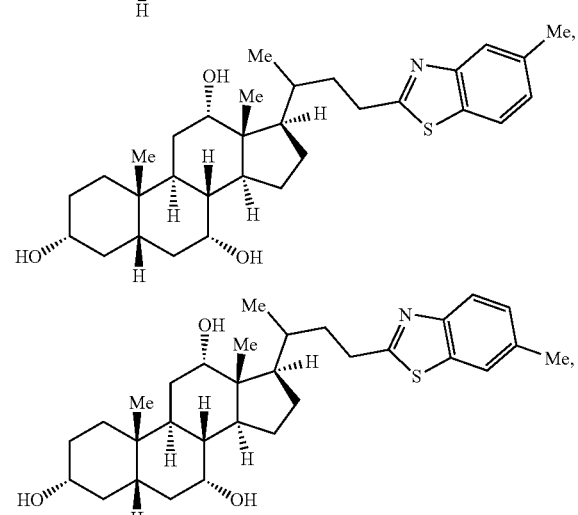
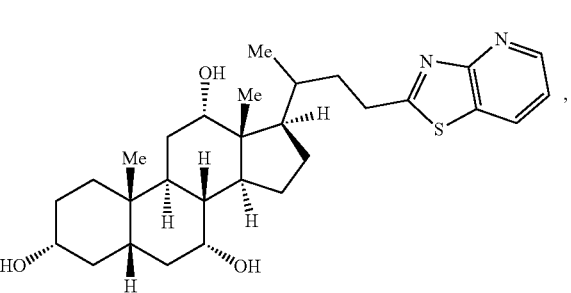
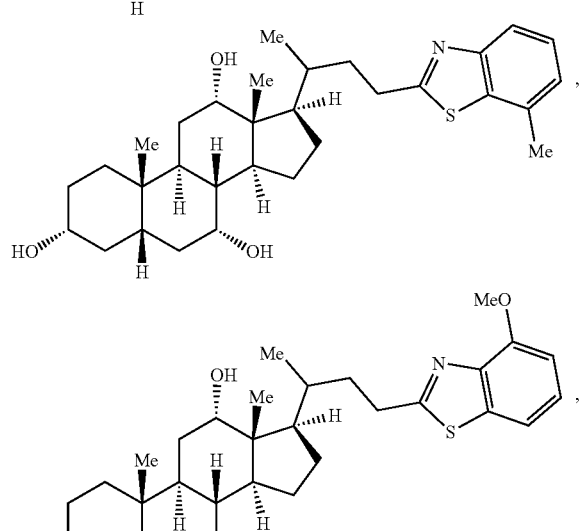
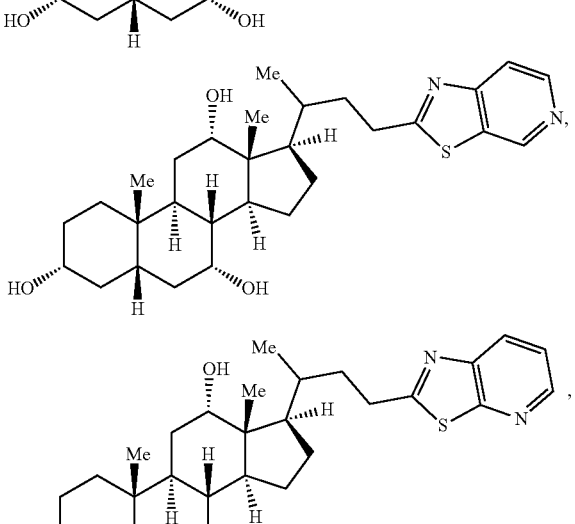

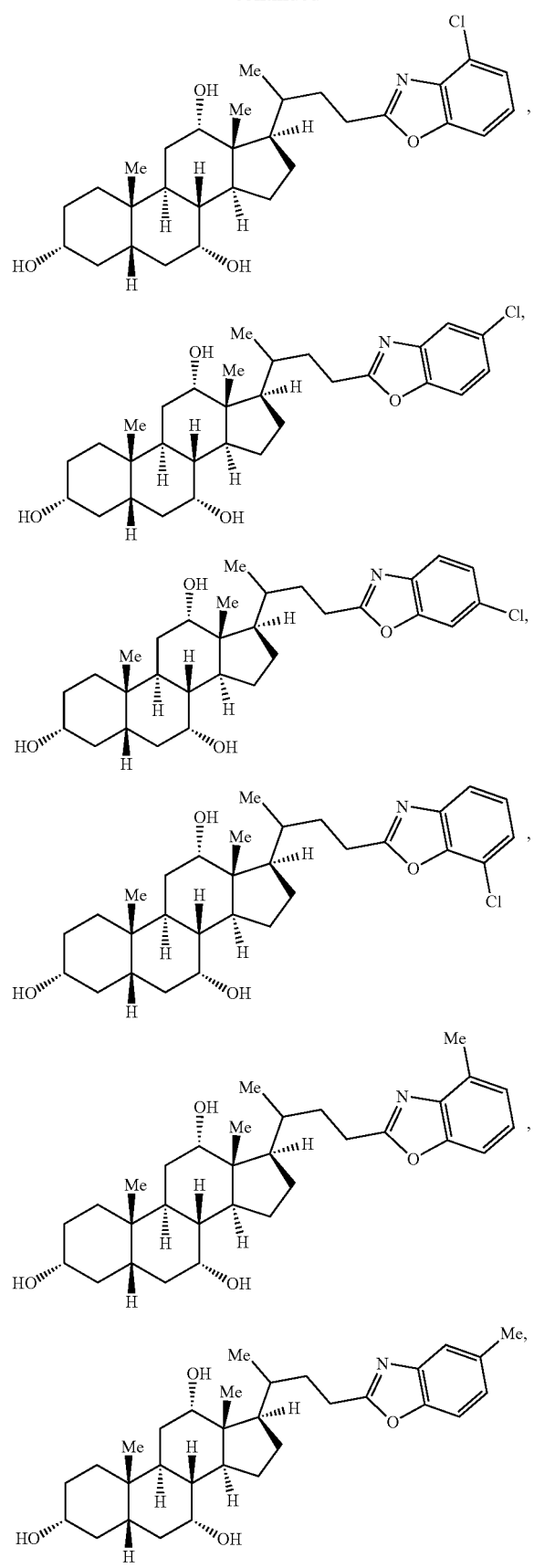
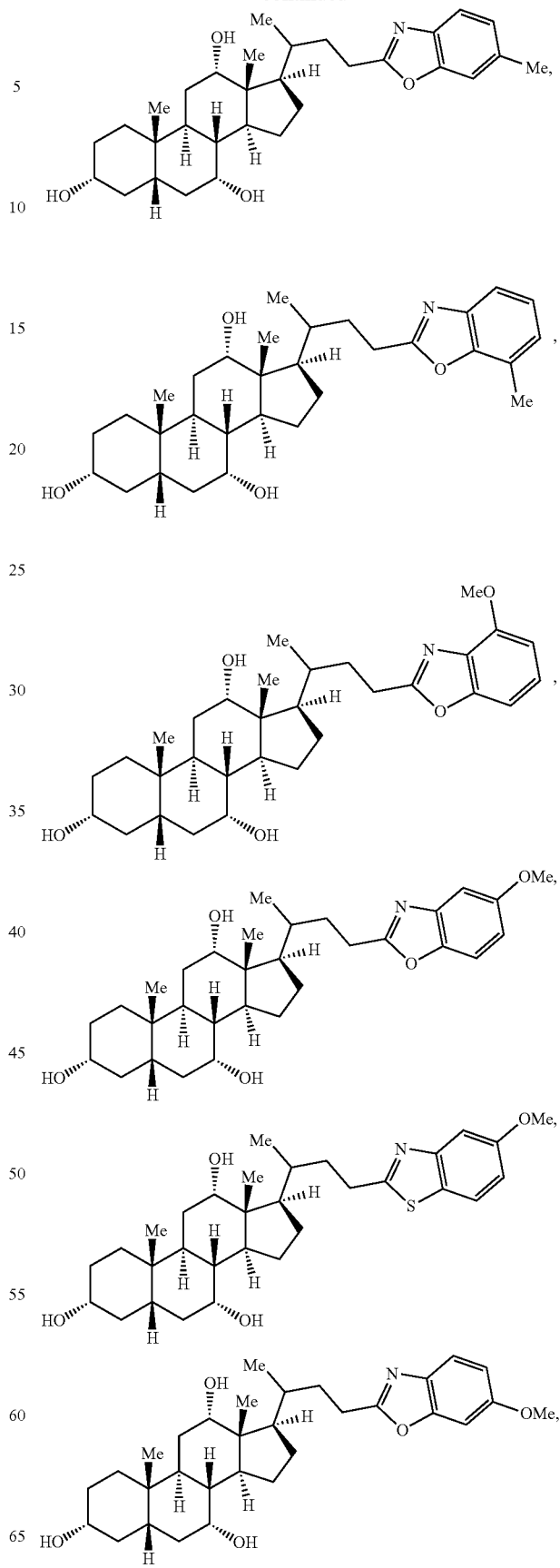

-continued

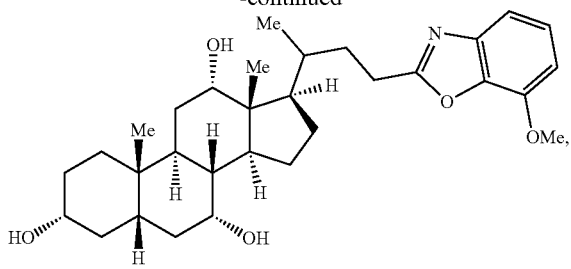

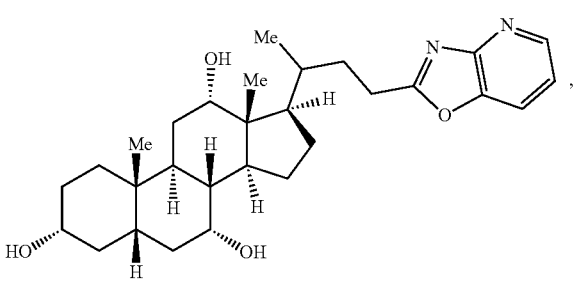

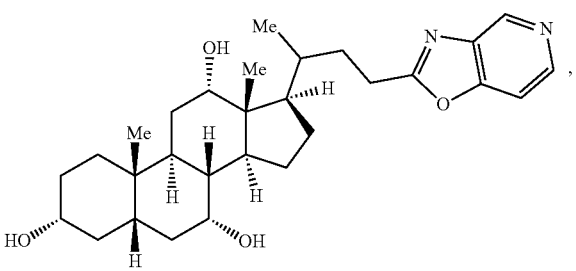

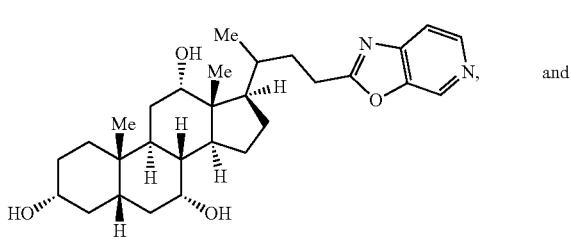

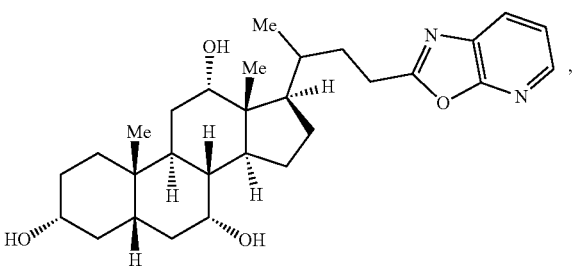

or a pharmaceutically acceptable salt thereof.

Also disclosed are methods for preventing or treating a disease or disorder caused by infection of *Clostridium difficile* in a subject in need thereof, the method comprising administering to the subject an effective amount of a compound having a structure represented by a formula:

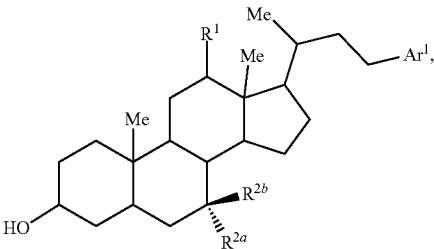

wherein each of $R^1$, $R^{2a}$, and $R^{2b}$ is independently selected from hydrogen and —OH; and wherein $Ar^1$ is a bicyclic heteroaryl having a structure represented by a formula selected from:

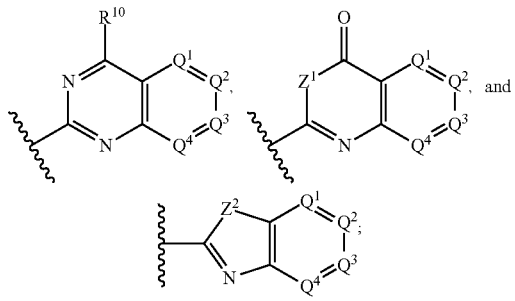

wherein $Z^1$ is selected from —O— and —NR$^{18}$—; wherein $R^{18}$, when present, is selected from hydrogen and C1-C4 alkyl; wherein $Z^2$ is selected from —O—, —S—, and —NR$^{19}$—; wherein $R^{19}$, when present, is selected from hydrogen and C1-C4 alkyl; wherein each of $Q^1$, $Q^2$, $Q^3$, and $Q^4$ is independently selected from —N= and —CR$^{20}$=; wherein each occurrence of $R^{20}$ is independently selected from hydrogen, halogen, C1-C4 alkyl, C1-C4 alkoxy, and phenyl; and wherein $R^{10}$ is selected from hydrogen, halogen, C1-C4 alkyl, C1-C4 alkoxy, and phenyl, or a pharmaceutically acceptable salt thereof.

Also disclosed are methods for inhibiting germination of a *Clostridium difficile* spore in a subject in need thereof, the method comprising administering to the subject an effective amount of a compound having a structure represented by a formula:

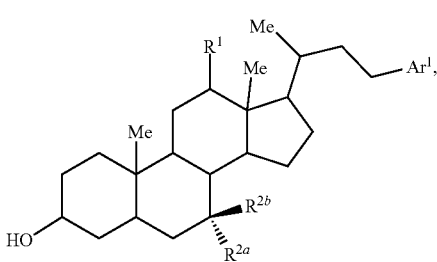

wherein each of $R^1$, $R^{2a}$, and $R^{2b}$ is independently selected from hydrogen and —OH; and wherein $Ar^1$ is a bicyclic heteroaryl having a structure represented by a formula selected from:

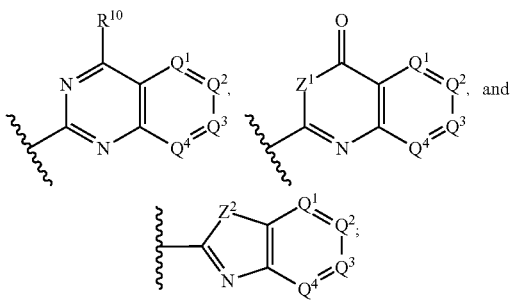

wherein $Z^1$ is selected from —O— and —NR$^{18}$—; wherein R$^{18}$, when present, is selected from hydrogen and C1-C4 alkyl; wherein $Z^2$ is selected from —O—, —S—, and —NR$^{19}$—; wherein R$^{19}$, when present, is selected from hydrogen and C1-C4 alkyl; wherein each of $Q^1$, $Q^2$, $Q^3$, and $Q^4$ is independently selected from —N═ and —CR$^{20}$═; wherein each occurrence of R$^{20}$ is independently selected from hydrogen, halogen, C1-C4 alkyl, C1-C4 alkoxy, and phenyl; and wherein R$^{10}$ is selected from hydrogen, halogen, C1-C4 alkyl, C1-C4 alkoxy, and phenyl, or a pharmaceutically acceptable salt thereof.

Also disclosed are kits comprising a compound having a structure represented by a formula:

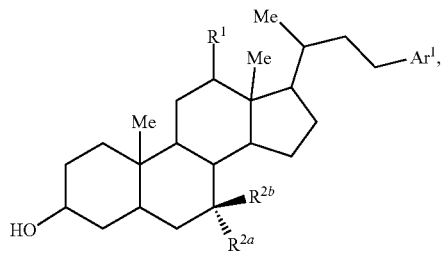

wherein each of R$^1$, R$^{2a}$, and R$^{2b}$ is independently selected from hydrogen and —OH; and wherein Ar$^1$ is a bicyclic heteroaryl having a structure represented by a formula selected from:

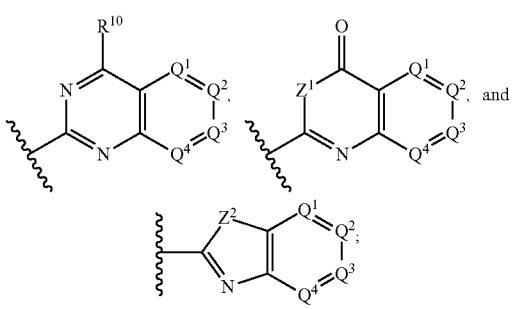

wherein $Z^1$ is selected from —O— and —NR$^{18}$—; wherein R$^{18}$, when present, is selected from hydrogen and C1-C4 alkyl; wherein $Z^2$ is selected from —O—, —S—, and —NR$^{19}$—; wherein R$^{19}$, when present, is selected from hydrogen and C1-C4 alkyl; wherein each of $Q^1$, $Q^2$, $Q^3$, and $Q^4$ is independently selected from —N═ and —CR$^{20}$═; wherein each occurrence of R$^{20}$ is independently selected from hydrogen, halogen, C1-C4 alkyl, C1-C4 alkoxy, and phenyl; and wherein R$^{10}$ is selected from hydrogen, halogen, C1-C4 alkyl, C1-C4 alkoxy, and phenyl, or a pharmaceutically acceptable salt thereof, and one or more of: (a) an agent known for use in feed compositions; (b) an antibiotic; (c) instructions for administering the compound for preventing or treating a disease or disorder caused by infection of *Clostridium difficile*; and (d) instructions for preventing or treating a disease or disorder caused by infection of *Clostridium difficile*.

Also disclosed are compounds having a structure represented by a formula:

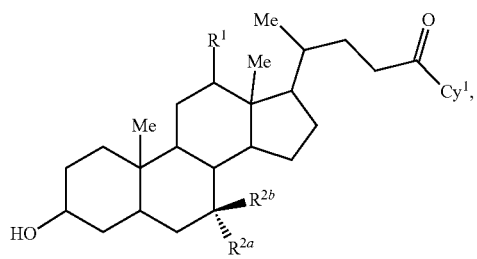

wherein each of R$^1$, R$^{2a}$, and R$^{2b}$ is independently selected from hydrogen and —OH; and wherein Cy$^1$ is a bicycle having a formula selected from:

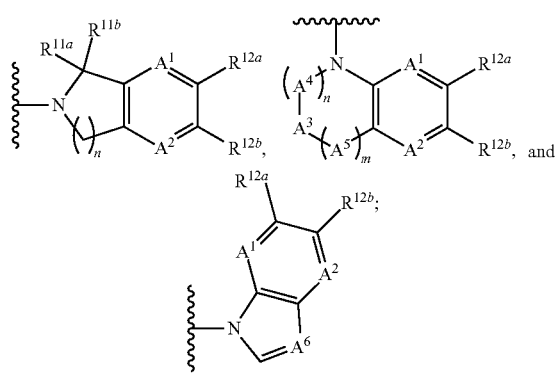

wherein each of n and m, when present, is independently 0, 1, or 2; wherein each of A$^1$ and A$^2$ is independently selected from —N═ and —CR$^{21}$═; wherein each occurrence of R$^{21}$ is independently selected from hydrogen, halogen, —NO$_2$, —CN, C1-C4 alkyl, C1-C4 alkoxy, C1-C4 haloalkyl, and —C(O)(C1-C4 alkyl); wherein A$^3$, when present, is selected from —O—, —S—, —NR$^{22}$—, and —C(R$^{23a}$)(R$^{23b}$)—; wherein R$^{22}$ is selected from hydrogen and C1-C4 alkyl; wherein each of R$^{23a}$ and R$^{23b}$ is independently selected from hydrogen and C1-C4 alkyl; wherein each of A$^4$ and A$^5$, when present, is independently —C(R$^{23c}$)(R$^{23d}$)—; wherein each of R$^{23c}$ and R$^{23d}$ is independently selected from hydrogen and C1-C4 alkyl; wherein A$^6$, when present, is selected from ═C(R$^{24}$)— and ═N—; wherein R$^{24}$, when present, is selected from hydrogen and C1-C4 alkyl; wherein each of R$^{11a}$ and R$^{11b}$, when present, is independently selected from hydrogen and C1-C4 alkyl; and wherein each of R$^{12a}$ and R$^{12b}$ is independently selected from hydrogen, halogen, —NO$_2$, —CN, C1-C4 alkyl, C1-C4 alkoxy, C1-C4 haloalkyl, and —C(O)(C1-C4 alkyl), or a pharmaceutically acceptable salt thereof.

Also disclosed are compounds selected from:

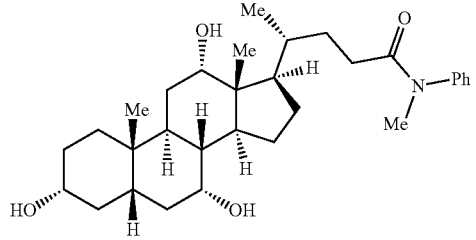

and

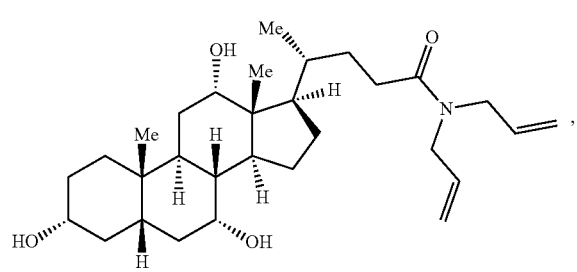

or a pharmaceutically acceptable salt thereof.

Also disclosed are methods for preventing or treating a disease caused by infection of *Clostridium difficile* in a subject in need thereof, the method comprising administering to the subject an effective amount of a compound having a structure represented by a formula:

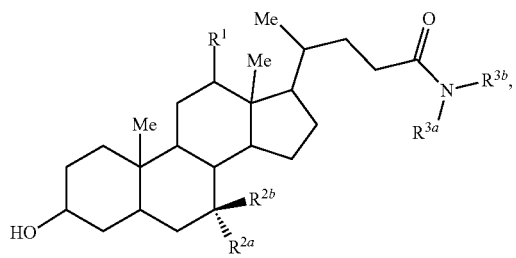

wherein each of $R^1$, $R^{2a}$, and $R^{2b}$ is independently selected from hydrogen and —OH; wherein each of $R^{3a}$ and $R^{3b}$ are independently selected from C1-C4 alkyl, C2-C4 alkenyl, and phenyl substituted with 0, 1, 2, or 3 groups independently selected from halogen, —NO$_2$, —CN, C1-C4 alkyl, C1-C4 haloalkyl, and —C(O)(C1-C4 alkyl), or wherein each of $R^{3a}$ and $R^{3b}$ together comprise a heterocycle having a structure represented by a formula selected from:

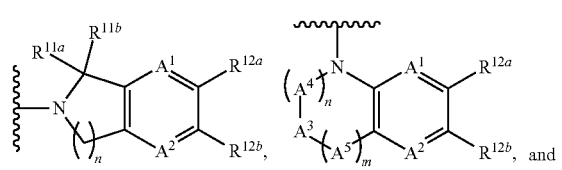

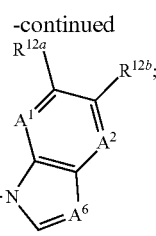

wherein each of n and m, when present, is independently 0, 1, or 2; wherein each of $A^1$ and $A^2$ is independently selected from —N= and —CR$^{21}$=; wherein each occurrence of $R^{21}$ is independently selected from hydrogen, halogen, —NO$_2$, —CN, C1-C4 alkyl, C1-C4 alkoxy, C1-C4 haloalkyl, and —C(O)(C1-C4 alkyl); wherein $A^3$, when present, is selected from —O—, —S—, —NR$^{22}$—, and —C(R$^{23a}$)(R$^{23b}$)—; wherein $R^{22}$ is selected from hydrogen and C1-C4 alkyl; wherein each of $R^{23a}$ and $R^{23b}$ is independently selected from hydrogen and C1-C4 alkyl; wherein each of $A^4$ and $A^5$, when present, is independently —C(R$^{23c}$)(R$^{23d}$)—; wherein each of $R^{23c}$ and $R^{23d}$ is independently selected from hydrogen and C1-C4 alkyl; wherein $A^6$, when present, is selected from =C(R$^{24}$)— and =N—; wherein $R^{24}$, when present, is selected from hydrogen and C1-C4 alkyl; wherein each of $R^{11a}$ and $R^{11b}$, when present, is independently selected from hydrogen and C1-C4 alkyl; and wherein each of $R^{12a}$ and $R^{12b}$ is independently selected from hydrogen, halogen, —NO$_2$, —CN, C1-C4 alkyl, C1-C4 haloalkyl, and —C(O)(C1-C4 alkyl), or a pharmaceutically acceptable salt thereof.

Also disclosed are methods for preventing or treating a disease caused by infection of *Clostridium difficile* in a subject in need thereof, the method comprising administering to the subject an effective amount of a compound selected from:

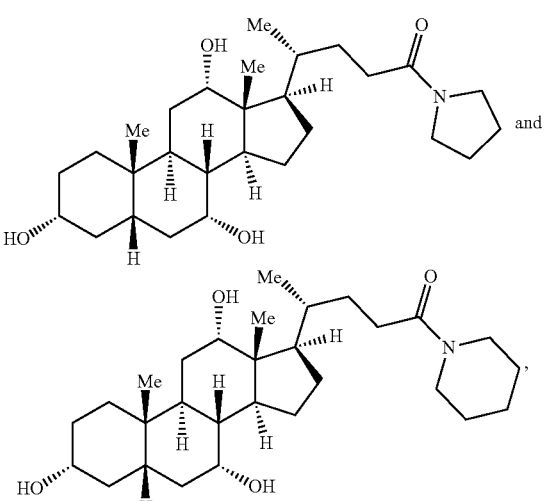

or a pharmaceutically acceptable salt thereof.

Also disclosed are methods for inhibiting germination of a *Clostridium difficile* spore in a subject in need thereof, the method comprising administering to the subject an effective amount of a compound having a structure represented by a formula:

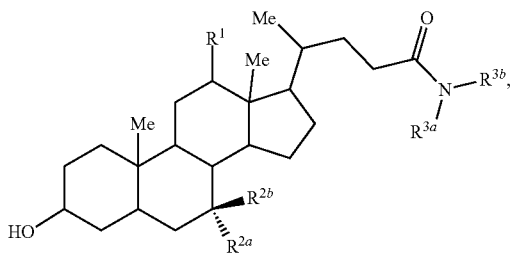

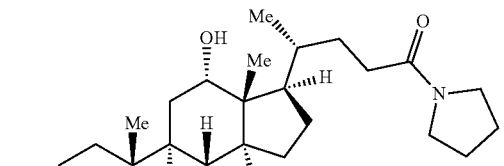

and

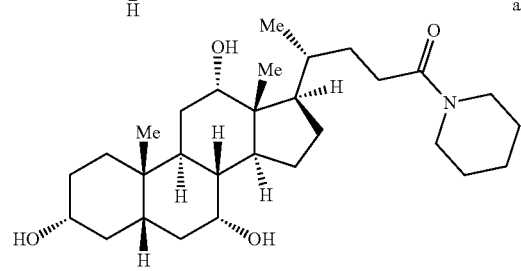

or a pharmaceutically acceptable salt thereof.

Also disclosed are kits comprising a compound having a structure represented by a formula:

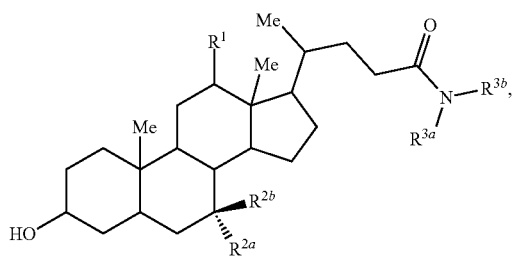

wherein each of $R^1$, $R^{2a}$, and $R^{2b}$ is independently selected from hydrogen and —OH; wherein each of $R^{3a}$ and $R^{3b}$ are independently selected from C1-C4 alkyl, C2-C4 alkenyl, and phenyl substituted with 0, 1, 2, or 3 groups independently selected from halogen, —NO$_2$, —CN, C1-C4 alkyl, C1-C4 haloalkyl, and —C(O)(C1-C4 alkyl), or wherein each of $R^{3a}$ and $R^{3b}$ together comprise a heterocycle having a structure represented by a formula selected from:

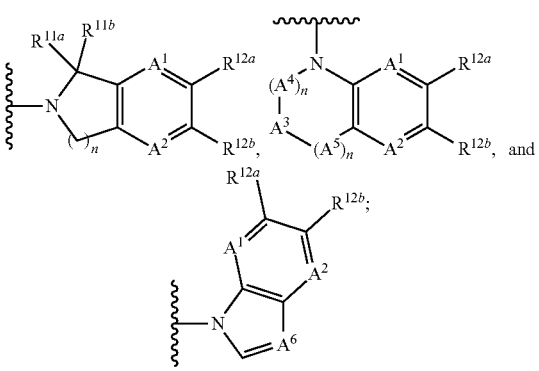

wherein each of n and m, when present, is independently 0, 1, or 2; wherein each of $A^1$ and $A^2$ is independently selected from —N= and —CR$^{21}$=; wherein each occurrence of $R^{21}$ is independently selected from wherein each of $R^1$, $R^{2a}$, and $R^{2b}$ is independently selected from hydrogen and —OH; wherein each of $R^{3a}$ and $R^{3b}$ are independently selected from C1-C4 alkyl, C2-C4 alkenyl, and phenyl substituted with 0, 1, 2, or 3 groups independently selected from halogen, —NO$_2$, —CN, C1-C4 alkyl, C1-C4 haloalkyl, and —C(O)(C1-C4 alkyl), or wherein each of $R^{3a}$ and $R^{3b}$ together comprise a heterocycle having a structure represented by a formula selected from:

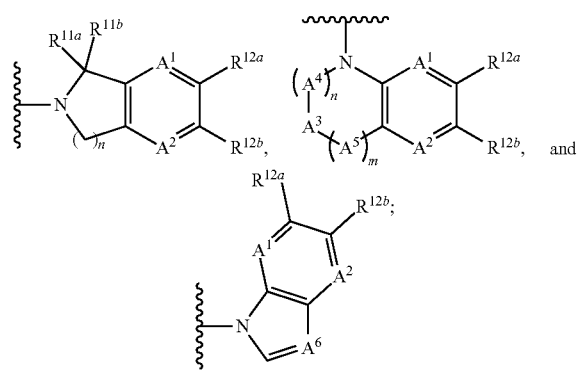

wherein each of n and m, when present, is independently 0, 1, or 2; wherein each of $A^1$ and $A^2$ is independently selected from —N= and —CR$^{21}$=; wherein each occurrence of $R^{21}$ is independently selected from hydrogen, halogen, —NO$_2$, —CN, C1-C4 alkyl, C1-C4 alkoxy, C1-C4 haloalkyl, and —C(O)(C1-C4 alkyl); wherein $A^3$, when present, is selected from —O—, —S—, —NR$^{22}$—, and —C(R$^{23a}$)(R$^{23b}$)—; wherein $R^{22}$ is selected from hydrogen and C1-C4 alkyl; wherein each of $R^{23a}$ and $R^{23b}$ is independently selected from hydrogen and C1-C4 alkyl; wherein each of $A^4$ and $A^5$, when present, is independently —C(R$^{23c}$)(R$^{23d}$)—; wherein each of $R^{23c}$ and $R^{23d}$ is independently selected from hydrogen and C1-C4 alkyl; wherein each of $R^{23a}$ and $R^{23b}$ is independently selected from hydrogen and C1-C4 alkyl; wherein $A^6$, when present, is selected from =C(R$^{24}$)— and =N—; wherein $R^{24}$, when present, is selected from hydrogen and C1-C4 alkyl; wherein each of $R^{11a}$ and $R^{11b}$, when present, is independently selected from hydrogen and C1-C4 alkyl; and wherein each of $R^{12a}$ and $R^{12b}$ is independently selected from hydrogen, halogen, —NO$_2$, —CN, C1-C4 alkyl, C1-C4 haloalkyl, and —C(O)(C1-C4 alkyl), or a pharmaceutically acceptable salt thereof.

Also disclosed are methods for inhibiting germination of a *Clostridium difficile* in a subject in need thereof, the method comprising administering to the subject an effective amount of a compound selected from:

hydrogen, halogen, —NO$_2$, —CN, C1-C4 alkyl, C1-C4 alkoxy, C1-C4 haloalkyl, and —C(O)(C1-C4 alkyl); wherein A$^3$, when present, is selected from —O—, —S—, —NR$^{22}$—, and —C(R$^{23a}$)(R$^{23b}$)—; wherein R$^{22}$ is selected from hydrogen and C1-C4 alkyl; wherein each of R$^{23a}$ and R$^{23b}$ is independently selected from hydrogen and C1-C4 alkyl; wherein each of A$^4$ and A$^5$, when present, is independently —C(R$^{23c}$)(R$^{23d}$)—; wherein each of R$^{23c}$ and R$^{23d}$ is independently selected from hydrogen and C1-C4 alkyl; wherein A$^6$, when present, is selected from =C(R$^{24}$)— and =N—; wherein R$^{24}$, when present, is selected from hydrogen and C1-C4 alkyl; wherein each of R$^{11a}$ and R$^{11b}$, when present, is independently selected from hydrogen and C1-C4 alkyl; and wherein each of R$^{12a}$ and R$^{12b}$ is independently selected from hydrogen, halogen, —NO$_2$, —CN, C1-C4 alkyl, C1-C4 haloalkyl, and —C(O)(C1-C4 alkyl), or a pharmaceutically acceptable salt thereof, and one or more of: (a) an agent known for use in feed compositions; (b) an antibiotic; (c) instructions for administering the compound for preventing or treating a disease or disorder caused by infection of *Clostridium difficile*; and (d) instructions for preventing or treating a disease or disorder caused by infection of *Clostridium difficile*.

Also disclosed are kits comprising a compound selected from:

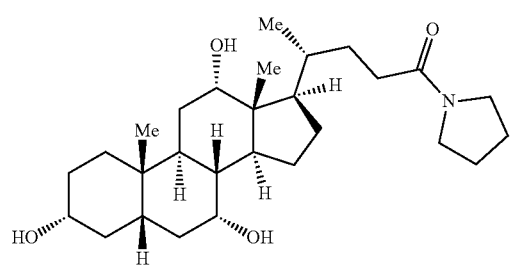

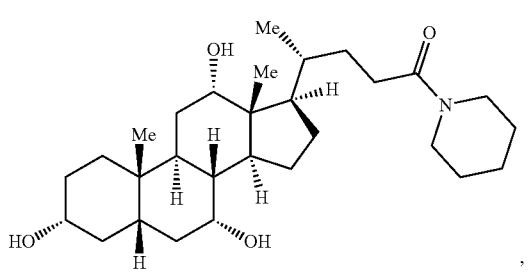

or a pharmaceutically acceptable salt thereof, and one or more of: (a) an agent known for use in feed compositions; (b) an antibiotic; (c) instructions for administering the compound for preventing or treating a disease or disorder caused by infection of *Clostridium difficile*; and (d) instructions for preventing or treating a disease or disorder caused by infection of *Clostridium difficile*.

Also disclosed are compounds selected from:

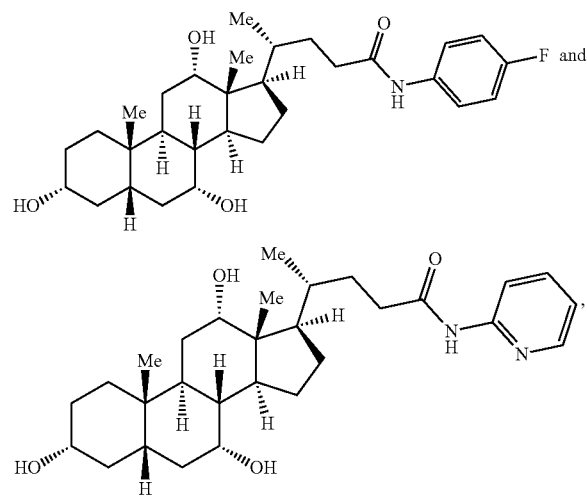

or a pharmaceutically acceptable salt thereof.

Also disclosed are methods for preventing or treating a disease caused by infection of *Clostridium difficile* in a subject in need thereof, the method comprising administering to the subject an effective amount of a compound selected from:

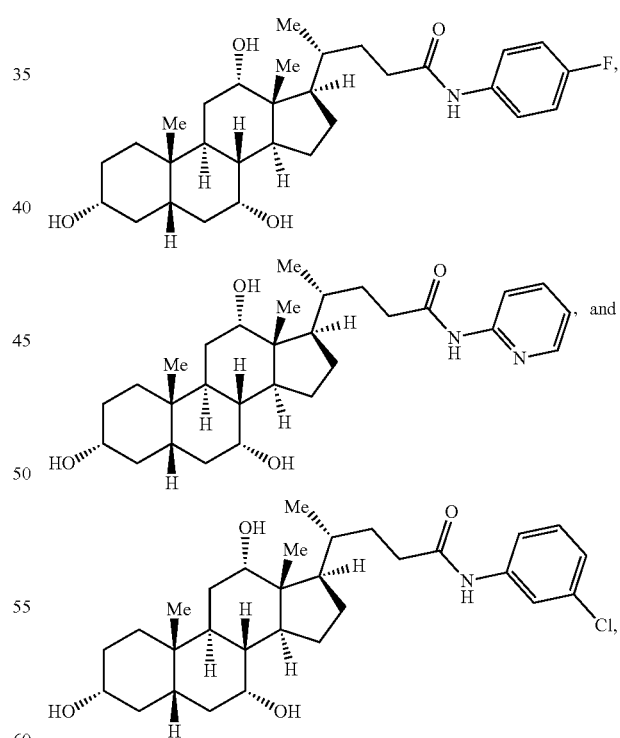

or a pharmaceutically acceptable salt thereof.

Also disclosed are methods for inhibiting germination of a *Clostridium difficile* in a subject in need thereof, the method comprising administering to the subject an effective amount of a compound selected from:

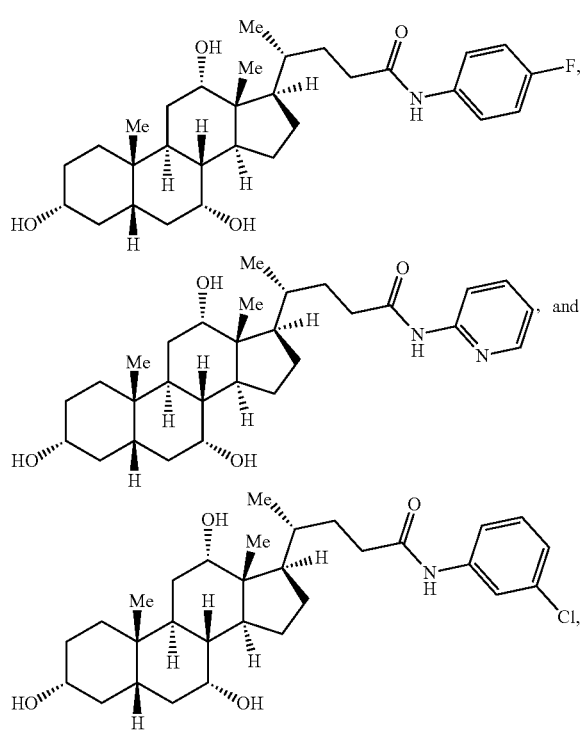

or a pharmaceutically acceptable salt thereof.

Also disclosed are kits comprising a compound selected from:

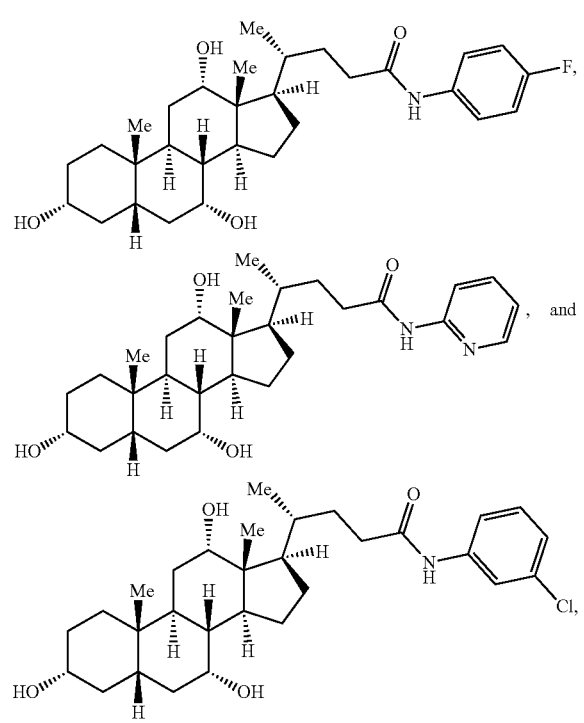

or a pharmaceutically acceptable salt thereof, and one or more of: (a) an agent known for use in feed compositions; (b) an antibiotic; (c) instructions for administering the compound for preventing or treating a disease or disorder caused by infection of *Clostridium difficile*; and (d) instructions for preventing or treating a disease or disorder caused by infection of *Clostridium difficile*.

Also disclosed are compositions comprising an effective amount of a disclosed compound, and a feed component.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

The accompanying FIGURES, which are incorporated in and constitute a part of this specification, illustrate several aspects and together with the description serve to explain the principles of the invention.

FIG. 1 shows representative structures of bile acids: cholic acid, chenodeoxycholic acid, deoxycholic acid, lithocholic acid, and ursodeoxycholic acid. FIG. 1 also shows CamSA and N-(Phenyl)-cholan-24-amide as potent inhibitors of the epidemic strain of *C. difficile* R202091.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

It is appreciated that certain features of the disclosure, which are, for clarity, described in the context of separate aspects, can also be provided in combination in a single aspect.

Conversely, various features of the disclosure which are, for brevity, described in the context of a single aspect, can also be provided separately or in any suitable subcombination.

For the terms "for example" and "such as," and grammatical equivalents thereof, the phrase "and without limitation" is understood to follow unless explicitly stated otherwise.

All measurements reported herein are understood to be modified by the term "about", whether or not the term is explicitly used, unless explicitly stated otherwise.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and salts hereof (e.g., pharmaceutically acceptable salts), can be found together with other substances such as water and solvents (e.g., hydrates and solvates).

Compounds provided herein also can include tautomeric forms. Tautomeric forms result from the swapping of a single bond with an adjacent double bond together with the concomitant migration of a proton. Tautomeric forms include prototropic tautomers that are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds provided herein can also include all isotopes of atoms occurring in the intermediates or final compounds. Isotopes include those atoms having the same atomic number but different mass numbers. For example, isotopes of hydrogen include hydrogen, tritium, and deuterium.

The phrase "pharmaceutically acceptable" is used herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Also provided herein are pharmaceutically acceptable salts of the compounds described herein. As used herein, the term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. In various aspects, a non-aqueous media like ether, ethyl acetate, alcohols (e.g., methanol, ethanol, iso-propanol, or butanol) or acetonitrile (ACN) ca a be used. Lists of suitable salts are found in Remington's Pharmaceutical Sciences, 17th ed., Mack Publishing Company, Easton, Pa., 1985, p. 1418 and Journal of Pharmaceutical Science, 66, 2 (1977). Conventional methods for preparing salt forms are described, for example, in Handbook of Pharmaceutical Salts: Properties, Selection, and Use, Wiley-VCH, 2002.

In some embodiments, a compound provided herein, or salt thereof, is substantially isolated. By "substantially isolated" is meant that the compound is at least partially or substantially separated from the environment in which it was formed or detected. Partial separation can include, for example, a composition enriched in the compound provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

As used herein, chemical structures that contain one or more stereocenters depicted with dashed and bold bonds (i.e., ) are meant to indicate absolute stereochemistry of the stereocenter(s) present in the chemical structure. As used herein, bonds symbolized by a simple line do not indicate a stereo-preference. Unless otherwise indicated to the contrary, chemical structures, which include one or more stereocenters, illustrated herein without indicating absolute or relative stereochemistry encompass all possible stereoisomeric forms of the compound (e.g., diastereomers and enantiomers) and mixtures thereof. Structures with a single bold or dashed line, and at least one additional simple line, encompass a single enantiomeric series of all possible diastereomers.

Resolution of racemic mixtures of compounds can be carried out using appropriate methods. An exemplary method includes fractional recrystallization using a chiral resolving acid that is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

The expressions "ambient temperature" and "room temperature" as used herein are understood in the art and refer generally to a temperature, e.g., a reaction temperature, that is about the temperature of the room in which the reaction is carried out, for example, a temperature from about 20° C. to about 30° C.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

The term "alkyl" includes substituted or unsubstituted straight-chain alkyl groups (e.g., methyl, ethyl, propyl, butyl, pentyl, hexyl, heptyl, octyl, nonyl, decyl, etc.) and branched-chain alkyl groups (iso propyl, tert-butyl, isobutyl, etc.), cycloalkyl (alicyclic) groups (cyclopropyl, cyclopentyl, cyclohexyl, cycloheptyl, cyclooctyl, etc.), alkyl substituted cycloalkyl groups, and cycloalkyl substituted alkyl groups. In certain embodiments, a straight chain or branched chain alkyl has six or fewer carbon atoms in its backbone (e.g., $C_{1-6}$ for straight chain; $C_{3-6}$ for branched chain). The term $C_{1-6}$ includes alkyl groups containing 1 to 6 carbon atoms. In certain embodiments, a straight chain alkyl has three or fewer carbon atoms in its backbone. The term $C_{1-3}$ includes alkyl groups containing one to three carbon atoms.

As used herein, "haloalkyl" means a hydrocarbon substituent, which is a linear or branched or cyclic alkyl, alkenyl or alkynyl substituted with one or more chloro, bromo, fluoro, or iodo atom(s). In some embodiments, a haloalkyl is a fluoroalkyl, wherein one or more of the hydrogen atoms have been substituted by fluoro. In some embodiments, haloalkyls are one to about three carbons in length (e.g., one to about two carbons in length, or one carbon in length).

The term "alkoxy" includes groups of the formula —OR, where R is an alkyl as defined herein. Non-limiting examples of alkoxy groups include methoxy, ethoxy, isopropoxy, tert-butoxy, and the like. In some embodiments, an alkoxy group can have from one to three carbons (e.g., methyoxy, ethoxy, or propoxy).

The term "haloalkoxy" includes group of the formula —OR, where R is a haloalkyl as defined herein. Examples of haloalkoxy groups include, without limitation, trifluoromethoxy, difluoromethoxy, etc.

"Alkylamino" includes groups of the formula —NR, where R is an alkyl as defined herein. Non-limiting examples of alkylamino groups include methylamino, ethylamino, isopropylamino, butylamino etc. In some embodiments, an alkylamino group can have from one to three carbons (e.g., methyoxy, ethoxy, or propoxy). The term "dialkylamino" includes groups of the formula —NR$_2$, where R is an alkyl as defined herein. In some embodiments, the alkyl groups of a dialkylamino independently can have one to three carbons.

In general, the term "aryl" includes substituted or unsubstituted aromatic rings, including 5- and 6-membered single-ring aromatic groups, such as benzene and phenyl. Further, the term "aryl" includes multicyclic aryl groups, e.g., tricyclic, bicyclic, such as naphthalene and anthracene. In some embodiments, aryls can have from six to ten (e.g., six, seven, eight, nine, or ten) ring atoms.

The term "heteroaryl" means a substituted or unsubstituted mono-, bi-, tri- or polycyclic group having four to 14 ring atoms, alternatively five, six, nine, or ten ring atoms; having six, ten, or 14 pi electrons shared in a cyclic array; wherein at least one ring in the system is aromatic, and at least one ring in the system contains one or more heteroatoms independently selected from the group consisting of N, O, and S. Exemplary heteroaryl groups include, for example, pyrrole, furan, thiophene, thiazole, isothiaozole, imidazole, triazole, tetrazole, pyrazole, oxazole, isooxazole, pyridine, pyrazine, pyridazine, and pyrimidine, and the like. Further, the term "heteroaryl" includes multicyclic heteroaryl groups, e.g., tricyclic or bicyclic groups, such as benzoxazole, benzodioxazole, benzothiazole, benzoimidazole, benzothiophene, methylenedioxyphenyl, quinoline, isoquinoline, napthyridine, indole, benzofuran, purine, benzofuran, quinazoline, deazapurine, indazole, or indolizine.

The term "heterocycloalkyl" includes substituted or unsubstituted groups, including but not limited to, three- to ten-membered single or multiple rings having one to five heteroatoms, for example, piperazine, pyrrolidine, piperidine, or homopiperazine. In certain embodiments, a heterocycloalkyl can have from four to ten ring atoms.

Methods for making compounds as described herein include those known in the art; such compounds also may be obtained commercially (e.g., from Sigma-Aldrich, St. Louis, MO). In some embodiments, benzoxazole derivatives can be generated by modifying the benzyl ring, azole ring, and/or side chain of MOB or 2-MTB, as indicated in Formula (I). Derivatives can include, for example, various benzoimidazoles (where x=N), benzoxazoles (where X=O), and benzothiazoles (where X=S). The derivative compounds can be tested for anti-germination activity, and then tested as NE prophylactics. Information gathered from such in vitro and in vivo screens can be used to direct further derivatization.

The term "substituted" means that an atom or group of atoms replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position. In some cases, two sites of substitution may come together to form a 3-10 membered cycloalkyl or heterocycloalkyl ring. Non-limiting examples of substituents include: $(C_1-C_6)$alkyl, halo, $(C_1-C_6)$haloalkyl, —CN, —$NR^8R^9$, —$NO_2$, —$O(C_1-C_6)$haloalkyl, —$OR^8$, —$OC(O)R^8$, —$C(O)R^8$, —$C(O)OR^8$, —$C(O)NR^8R^9$, —$SR^8$, —$S(O)R^8$, —$SO_2R^8$, —$SO_2NR^8R^9$, $(C_3-C_7)$ cycloalkyl, $(C_3-C_7)$heterocycloalkyl, $(C_5-C_{14})$aryl, and $(C_5-C_{14})$heteroaryl, wherein $R^8$ and $R^9$ are independently selected from H and $(C_1-C_6)$alkyl.

It is to be noted that this document encompasses not only the various isomers of the compounds that may exist, but also the various mixtures of isomers that may be formed, as well as any enantiomers and tautomers that may exist.

In addition, the scope of this document also encompasses solvates and salts of the compounds described herein, as well as prodrugs of the compounds, such as esters, amides, and acylated groups, among others. In some embodiments, for example, this document provides prodrugs of the compounds disclosed herein, which may contain, for example, acylated phenols or acyl derivatives of amines. By "prodrug" is meant, for example, any compound (whether itself active or inactive) that is converted chemically in vivo into a biologically active compound as provided herein, following administration of the prodrug to a subject. In some embodiments, a prodrug is a covalently bonded carrier that releases the active parent drug when administered to a subject. Prodrugs can be prepared by modifying functional groups present in the compounds in such a way that the modifications are cleaved, either in routine manipulation or in vivo, to the parent compounds. Prodrugs can include compounds in which hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, without limitation, acetate, formate and benzoate derivatives of alcohol and amine functional groups in the compounds provided herein. The suitability and techniques involved in making and using prodrugs are discussed in Higuchi and Stella, "Pro-drugs as Novel Delivery Systems," Vol. 14 of the ACS Symposium Series, and in *Bioreversible Carriers in Drug Design*, ed. Edward B. Roche, American Pharmaceutical Association and Pergamon Press, 1987, both of which are hereby incorporated by reference in their entirety.

The phrase "pharmaceutically acceptable" is used herein to refer to those compounds, materials, compositions, and/or dosage forms that are, within the scope of sound medical judgment, suitable for use in contact with the tissues of animals without excessive toxicity, irritation, allergic response, or other problem or complication, commensurate with a reasonable benefit/risk ratio. Examples of pharmaceutically acceptable salts of the compounds provided herein include acid addition salts and base salts of the compounds.

B. COMPOUNDS

In one aspect, the invention relates to compounds useful in preventing or treating diseases or disorders associated with infection caused by *C. difficile*, such as, for example, severe diarrhea and colitis. In a further aspect, the disclosed compounds are useful in preventing diseases or disorders associated with infection caused by *C. difficile*. In a still further aspect, the disclosed compounds are useful in treating diseases or disorders associated with infection caused by *C. difficile*.

In one aspect, the disclosed compounds exhibit inhibition of germination of *C. difficile* spores.

In one aspect, the compounds of the invention are useful in the prevention of diseases associated with infection caused by *C. difficile*, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

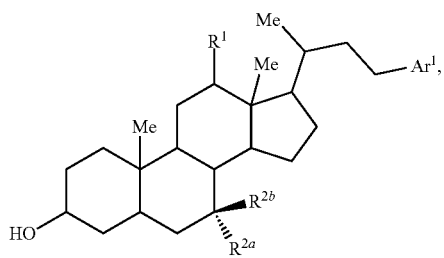

wherein each of $R^1$, $R^{2a}$, and $R^{2b}$ is independently selected from hydrogen and —OH; and wherein $Ar^1$ is a bicyclic heteroaryl having a structure represented by a formula selected from:

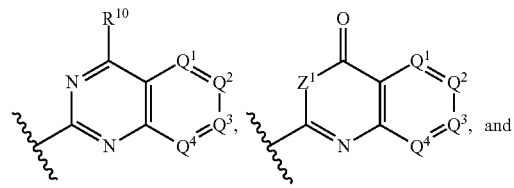

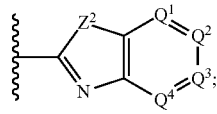

wherein $Z^1$ is selected from —O— and —NR$^{18}$—; wherein $R^{18}$, when present, is selected from hydrogen and C1-C4 alkyl; wherein $Z^2$ is selected from —O—, —S—, and —NR$^{19}$—; wherein $R^{19}$, when present, is selected from hydrogen and C1-C4 alkyl; wherein each of $Q^1$, $Q^2$, $Q^3$, and $Q^4$ is independently selected from —N= and —CR$^{20}$=; wherein each occurrence of $R^{20}$ is independently selected from hydrogen, halogen, C1-C4 alkyl, C1-C4 alkoxy, and phenyl; and wherein $R^{10}$ is selected from hydrogen, halogen, C1-C4 alkyl, C1-C4 alkoxy, C1-C4 haloalkyl, C1-C4 thioalkyl, and phenyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; provided that when $Ar^1$ is:

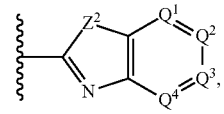

then: (a) at least one of $Q^1$, $Q^2$, $Q^3$, and $Q^4$ is —N= and at least one of $Q^1$, $Q^2$, $Q^3$, and $Q^4$ is —CR$^{20}$=, wherein $R^{20}$ is not hydrogen; or (b) at least two of $Q^1$, $Q^2$, $Q^3$, and $Q^4$ is —CR$^{20}$=, wherein at least two occurrences of $R^{20}$ are not hydrogen, or a pharmaceutically acceptable salt thereof.

In one aspect, disclosed are compounds selected from:

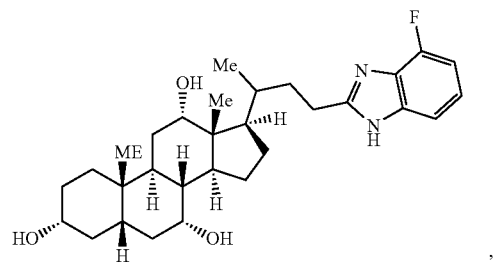

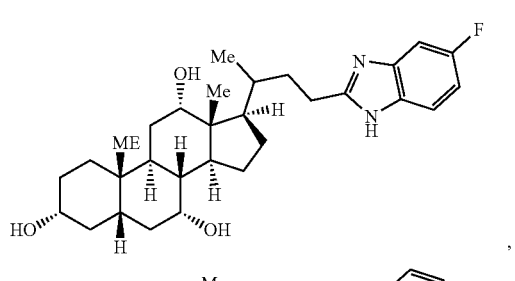

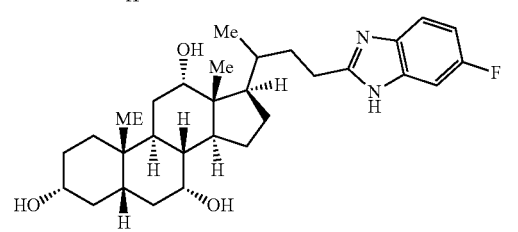

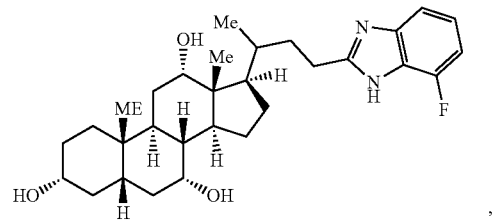

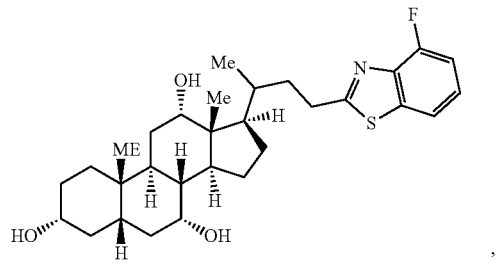

35
-continued
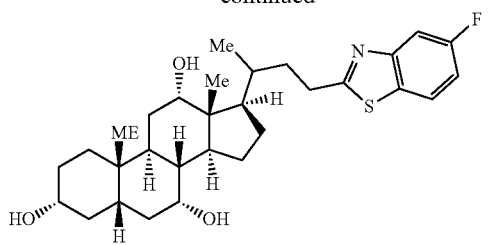
,
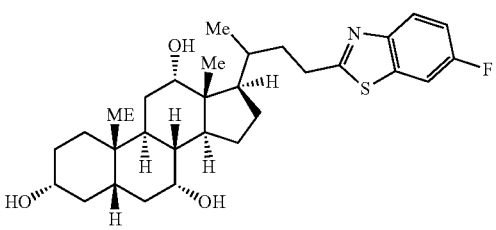
,
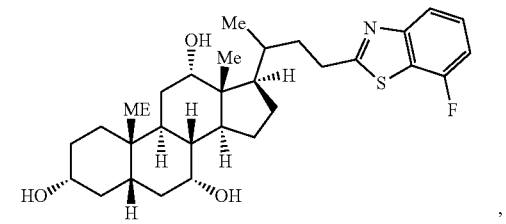
,
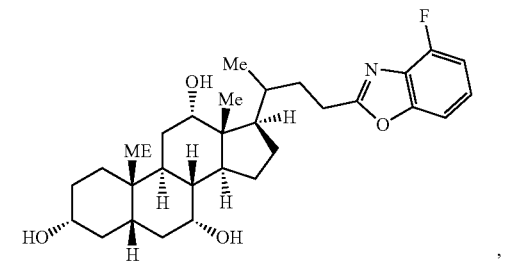
,
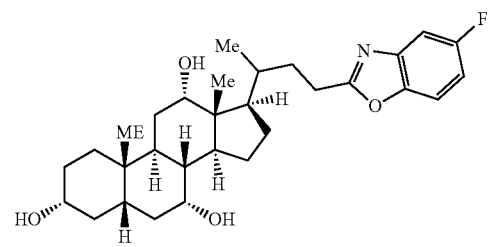
,
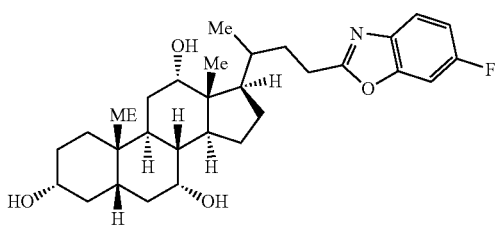
,
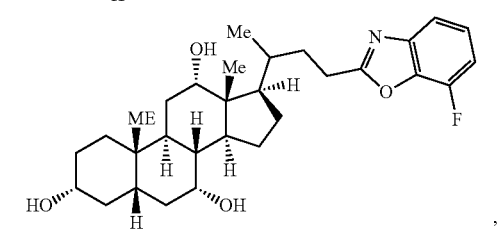
,
36
-continued
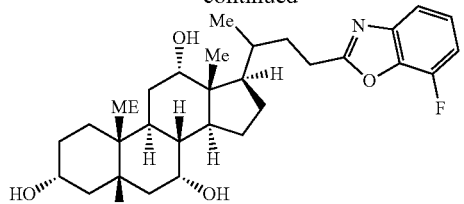
,
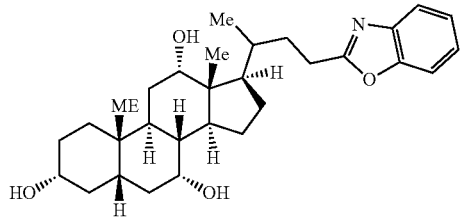
,
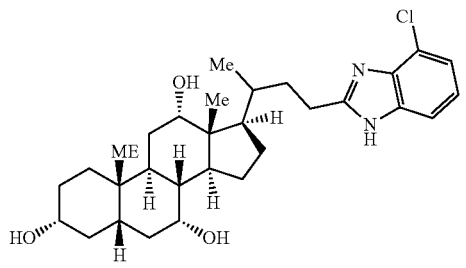
,

,
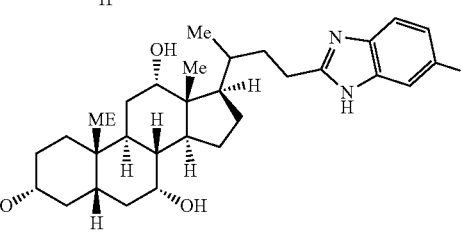
,
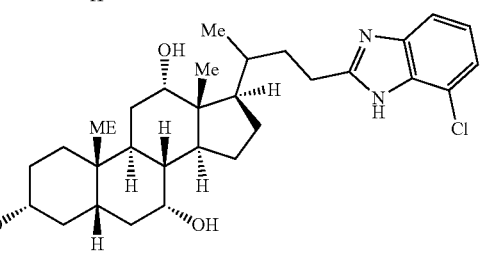
,
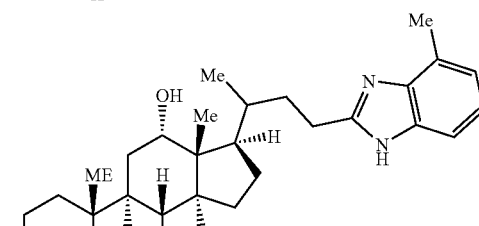
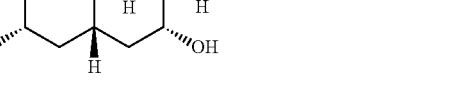

-continued
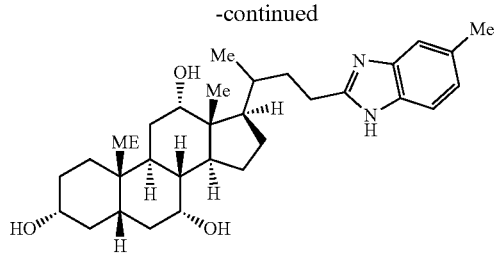
,
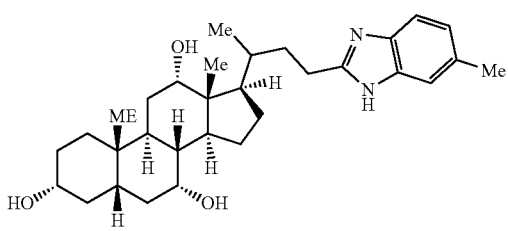
,
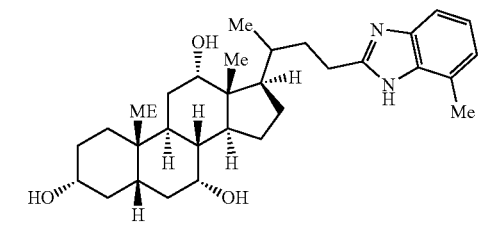
,
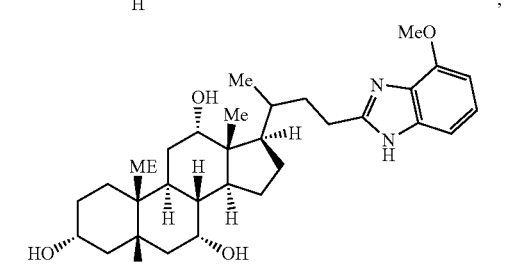
,
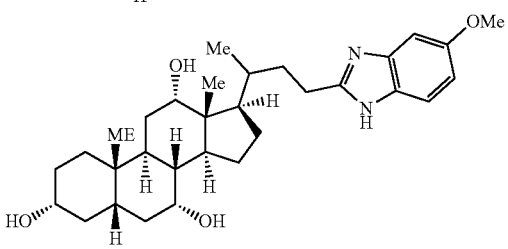
,
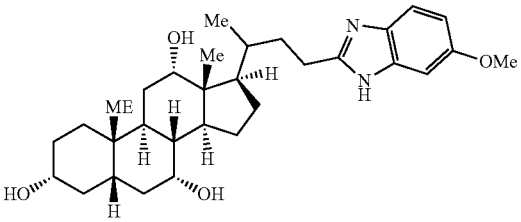
,
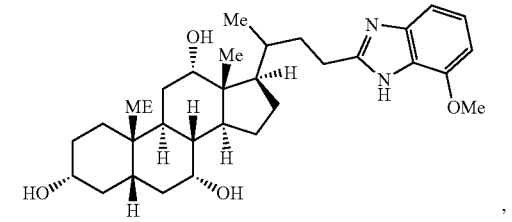
,
-continued
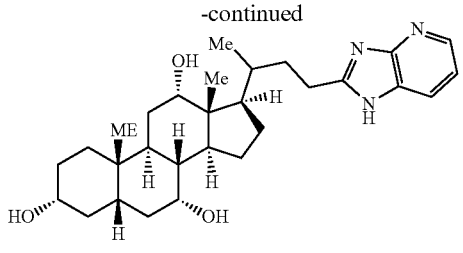
,
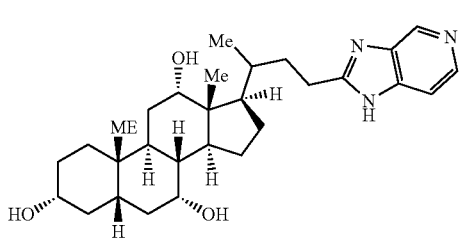
,
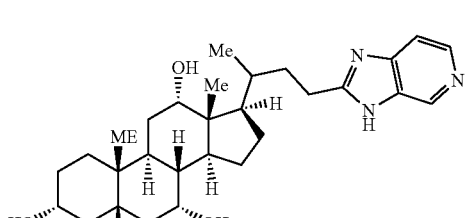
,
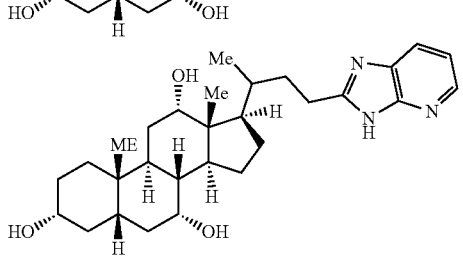
,
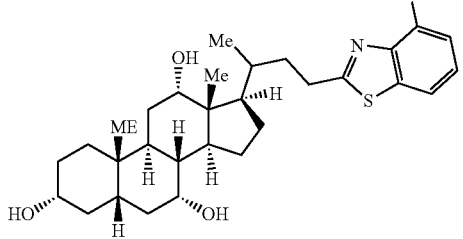
,
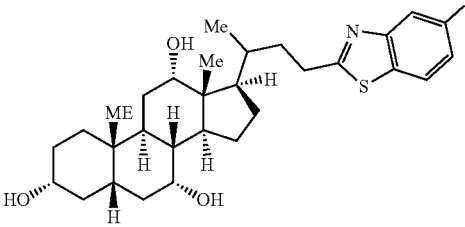
,
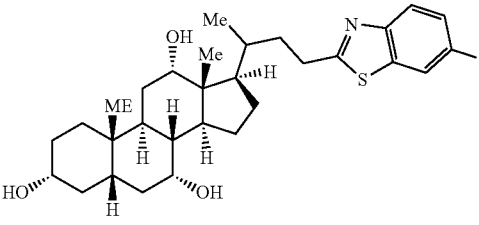
,

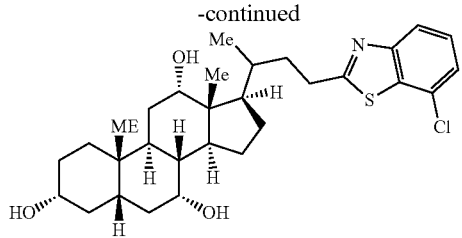,
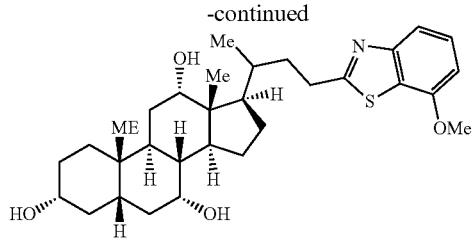,
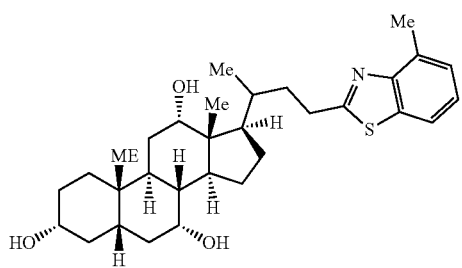,
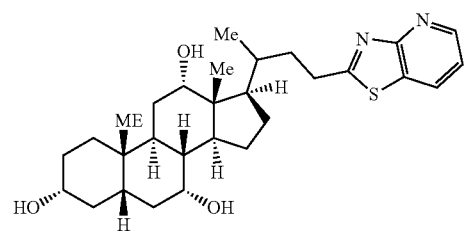,
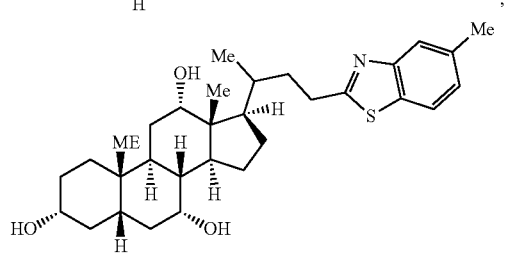,
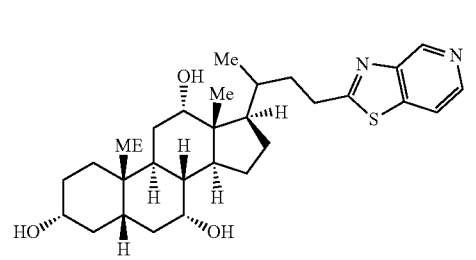,
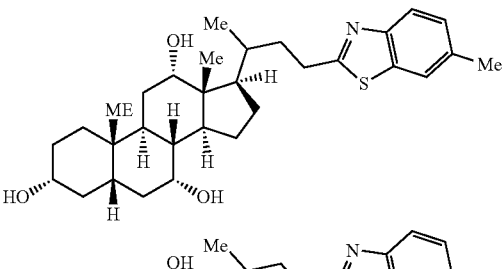,
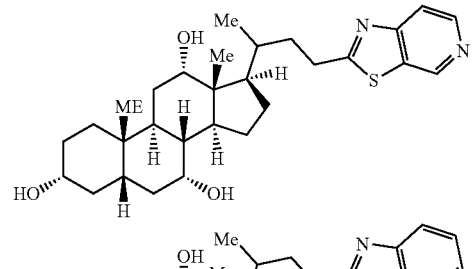,
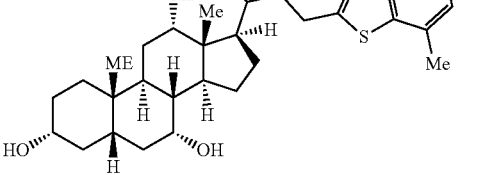,
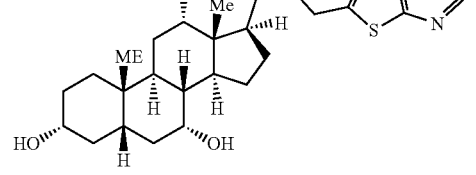,
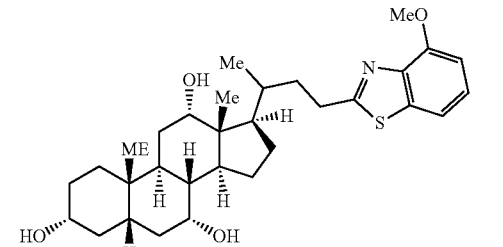,
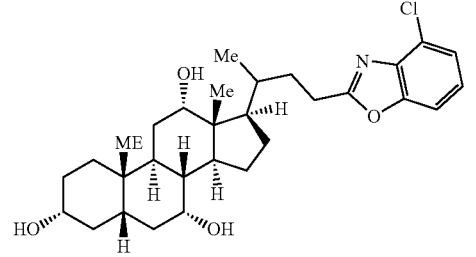,
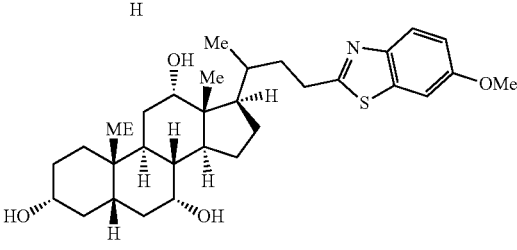,
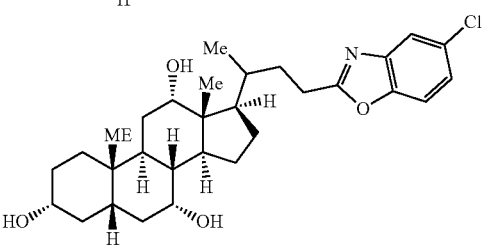,

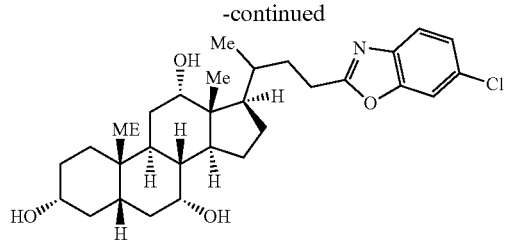
,
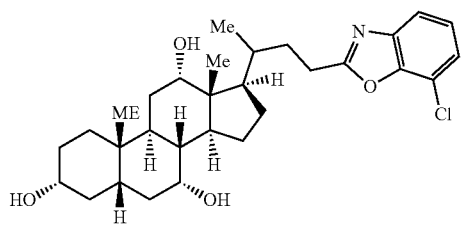
,
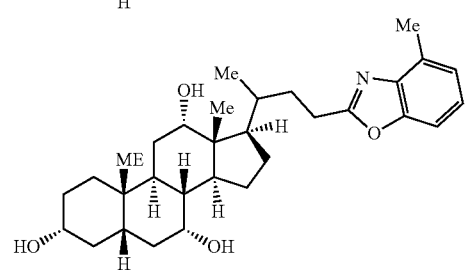
,
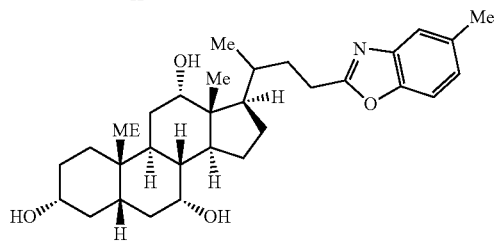
,
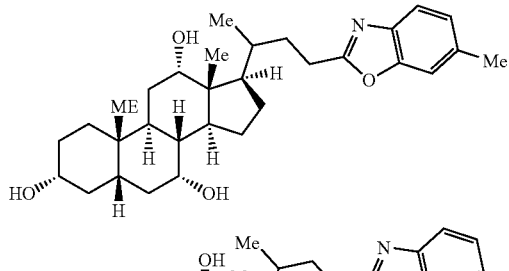
,
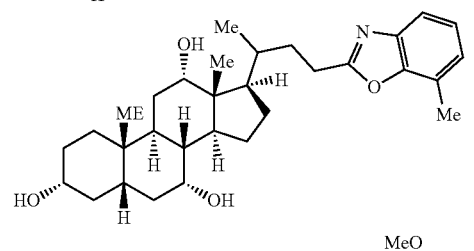
,
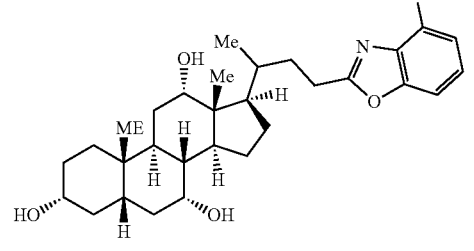
,
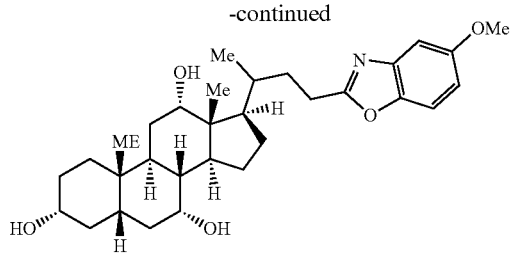
,
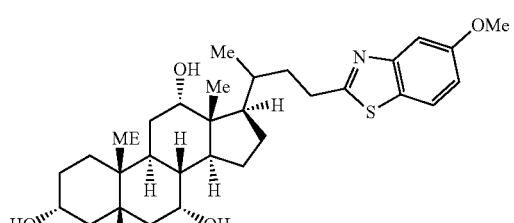
,
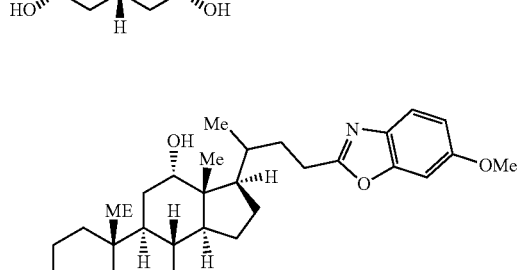
,
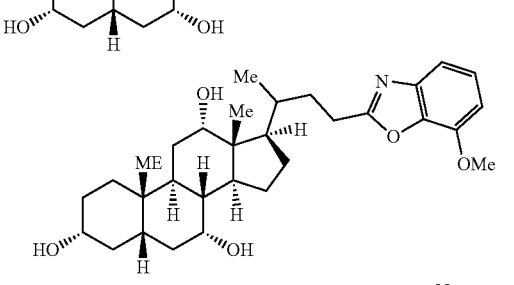
,
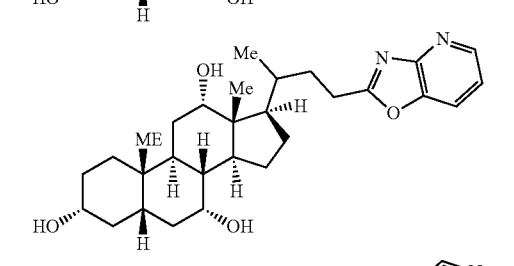
,
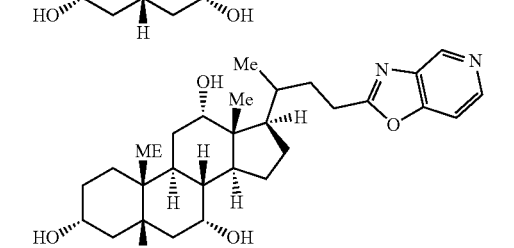
,
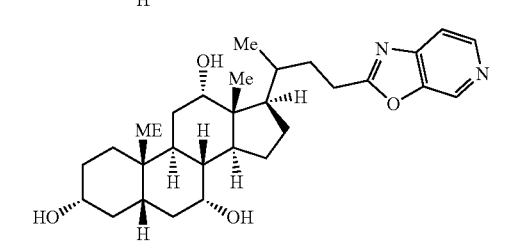
, -continued

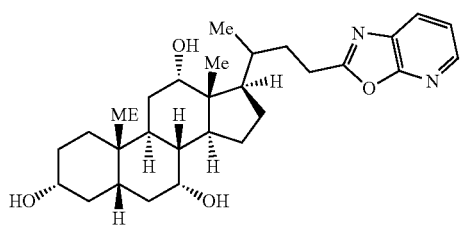, or a pharmaceutically acceptable salt thereof.

In a further aspect, the compound has a structure represented by a formula:

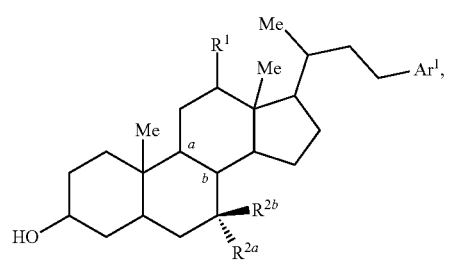

wherein the hydrogen atoms located at positions a and b are optionally present in the trans or in the cis configuration. Thus, in various aspects, the hydrogen atoms located at positions a and b are in the cis configuration. Alternatively, in various aspects, the hydrogen atoms located at positions a and b are in the trans configuration.

In a further aspect, the compound has a structure represented by a formula:

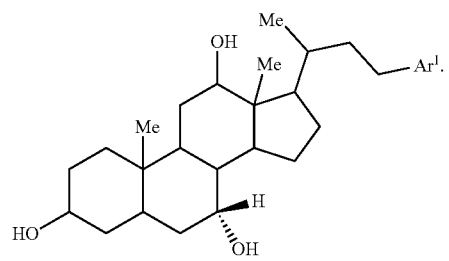

In a further aspect, the compound has a structure represented by a formula:

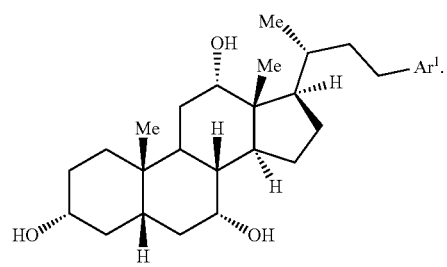

In a further aspect, the compound is:

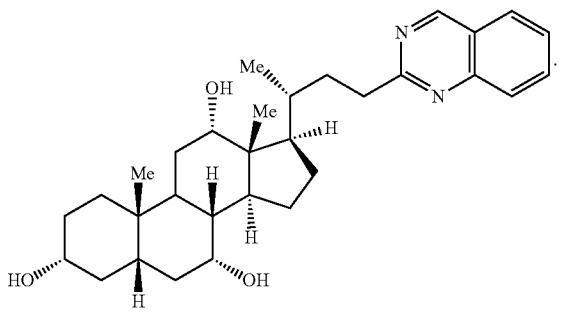

In a further aspect, the compound is selected from:

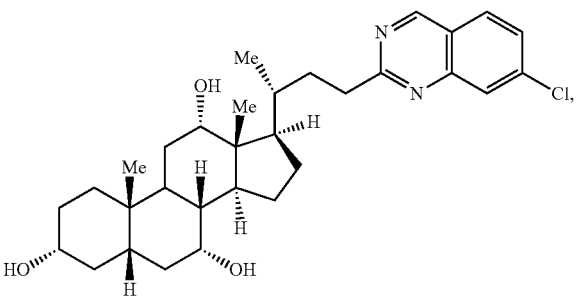

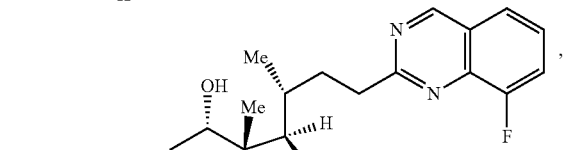

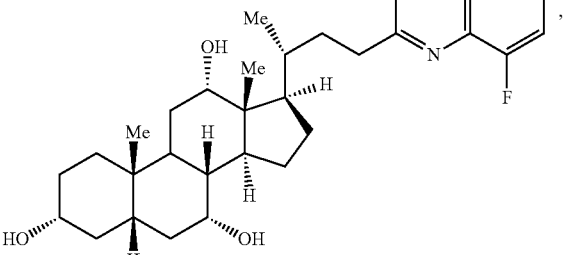

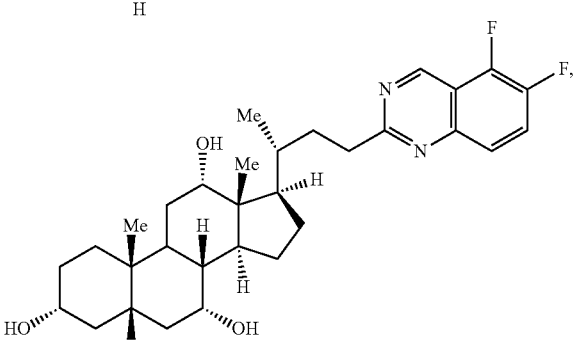

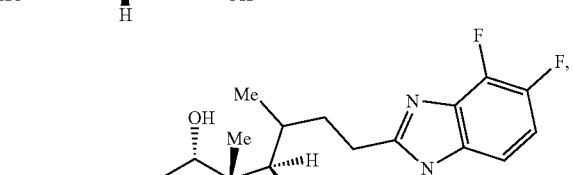

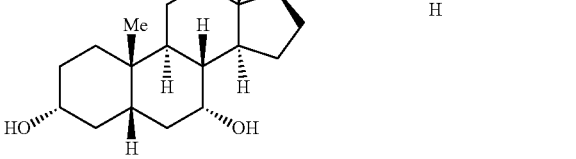

-continued
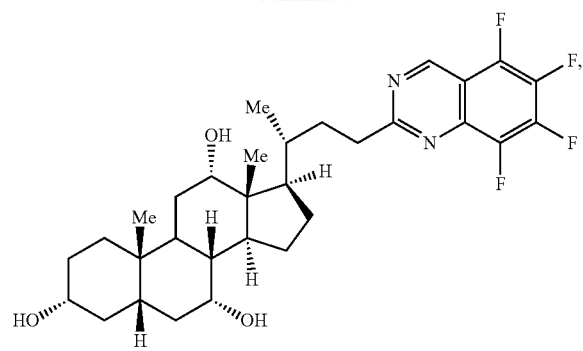
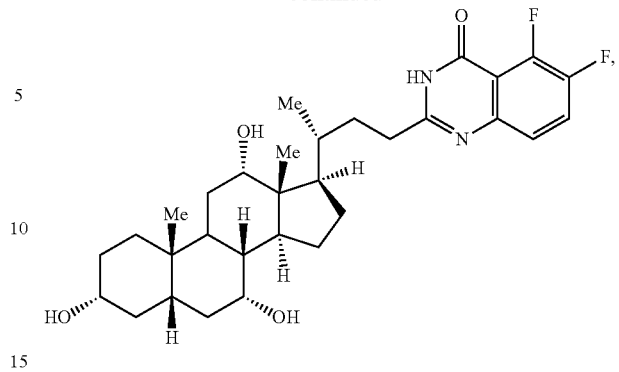
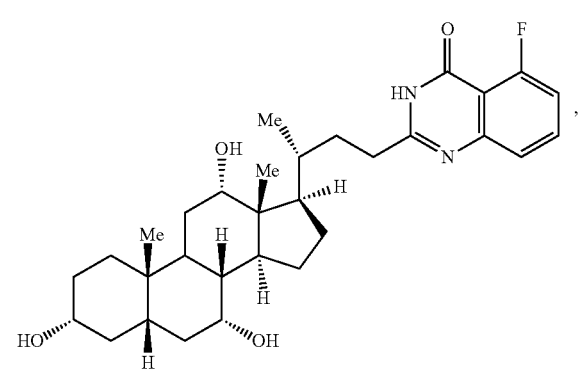
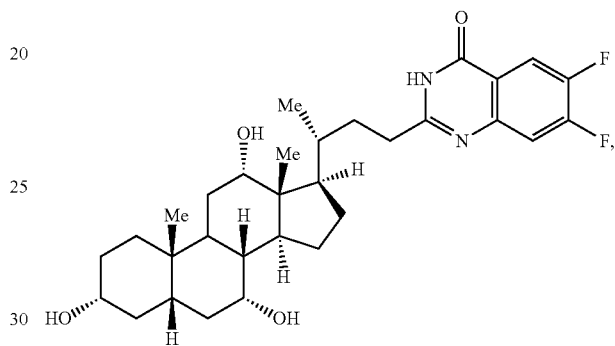
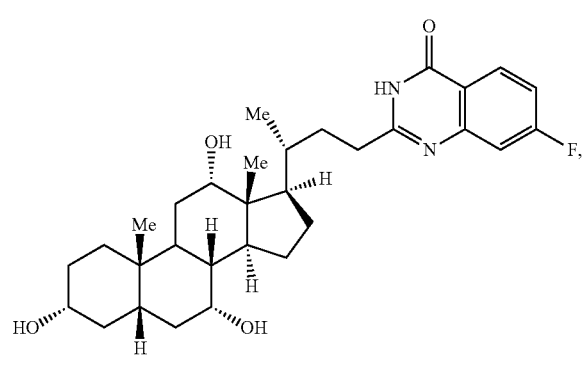
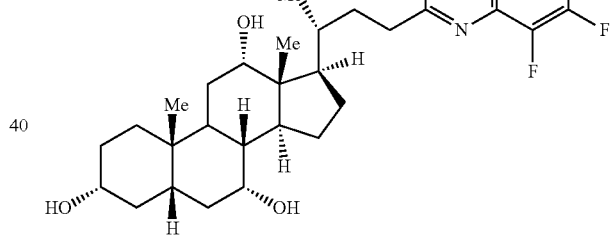
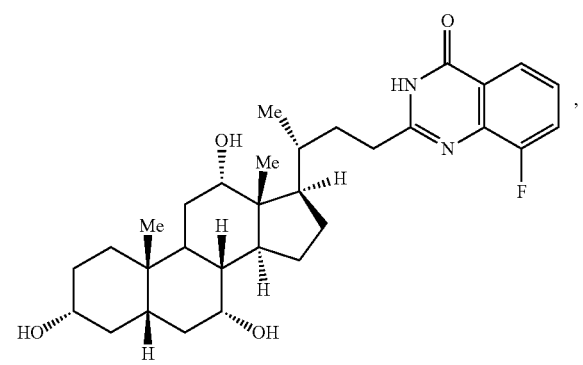
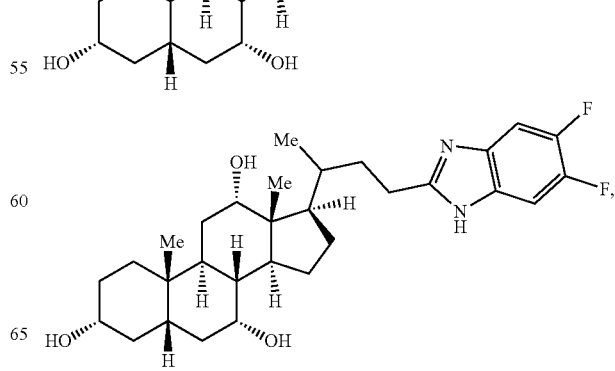

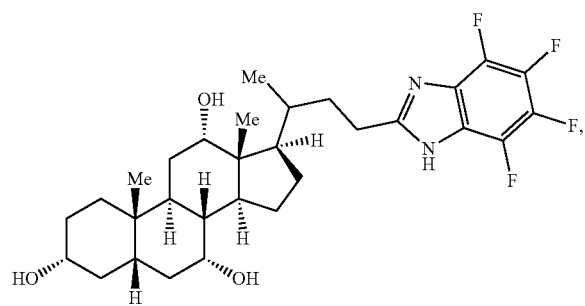
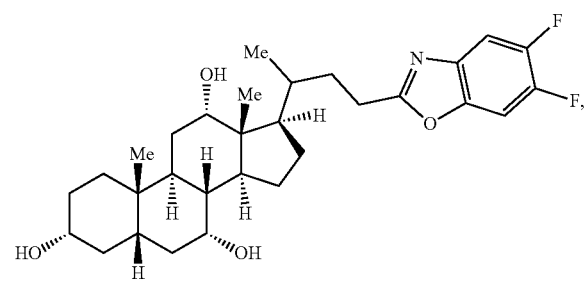
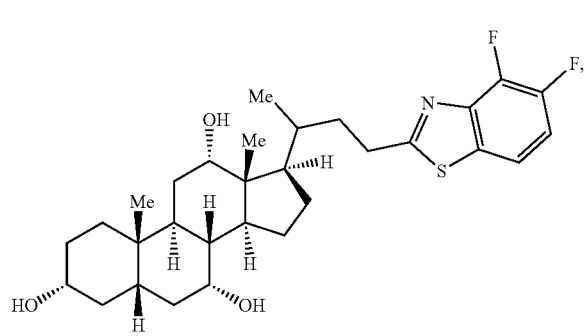
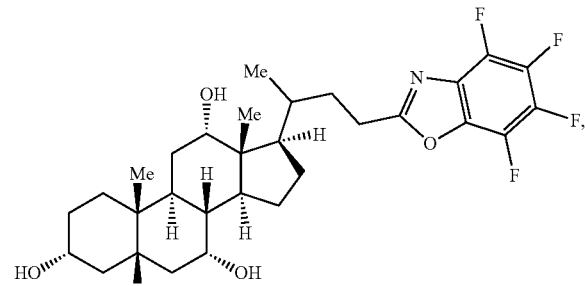
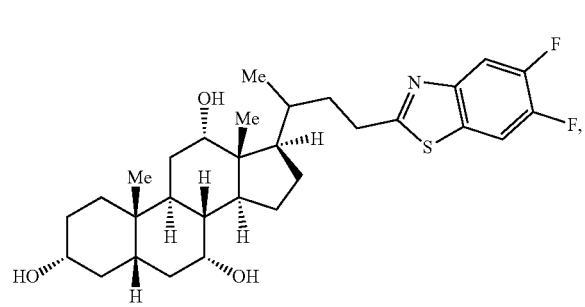
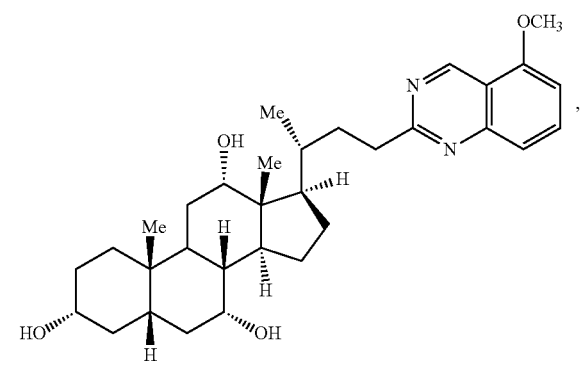
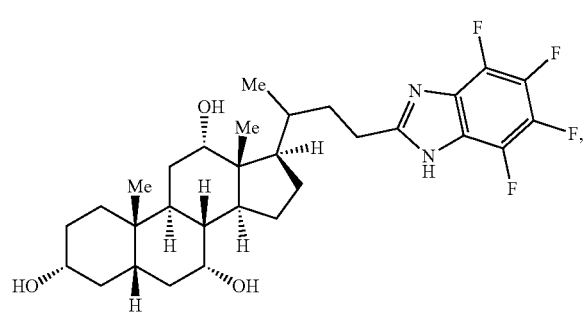
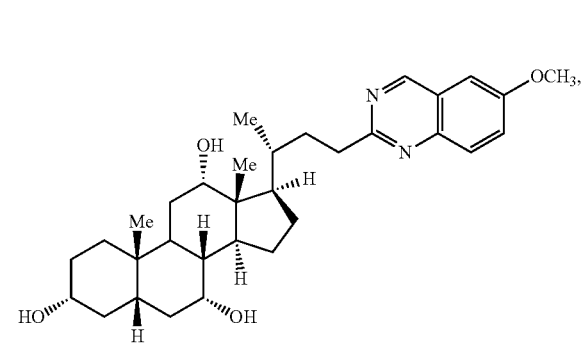
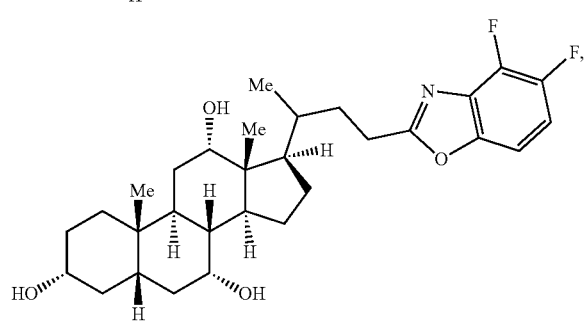
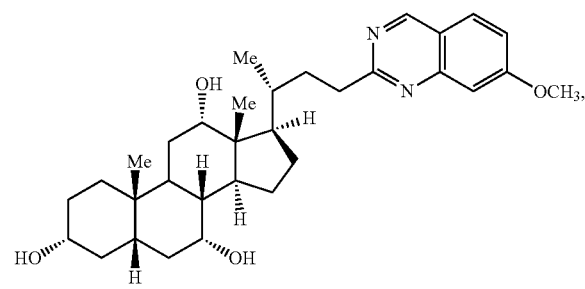

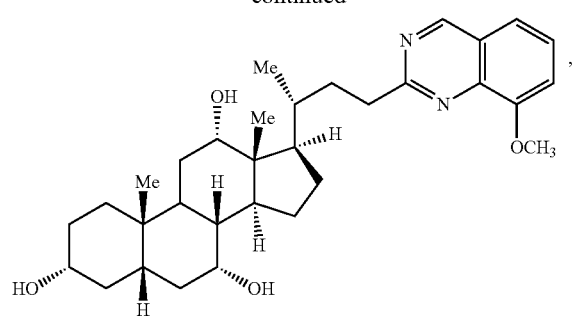,
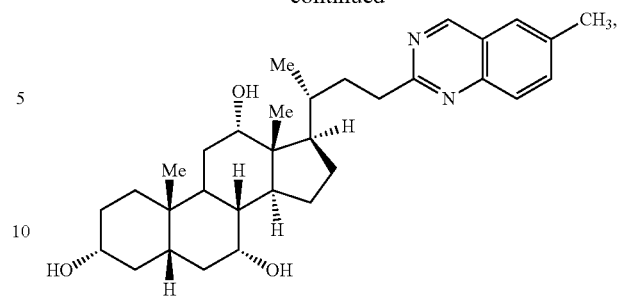,
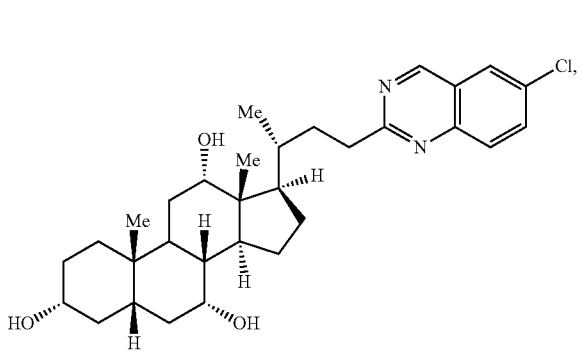,
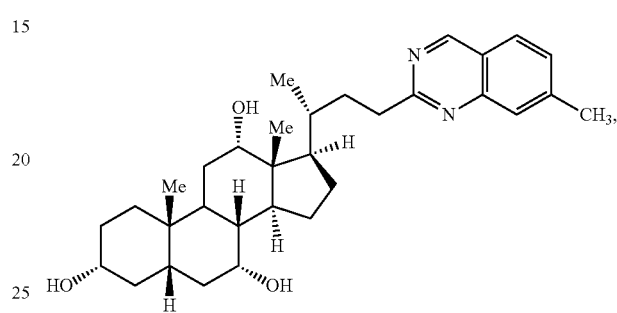,
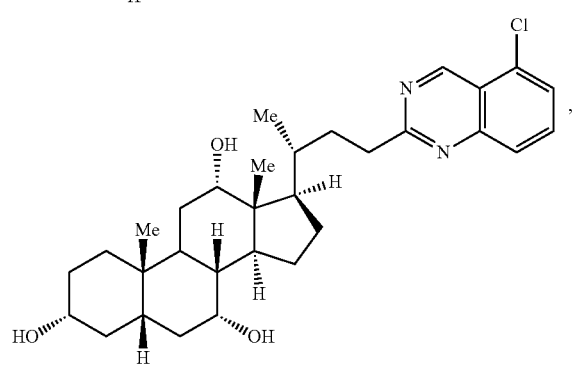,
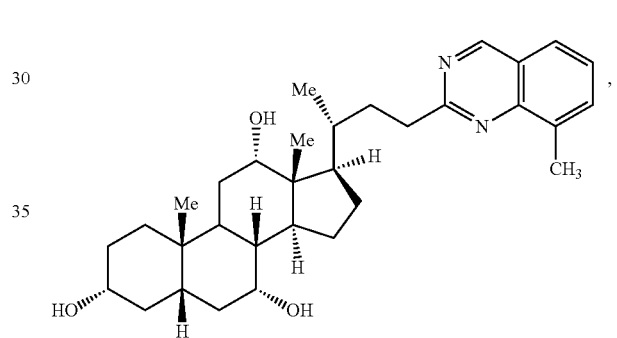,
,
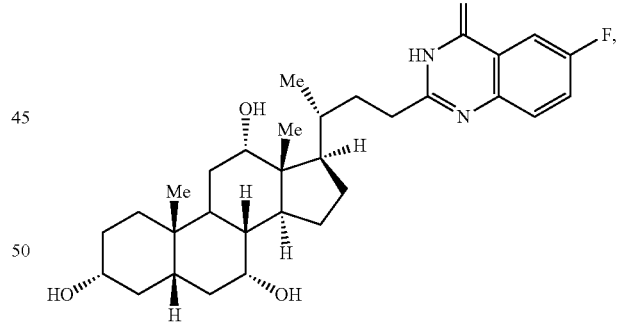,
,
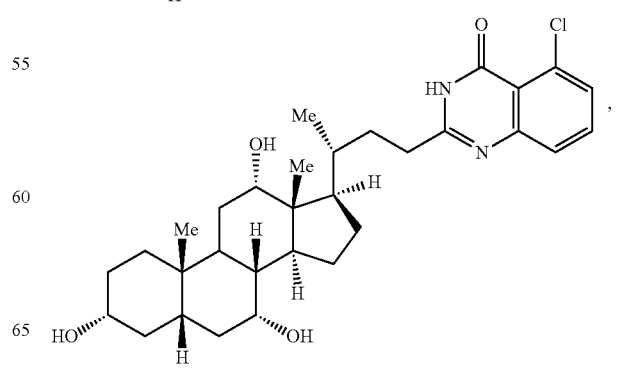, -continued
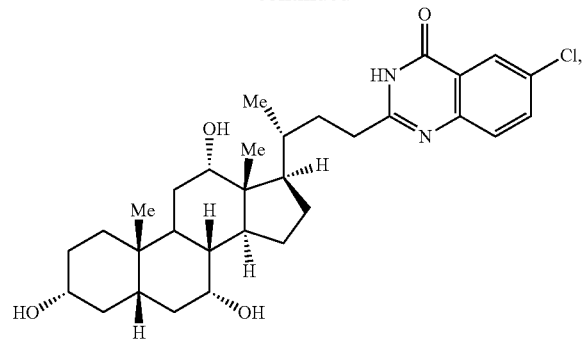
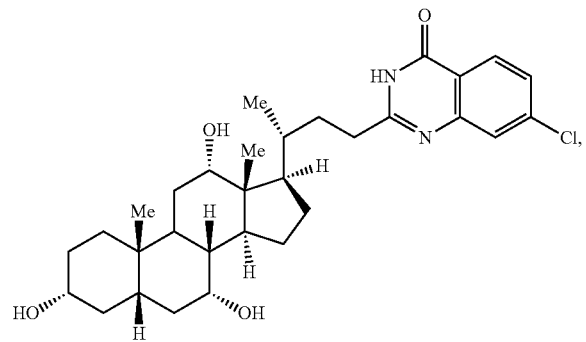
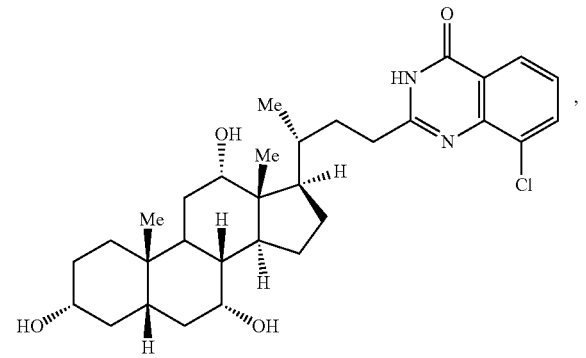
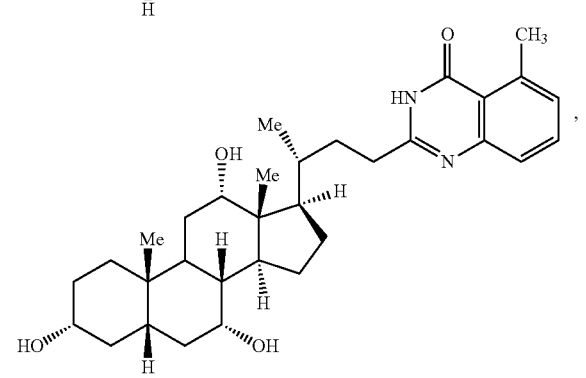
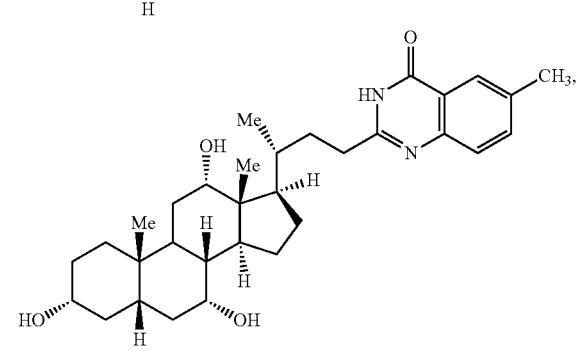
-continued
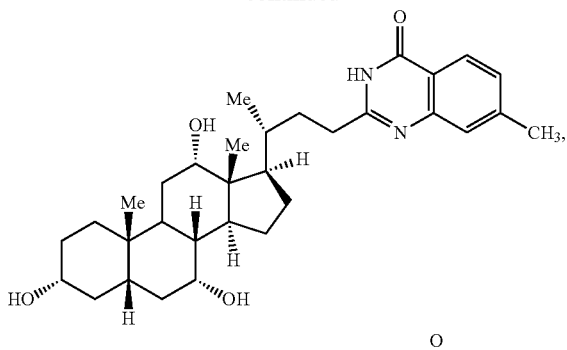
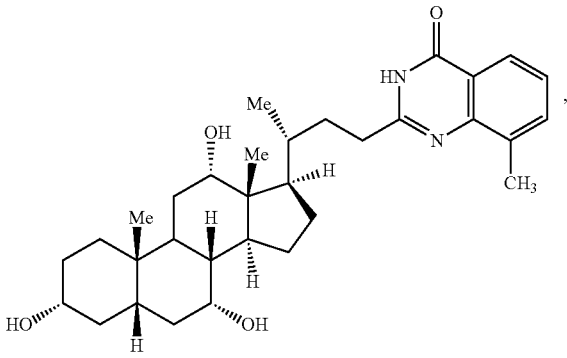
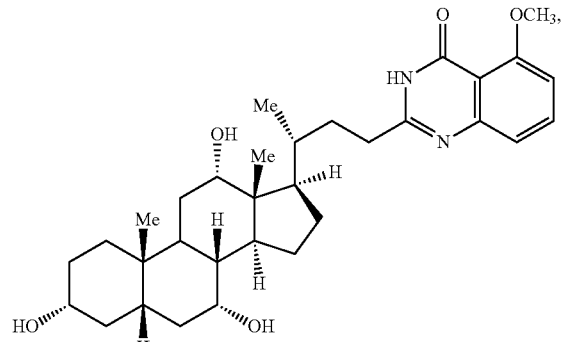
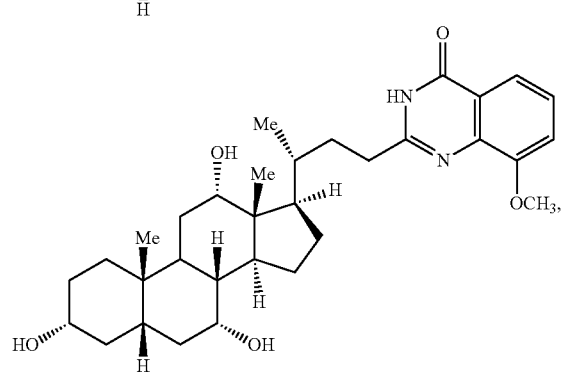
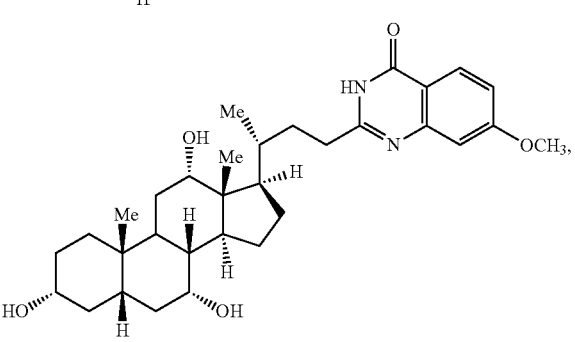

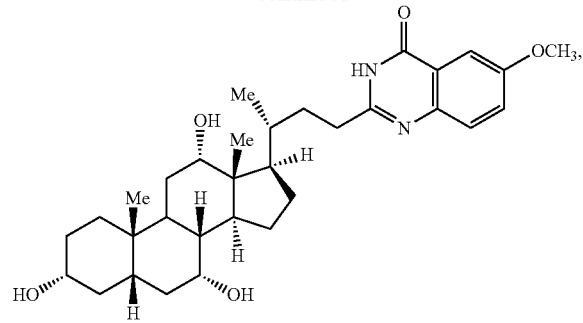
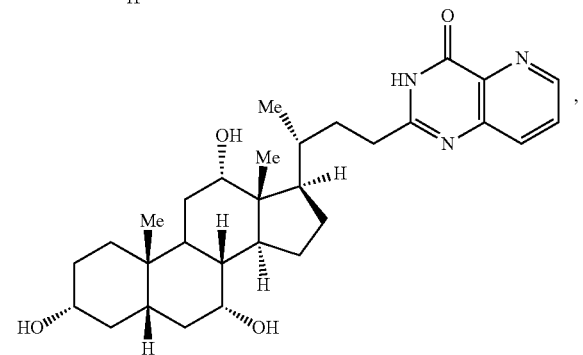
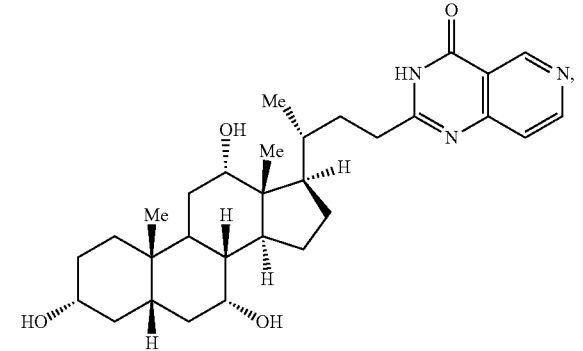
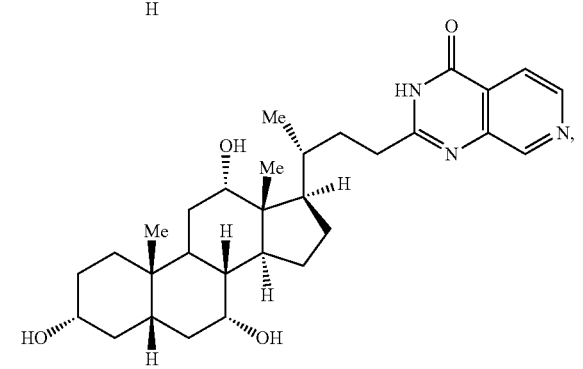
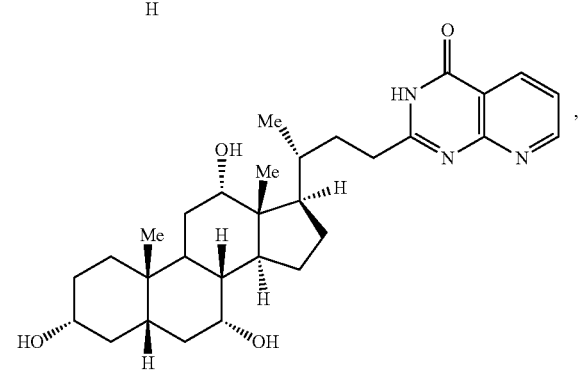
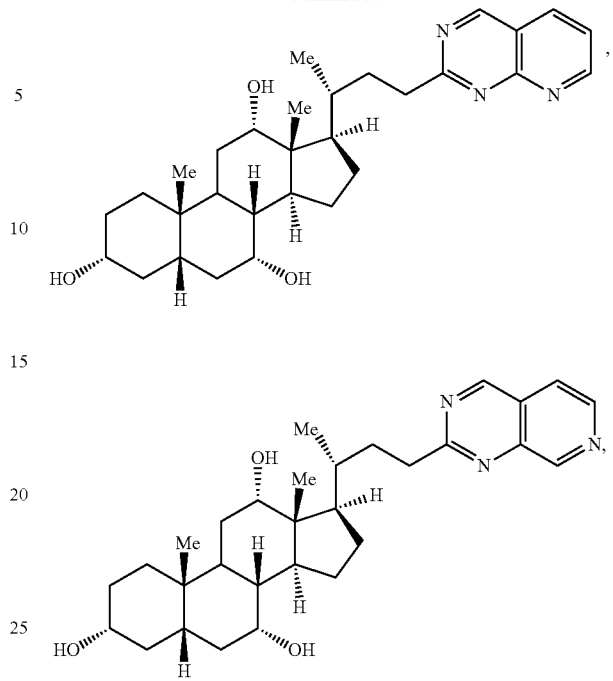
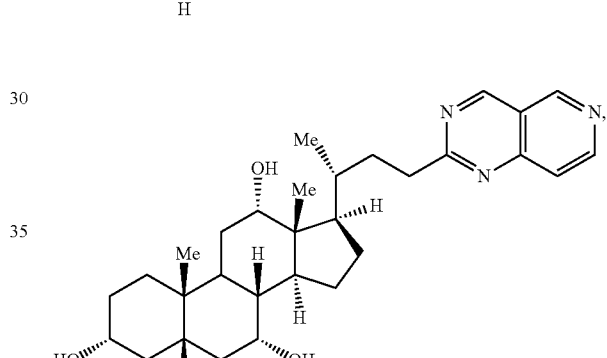
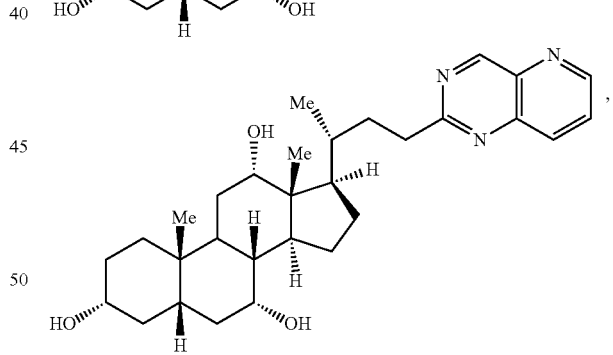
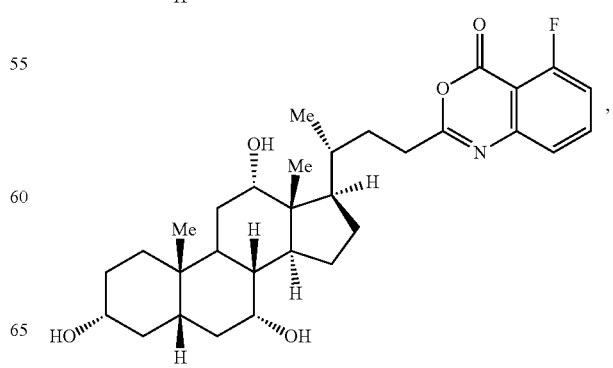

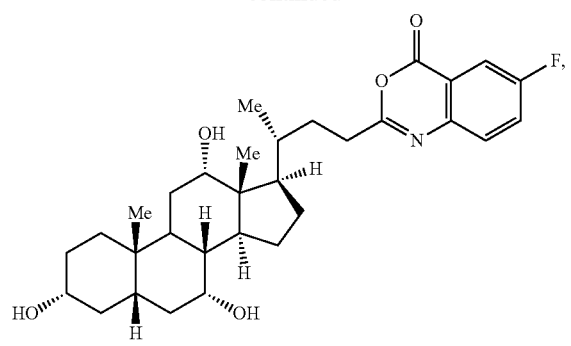
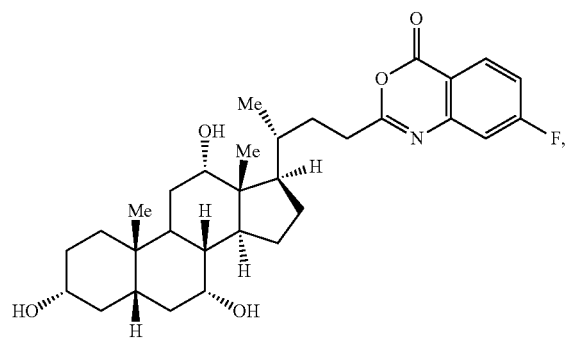
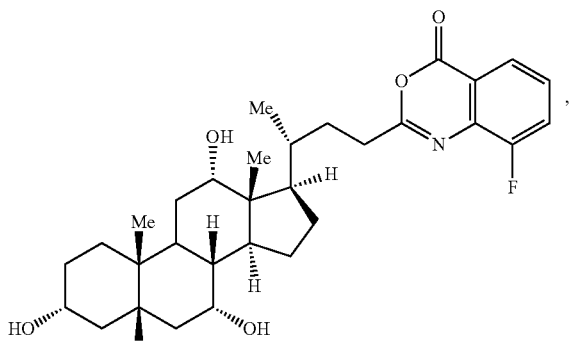
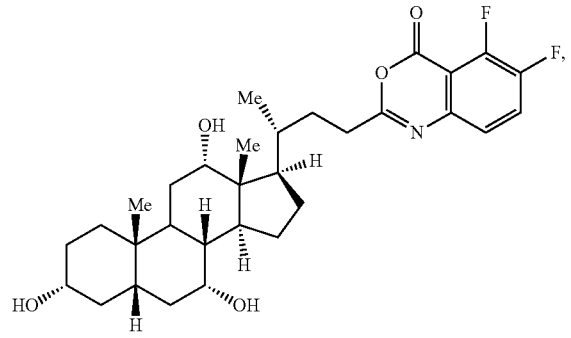
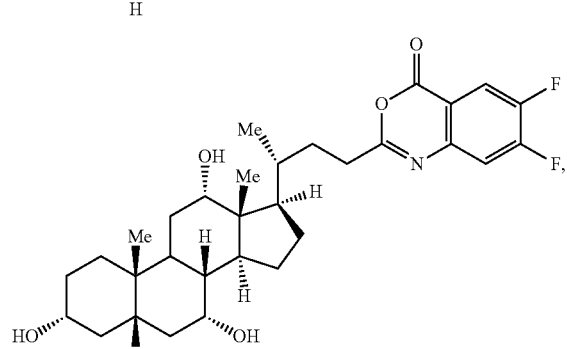
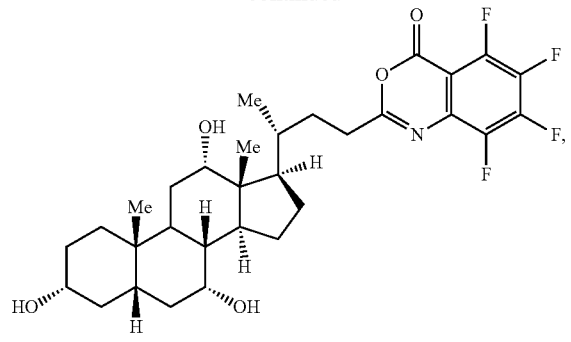
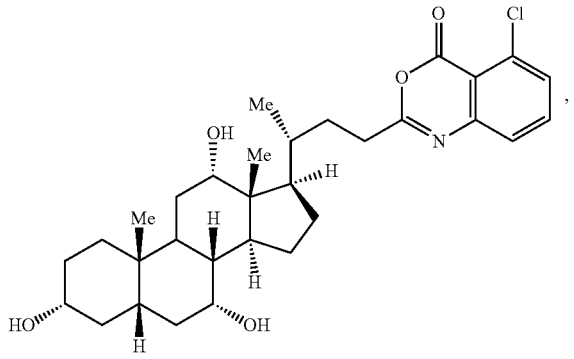
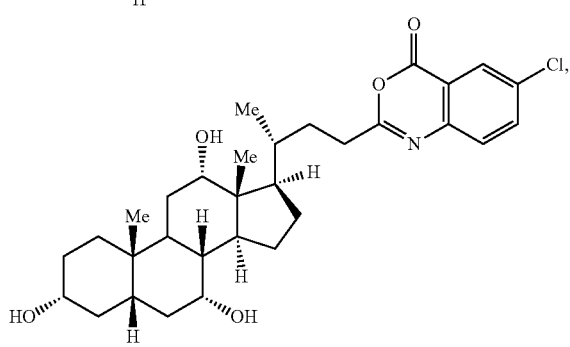
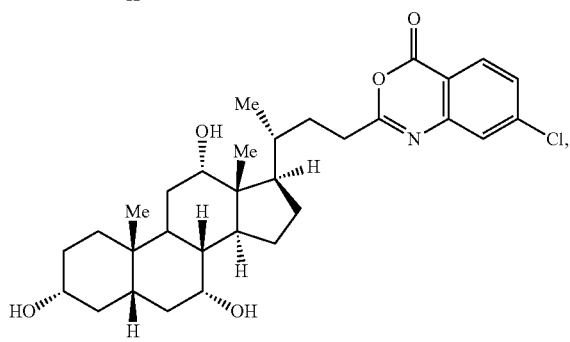
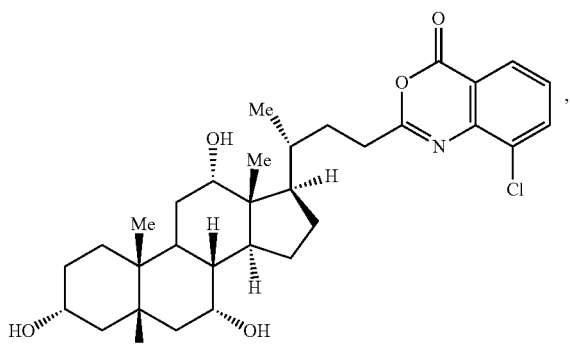

57
-continued
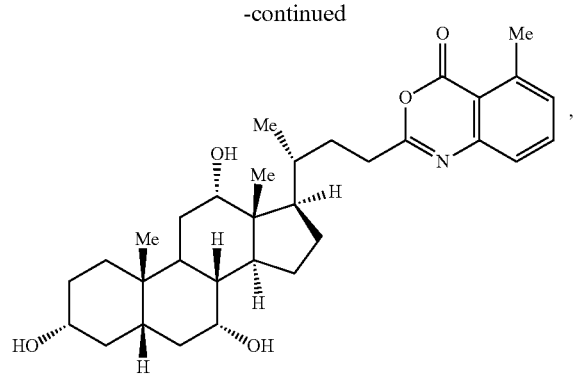
,
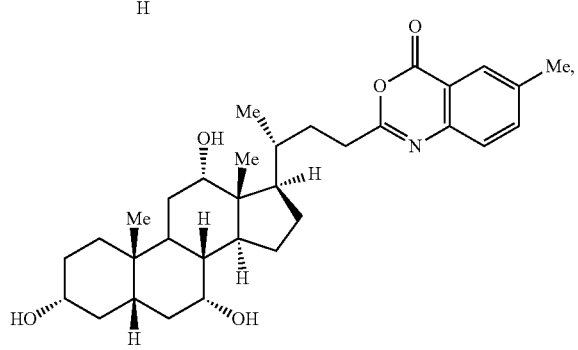
,
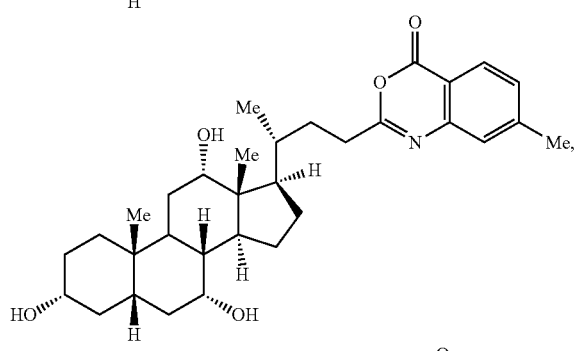
,
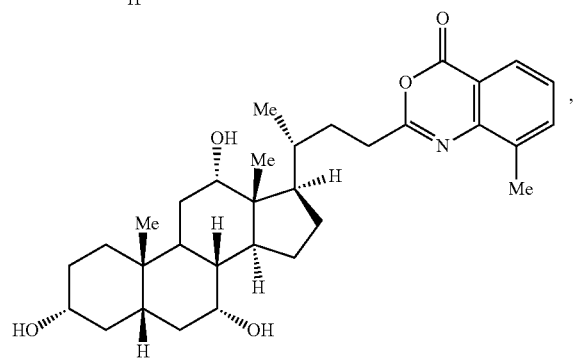
,
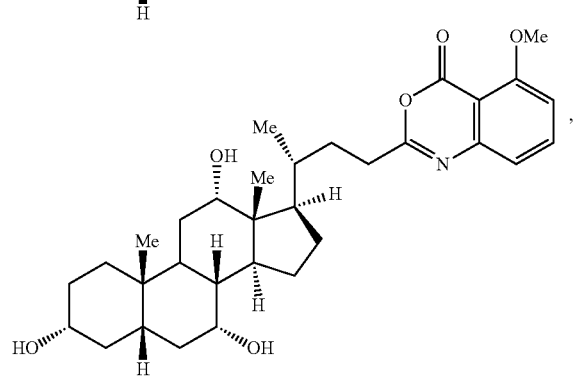
,
58
-continued
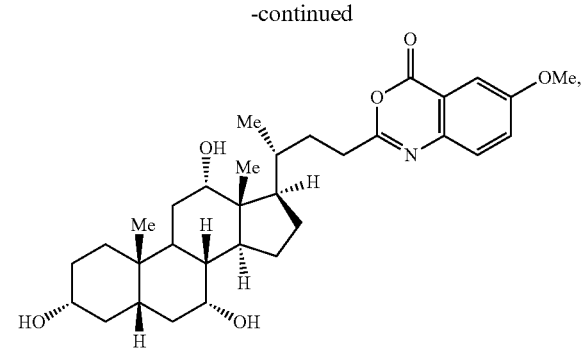
,
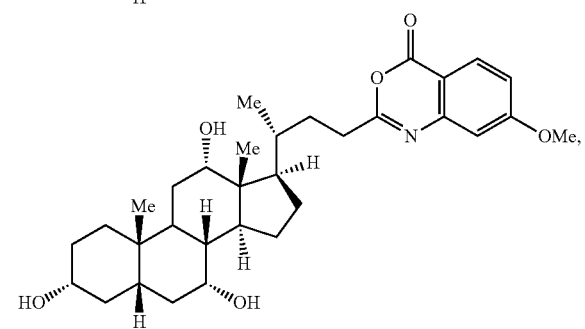
,
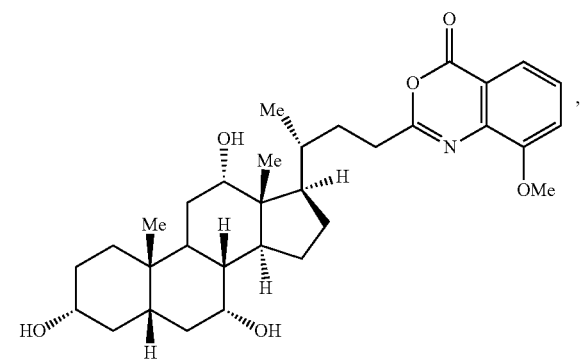
,
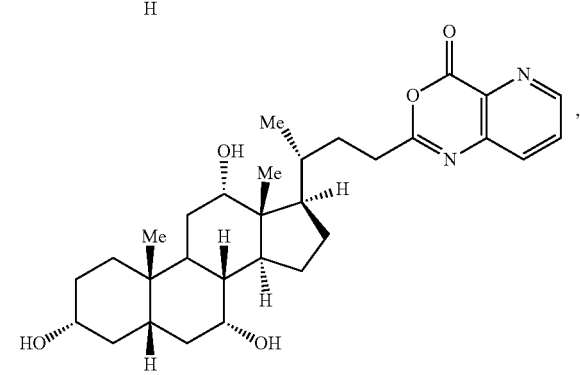
,
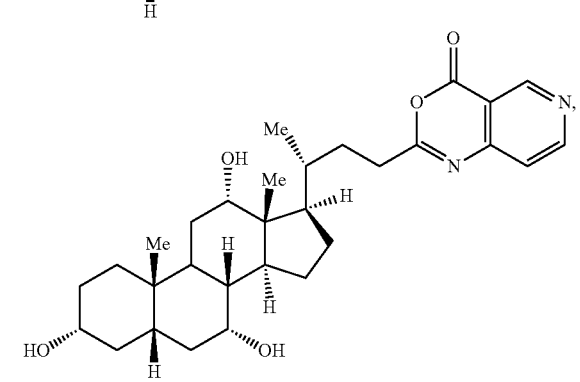
,

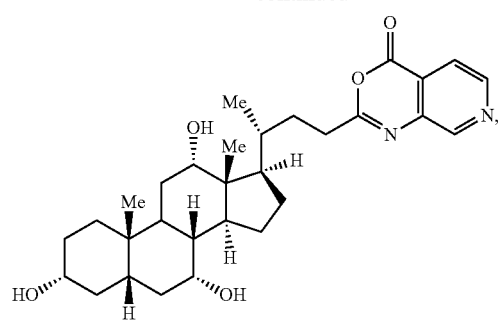
and
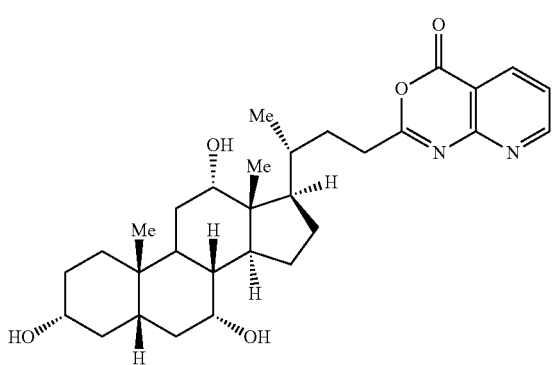
In a further aspect, the compound is selected from:
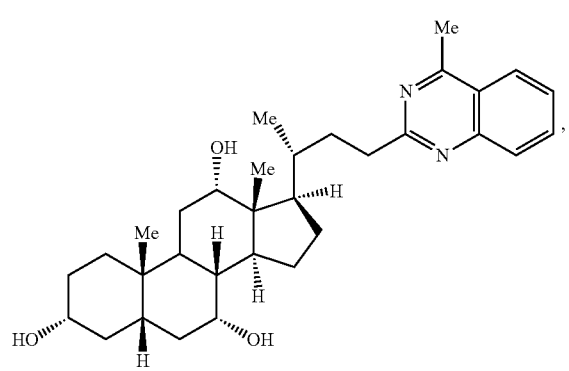
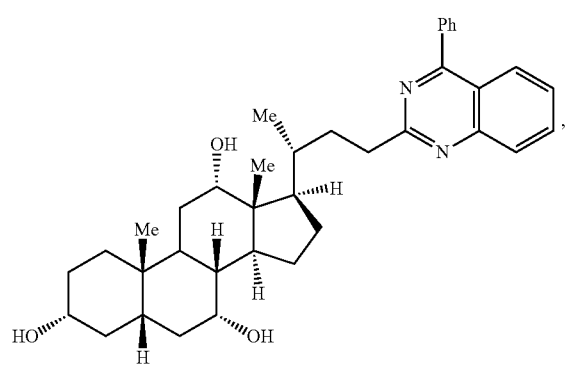
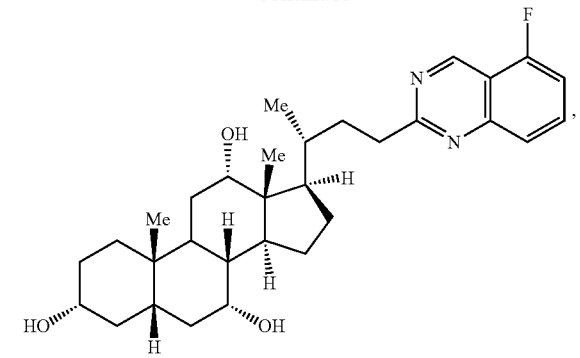
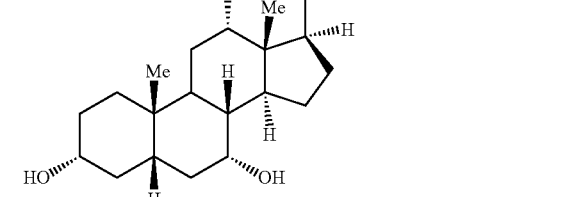
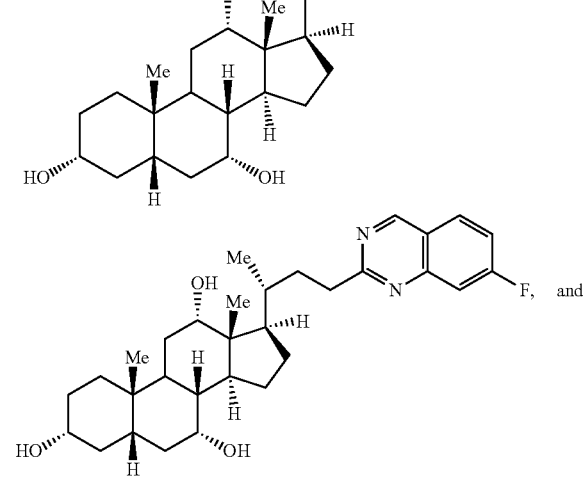

In a further aspect, the compound is:
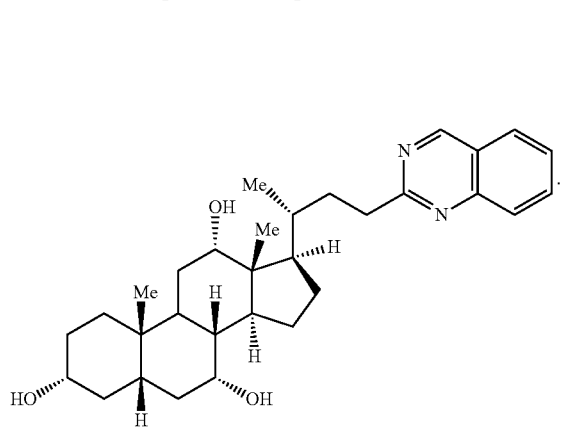
In a further aspect, the compound has a structure represented by a formula:
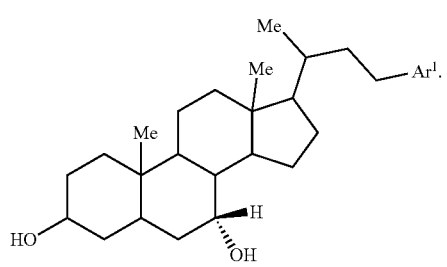
In a further aspect, the compound has a structure represented by a formula:
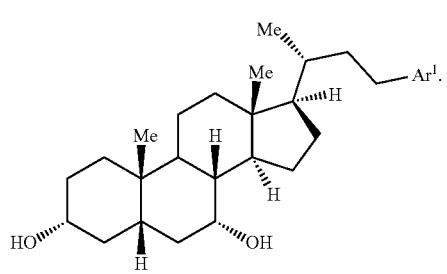
In a further aspect, the compound is selected from:
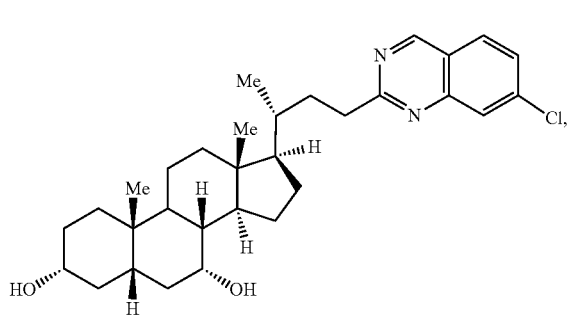
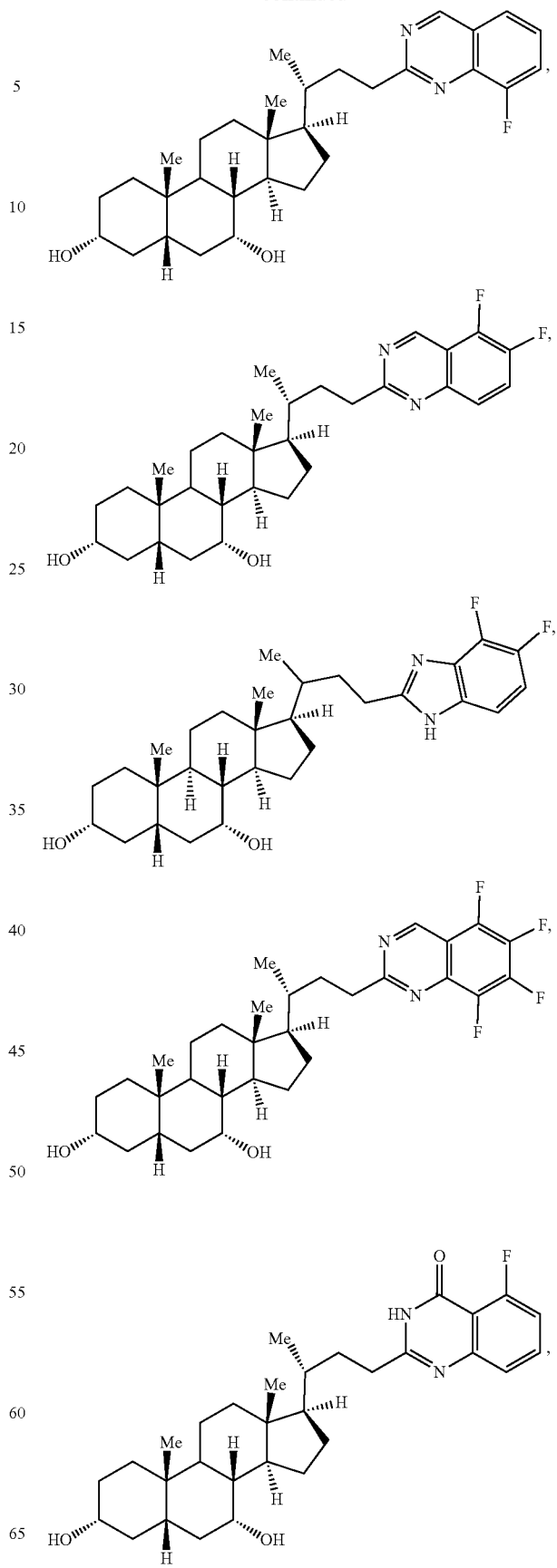

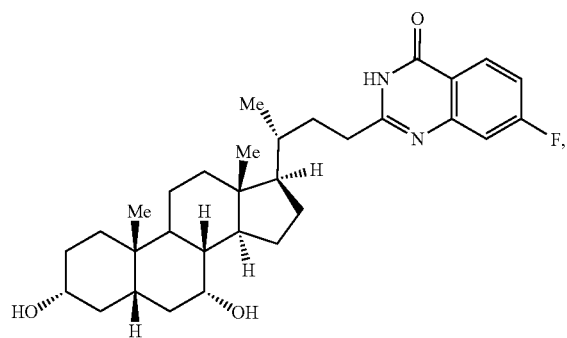
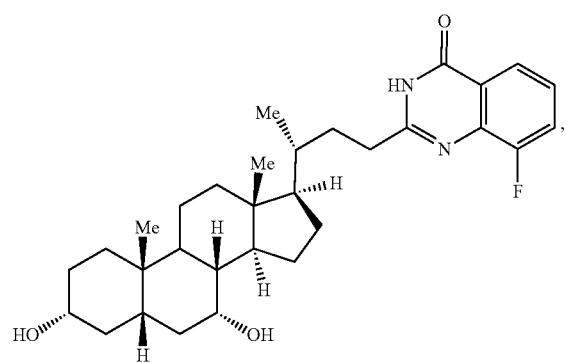
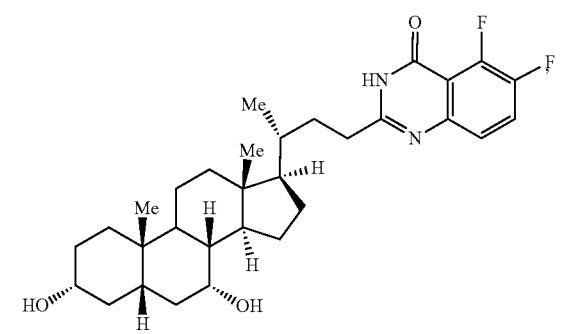
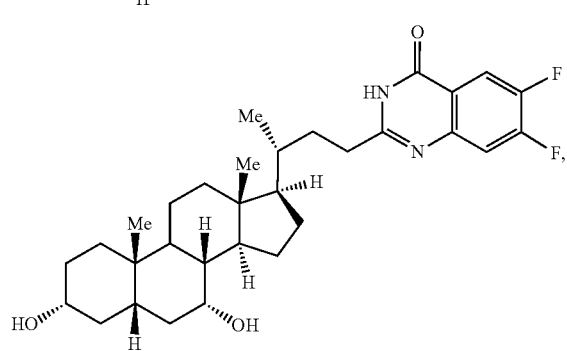
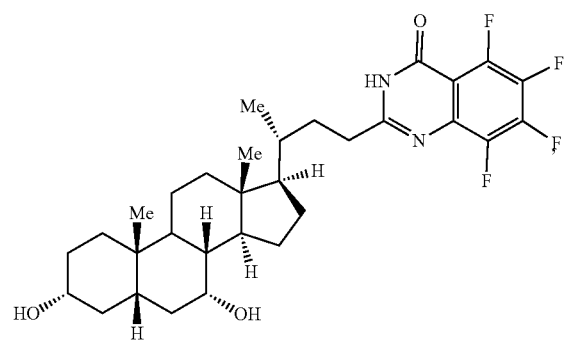
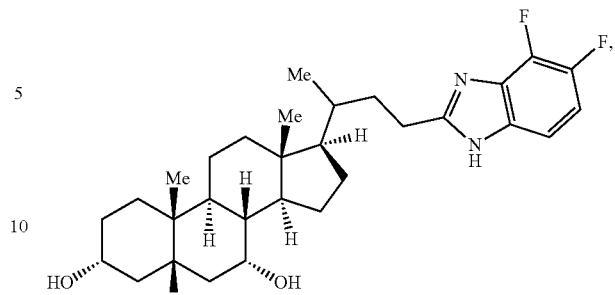
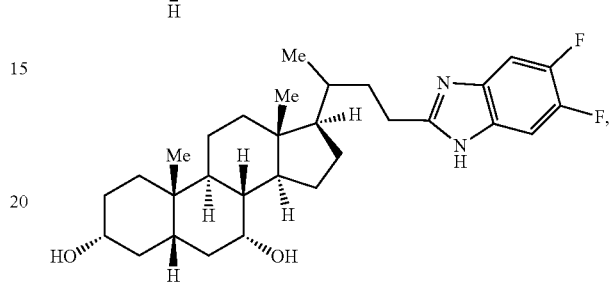
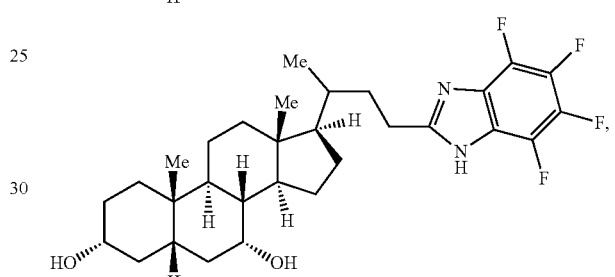
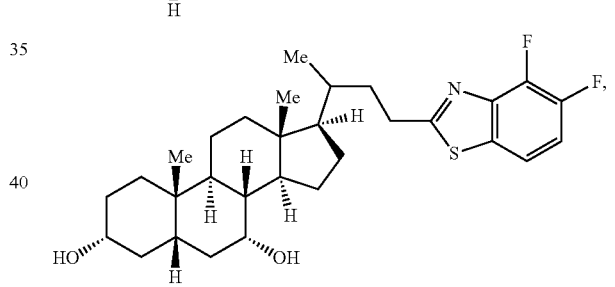
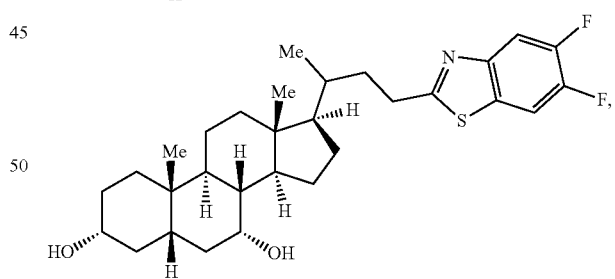
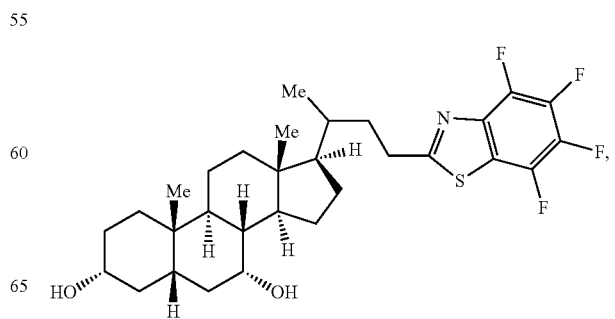

65
-continued
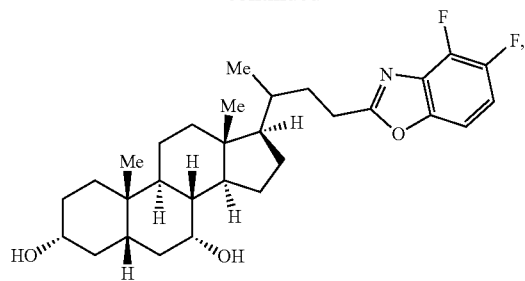
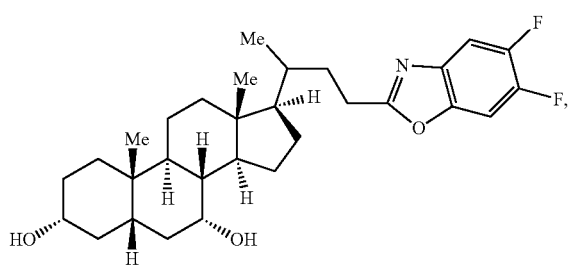
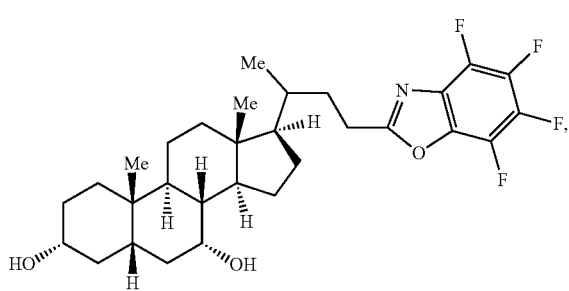
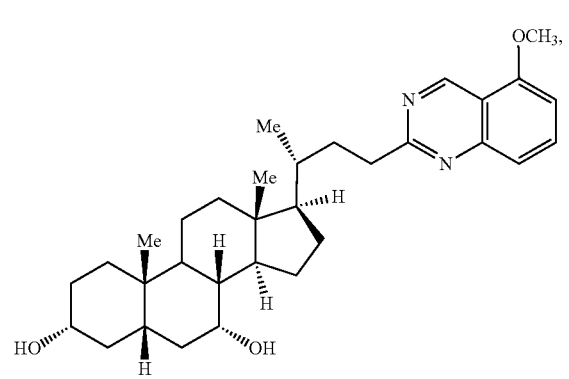
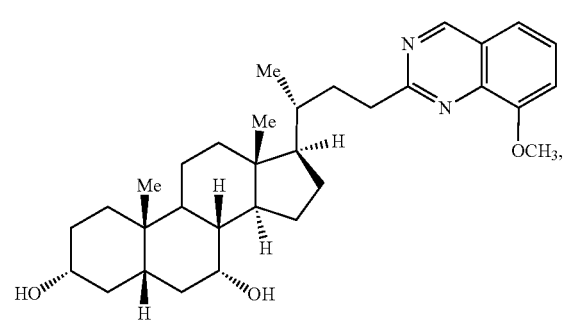
66
-continued
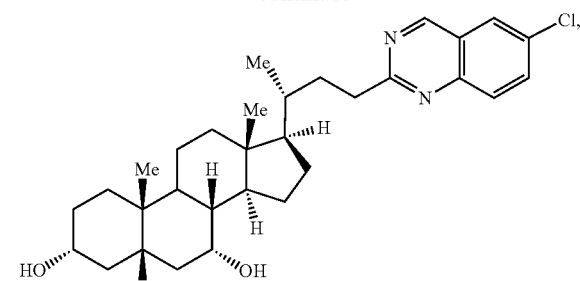
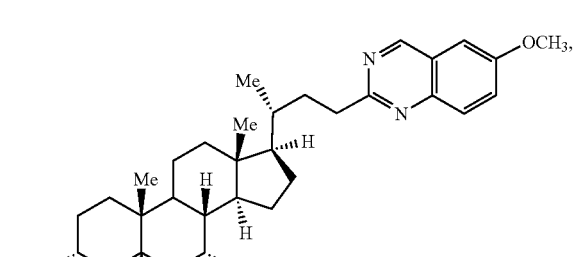
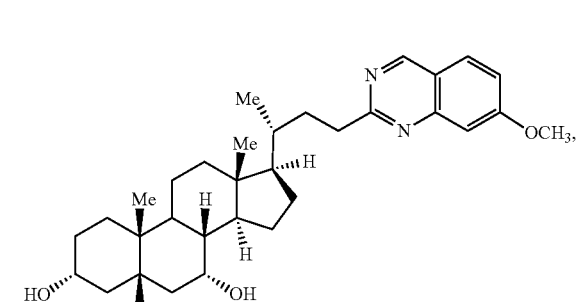
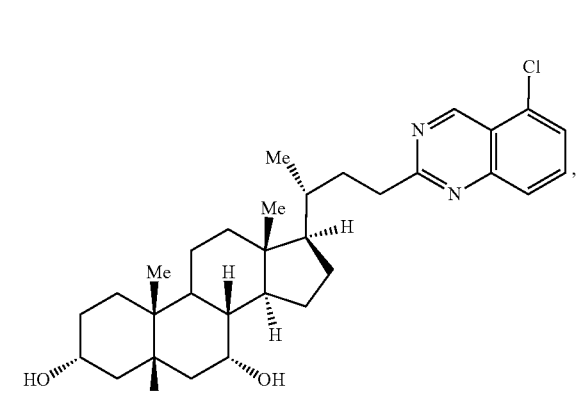
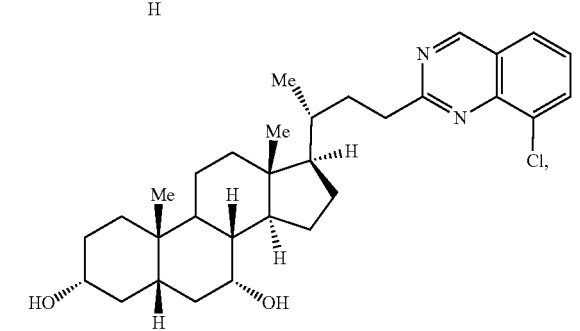

-continued
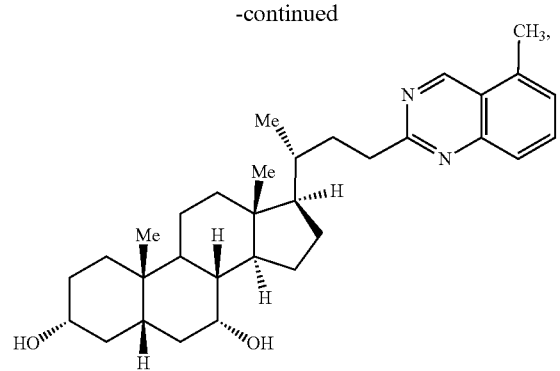
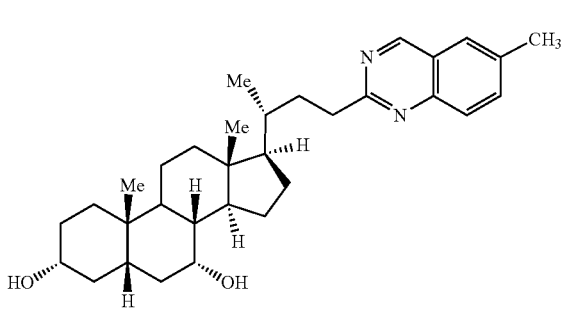
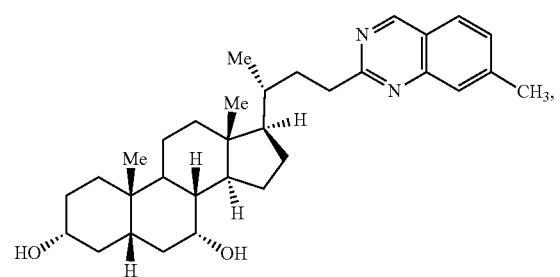
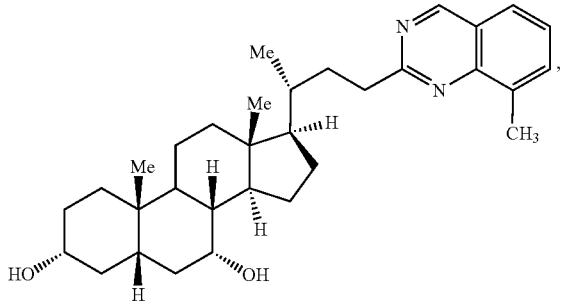
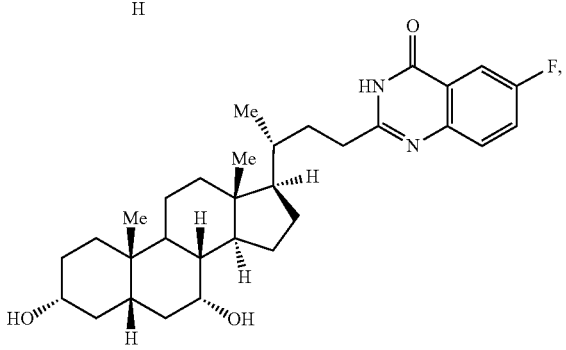
-continued
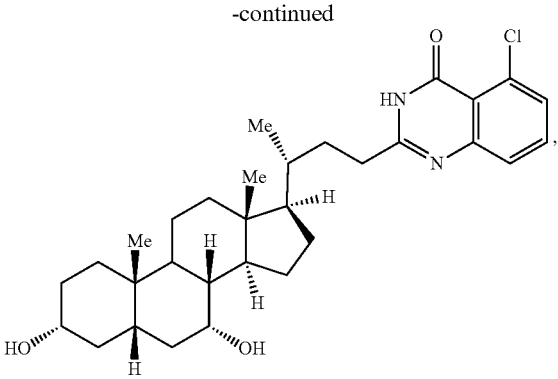
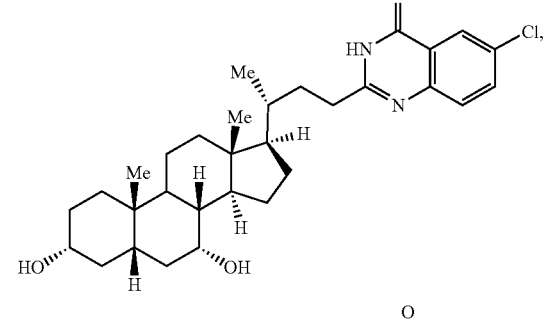
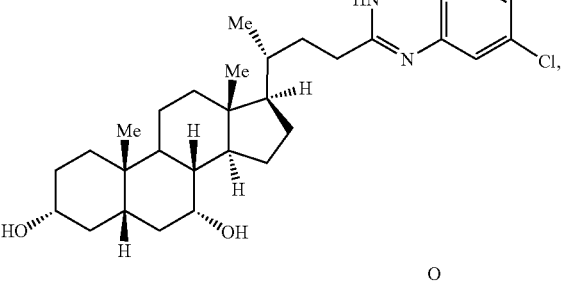
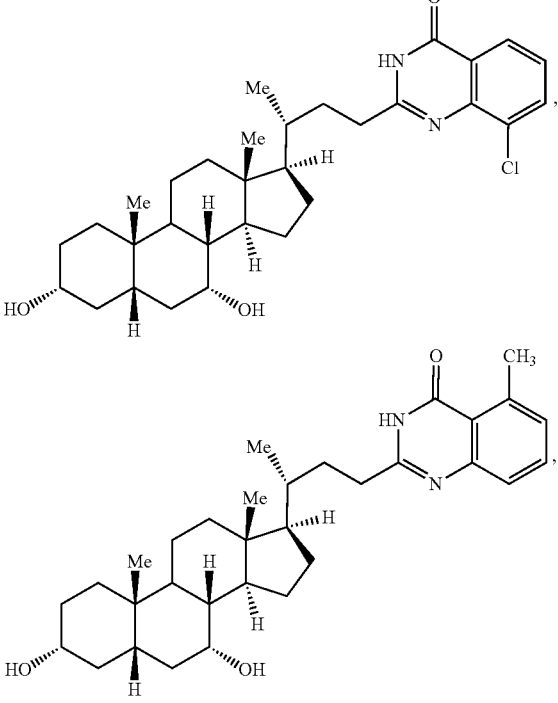
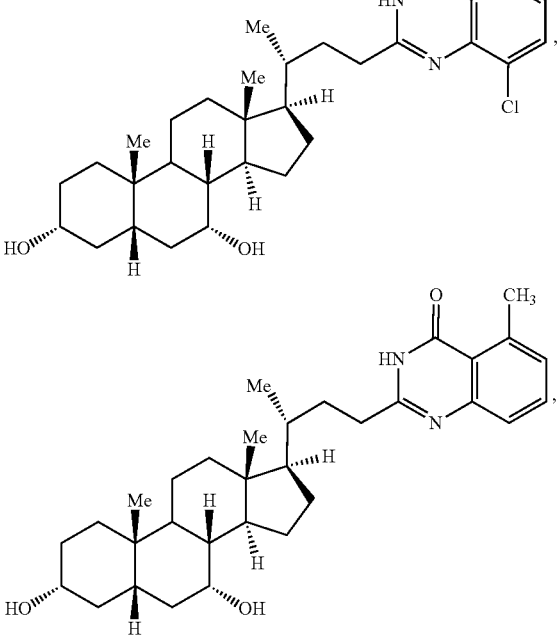

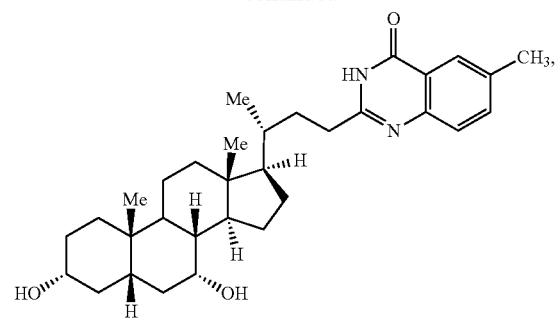
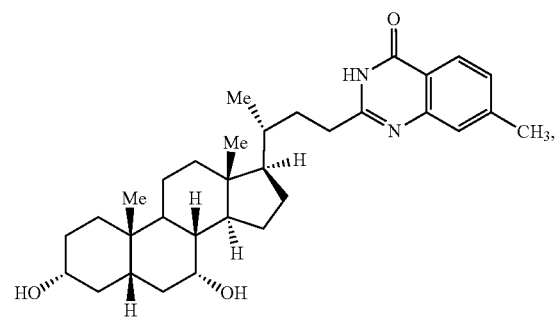
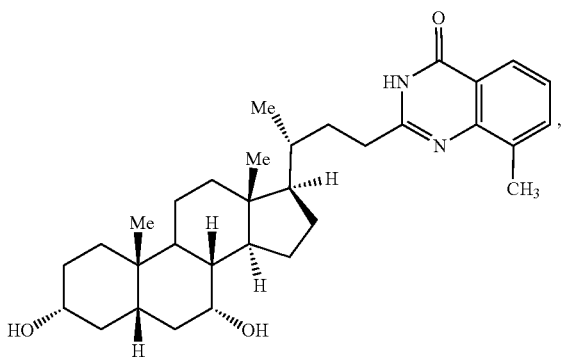
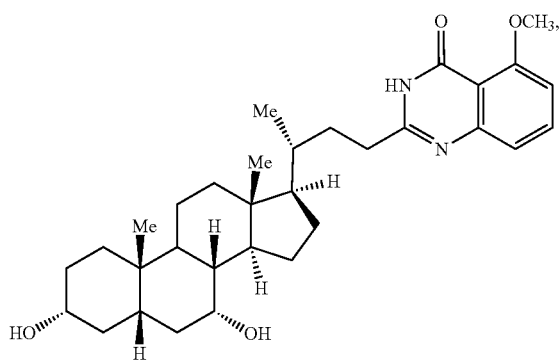
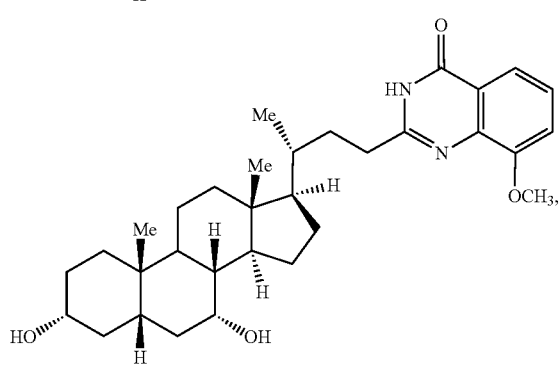
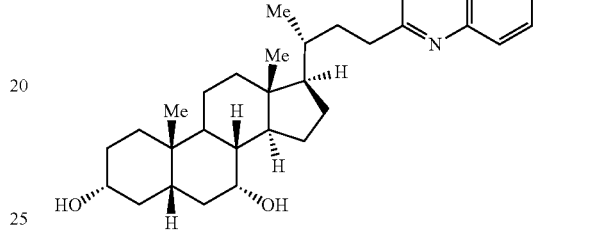
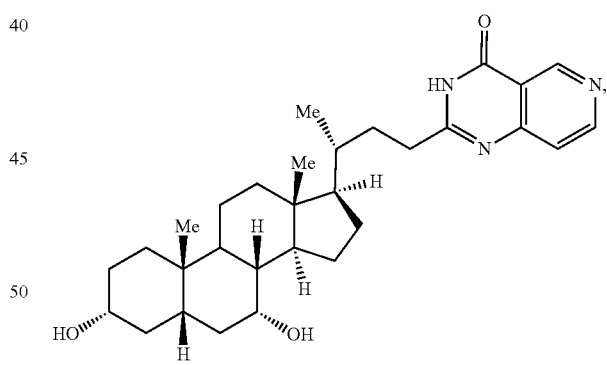
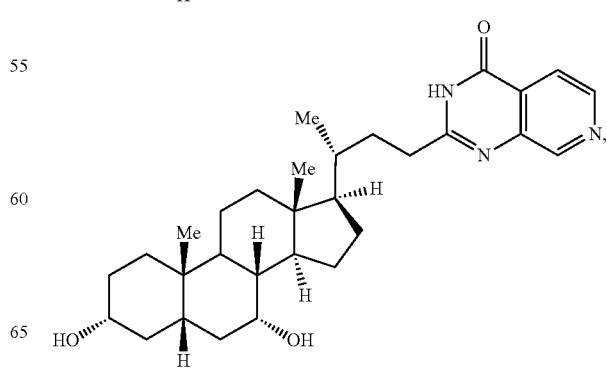

71
-continued
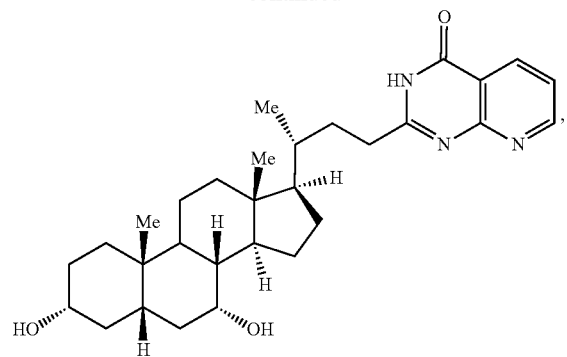
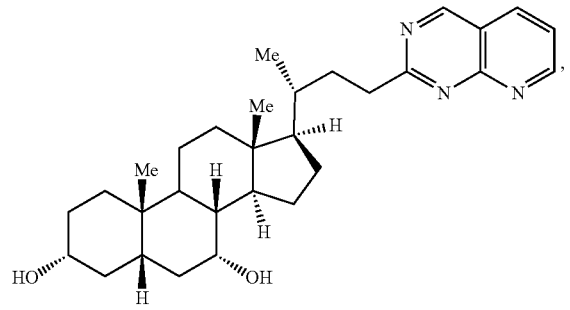
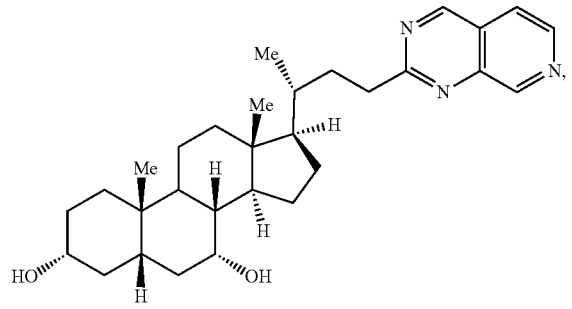
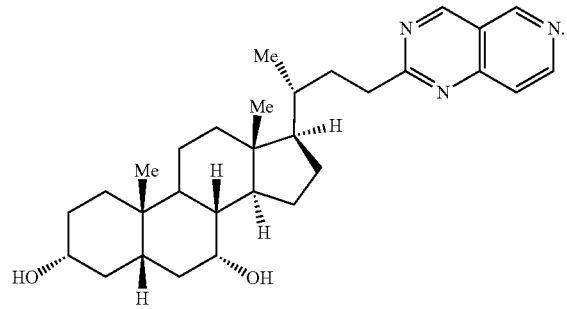
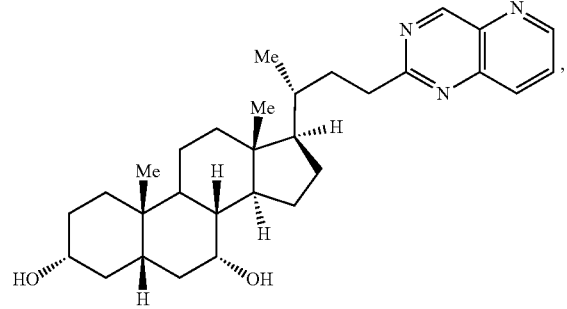
72
-continued
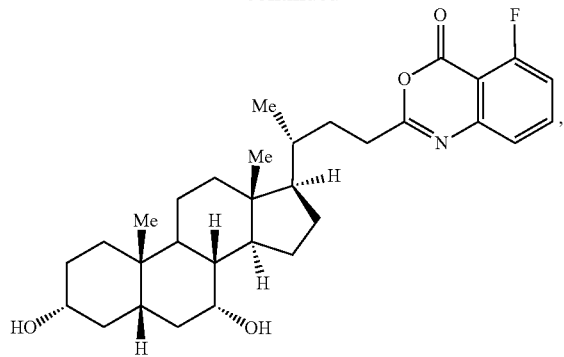
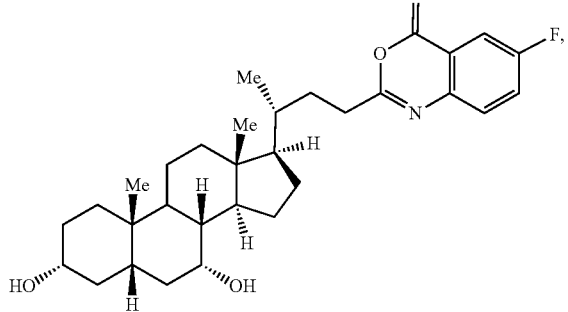
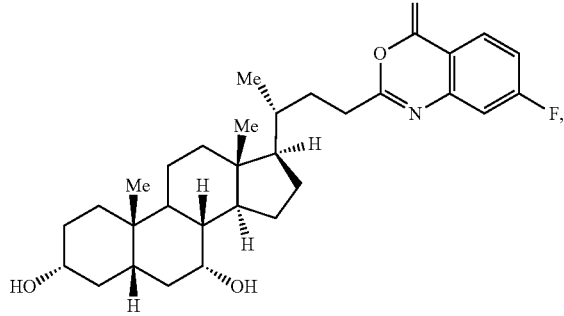
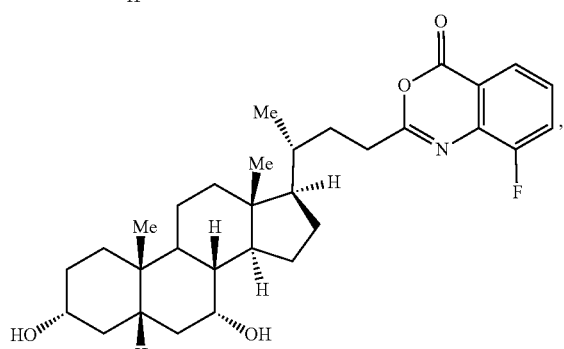
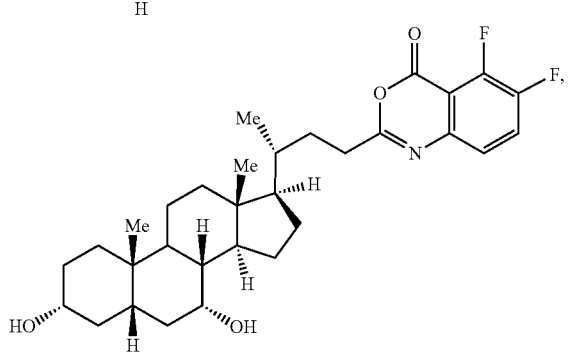

73
-continued
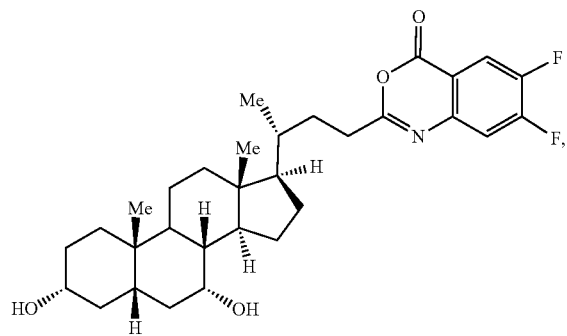
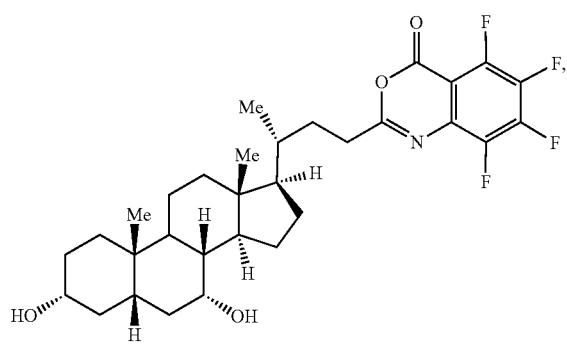
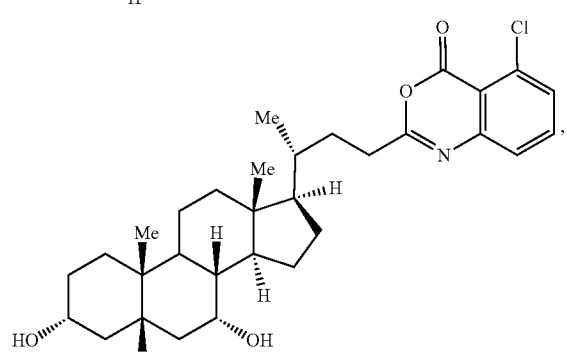
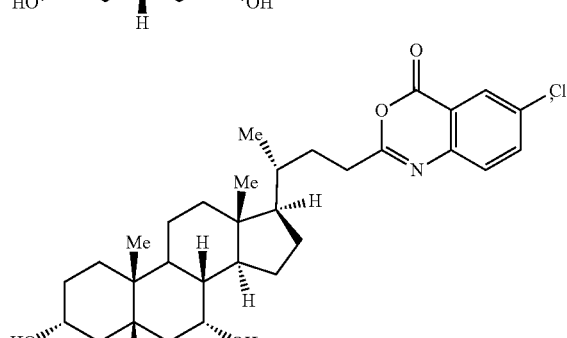
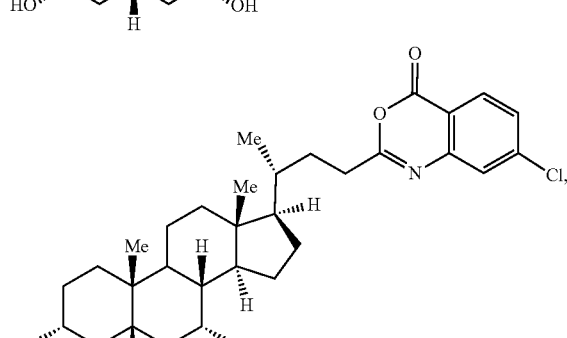
74
-continued
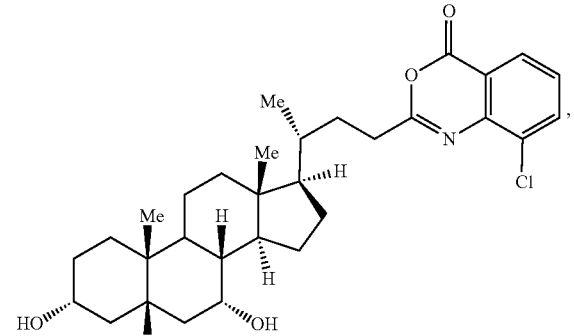
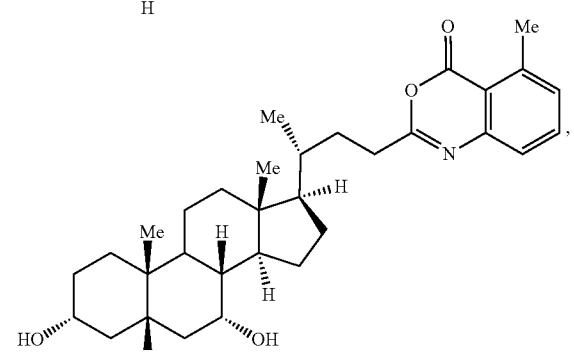
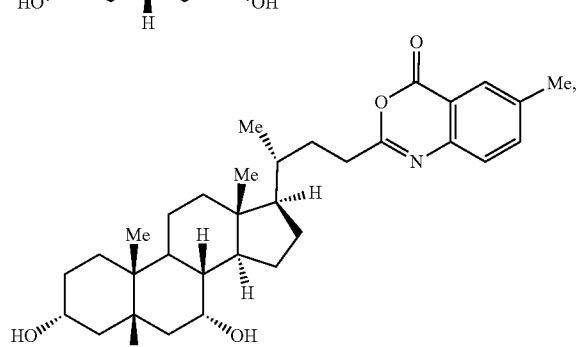
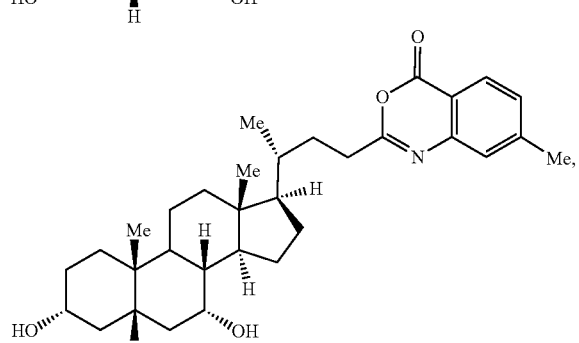
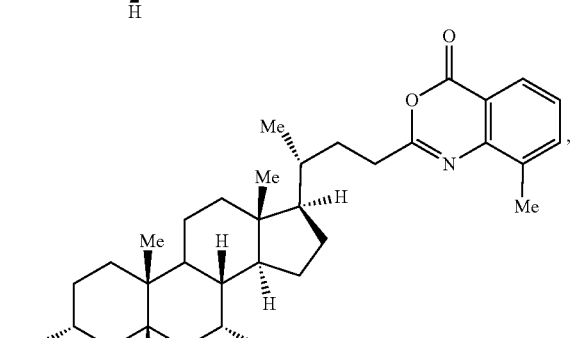

75
-continued
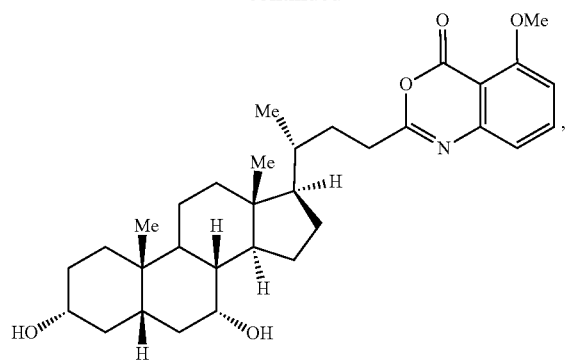
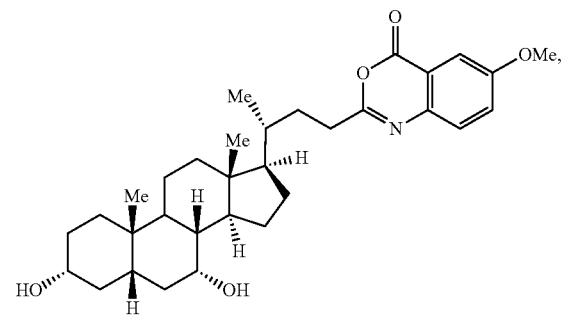
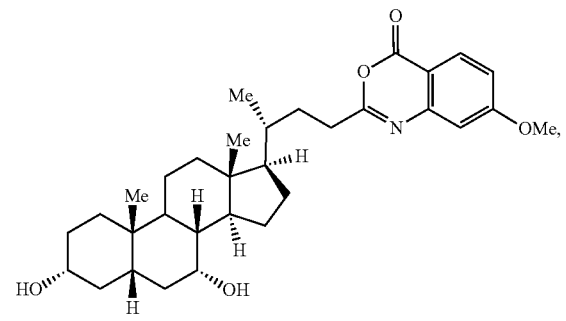
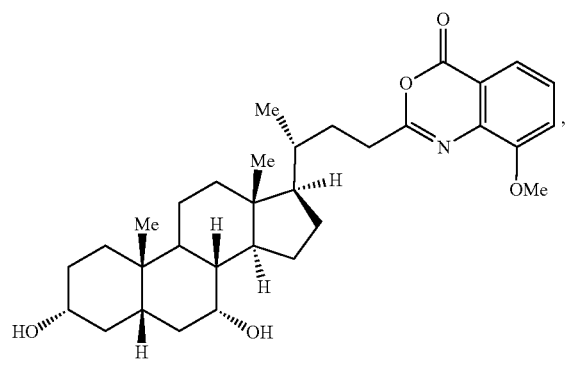
76
-continued

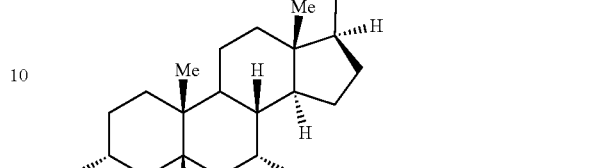
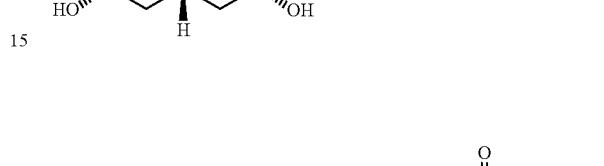
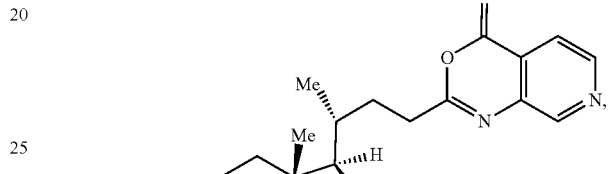
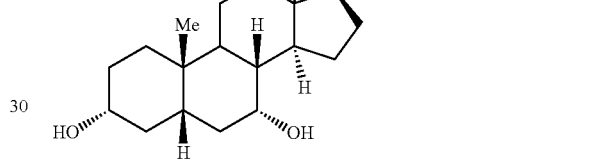

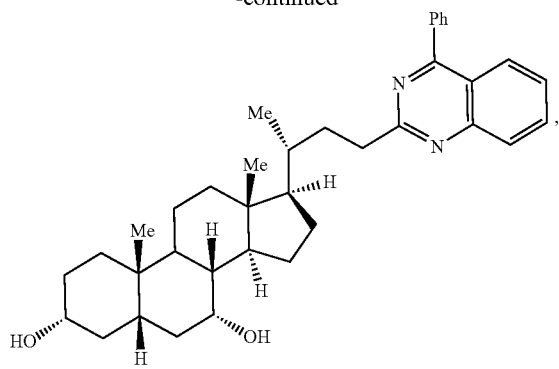
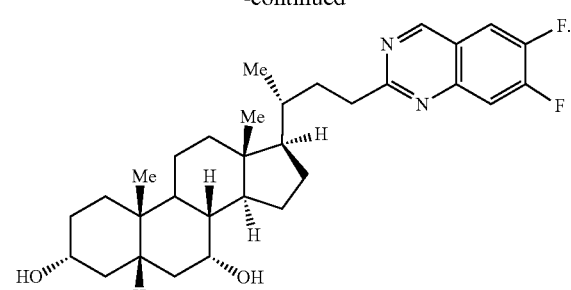
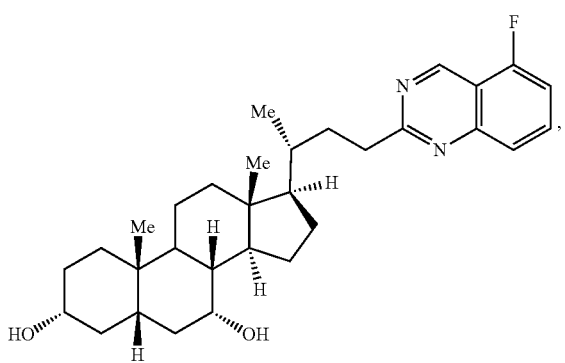
In a further aspect, the compound has a structure represented by a formula:
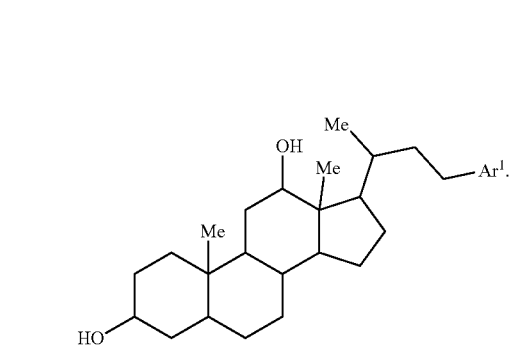
In a further aspect, the compound has a structure represented by a formula:
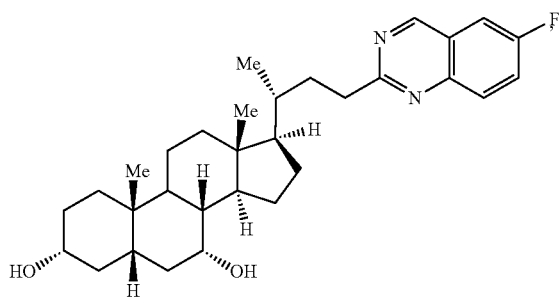
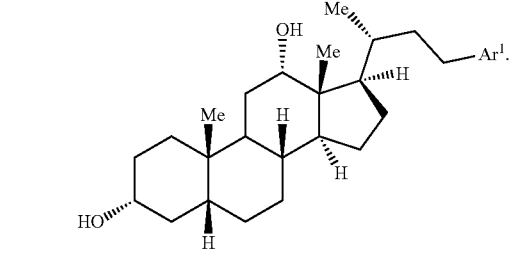
In a further aspect, the compound is selected from:
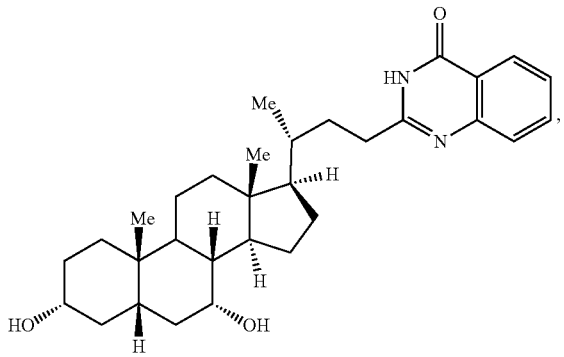
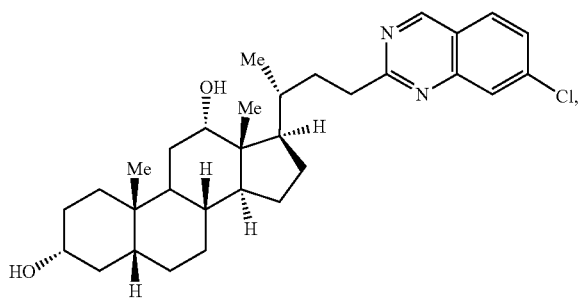

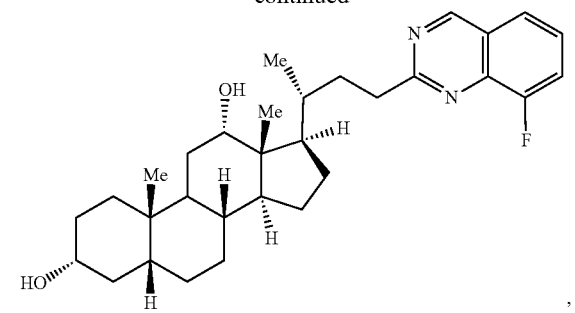
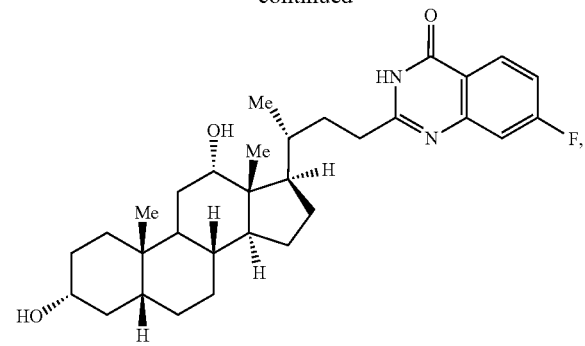

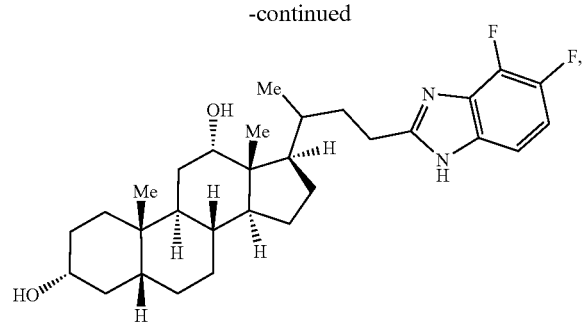
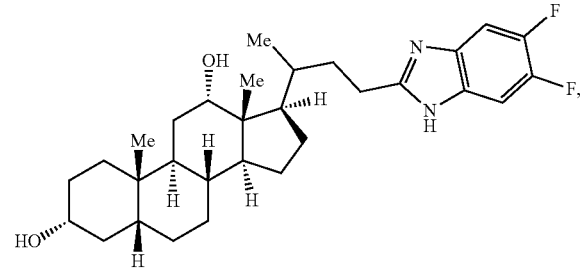
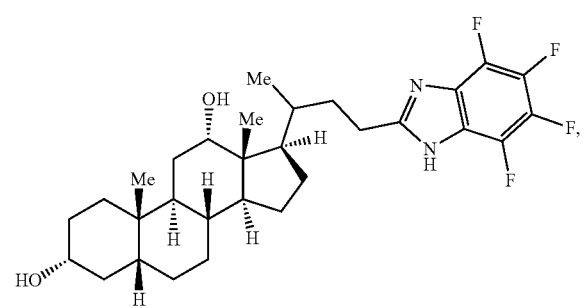
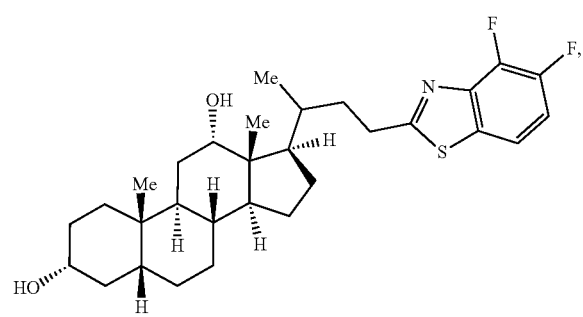
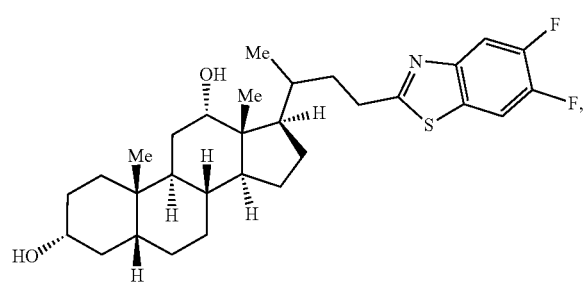
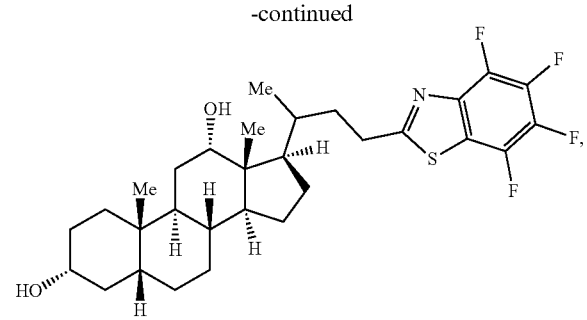
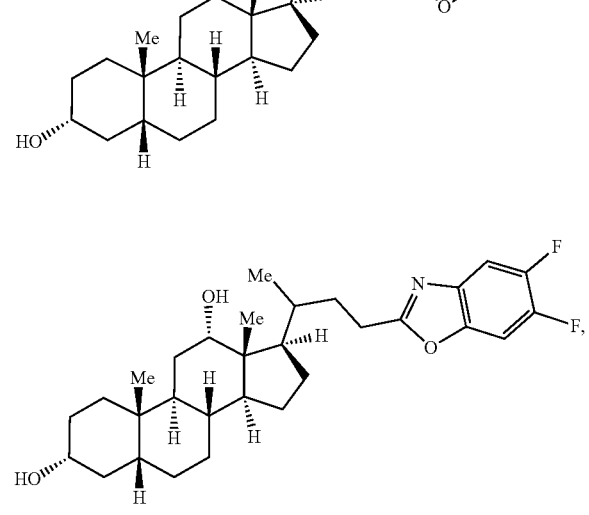
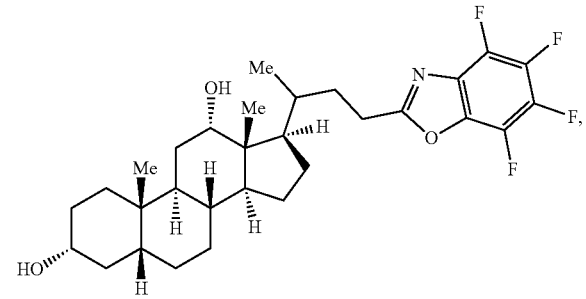
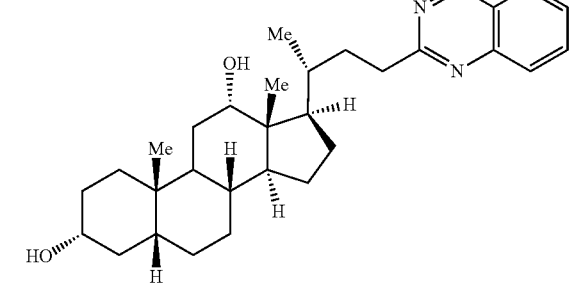

-continued
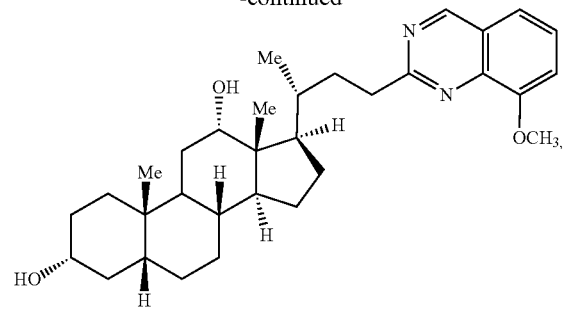
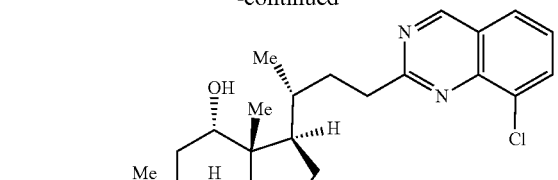
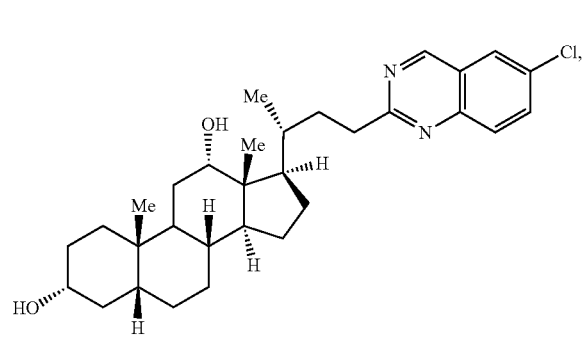
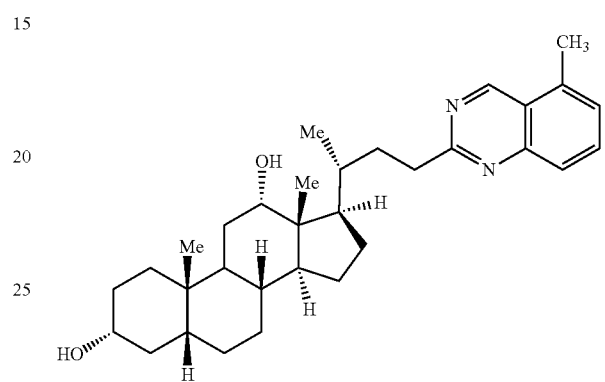
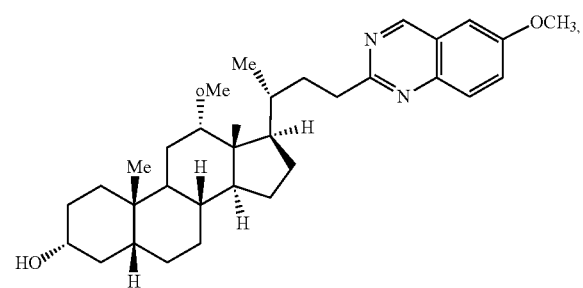
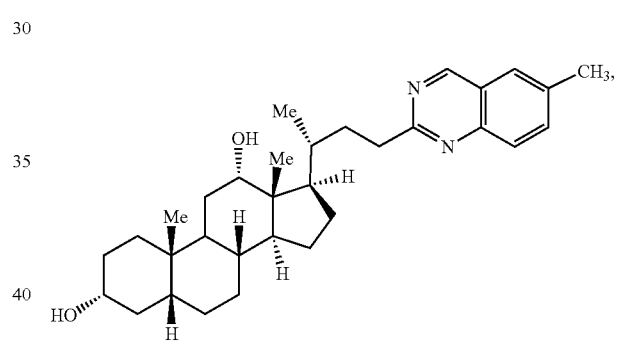
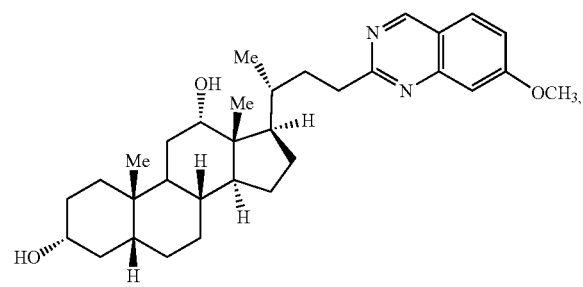
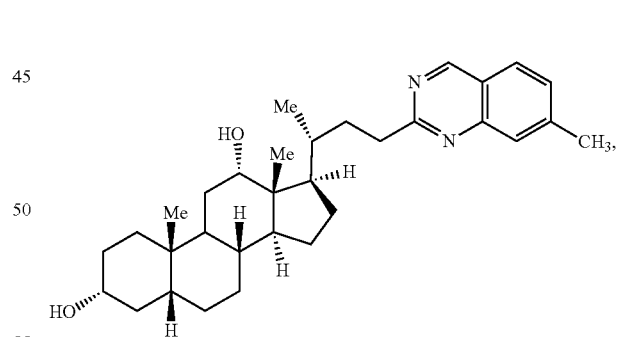
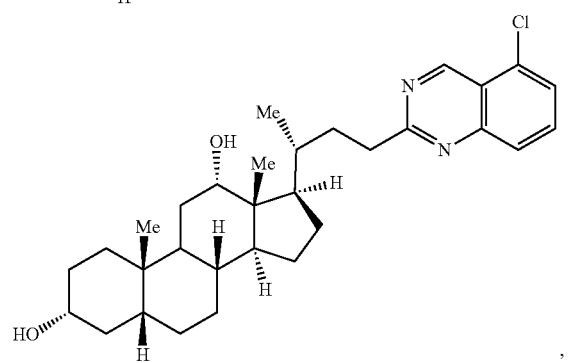
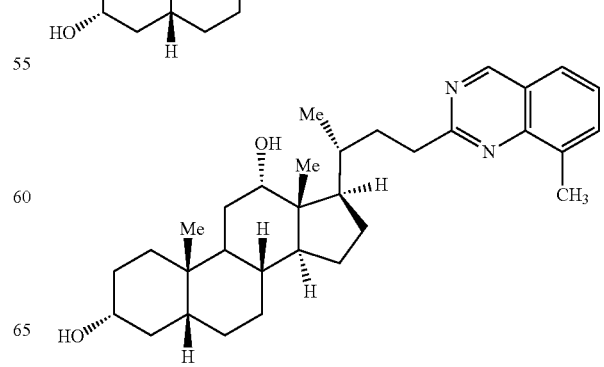

-continued
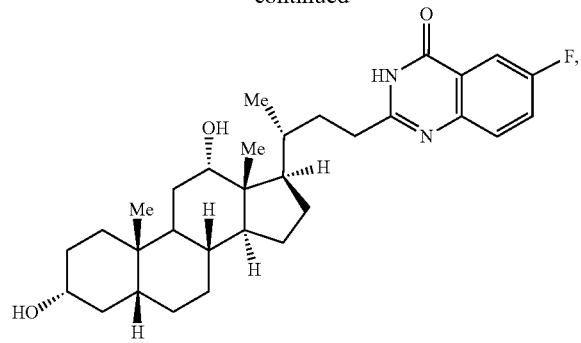
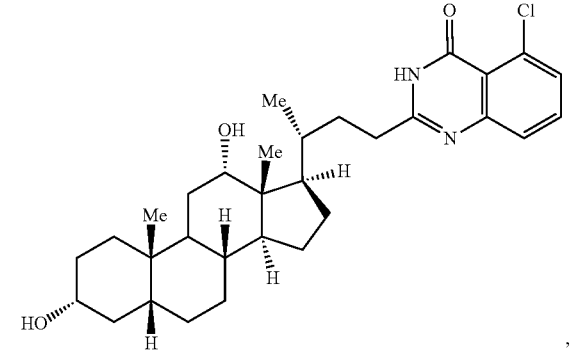
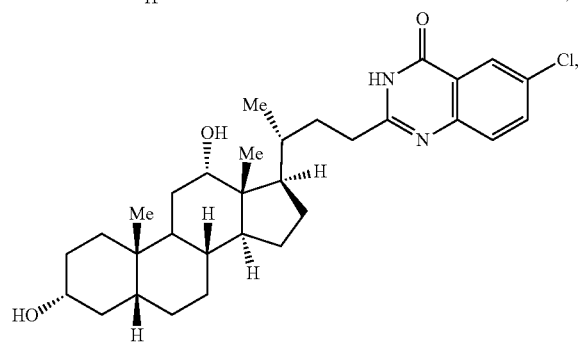
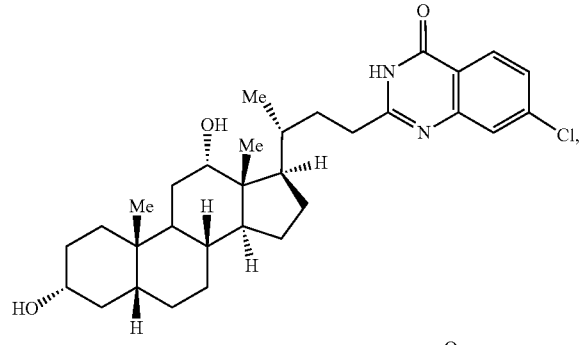
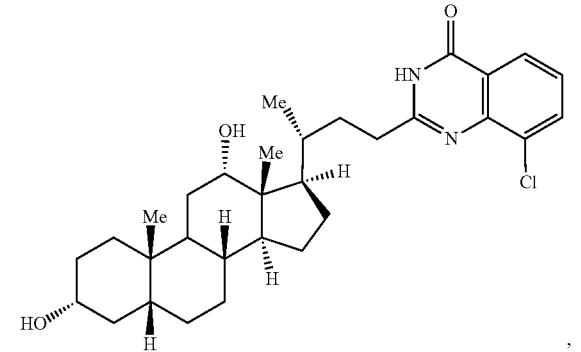
-continued
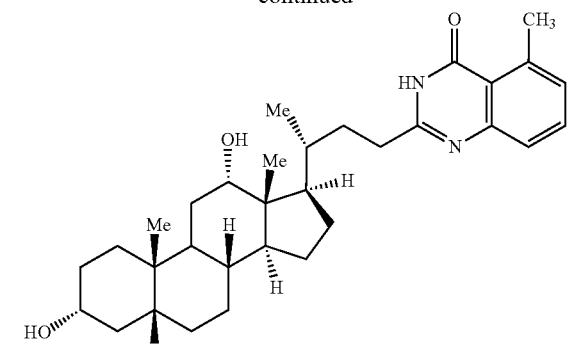
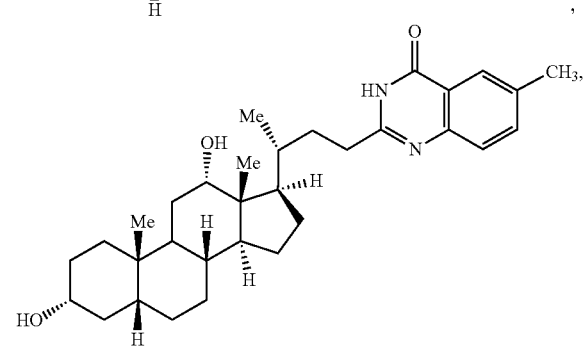
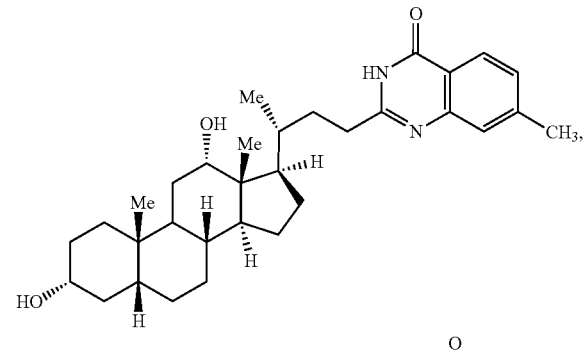
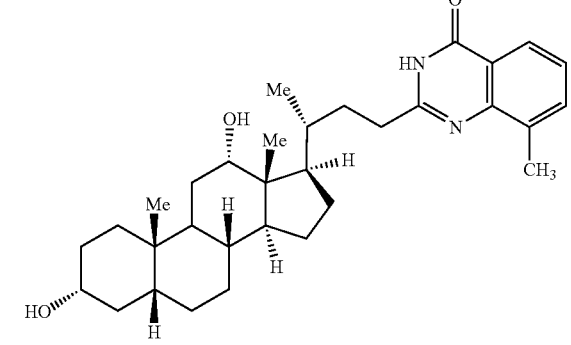
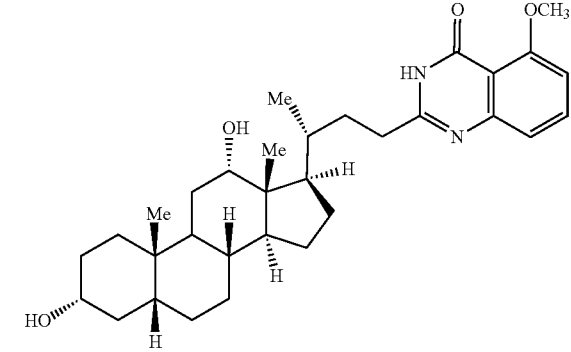

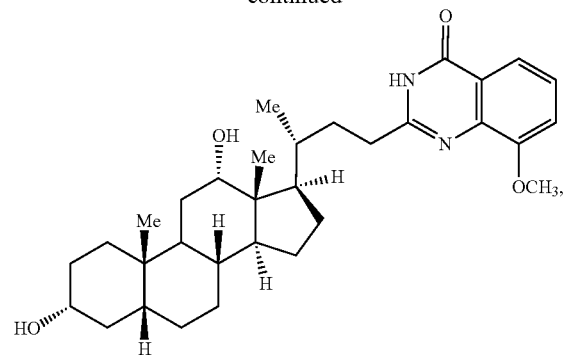
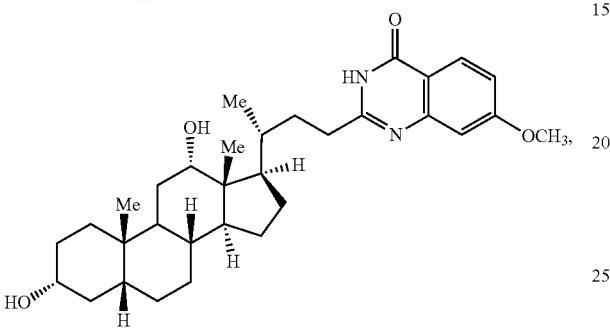
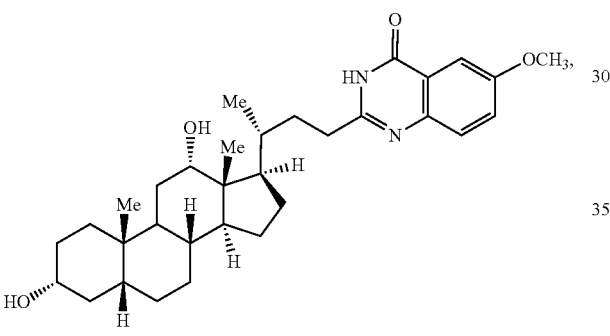
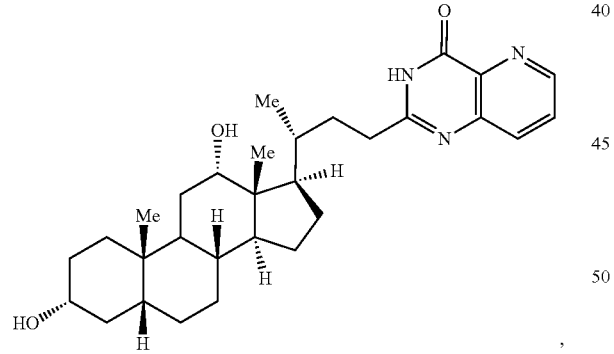
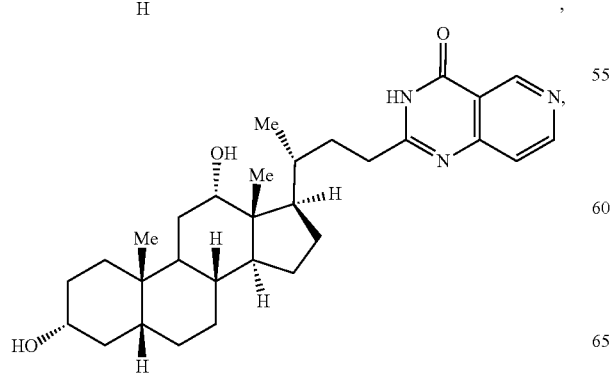
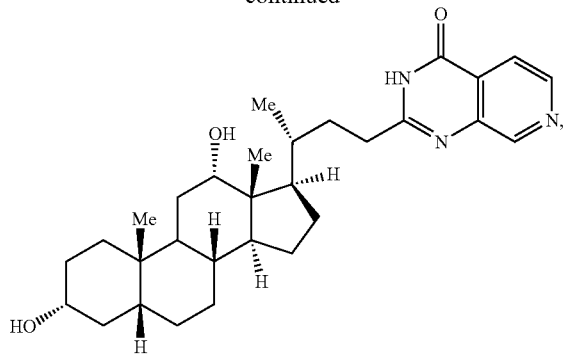
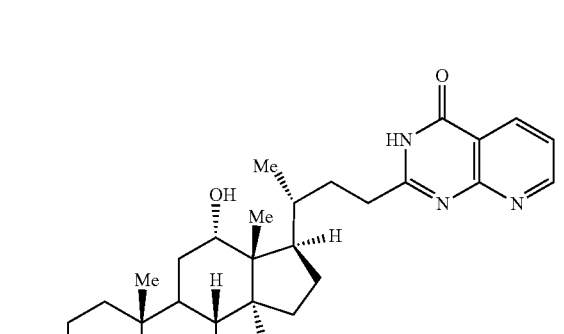
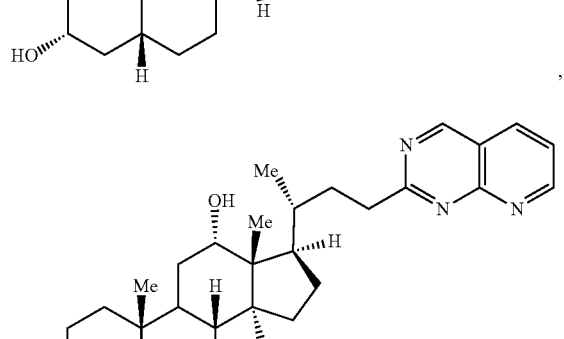
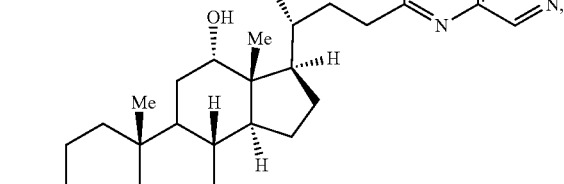
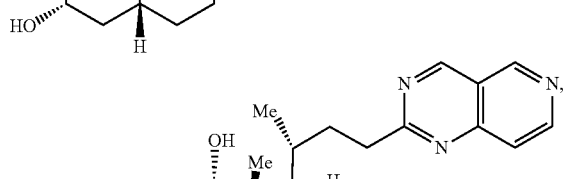
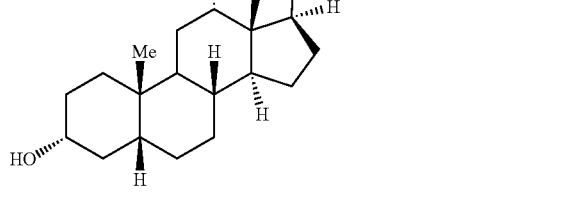

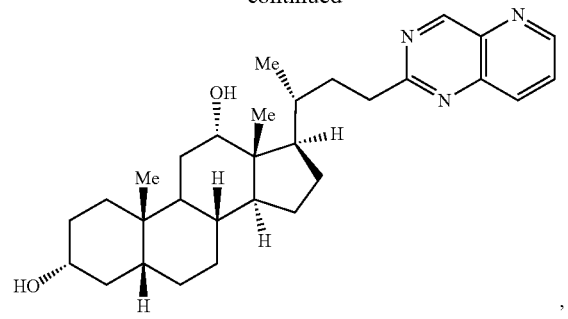
,

,
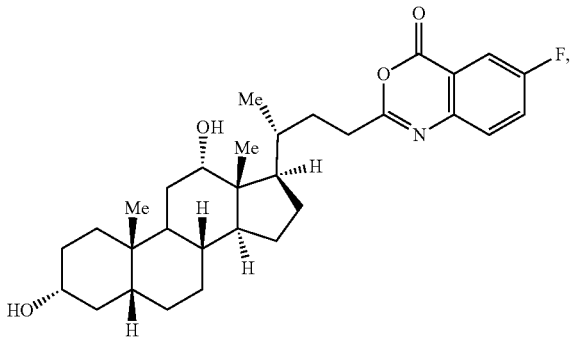
,
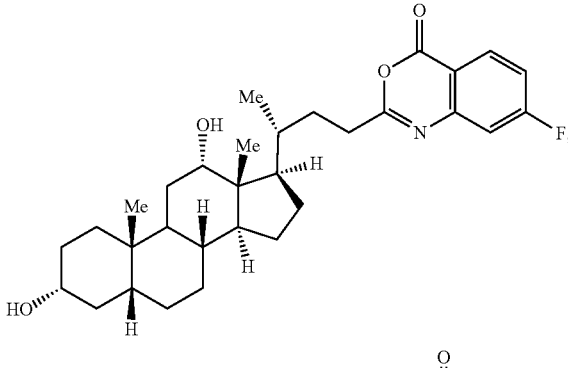
,
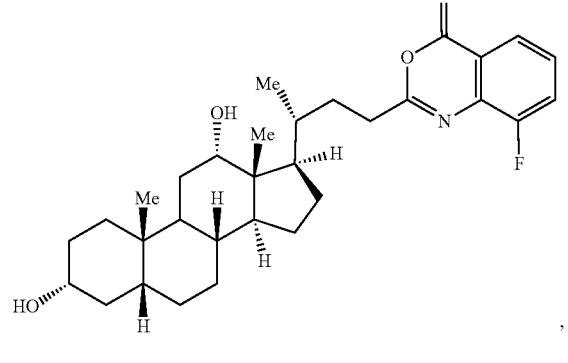
,
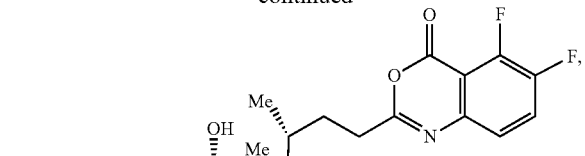
,

,

,

,

,

,

, 91
-continued
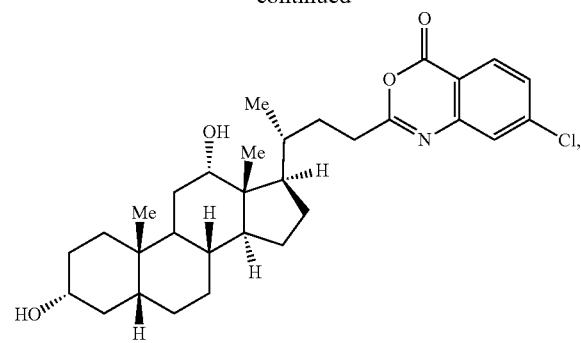
,
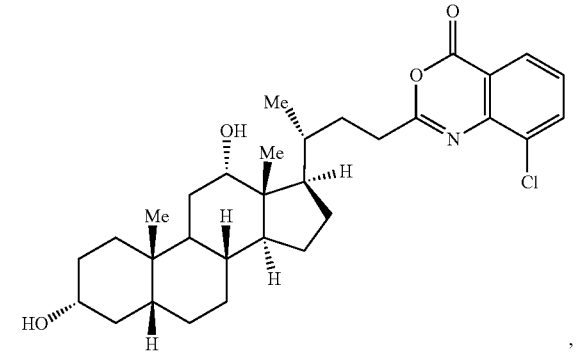
,
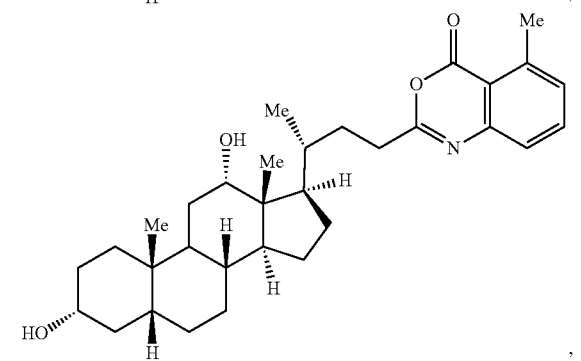
,
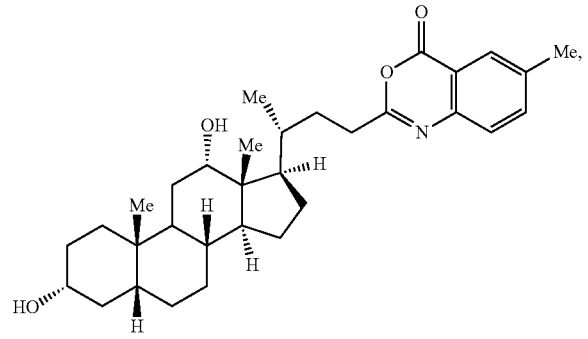
,
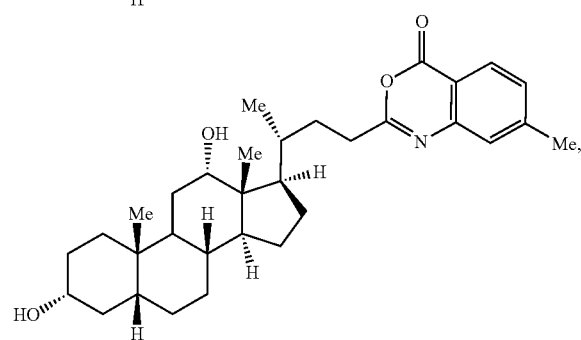
,
92
-continued
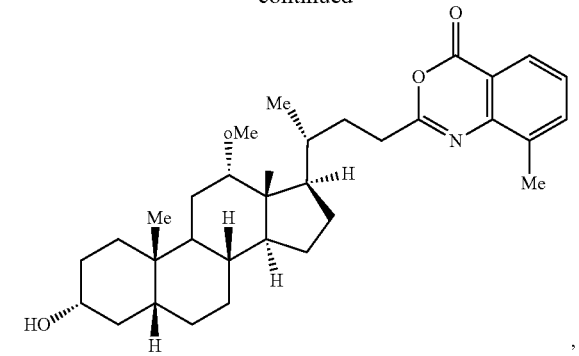
,

,
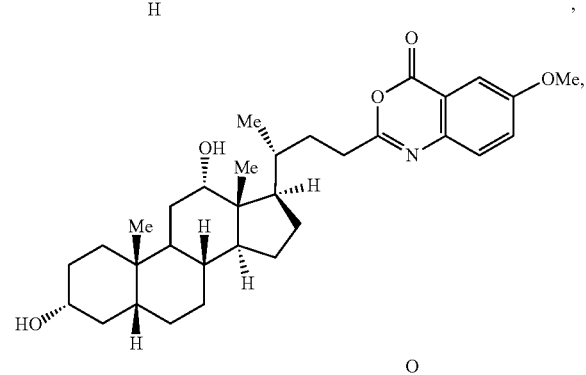
,
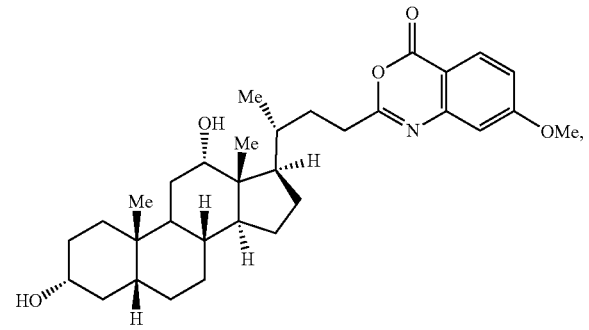
,
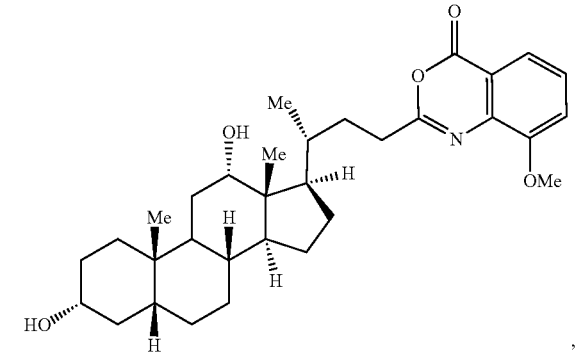
, 93
-continued
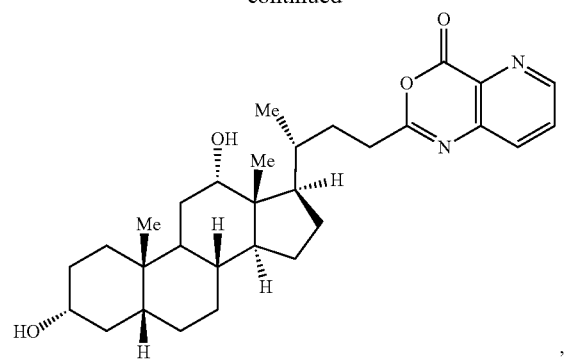
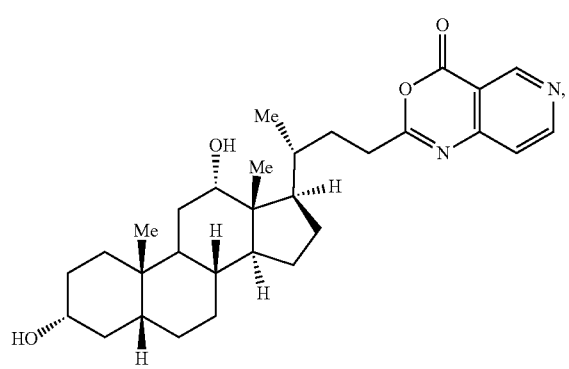
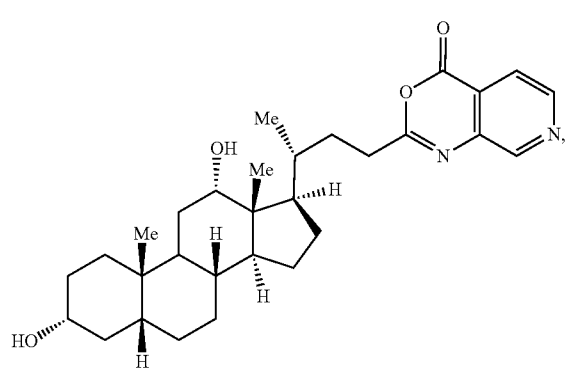
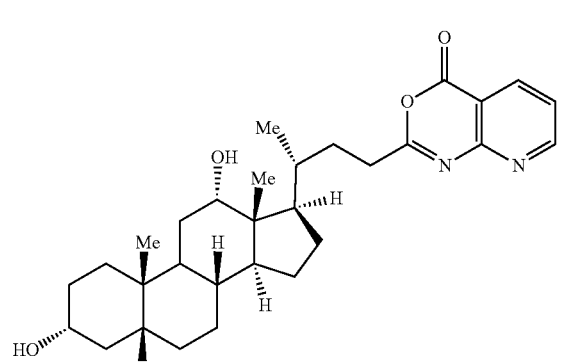
94
-continued
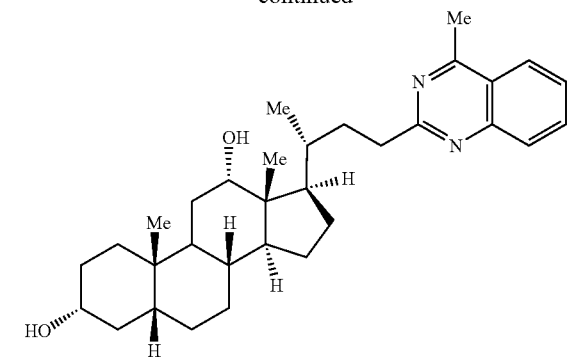
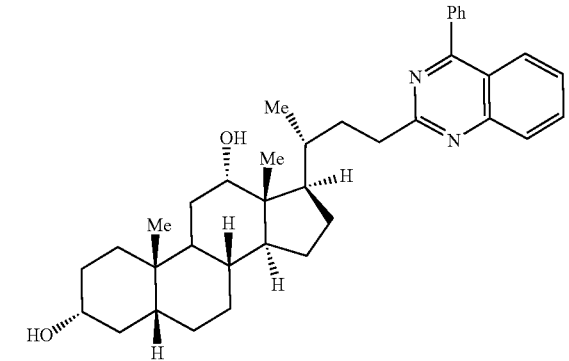
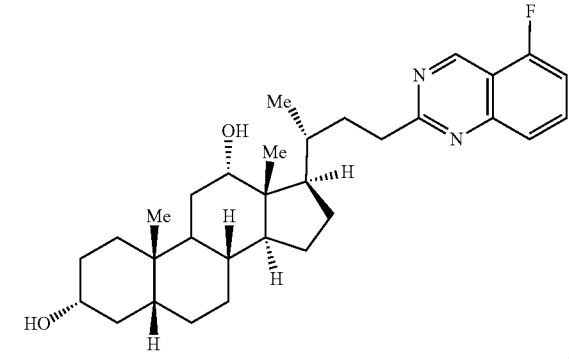
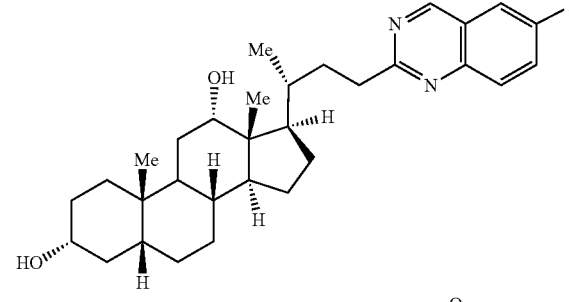
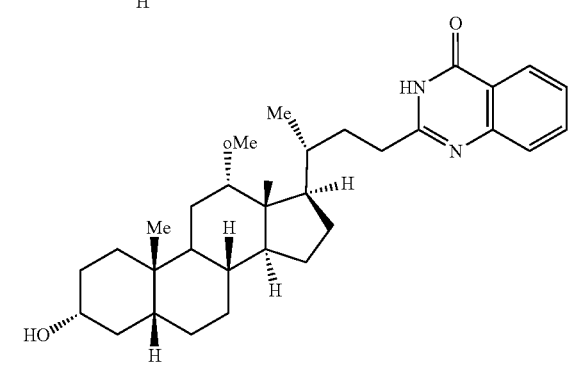

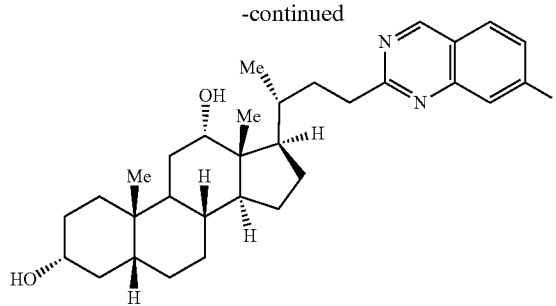
and
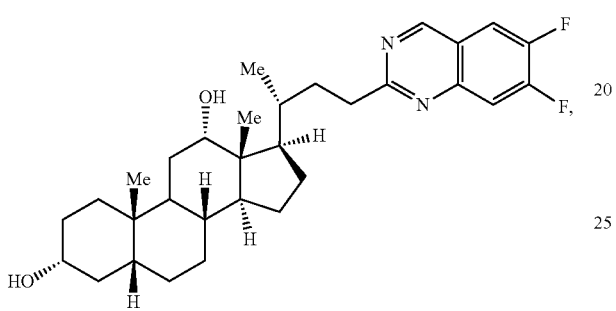
In a further aspect, the compound has a structure represented by a formula:
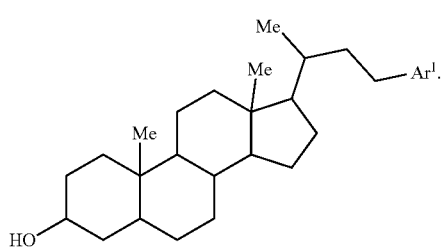
In a further aspect, the compound has a structure represented by a formula:
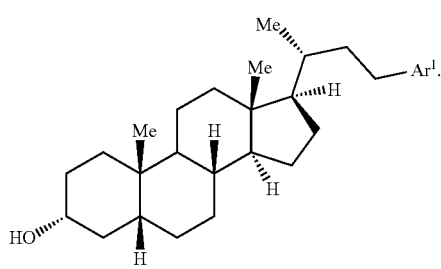
In a further aspect, the compound has a structure represented by a formula:
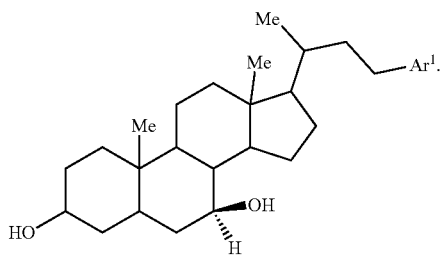
In a further aspect, the compound has a structure represented by a formula:
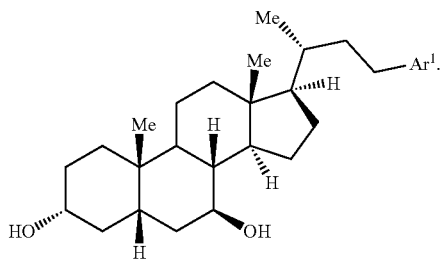
In a further aspect, the compound is selected from:
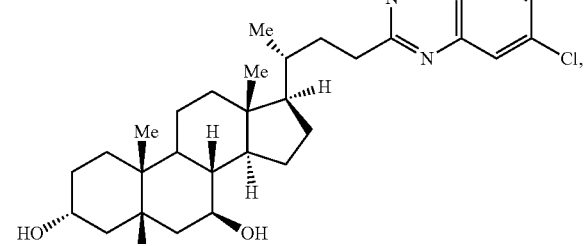
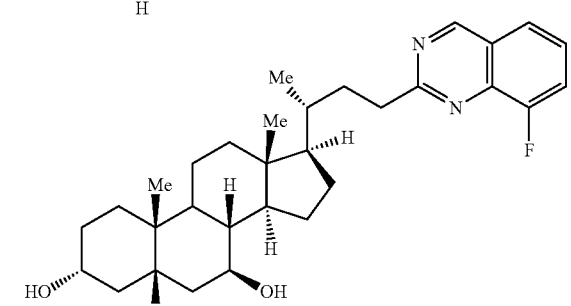
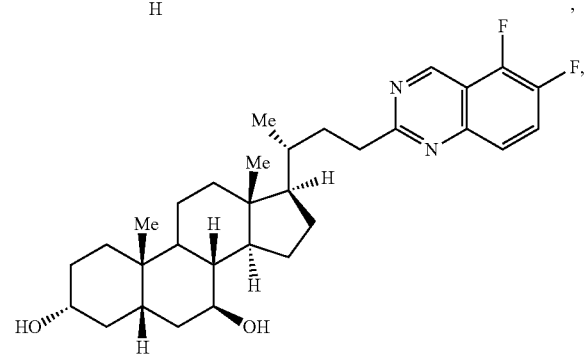

97
-continued
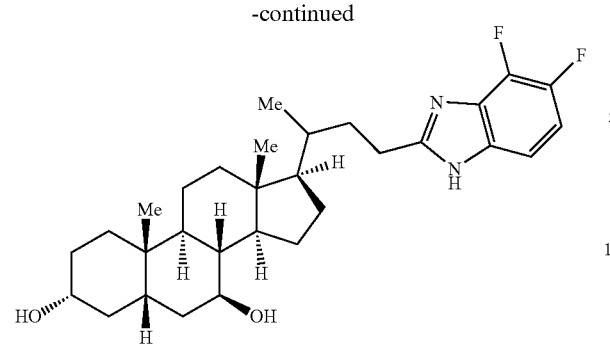
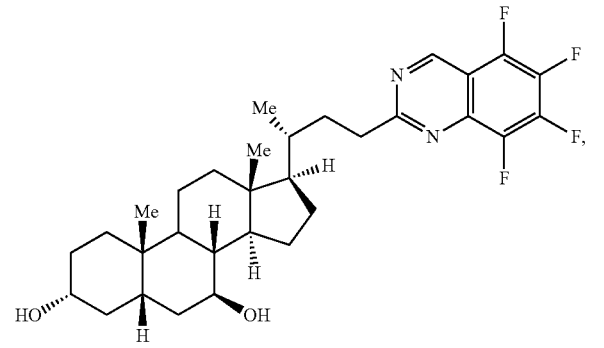
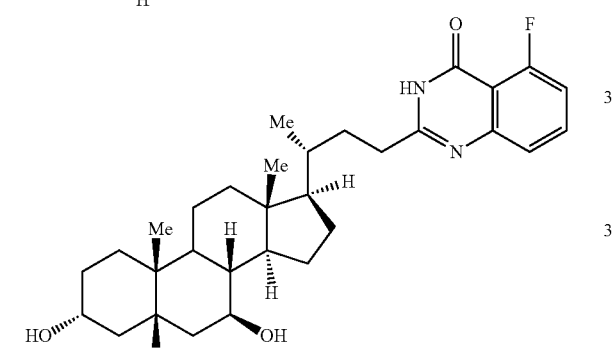
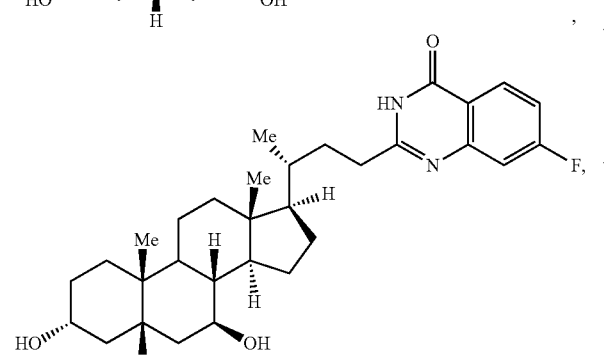
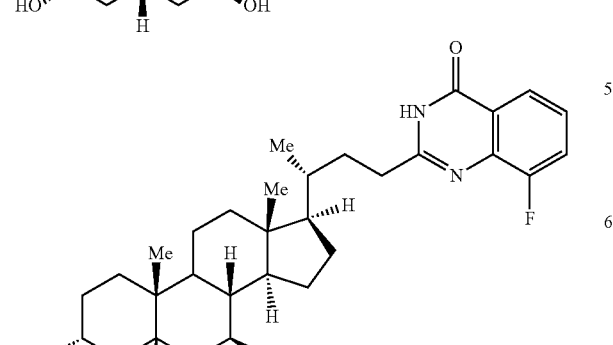
98
-continued
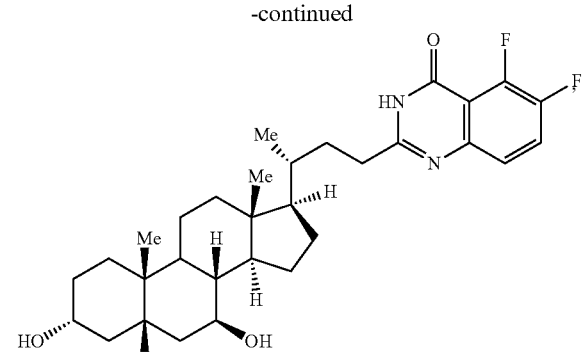
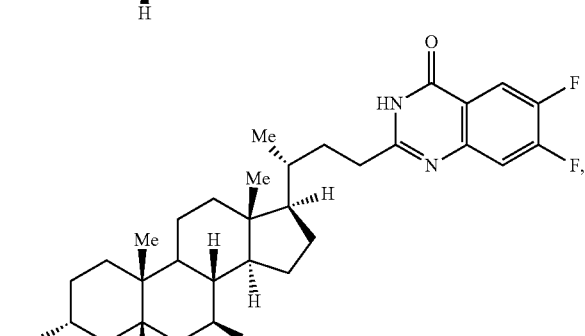
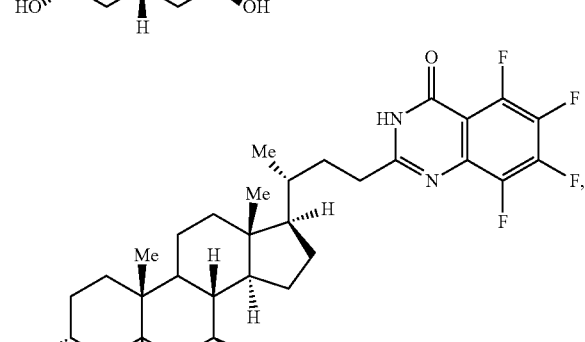
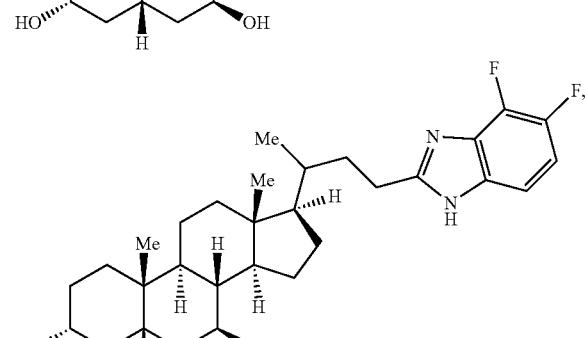
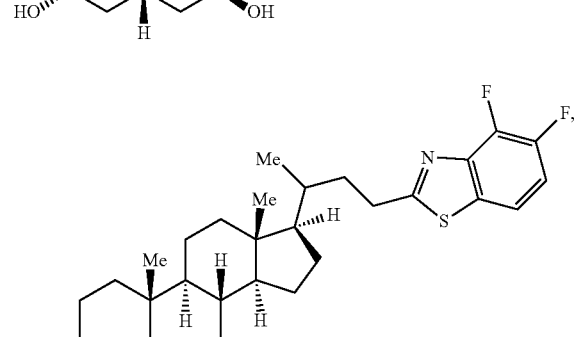

99
-continued
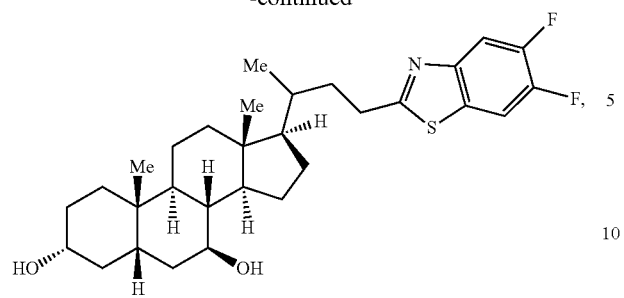
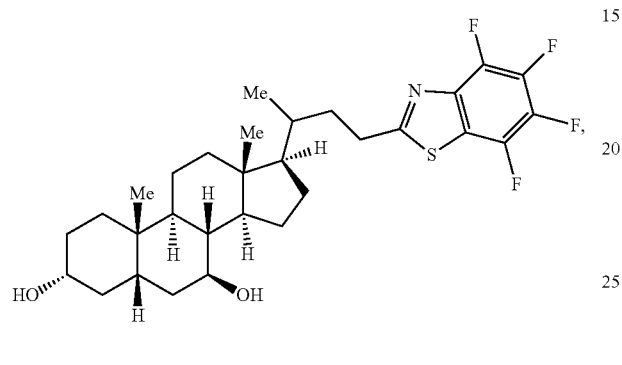
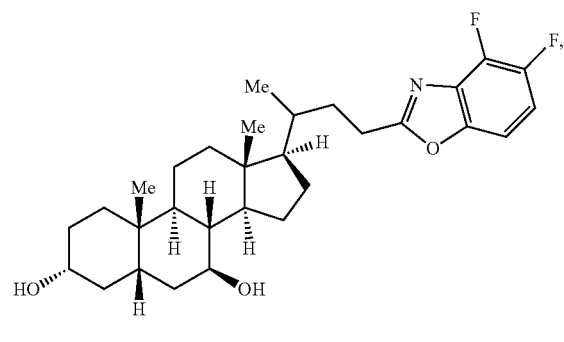
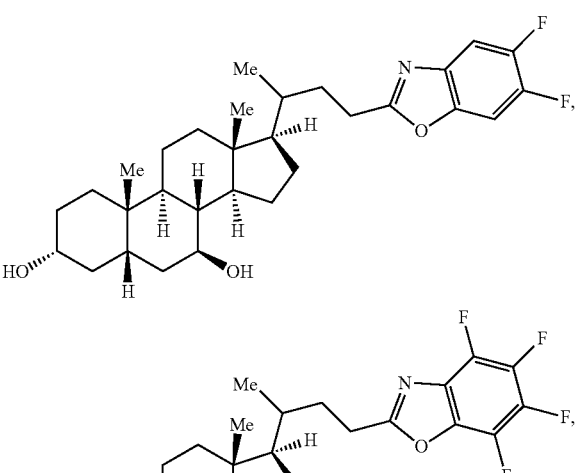
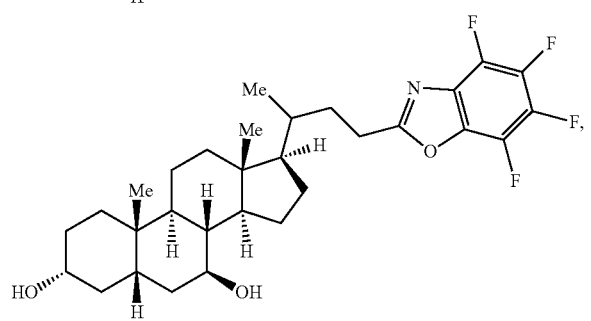
100
-continued
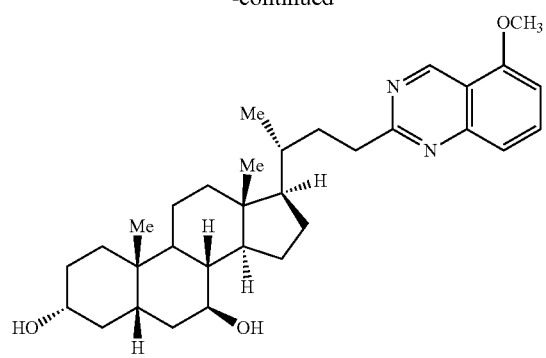
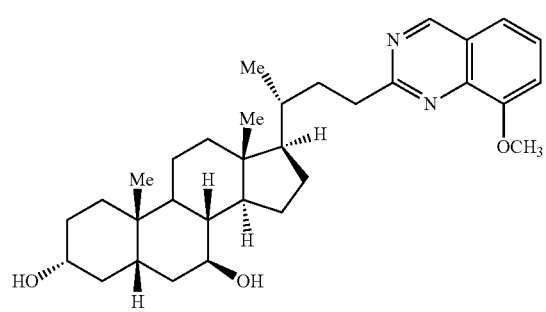
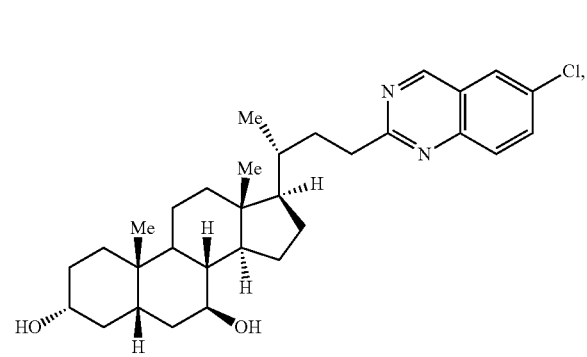
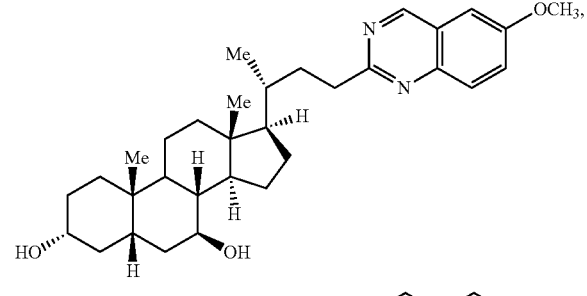
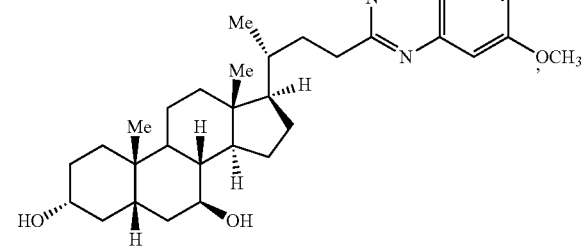

101
-continued
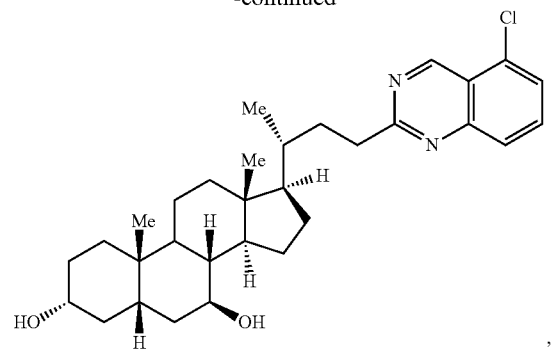
,
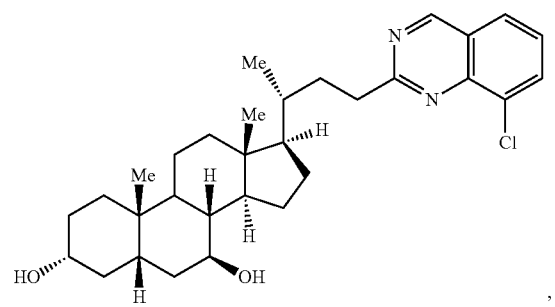
,
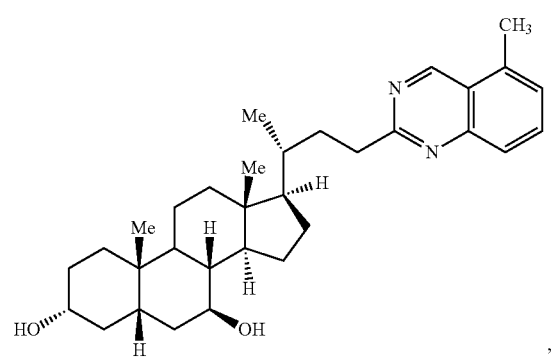
,
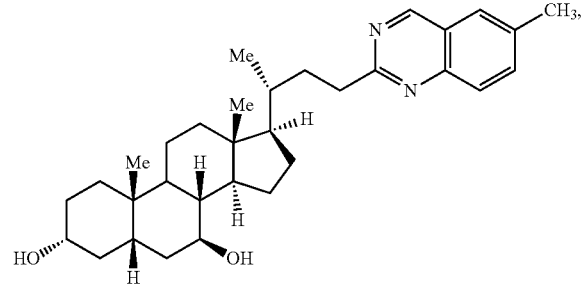
,
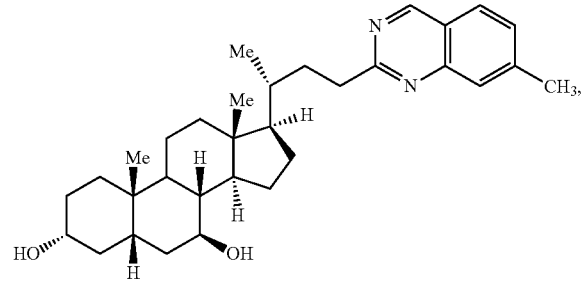
,
102
-continued
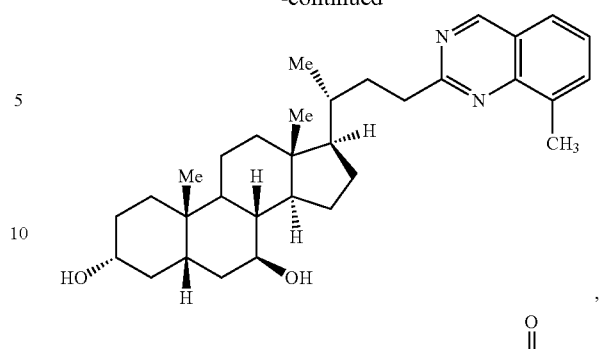
,
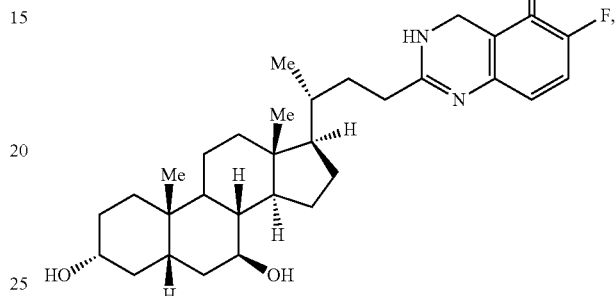
,
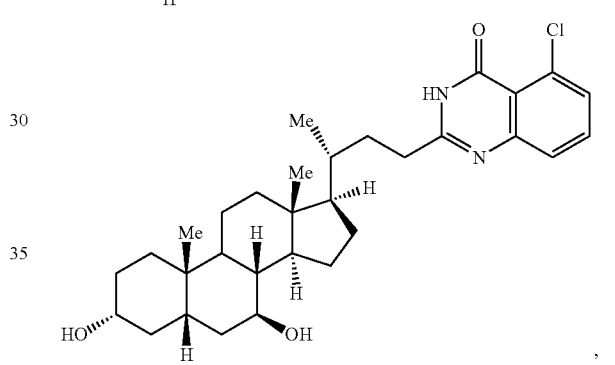
,
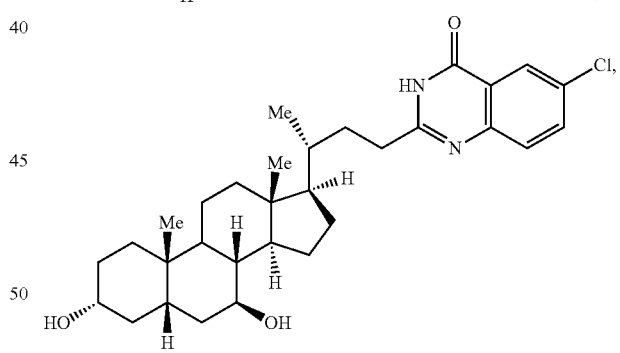
,
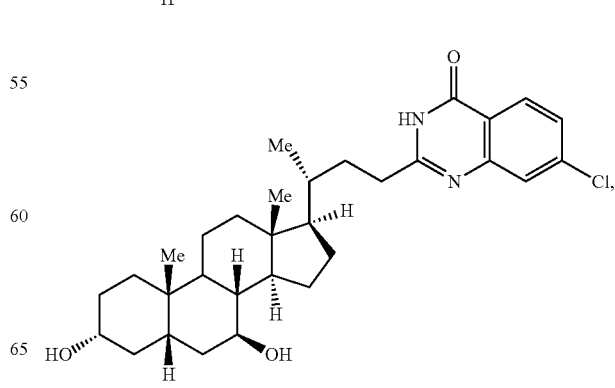

103
-continued
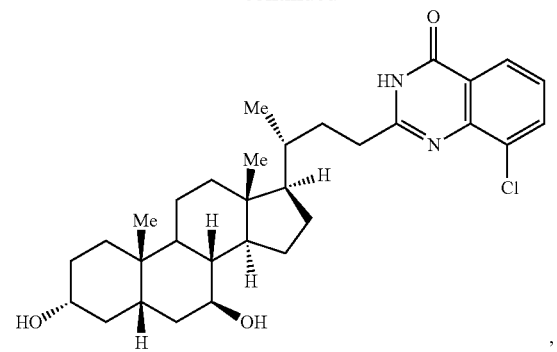
,
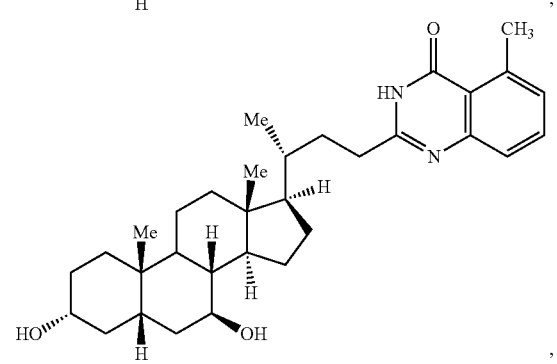
,
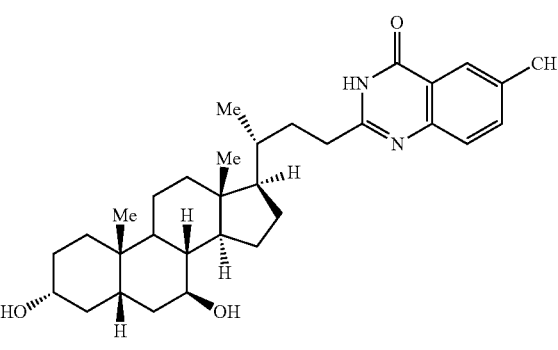
,
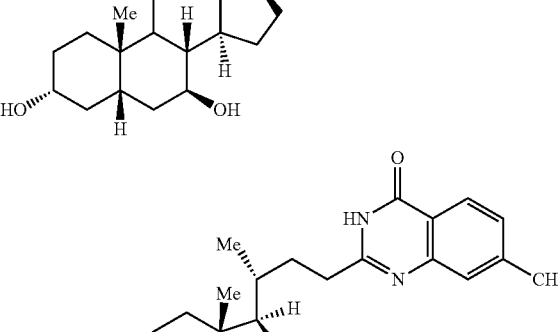
,
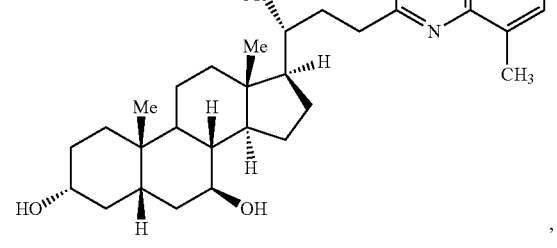
,
104
-continued
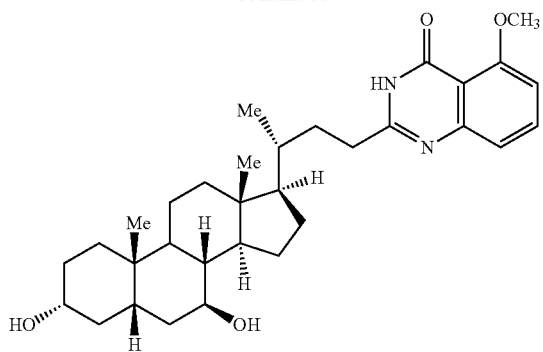
,
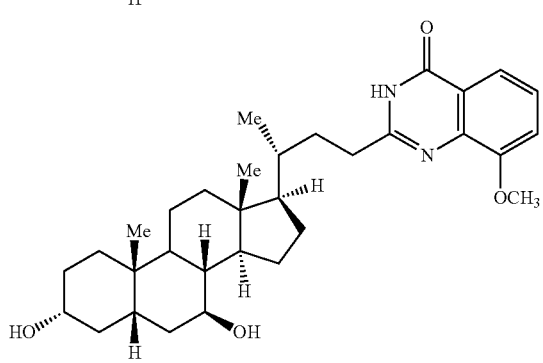
,
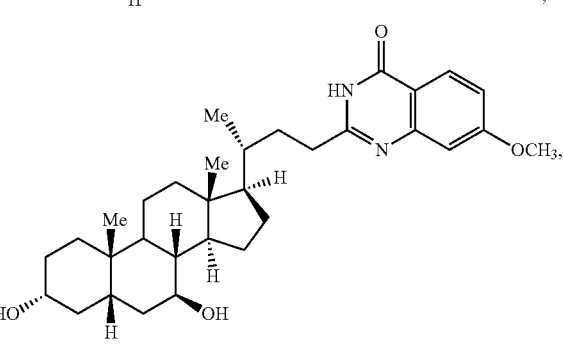
,
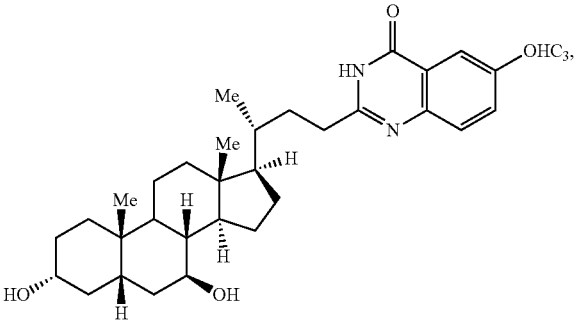
,
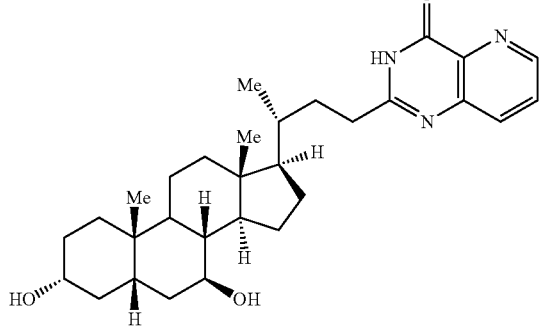
,

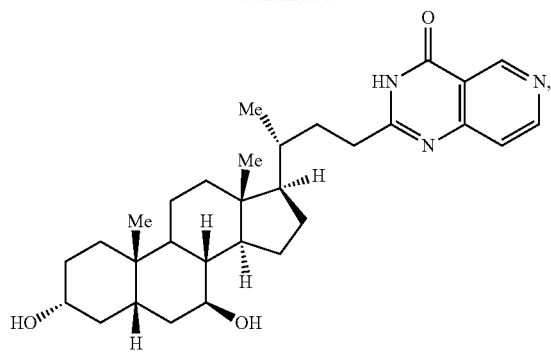
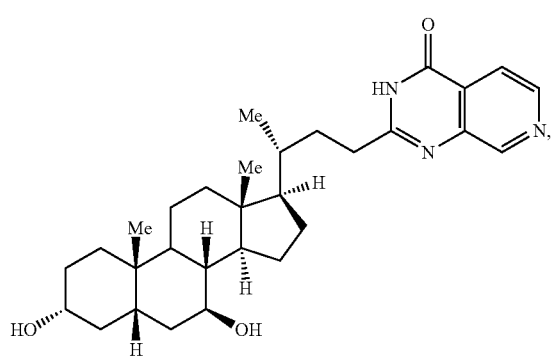
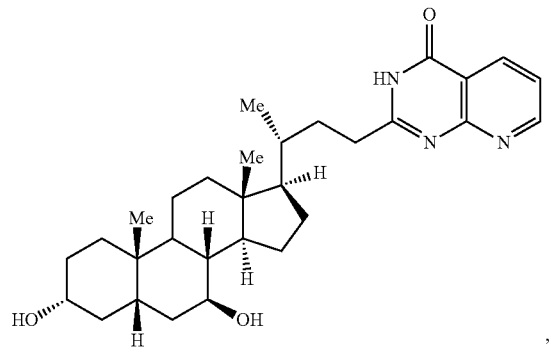
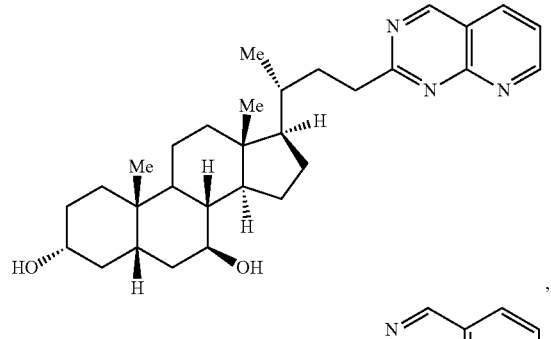
,
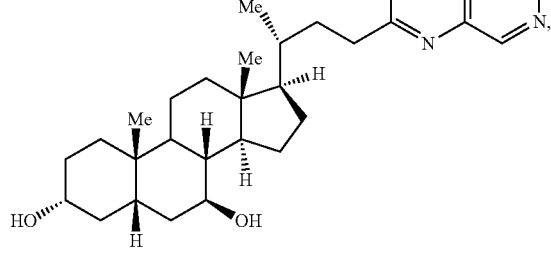
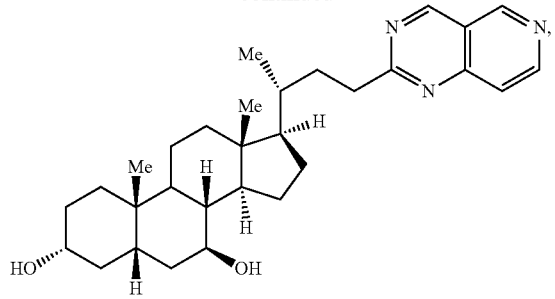
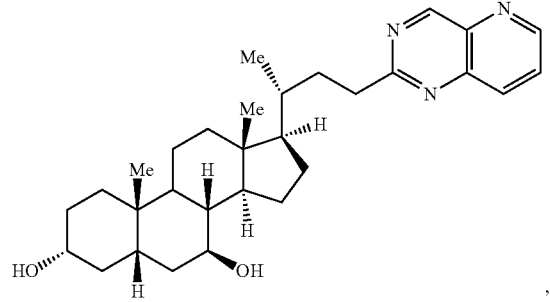
,
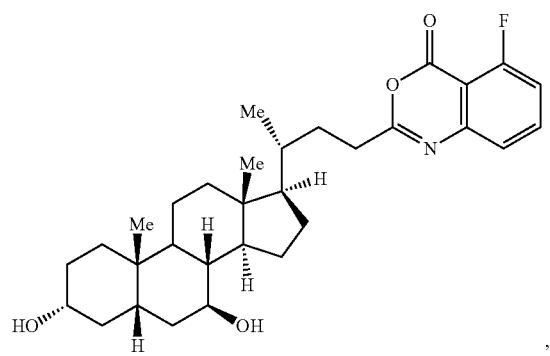
,
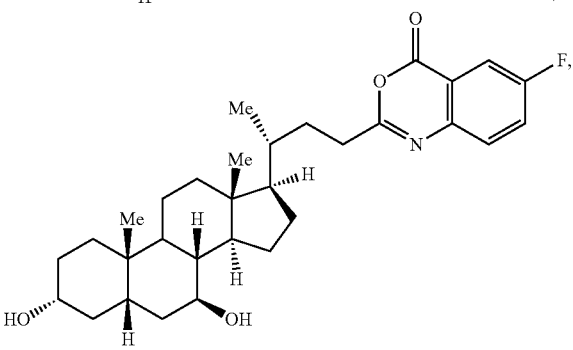
,
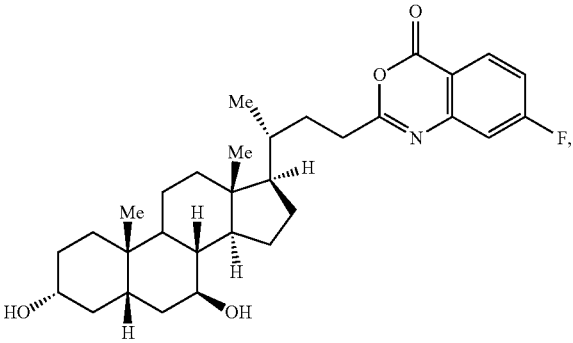

107
-continued
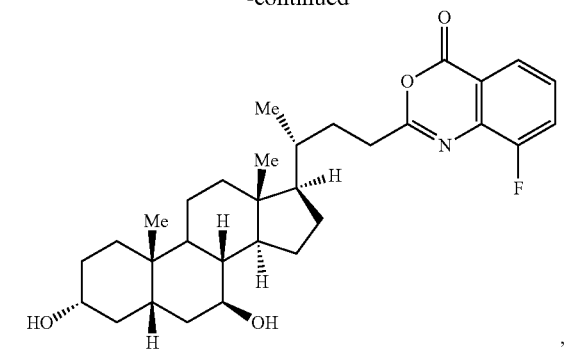
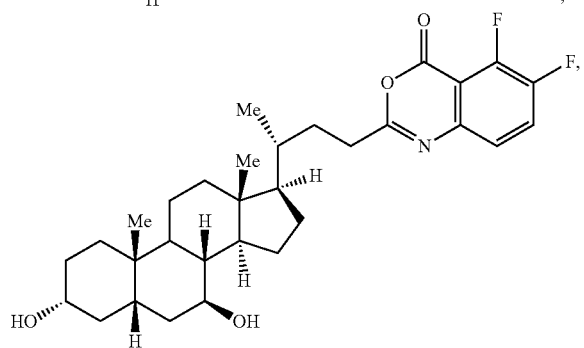
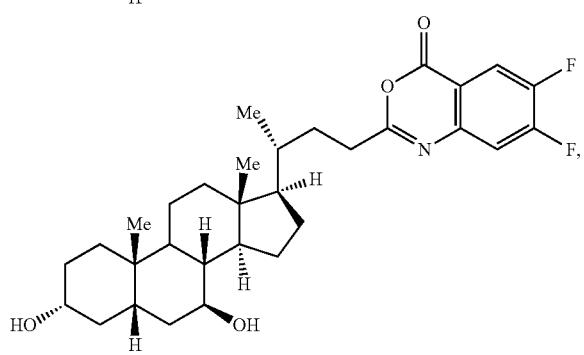
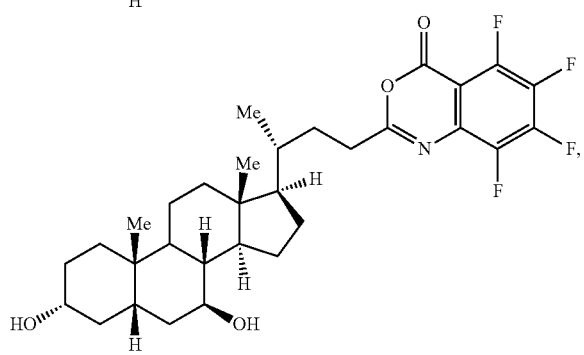
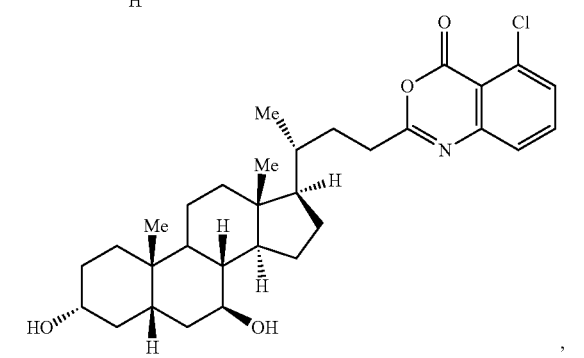
108
-continued
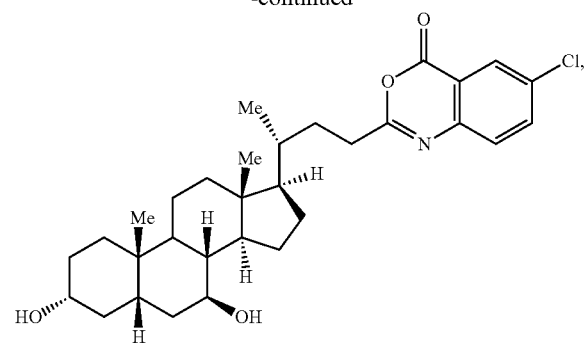
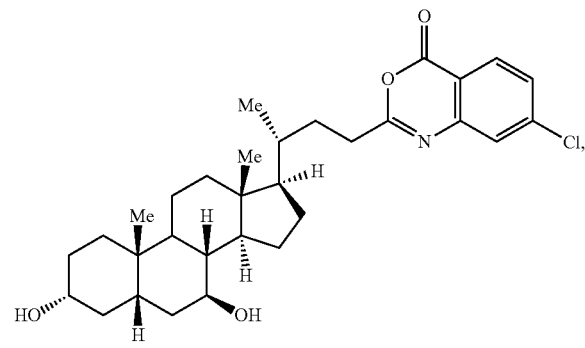
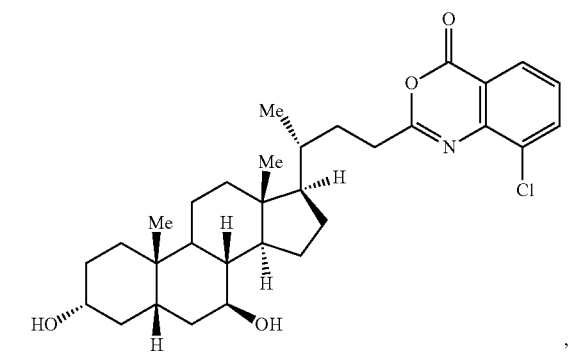
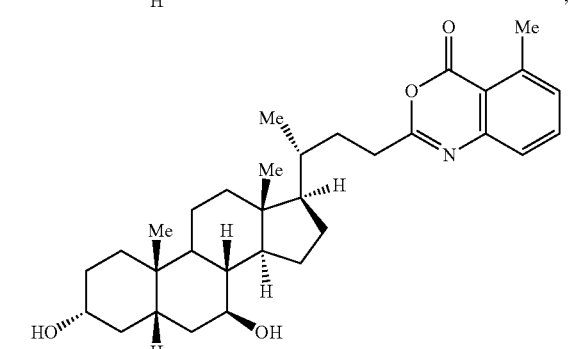
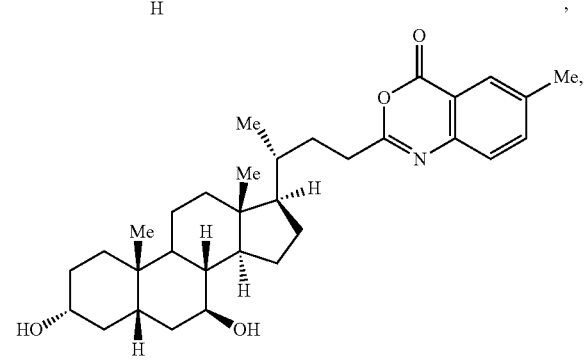

-continued
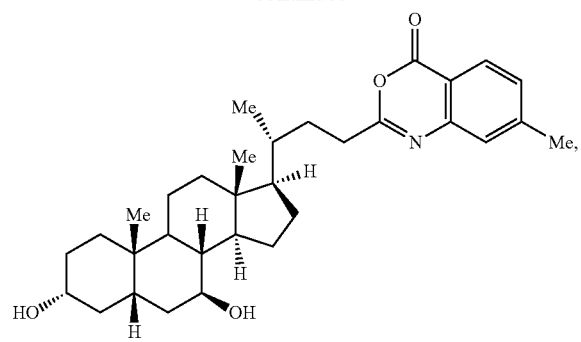
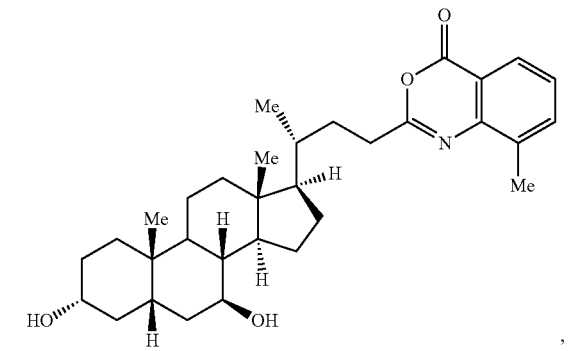
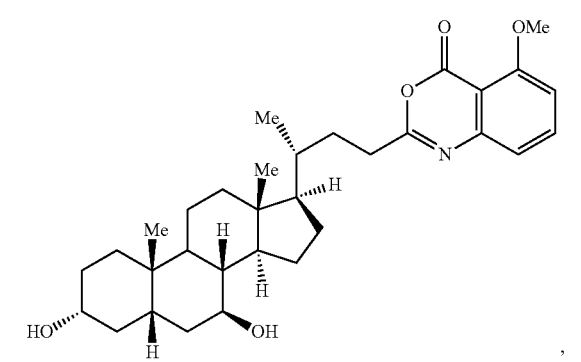
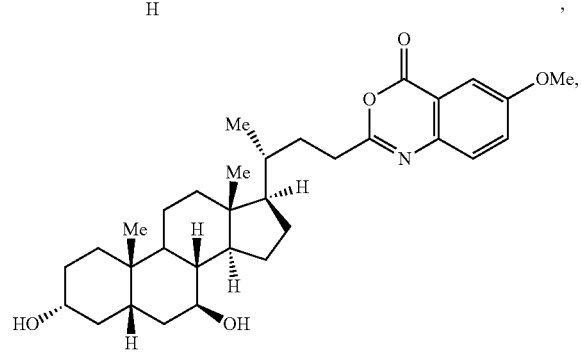
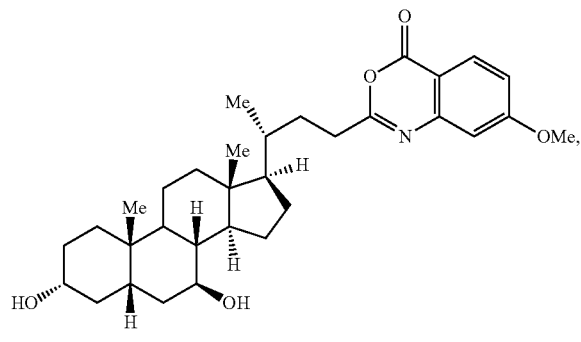
-continued
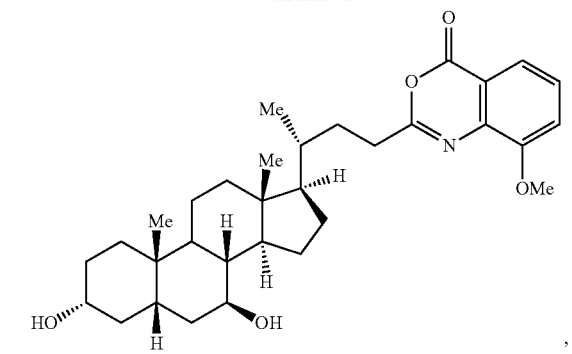
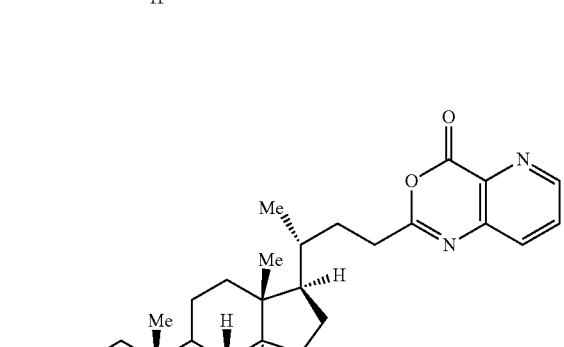
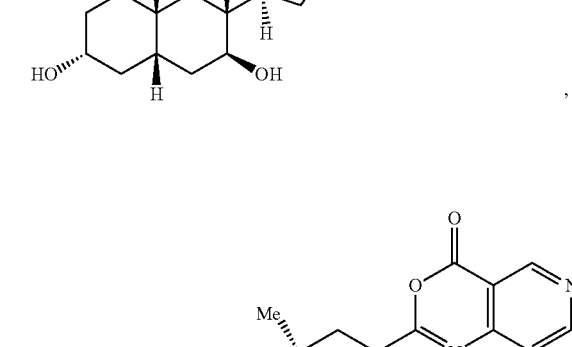
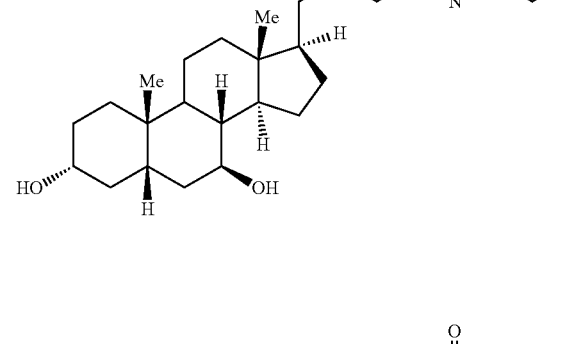
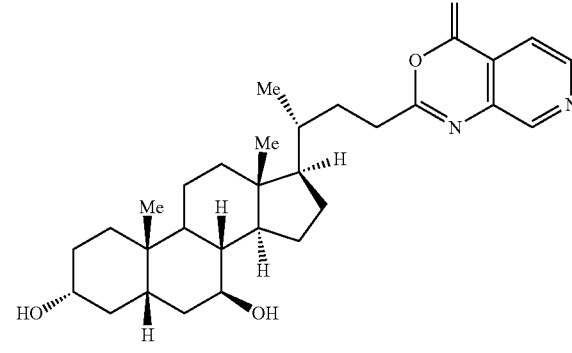

-continued
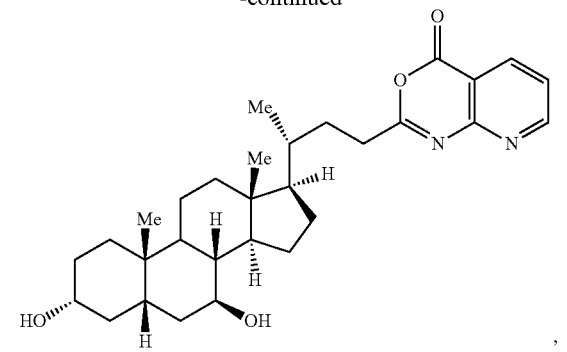
,
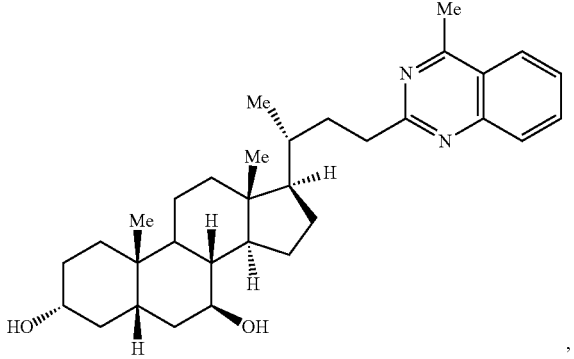
,
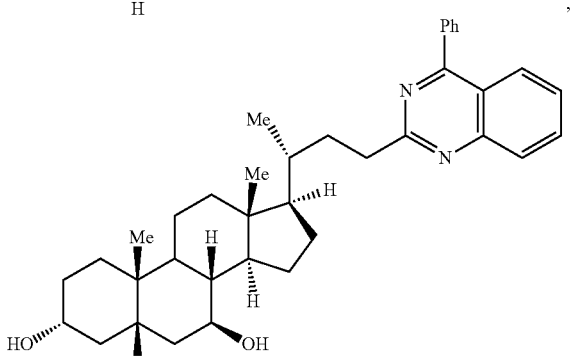
,
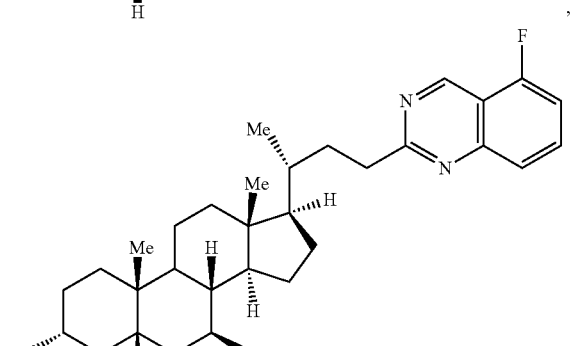
,
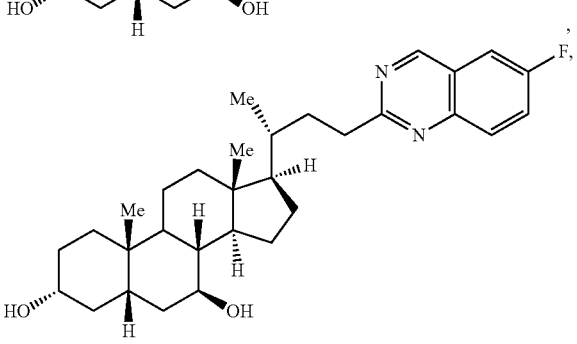
,
-continued
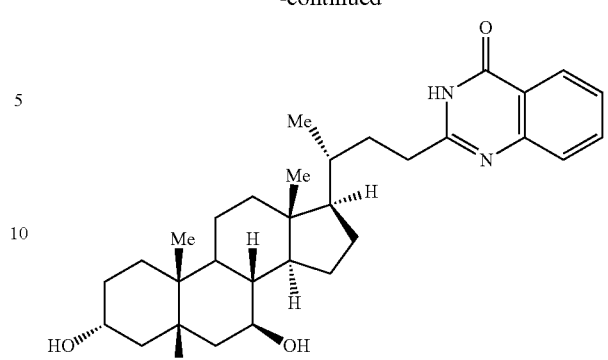
,
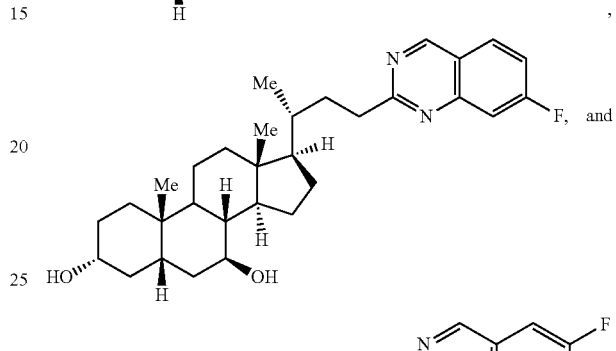
, and
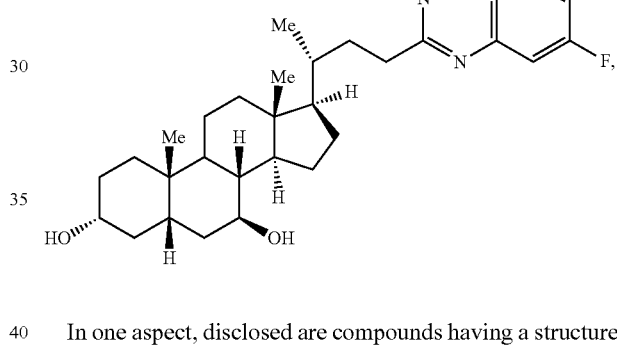
In one aspect, disclosed are compounds having a structure represented by a formula:
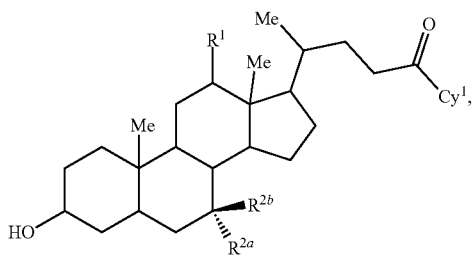
wherein each of $R^1$, $R^{2a}$, and $R^{2b}$ is independently selected from hydrogen and —OH; and wherein $Cy^1$ is a bicycle having a formula selected from:
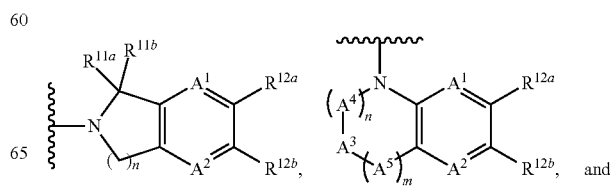
and

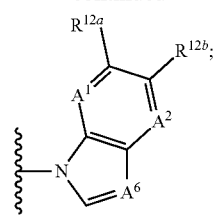

wherein each of n and m, when present, is independently 0, 1, or 2; wherein each of $A^1$ and $A^2$ is independently selected from —N= and —CR$^{21}$=; wherein each occurrence of $R^{21}$ is independently selected from hydrogen, halogen, —NO$_2$, —CN, C1-C4 alkyl, C1-C4 alkoxy, C1-C4 haloalkyl, and —C(O)(C1-C4 alkyl); wherein $A^3$, when present, is selected from —O—, —S—, —NR$^{22}$—, and —C(R$^{23a}$)(R$^{23b}$)—; wherein $R^{22}$ is selected from hydrogen and C1-C4 alkyl; wherein each of $R^{23a}$ and $R^{23b}$ is independently selected from hydrogen and C1-C4 alkyl; wherein each of $A^4$ and $A^5$, when present, is independently —C(R$^{23c}$)(R$^{23d}$)—; wherein each of $R^{23c}$ and $R^{23d}$ is independently selected from hydrogen and C1-C4 alkyl; wherein $A^6$, when present, is selected from =C(R$^{24}$)— and =N—; wherein $R^{24}$, when present, is selected from hydrogen and C1-C4 alkyl; wherein each of $R^{1a}$ and $R^{11b}$, when present, is independently selected from hydrogen and C1-C4 alkyl; and wherein each of $R^{12a}$ and $R^{12b}$ is independently selected from hydrogen, halogen, —NO$_2$, —CN, C1-C4 alkyl, C1-C4 alkoxy, C1-C4 haloalkyl, and —C(O)(C1-C4 alkyl), or a pharmaceutically acceptable salt thereof.

In one aspect, disclosed are compounds selected from:

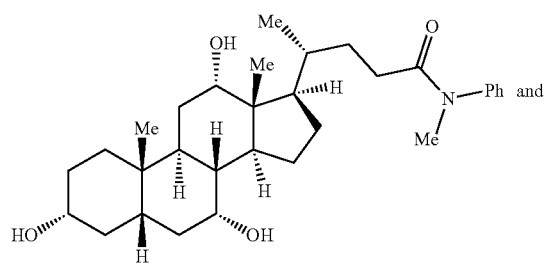

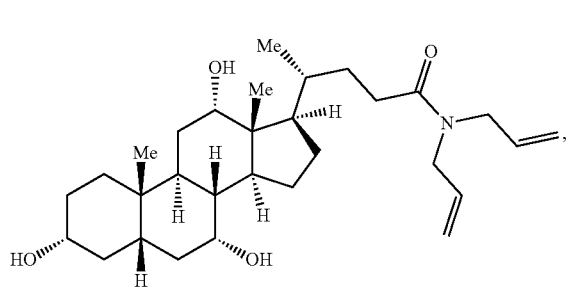

or a pharmaceutically acceptable salt thereof.

In a further aspect, the compound has a structure represented by a formula:

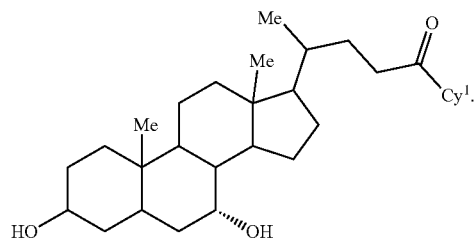

In a further aspect, the compound has a structure represented by a formula:

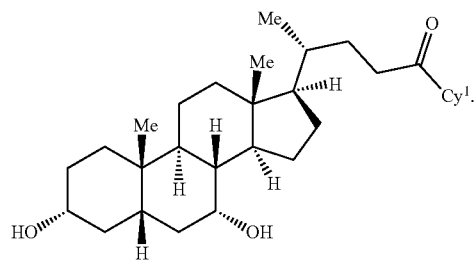

In a further aspect, the compound is selected from:

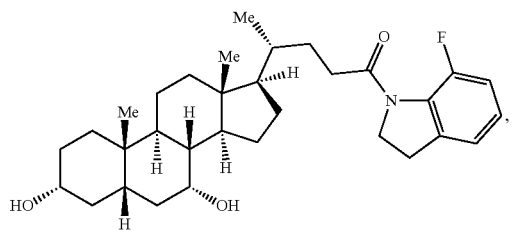

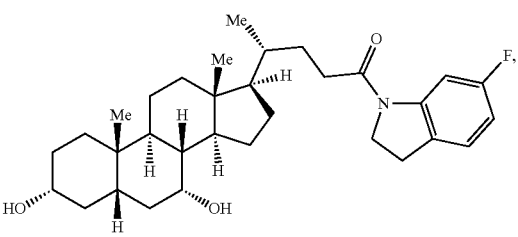

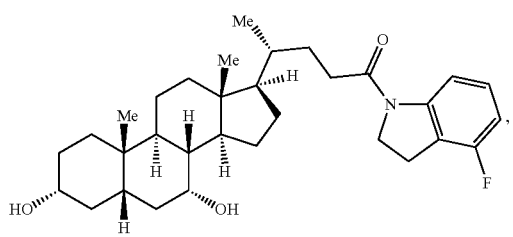

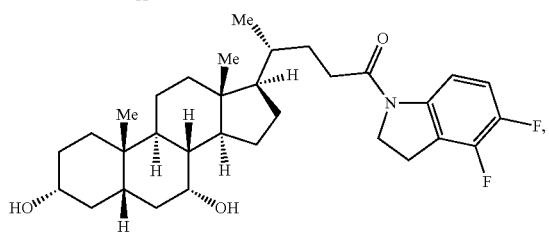

115
-continued
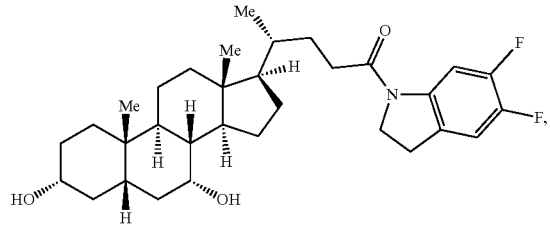
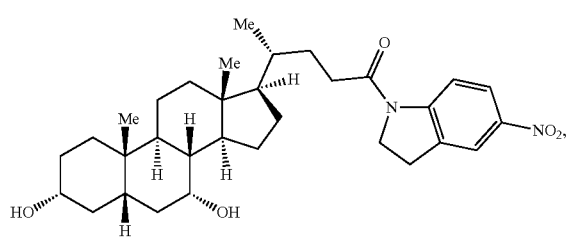
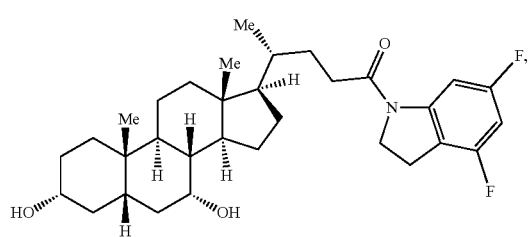
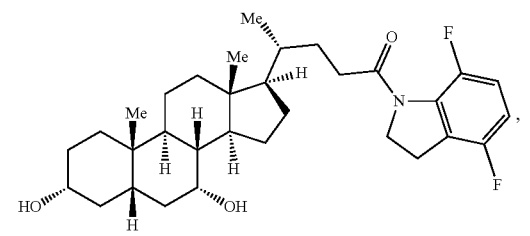
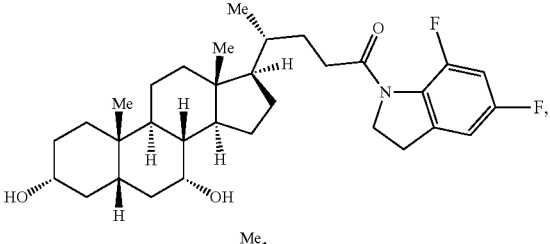
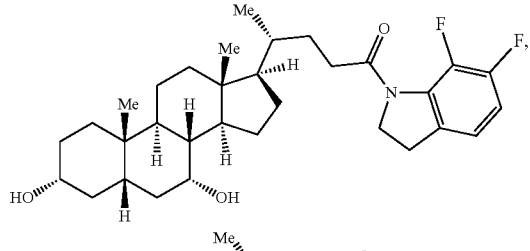
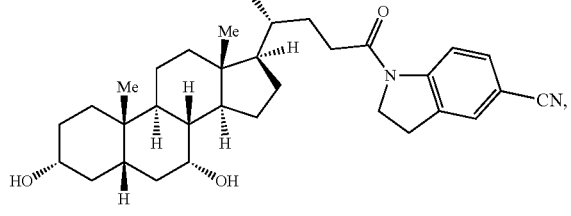
116
-continued
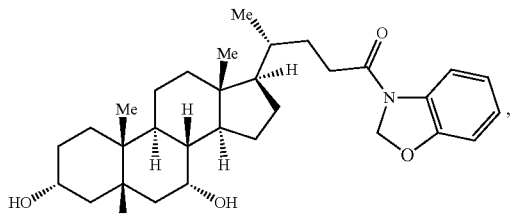
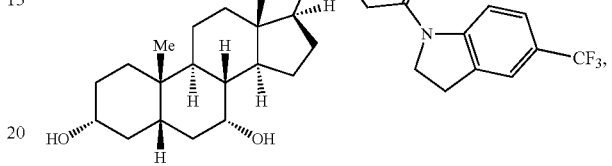
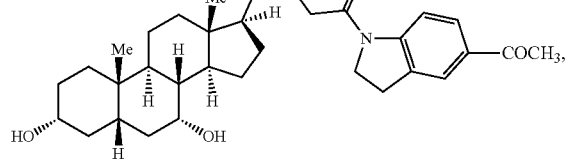
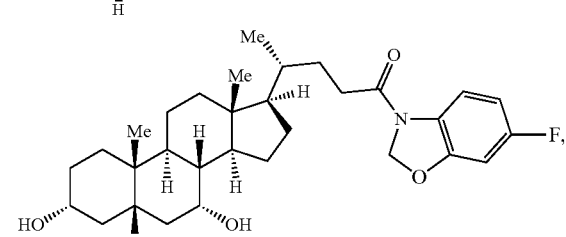
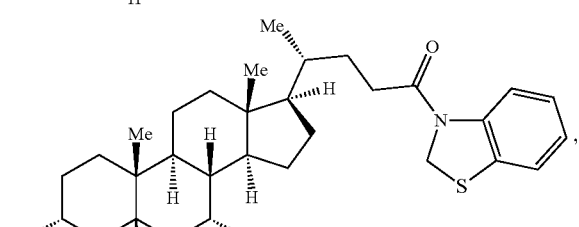
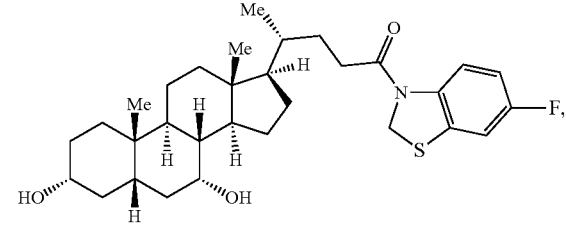
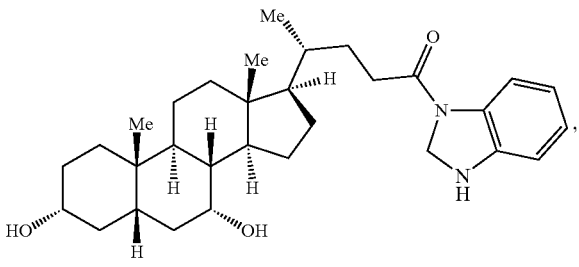

-continued
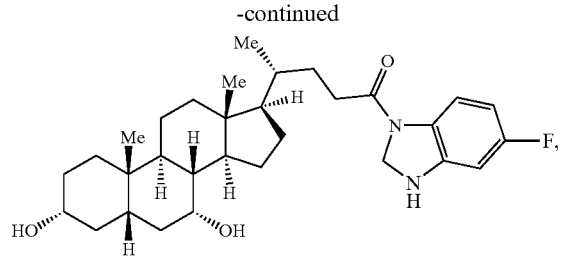
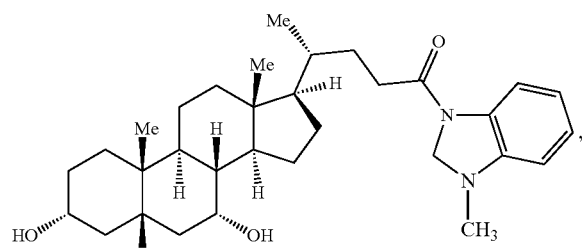
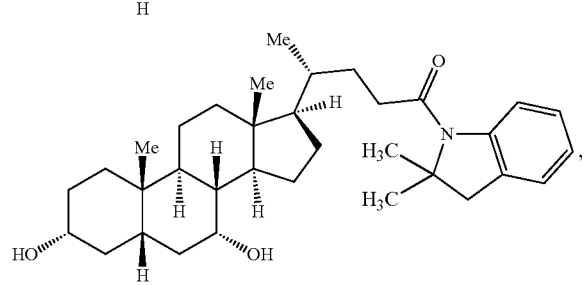
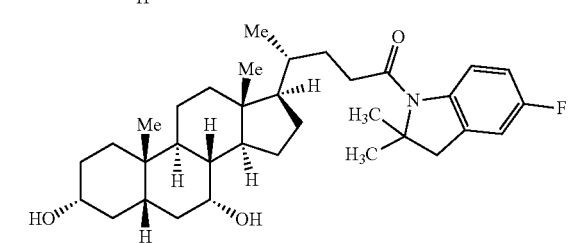
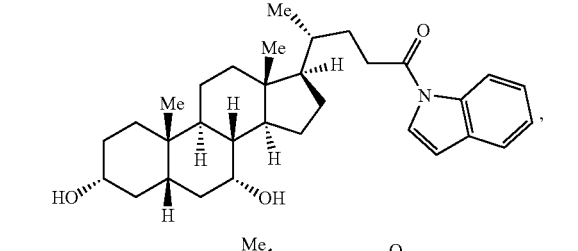
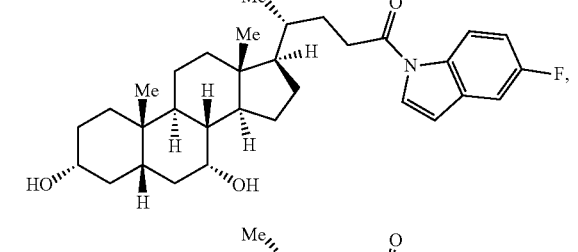
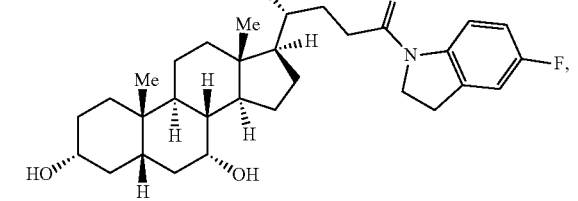
-continued
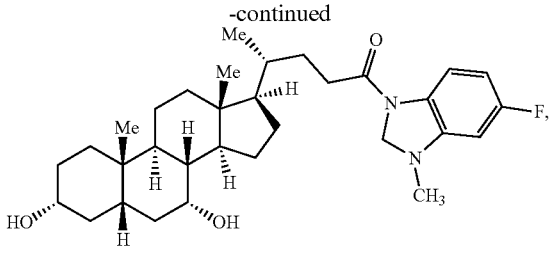
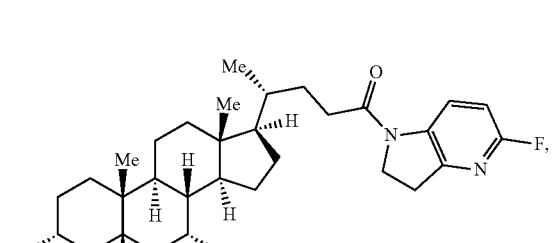
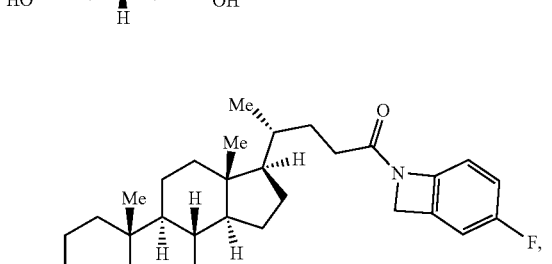
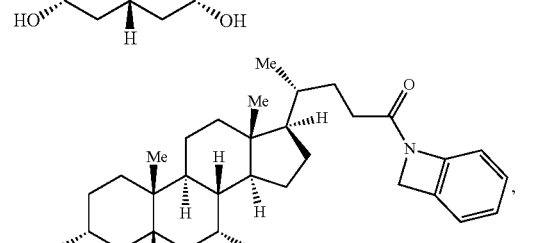
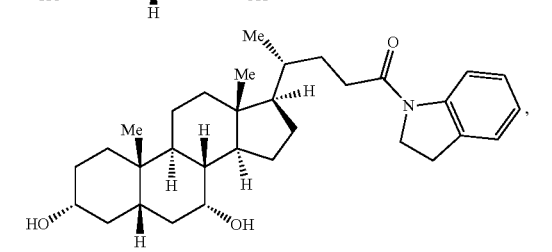
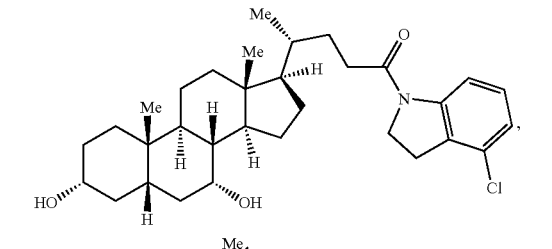
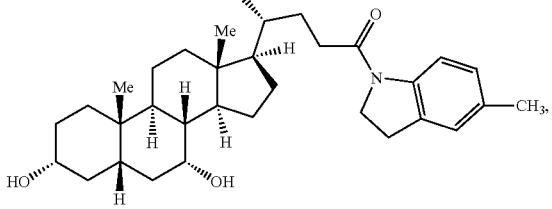

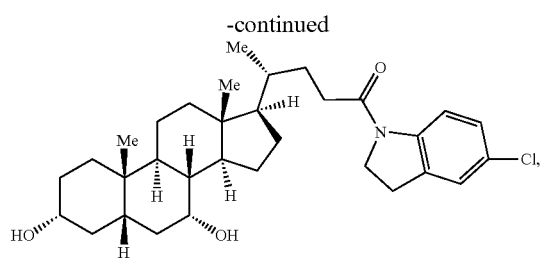
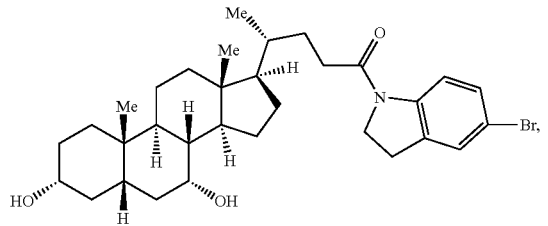
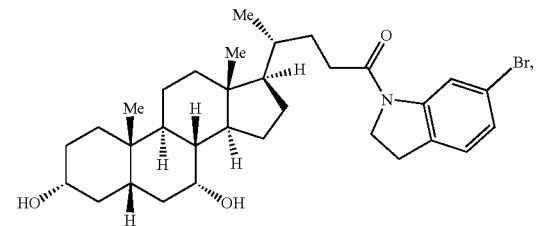
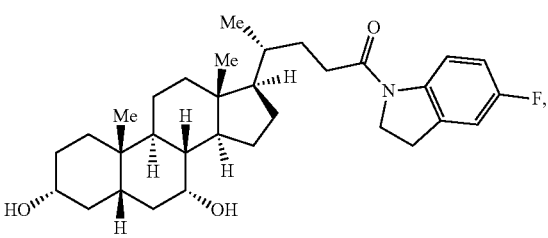
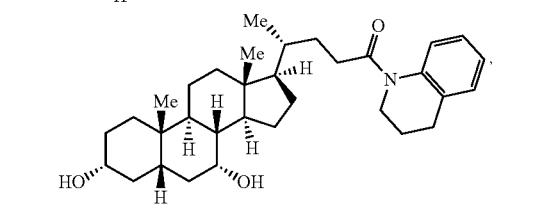
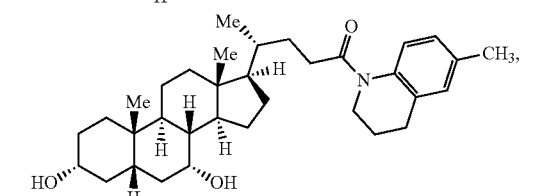
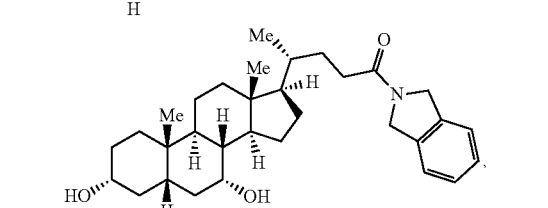
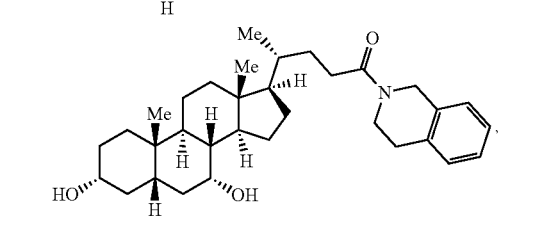
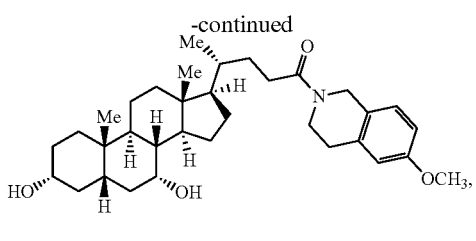
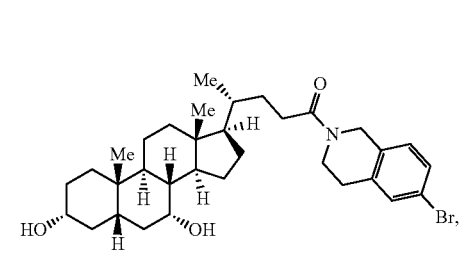
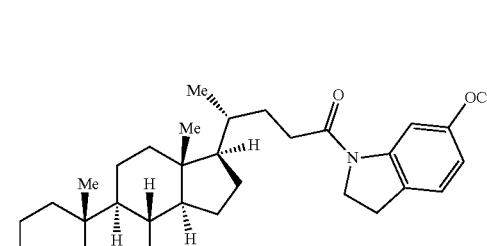
In a further aspect, the compound has a structure represented by a formula:
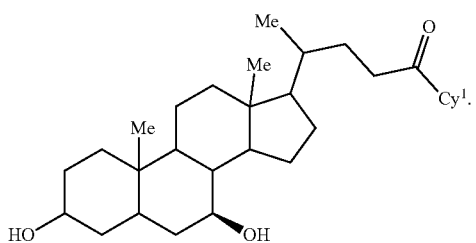
In a further aspect, the compound has a structure represented by a formula:
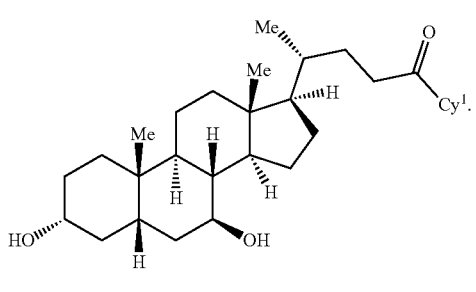

In a further aspect, the compound is selected from:
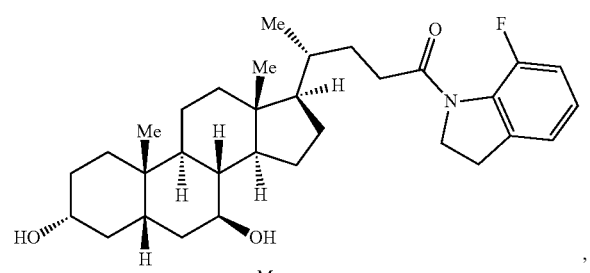
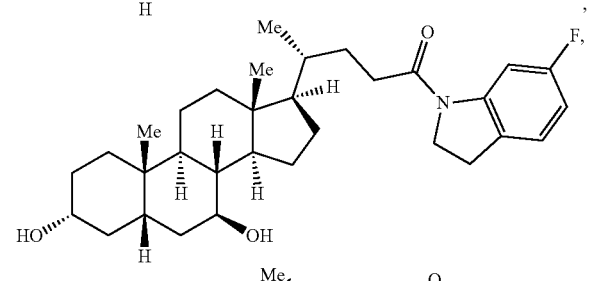
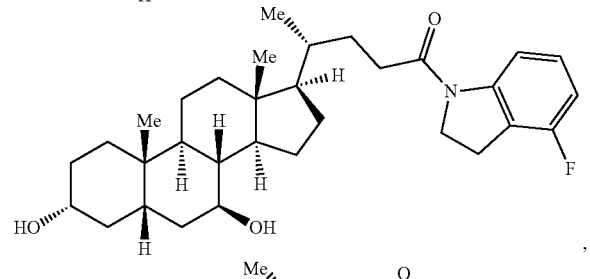
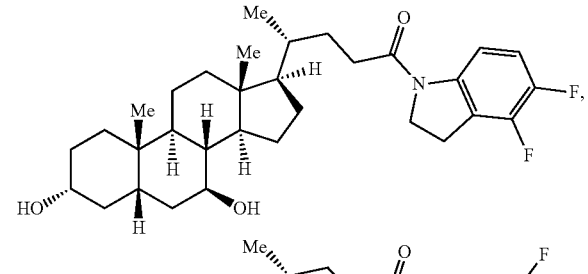
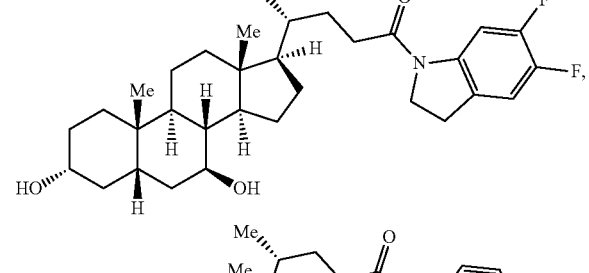
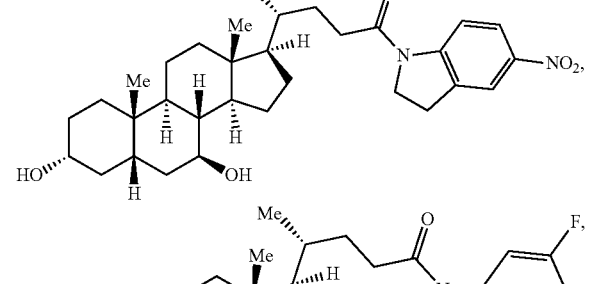
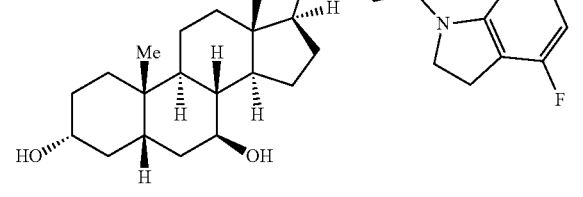
-continued
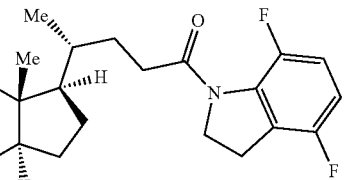
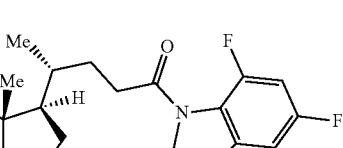
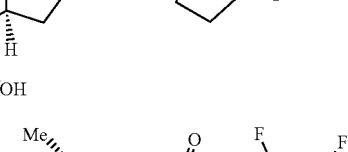
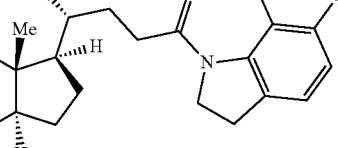
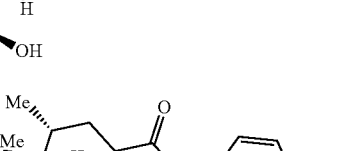
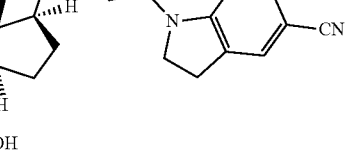
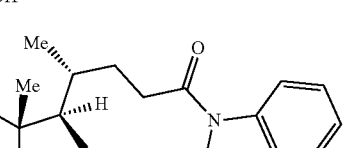
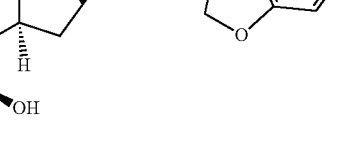
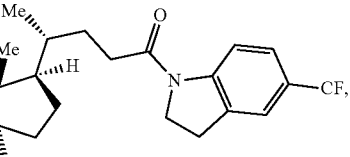
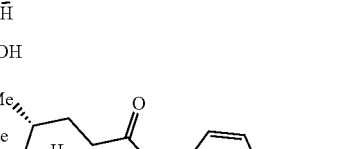
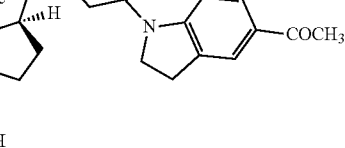

123
-continued
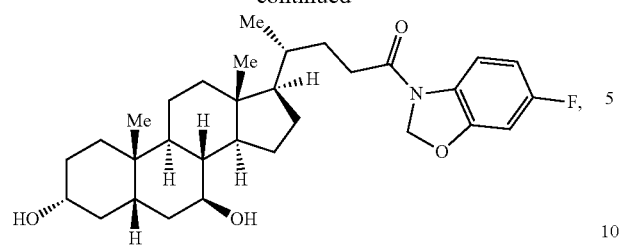
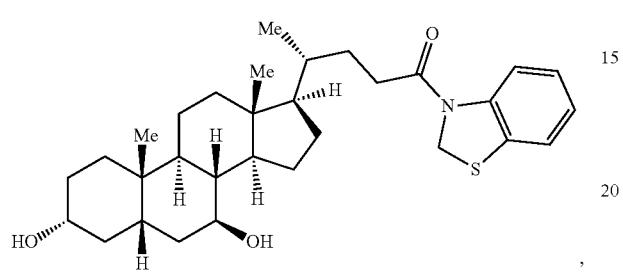
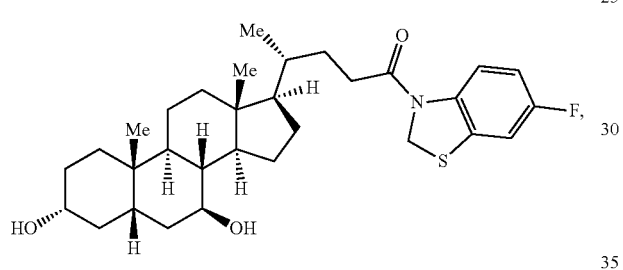
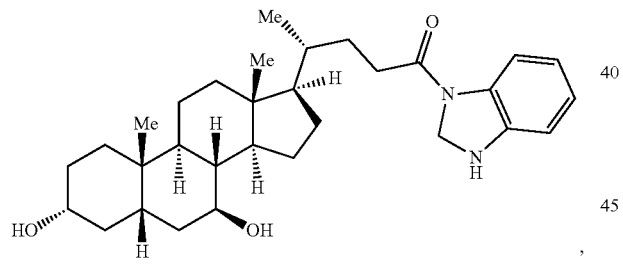
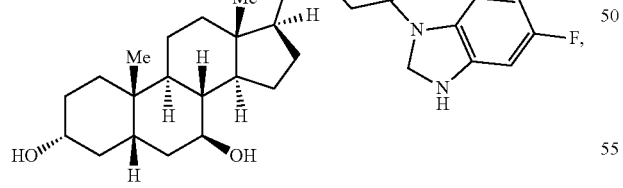
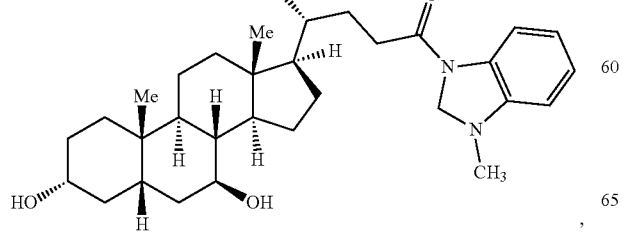
124
-continued
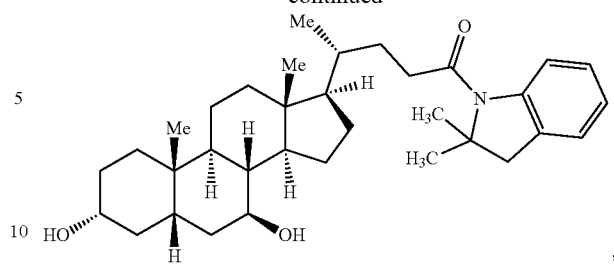
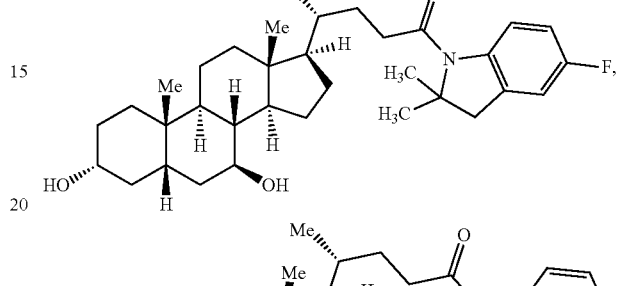
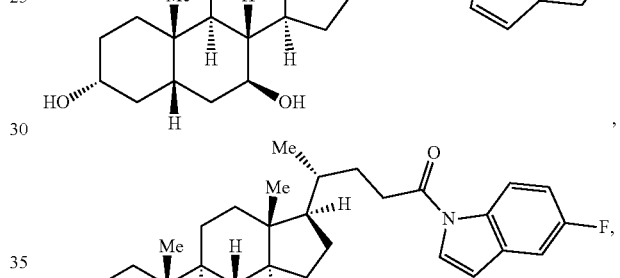
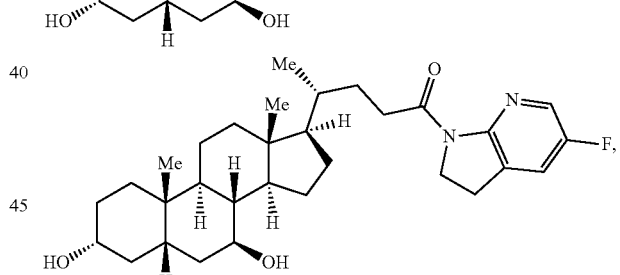
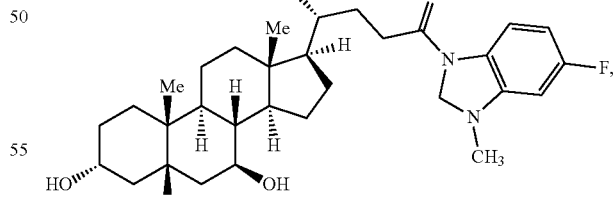
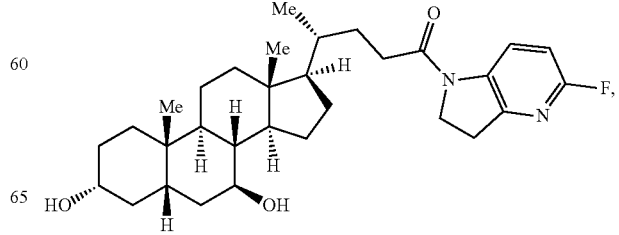

125
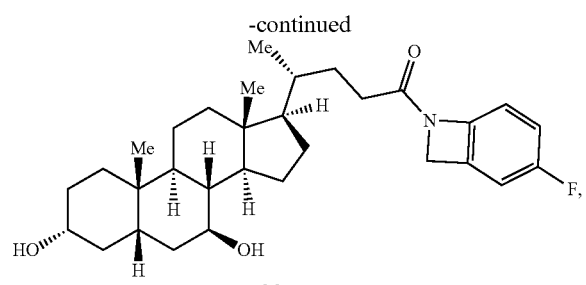
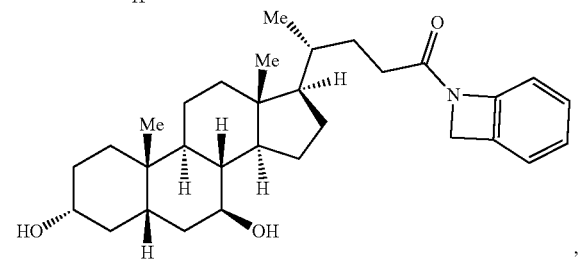
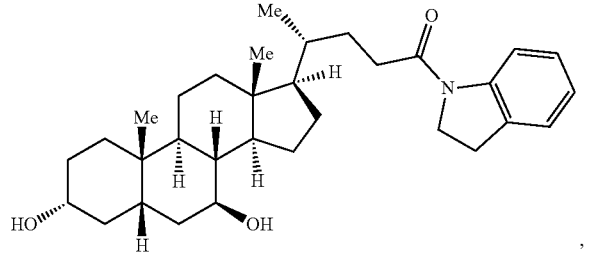
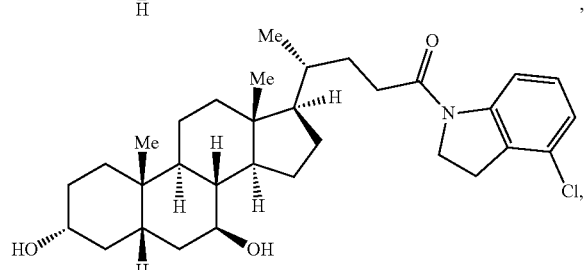
,
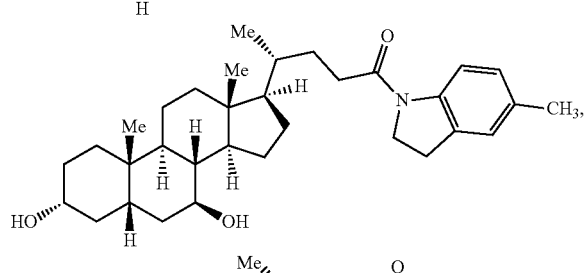
,
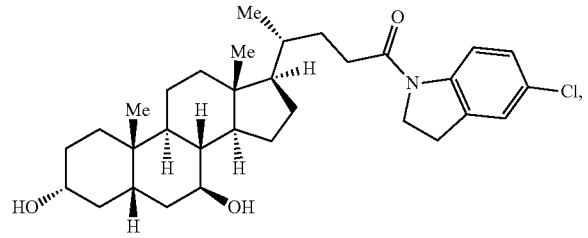
,
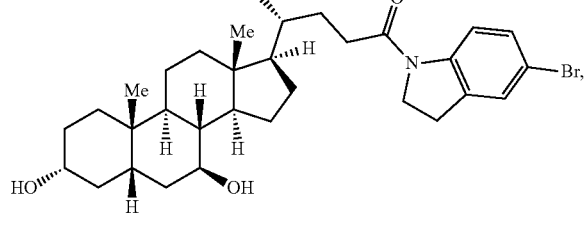
126
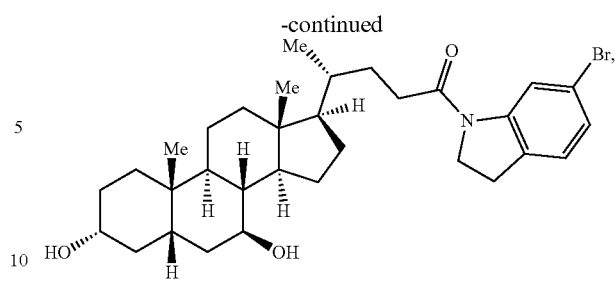
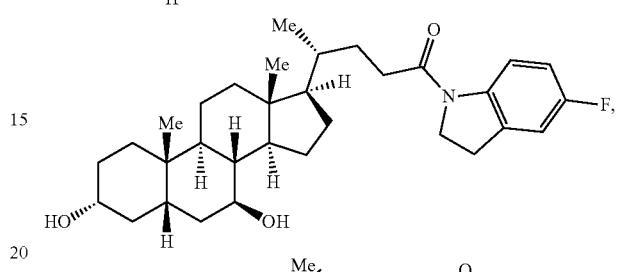
,

,
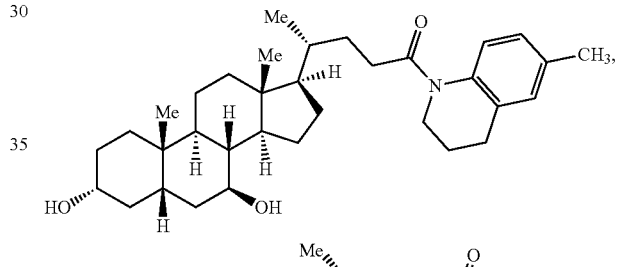
,
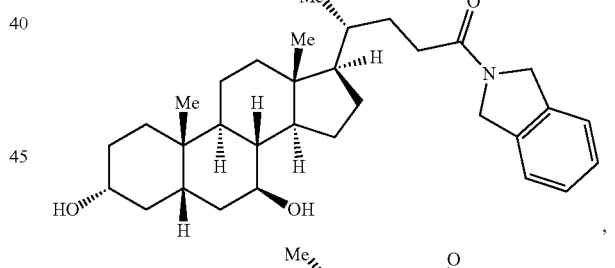
,
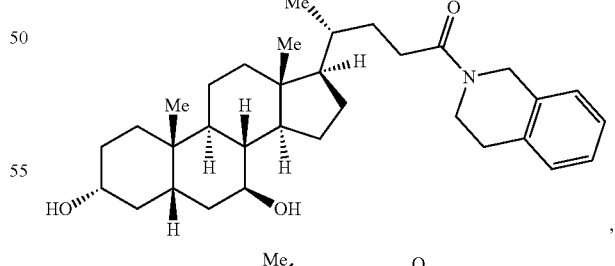
,
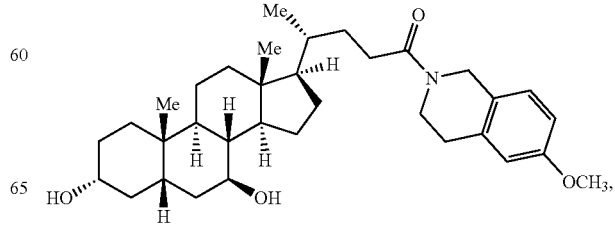

-continued
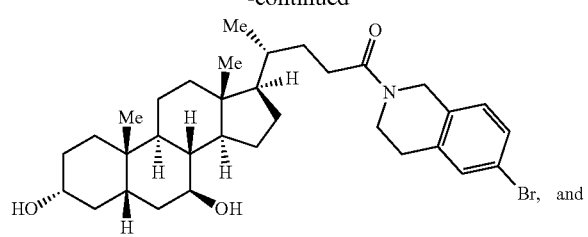
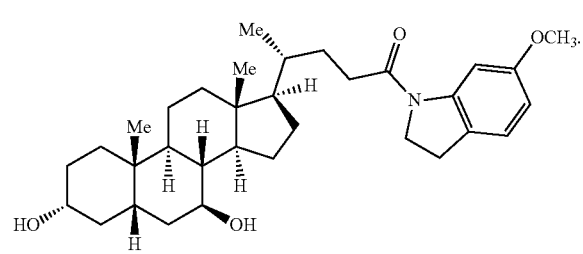
In a further aspect, the compound has a structure represented by a formula:
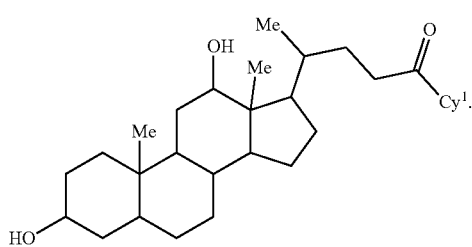
In a further aspect, the compound has a structure represented by a formula:
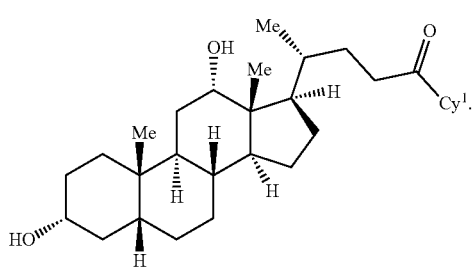
In a further aspect, the compound is selected from:
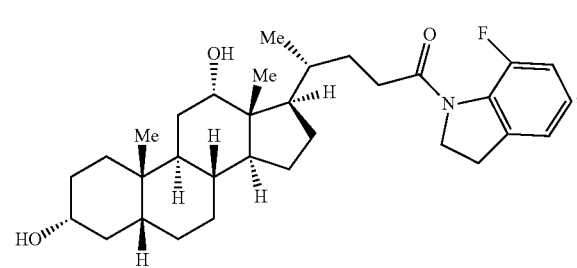
-continued
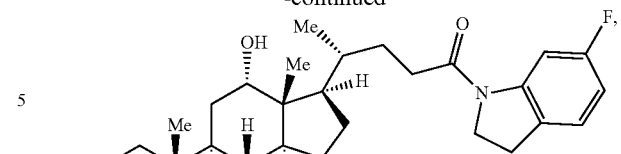
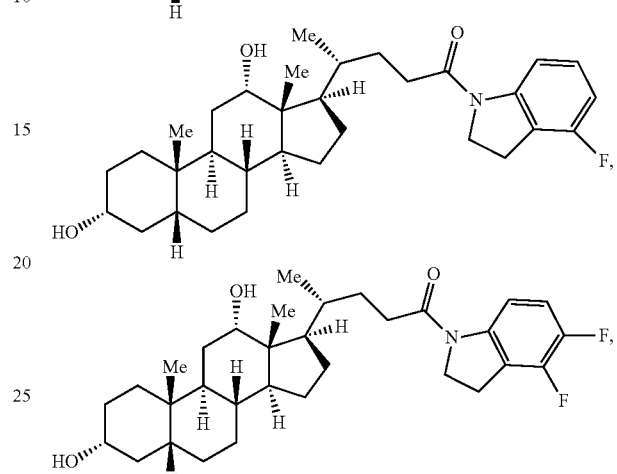
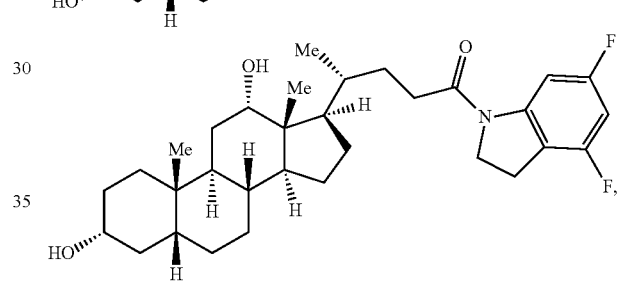
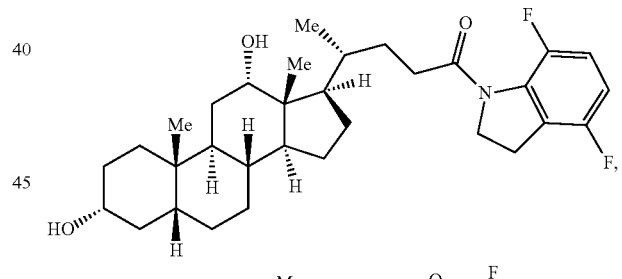
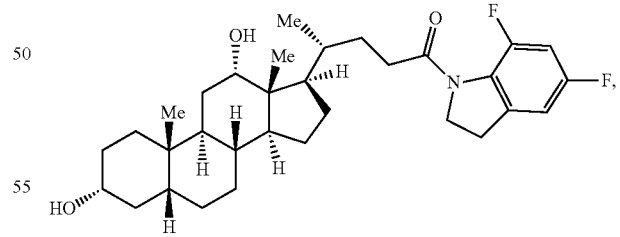

129
-continued
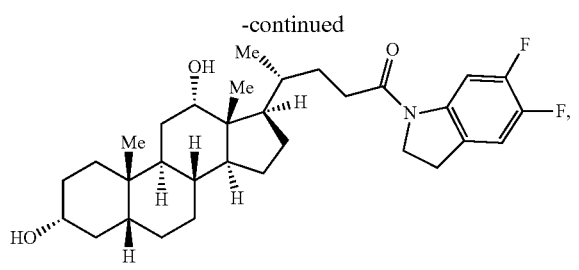
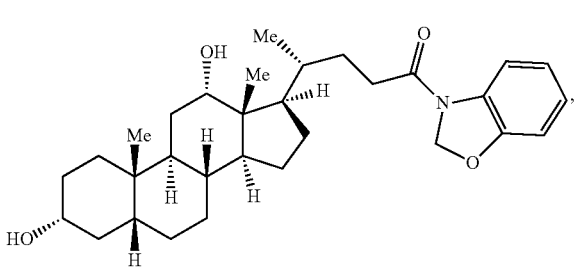
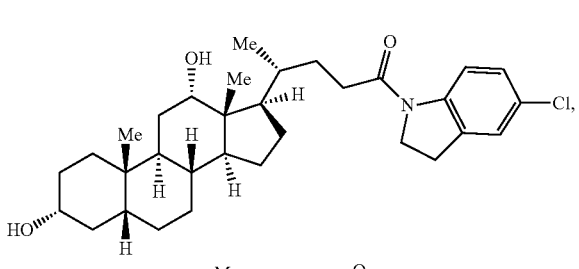
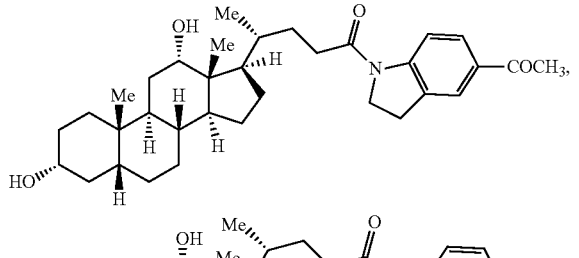
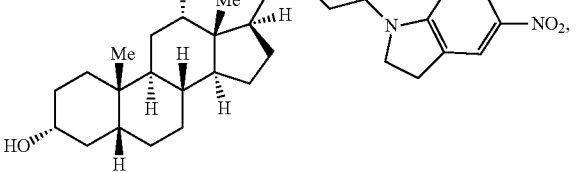
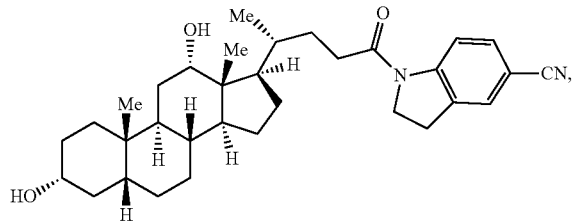
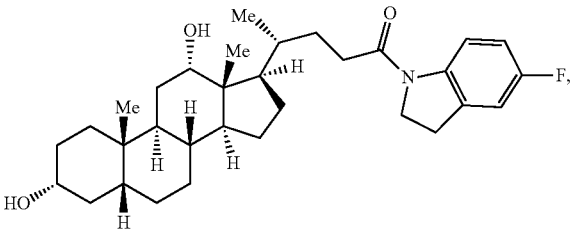
130
-continued
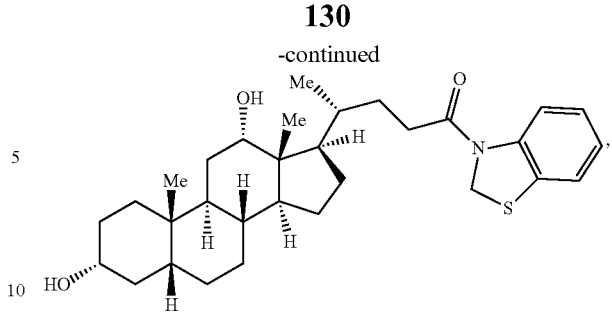
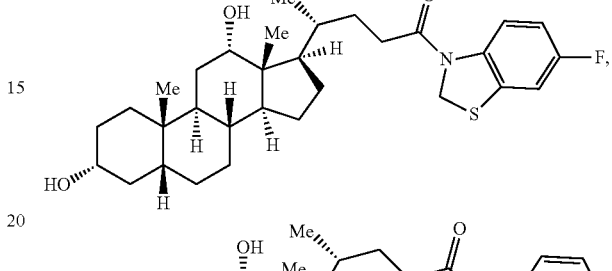
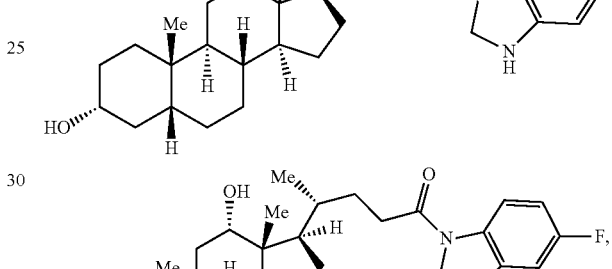
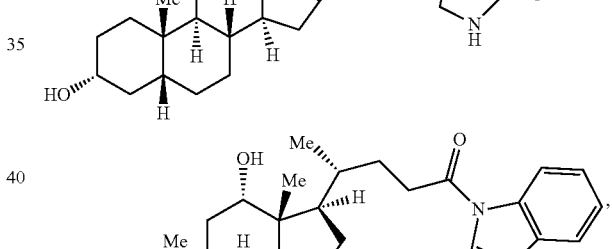
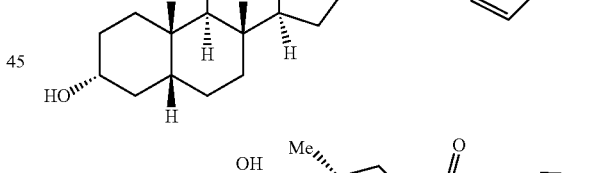
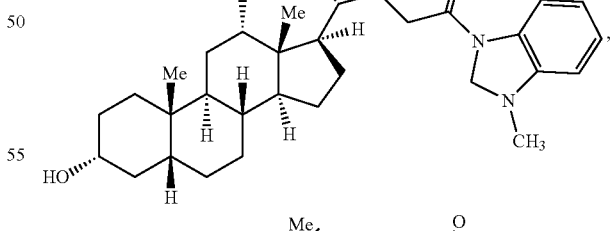
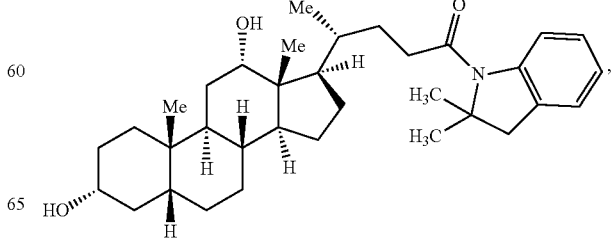

131
-continued
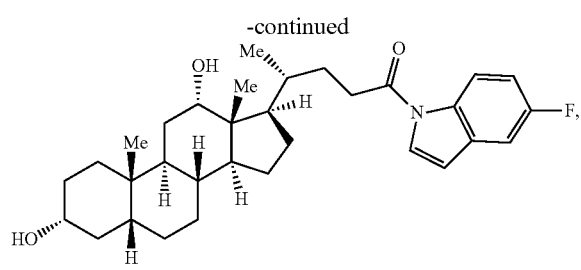
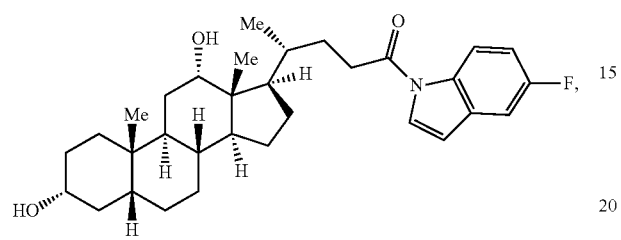
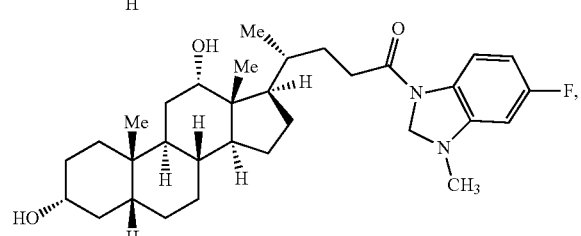
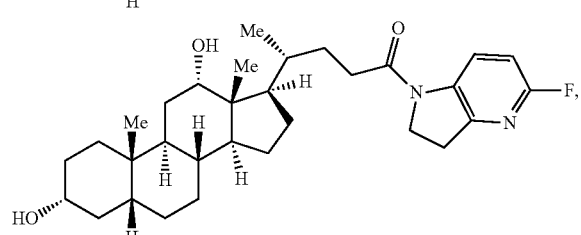
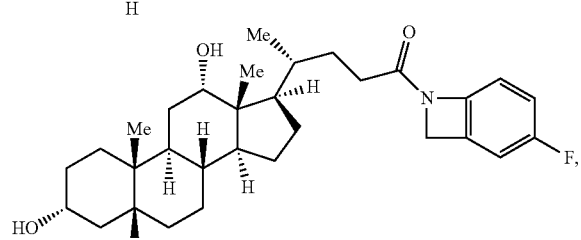
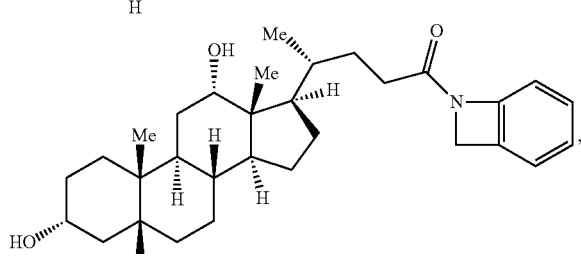
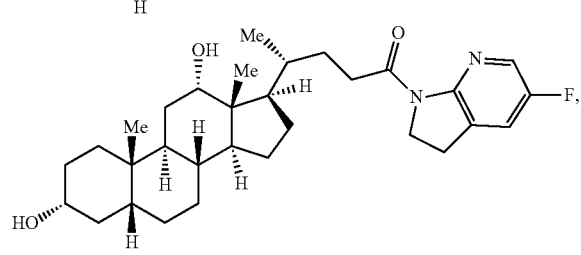
132
-continued
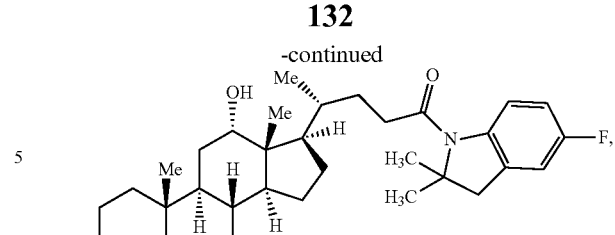
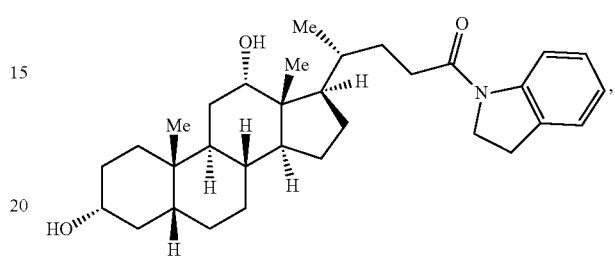
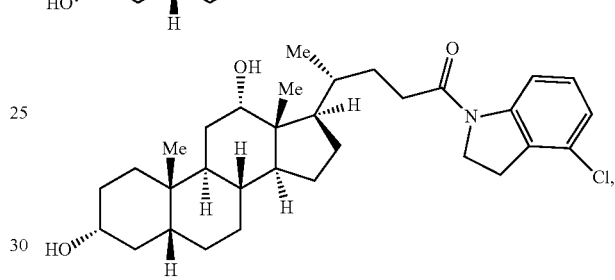
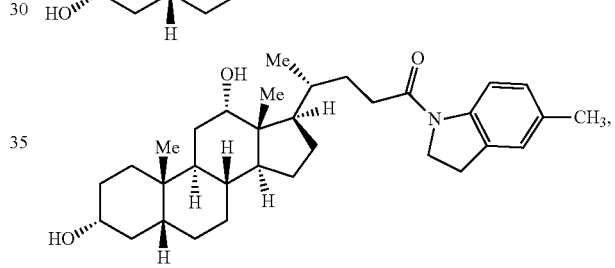
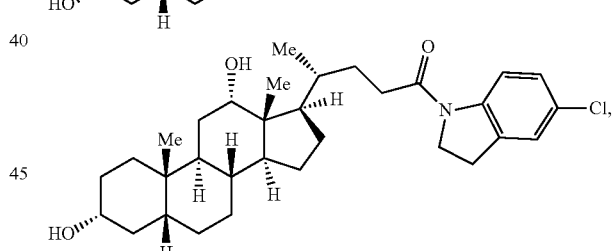
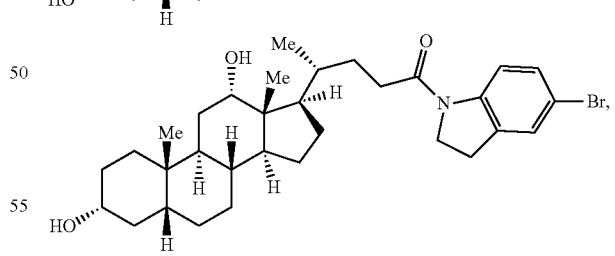
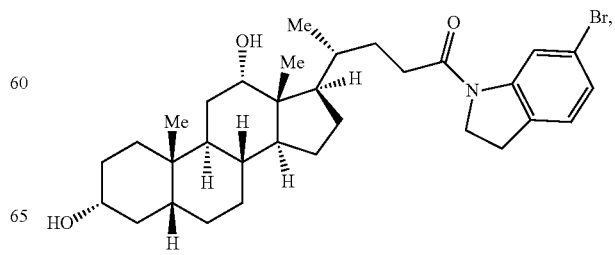

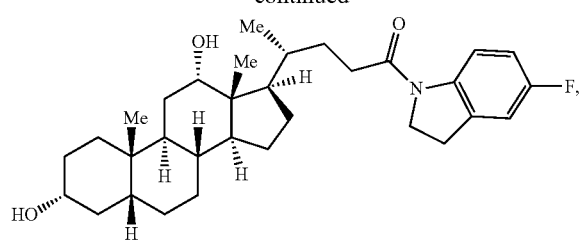
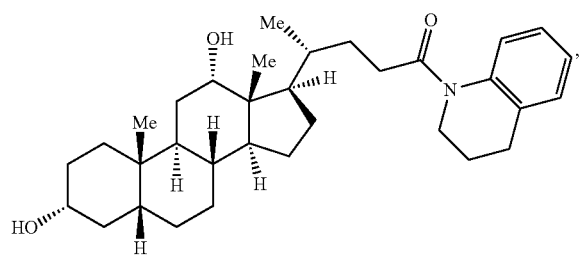
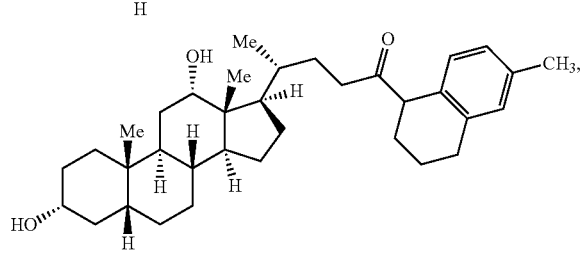
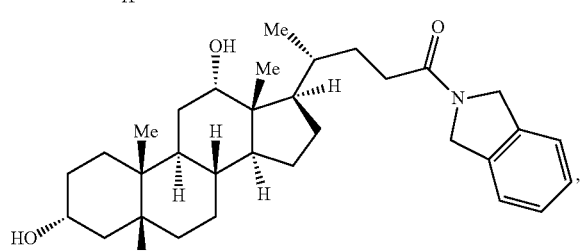
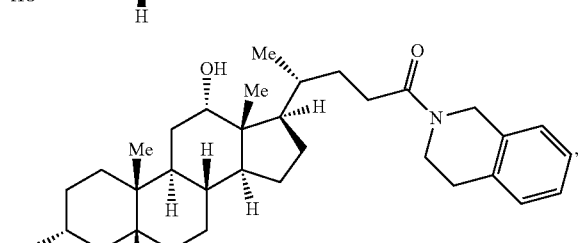
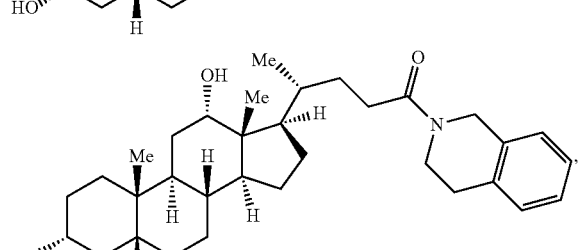

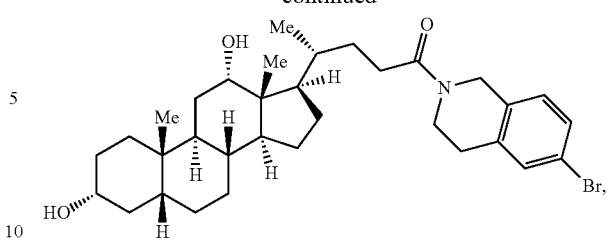
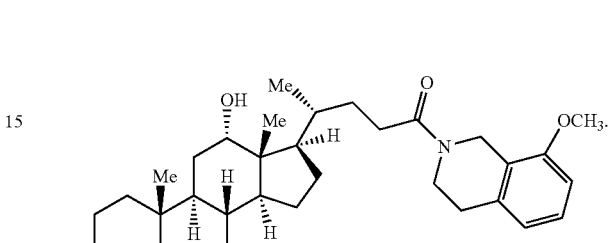
In a further aspect, the compound has a structure represented by a formula:
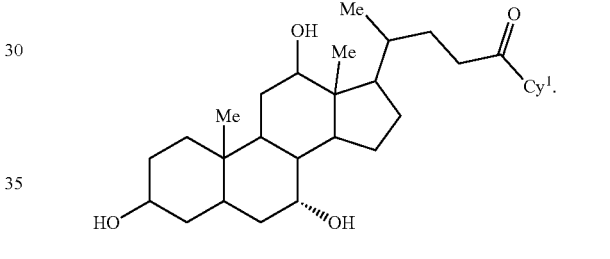
In a further aspect, the compound has a structure represented by a formula:
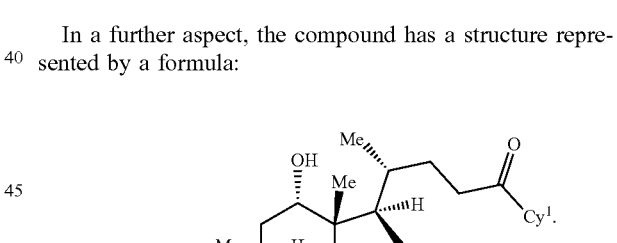
In a further aspect, the compound is selected from:
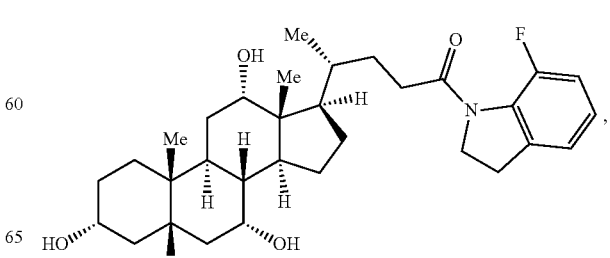

135
-continued
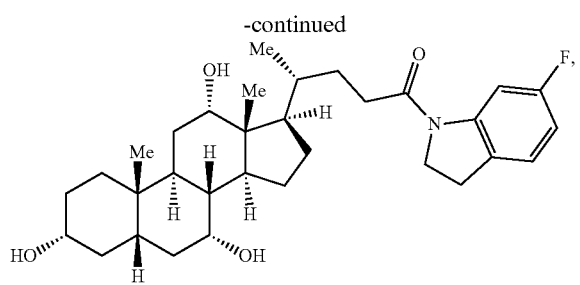
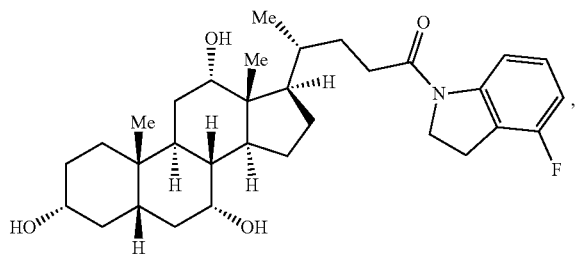
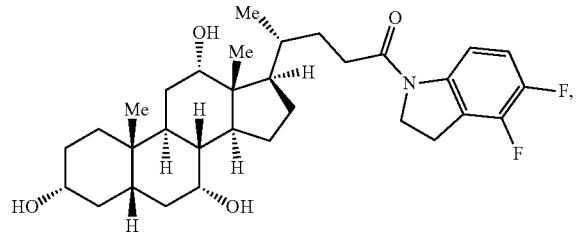
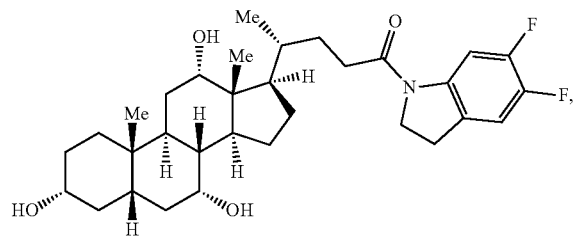
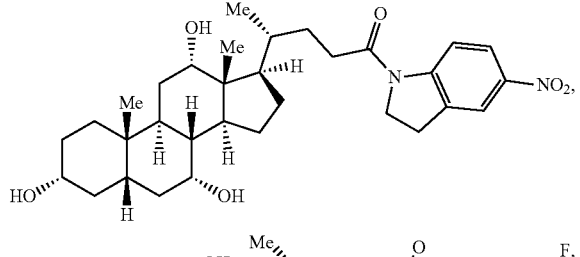
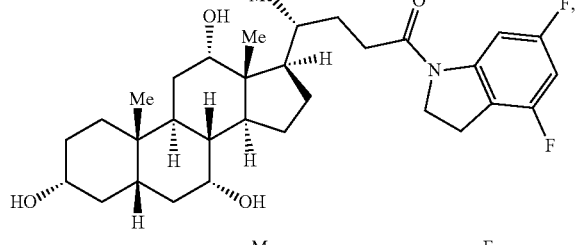
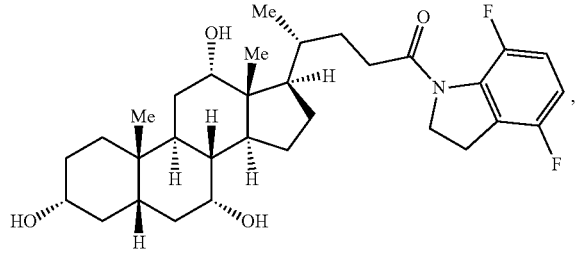
136
-continued
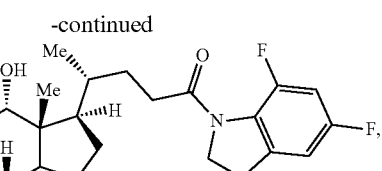
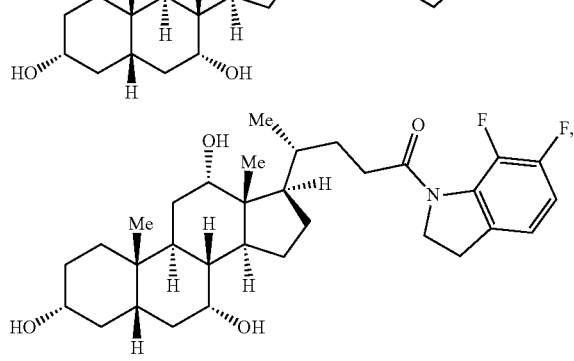
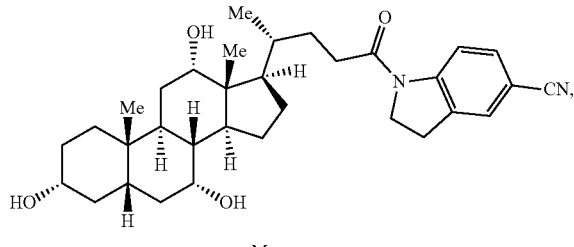
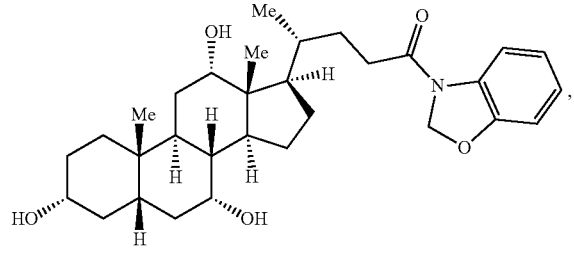
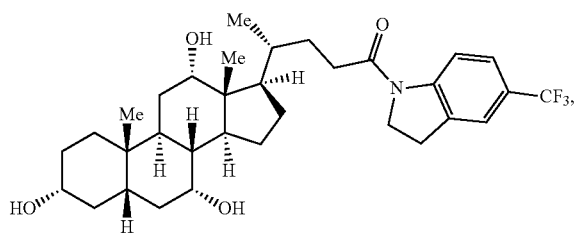
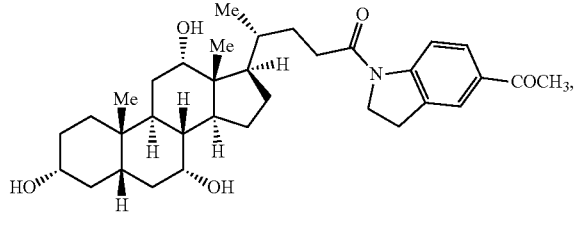
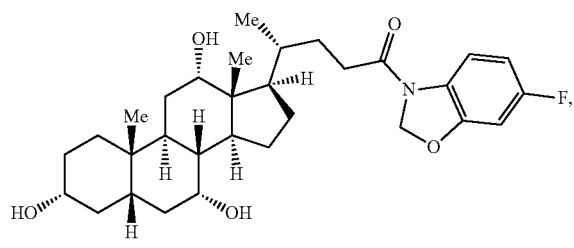

-continued
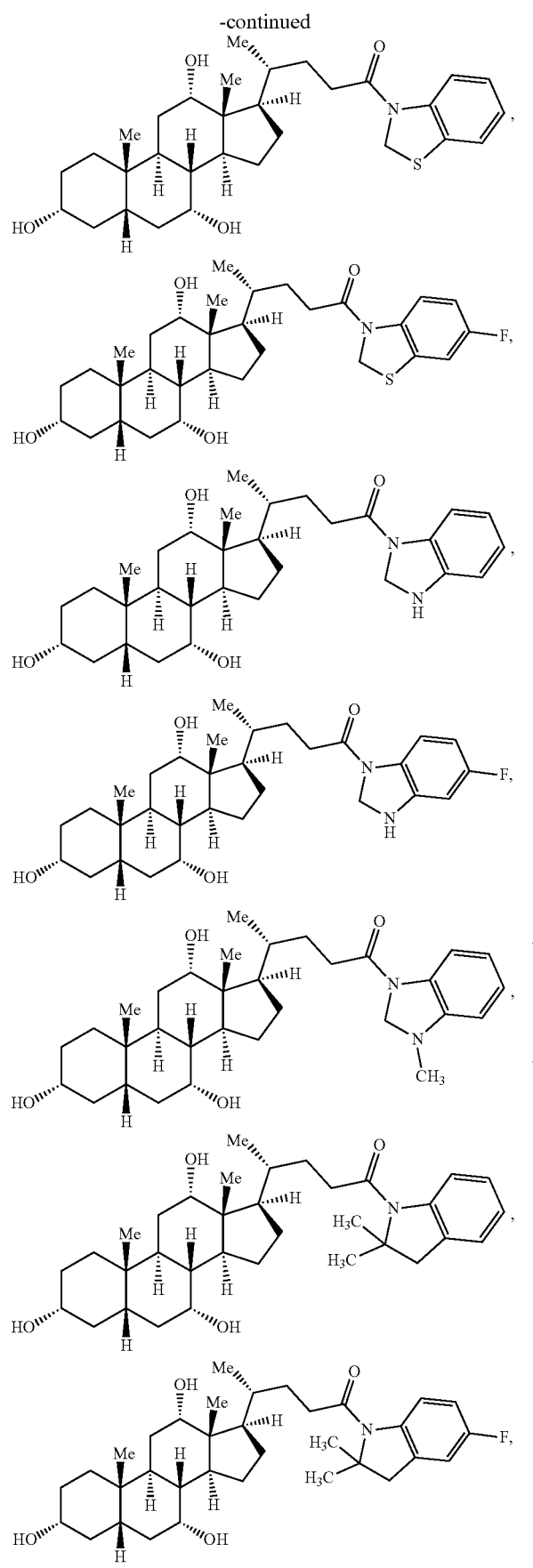
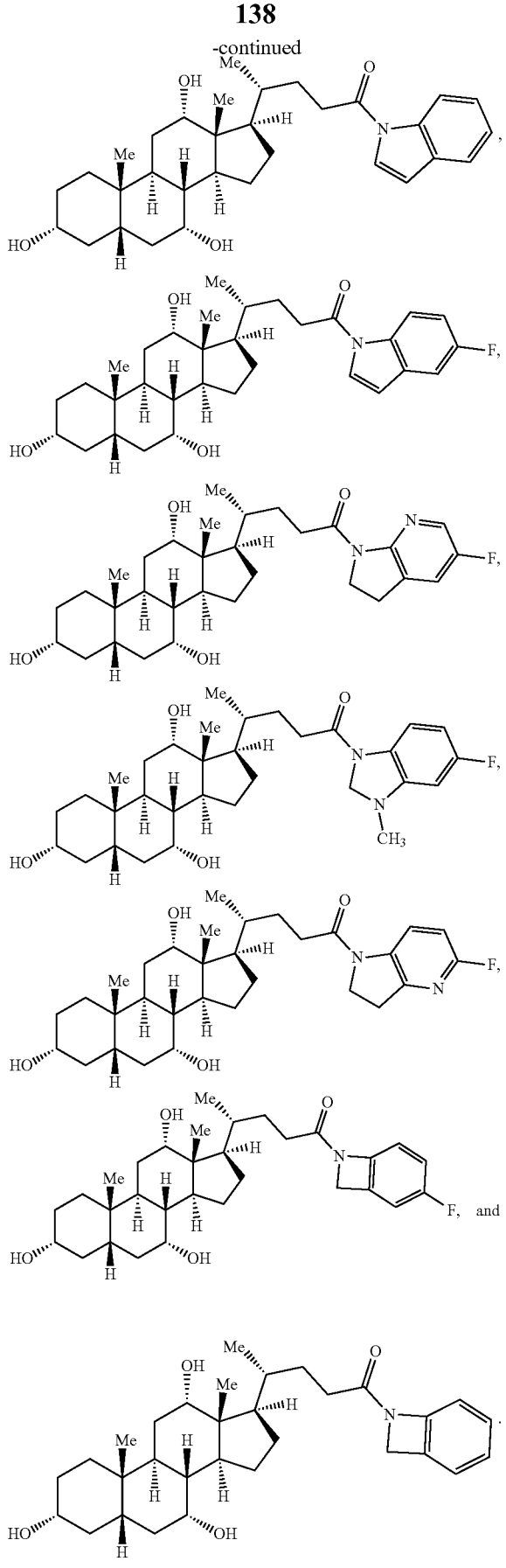

In a further aspect, the compound is selected from:
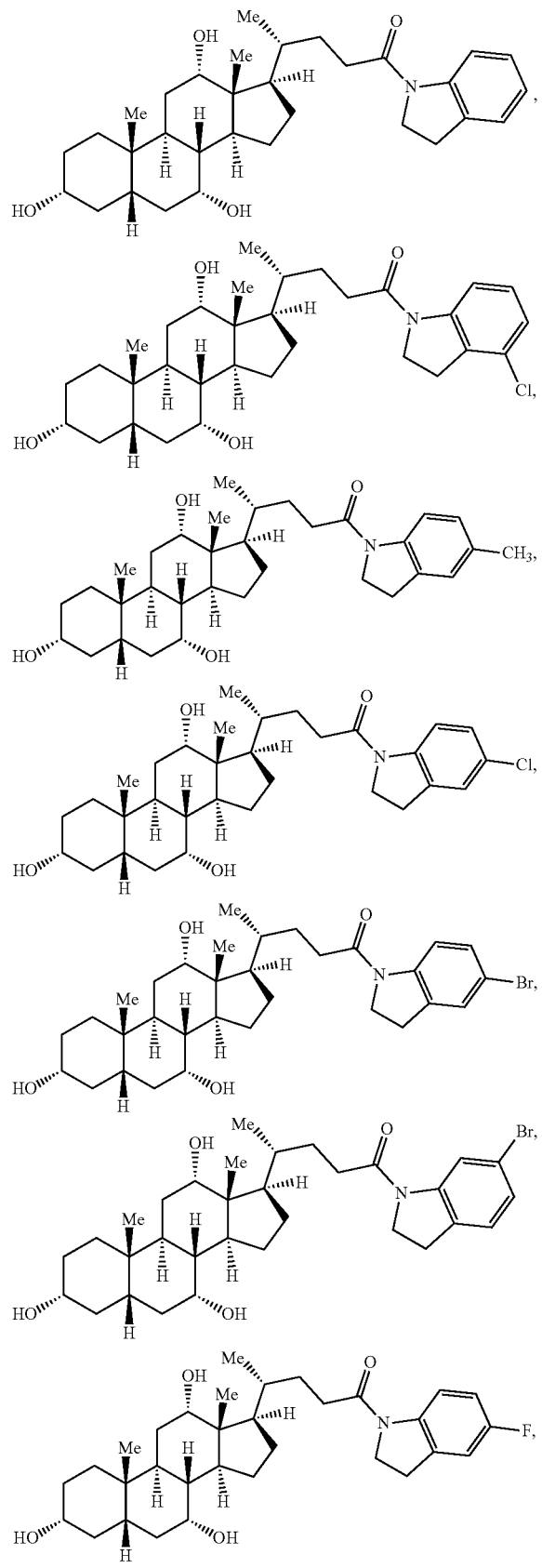
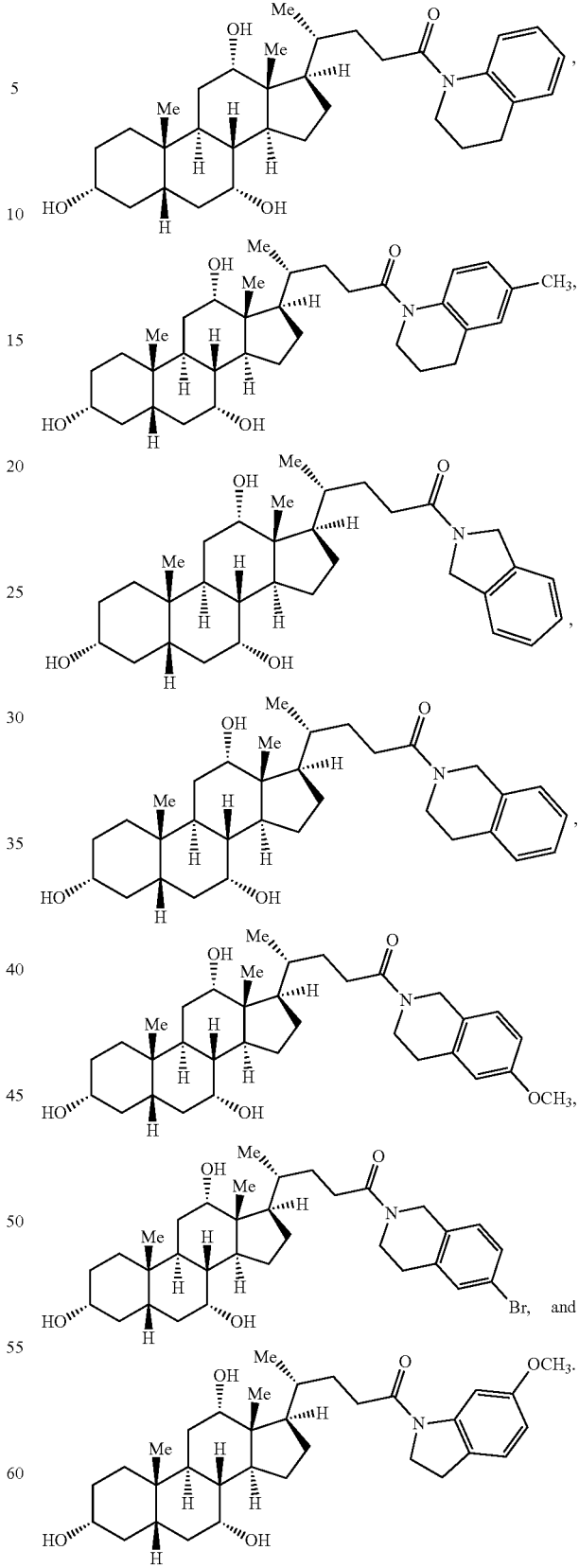
In a further aspect, the compound has a structure represented by a formula:

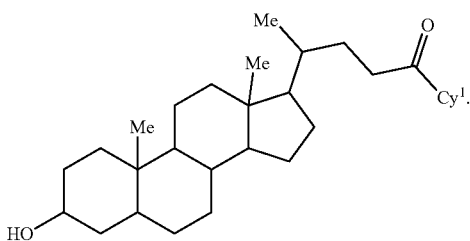

In a further aspect, the compound has a structure represented by a formula:

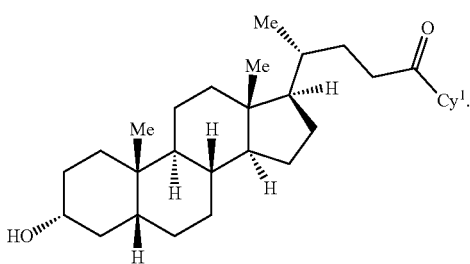

In one aspect, disclosed are compounds selected from:

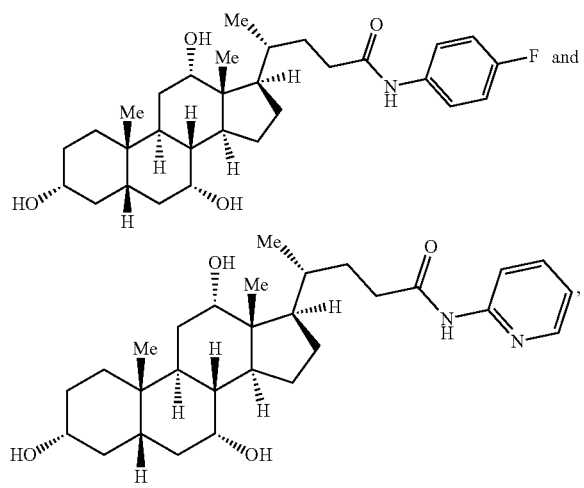

or a pharmaceutically acceptable salt thereof.

In one aspect, each of n and m, when present, is independently 0, 1, or 2. In a further aspect, each of n and m, when present, is independently 0 or 1. In a still further aspect, each of n and m, when present, is independently 1 or 2. In yet a further aspect, each of n and m, when present, is independently 0 or 2. In an even further aspect, each of n and m, when present, is 2. In a still further aspect, each of n and m, when present, is 1. In yet a further aspect, each of n and m, when present, is 0.

In various aspects, n, when present, is 0, 1, or 2. In a further aspect, n, when present, is 0 or 1. In a still further aspect, n, when present, is 1 or 2. In yet a further aspect, n, when present, is 0 or 2. In an even further aspect, n, when present, is 2. In a still further aspect, n, when present, is 1. In yet a further aspect, n, when present, is 0.

In various aspects, m, when present, is 0, 1, or 2. In a further aspect, m, when present, is 0 or 1. In a still further aspect, m, when present, is 1 or 2. In yet a further aspect, m, when present, is 0 or 2. In an even further aspect, m, when present, is 2. In a still further aspect, m, when present, is 1. In yet a further aspect, m, when present, is 0.

A. $A^1$ and $A^2$ Groups

In one aspect, each of $A^1$ and $A^2$ is independently selected from —N═ and —$CR^{21}$═. In a further aspect, each of $A^1$ and $A^2$ is —N═. In a still further aspect, each of $A^1$ and $A^2$ is —$CR^{21}$═.

In various aspects, $A^1$ is —N═ and $A^2$ is —$CR^{21}$═. In a further aspect, $A^2$ is —N═ and $A^1$ is —$CR^{21}$═.

b. $A^3$ Groups

In one aspect, $A^3$, when present, is selected from —O—, —S—, and —$NR^{22}$—. In a further aspect, $A^3$, when present, is selected from —O— and —S—. In a still further aspect, $A^3$, when present, is selected from —O— and —$NR^{22}$—. In yet a further aspect, $A^3$, when present, is selected from —S— and —$NR^{22}$—. In an even further aspect, $A^3$, when present, is —O—. In a still further aspect, $A^3$, when present, is —S—. In yet a further aspect, $A^3$, when present, is —$NR^{22}$—.

c. $A^4$ and $R^5$ Groups

In one aspect, each of $A^4$ and $A^5$, when present, is independently —$C(R^{23a})(R^{23b})$—.

d. $A^6$ Groups

In one aspect, $A^6$, when present, is selected from ═$C(R^{24})$— and ═N—. In a further aspect, $A^6$, when present, is ═$C(R^{24})$—. In a still further aspect, $A^6$, when present, is ═N—.

e. $Q^1$, $Q^2$, $Q^3$, and $Q^4$ Groups

In one aspect, each of $Q^1$, $Q^2$, $Q^3$, and $Q^4$ is independently selected from —N═ and —$CR^{20}$═. In a further aspect, each of $Q^1$, $Q^2$, $Q^3$, and $Q^4$ is —N═. In a still further aspect, each of $Q^1$, $Q^2$, $Q^3$, and $Q^4$ is —$CR^{20}$═.

In various aspects, each of $Q^1$, $Q^2$, and $Q^3$ is —N═ and $Q^4$ is —$CR^{20}$═. In a further aspect, each of $Q^1$, $Q^2$, and $Q^3$ is —$CR^{20}$═ and $Q^4$ is —N═.

In various aspects, each of $Q^1$, $Q^2$, and $Q^4$ is —N═ and $Q^3$ is —$CR^{20}$═. In a further aspect, each of $Q^1$, $Q^2$, and $Q^4$ is —$CR^{20}$═ and $Q^3$ is —N═.

In various aspects, each of $Q^1$, $Q^3$, and $Q^4$ is —N═ and $Q^2$ is —$CR^{20}$═. In a further aspect, each of $Q^1$, $Q^3$, and $Q^4$ is —$CR^{20}$═ and $Q^2$ is —N═.

In various aspects, each of $Q^2$, $Q^3$, and $Q^4$ is —N═ and $Q^1$ is —$CR^{20}$═. In a further aspect, each of $Q^2$, $Q^3$, and $Q^4$ is —$CR^{20}$═ and $Q^1$ is —N═.

In various aspects, each of $Q^1$ and $Q^2$ is —N═ and each of $Q^3$ and $Q^4$ is —$CR^{20}$═. In a further aspect, each of $Q^1$ and $Q^2$ is —$CR^{20}$═ and each of $Q^3$ and $Q^4$ is —N═.

In various aspects, each of $Q^1$ and $Q^3$ is —N═ and each of $Q^2$ and $Q^4$ is —$CR^{20}$═. In a further aspect, each of $Q^1$ and $Q^3$ is —$CR^{20}$═ and each of $Q^2$ and $Q^4$ is —N═.

In various aspects, each of $Q^1$ and $Q^4$ is —N═ and each of $Q^2$ and $Q^3$ is —$CR^{20}$═. In a further aspect, each of $Q^1$ and $Q^4$ is —$CR^{20}$═ and each of $Q^2$ and $Q^3$ is —N═.

In various aspects, each of $Q^2$ and $Q^3$ is —N═ and each of $Q^1$ and $Q^4$ is —$CR^{20}$═. In a further aspect, each of $Q^2$ and $Q^3$ is —$CR^{20}$═ and each of $Q^1$ and $Q^4$ is —N═.

In various aspects, each of $Q^2$ and $Q^4$ is —N═ and each of $Q^1$ and $Q^3$ is —$CR^{20}$═. In a further aspect, each of $Q^2$ and $Q^4$ is —$CR^{20}$═ and each of $Q^1$ and $Q^3$ is —N═.

In various aspects, each of $Q^3$ and $Q^4$ is —N═ and each of $Q^1$ and $Q^2$ is —$CR^{20}$═. In a further aspect, each of $Q^3$ and $Q^4$ is —$CR^{20}$═ and each of $Q^1$ and $Q^2$ is —N═.

f. $Z^1$ Groups

In one aspect, $Z^1$ is selected from —O— and —NR$^{18}$—. In a further aspect, $Z^1$ is —O—. In a still further aspect, $Z^1$ is —NR$^{18}$—.

g. $Z^2$ Groups

In one aspect, $Z^2$ is selected from —O—, —S—, and —NR$^{19}$—. In a further aspect, $Z^2$ is selected from —O— and —NR$^{19}$—. In a still further aspect, $Z^2$ is selected from —S— and —NR$^{19}$—.

In yet a further aspect, $Z^2$ is selected from —O— and —S—.

In a further aspect, $Z^2$ is —O—. In a still further aspect, $Z^2$ is —S—. In yet a further aspect, $Z^2$ is —NR$^{19}$—.

h. $R^1$, $R^{2a}$, and $R^{2b}$ Groups

In one aspect, each of $R^1$, $R^{2a}$, and $R^{2b}$ is independently selected from hydrogen and —OH. In a further aspect, each of $R^1$, $R^{2a}$, and $R^{2b}$ is —OH. In a still further aspect, each of $R^1$, $R^{2a}$, and $R^{2b}$ is hydrogen.

In various aspects, each of $R^1$ and $R^{2a}$ is hydrogen and $R^{2b}$ is —OH. In a further aspect, each of $R^1$ and $R^{2a}$ is —OH and $R^{2b}$ is hydrogen.

In various aspects, each of $R^1$ and $R^{2b}$ is hydrogen and $R^{2a}$ is —OH. In a further aspect, each of $R^1$ and $R^{2b}$ is —OH and $R^{2a}$ is hydrogen.

In various aspects, each of $R^{2a}$ and $R^{2b}$ is hydrogen and $R^1$ is —OH. In a further aspect, each of $R^{2a}$ and $R^{2b}$ is —OH and $R^1$ is hydrogen.

In various aspects, one of $R^1$, $R^{2a}$, and $R^{2b}$ is —OH, and two of $R^1$, $R^{2a}$, and $R^{2b}$ are hydrogen. In a further aspect, two of $R^1$, $R^{2a}$, and $R^{2b}$ are —OH, and one of $R^1$, $R^{2a}$, and $R^{2b}$ is hydrogen.

i. $R^{3a}$ and $R^{3b}$ Groups

In one aspect, each of $R^{3a}$ and $R^{3b}$ are independently selected from C1-C4 alkyl, C2-C4 alkenyl, and phenyl substituted with 0, 1, 2, or 3 groups independently selected from halogen, —NO$_2$, —CN, C1-C4 alkyl, C1-C4 haloalkyl, and —C(O)(C1-C4 alkyl), or wherein each of $R^{3a}$ and $R^{3b}$ together comprise a heterocycle having a structure represented by a formula selected from:

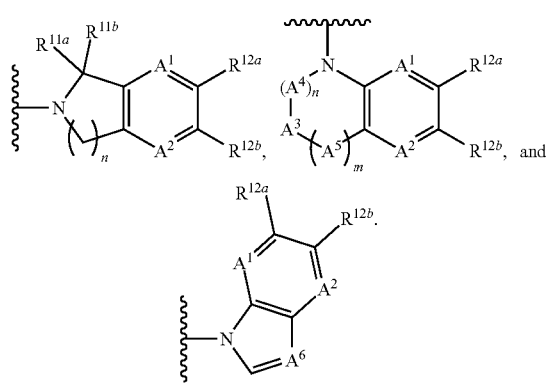

In various aspects, each of $R^{3a}$ and $R^{3b}$ are independently selected from C1-C4 alkyl, C2-C4 alkenyl, and phenyl substituted with 0, 1, 2, or 3 groups independently selected from halogen, —NO$_2$, —CN, C1-C4 alkyl, C1-C4 haloalkyl, and —C(O)(C1-C4 alkyl). In a further aspect, each of $R^{3a}$ and $R^{3b}$ are independently selected from methyl, ethyl, n-propyl, isopropyl, ethenyl, n-propenyl, isopropenyl, and phenyl substituted with 0, 1, 2, or 3 groups independently selected from halogen, —NO$_2$, —CN, C1-C4 alkyl, C1-C4 haloalkyl, and —C(O)(C1-C4 alkyl). In a still further aspect, each of $R^{3a}$ and $R^{3b}$ are independently selected from methyl, ethyl, ethenyl, and phenyl substituted with 0, 1, 2, or 3 groups independently selected from halogen, —NO$_2$, —CN, C1-C4 alkyl, C1-C4 haloalkyl, and —C(O)(C1-C4 alkyl). In yet a further aspect, each of $R^{3a}$ and $R^{3b}$ are independently selected from methyl and phenyl substituted with 0, 1, 2, or 3 groups independently selected from halogen, —NO$_2$, —CN, C1-C4 alkyl, C1-C4 haloalkyl, and —C(O)(C1-C4 alkyl).

In various aspects, each of $R^{3a}$ and $R^{3b}$ are independently selected from C1-C4 alkyl and C2-C4 alkenyl. In a further aspect, each of $R^{3a}$ and $R^{3b}$ are independently selected from methyl, ethyl, n-propyl, isopropyl, ethenyl, n-propenyl, and isopropenyl. In a still further aspect, each of $R^{3a}$ and $R^{3b}$ are independently selected from methyl, ethyl, and ethenyl. In yet a further aspect, each of $R^{3a}$ and $R^{3b}$ are methyl.

In various aspects, each of $R^{3a}$ and $R^{3b}$ are independently selected from C1-C4 alkyl. In a further aspect, each of $R^{3a}$ and $R^{3b}$ are independently selected from methyl, ethyl, n-propyl, and isopropyl. In a still further aspect, each of $R^{3a}$ and $R^{3b}$ are independently selected from methyl and ethyl. In yet a further aspect, each of $R^{3a}$ and $R^{3b}$ are ethyl.

In various aspects, each of $R^{3a}$ and $R^{3b}$ are independently selected from C2-C4 alkenyl. In a further aspect, each of $R^{3a}$ and $R^{3b}$ are independently selected from ethenyl, n-propenyl, and isopropenyl. In a still further aspect, each of $R^{3a}$ and $R^{3b}$ are ethenyl.

In various aspects, each of $R^{3a}$ and $R^{3b}$ are —CH$_2$CH=CH$_2$.

In various aspects, each of $R^{3a}$ and $R^{3b}$ are independently selected from C1-C4 alkyl and phenyl substituted with 0, 1, 2, or 3 groups independently selected from halogen, —NO$_2$, —CN, C1-C4 alkyl, C1-C4 haloalkyl, and —C(O)(C1-C4 alkyl). In a further aspect, each of $R^{3a}$ and $R^{3b}$ are independently selected from methyl, ethyl, n-propyl, isopropyl, and phenyl substituted with 0, 1, 2, or 3 groups independently selected from halogen, —NO$_2$, —CN, C1-C4 alkyl, C1-C4 haloalkyl, and —C(O)(C1-C4 alkyl). In a still further aspect, each of $R^{3a}$ and $R^{3b}$ are independently selected from methyl, ethyl, and phenyl substituted with 0, 1, 2, or 3 groups independently selected from halogen, —NO$_2$, —CN, C1-C4 alkyl, C1-C4 haloalkyl, and —C(O)(C1-C4 alkyl). In yet a further aspect, each of $R^{3a}$ and $R^{3b}$ are independently selected from methyl and phenyl substituted with 0, 1, 2, or 3 groups independently selected from halogen, —NO$_2$, —CN, C1-C4 alkyl, C1-C4 haloalkyl, and —C(O)(C1-C4 alkyl).

In various aspects, each of $R^{3a}$ and $R^{3b}$ are independently selected from C1-C4 alkyl and unsubstituted phenyl. In a further aspect, each of $R^{3a}$ and $R^{3b}$ are independently selected from methyl, ethyl, n-propyl, isopropyl, and unsubstituted phenyl. In a still further aspect, each of $R^{3a}$ and $R^{3b}$ are independently selected from methyl, ethyl, and unsubstituted phenyl. In yet a further aspect, each of $R^{3a}$ and $R^{3b}$ are independently selected from methyl and unsubstituted phenyl.

In various aspects, one of $R^{3a}$ and $R^{3b}$ is methyl and the other is unsubstituted phenyl.

In various aspect, each of $R^{3a}$ and $R^{3b}$ are independently phenyl substituted with 0, 1, 2, or 3 groups independently selected from halogen, —NO$_2$, —CN, C1-C4 alkyl, C1-C4 haloalkyl, and —C(O)(C1-C4 alkyl). In a further aspect, each of $R^{3a}$ and $R^{3b}$ are independently phenyl substituted with 0, 1, or 2 groups independently selected from halogen, —NO$_2$, —CN, C1-C4 alkyl, C1-C4 haloalkyl, and —C(O)(C1-C4 alkyl). In a still further aspect, each of $R^{3a}$ and $R^{3b}$ are independently phenyl substituted with 0 or 1 group selected from halogen, —NO$_2$, —CN, C1-C4 alkyl, C1-C4 haloalkyl, and —C(O)(C1-C4 alkyl). In yet a further aspect, each of $R^{3a}$ and $R^{3b}$ are independently phenyl monosubstituted with a group selected from halogen, —NO$_2$, —CN, C1-C4 alkyl, C1-C4 haloalkyl, and —C(O)(C1-C4 alkyl).

In an even further aspect, each of $R^{3a}$ and $R^{3b}$ are unsubstituted phenyl.

In various aspects, each of $R^{3a}$ and $R^{3b}$ together comprise a heterocycle having a structure represented by a formula selected from:

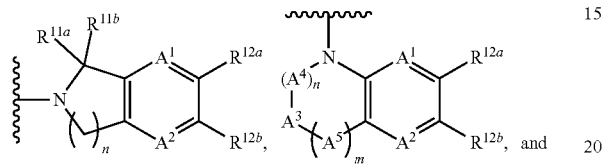

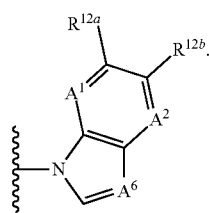

In various aspects, each of $R^{3a}$ and $R^{3b}$ together comprise a heterocycle having a structure represented by a formula:

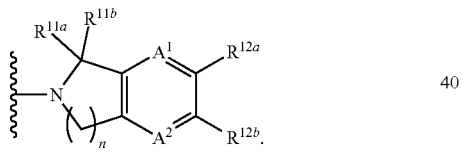

In various aspects, each of $R^{3a}$ and $R^{3b}$ together comprise a heterocycle having a structure represented by a formula:

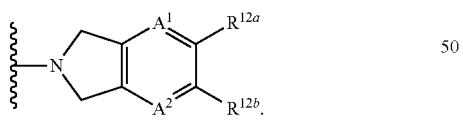

In various aspects, each of $R^{3a}$ and $R^{3b}$ together comprise a heterocycle having a structure represented by a formula:

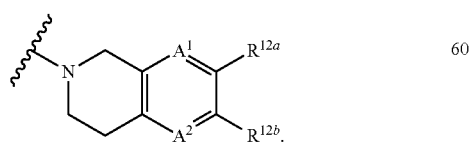

In various aspects, each of $R^{3a}$ and $R^{3b}$ together comprise a heterocycle having a structure represented by a formula:

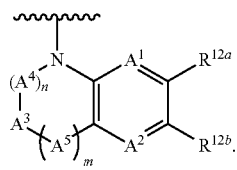

In various aspects, each of $R^{3a}$ and $R^{3b}$ together comprise a heterocycle having a structure represented by a formula:

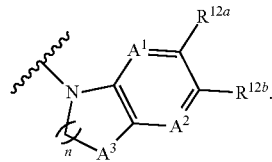

In various aspects, each of $R^{3a}$ and $R^{3b}$ together comprise a heterocycle having a structure represented by a formula selected from:

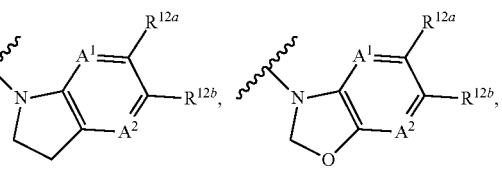

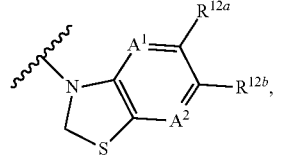

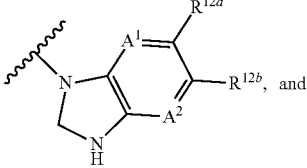

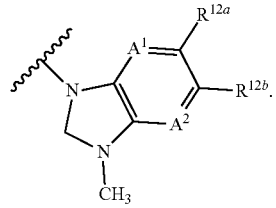

In various aspects, each of $R^{3a}$ and $R^{3b}$ together comprise a heterocycle having a structure represented by a formula selected from:

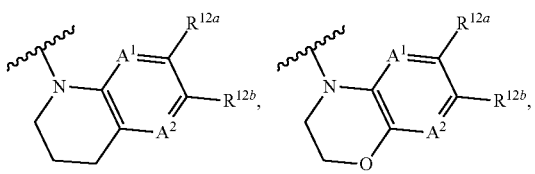

-continued

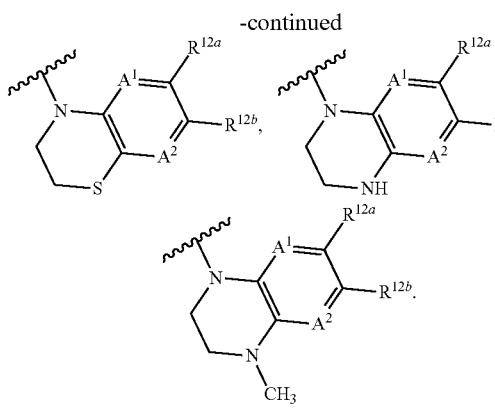

In various aspects, each of $R^{3a}$ and $R^{3b}$ together comprise a heterocycle having a structure represented by a formula:

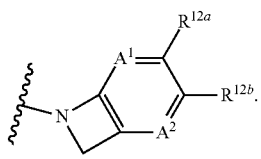

In various aspects, each of $R^{3a}$ and $R^{3b}$ together comprise a heterocycle having a structure represented by a formula:

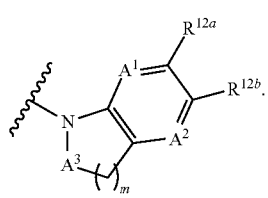

In various aspects, each of $R^{3a}$ and $R^{3b}$ together comprise a heterocycle having a structure represented by a formula:

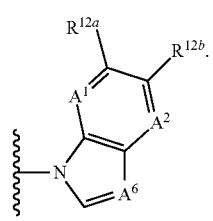

In various aspects, each of $R^{3a}$ and $R^{3b}$ together comprise a heterocycle having a structure represented by a formula:

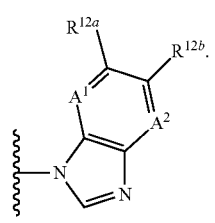

In various aspects, each of $R^{3a}$ and $R^{3b}$ together comprise a heterocycle having a structure represented by a formula:

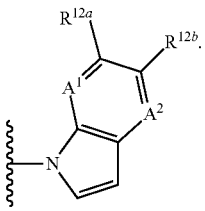

j. $R^{10}$ Groups

In one aspect, $R^{10}$ is selected from hydrogen, halogen, C1-C4 alkyl, C1-C4 alkoxy, C1-C4 haloalkyl, C1-C4 thioalkyl, and phenyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{10}$ is selected from hydrogen, —F, —Cl, —Br, methyl, ethyl, n-propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —SCH$_3$, —SCH$_2$CH$_3$, —S(CH$_2$)$_2$CH$_3$, —SCH(CH$_3$)$_2$, and phenyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{10}$ is selected from hydrogen, —F, —Cl, —Br, methyl, ethyl, —OCH$_3$, —OCH$_2$CH$_3$, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —SCH$_3$, —SCH$_2$CH$_3$, and phenyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{10}$ is selected from hydrogen, —F, —Cl, —Br, methyl, ethyl, —OCH$_3$, —CH$_2$F, —CH$_2$Cl, —CH$_2$Br, —CHF$_2$, —CF$_3$, —CHCl$_2$, —CCl$_3$, —CHBr$_2$, —CBr$_3$, —SCH$_3$, and phenyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, $R^{10}$ is selected from hydrogen, halogen, C1-C4 alkyl, C1-C4 alkoxy, C1-C4 haloalkyl, and C1-C4 thioalkyl. In a further aspect, $R^{10}$ is selected from hydrogen, —F, —Cl, —Br, methyl, ethyl, n-propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl₃, —CHBr₂, —CBr₃, —CH₂CHF₂, —CH₂CF₃, —CH₂CHCl₂, —CH₂CCl₃, —CH₂CHBr₂, —CH₂CBr₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —SCH₃, —SCH₂CH₃, —S(CH₂)₂CH₃, and —SCH(CH₃)₂. In a still further aspect, $R^{10}$ is selected from hydrogen, —F, —Cl, —Br, methyl, ethyl, —OCH₃, —OCH₂CH₃, —CH₂F, —CH₂Cl, —CH₂Br, —CH₂CH₂F, —CH₂CH₂Cl, —CH₂CH₂Br, —CHF₂, —CF₃, —CHCl₂, —CCl₃, —CHBr₂, —CBr₃, —CH₂CHF₂, —CH₂CF₃, —CH₂CHCl₂, —CH₂CCl₃, —CH₂CHBr₂, —CH₂CBr₃, —SCH₃, and —SCH₂CH₃. In yet a further aspect, $R^{10}$ is selected from hydrogen, —F, —Cl, —Br, methyl, ethyl, —OCH₃, —CH₂F, —CH₂Cl, —CH₂Br, —CHF₂, —CF₃, —CHCl₂, —CCl₃, —CHBr₂, —CBr₃, and —SCH₃.

In various aspects, $R^{10}$ is selected from hydrogen and C1-C4 alkoxy. In a further aspect, $R^{10}$ is selected from hydrogen, —OCH₃, —OCH₂CH₃, —O(CH₂)₂CH₃, and —OCH(CH₃)₂. In a still further aspect, $R^{10}$ is selected from hydrogen, —OCH₃, and —OCH₂CH₃. In yet a further aspect, $R^{10}$ is selected from hydrogen and —OCH₃.

In various aspects, $R^{10}$ is selected from hydrogen and C1-C4 haloalkyl. In a further aspect, $R^{10}$ is selected from hydrogen, —CH₂F, —CH₂Cl, —CH₂Br, —CH₂CH₂F, —CH₂CH₂Cl, —CH₂CH₂Br, —(CH₂)₂CH₂F, —(CH₂)₂CH₂Cl, —(CH₂)₂CH₂Br, —CHF₂, —CF₃, —CHCl₂, —CCl₃, —CHBr₂, —CBr₃, —CH₂CHF₂, —CH₂CF₃, —CH₂CHCl₂, —CH₂CCl₃, —CH₂CHBr₂, —CH₂CBr₃, —(CH₂)₂CHF₂, —(CH₂)₂CF₃, —(CH₂)₂CHCl₂, —(CH₂)₂CCl₃, —(CH₂)₂CHBr₂, and —(CH₂)₂CBr₃. In a still further aspect, $R^{10}$ is selected from hydrogen, —CH₂F, —CH₂Cl, —CH₂Br, —CH₂CH₂F, —CH₂CH₂Cl, —CH₂CH₂Br, —CHF₂, —CF₃, —CHCl₂, —CCl₃, —CHBr₂, —CBr₃, —CH₂CHF₂, —CH₂CF₃, —CH₂CHCl₂, —CH₂CCl₃, —CH₂CHBr₂, and —CH₂CBr₃. In yet a further aspect, $R^{10}$ is selected from hydrogen, —CH₂F, —CH₂Cl, —CH₂Br, —CHF₂, —CF₃, —CHCl₂, —CCl₃, —CHBr₂, and —CBr₃.

In various aspects, $R^{10}$ is selected from hydrogen and C1-C4 thioalkyl. In a further aspect, $R^{10}$ is selected from hydrogen, —SCH₃, —SCH₂CH₃, —S(CH₂)₂CH₃, and —SCH(CH₃)₂. In a still further aspect, $R^{10}$ is selected from hydrogen, —SCH₃, and —SCH₂CH₃. In yet a further aspect, $R^{10}$ is selected from hydrogen and —SCH₃.

In various aspects, $R^{10}$ is selected from hydrogen, halogen, and C1-C4 alkyl. In a further aspect, $R^{10}$ is selected from hydrogen, —F, —Cl, —Br, methyl, ethyl, n-propyl, and isopropyl. In a still further aspect, $R^{10}$ is selected from hydrogen, —F, —Cl, methyl, and ethyl. In yet a further aspect, $R^{10}$ is selected from hydrogen, —F, and methyl.

In various aspects, $R^{10}$ is selected from hydrogen and C1-C4 alkyl. In a further aspect, $R^{10}$ is selected from hydrogen, methyl, ethyl, n-propyl, and isopropyl. In a still further aspect, $R^{10}$ is selected from hydrogen, methyl, and ethyl. In yet a further aspect, $R^{10}$ is selected from hydrogen and methyl.

In various aspects, $R^{10}$ is C1-C4 alkyl. In a further aspect, $R^{10}$ is selected from methyl, ethyl, n-propyl, and isopropyl. In a still further aspect, $R^{10}$ is selected from methyl and ethyl. In yet a further aspect, $R^{10}$ is methyl.

In various aspects, $R^{10}$ is selected from hydrogen and halogen. In a further aspect, $R^{10}$ is selected from hydrogen, —F, —Cl, and —Br. In a still further aspect, $R^{10}$ is selected from hydrogen, —F, and —Cl. In yet a further aspect, $R^{10}$ is selected from hydrogen and —F.

In various aspects, $R^{10}$ is phenyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{10}$ is phenyl substituted with 0, 1, or 2 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{10}$ is phenyl substituted with 0 or 1 group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{10}$ is phenyl monosubstituted with a group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{10}$ is unsubstituted phenyl.

k. $R^{11a}$ and $R^{11b}$ Groups

In one aspect, each of $R^{11a}$ and $R^{11b}$, when present, is independently selected from hydrogen and C1-C4 alkyl. In a further aspect, each of $R^{11a}$ and $R^{11b}$, when present, is independently selected from hydrogen, methyl, ethyl, n-propyl, and isopropyl. In a still further aspect, each of $R^{11a}$ and $R^{11b}$, when present, is independently selected from hydrogen, methyl, and ethyl. In yet a further aspect, each of $R^{11a}$ and $R^{11b}$, when present, is independently selected from hydrogen and ethyl. In an even further aspect, each of $R^{11a}$ and $R^{11b}$, when present, is independently selected from hydrogen and methyl.

In various aspects, each of $R^{11a}$ and $R^{11b}$, when present, is independently C1-C4 alkyl. In a further aspect, each of $R^{11a}$ and $R^{11b}$, when present, is independently selected from methyl, ethyl, n-propyl, and isopropyl. In a still further aspect, each of $R^{11a}$ and $R^{11b}$, when present, is independently selected from methyl and ethyl. In yet a further aspect, each of $R^{11a}$ and $R^{11b}$, when present, is ethyl. In an even further aspect, each of $R^{11a}$ and $R^{11b}$, when present, is methyl.

In various aspects, each of $R^{11a}$ and $R^{11b}$, when present, is hydrogen.

l. $R^{12a}$ and $R^{12b}$ Groups

In one aspect, each of $R^{12a}$ and $R^{12b}$ is independently selected from hydrogen, halogen, —NO₂, —CN, C1-C4 alkyl, C1-C4 alkoxy, C1-C4 haloalkyl, and —C(O)(C1-C4 alkyl). In a further aspect, each of $R^{12a}$ and $R^{12b}$ is independently selected from hydrogen, —F, —Cl, —Br, —NO₂, —CN, methyl, ethyl, n-propyl, isopropyl, —OCH₃, —OCH₂CH₃, —O(CH₂)₂CH₃, —OCH(CH₃)₂, —CH₂F, —CH₂Cl, —CH₂Br, —CH₂CH₂F, —CH₂CH₂Cl, —CH₂CH₂Br, —(CH₂)₂CH₂F, —(CH₂)₂CH₂Cl, —(CH₂)₂CH₂Br, —CHF₂, —CF₃, —CHCl₂, —CCl₃, —CHBr₂, —CBr₃, —CH₂CHF₂, —CH₂CF₃, —CH₂CHCl₂, —CH₂CCl₃, —CH₂CHBr₂, —CH₂CBr₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —C(O)CH₃, —C(O)CH₂CH₃, —C(O)(CH₂)₂CH₃, and —C(O)CH(CH₃)₂. In a still further aspect, each of $R^{12a}$ and $R^{12b}$ is independently selected from hydrogen, —F, —Cl, —NO₂, —CN, methyl, ethyl, —OCH₃, —OCH₂CH₃, —CH₂F, —CH₂Cl, —CH₂Br, —CH₂CH₂F, —CH₂CH₂Cl, —CH₂CH₂Br, —CHF₂, —CF₃, —CHCl₂, —CCl₃, —CHBr₂, —CBr₃, —CH₂CHF₂, —CH₂CF₃, —CH₂CHCl₂, —CH₂CCl₃, —CH₂CHBr₂, —CH₂CBr₃, —C(O)CH₃, and —C(O)CH₂CH₃. In yet a further aspect, each of $R^{12a}$ and $R^{12b}$ is independently selected from hydrogen, —F, —Cl, —NO$_2$, —CN, methyl, —OCH$_3$, —CH$_2$F, —CH$_2$Cl, —CH$_2$Br, —CHF$_2$, —CF$_3$, —CHCl$_2$, —CCl$_3$, —CHBr$_2$, —CBr$_3$, and —C(O)CH$_3$.

In various aspects, each of $R^{12a}$ and $R^{12b}$ is independently selected from hydrogen, halogen, —NO$_2$, —CN, and —C(O)(C1-C4 alkyl). In a further aspect, each of $R^{12a}$ and $R^{12b}$ is independently selected from hydrogen, —F, —Cl, —Br, —NO$_2$, —CN, —C(O)CH$_3$, —C(O)CH$_2$CH$_3$, —C(O)(CH$_2$)$_2$CH$_3$, and —C(O)CH(CH$_3$)$_2$. In a still further aspect, each of $R^{12a}$ and $R^{12b}$ is independently selected from hydrogen, —F, —Cl, —NO$_2$, —CN, —C(O)CH$_3$, and —C(O)CH$_2$CH$_3$. In yet a further aspect, each of $R^{12a}$ and $R^{12b}$ is independently selected from hydrogen, —F, —Cl, —NO$_2$, —CN, and —C(O)CH$_3$.

In various aspects, each of $R^{12a}$ and $R^{12b}$ is independently selected from hydrogen, halogen, —NO$_2$, —CN, and C1-C4 haloalkyl. In a further aspect, each of $R^{12a}$ and $R^{12b}$ is independently selected from hydrogen, —F, —Cl, —Br, —NO$_2$, —CN, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, and —(CH$_2$)$_2$CBr$_3$. In a still further aspect, each of $R^{12a}$ and $R^{12b}$ is independently selected from hydrogen, —F, —Cl, —NO$_2$, —CN, —CH$_2$F, —CH$_2$Cl, H—CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, and —CH$_2$CBr$_3$. In yet a further aspect, each of $R^{12a}$ and $R^{12b}$ is independently selected from hydrogen, —F, —Cl, —NO$_2$, —CN, —CH$_2$F, —CH$_2$Cl, —CH$_2$Br, —CHF$_2$, —CF$_3$, —CHCl$_2$, —CCl$_3$, —CHBr$_2$, and —CBr$_3$.

In various aspects, each of $R^{12a}$ and $R^{12b}$ is independently selected from hydrogen, halogen, —NO$_2$, —CN, and C1-C4 alkoxy. In a further aspect, each of $R^{12a}$ and $R^{12b}$ is independently selected from hydrogen, —F, —Cl, —Br, —NO$_2$, —CN, —OCH$_3$, —OCH$_2$CH$_3$, —O(CH$_2$)$_2$CH$_3$, and —OCH(CH$_3$)$_2$. In a still further aspect, each of $R^{12a}$ and $R^{12b}$ is independently selected from hydrogen, —F, —Cl, —NO$_2$, —CN, —OCH$_3$, and —OCH$_2$CH$_3$. In yet a further aspect, each of $R^{12a}$ and $R^{12b}$ is independently selected from hydrogen, —F, —Cl, —NO$_2$, —CN, and —OCH$_3$.

In various aspects, each of $R^{12a}$ and $R^{12b}$ is independently selected from hydrogen, halogen, —NO$_2$, —CN, and C1-C4 alkyl. In a further aspect, each of $R^{12a}$ and $R^{12b}$ is independently selected from hydrogen, —F, —Cl, —Br, —NO$_2$, —CN, methyl, ethyl, n-propyl, and isopropyl. In a still further aspect, each of $R^{12a}$ and $R^{12b}$ is independently selected from hydrogen, —F, —Cl, —NO$_2$, —CN, methyl, and ethyl. In yet a further aspect, each of $R^{12a}$ and $R^{12b}$ is independently selected from hydrogen, —F, —Cl, —NO$_2$, —CN, and methyl.

In various aspects, each of $R^{12a}$ and $R^{12b}$ is independently selected from hydrogen and C1-C4 alkyl. In a further aspect, each of $R^{12a}$ and $R^{12b}$ is independently selected from hydrogen, methyl, ethyl, n-propyl, and isopropyl. In a still further aspect, each of $R^{12a}$ and $R^{12b}$ is independently selected from hydrogen, methyl, and ethyl. In yet a further aspect, each of $R^{12a}$ and $R^{12b}$ is independently selected from hydrogen and methyl.

In various aspects, each of $R^{12a}$ and $R^{12b}$ is independently selected from hydrogen and halogen. In a further aspect, each of $R^{12a}$ and $R^{12b}$ is independently selected from hydrogen, —F, —Cl, and —Br. In a still further aspect, each of $R^{12a}$ and $R^{12b}$ is independently selected from hydrogen, —F, and —Cl. In yet a further aspect, each of $R^{12a}$ and $R^{12b}$ is independently selected from hydrogen and —F.

In various aspects, each of $R^{12a}$ and $R^{12b}$ is hydrogen.

m. $R^{18}$ Groups

In one aspect, $R^{18}$, when present, is selected from hydrogen and C1-C4 alkyl. In a further aspect, $R^{18}$, when present, is selected from hydrogen, methyl, ethyl, n-propyl, and isopropyl. In a still further aspect, $R^{18}$, when present, is selected from hydrogen, methyl, and ethyl. In yet a further aspect, $R^{18}$, when present, is selected from hydrogen and ethyl. In an even further aspect, $R^{18}$, when present, is selected from hydrogen and methyl.

In various aspects, $R^{18}$, when present, is C1-C4 alkyl. In a further aspect, $R^{18}$, when present, is selected from methyl, ethyl, n-propyl, and isopropyl. In a still further aspect, $R^{18}$, when present, is selected from methyl and ethyl. In yet a further aspect, $R^{18}$, when present, is ethyl. In an even further aspect, $R^{18}$, when present, is methyl.

In various aspects, $R^{18}$, when present, is hydrogen.

n. $R^{19}$ Groups

In one aspect, $R^{19}$, when present, is selected from hydrogen and C1-C4 alkyl. In a further aspect, $R^{19}$, when present, is selected from hydrogen, methyl, ethyl, n-propyl, and isopropyl. In a still further aspect, $R^{19}$, when present, is selected from hydrogen, methyl, and ethyl. In yet a further aspect, $R^{19}$, when present, is selected from hydrogen and ethyl. In an even further aspect, $R^{19}$, when present, is selected from hydrogen and methyl.

In various aspects, $R^{19}$, when present, is C1-C4 alkyl. In a further aspect, $R^{19}$, when present, is selected from methyl, ethyl, n-propyl, and isopropyl. In a still further aspect, $R^{19}$, when present, is selected from methyl and ethyl. In yet a further aspect, $R^{19}$, when present, is ethyl. In an even further aspect, $R^{19}$, when present, is methyl.

In various aspects, $R^{19}$, when present, is hydrogen.

o. $R^{20}$ Groups

In one aspect, each occurrence of $R^{20}$ is independently selected from hydrogen, halogen, C1-C4 alkyl, C1-C4 alkoxy, and phenyl. In a further aspect, each occurrence of $R^{20}$ is independently selected from hydrogen, —F, —Cl, —Br, methyl, ethyl, n-propyl, isopropyl, methoxy, ethoxy, n-propoxy, isopropoxy, and phenyl. In a still further aspect, each occurrence of $R^{20}$ is independently selected from hydrogen, —F, —Cl, methyl, ethyl, methoxy, ethoxy, and phenyl. In yet a further aspect, each occurrence of $R^{20}$ is independently selected from hydrogen, —F, —Cl, methyl, methoxy, and phenyl.

In various aspects, each occurrence of $R^{20}$ is independently selected from hydrogen, halogen, C1-C4 alkyl, and phenyl. In a further aspect, each occurrence of $R^{20}$ is independently selected from hydrogen, —F, —Cl, —Br, methyl, ethyl, n-propyl, isopropyl, and phenyl. In a still further aspect, each occurrence of $R^{20}$ is independently selected from hydrogen, —F, —Cl, methyl, ethyl, and phenyl. In yet a further aspect, each occurrence of $R^{20}$ is independently selected from hydrogen, —F, —Cl, methyl, and phenyl.

In various aspects, each occurrence of $R^{20}$ is independently selected from hydrogen, halogen, C1-C4 alkoxy, and phenyl. In a further aspect, each occurrence of $R^{20}$ is independently selected from hydrogen, —F, —Cl, —Br, methoxy, ethoxy, n-propoxy, isopropoxy, and phenyl. In a still further aspect, each occurrence of $R^{20}$ is independently selected from hydrogen, —F, —Cl, methoxy, ethoxy, and phenyl. In yet a further aspect, each occurrence of $R^{20}$ is independently selected from hydrogen, —F, —Cl, methoxy, and phenyl.

In various aspects, In various aspects, each occurrence of $R^{20}$ is independently selected from hydrogen and C1-C4 alkoxy. In a further aspect, each occurrence of $R^{20}$ is independently selected from hydrogen, methoxy, ethoxy, n-propoxy, and isopropoxy. In a still further aspect, each occurrence of $R^{20}$ is independently selected from hydrogen, methoxy, and ethoxy. In yet a further aspect, each occurrence of $R^{20}$ is independently selected from hydrogen and methoxy.

In various aspects, each occurrence of $R^{20}$ is independently selected from hydrogen and C1-C4 alkyl. In a further aspect, each occurrence of $R^{20}$ is independently selected from hydrogen, methyl, ethyl, n-propyl, and isopropyl. In a still further aspect, each occurrence of $R^{20}$ is independently selected from hydrogen, methyl, and ethyl. In yet a further aspect, each occurrence of $R^{20}$ is independently selected from hydrogen and methyl.

In various aspects, each occurrence of $R^{20}$ is independently selected from hydrogen and halogen. In a further aspect, each occurrence of $R^{20}$ is independently selected from hydrogen, —F, —Cl, and —Br. In a still further aspect, each occurrence of $R^{20}$ is independently selected from hydrogen, —F, and —Cl. In yet a further aspect, each occurrence of $R^{20}$ is independently selected from hydrogen and —F.

In various aspects, each occurrence of $R^{20}$ is independently selected from hydrogen and phenyl. In a further aspect, each occurrence of $R^{20}$ is phenyl. In a still further aspect, each occurrence of $R^{20}$ is hydrogen.

p. $R^{21}$ Groups

In one aspect, each occurrence of $R^{21}$ is independently selected from hydrogen, halogen, —NO$_2$, —CN, C1-C4 alkyl, C1-C4 alkoxy, C1-C4 haloalkyl, and —C(O)(C1-C4 alkyl). In a further aspect, each occurrence of $R^2$ is independently selected from hydrogen, —F, —Cl, —Br, —NO$_2$, —CN, methyl, ethyl, n-propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —C(O)CH$_3$, —C(O)CH$_2$CH$_3$, —C(O)(CH$_2$)$_2$CH$_3$, and —C(O)CH(CH$_3$)$_2$. In a still further aspect, each occurrence of $R^2$ is independently selected from hydrogen, —F, —Cl, —NO$_2$, —CN, methyl, ethyl, —OCH$_3$, —OCH$_2$CH$_3$, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —C(O)CH$_3$, and —C(O)CH$_2$CH$_3$. In yet a further aspect, each occurrence of $R^{21}$ is independently selected from hydrogen, —F, —Cl, —NO$_2$, —CN, methyl, —OCH$_3$, —CH$_2$F, —CH$_2$Cl, —CH$_2$Br, —CHF$_2$, —CF$_3$, —CHCl$_2$, —CCl$_3$, —CHBr$_2$, —CBr$_3$, and —C(O)CH$_3$.

In various aspects, each occurrence of $R^{21}$ is independently selected from hydrogen, halogen, —NO$_2$, —CN, and —C(O)(C1-C4 alkyl). In a further aspect, each occurrence of $R^{21}$ is independently selected from hydrogen, —F, —Cl, —Br, —NO$_2$, —CN, —C(O)CH$_3$, —C(O)CH$_2$CH$_3$, —C(O)(CH$_2$)$_2$CH$_3$, and —C(O)CH(CH$_3$)$_2$. In a still further aspect, each occurrence of $R^{21}$ is independently selected from hydrogen, —F, —Cl, —NO$_2$, —CN, —C(O)CH$_3$, and —C(O)CH$_2$CH$_3$. In yet a further aspect, each occurrence of $R^{21}$ is independently selected from hydrogen, —F, —Cl, —NO$_2$, —CN, and —C(O)CH$_3$.

In various aspects, each occurrence of $R^{21}$ is independently selected from hydrogen, halogen, —NO$_2$, —CN, and C1-C4 haloalkyl. In a further aspect, each of $R^{12a}$ and $R^{12b}$ is independently selected from hydrogen, —F, —Cl, —Br, —NO$_2$, —CN, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, and —(CH$_2$)$_2$CBr$_3$. In a still further aspect, each occurrence of $R^{21}$ is independently selected from hydrogen, —F, —Cl, —NO$_2$, —CN, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, and —CH$_2$CBr$_3$. In yet a further aspect, each occurrence of $R^{21}$ is independently selected from hydrogen, —F, —Cl, —NO$_2$, —CN, —CH$_2$F, —CH$_2$Cl, —CH$_2$Br, —CHF$_2$, —CF$_3$, —CHCl$_2$, —CCl$_3$, —CHBr$_2$, and —CBr$_3$.

In various aspects, each occurrence of $R^{21}$ is independently selected from hydrogen, halogen, —NO$_2$, —CN, and C1-C4 alkoxy. In a further aspect, each occurrence of $R^{21}$ is independently selected from hydrogen, —F, —Cl, —Br, —NO$_2$, —CN, —OCH$_3$, —OCH$_2$CH$_3$, —O(CH$_2$)$_2$CH$_3$, and —OCH(CH$_3$)$_2$. In a still further aspect, each occurrence of $R^{21}$ is independently selected from hydrogen, —F, —Cl, —NO$_2$, —CN, —OCH$_3$, and —OCH$_2$CH$_3$. In yet a further aspect, each occurrence of $R^{21}$ is independently selected from hydrogen, —F, —Cl, —NO$_2$, —CN, and —OCH$_3$.

In various aspects, each occurrence of $R^{21}$ is independently selected from hydrogen, halogen, —NO$_2$, —CN, and C1-C4 alkyl. In a further aspect, each occurrence of $R^{21}$ is independently selected from hydrogen, —F, —Cl, —Br, —NO$_2$, —CN, methyl, ethyl, n-propyl, and isopropyl. In a still further aspect, each occurrence of $R^{21}$ is independently selected from hydrogen, —F, —Cl, —NO$_2$, —CN, methyl, and ethyl. In yet a further aspect, each occurrence of $R^{21}$ is independently selected from hydrogen, —F, —Cl, —NO$_2$, —CN, and methyl.

In various aspects, each occurrence of $R^{21}$ is independently selected from hydrogen and C1-C4 alkyl. In a further aspect, each occurrence of $R^{21}$ is independently selected from hydrogen, methyl, ethyl, n-propyl, and isopropyl. In a still further aspect, each occurrence of $R^{21}$ is independently selected from hydrogen, methyl, and ethyl. In yet a further aspect, each occurrence of $R^{21}$ is independently selected from hydrogen and methyl.

In various aspects, each occurrence of $R^{21}$ is independently selected from hydrogen and halogen. In a further aspect, each occurrence of $R^{21}$ is independently selected from hydrogen, —F, —Cl, and —Br. In a still further aspect, each occurrence of $R^{21}$ is independently selected from hydrogen, —F, and —Cl. In yet a further aspect, each occurrence of $R^{21}$ is independently selected from hydrogen and —F.

In various aspects, each occurrence of $R^{21}$ is hydrogen.

q. $R^{22}$ Groups

In one aspect, $R^{22}$ is selected from hydrogen and C1-C4 alkyl. In a further aspect, $R^{22}$ is selected from hydrogen, methyl, ethyl, n-propyl, and isopropyl. In a still further aspect, $R^{22}$ is selected from hydrogen, methyl, and ethyl. In yet a further aspect, $R^{22}$ is selected from hydrogen and ethyl. In an even further aspect, $R^{22}$ is selected from hydrogen and methyl.

In various aspects, $R^{22}$ is C1-C4 alkyl. In a further aspect, $R^{22}$ is selected from methyl, ethyl, n-propyl, and isopropyl. In a still further aspect, $R^{22}$ is selected from methyl and ethyl. In yet a further aspect, $R^{22}$ is ethyl. In an even further aspect, $R^{22}$ is methyl.

In various aspects, $R^{22}$ is hydrogen.

r. $R^{23a}$ and $R^{23b}$ Groups

In one aspect, each of $R^{23a}$ and $R^{23b}$ is independently selected from hydrogen and C1-C4 alkyl. In a further aspect, each of $R^{23a}$ and $R^{23b}$ is independently selected from hydrogen, methyl, ethyl, n-propyl, and isopropyl. In a still further aspect, each of $R^{23a}$ and $R^{23b}$ is independently selected from hydrogen, methyl, and ethyl. In yet a further aspect, each of $R^{23a}$ and $R^{23b}$ is independently selected from hydrogen and ethyl. In an even further aspect, each of $R^{23a}$ and $R^{23b}$ is independently selected from hydrogen and methyl.

In various aspects, each of $R^{23a}$ and $R^{23b}$ is independently C1-C4 alkyl. In a further aspect, each of $R^{23a}$ and $R^{23b}$ is independently selected from methyl, ethyl, n-propyl, and isopropyl. In a still further aspect, each of $R^{23a}$ and $R^{23b}$ is independently selected from methyl and ethyl. In yet a further aspect, each of $R^{23a}$ and $R^{23b}$ is ethyl. In an even further aspect, each of $R^{23a}$ and $R^{23b}$ is methyl.

In various aspects, each of $R^{23a}$ and $R^{23b}$ is hydrogen.

s. $R^{23c}$ and $R^{23d}$ Groups

In one aspect, each of $R^{23c}$ and $R^{23d}$ is independently selected from hydrogen and C1-C4 alkyl. In a further aspect, each of $R^{23c}$ and $R^{23d}$ is independently selected from hydrogen, methyl, ethyl, n-propyl, and isopropyl. In a still further aspect, each of $R^{23c}$ and $R^{23d}$ is independently selected from hydrogen, methyl, and ethyl. In yet a further aspect, each of $R^{23c}$ and $R^{23d}$ is independently selected from hydrogen and ethyl. In an even further aspect, each of $R^{23c}$ and $R^{23d}$ is independently selected from hydrogen and methyl.

In various aspects, each of $R^{23c}$ and $R^{23d}$ is independently C1-C4 alkyl. In a further aspect, each of $R^{23c}$ and $R^{23d}$ is independently selected from methyl, ethyl, n-propyl, and isopropyl. In a still further aspect, each of $R^{23c}$ and $R^{23d}$ is independently selected from methyl and ethyl. In yet a further aspect, each of $R^{23c}$ and $R^{23d}$ is ethyl. In an even further aspect, each of $R^{23c}$ and $R^{23d}$ is methyl.

In various aspects, each of $R^{23c}$ and $R^{23d}$ is hydrogen.

t. $R^{24}$ Groups

In one aspect, $R^{24}$, when present, is selected from hydrogen and C1-C4 alkyl. In a further aspect, $R^{24}$, when present, is selected from hydrogen, methyl, ethyl, n-propyl, and isopropyl. In a still further aspect, $R^{24}$, when present, is selected from hydrogen, methyl, and ethyl. In yet a further aspect, $R^{24}$, when present, is selected from hydrogen and ethyl. In an even further aspect, $R^{24}$, when present, is selected from hydrogen and methyl.

In various aspects, $R^{24}$, when present, is C1-C4 alkyl. In a further aspect, $R^{24}$, when present, is selected from methyl, ethyl, n-propyl, and isopropyl. In a still further aspect, $R^{24}$, when present, is selected from methyl and ethyl. In yet a further aspect, $R^{24}$, when present, is ethyl. In an even further aspect, $R^{24}$, when present, is methyl.

In various aspects, $R^{24}$, when present, is hydrogen.

u. $Ar^1$ Groups

In one aspect, $Ar^1$ is a bicyclic heteroaryl having a structure represented by a formula selected from:

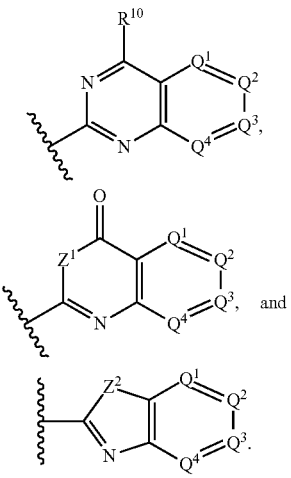

In one aspect, $Ar^1$ is:

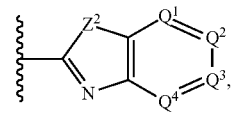

and either: (a) at least one of $Q^1$, $Q^2$, $Q^3$, and $Q^4$ is —N= and at least one of $Q^1$, $Q^2$, $Q^3$, and $Q^4$ is —CR$^{20}$=, wherein $R^{20}$ is not hydrogen; or (b) at least two of $Q^1$, $Q^2$, $Q^3$, and $Q^4$ is —CR$^{20}$=, wherein at least two occurrences of $R^{20}$ are not hydrogen.

Thus, in one aspect, $Ar^1$ is a bicyclic heteroaryl having a structure represented by a formula:

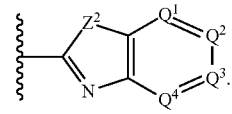

In various aspects, $Ar^1$ is:

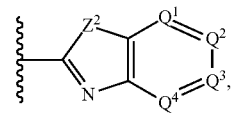

at least one of $Q^1$, $Q^2$, $Q^3$, and $Q^4$ is —N=, and at least one of $Q^1$, $Q^2$, $Q^3$, and $Q^4$ is —CR$^{20}$=, wherein $R^{20}$ is not hydrogen.

In various aspects, $Ar^1$ is:

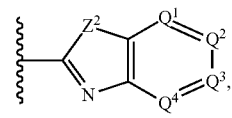

and at least two of $Q^1$, $Q^2$, $Q^3$, and $Q^4$ is —CR$^{20}$=, wherein at least two occurrences of $R^{20}$ are not hydrogen.

In various aspects, Ar¹ is selected from:
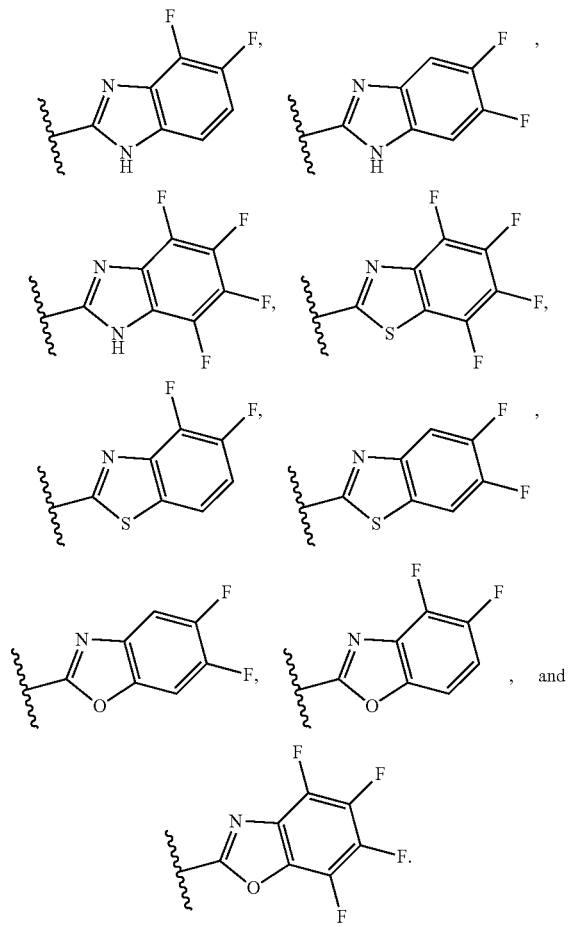
In various aspects, Ar¹ is a bicyclic heteroaryl having a structure represented by a formula selected from:
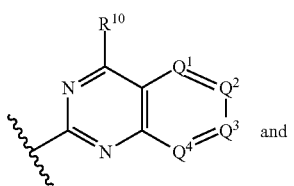
In various aspects, Ar¹ is a bicyclic heteroaryl having a structure:
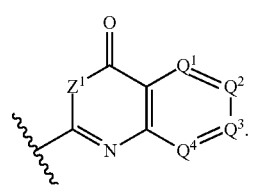
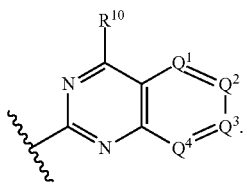
In various aspects, Ar¹ is selected from:
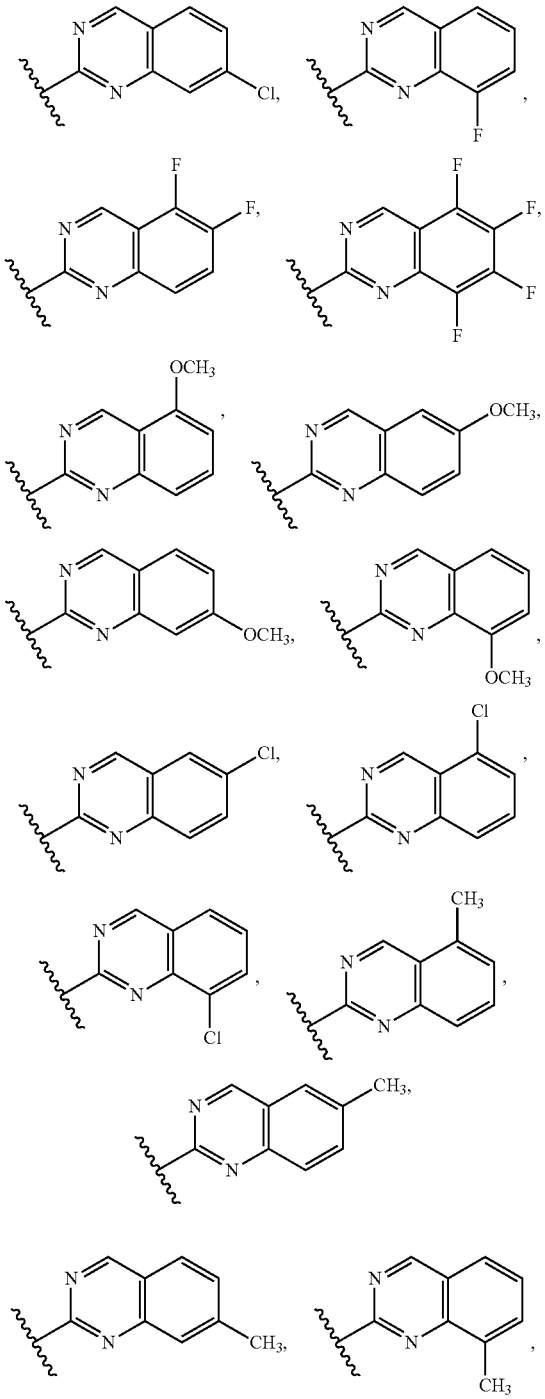

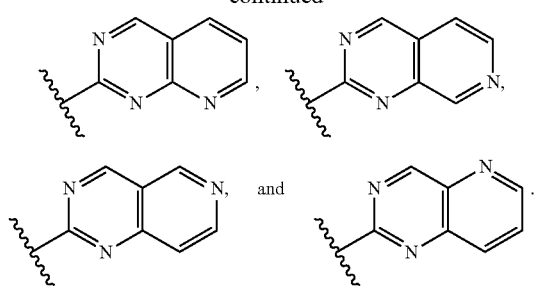
In various aspects, Ar¹ is a bicyclic heteroaryl having a structure:
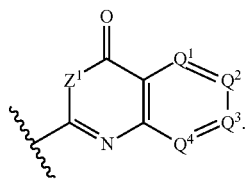
In various aspects, Ar¹ is selected from:
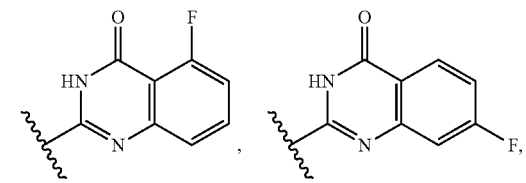
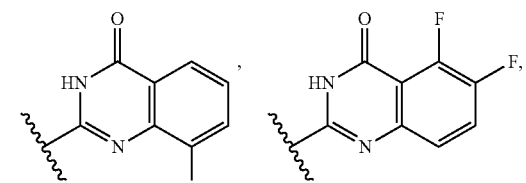
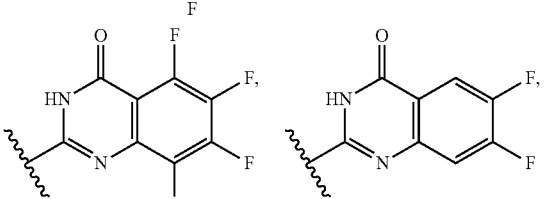
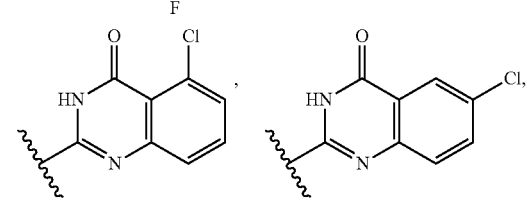
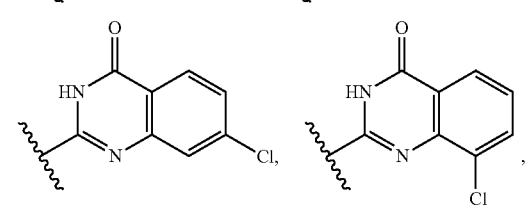
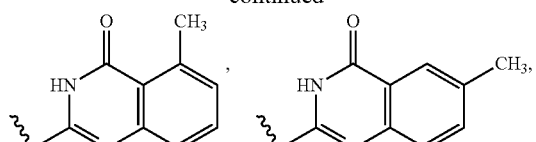
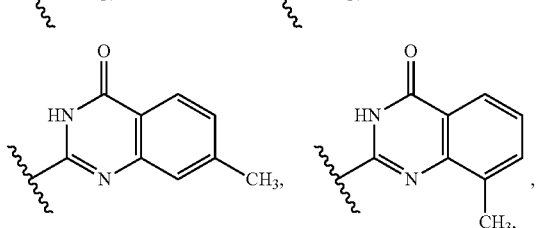
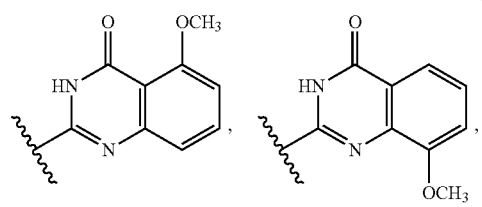
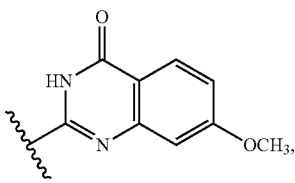
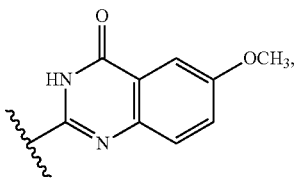
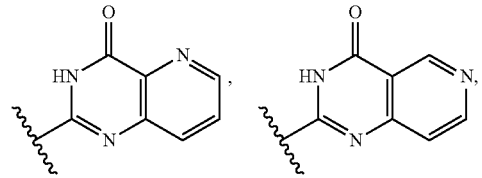
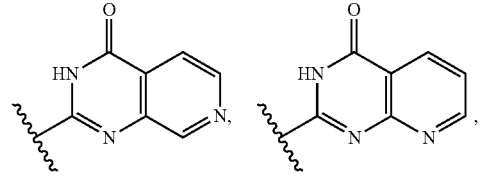
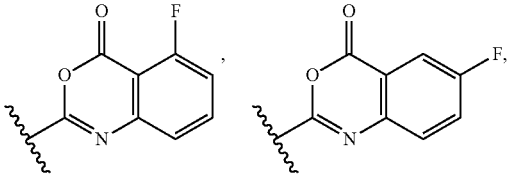
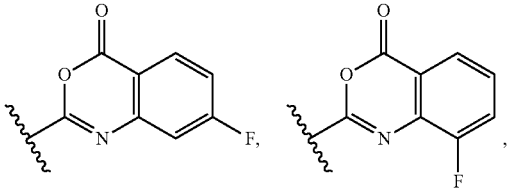

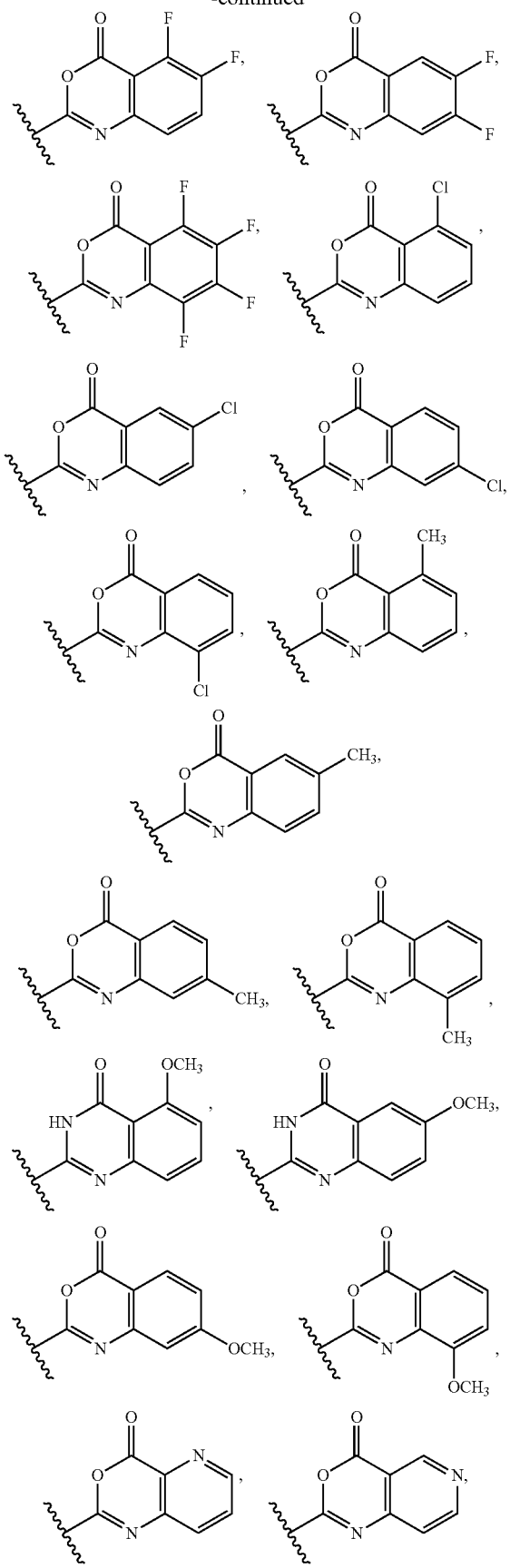
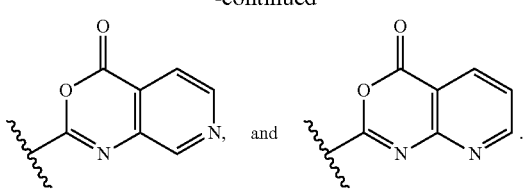
v. Cy¹ Groups
In one aspect, Cy¹ is a bicycle having a formula selected from:
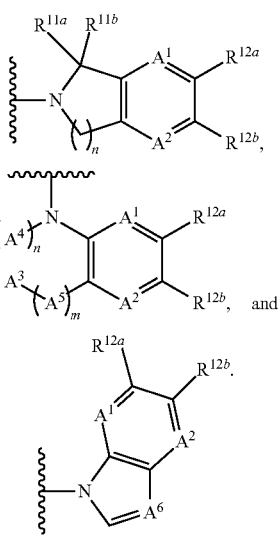
In various aspects, Cy¹ is a bicycle having a formula:
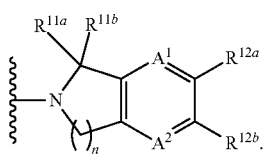
In various aspects, Cy¹ is a bicycle having a formula:
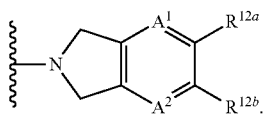
In various aspects, Cy¹ is a bicycle having a formula:
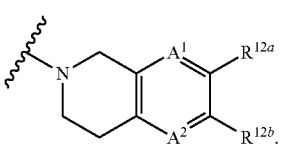

In various aspects, Cy¹ is a bicycle having a formula:

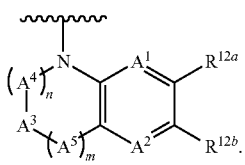

In various aspects, Cy¹ is a bicycle having a formula:

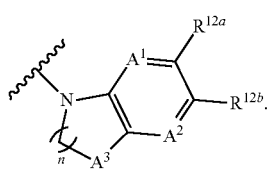

In various aspects, Cy¹ is a bicycle having a formula selected from:

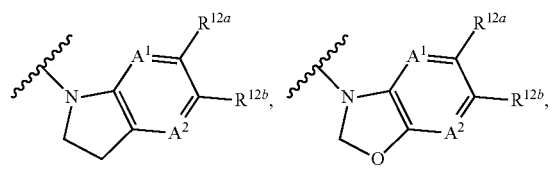

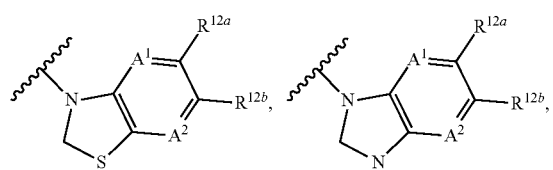

and 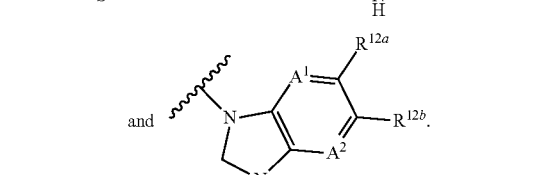

In various aspects, Cy¹ is a bicycle having a formula selected from:

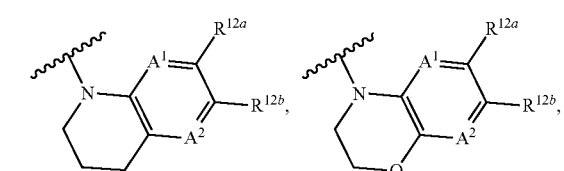

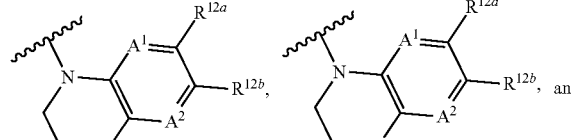, and

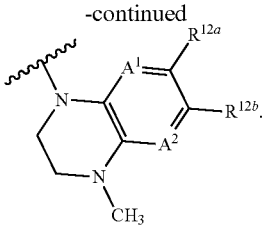

In various aspects, Cy¹ is a bicycle having a formula:

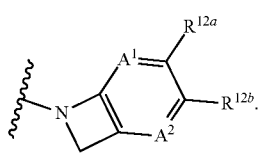

In various aspects, Cy¹ is a bicycle having a formula:

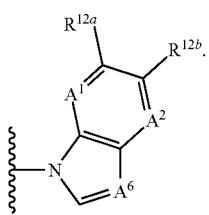

In various aspects, Cy¹ is a bicycle having a formula:

In various aspects, Cy¹ is a bicycle having a formula:

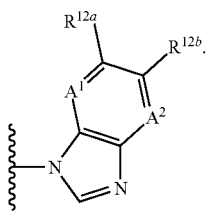

In various aspects, $Cy^1$ is a bicycle having a formula:
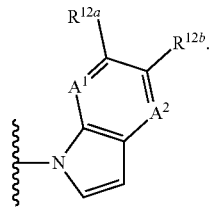
2. Example Compounds
In one aspect, a compound can be present as one or more of the following structures:
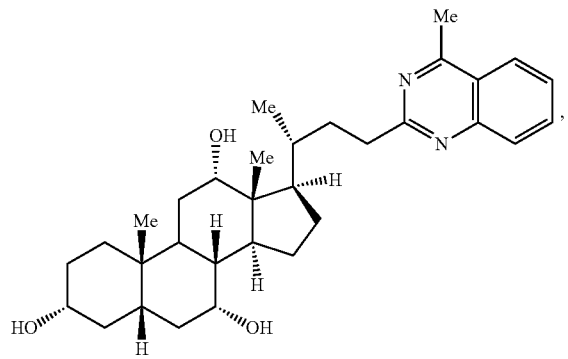
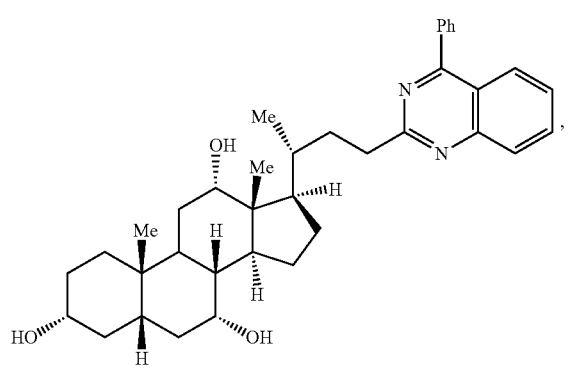
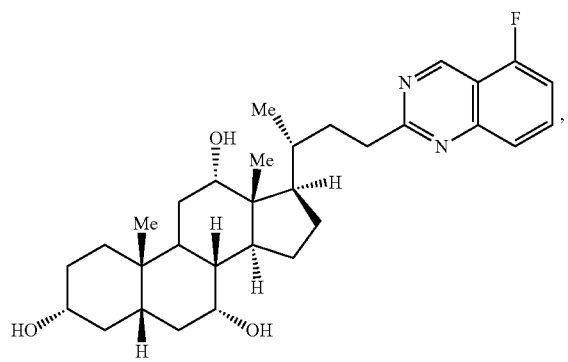
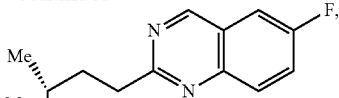
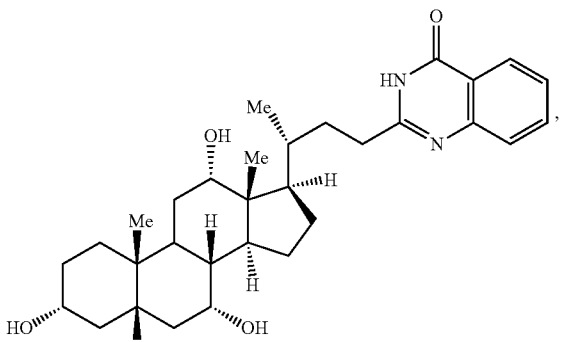
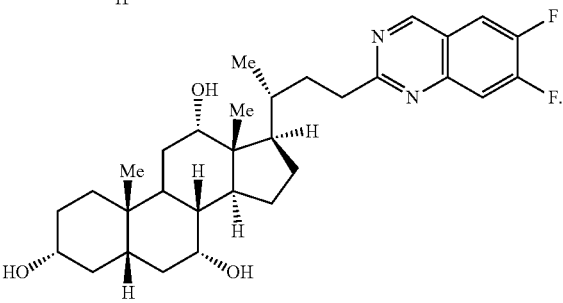
In one aspect, a compound can be present as:
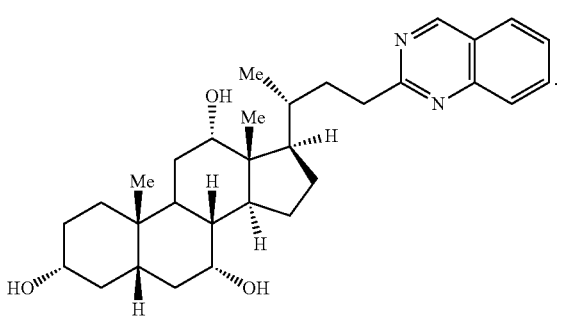

In one aspect, a compound can be present as:
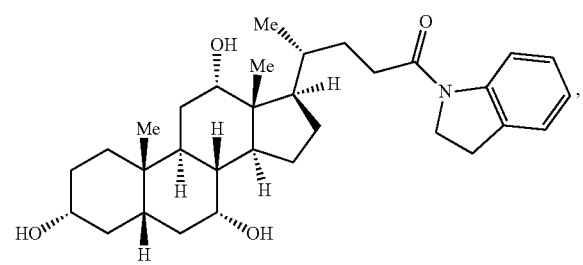,
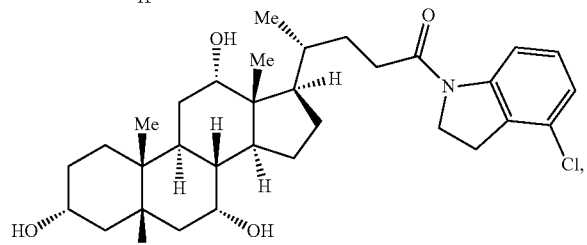,
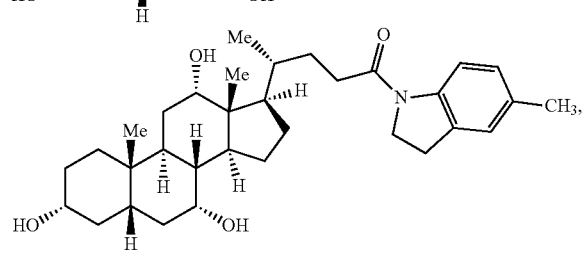,
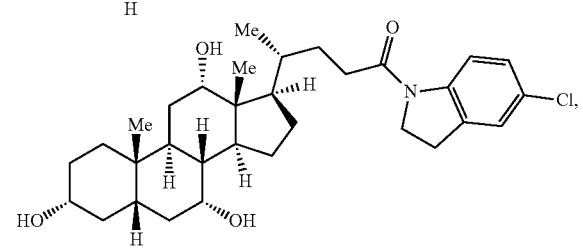,
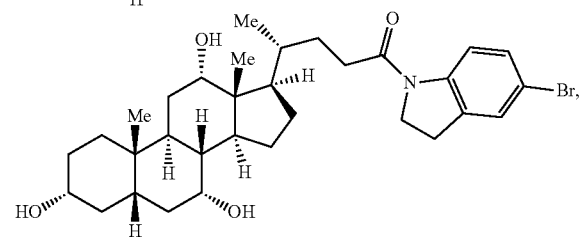,
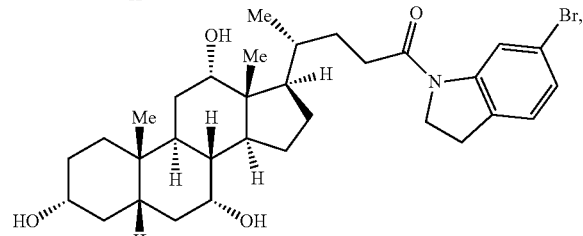,
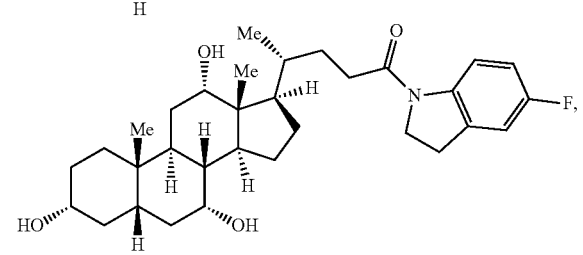,
-continued
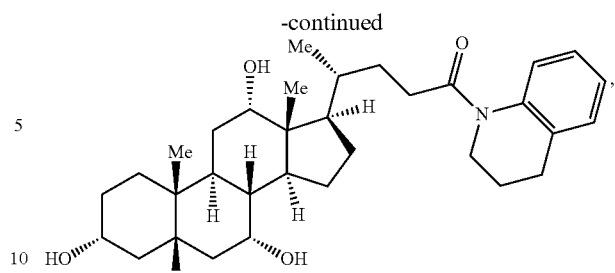,
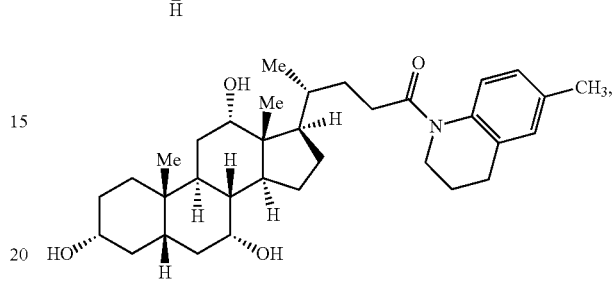,
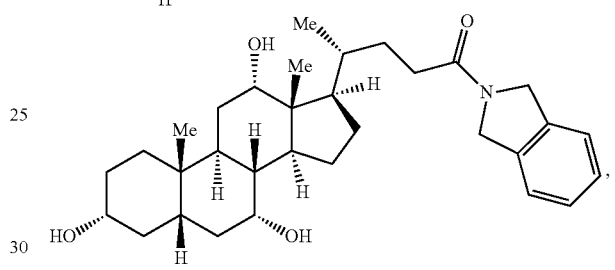,
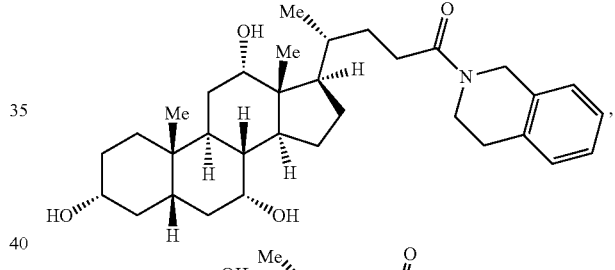,
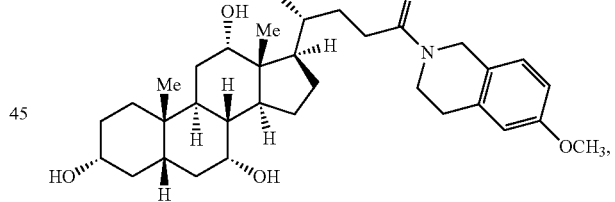,
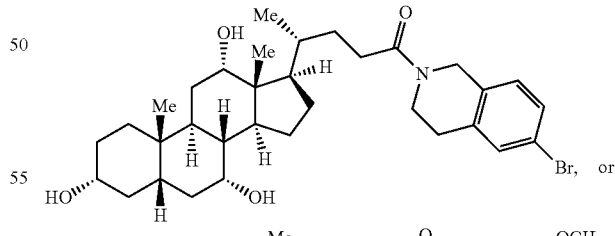, or
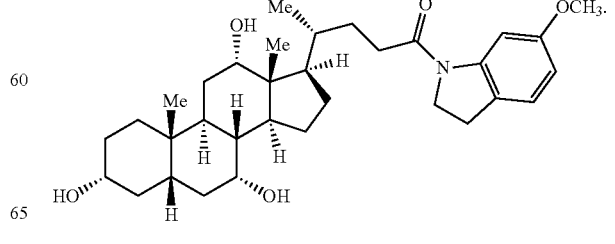.

In one aspect, a compound can be present as:
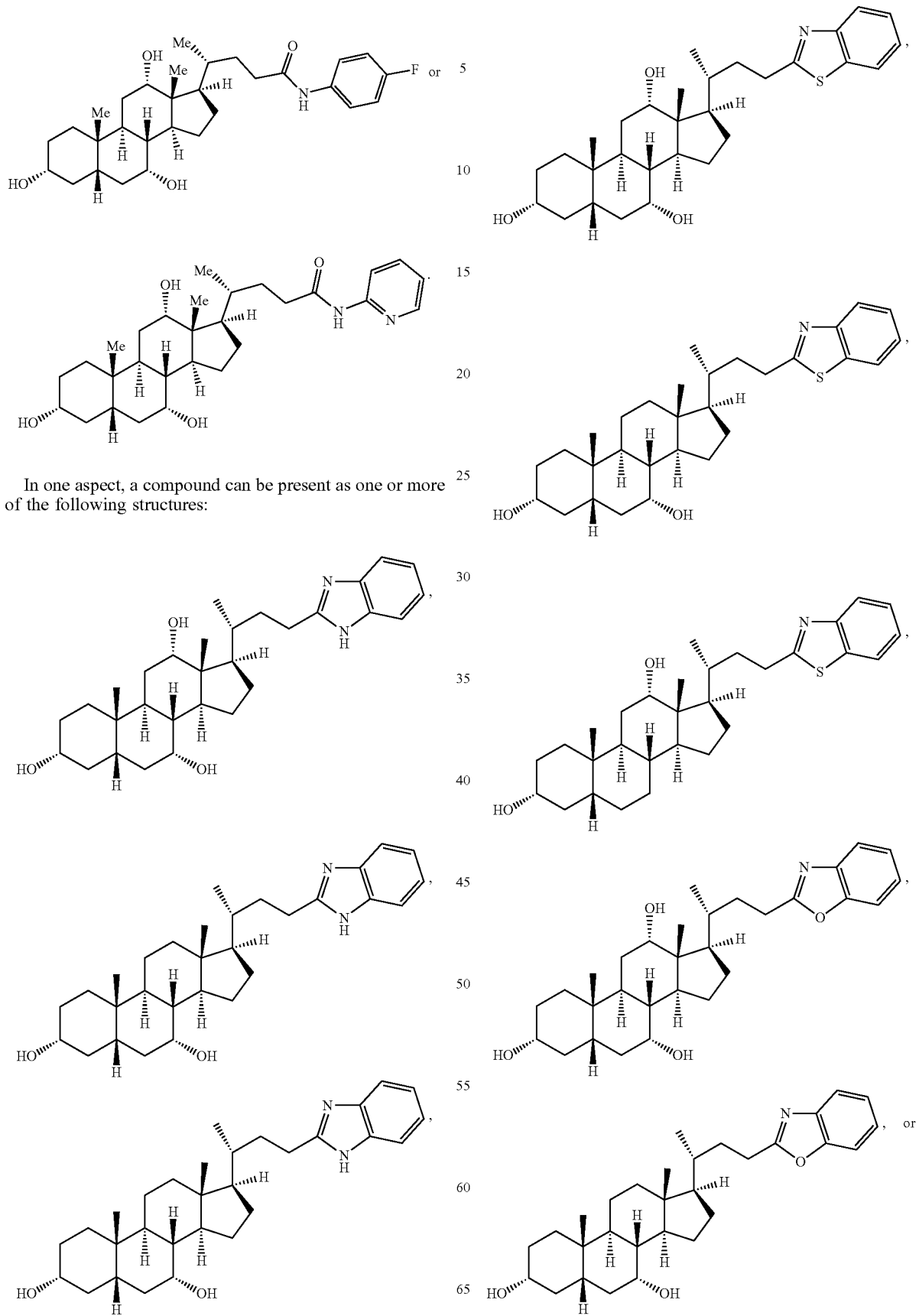
In one aspect, a compound can be present as one or more of the following structures:
-continued

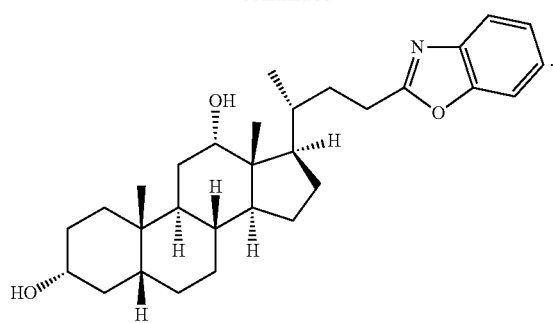
In one aspect, a compound can be present as one or more of the following structures:
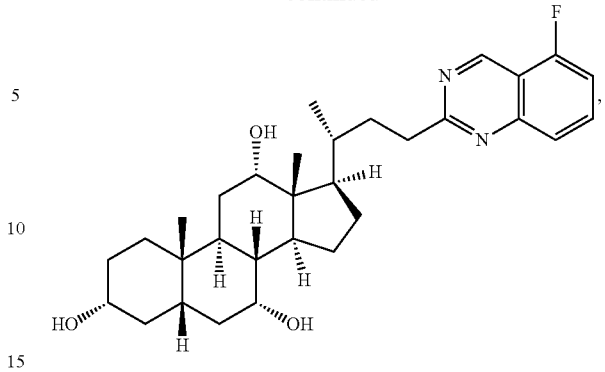
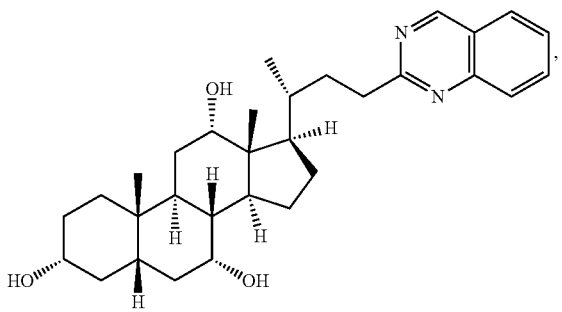
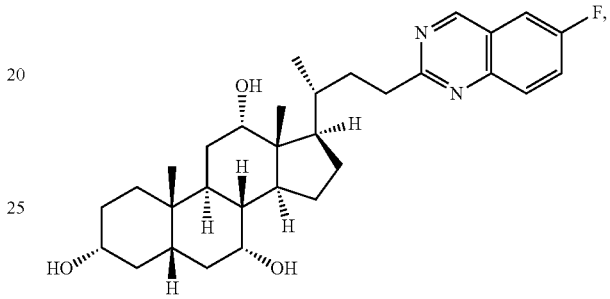
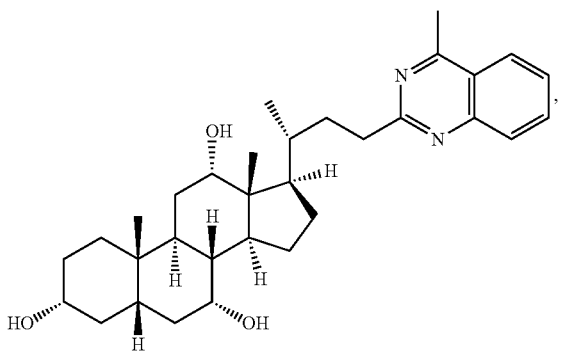
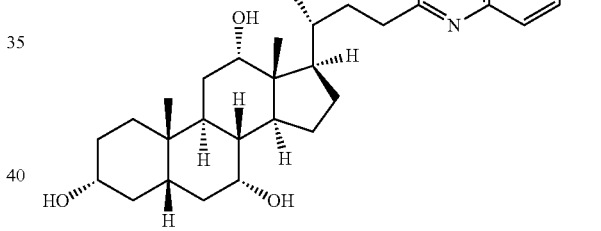
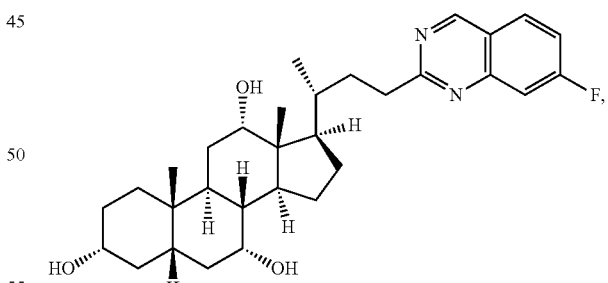
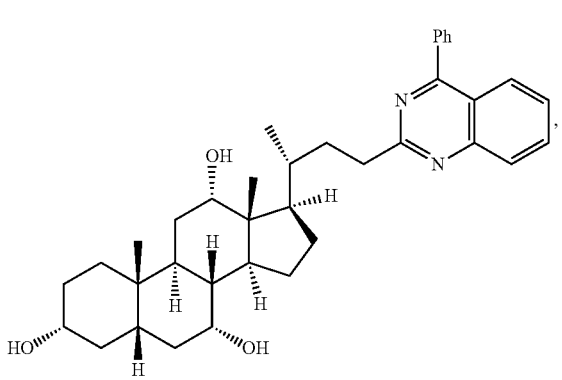
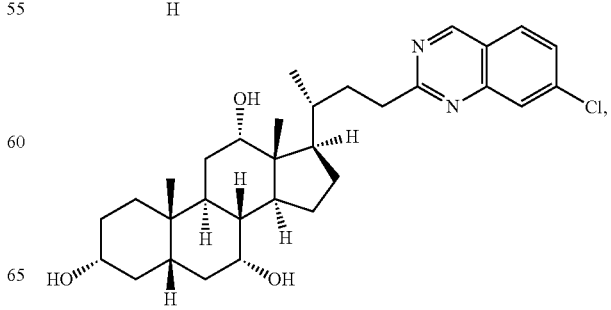

-continued

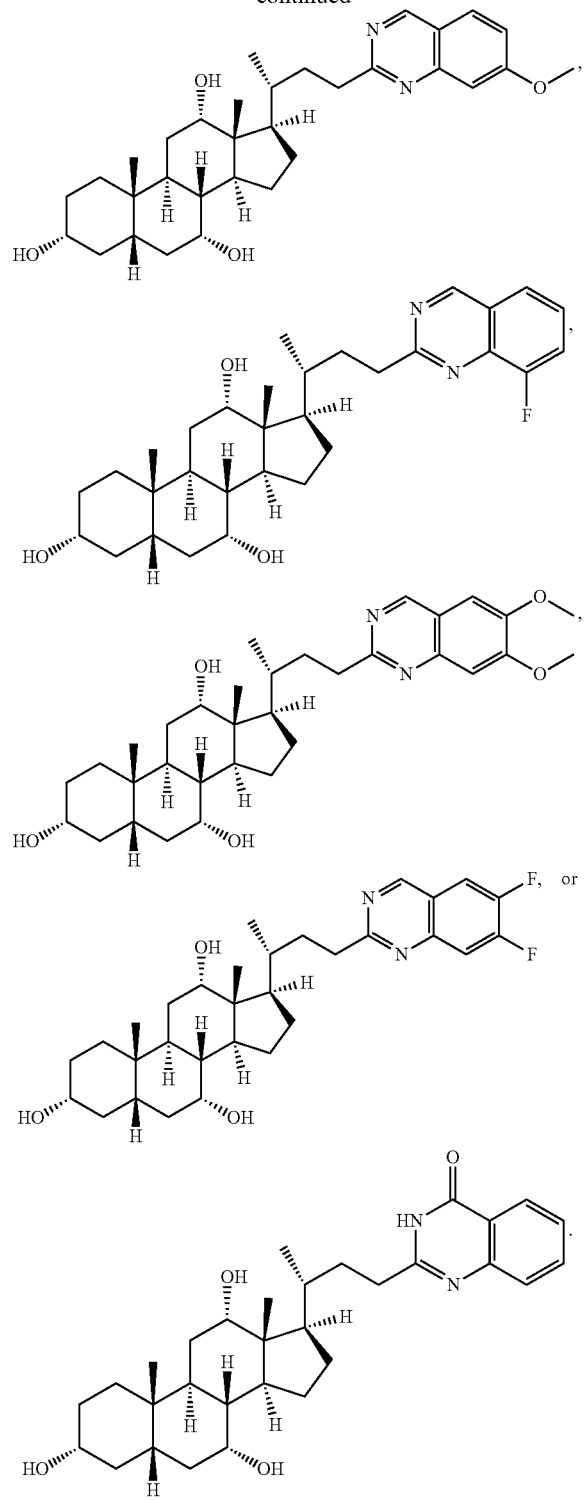

3. Prophetic Compound Examples

The following compound examples are prophetic, and can be prepared using the synthesis methods described herein above and other general methods as needed as would be known to one skilled in the art. It is anticipated that the prophetic compounds would be active as inhibitors of germination of *C. difficile* spores, and such activity can be determined using the assay methods described herein.

In one aspect, a compound can be selected from:

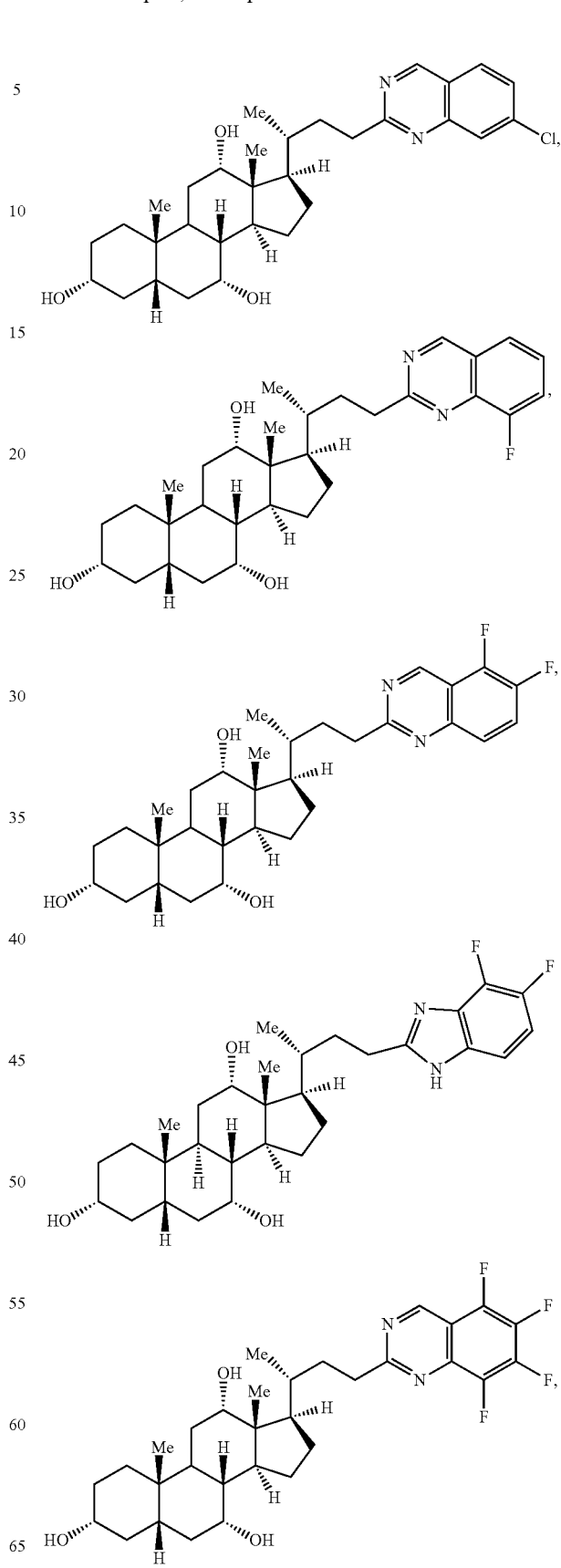

175
-continued
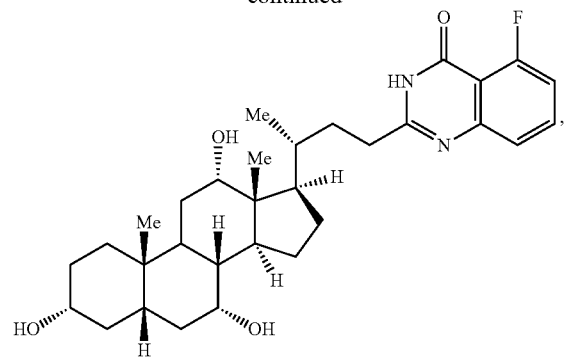
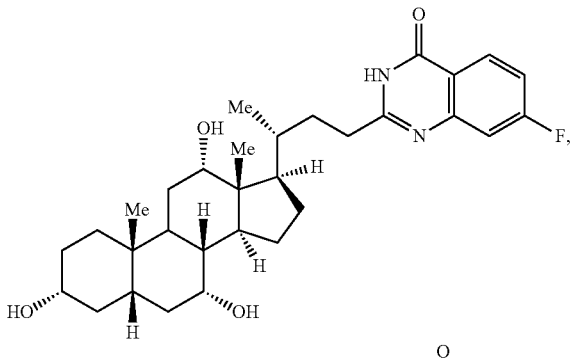
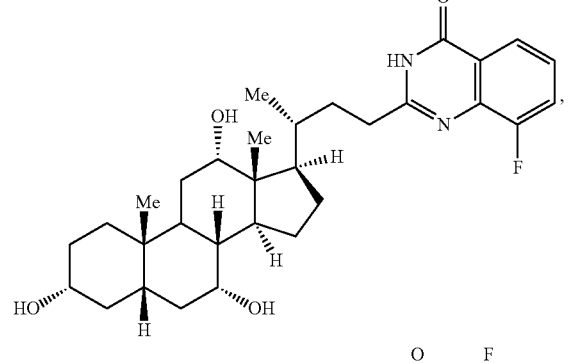
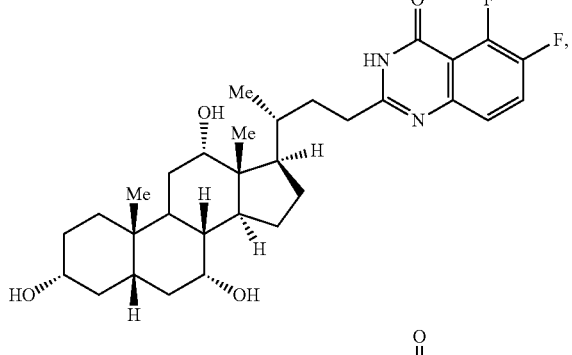
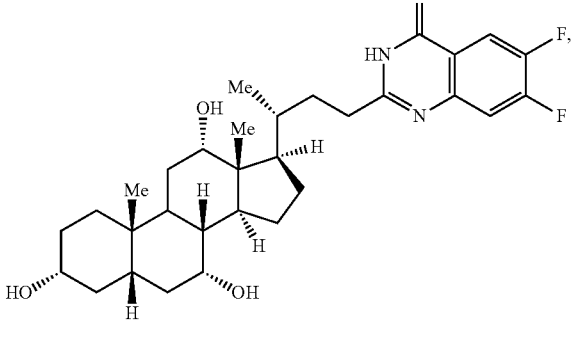
176
-continued
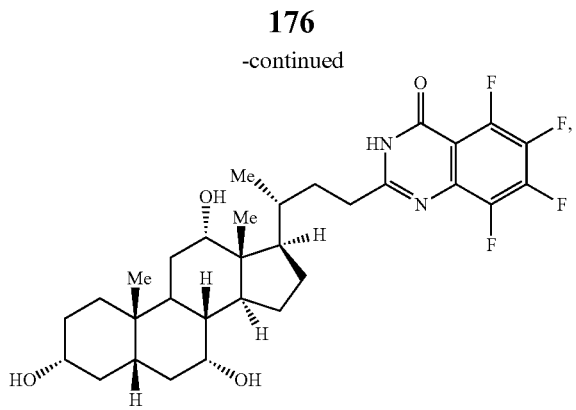
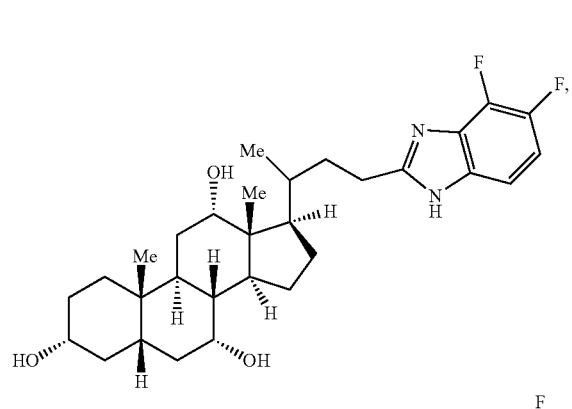
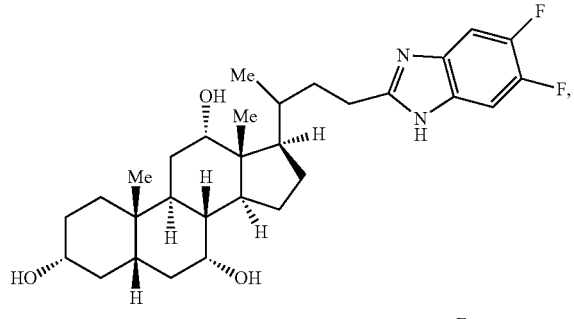
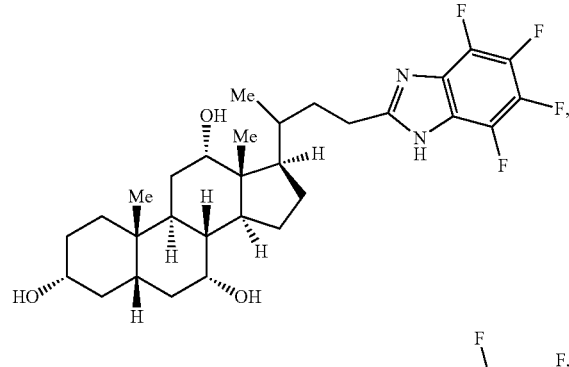
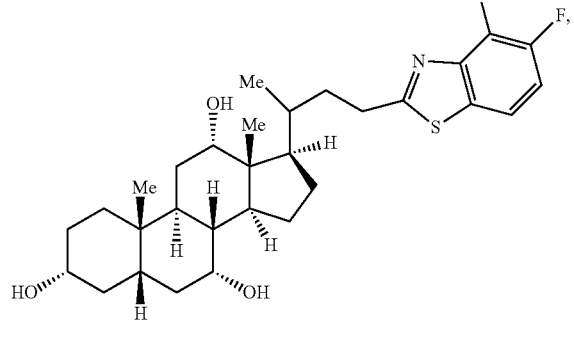

177
-continued
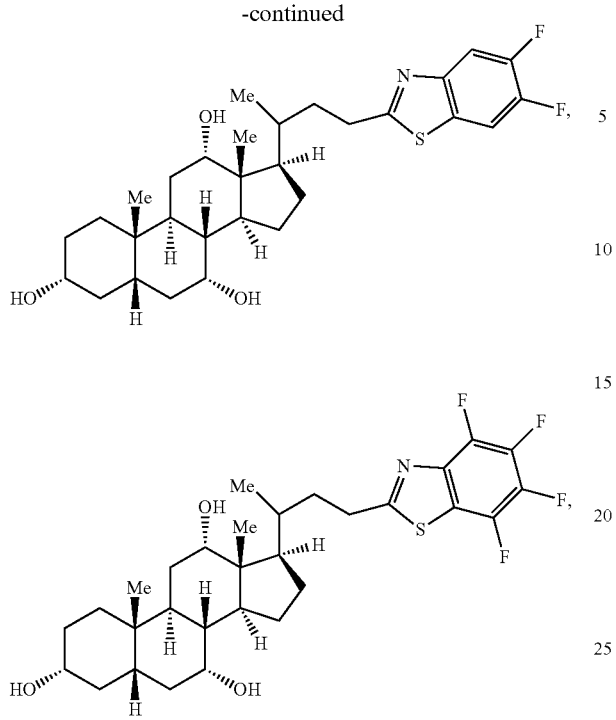
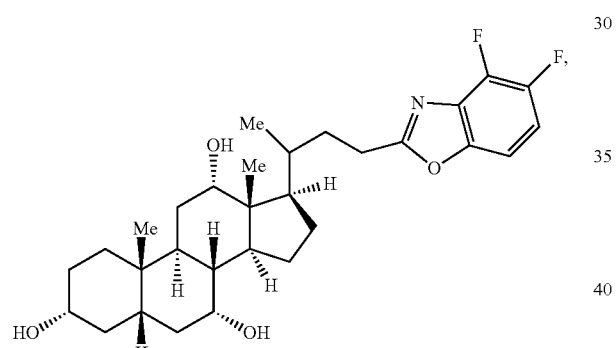
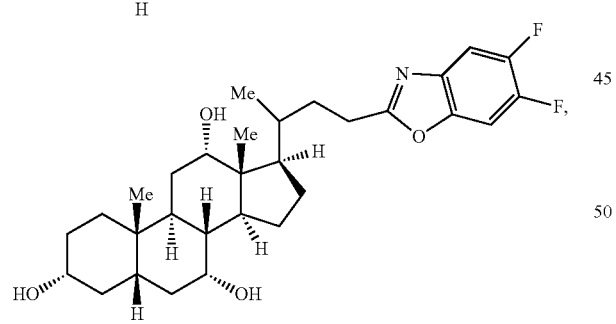
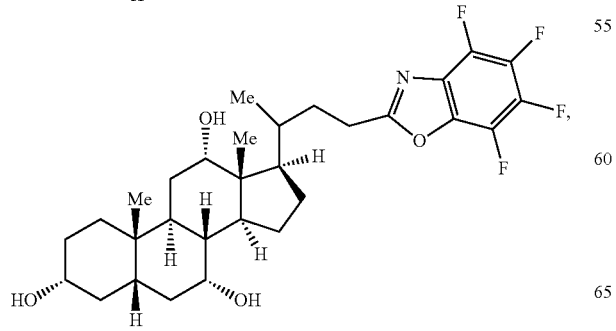
178
-continued
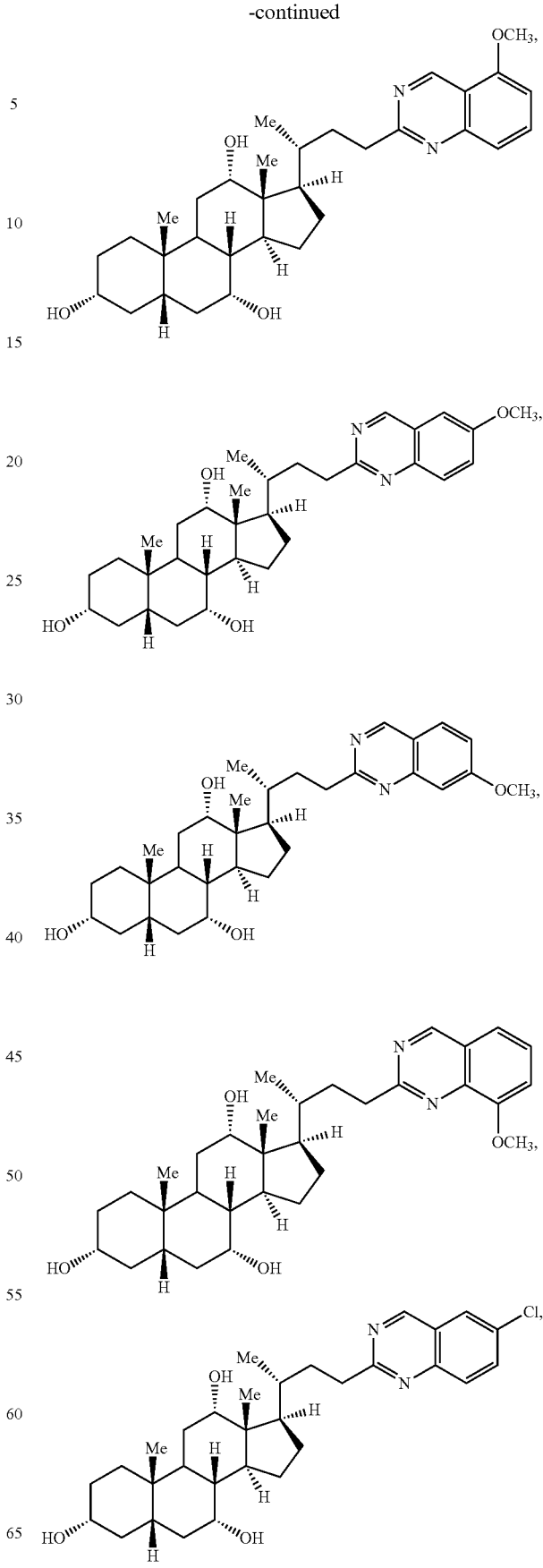

179
-continued
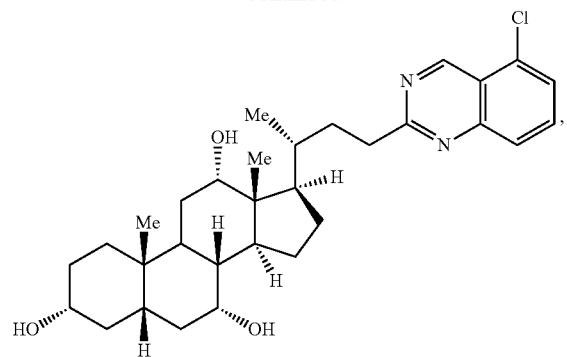
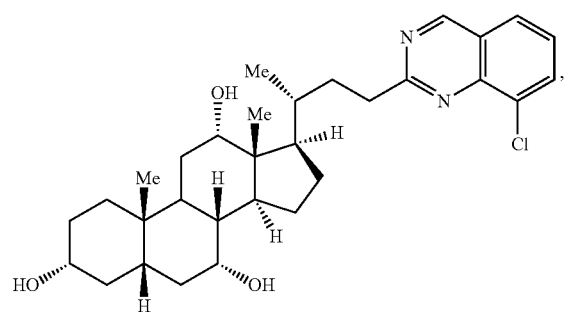
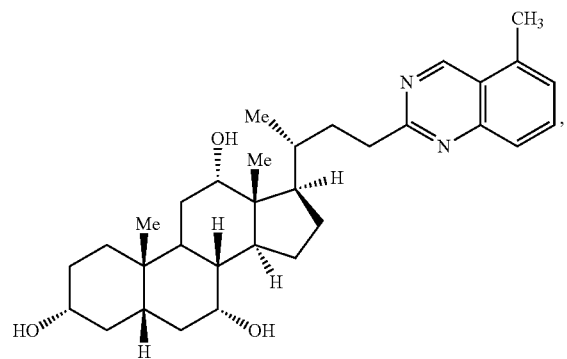
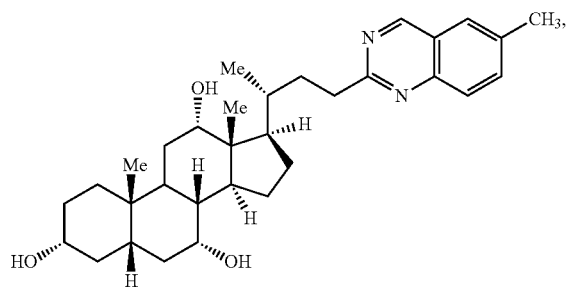
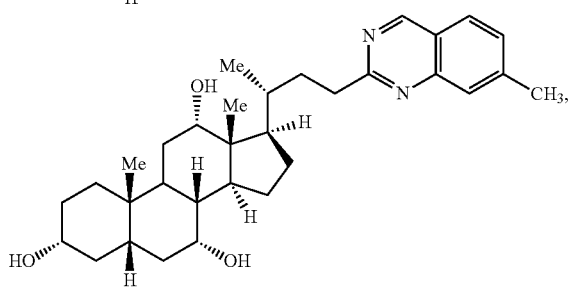
180
-continued
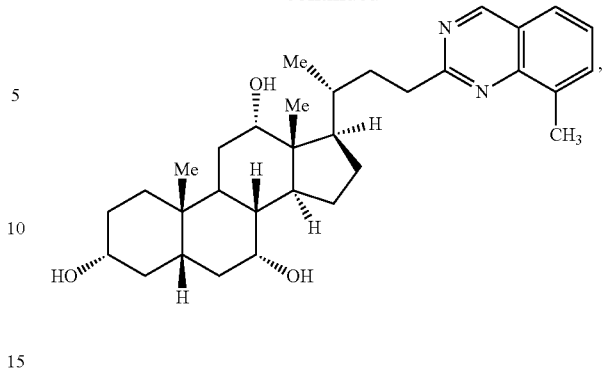
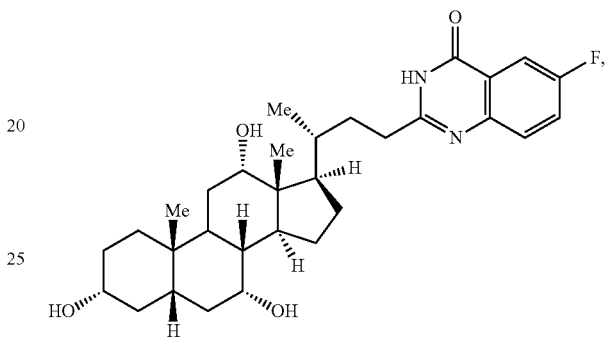
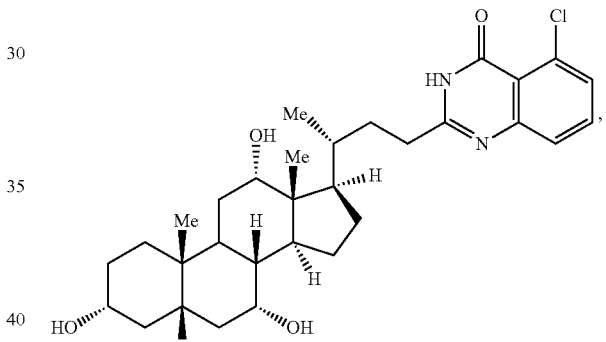
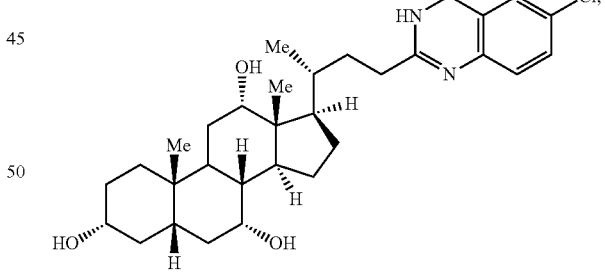
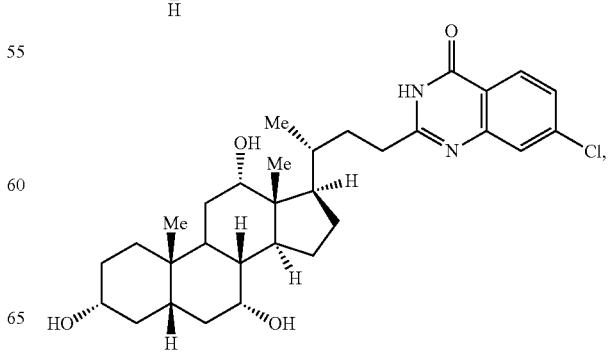

-continued
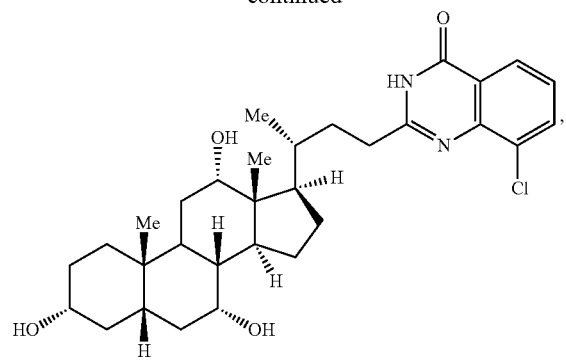
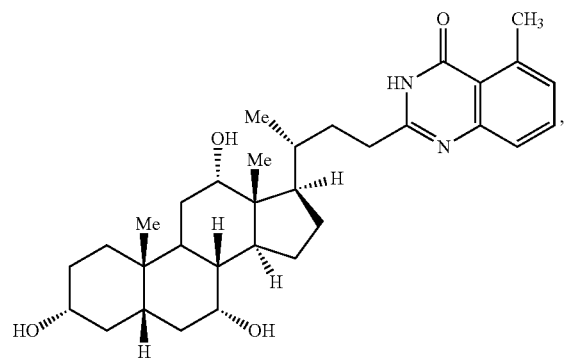
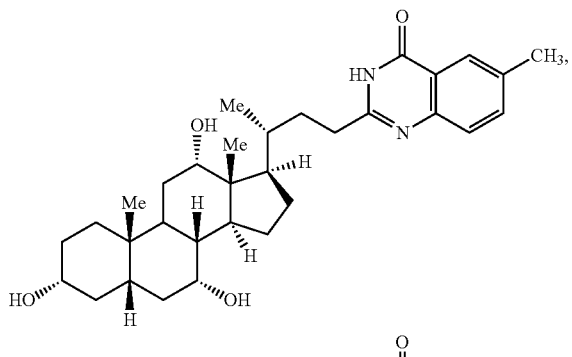
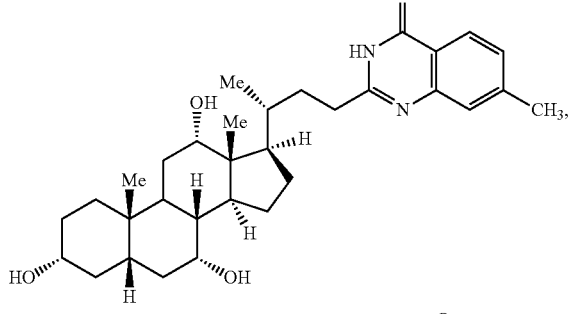
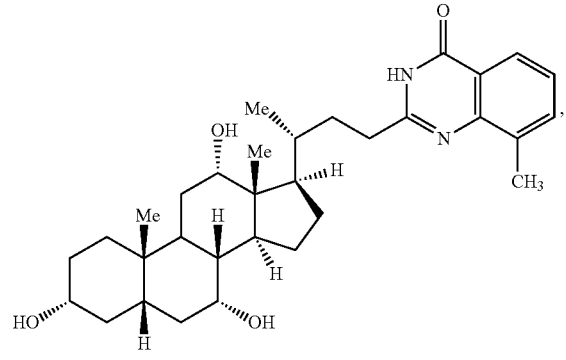
-continued
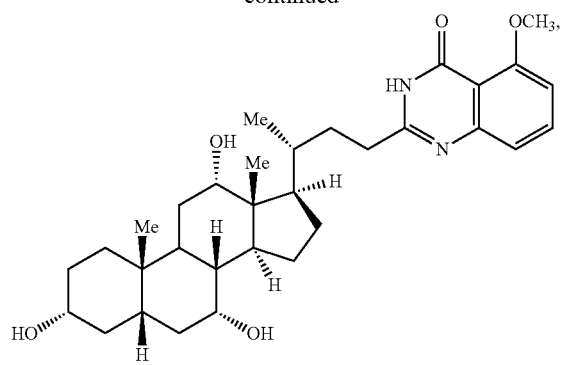
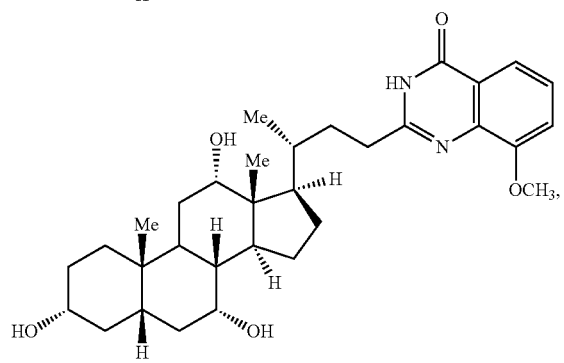
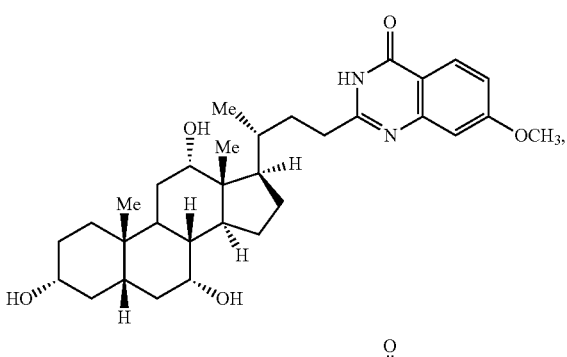
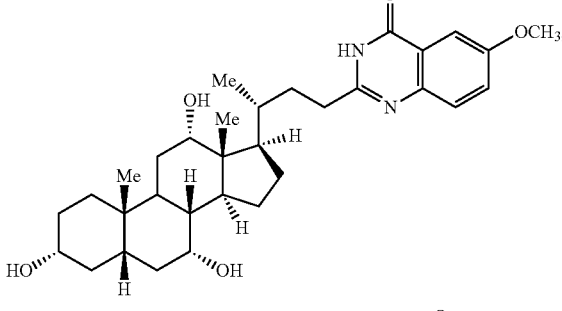
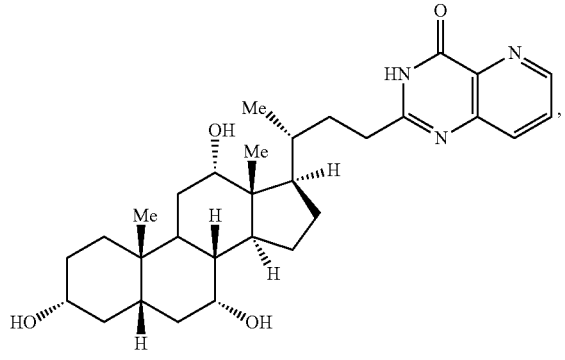

183
-continued
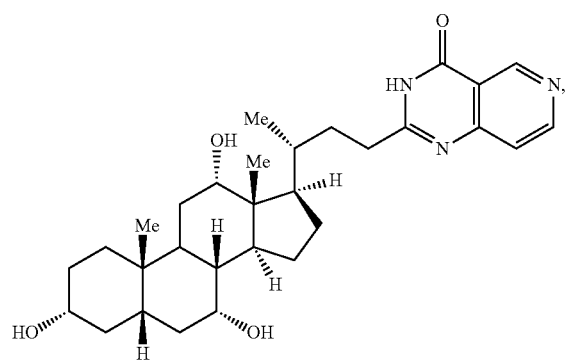
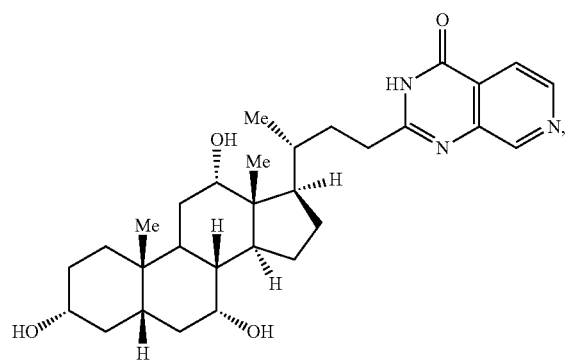
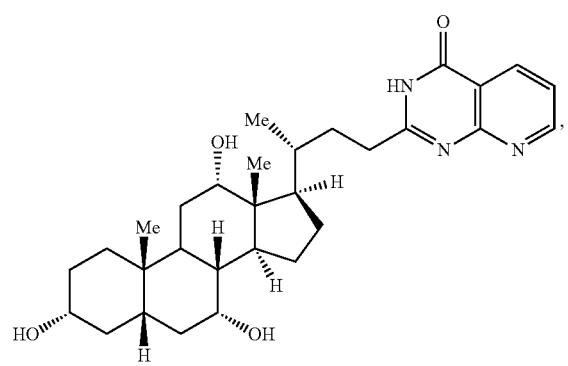
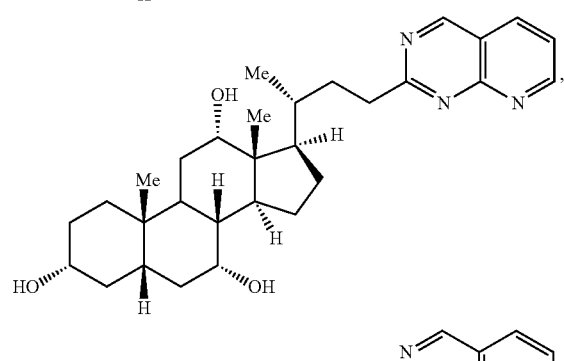
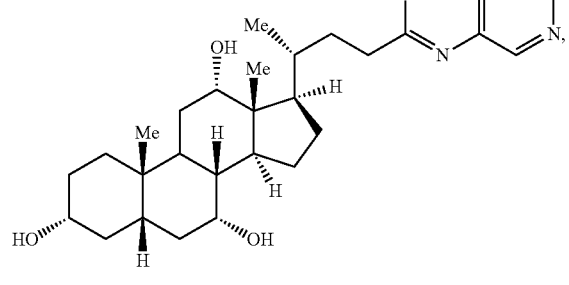
184
-continued
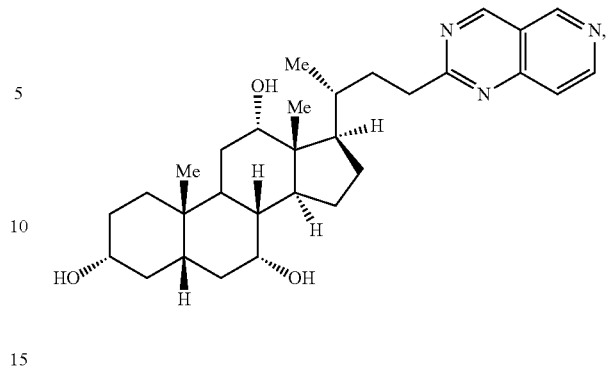

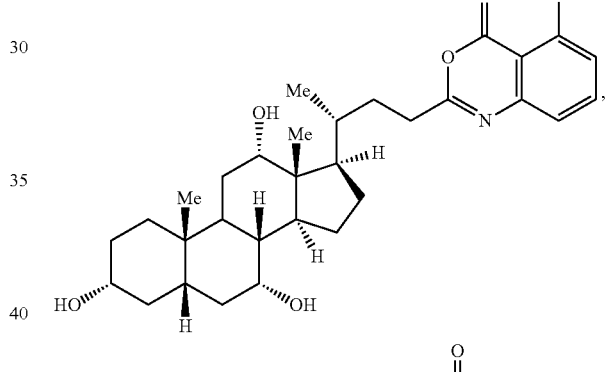
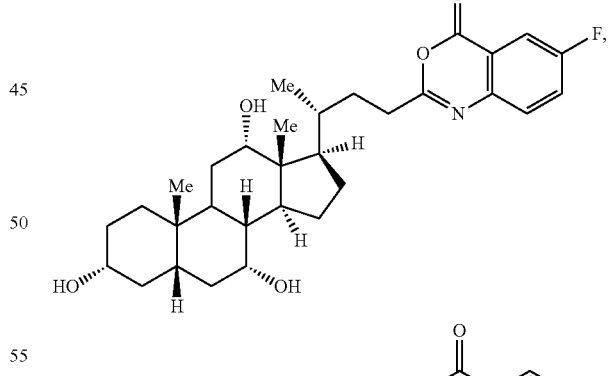
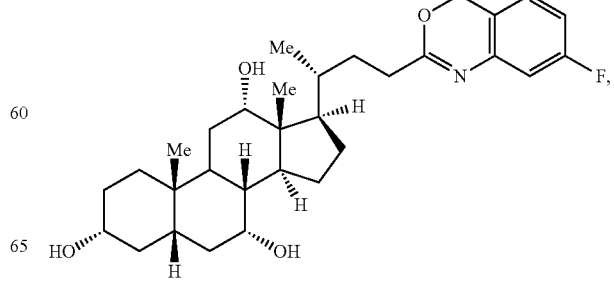

-continued
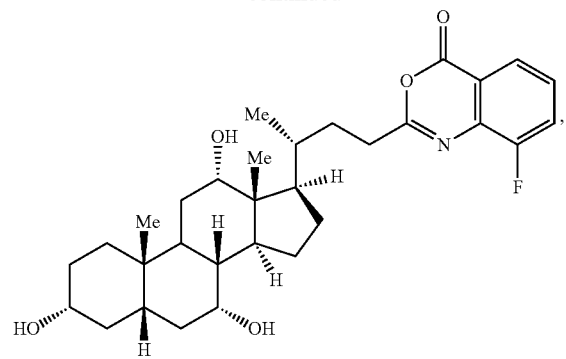
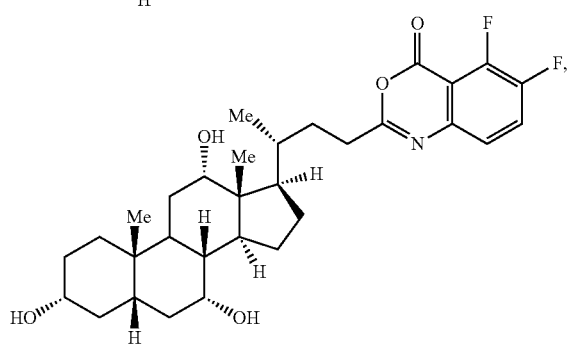
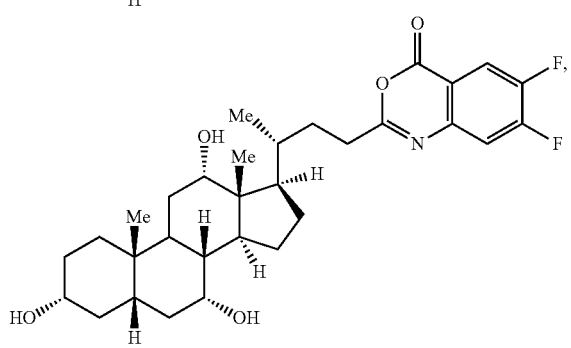
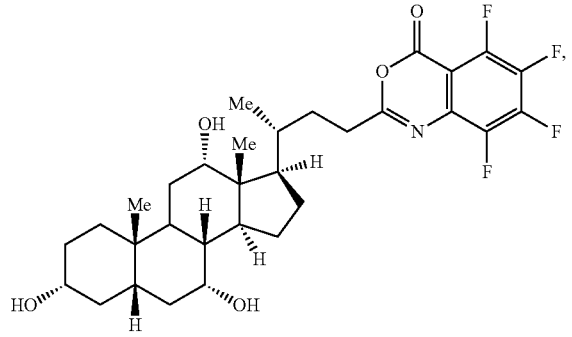
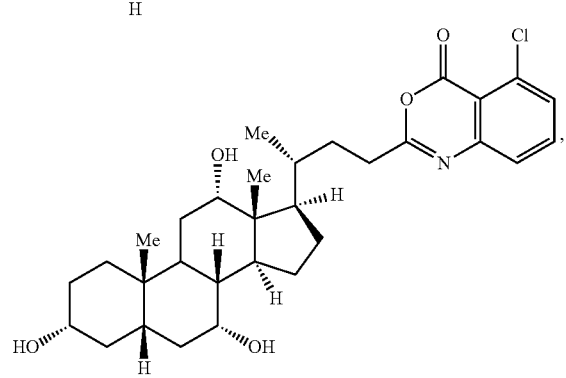
-continued
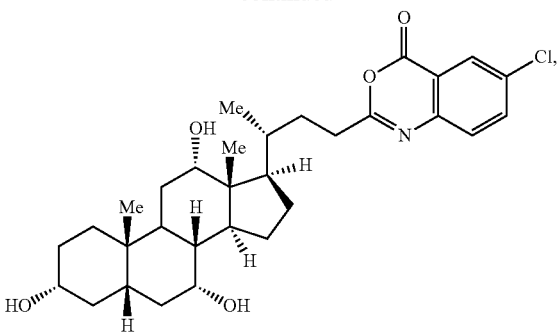
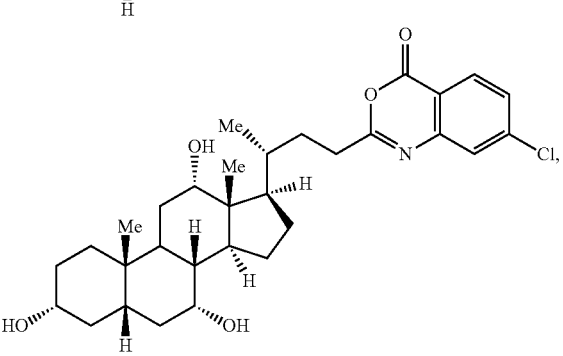
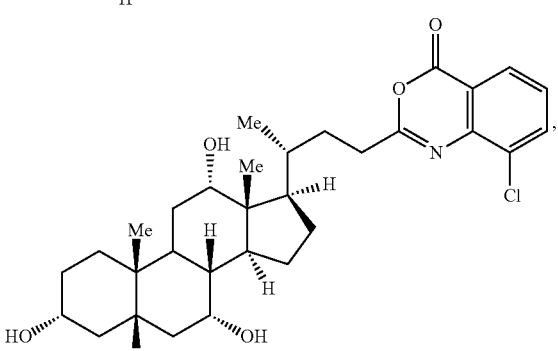
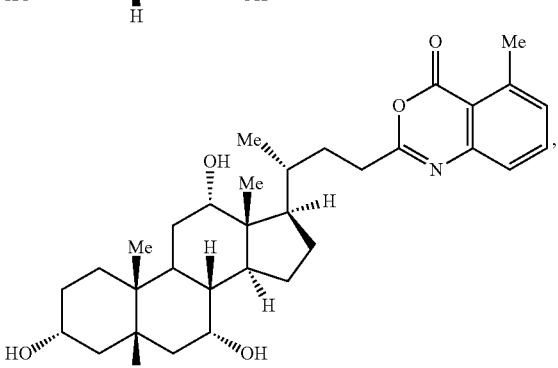
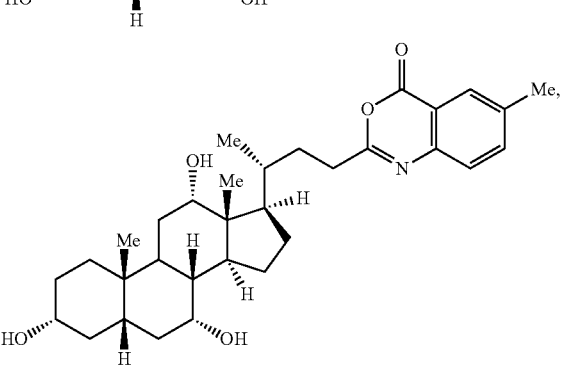

187
-continued
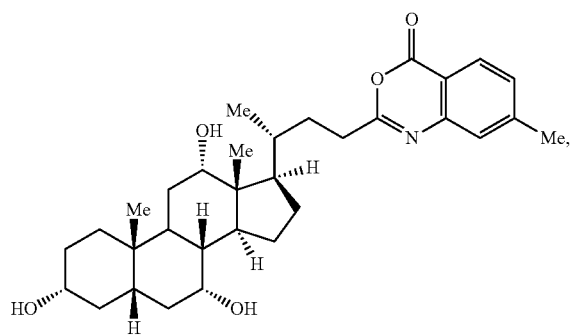
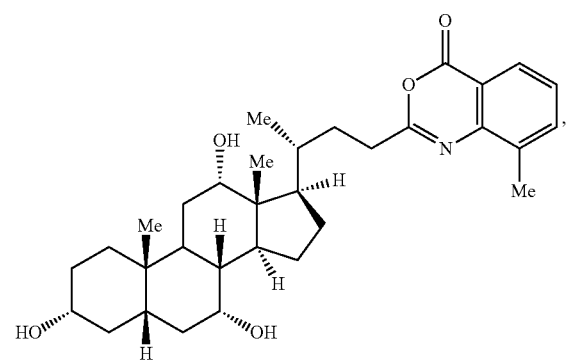
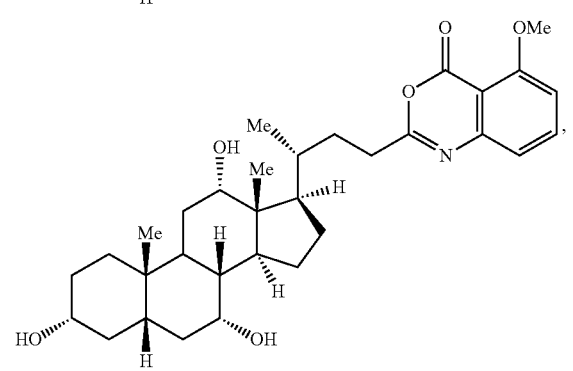
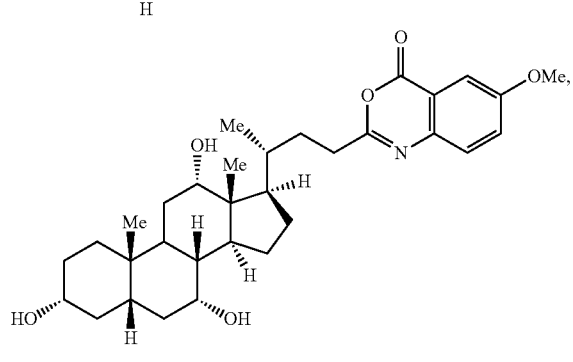
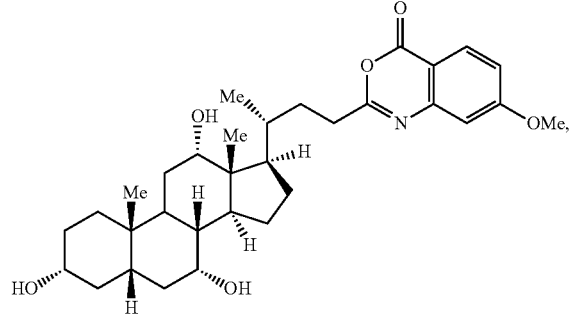
188
-continued
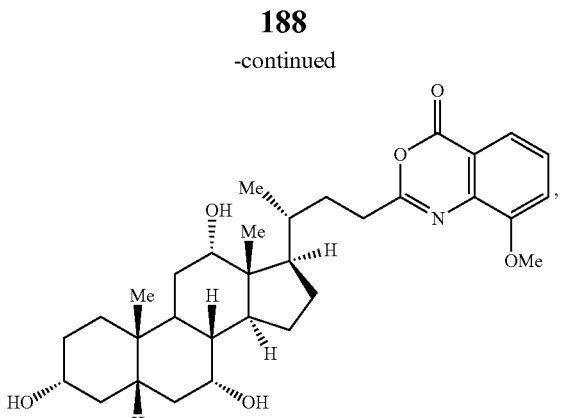
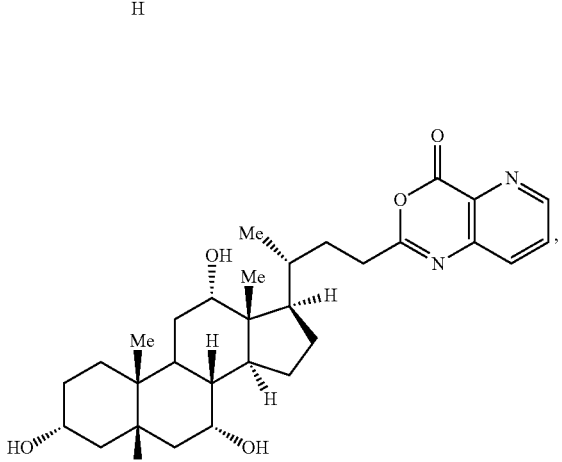
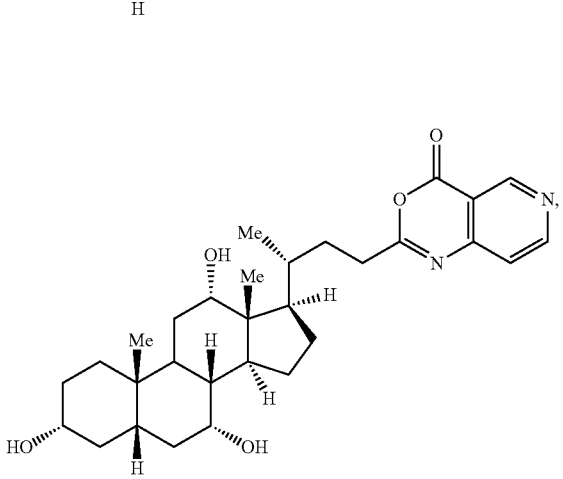
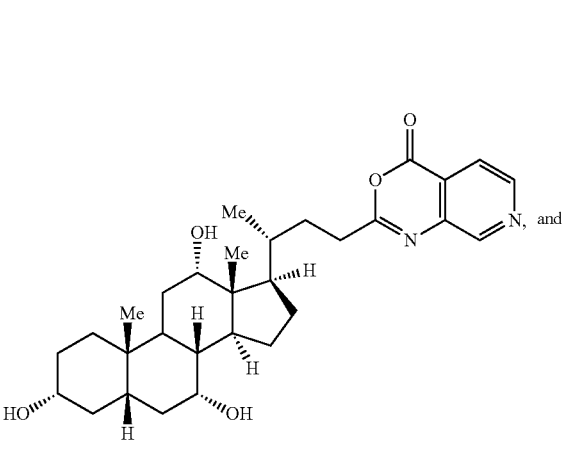

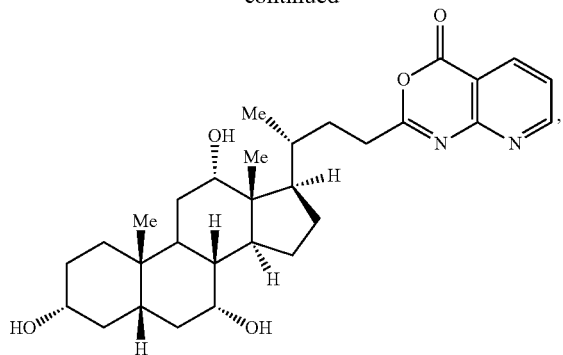
or a pharmaceutically acceptable salt thereof.
In one aspect, a compound can be selected from:
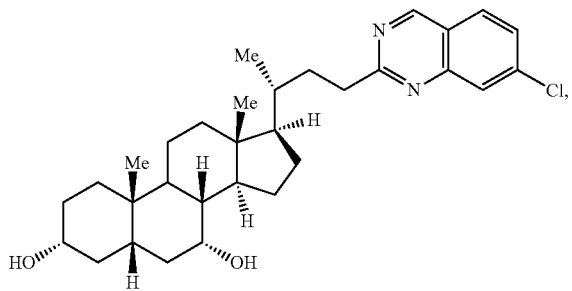
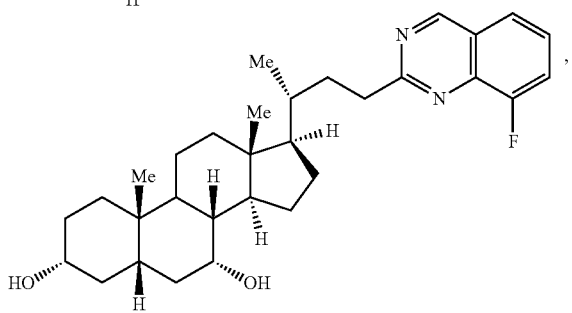
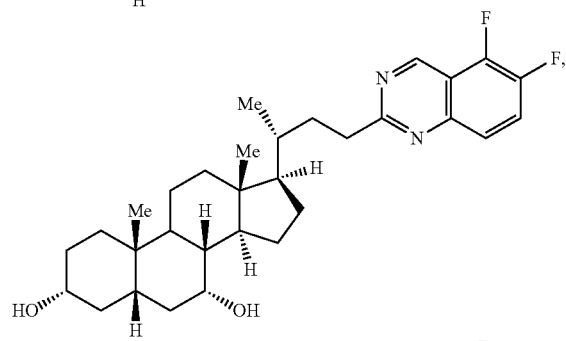
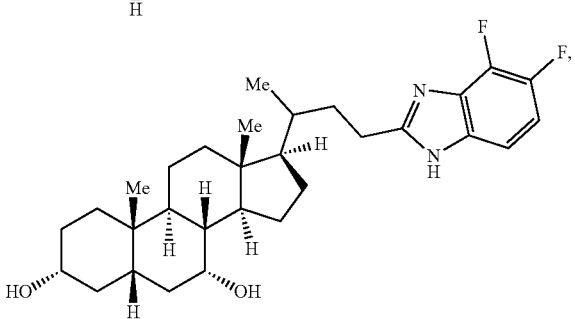
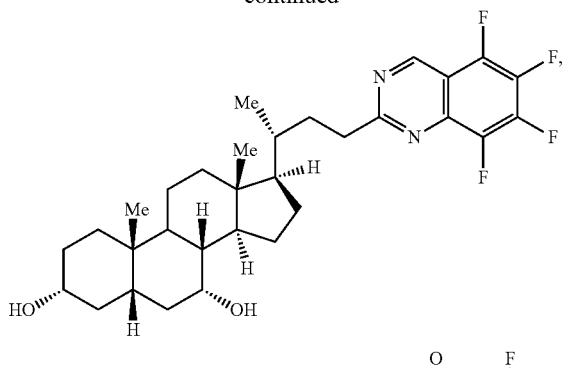
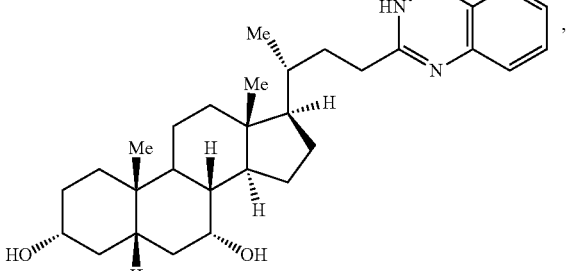
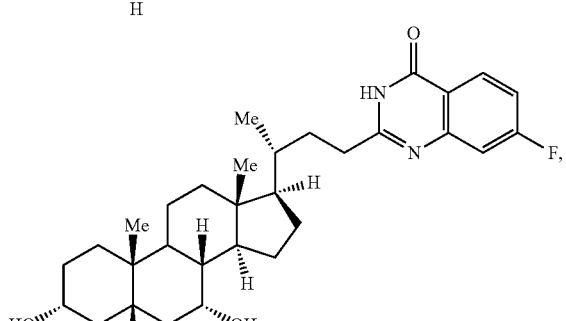
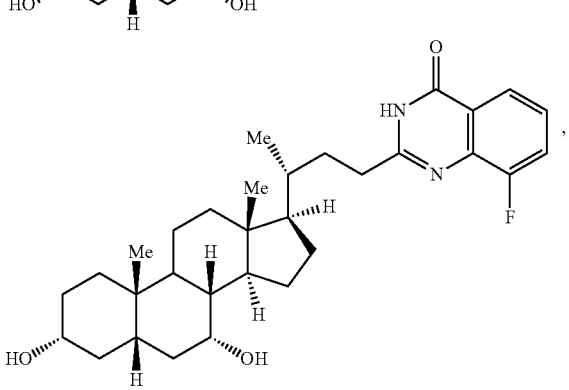
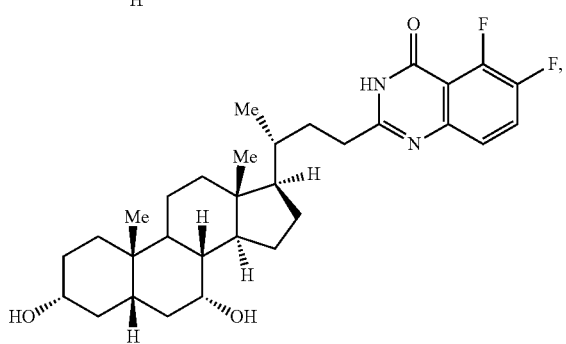

191
-continued
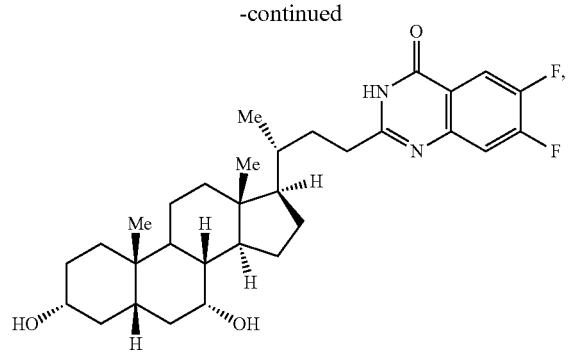
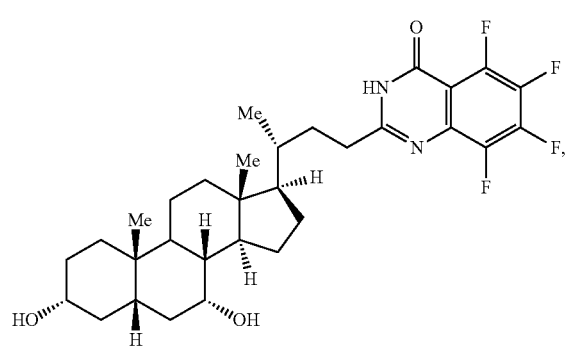
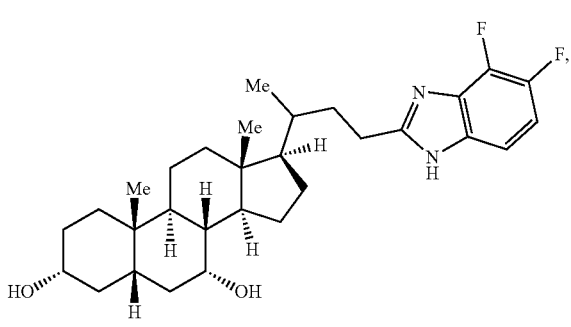
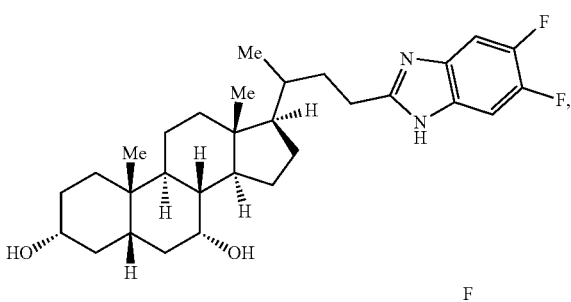
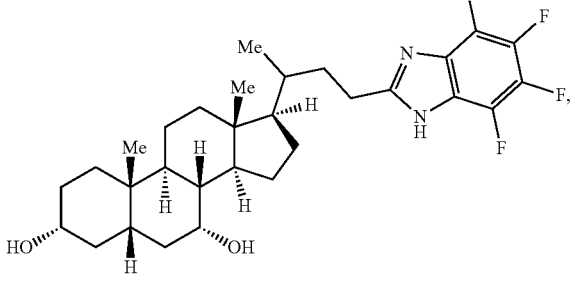
192
-continued
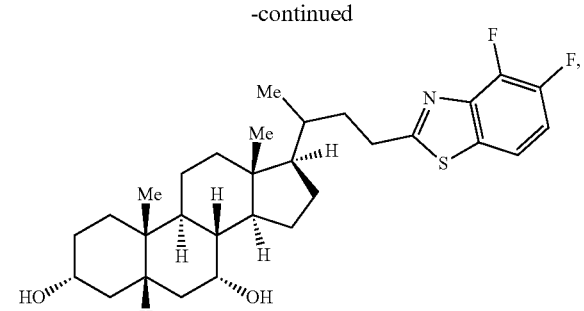
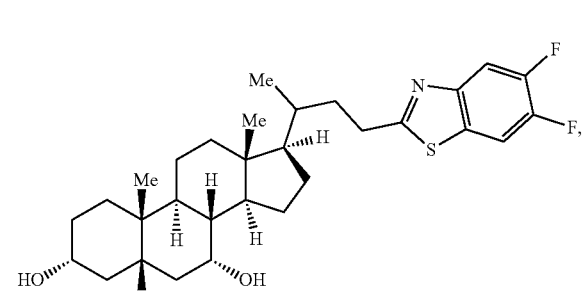
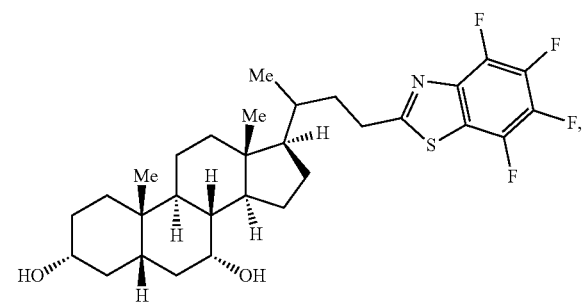
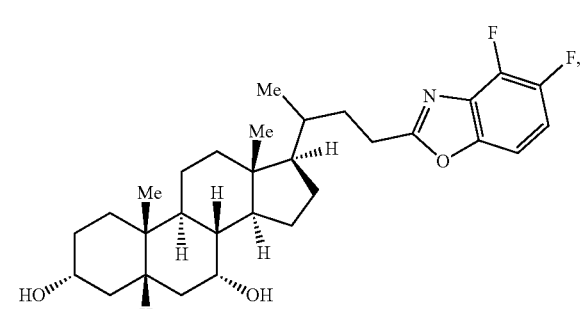
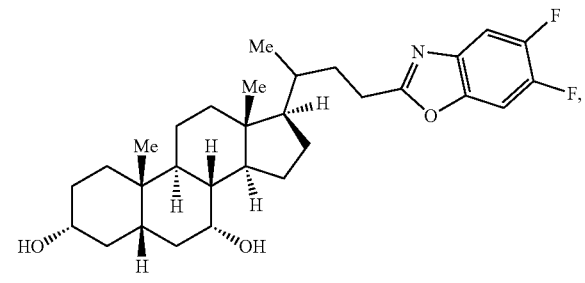

193
-continued
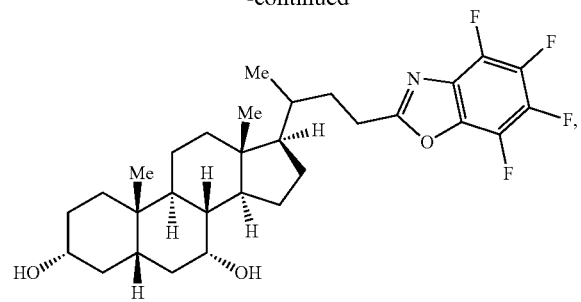
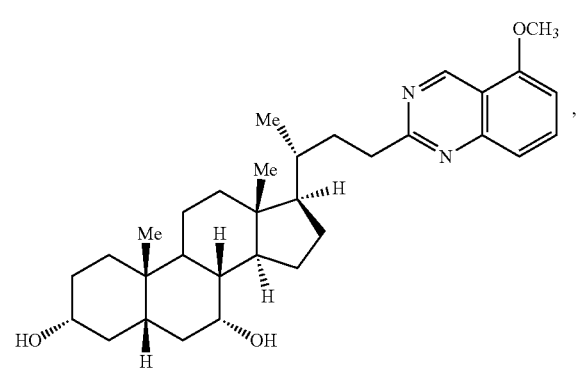
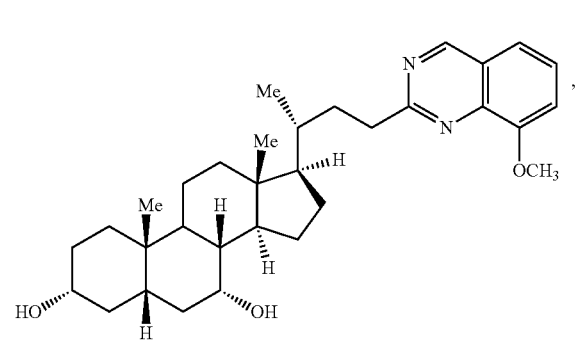
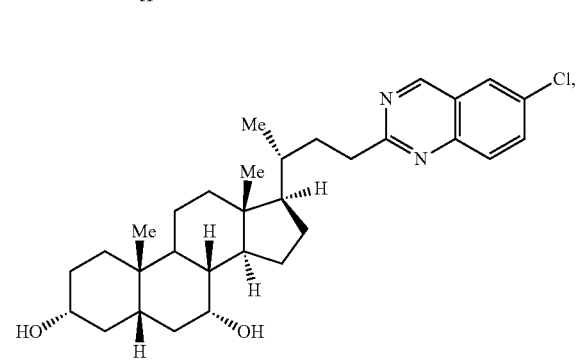
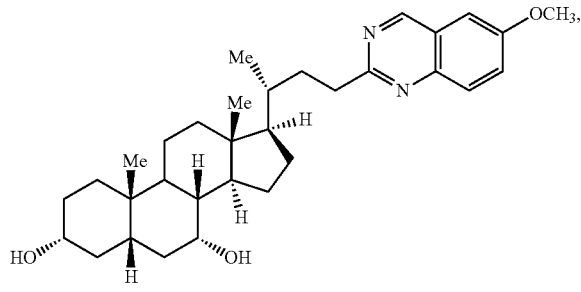
194
-continued
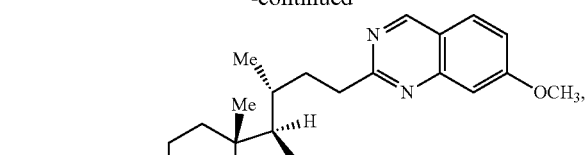
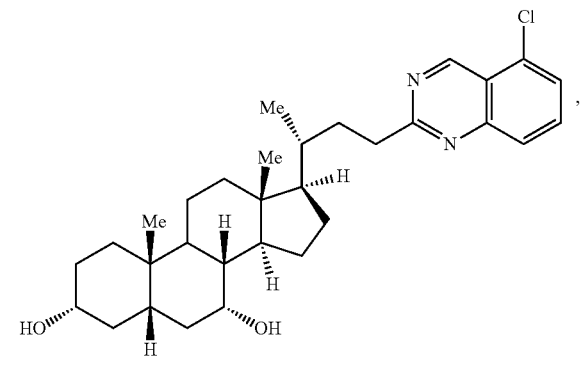
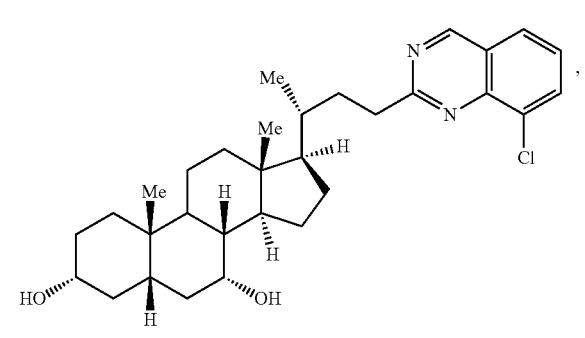
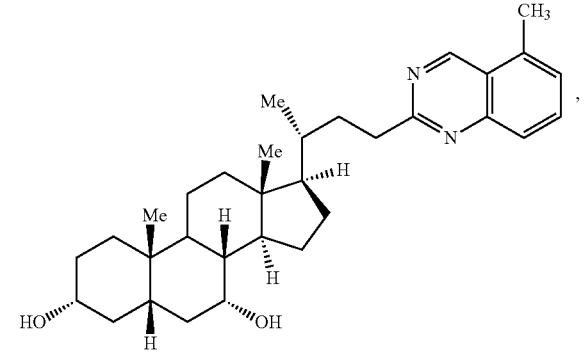
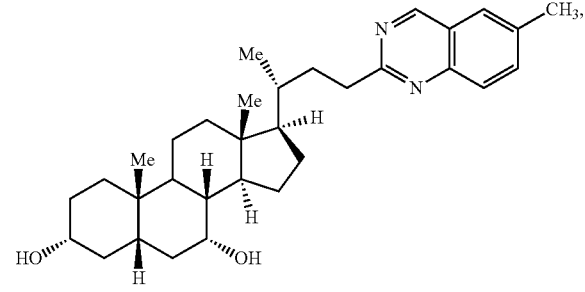

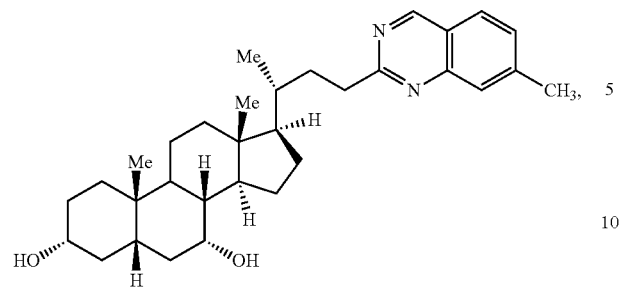
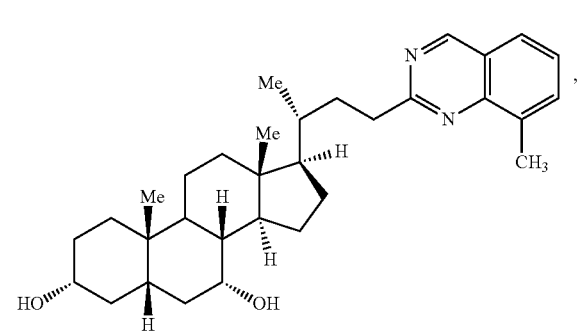
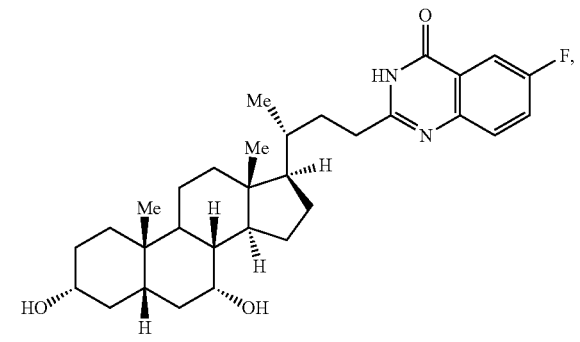
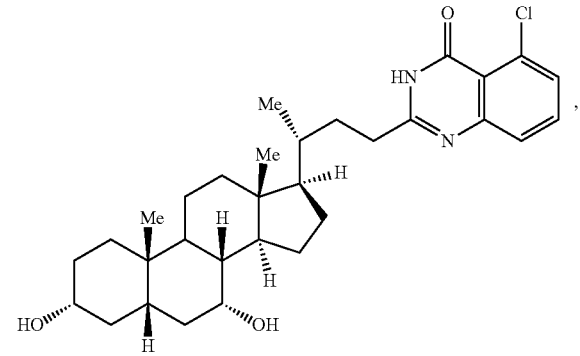
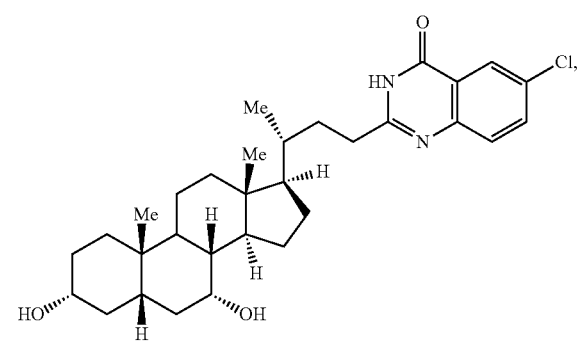
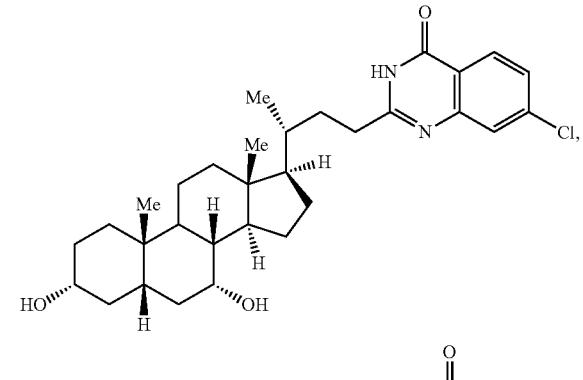
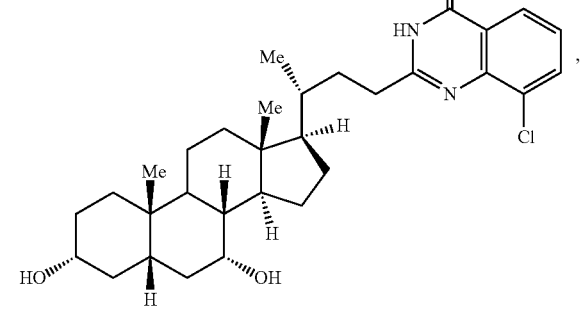
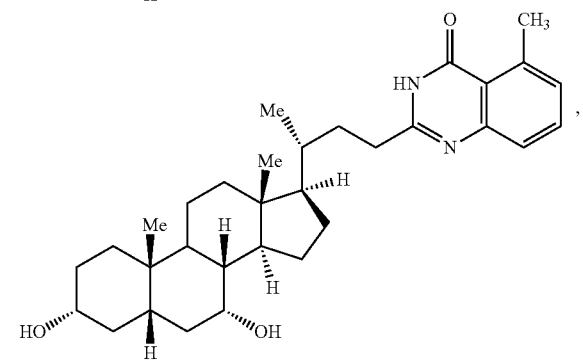
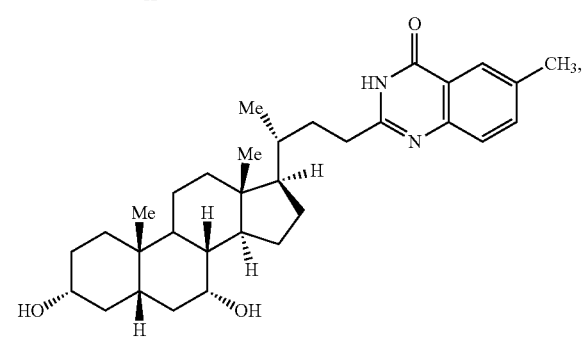
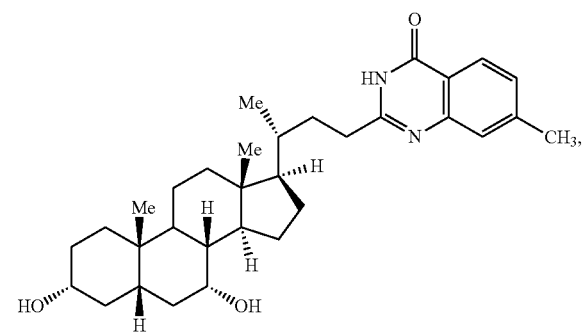

197
-continued
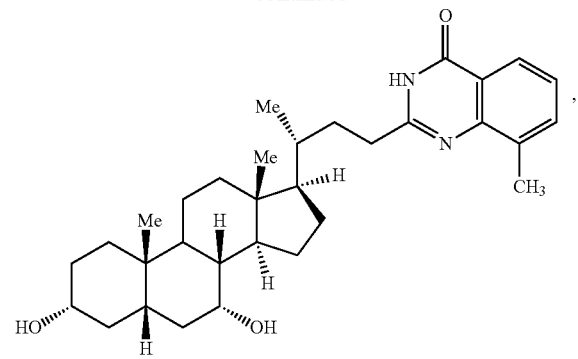
,
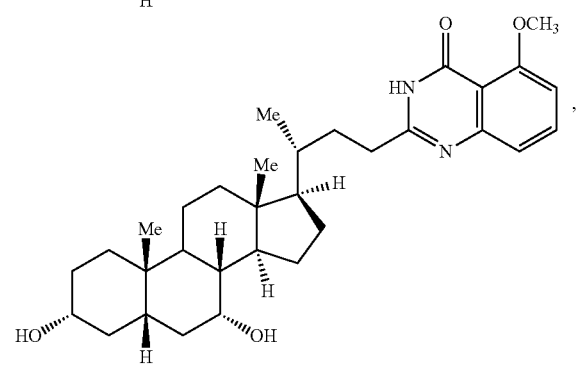
,
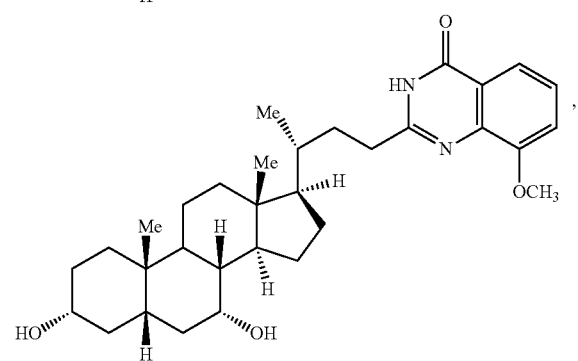
,
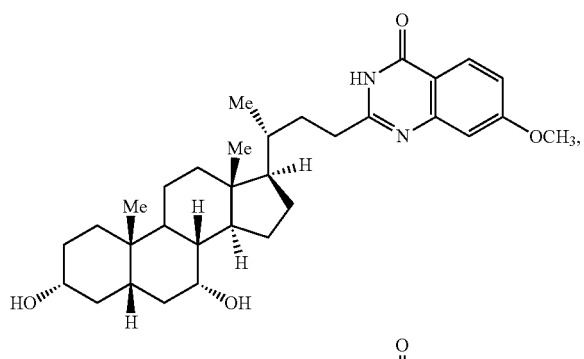
,
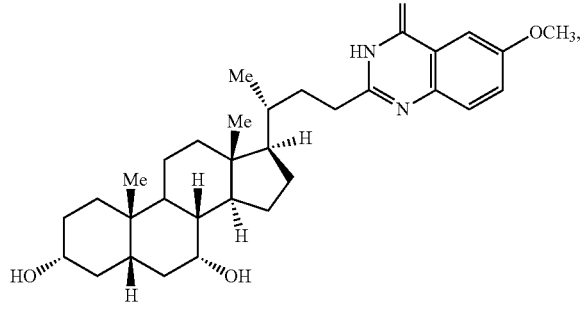
198
-continued
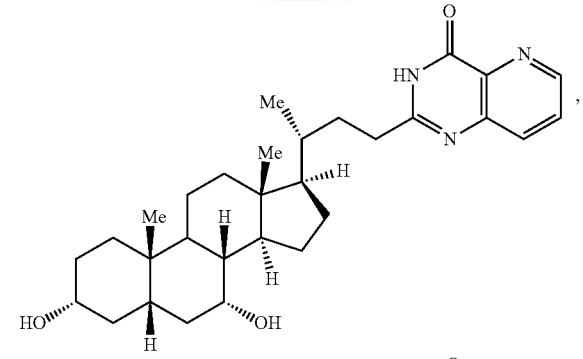
,
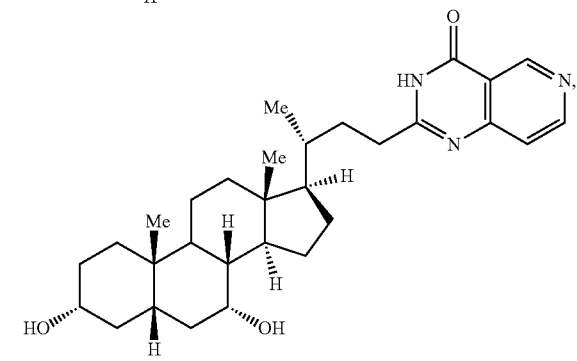
,
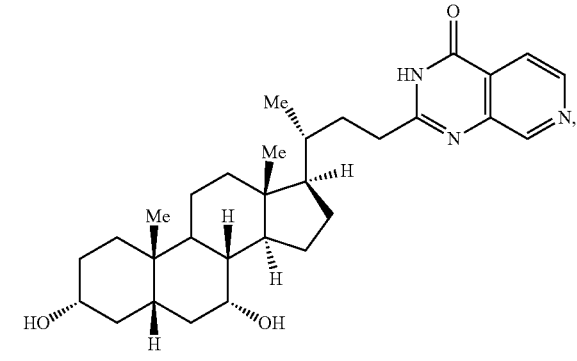
,
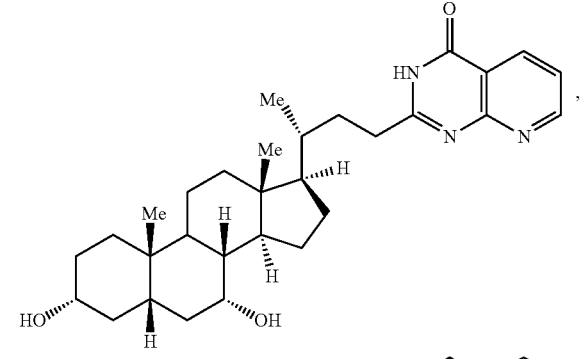
,
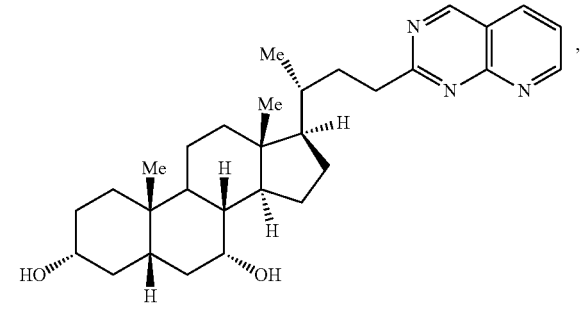
, 199
-continued
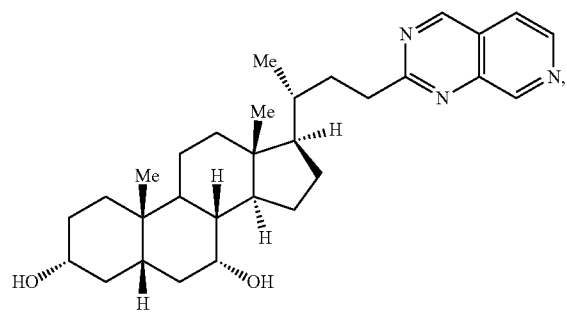
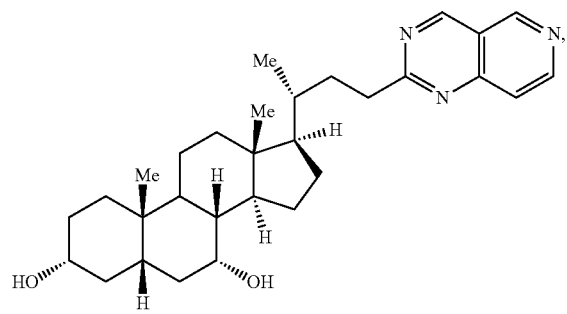
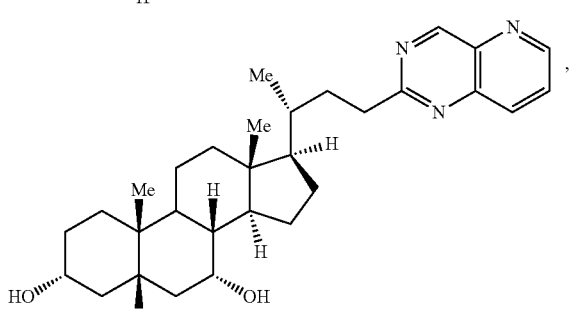
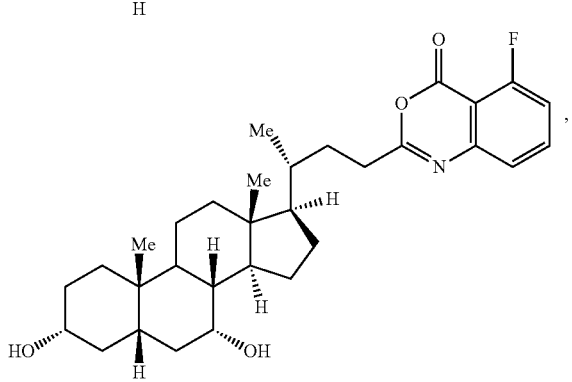
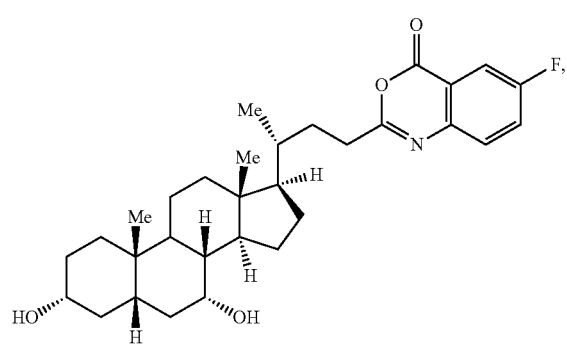
200
-continued
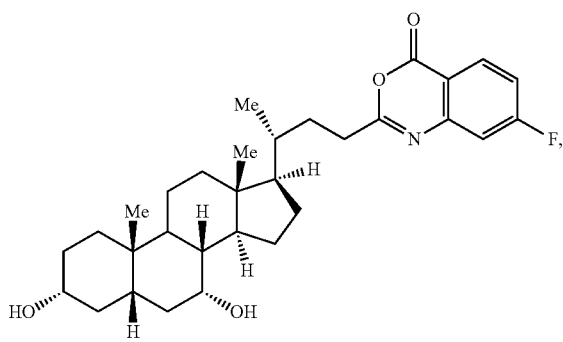
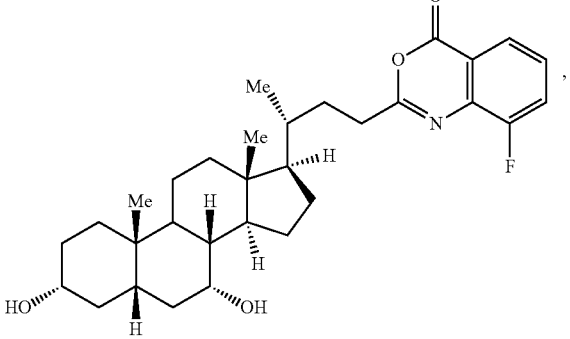
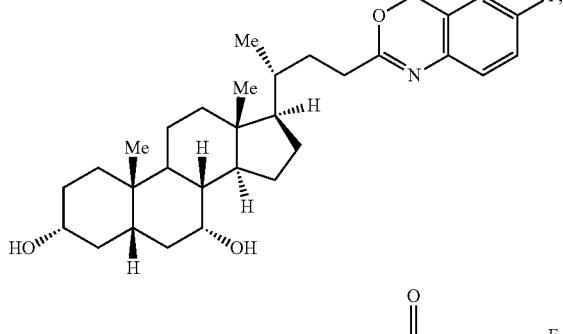
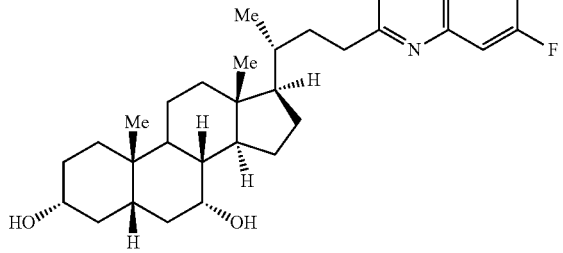
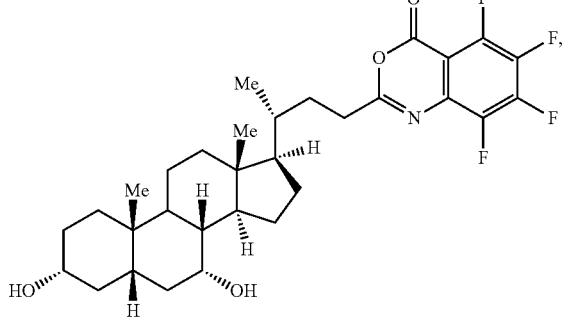

201
-continued
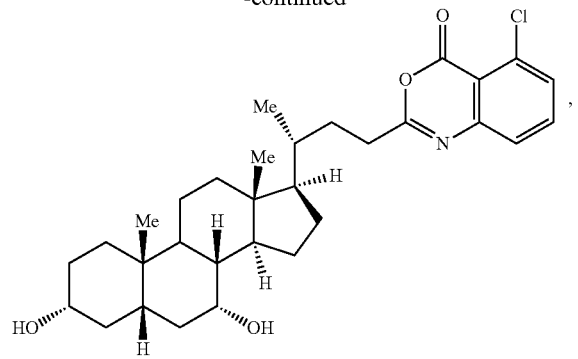
,
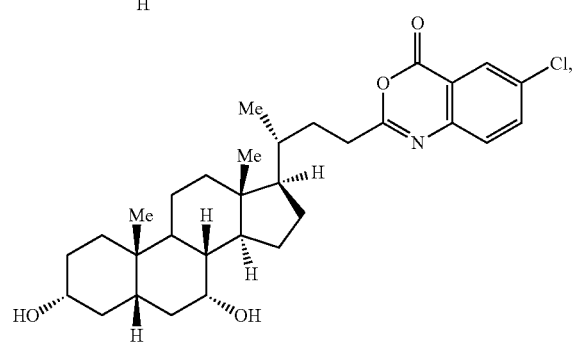
,
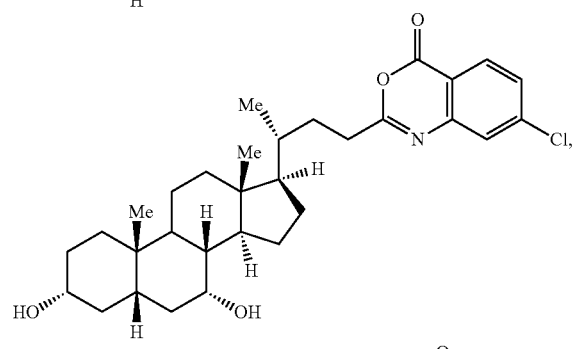
,
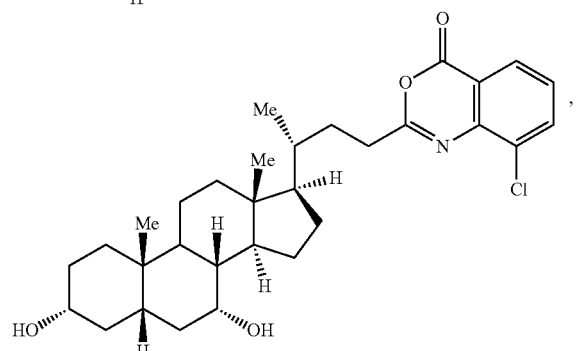
,
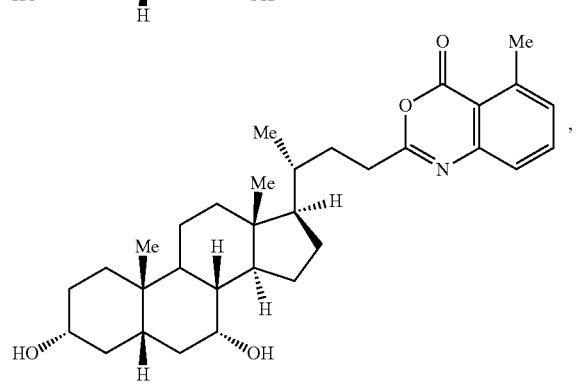
,
202
-continued
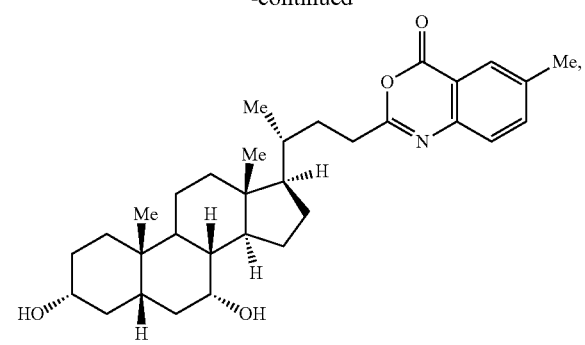
,
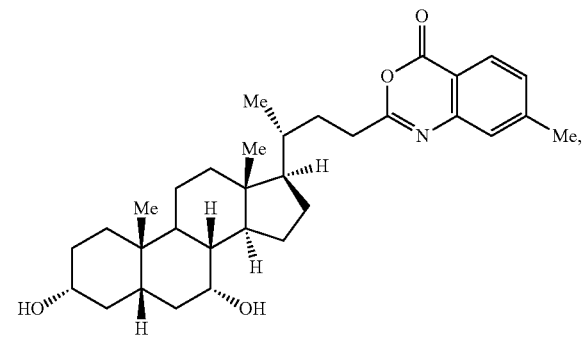
,
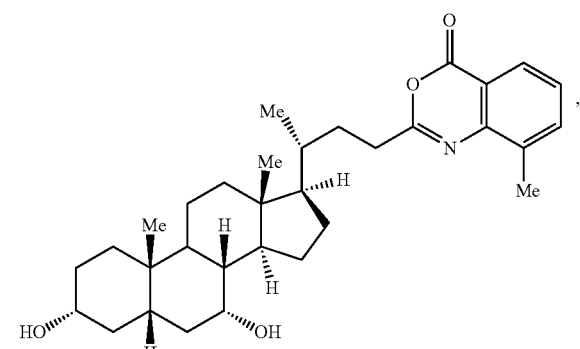
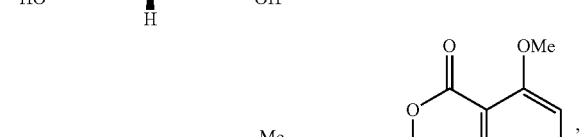
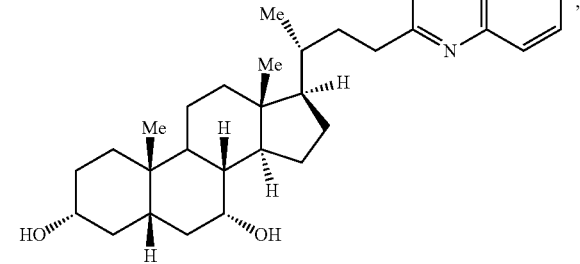
,
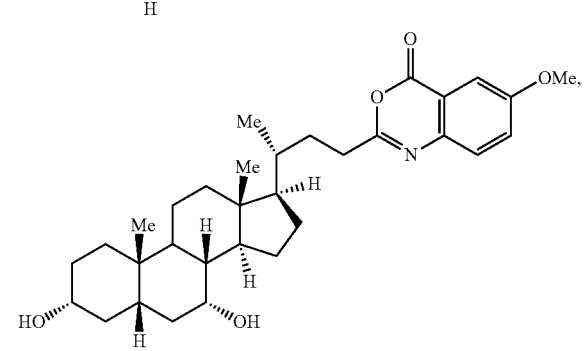
, 203
-continued
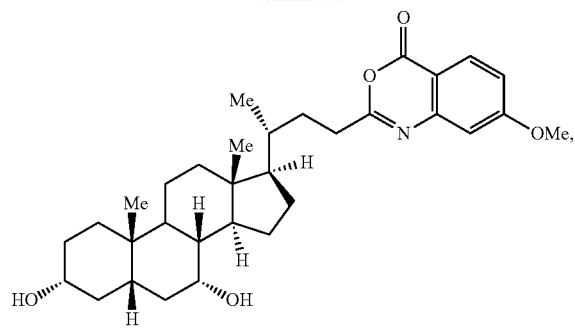
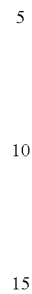
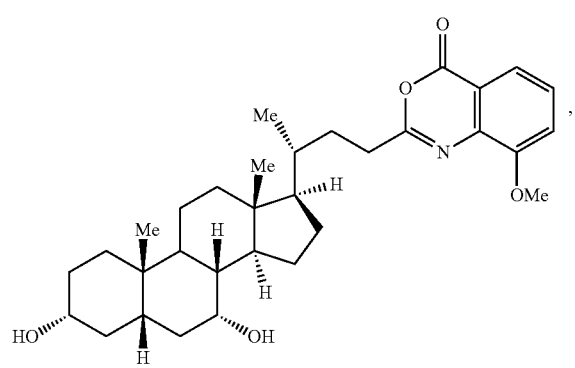
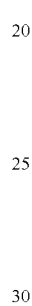
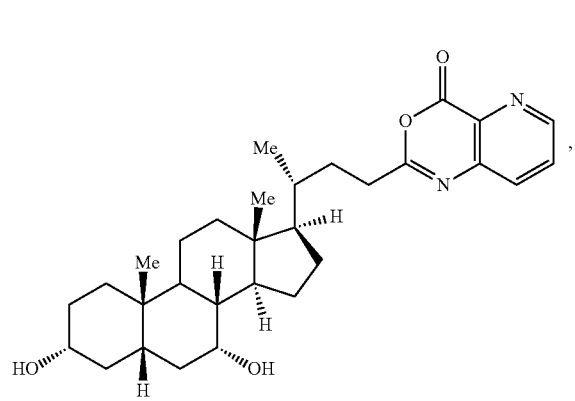
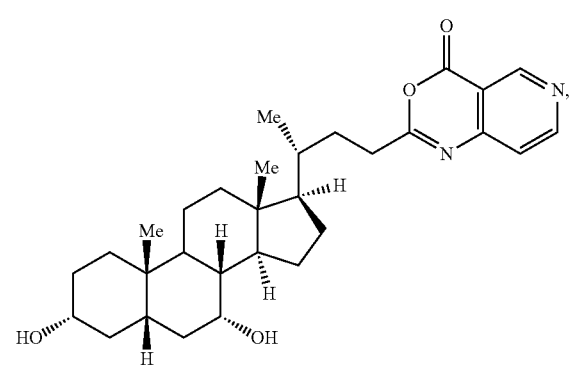
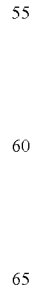
204
-continued
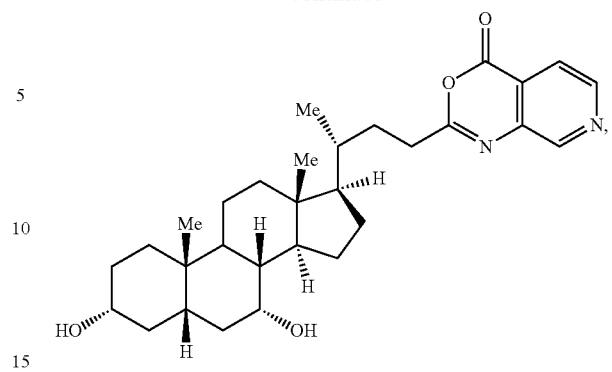
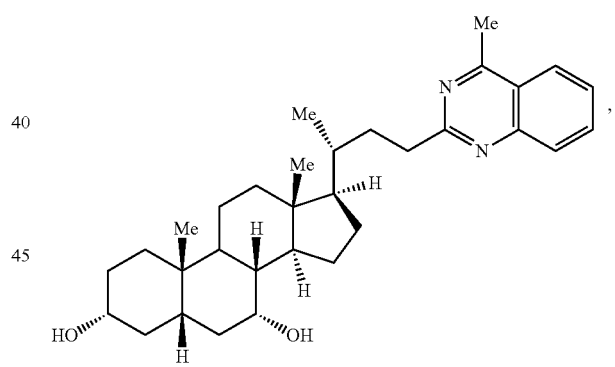
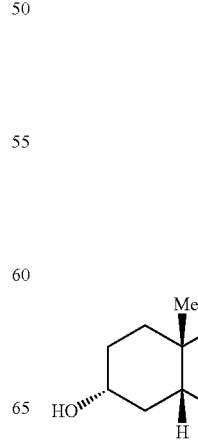

-continued
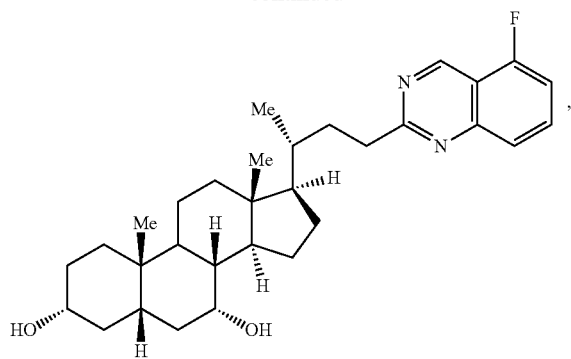
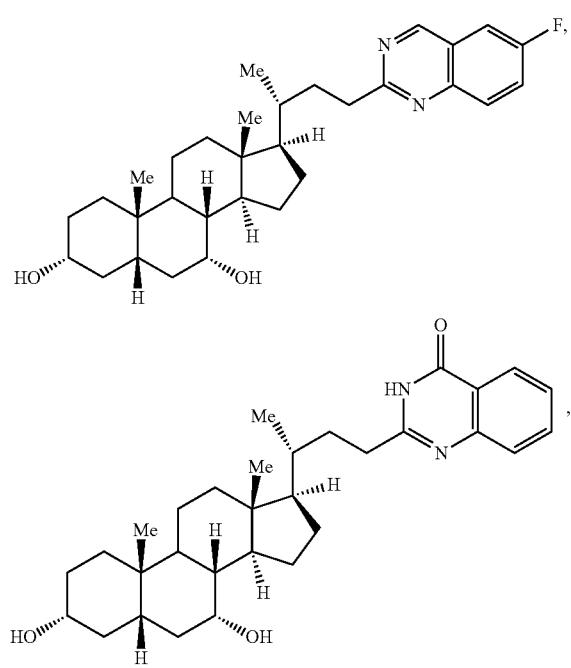
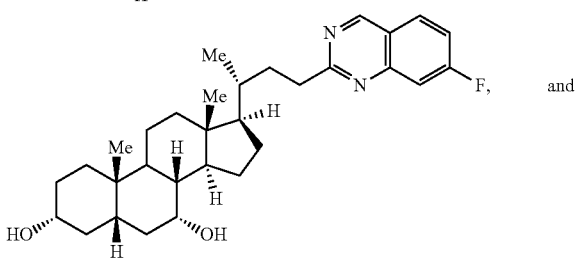
or a pharmaceutically acceptable salt thereof.
In one aspect, a compound can be selected from:
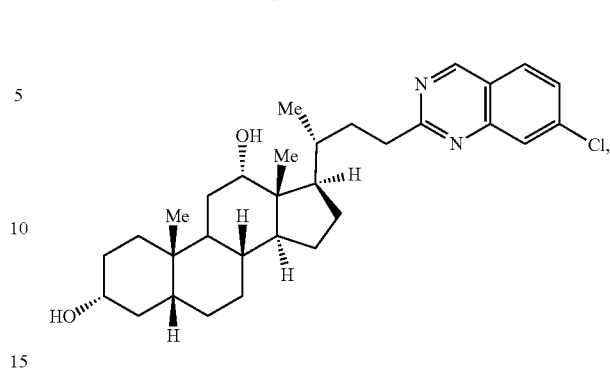
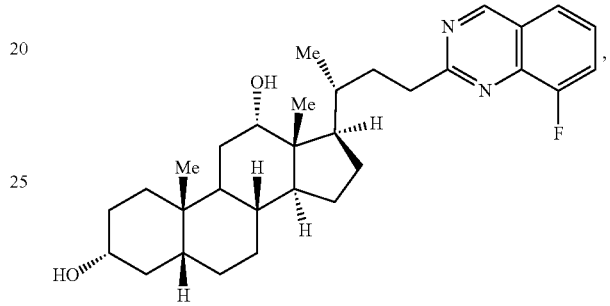
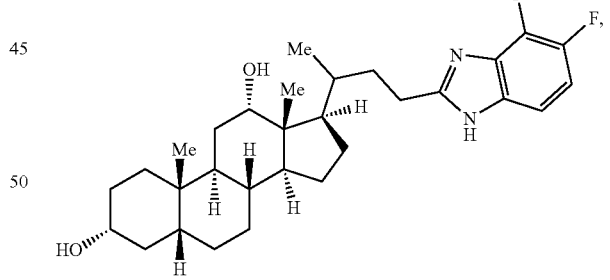
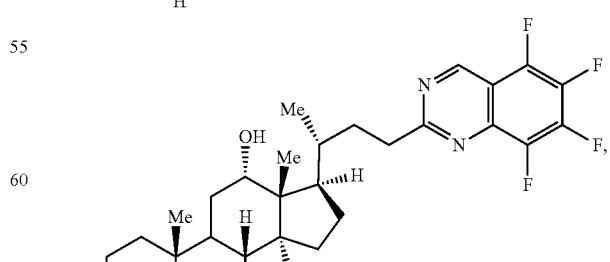
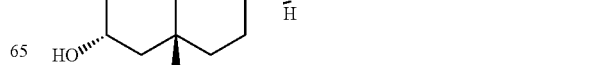

207
-continued
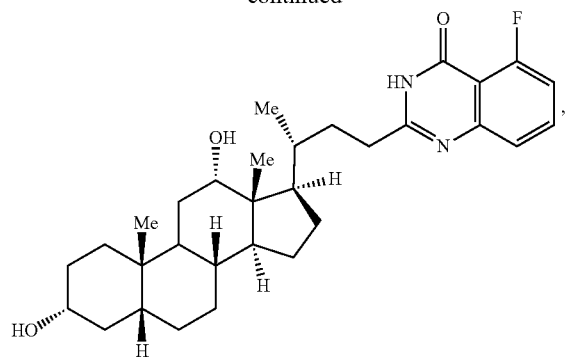
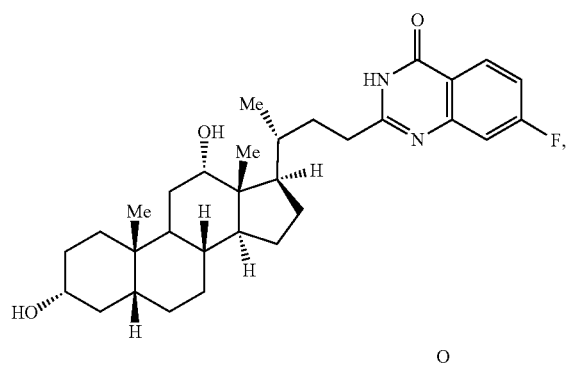
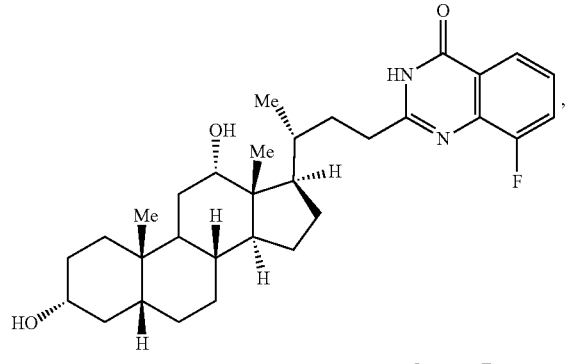
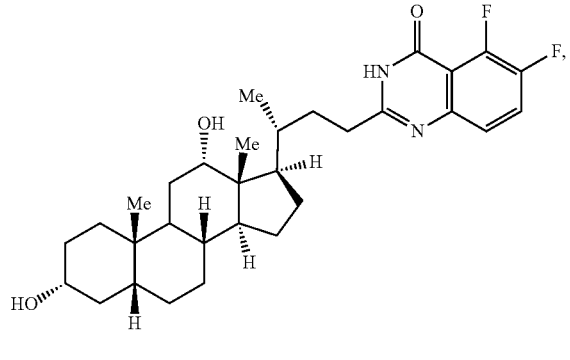
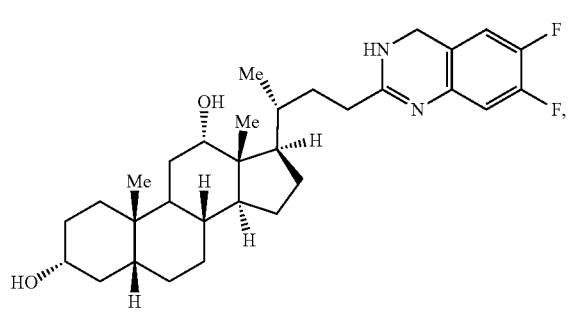
208
-continued
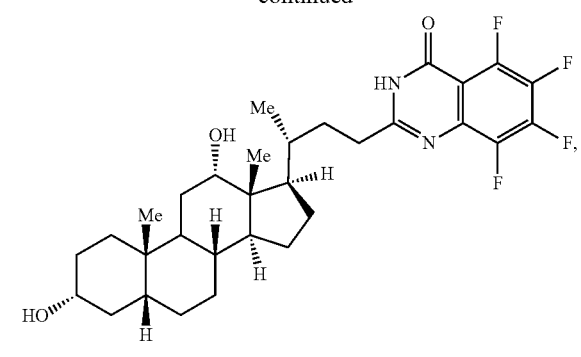
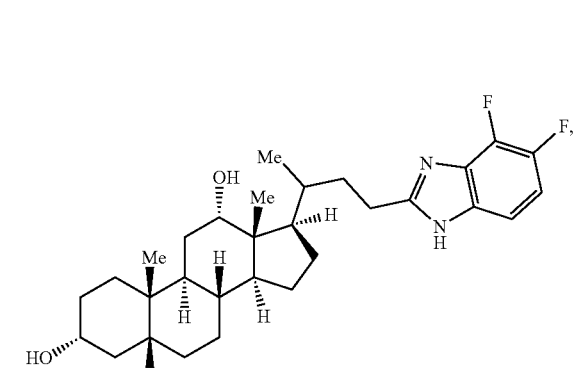
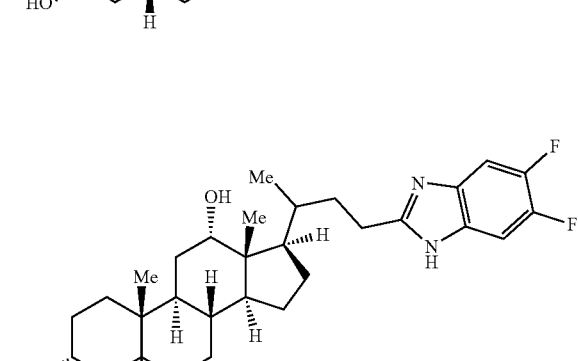
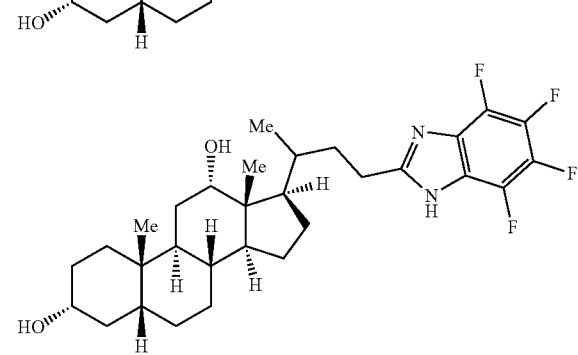
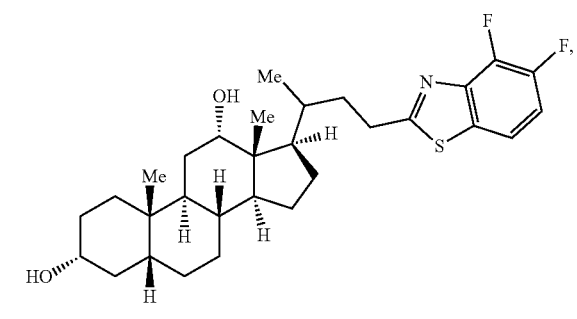

209
-continued
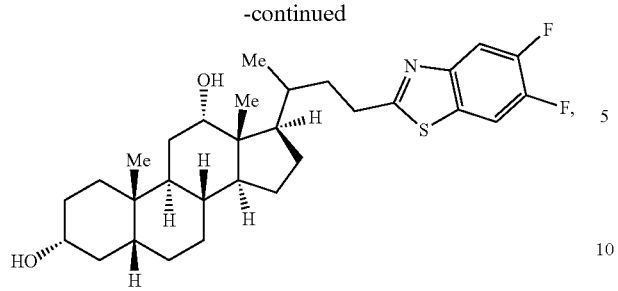
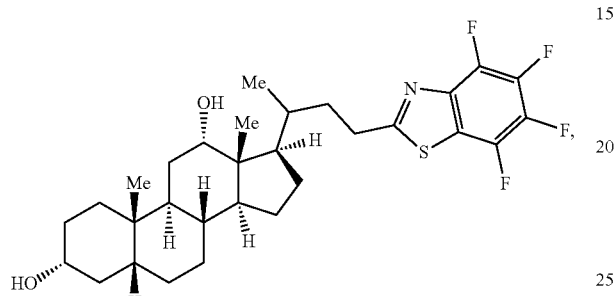
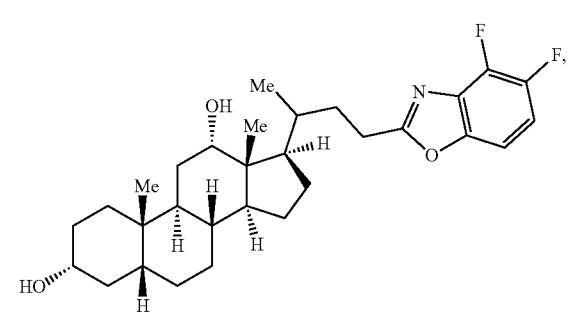
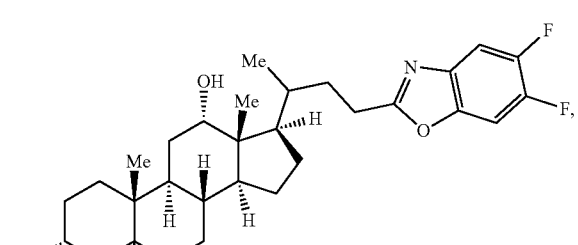
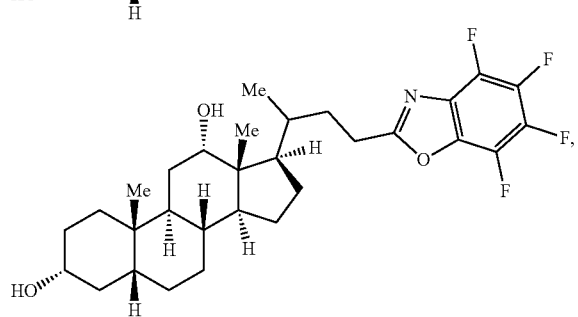
210
-continued
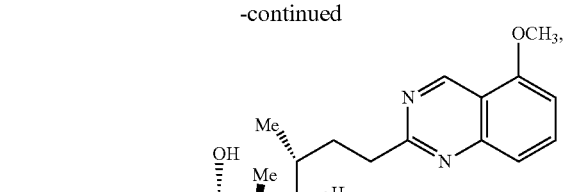
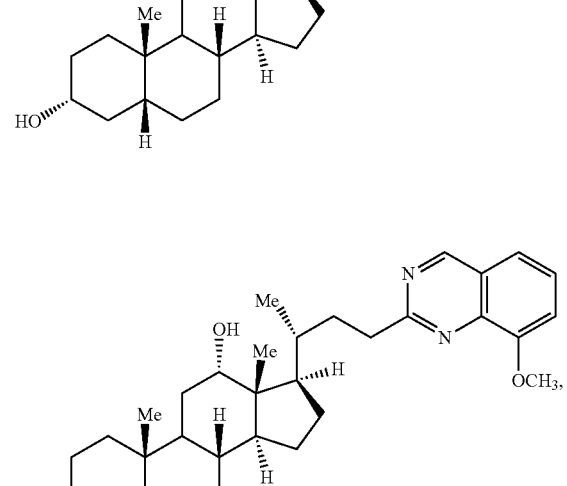
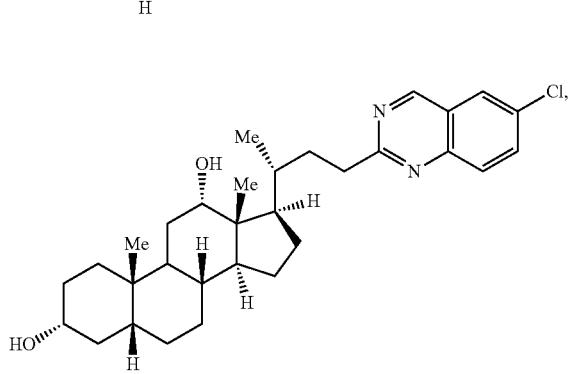
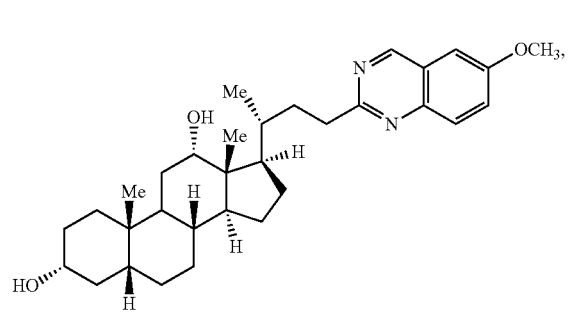
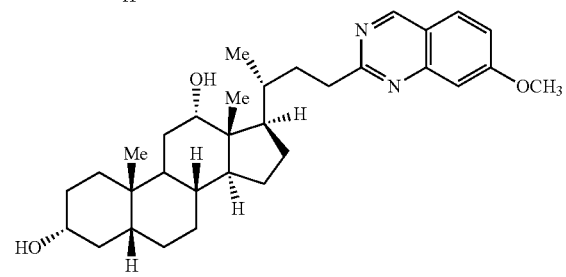

211
-continued
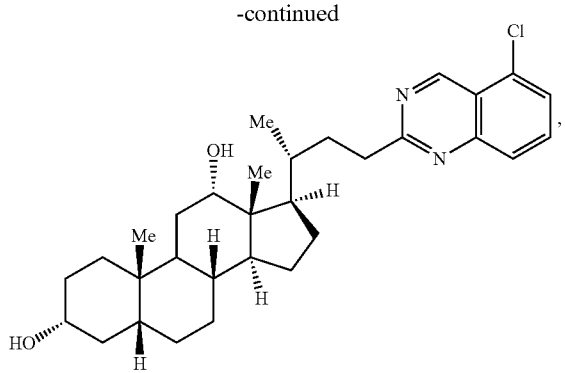
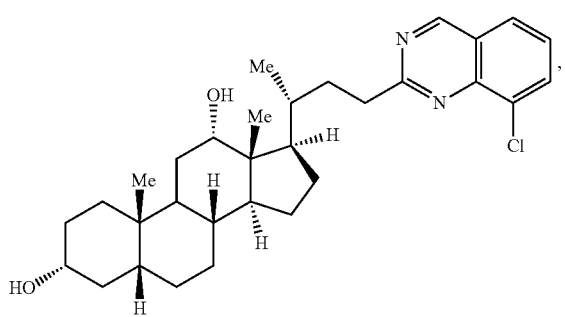
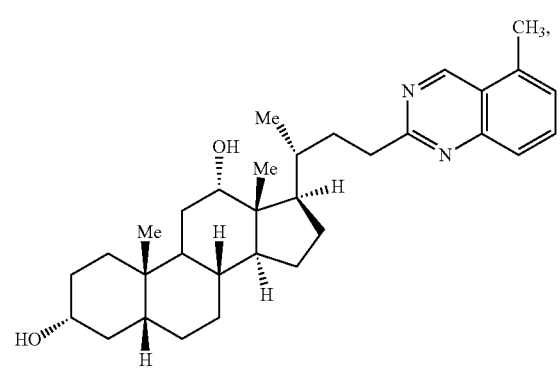
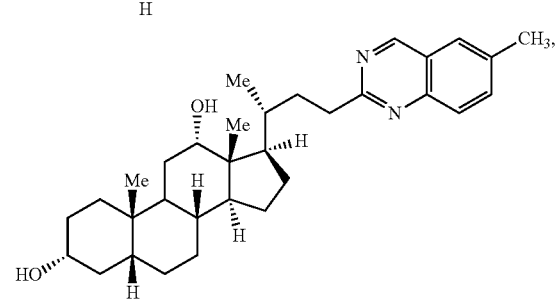
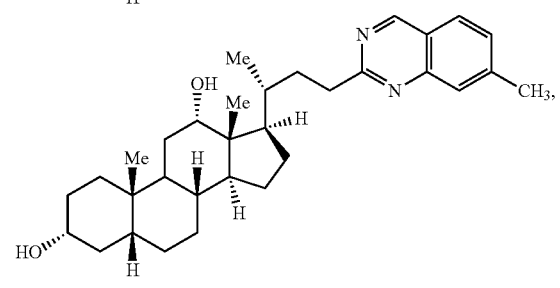
212
-continued
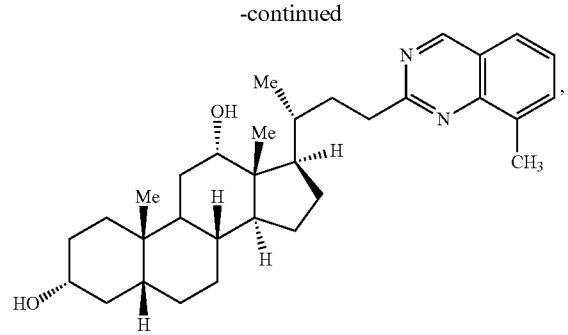
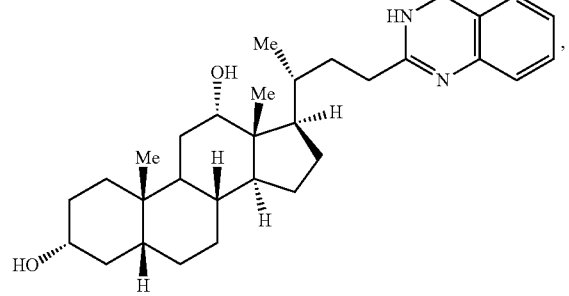
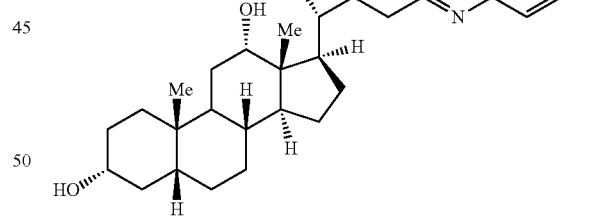
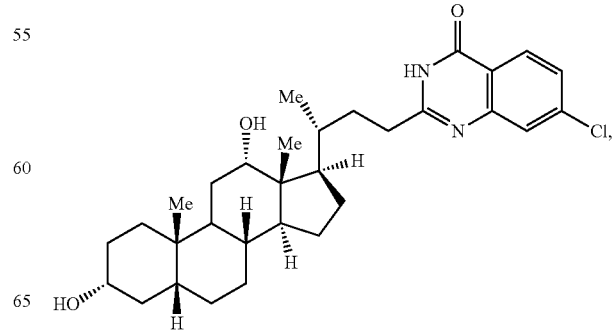

213
-continued
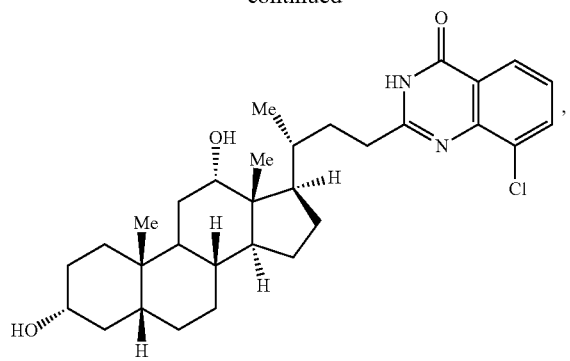
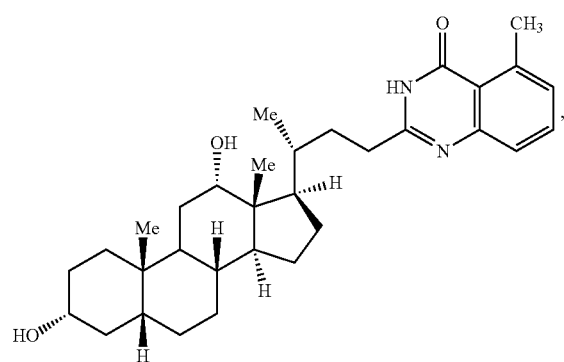
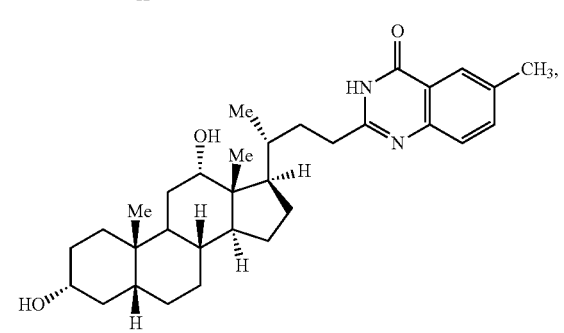
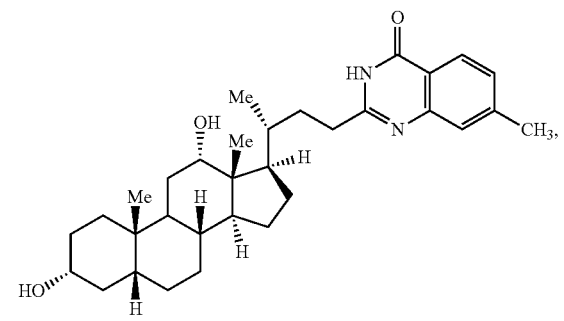
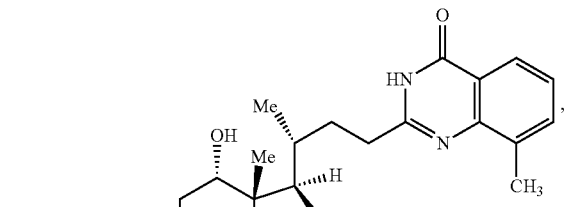
214
-continued
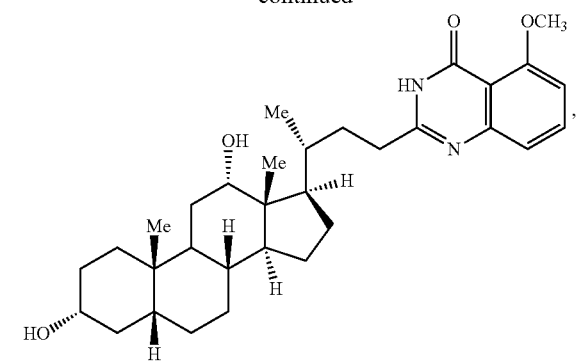
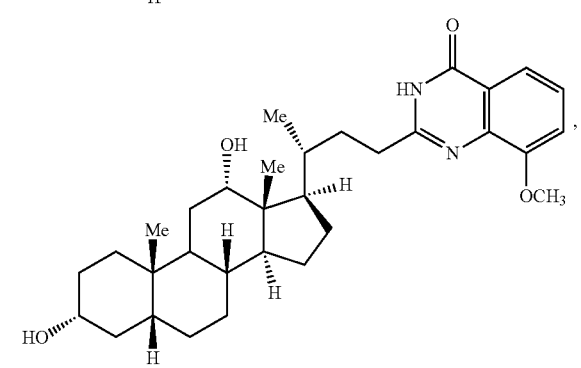
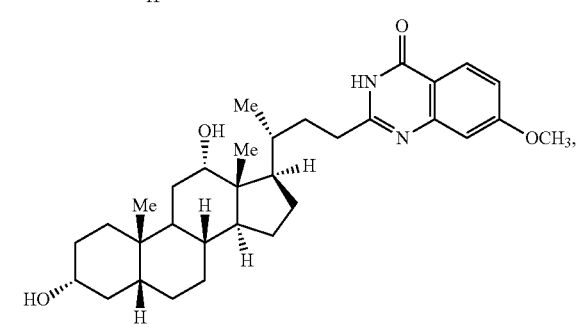
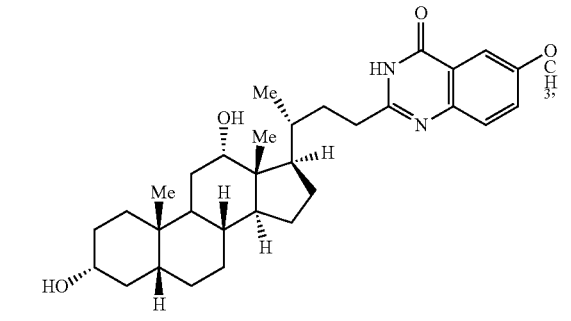
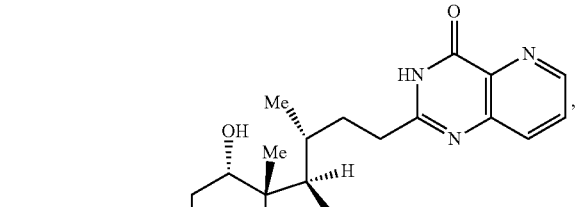

215
-continued
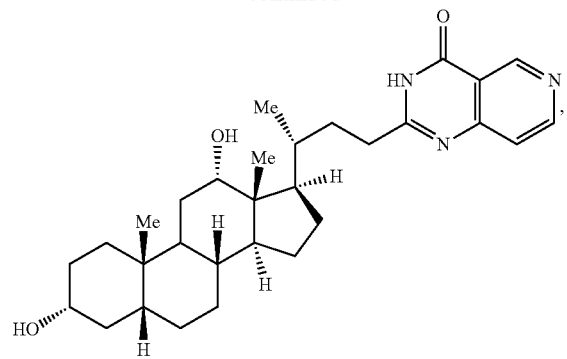
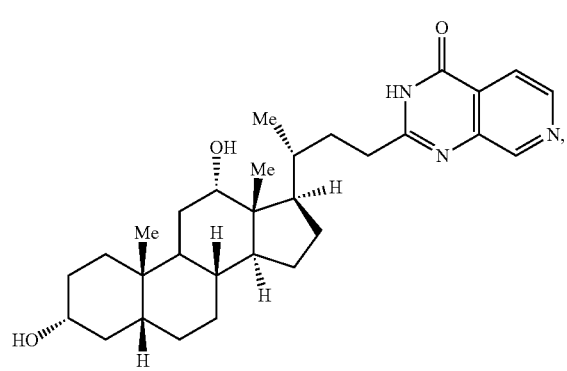
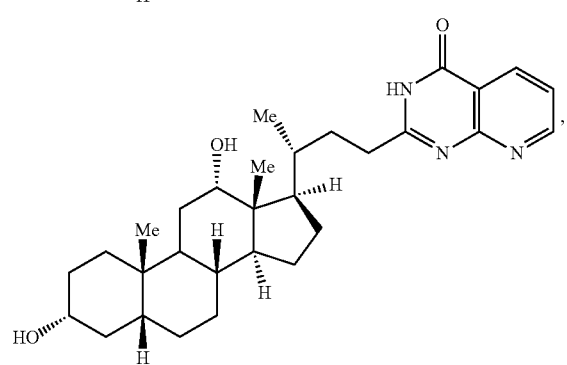
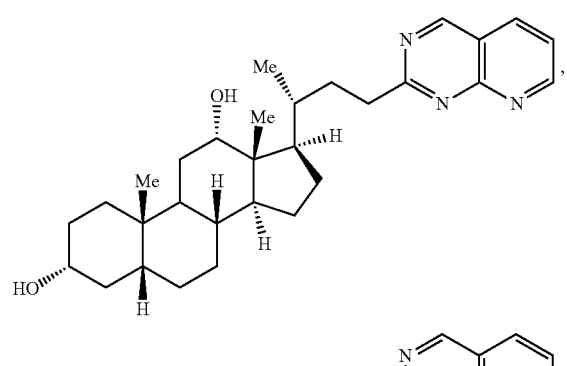
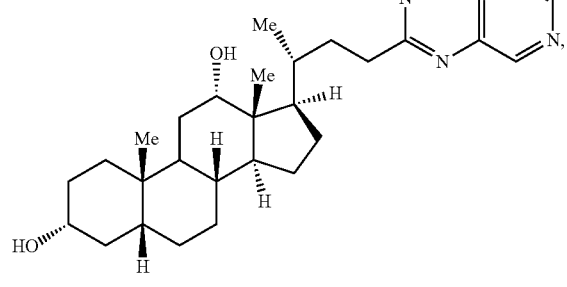
216
-continued
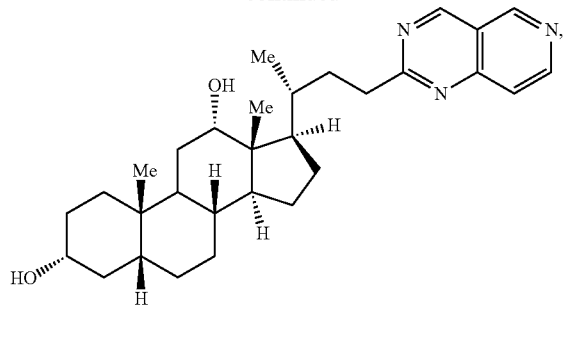
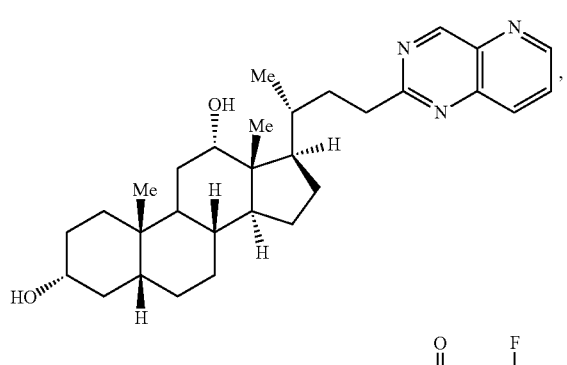
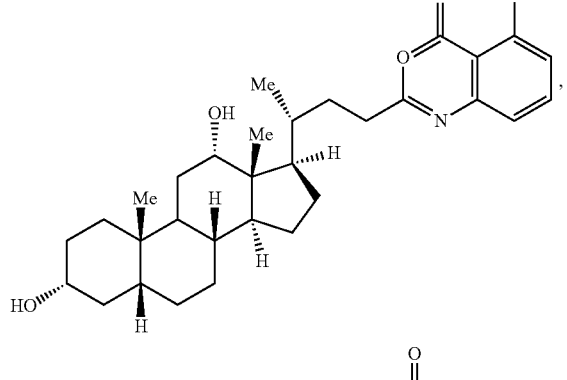
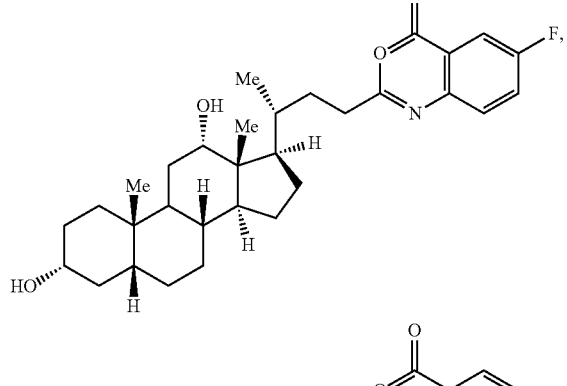
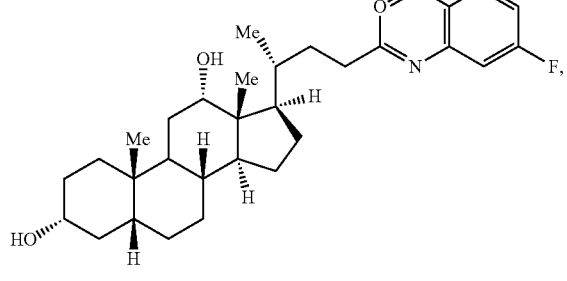

217
-continued
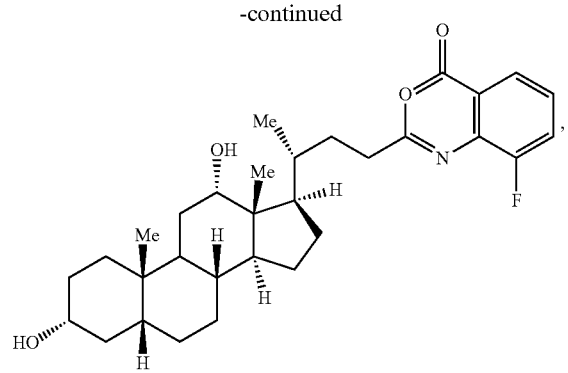
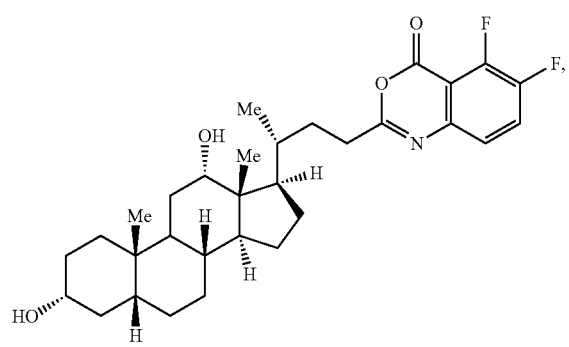
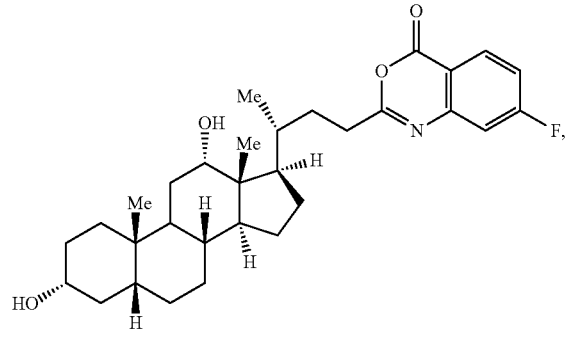
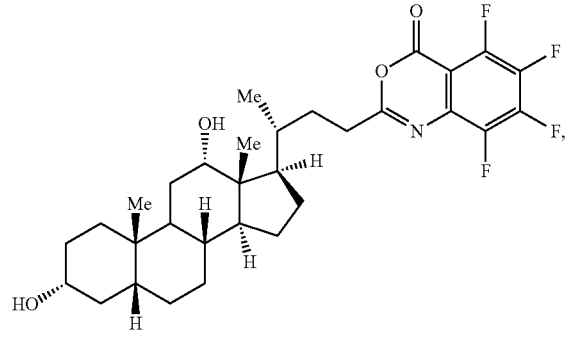
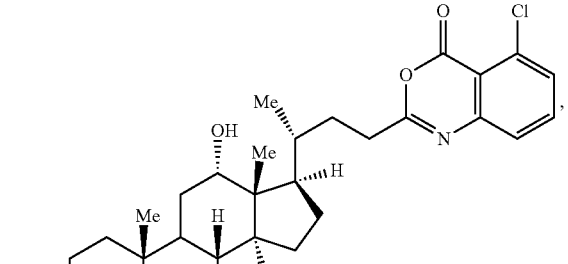
218
-continued
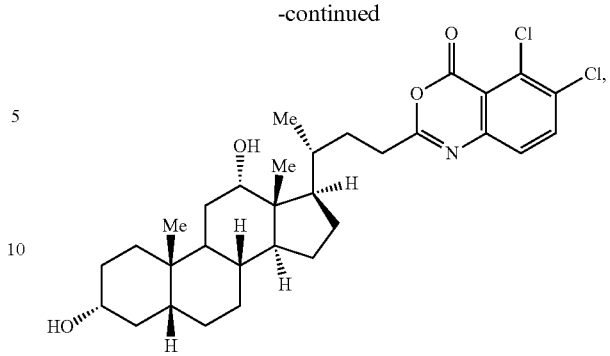
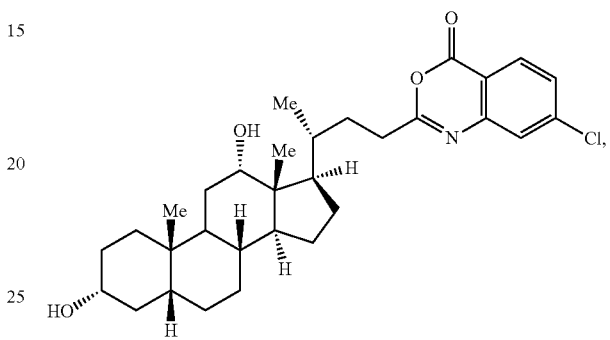
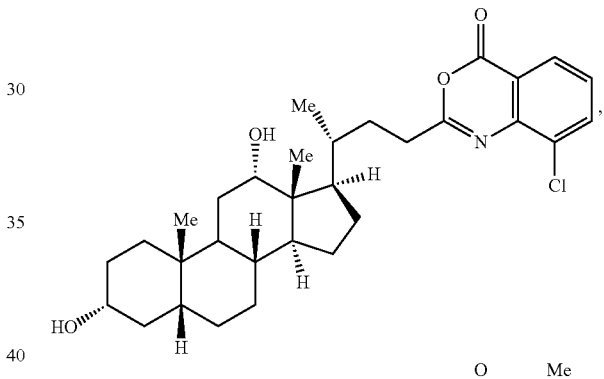
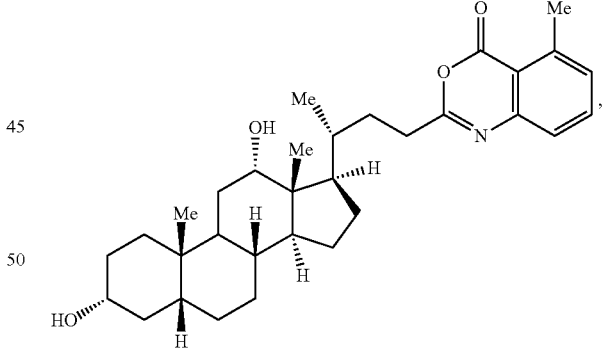
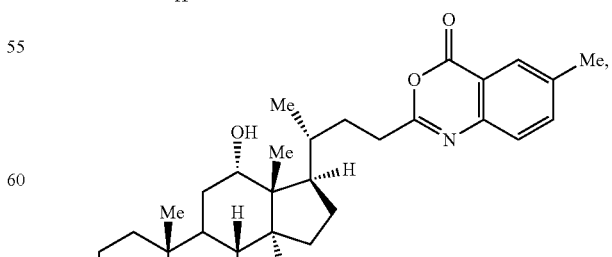

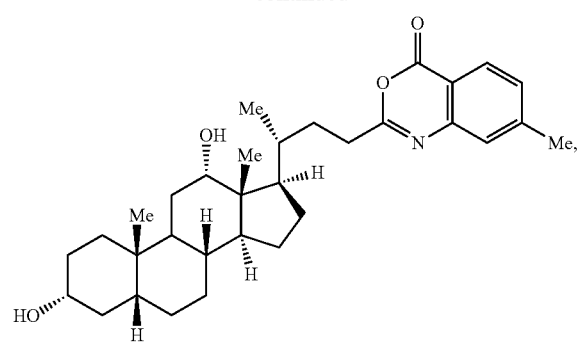
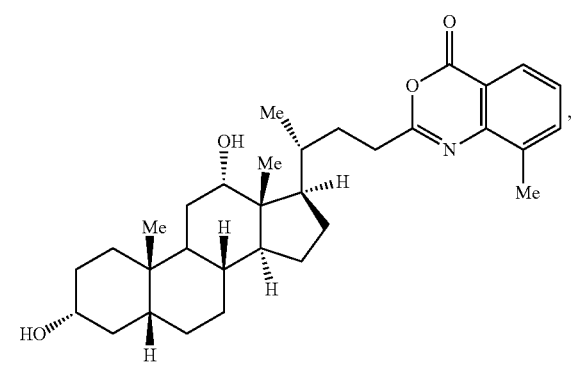
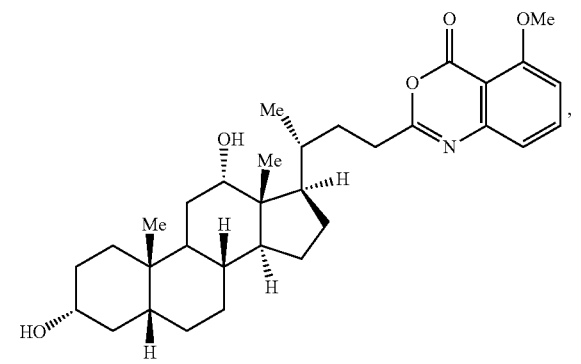
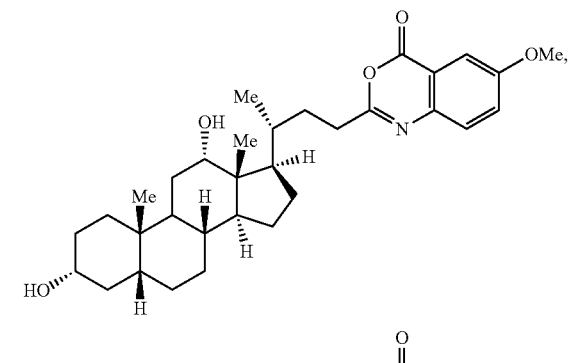
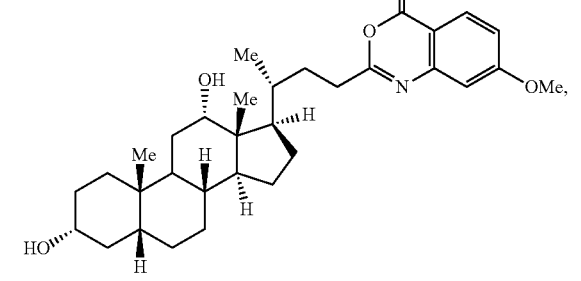
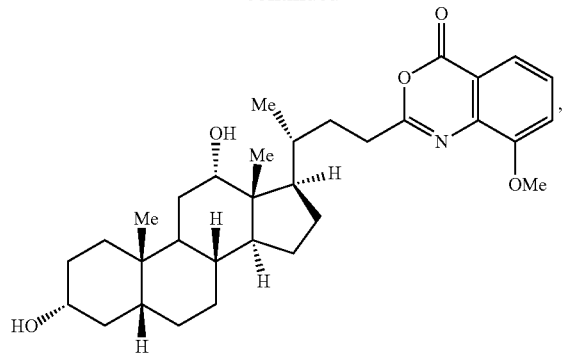
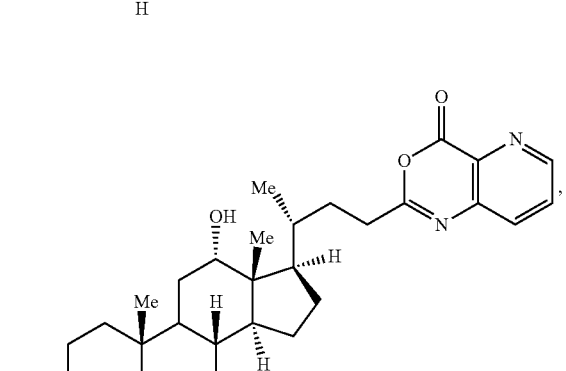
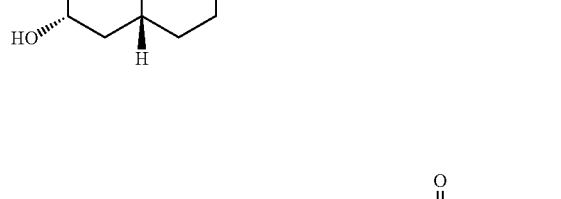
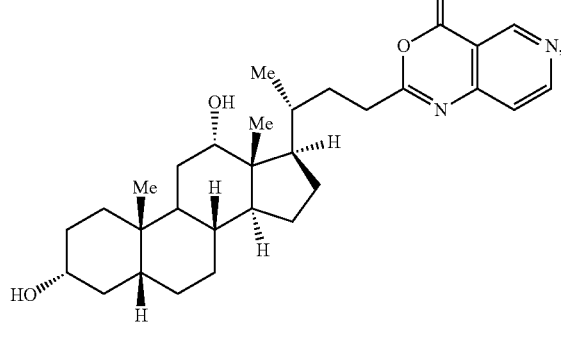
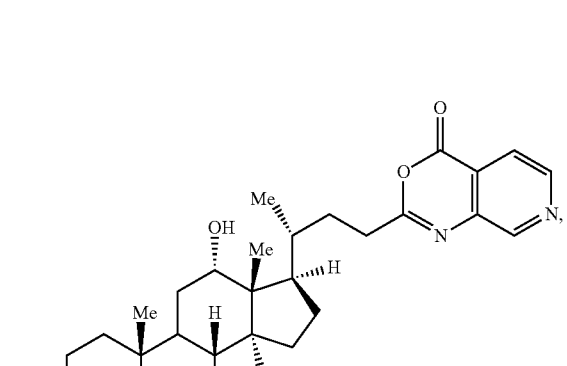

221
-continued
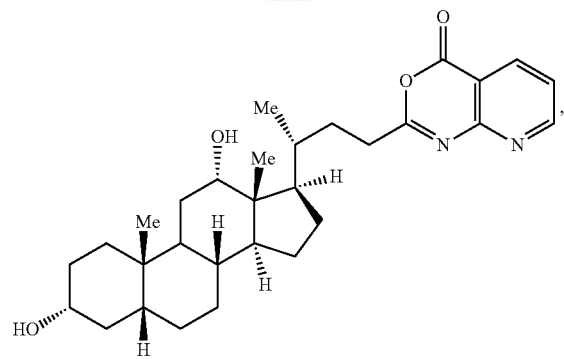
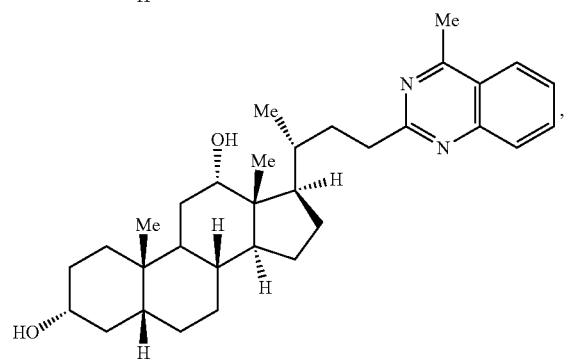
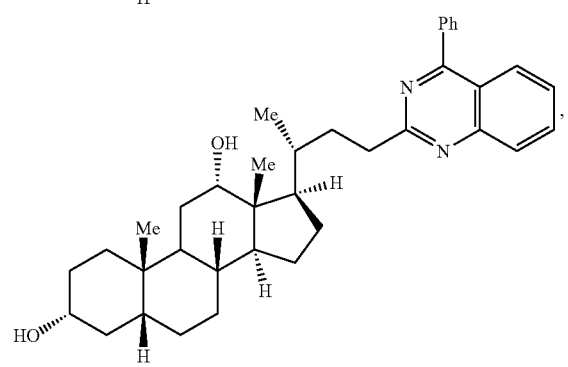
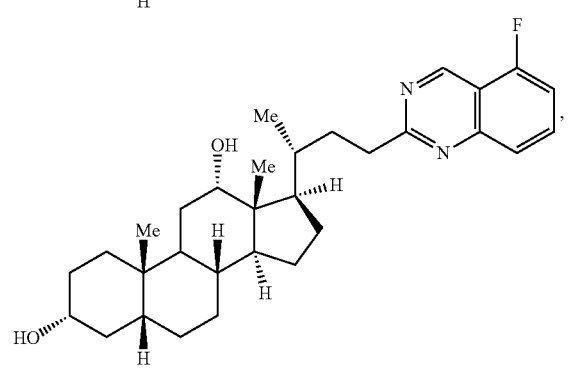
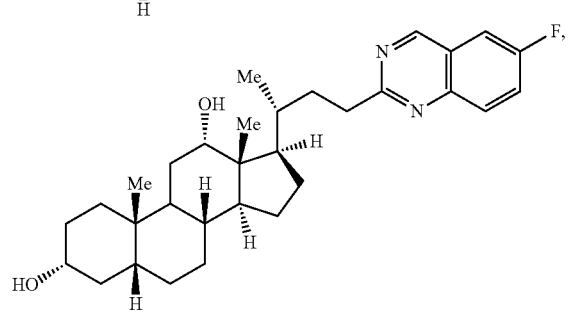
222
-continued
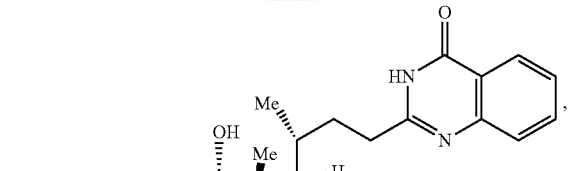
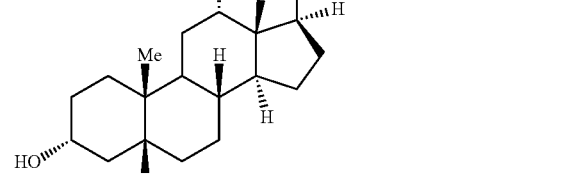
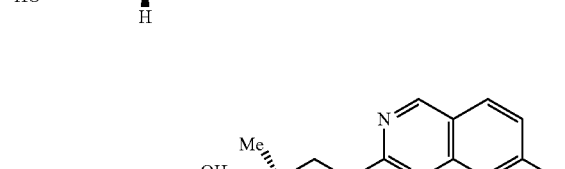
and
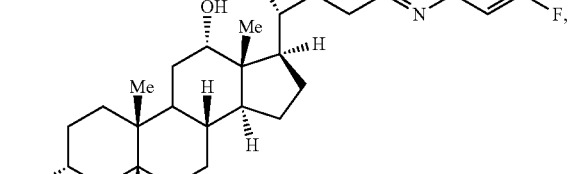
or a pharmaceutically acceptable salt thereof.
In one aspect, a compound can be selected from:
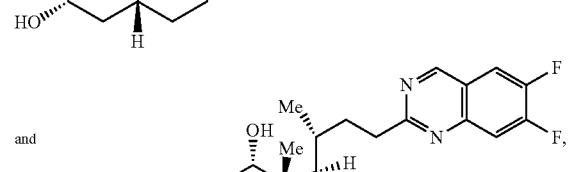
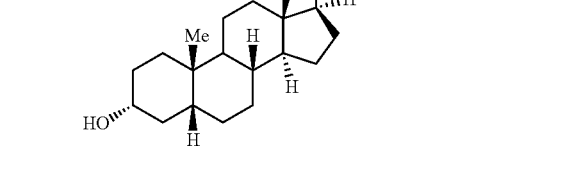
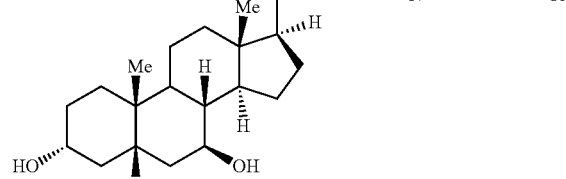
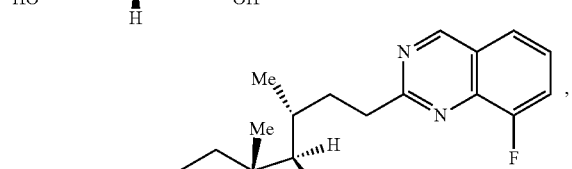
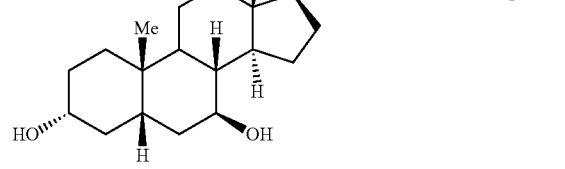

223
-continued
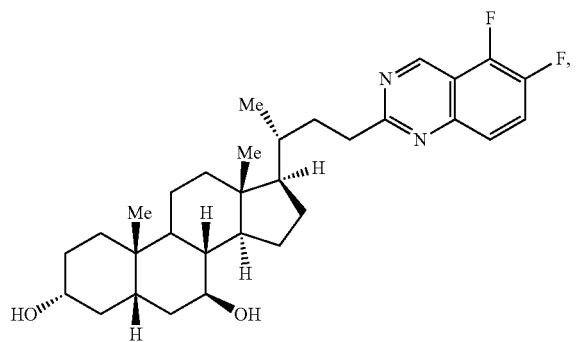
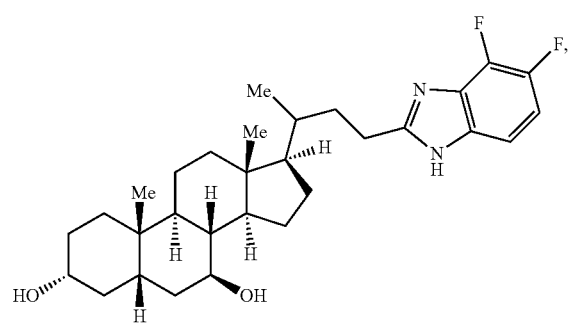
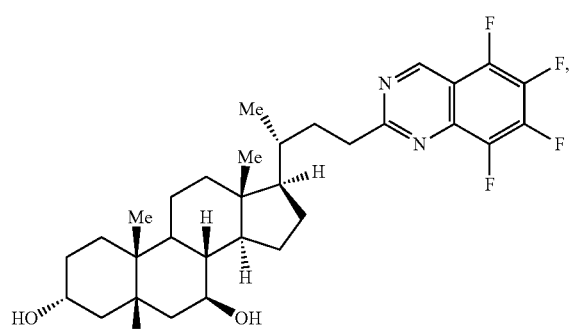
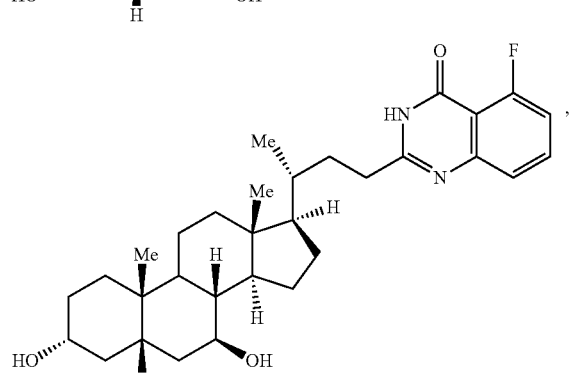
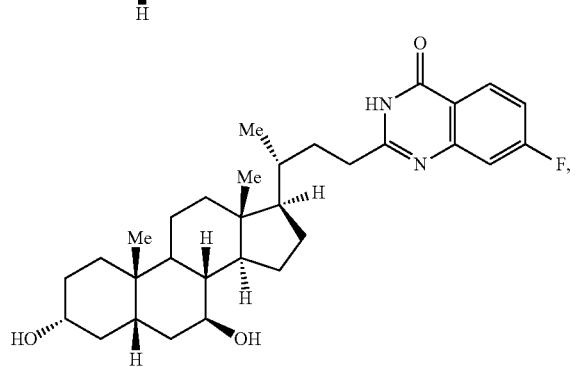
224
-continued
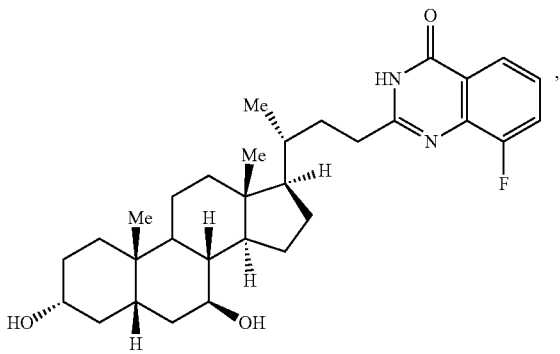
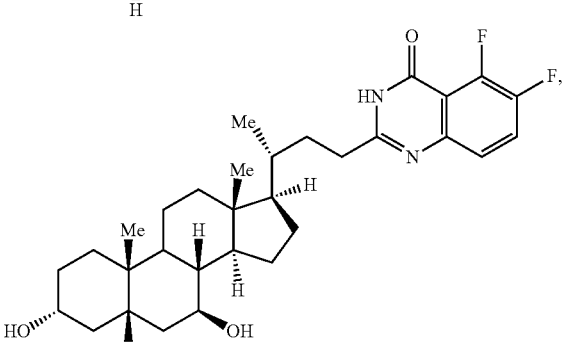
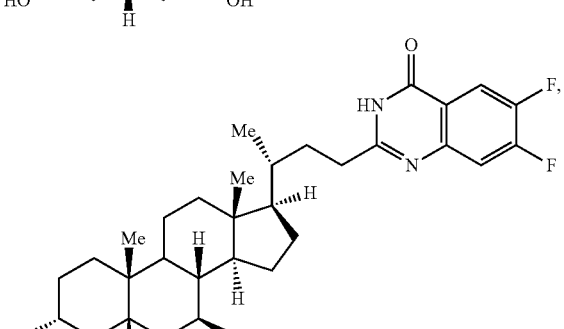
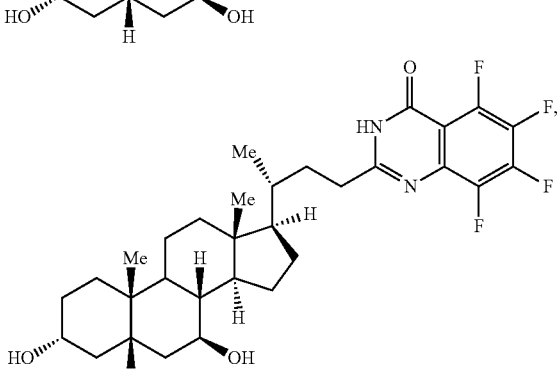
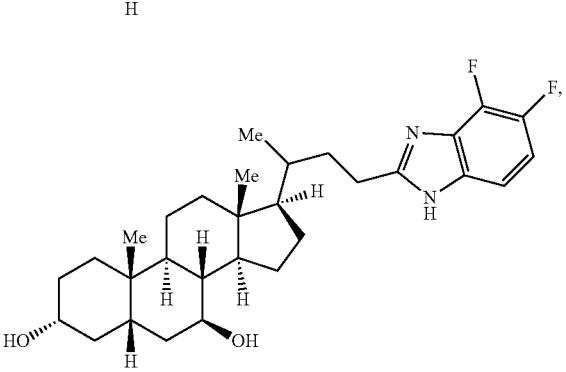

225
-continued
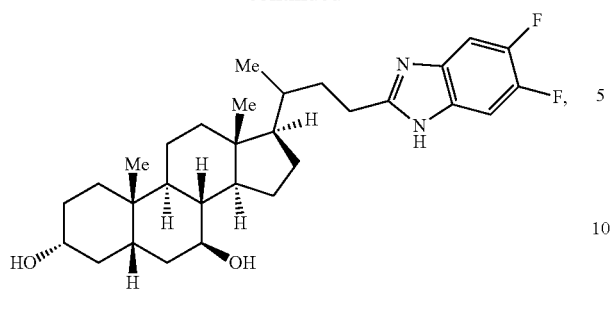
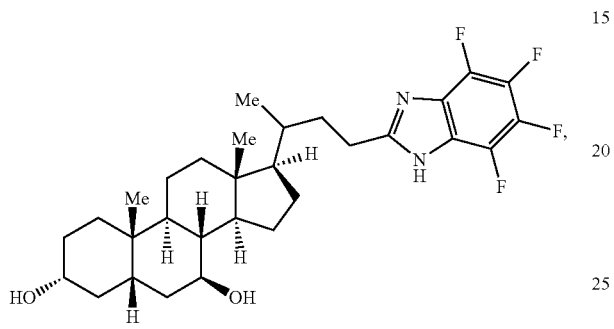
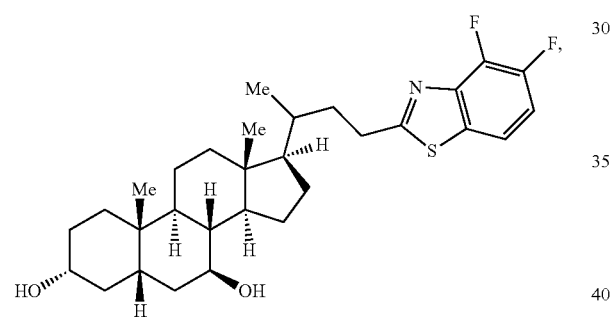
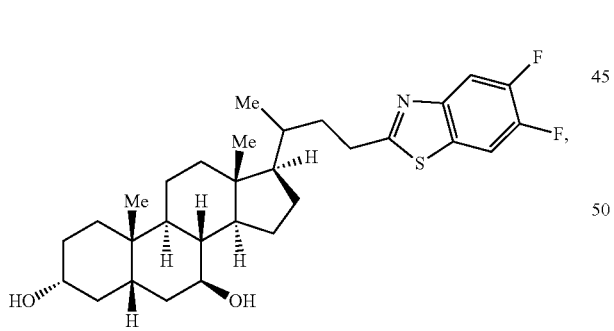
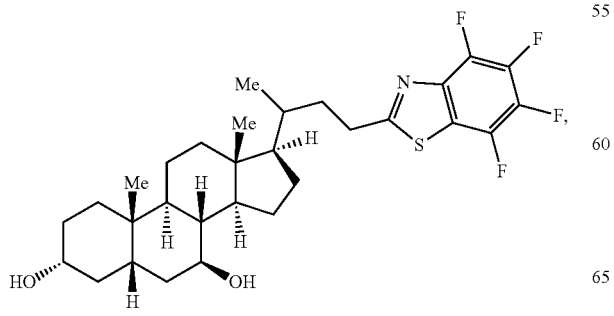
226
-continued
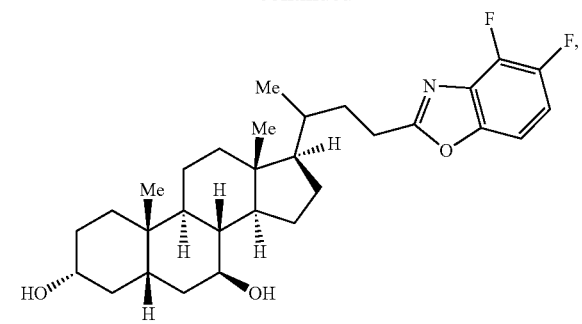
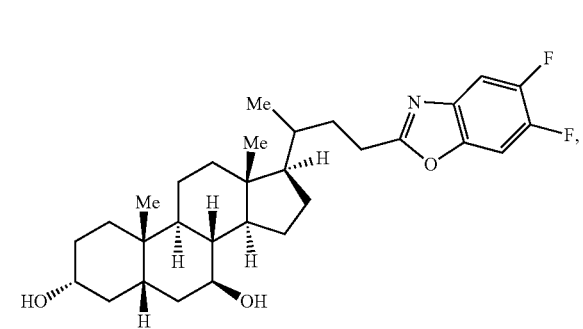
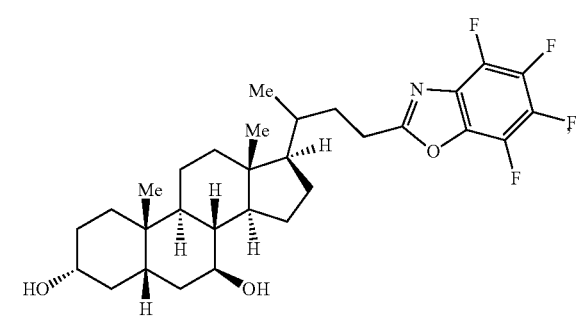
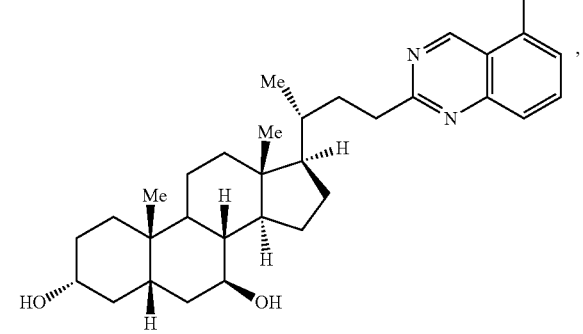
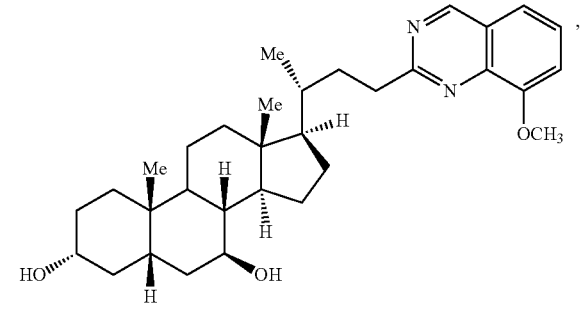

227
-continued
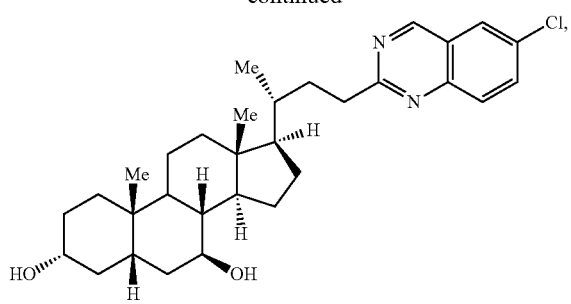
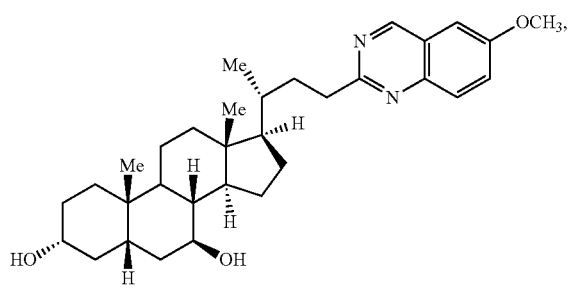
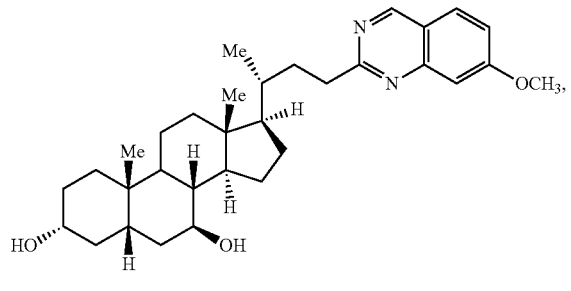
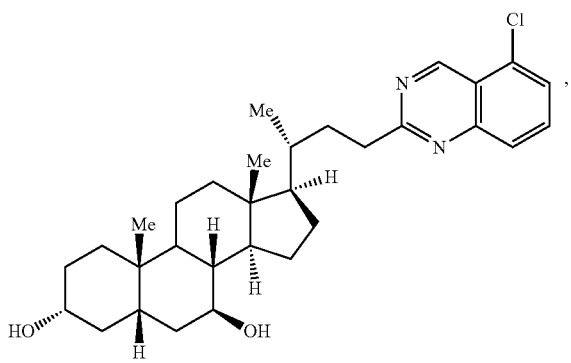
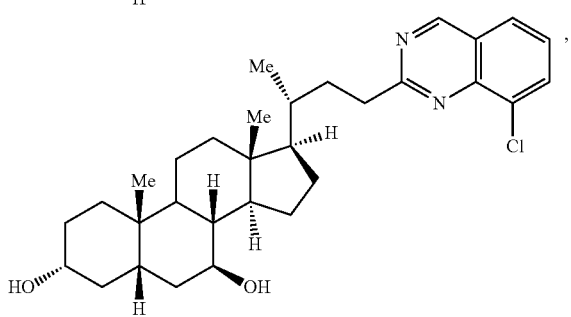
228
-continued
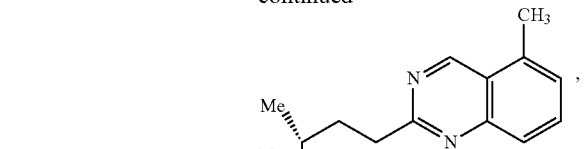
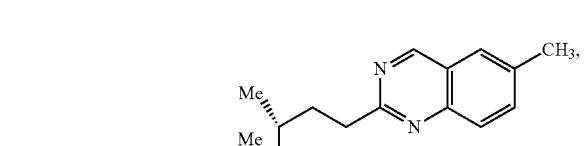
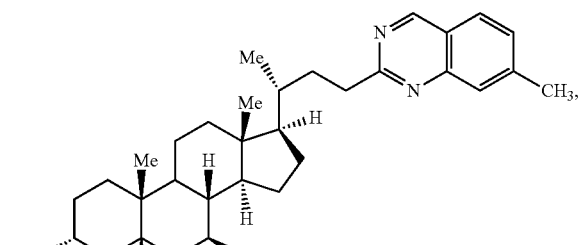
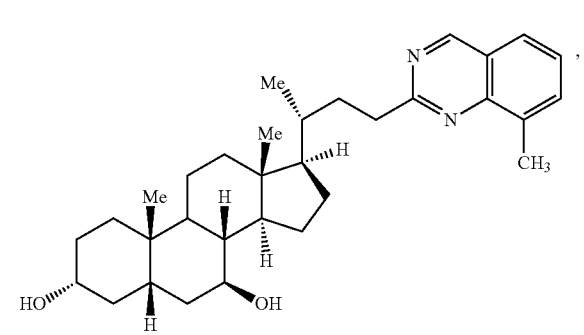
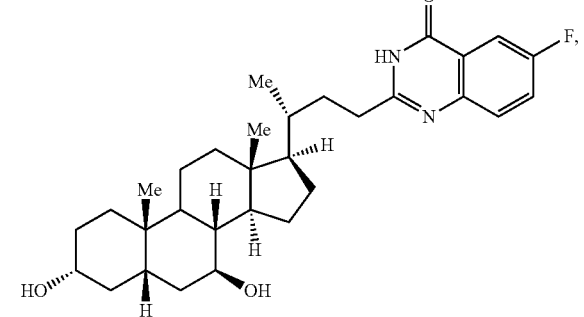

229
-continued
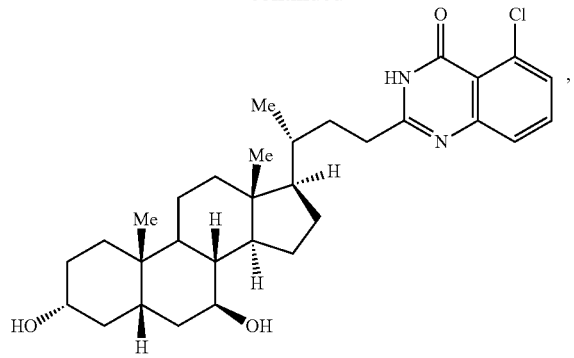
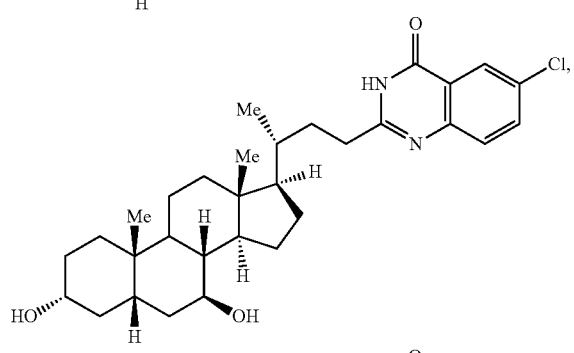
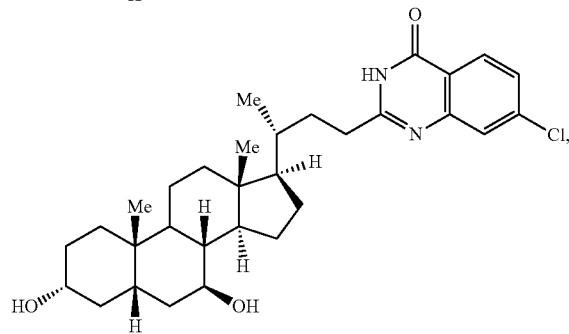
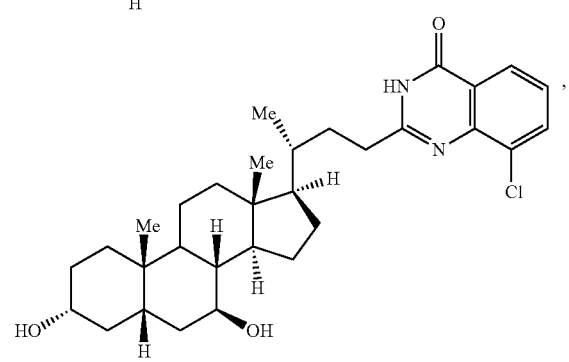
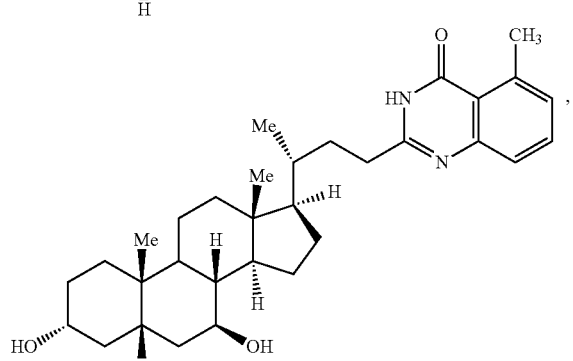
230
-continued
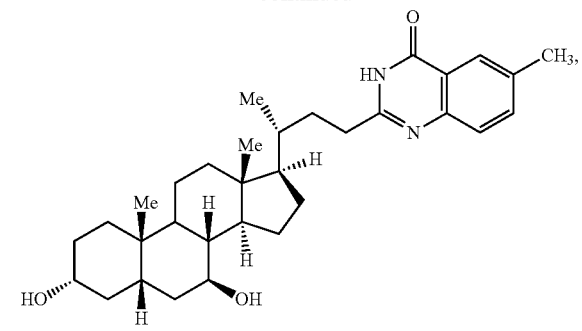
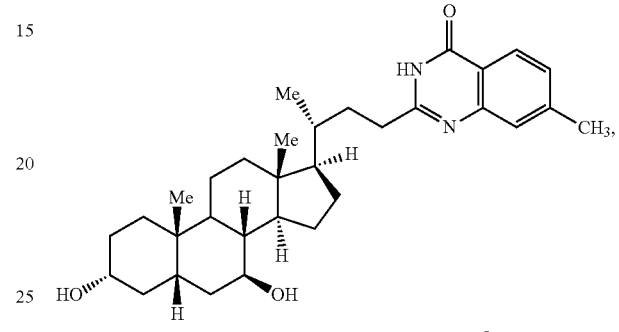
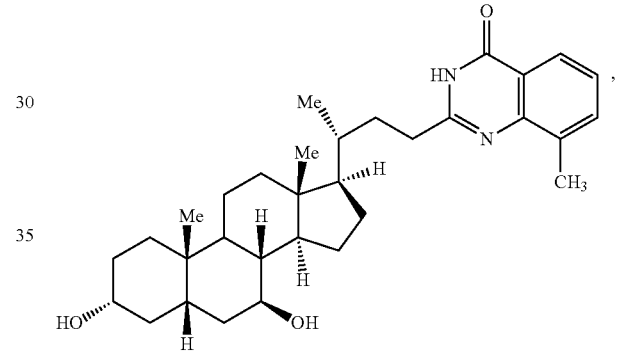
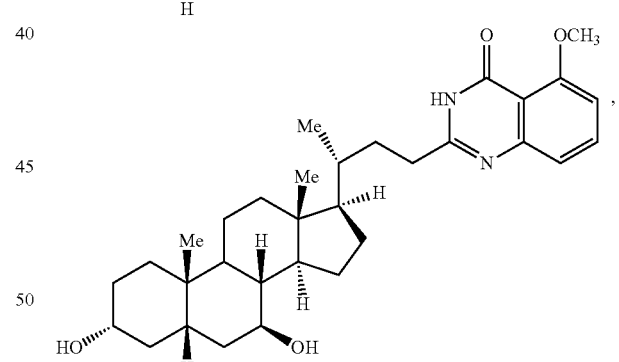
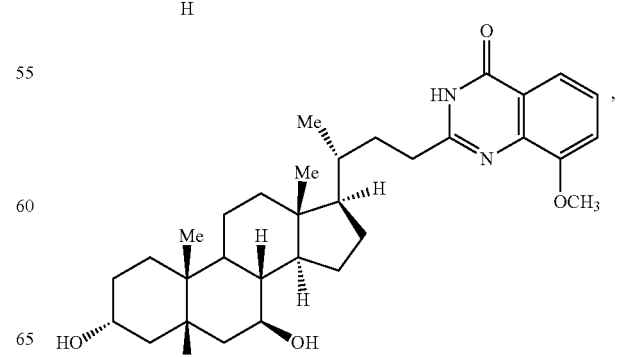

231
-continued
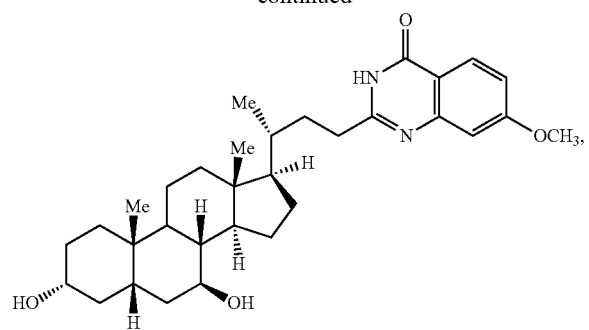
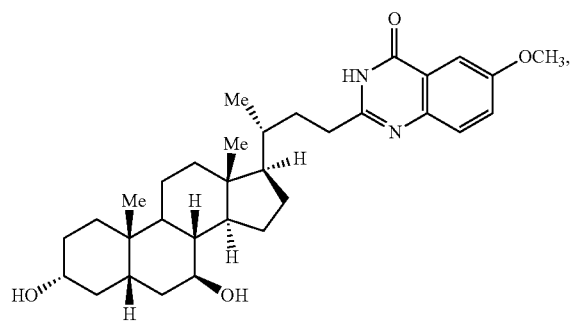
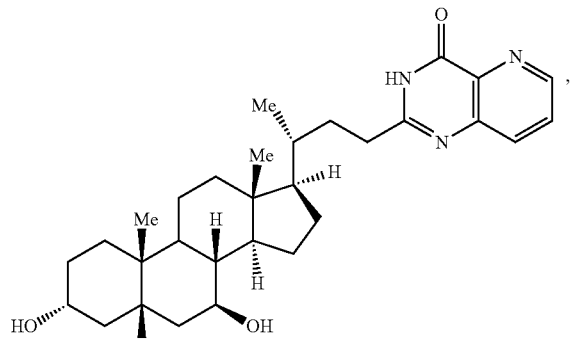
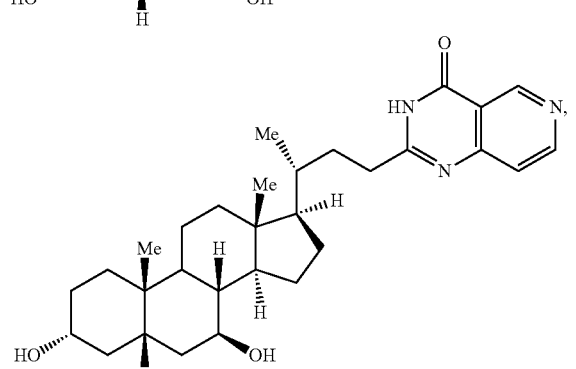
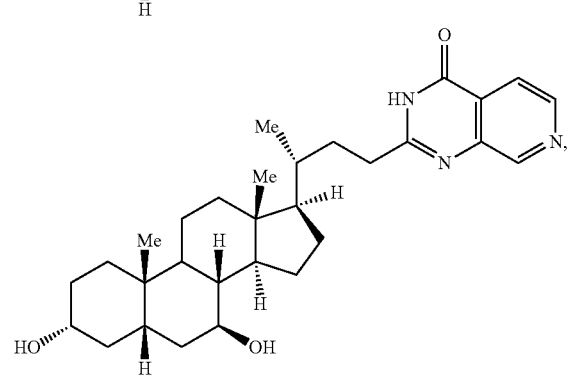
232
-continued
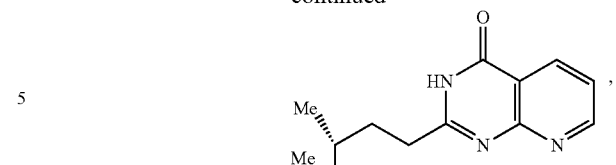
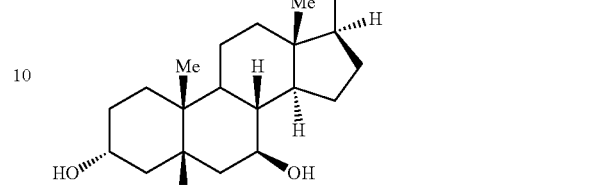
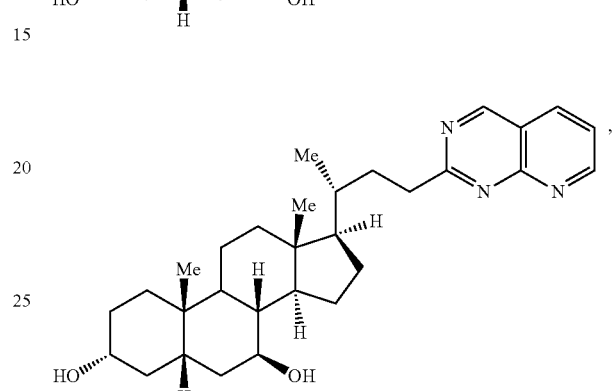
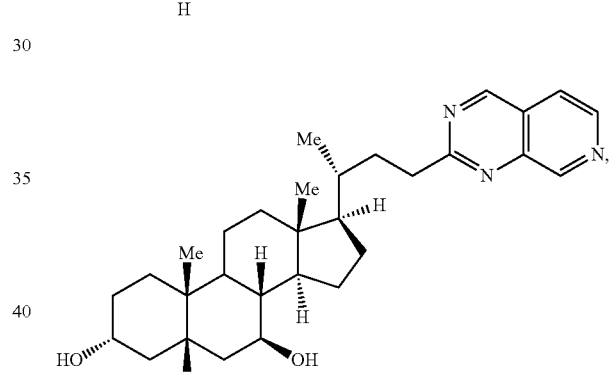
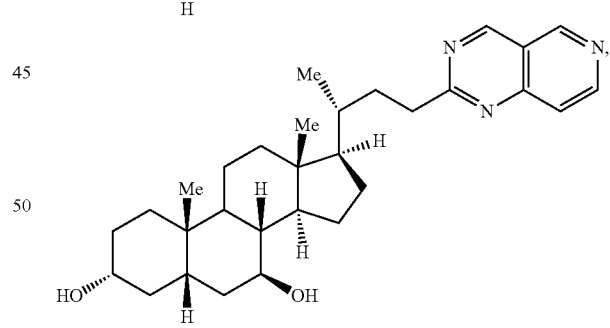
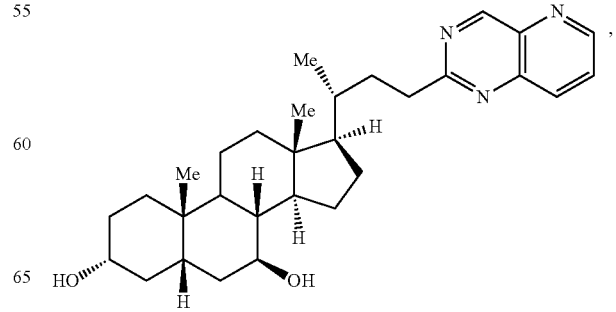

233
-continued
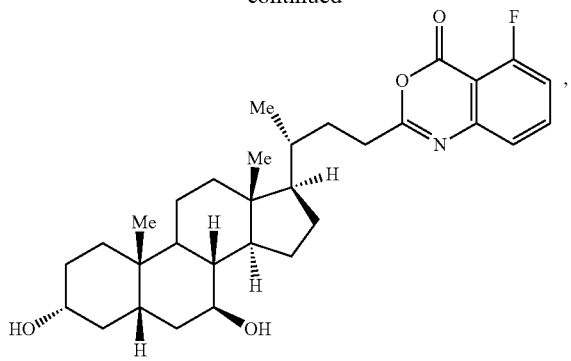
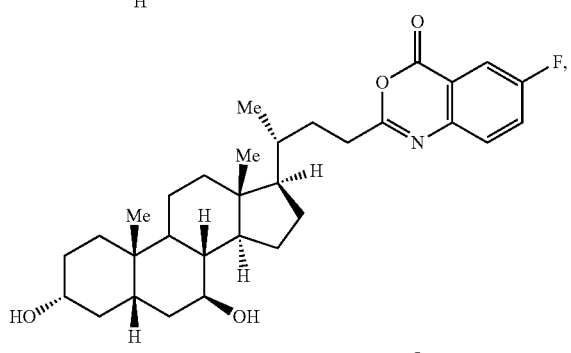
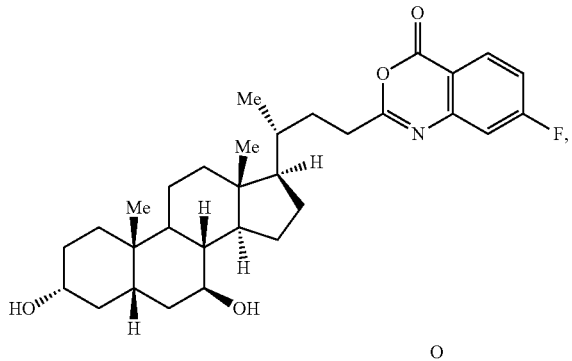
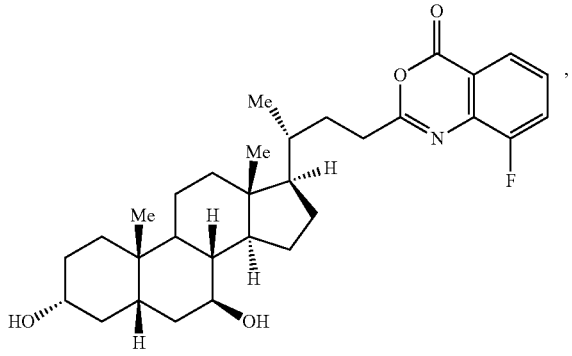
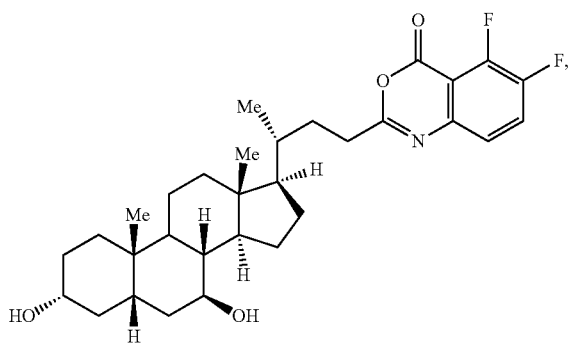
234
-continued
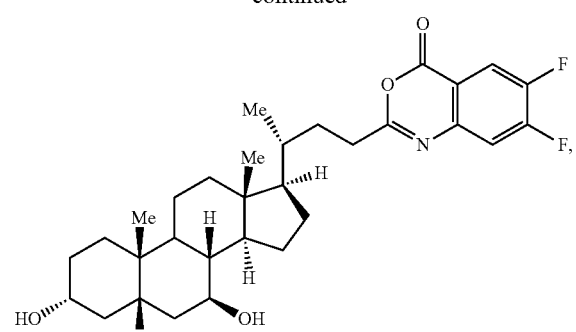
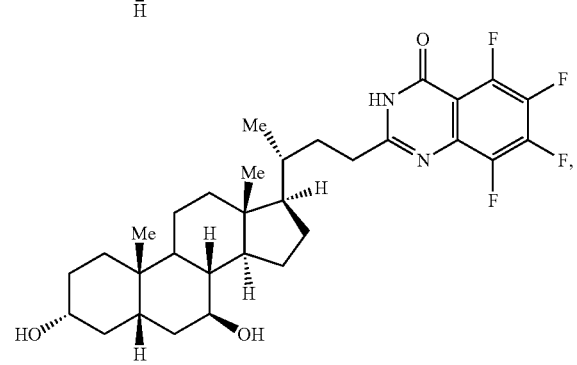
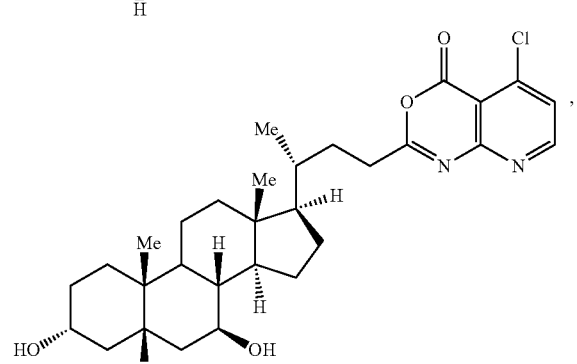
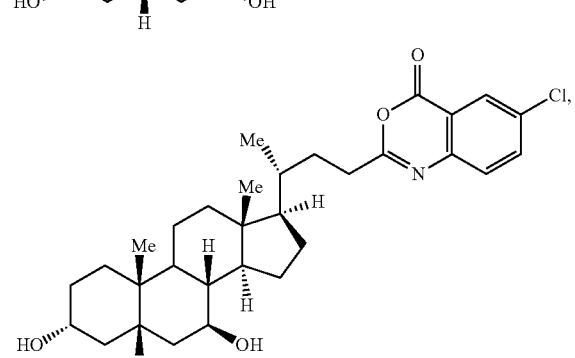
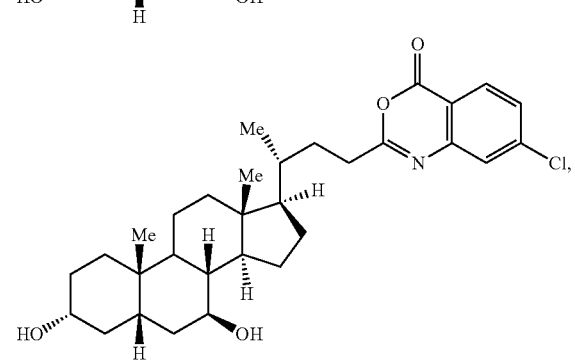

235
-continued
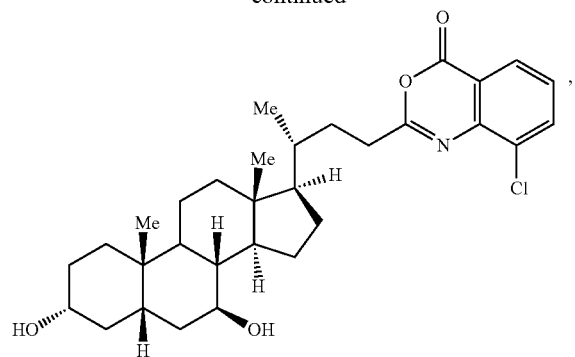
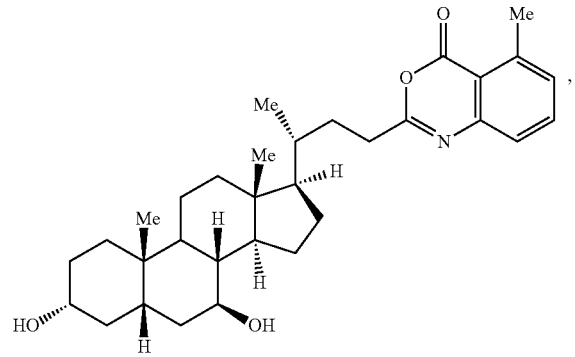
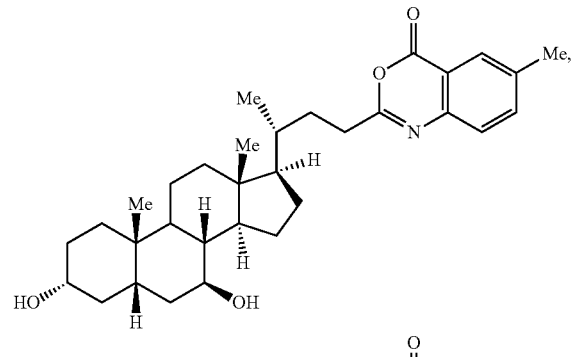
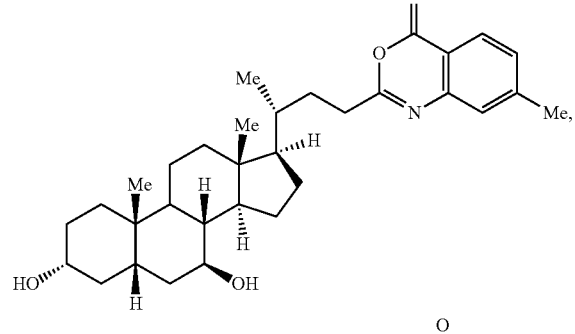
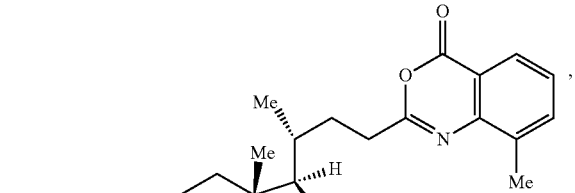
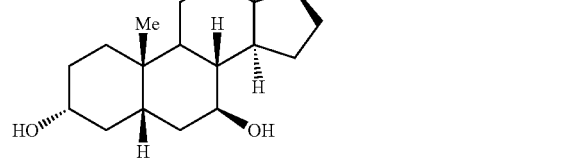
236
-continued
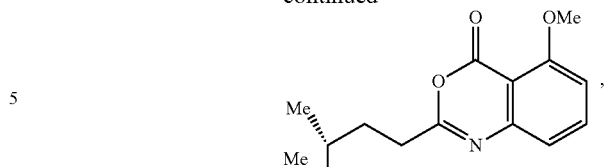
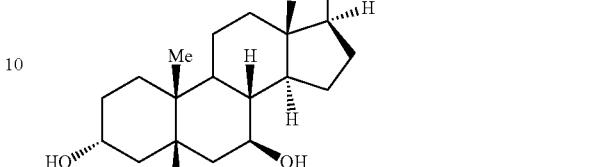
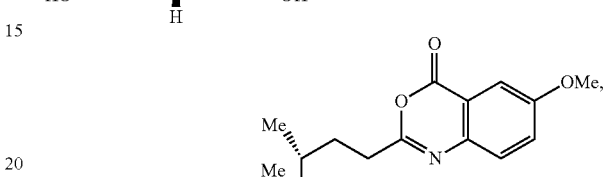
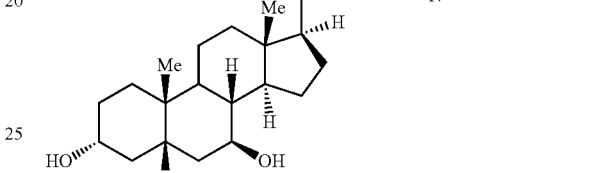
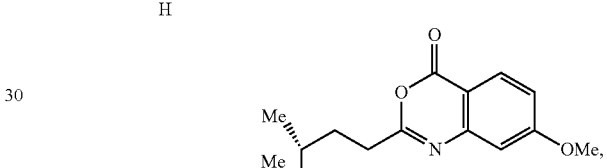
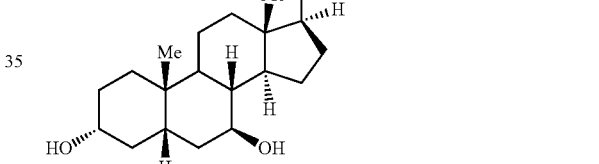
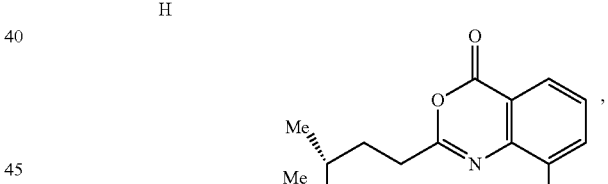
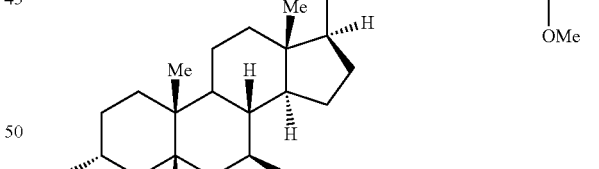
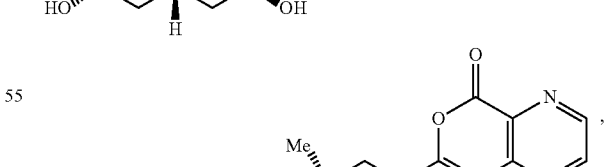
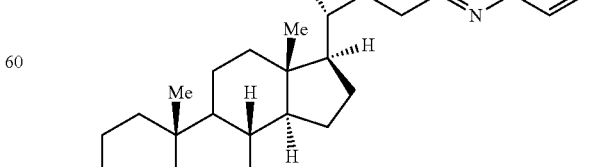
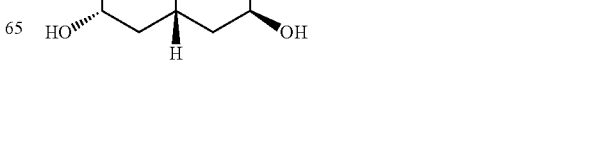

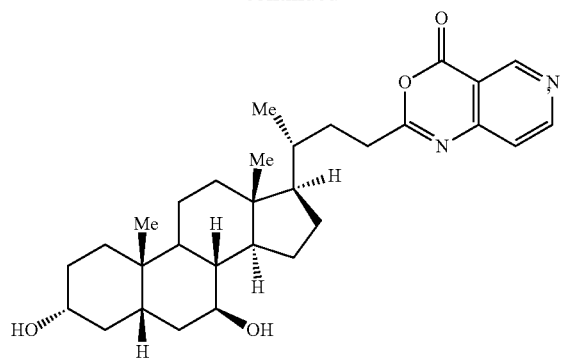
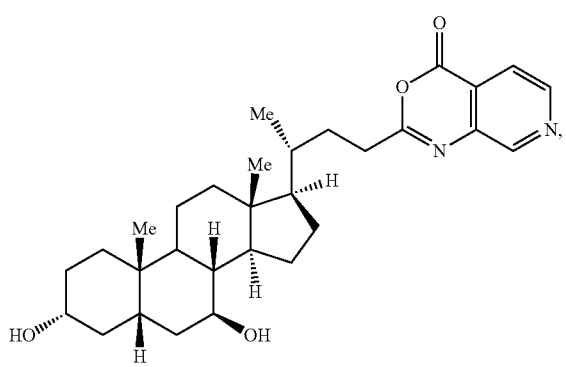
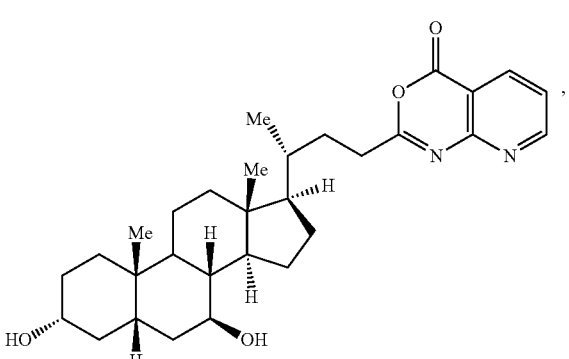
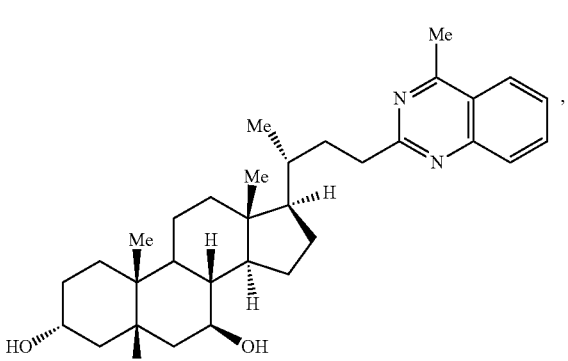
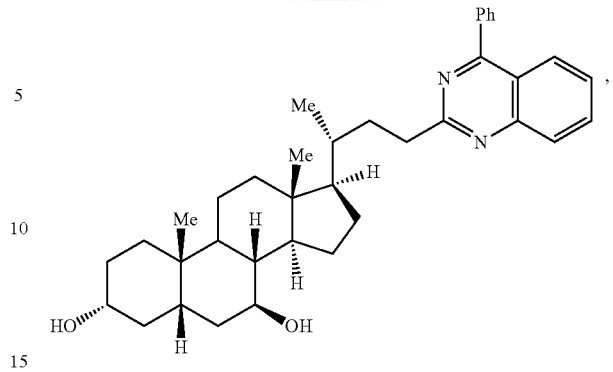

-continued
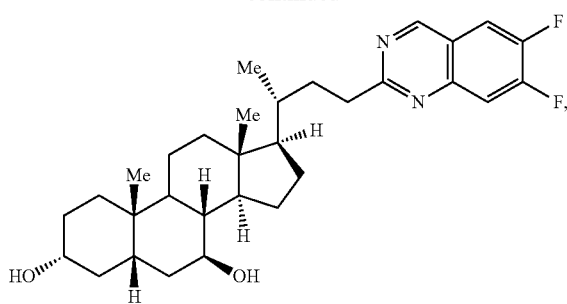
or a pharmaceutically acceptable salt thereof.
In one aspect, a compound can be selected from:
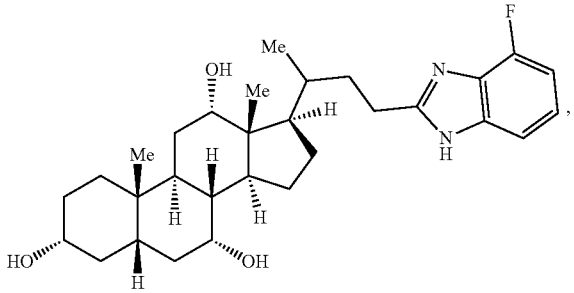
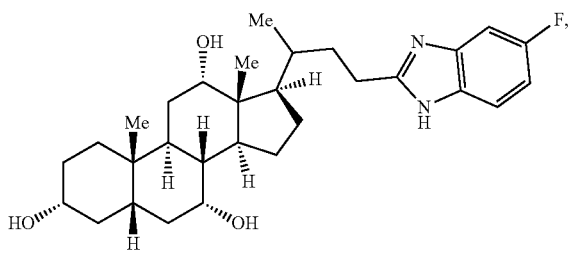
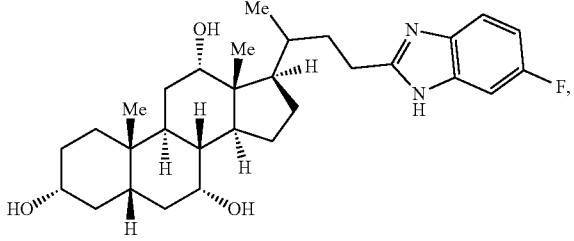
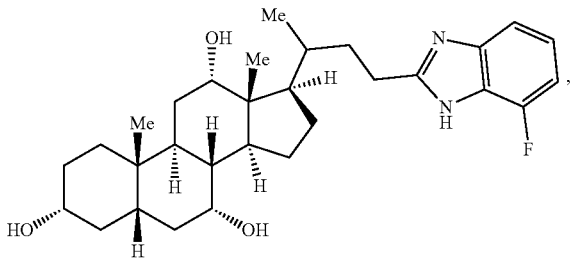
-continued
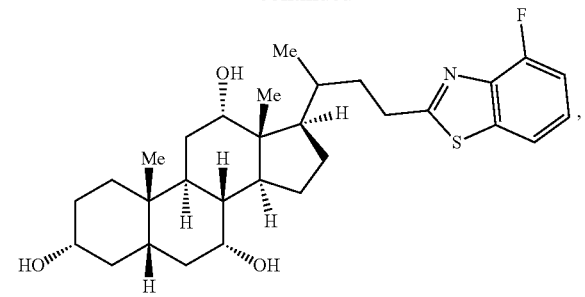

241
-continued
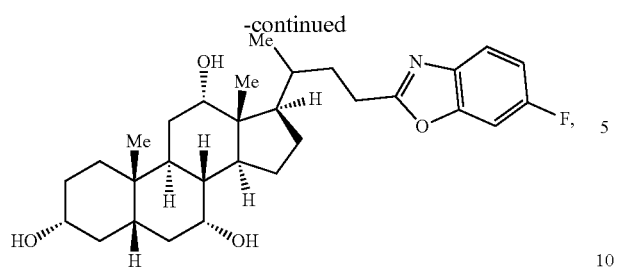
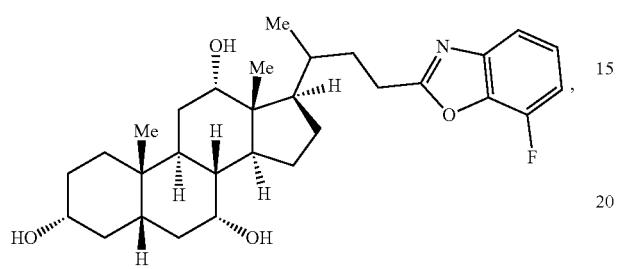
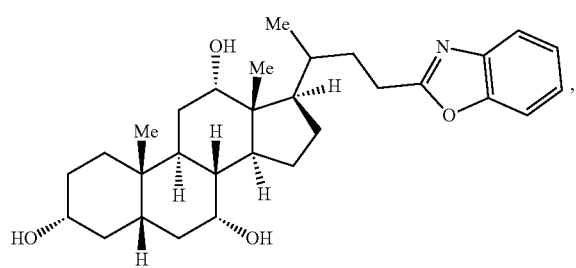
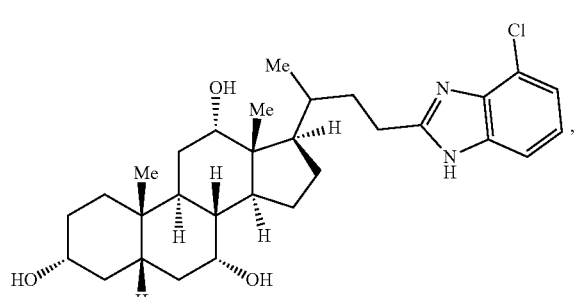
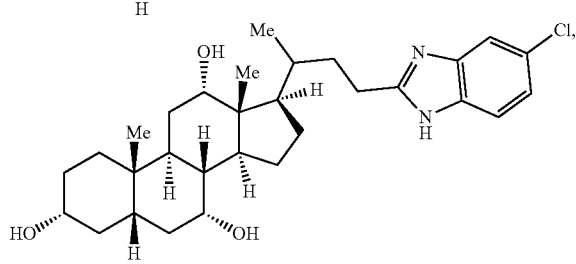
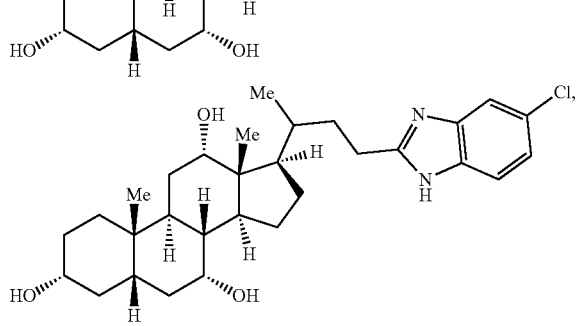
242
-continued
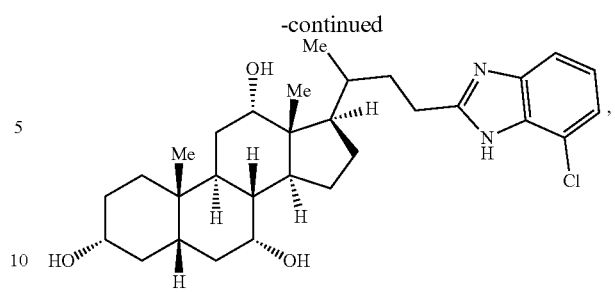
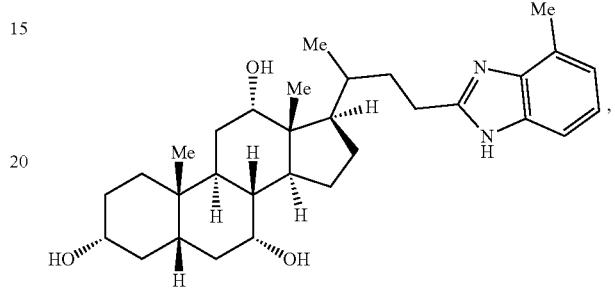
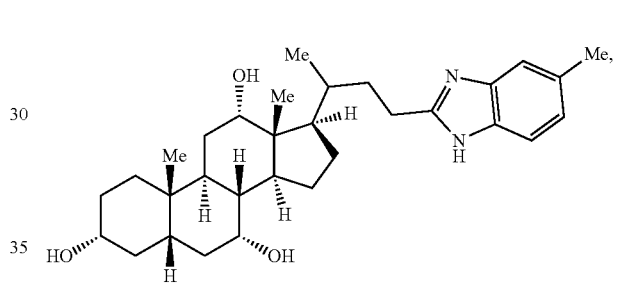
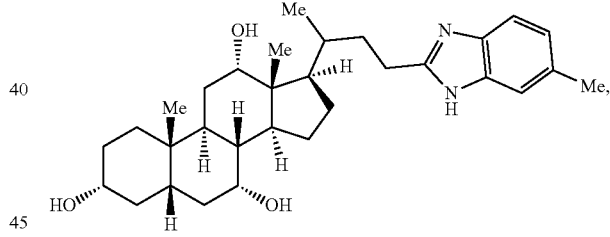
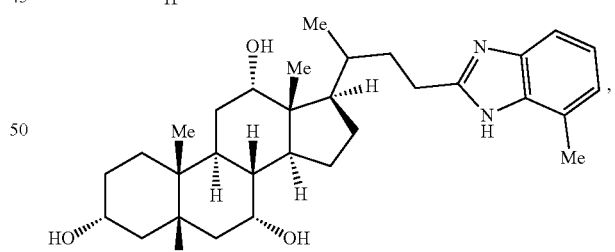
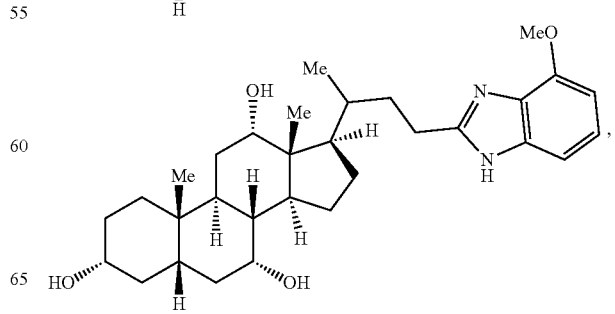

-continued
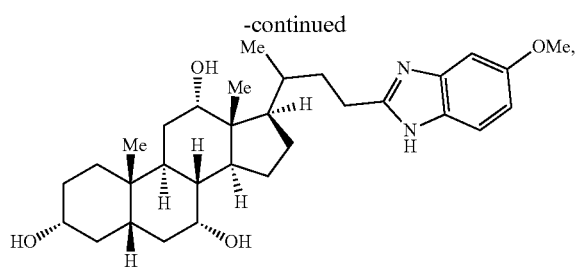
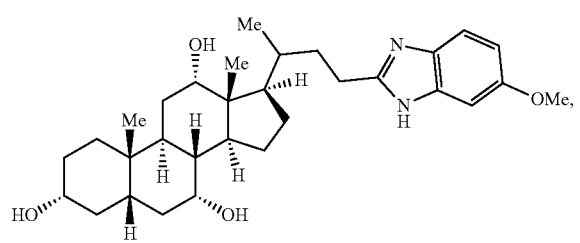
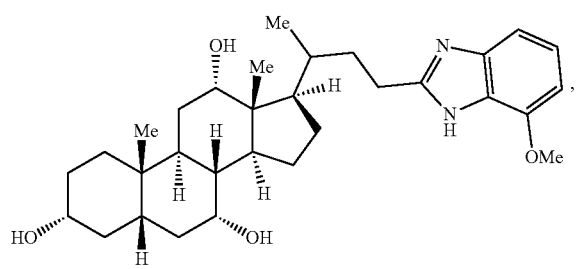
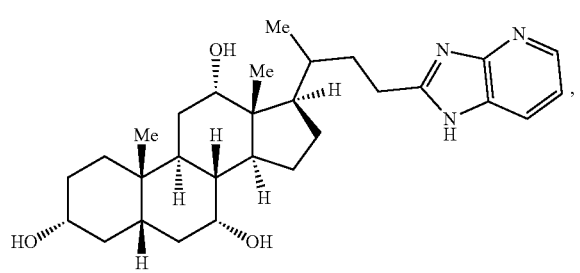
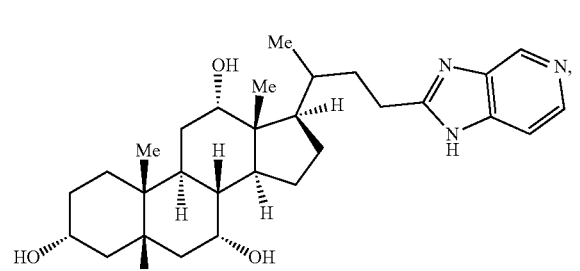
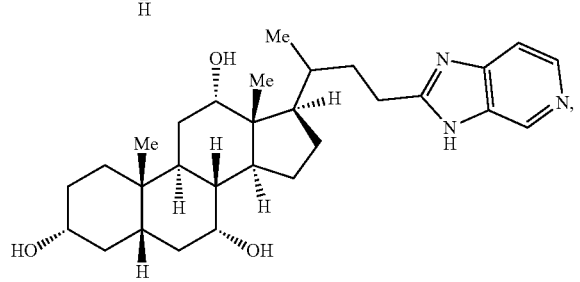
-continued
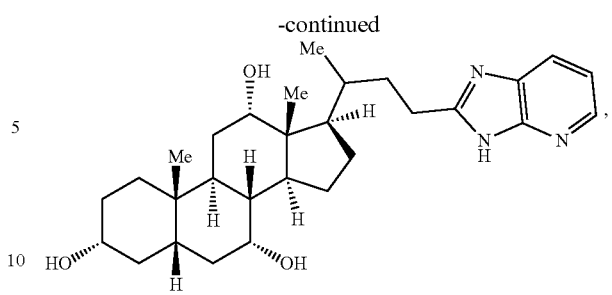
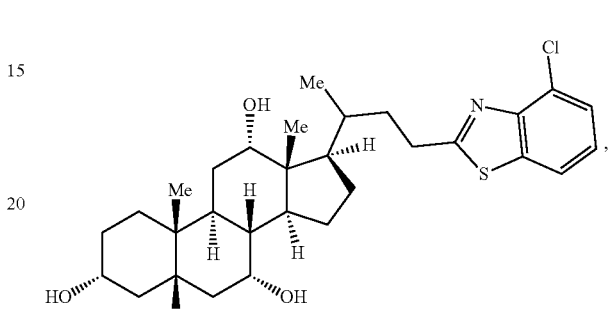
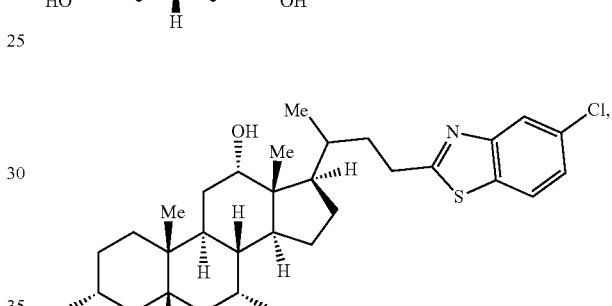
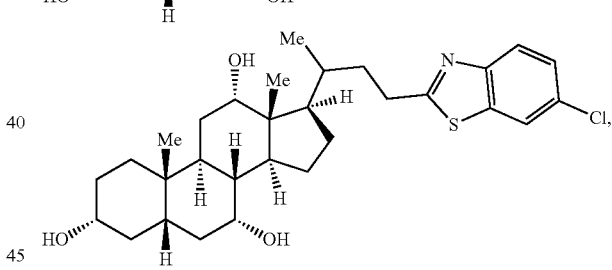
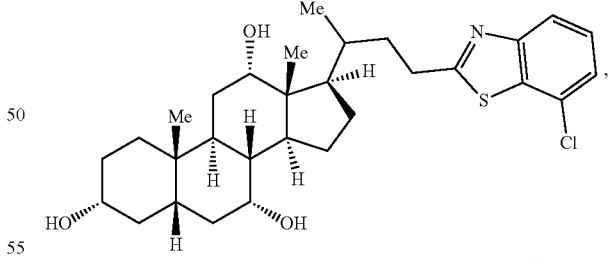
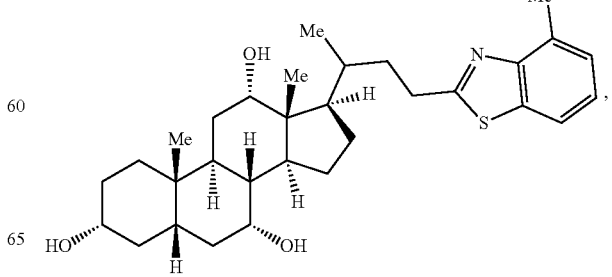

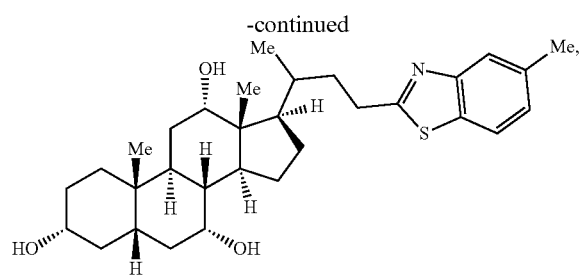
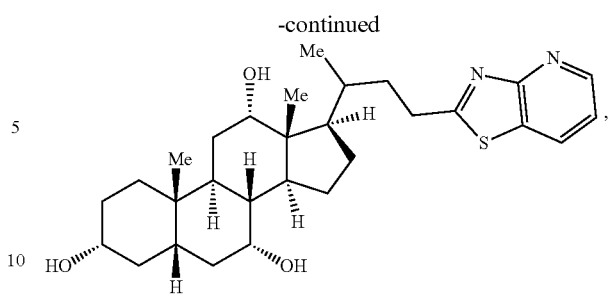
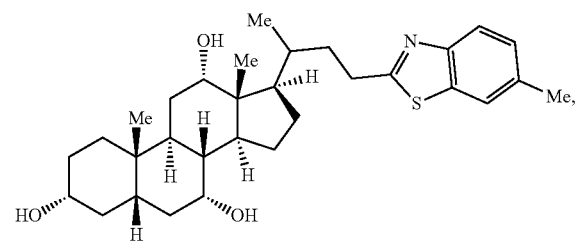
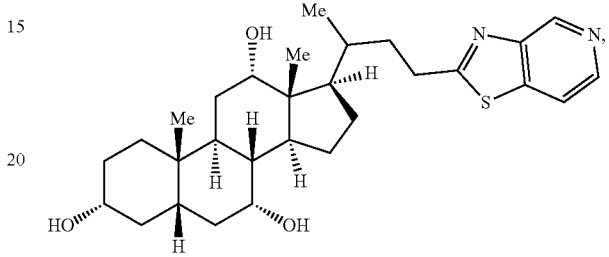
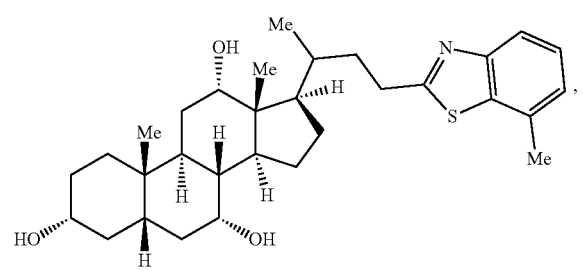
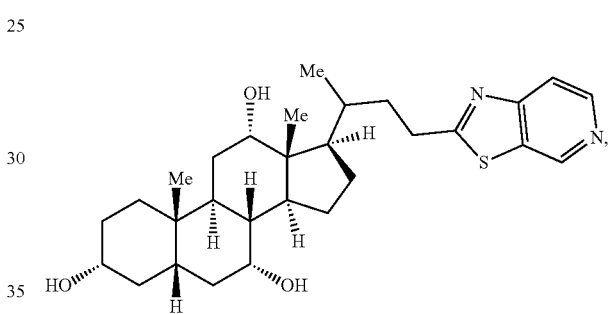
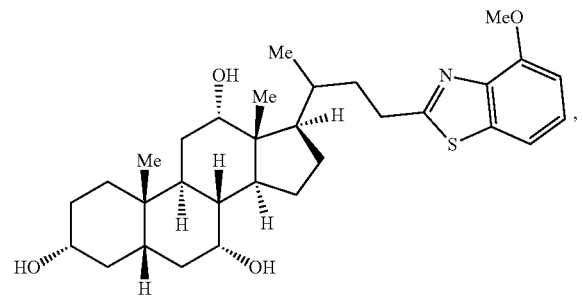
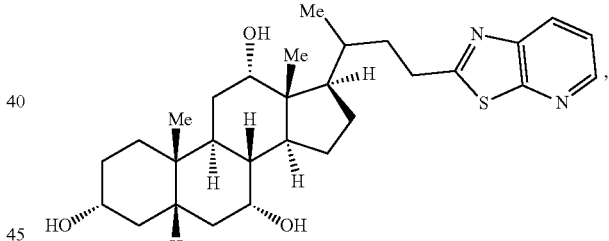
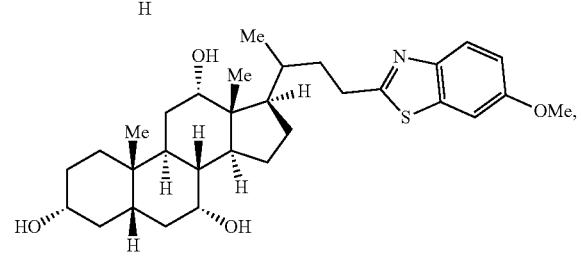
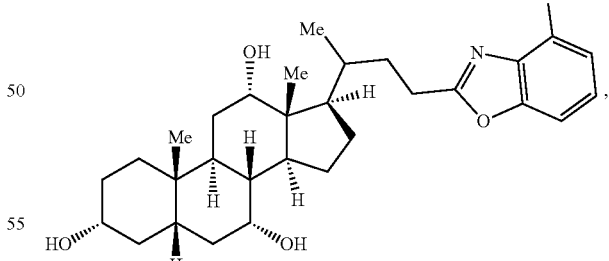
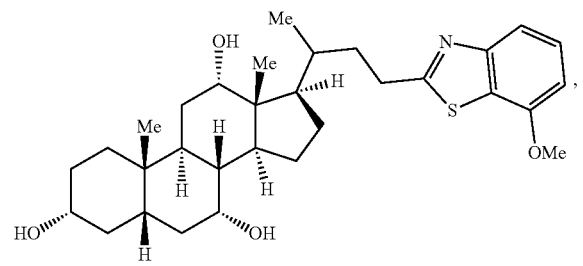
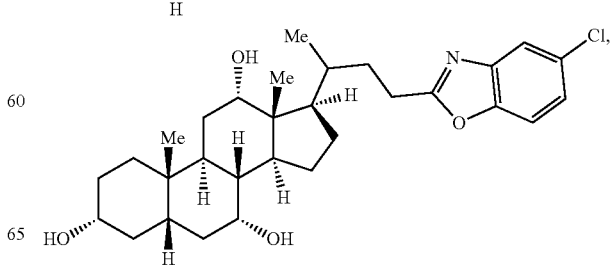

247
-continued
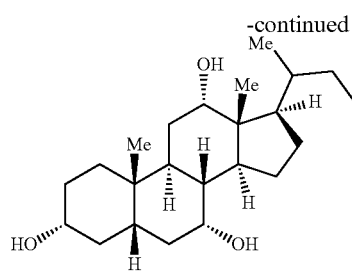
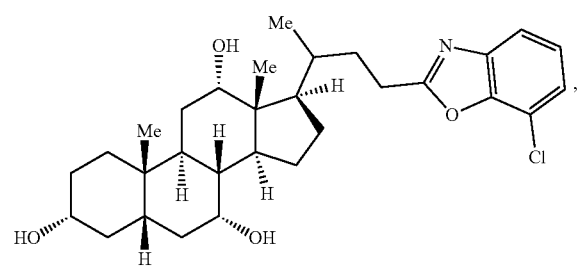
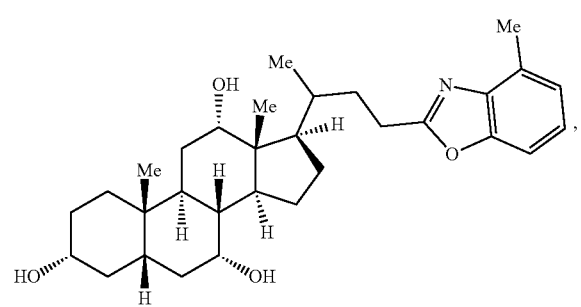
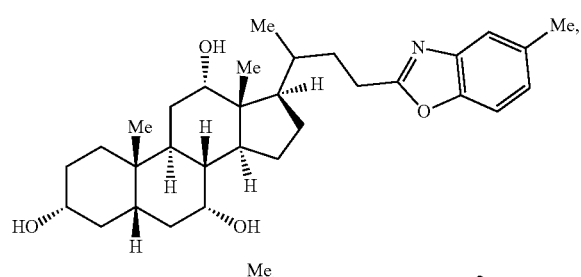
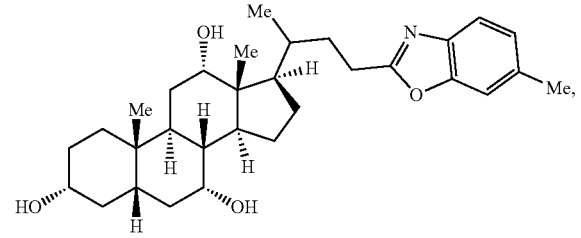
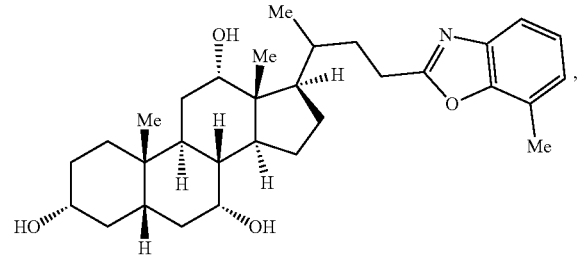
248
-continued
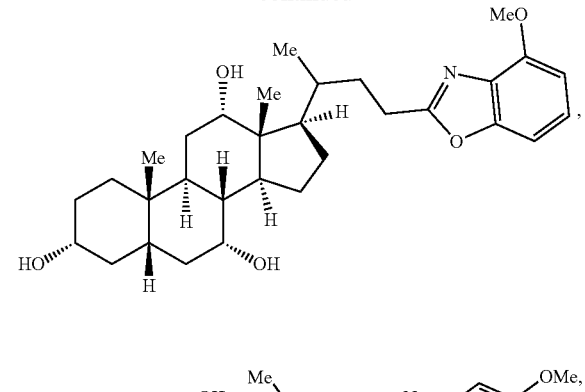
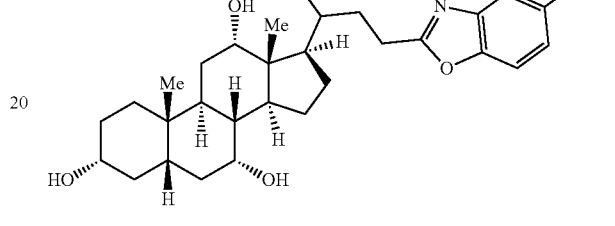
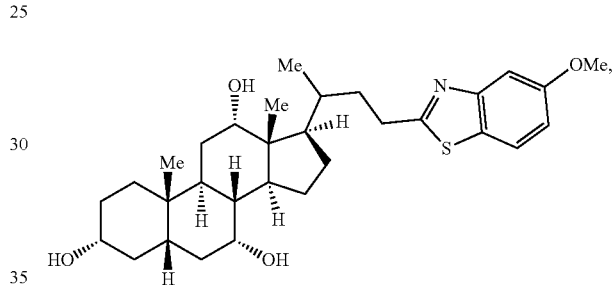
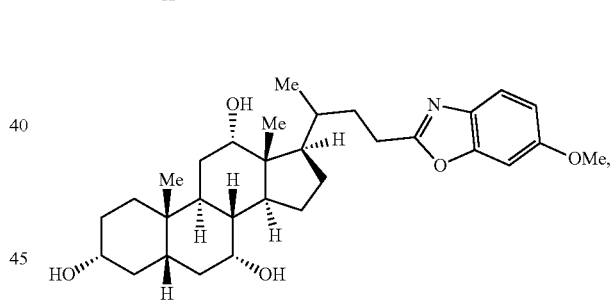
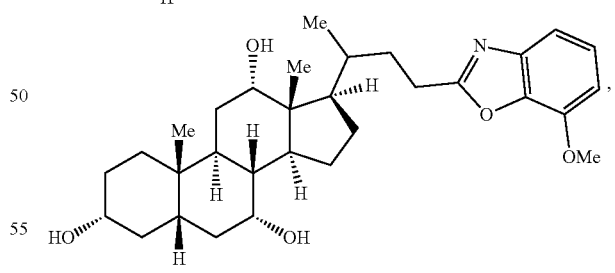
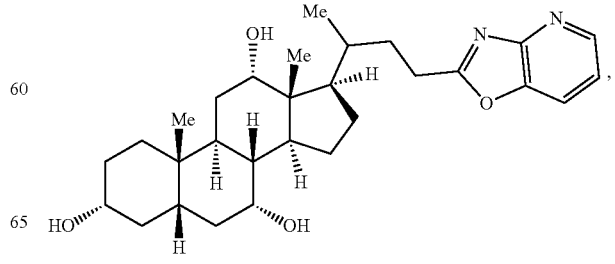

-continued
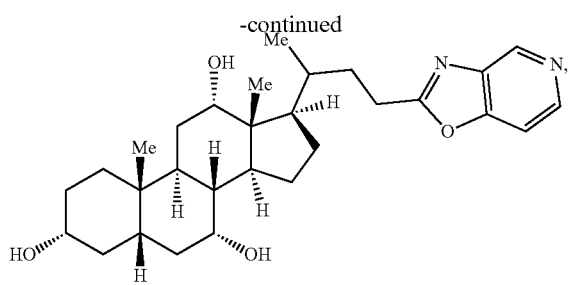
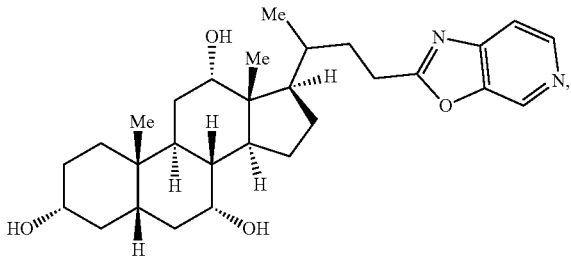
and
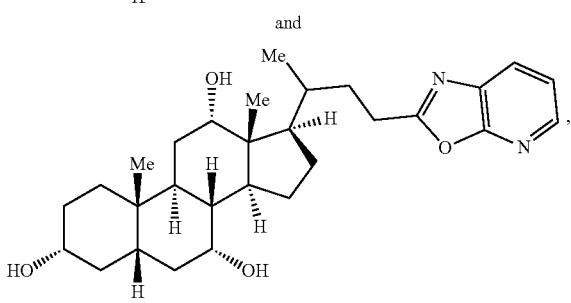
or a pharmaceutically acceptable salt thereof.
In one aspect, a compound can be selected from:
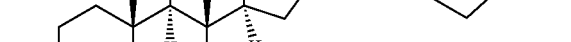
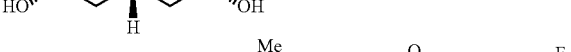
-continued
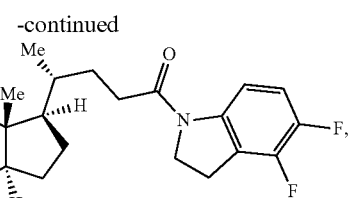
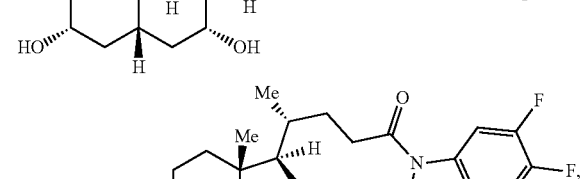
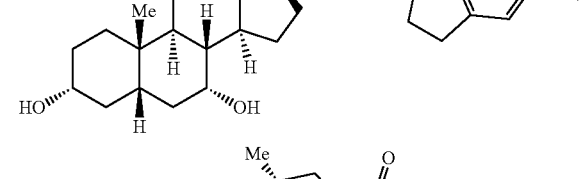
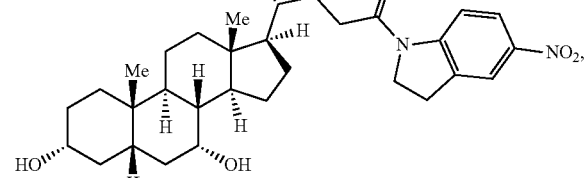
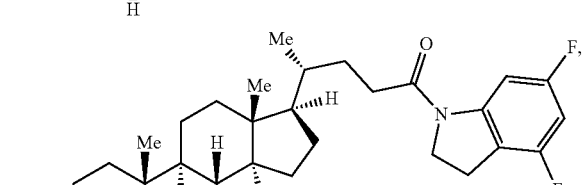
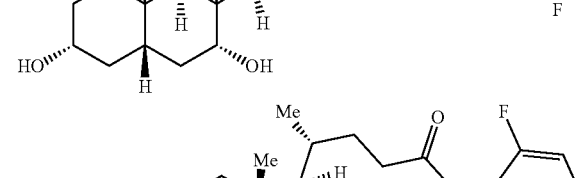
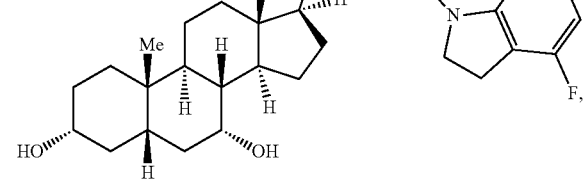
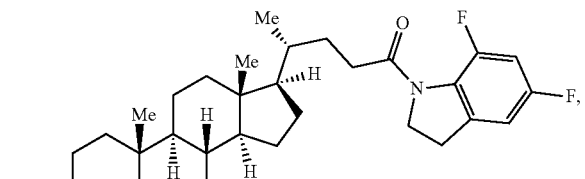
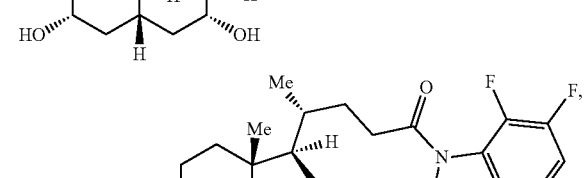
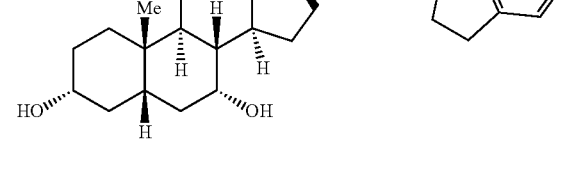

-continued
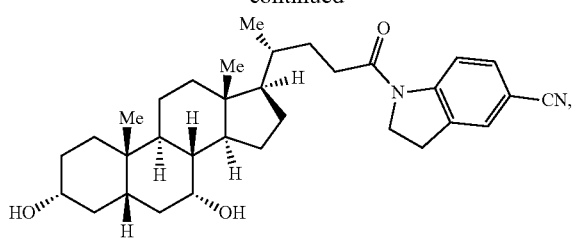
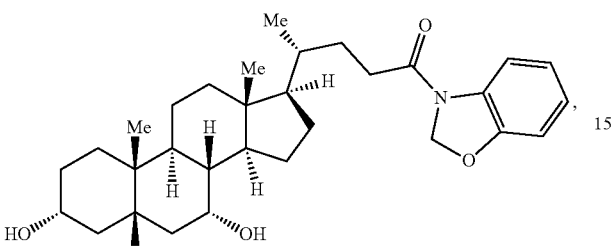
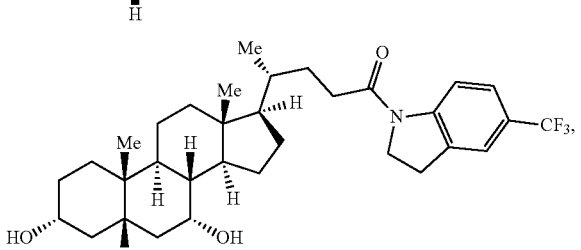
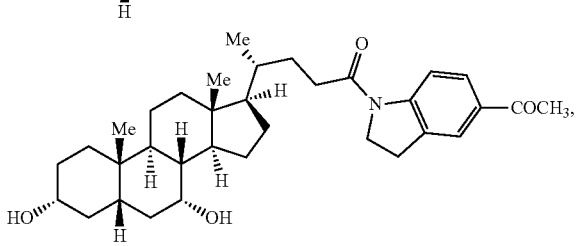
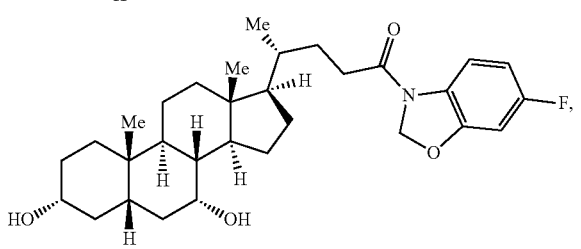
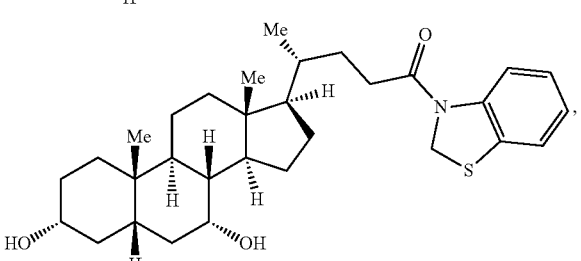
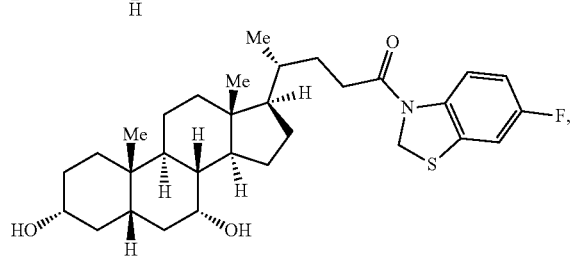
-continued
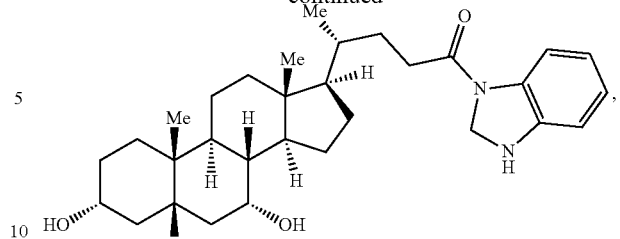
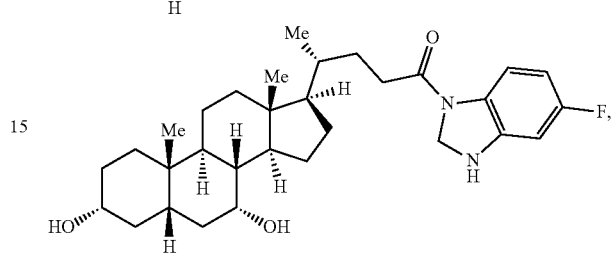
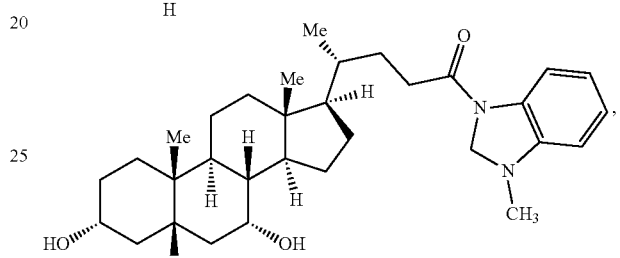
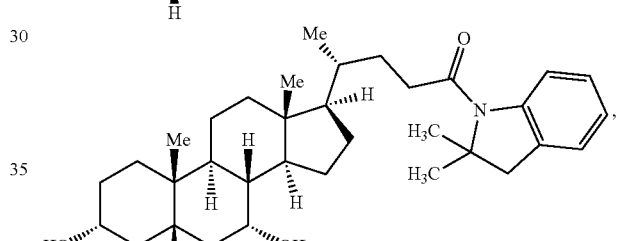
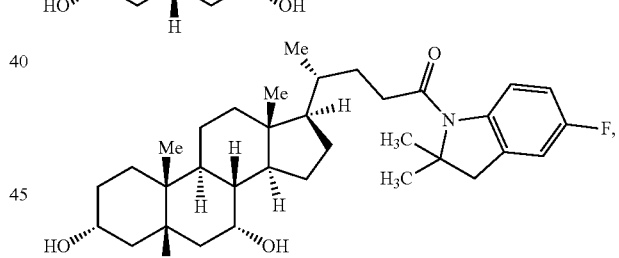
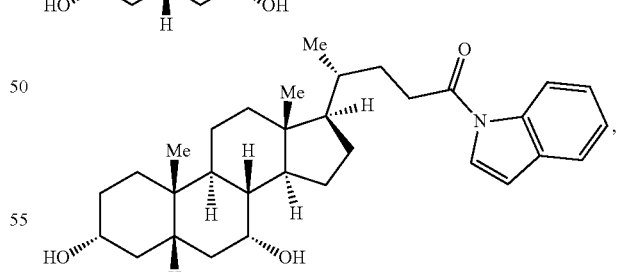
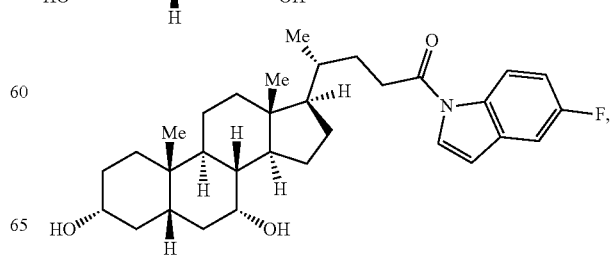

-continued
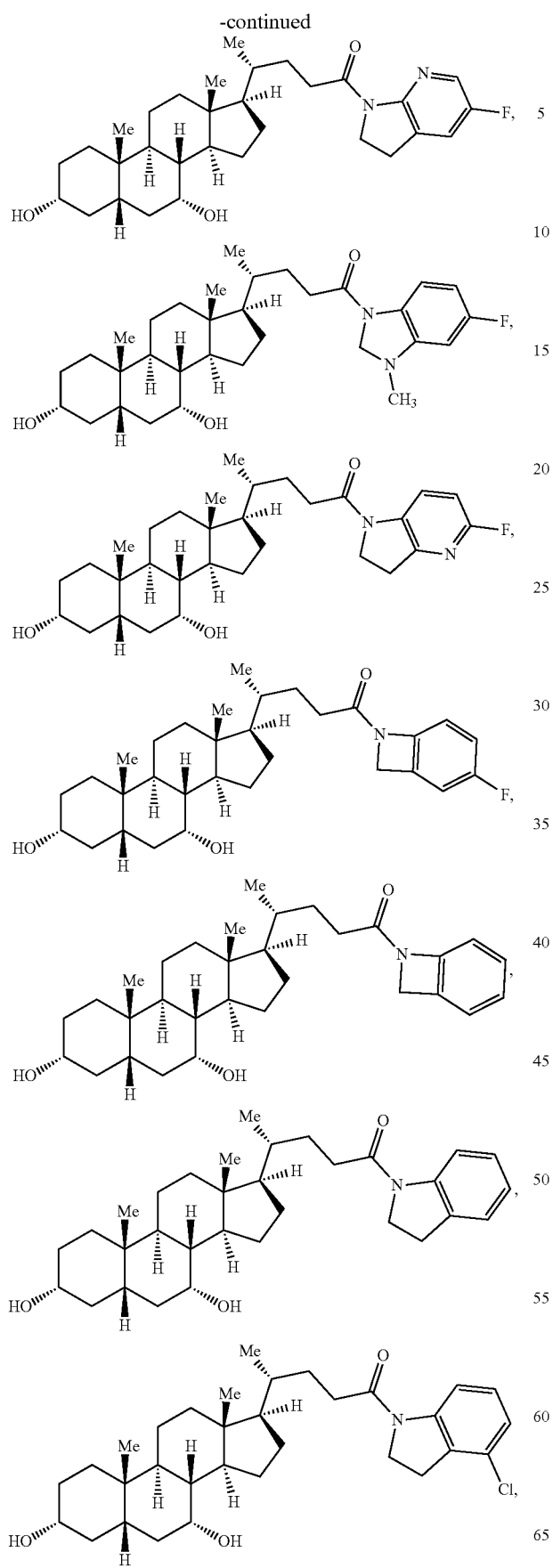
-continued
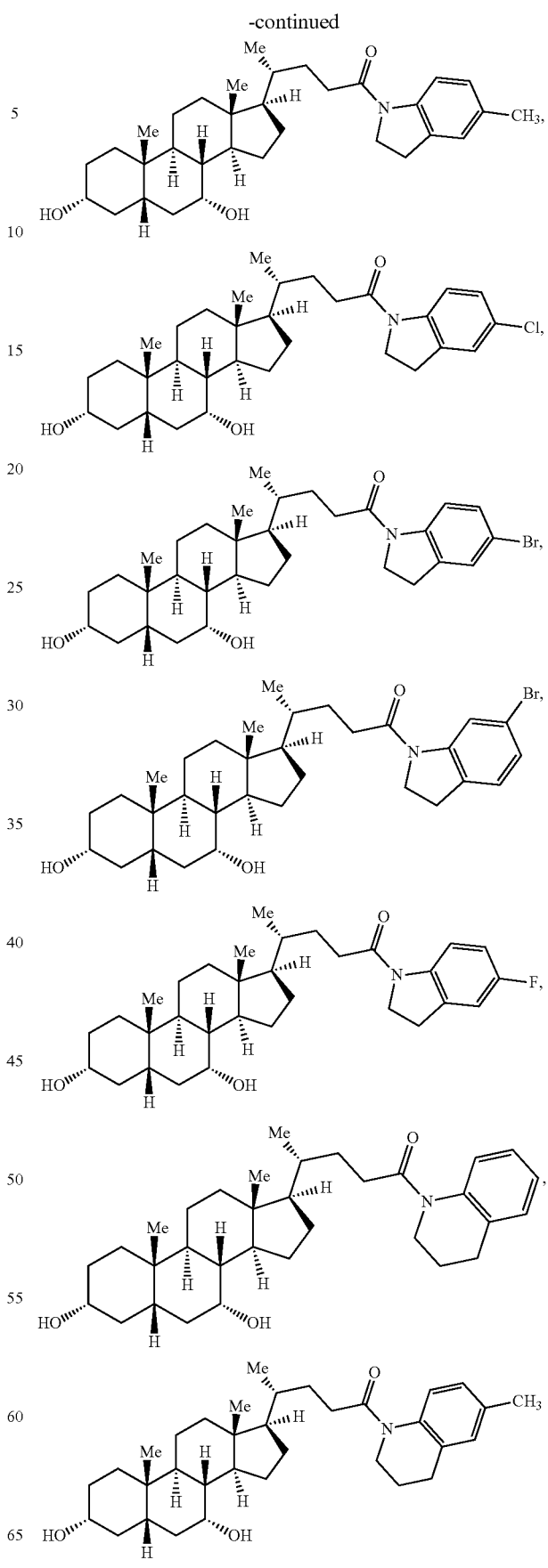

-continued
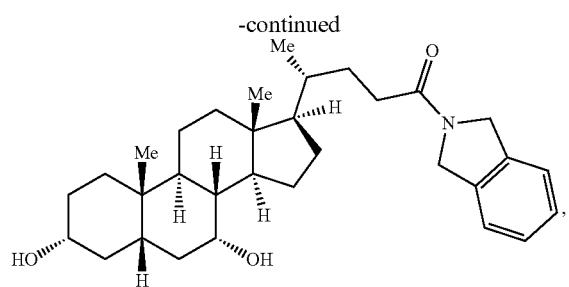
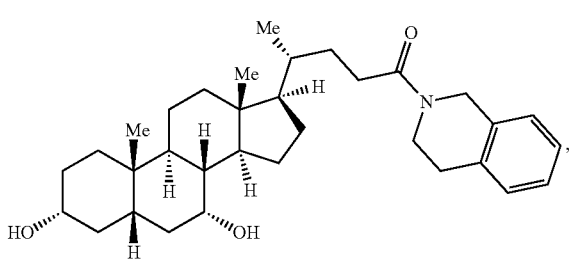
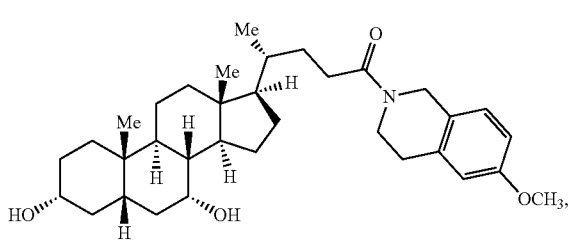
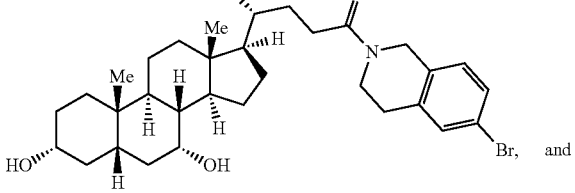
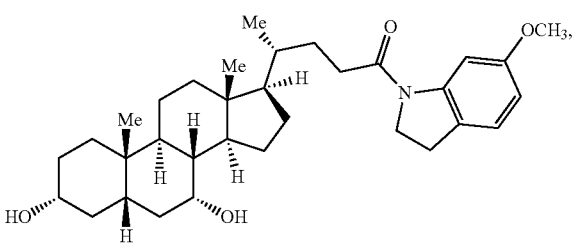
or a pharmaceutically acceptable salt thereof.
In one aspect, a compound can be selected from:
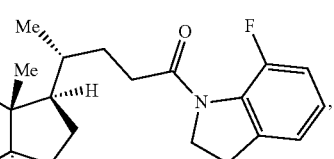
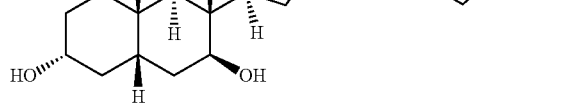
-continued
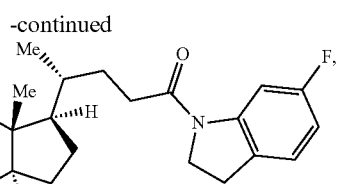
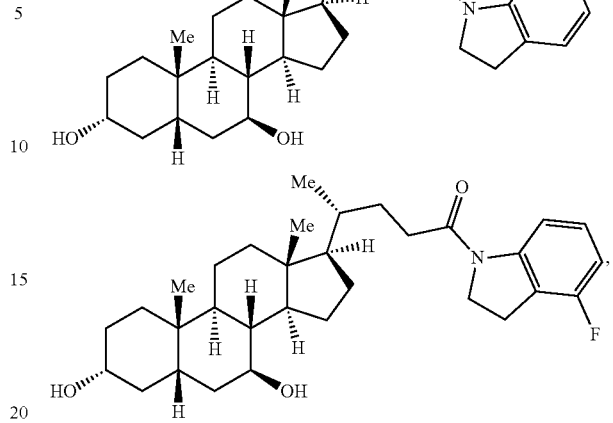
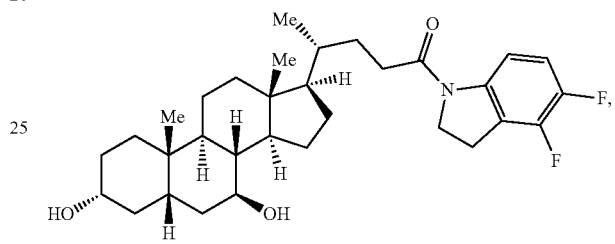
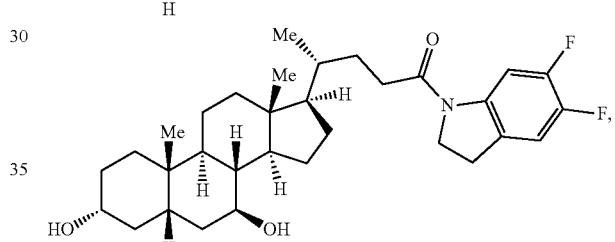
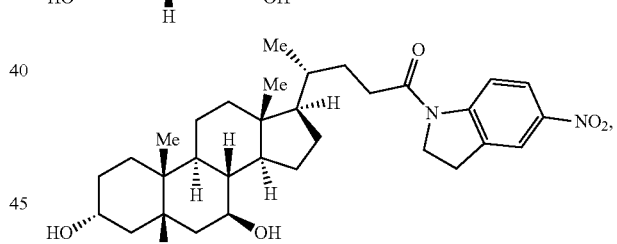
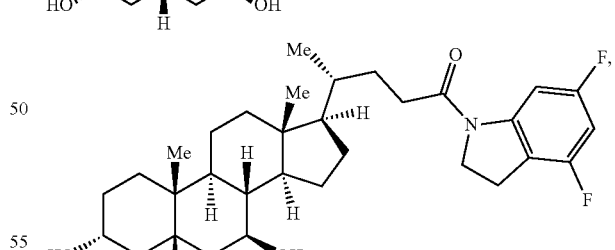
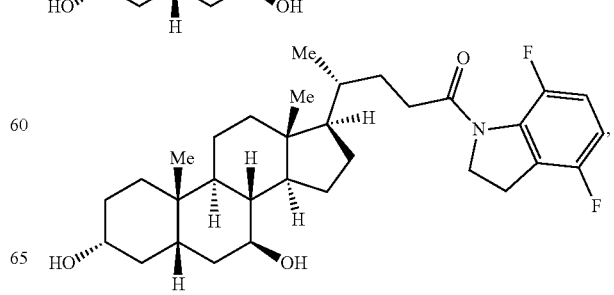

257
-continued
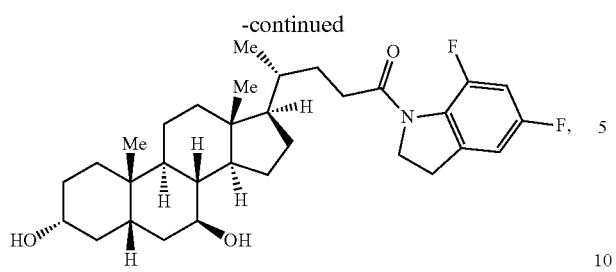
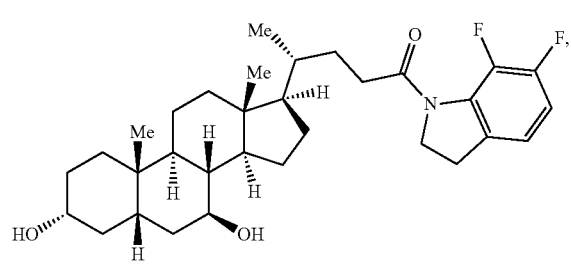
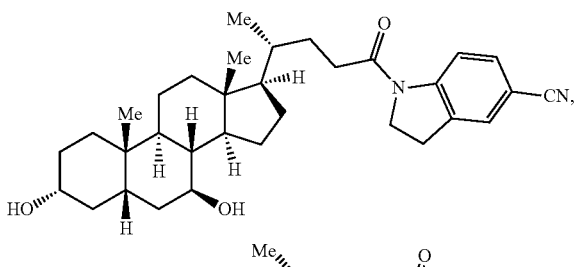
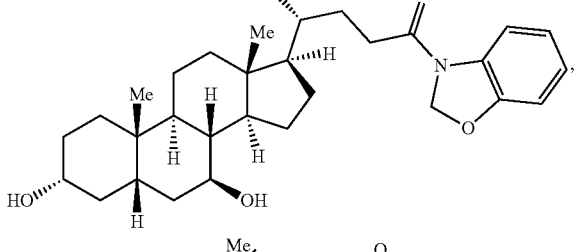
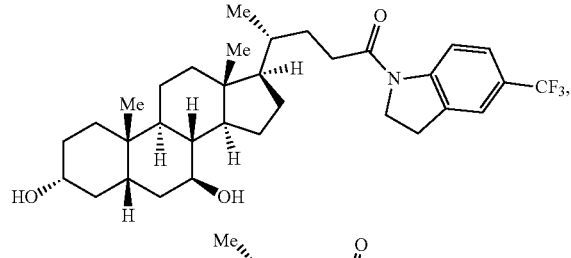
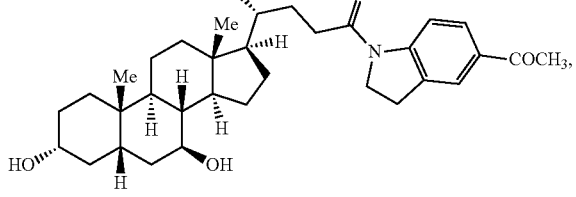
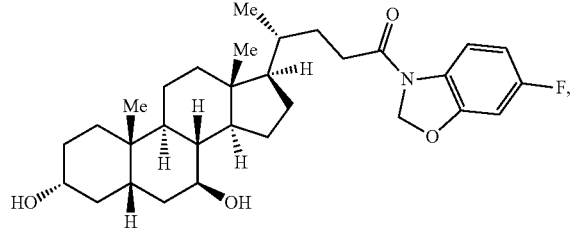
258
-continued
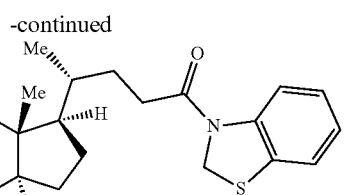
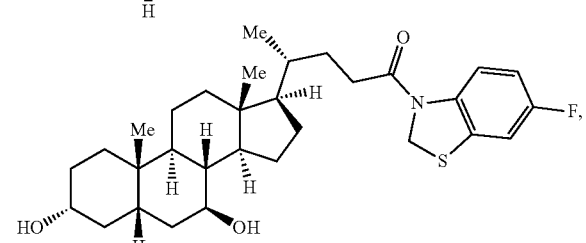
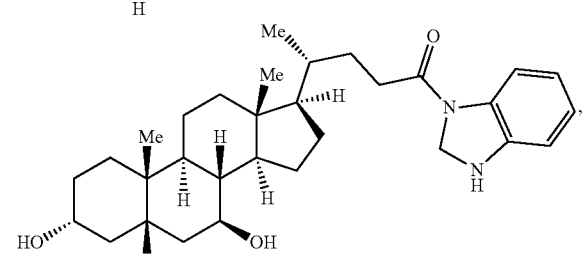
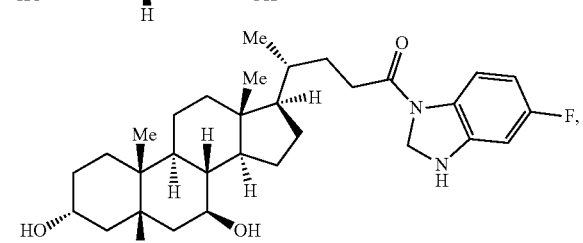
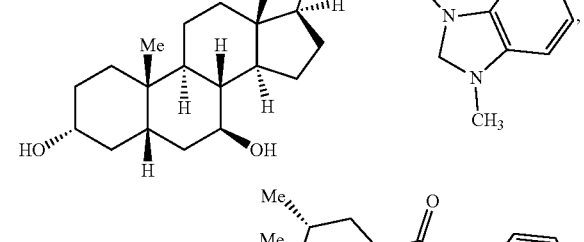
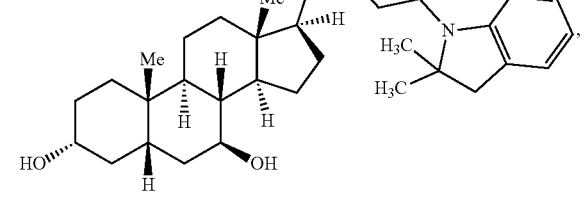

-continued
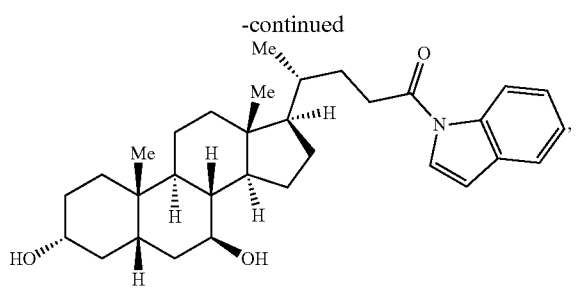
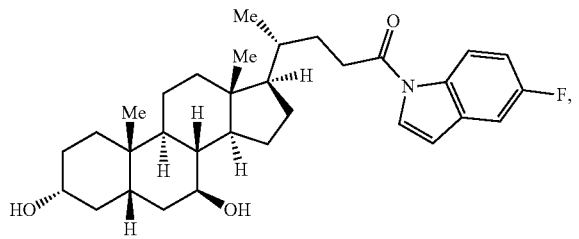
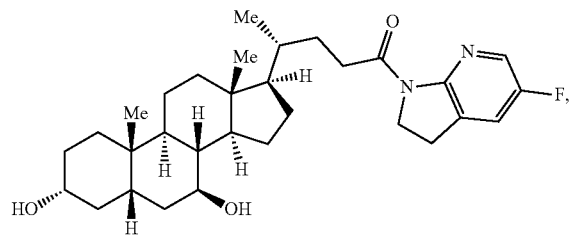
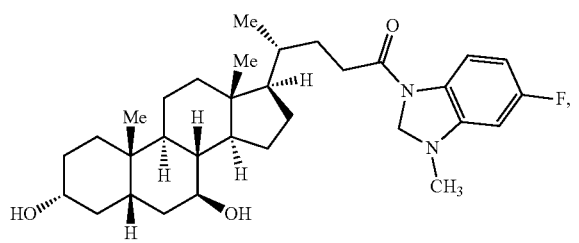
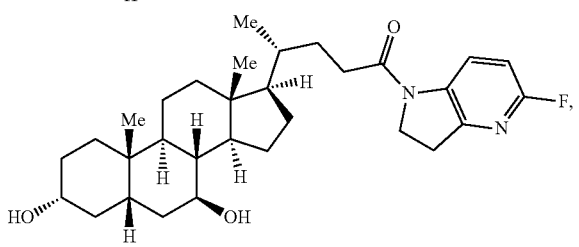
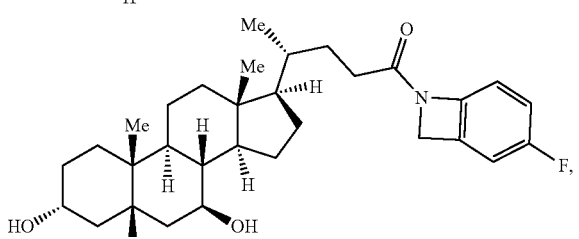
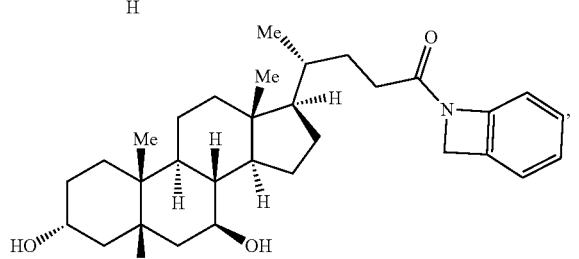
-continued
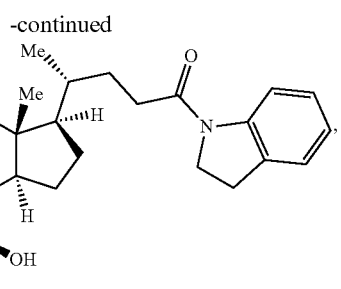
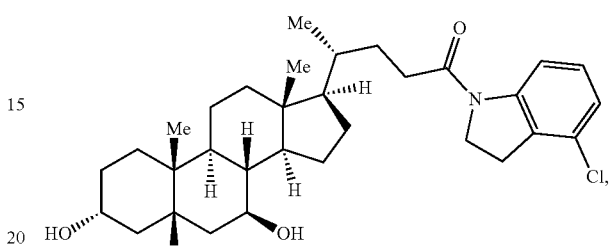
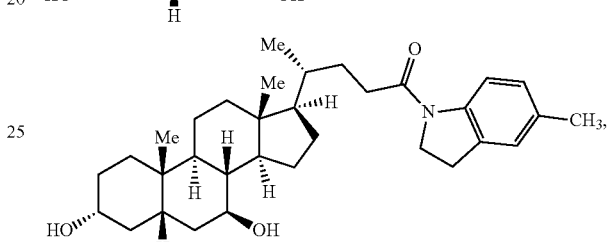
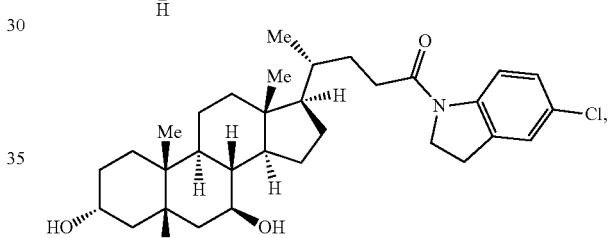
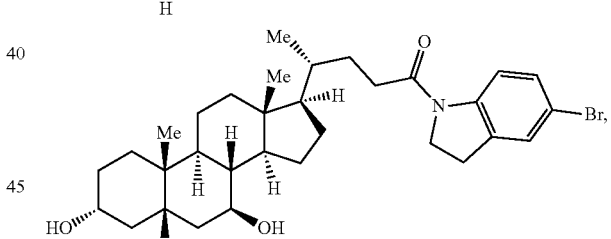
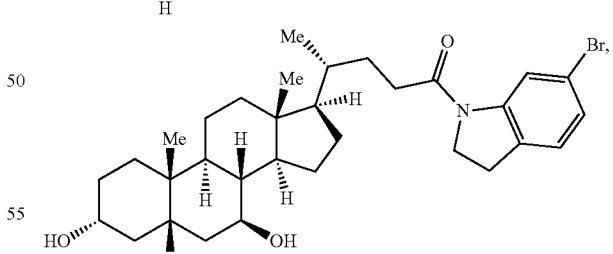
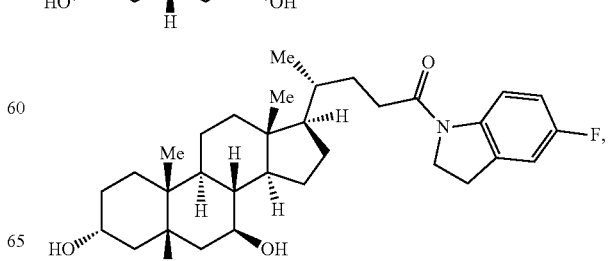

-continued
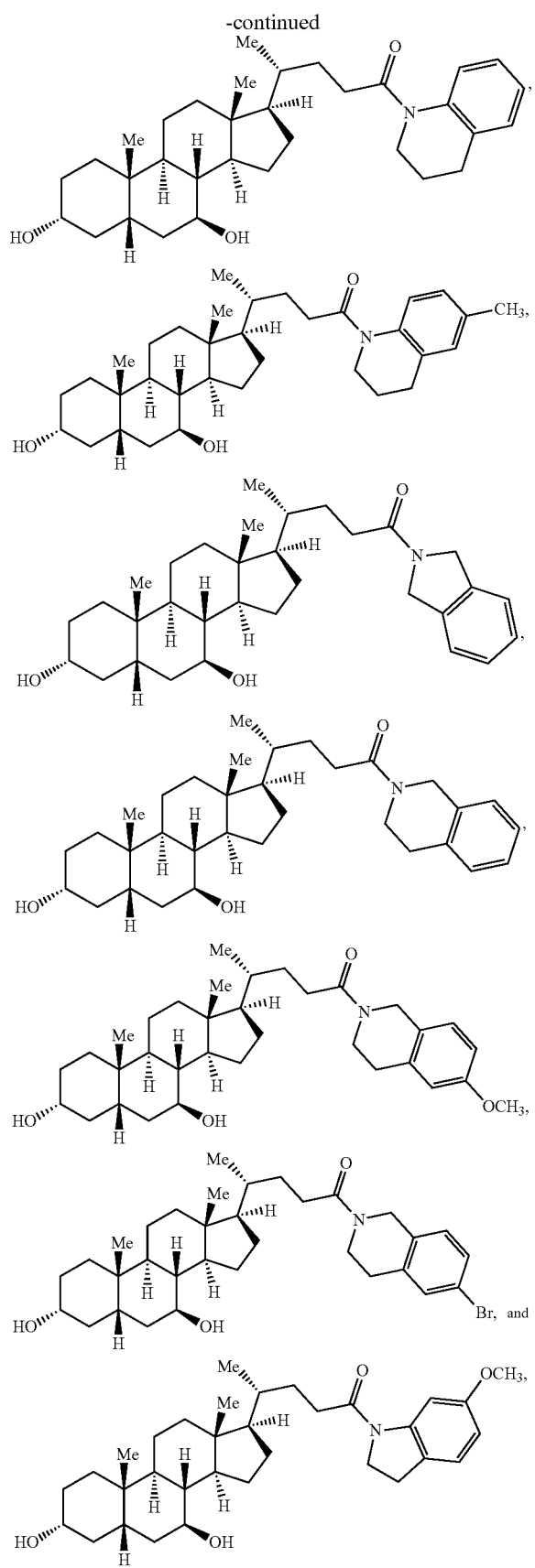
or a pharmaceutically acceptable salt thereof.
In one aspect, a compound can be selected from:
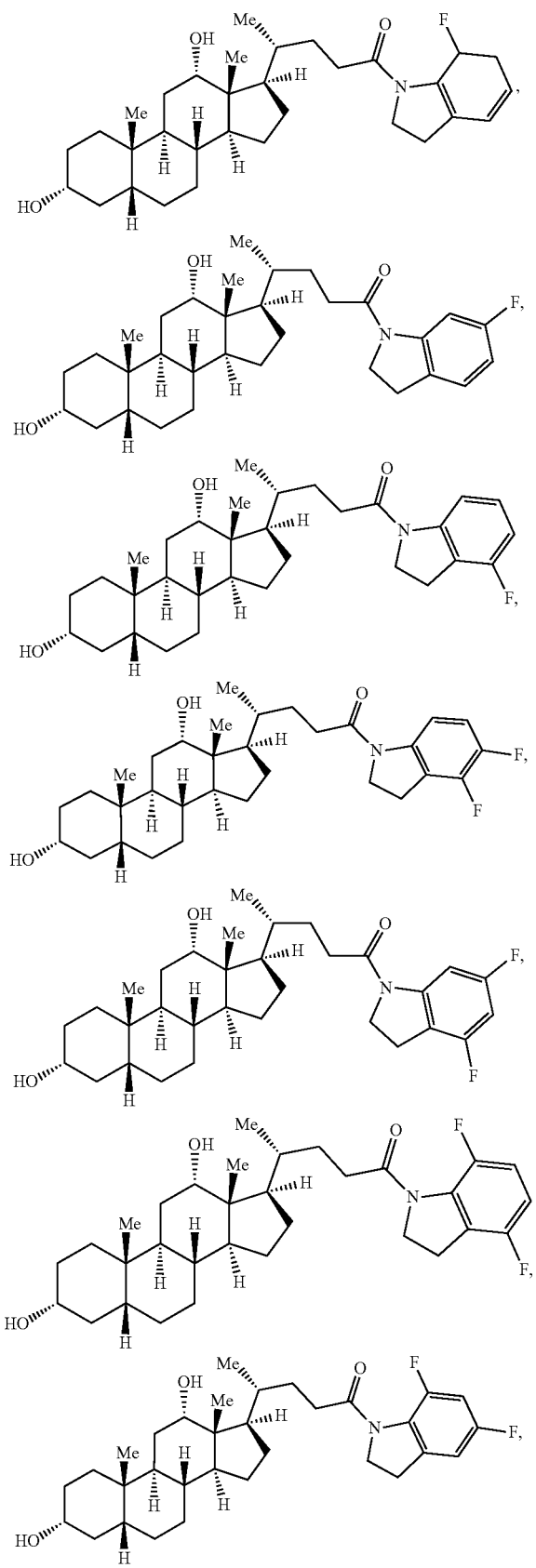

263
-continued
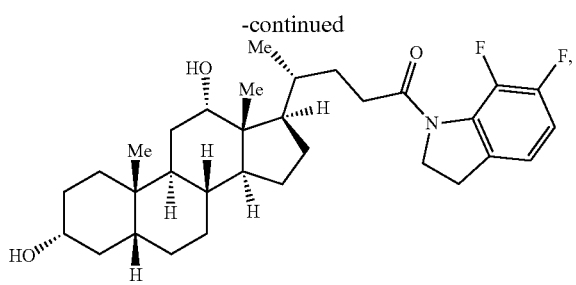
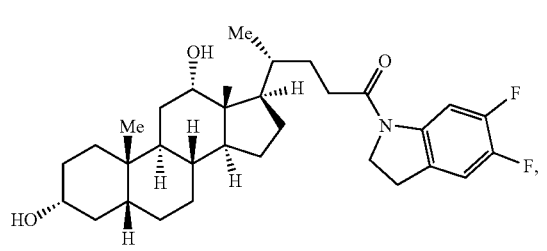
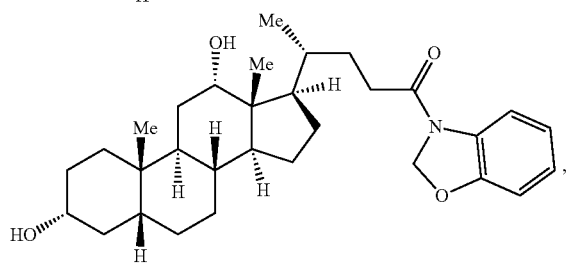
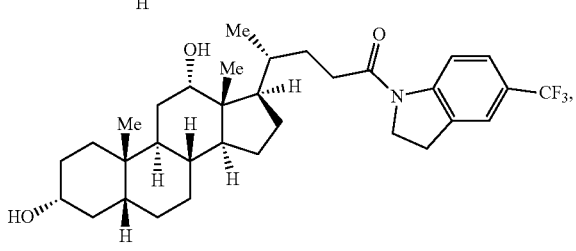
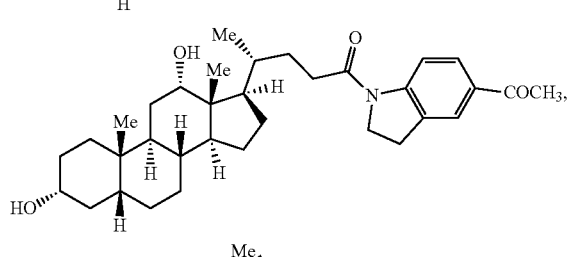
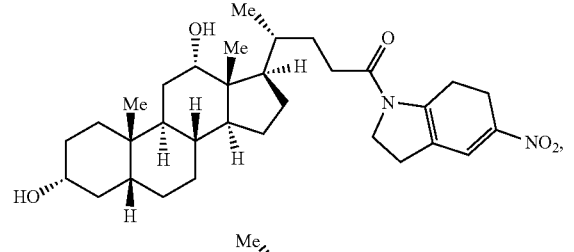
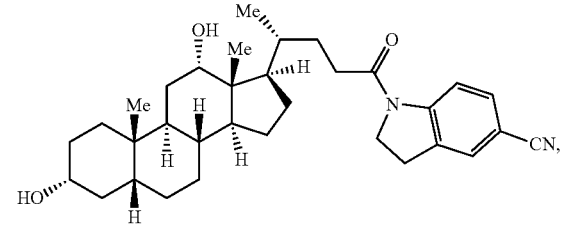
264
-continued
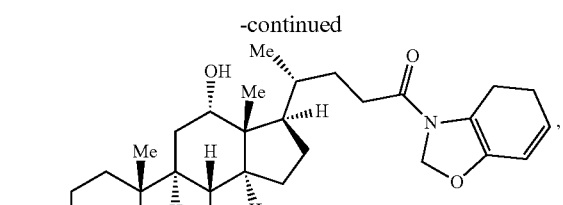
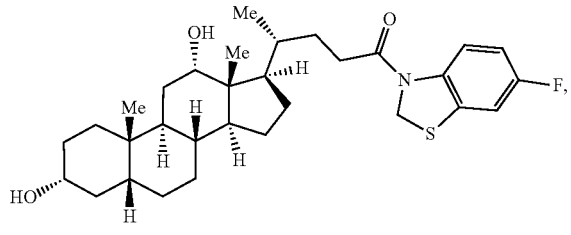
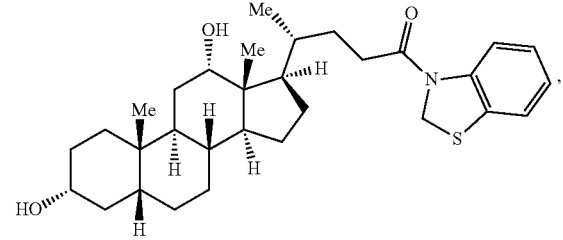
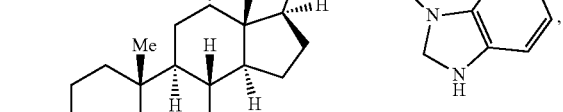
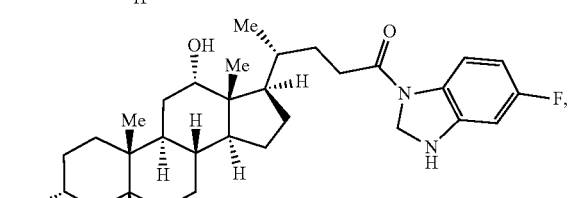
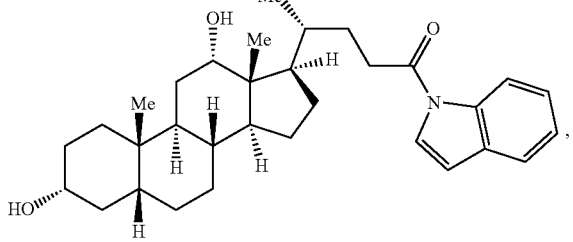
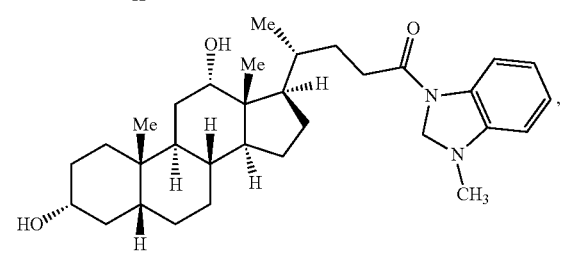

265
-continued
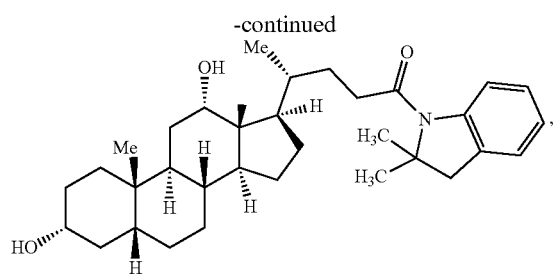
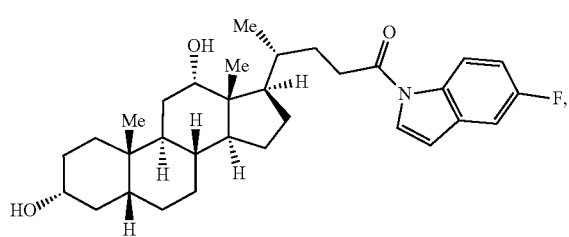
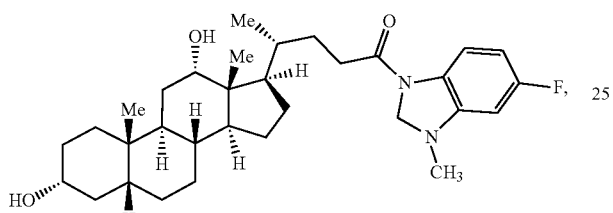
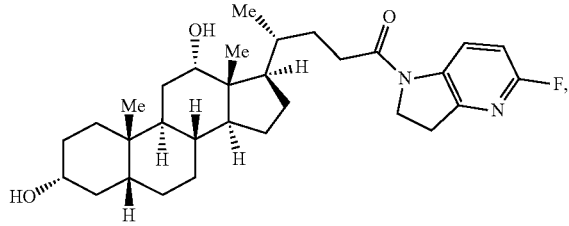
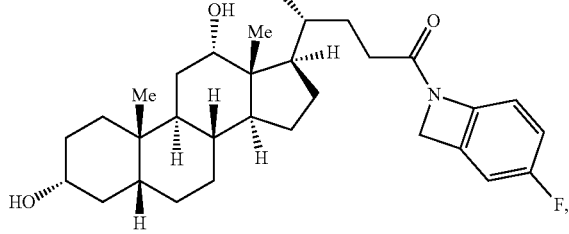
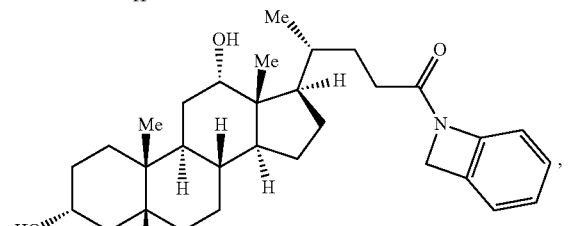
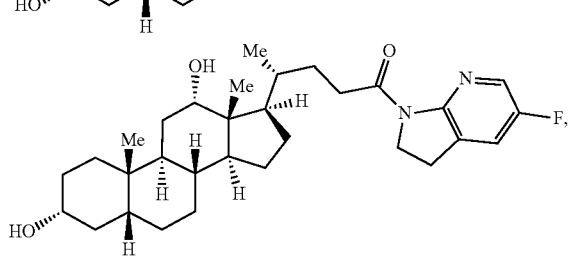
266
-continued
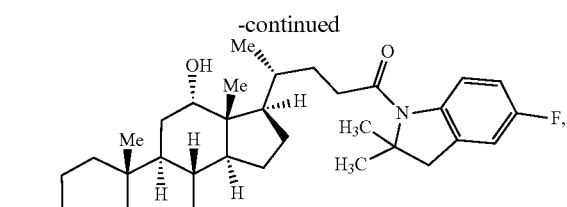
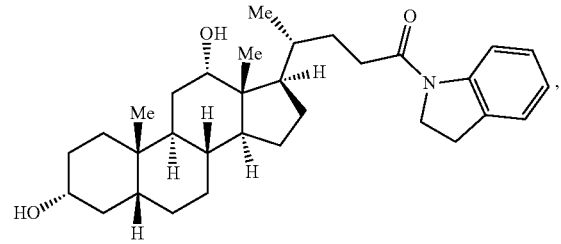
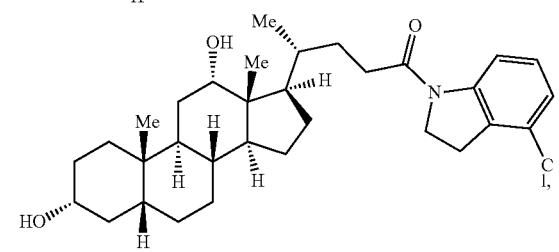
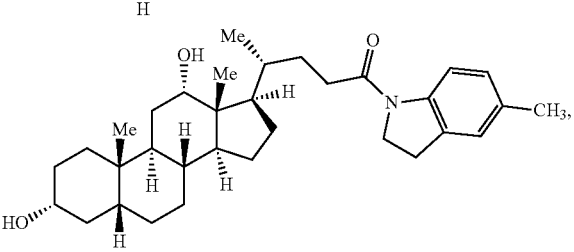
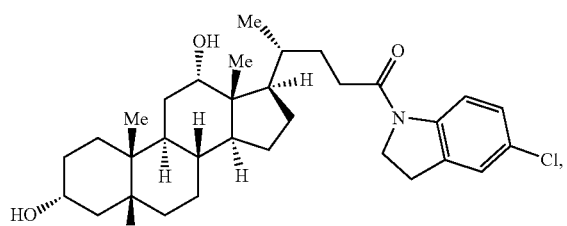
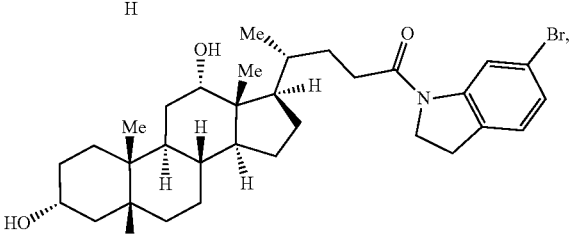
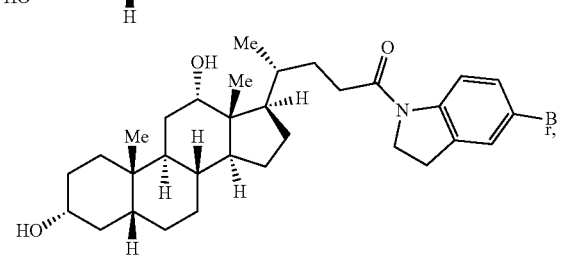

267
-continued
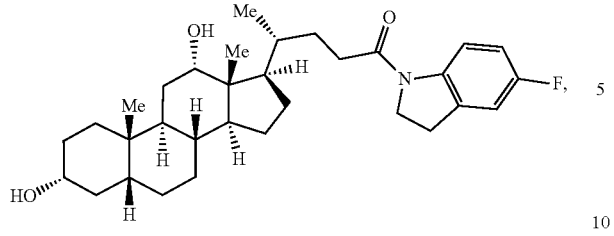
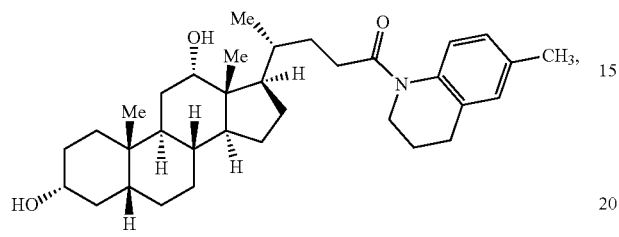
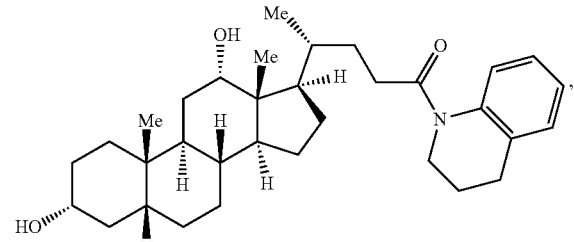
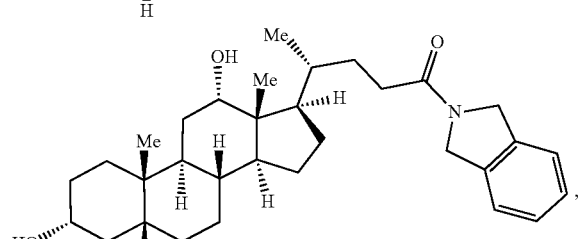
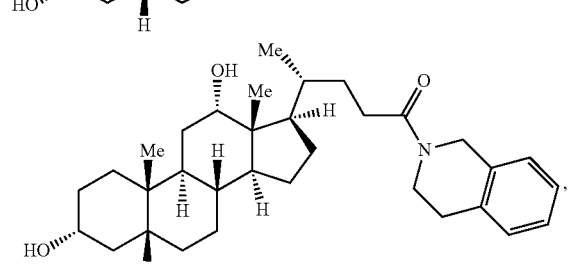
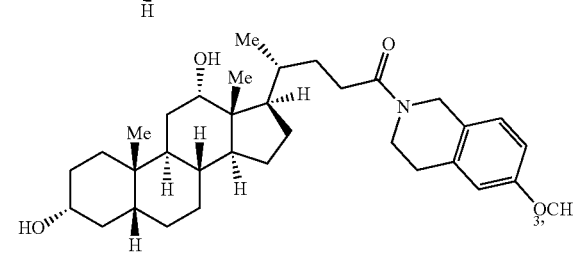
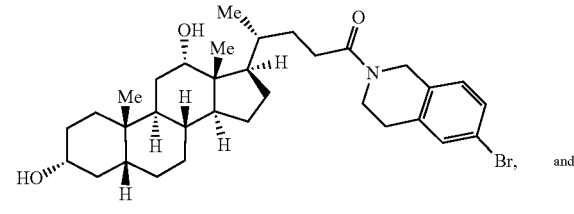
268
-continued
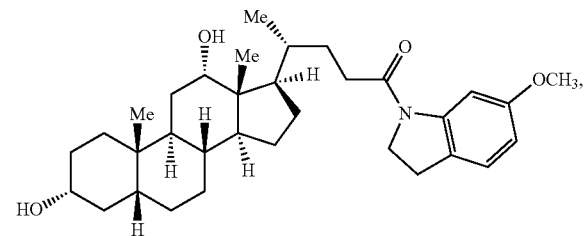
or a pharmaceutically acceptable salt thereof.
In one aspect, a compound can be selected from:
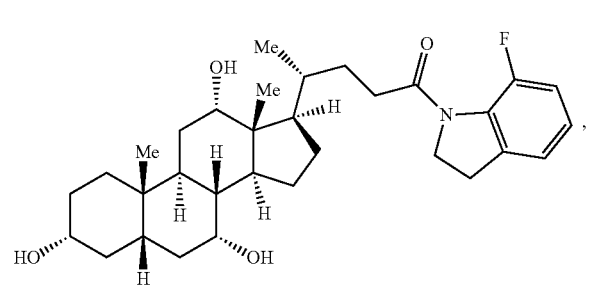
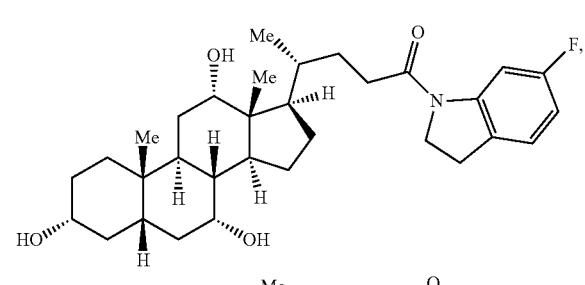
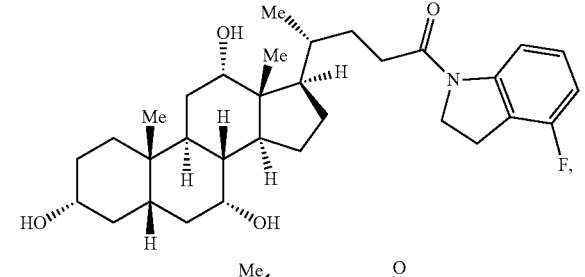
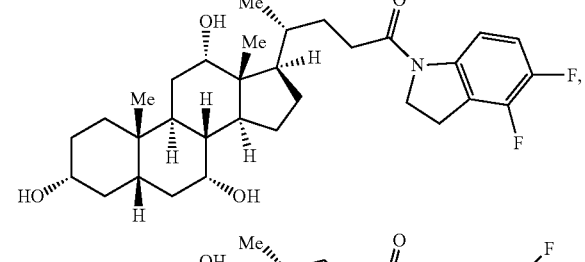
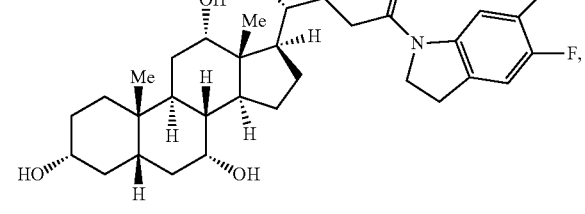

269
-continued
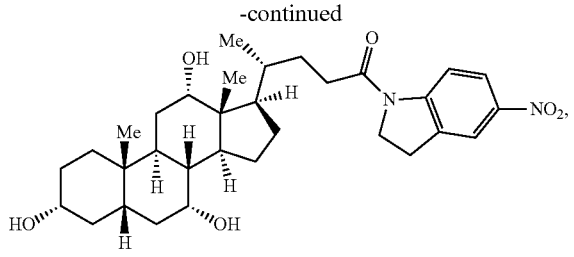
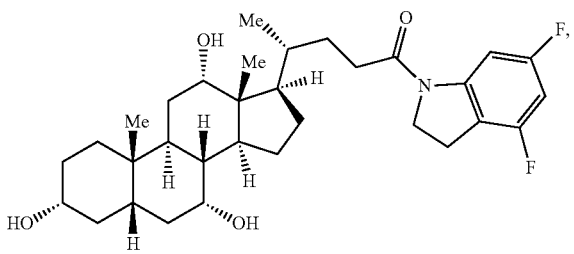
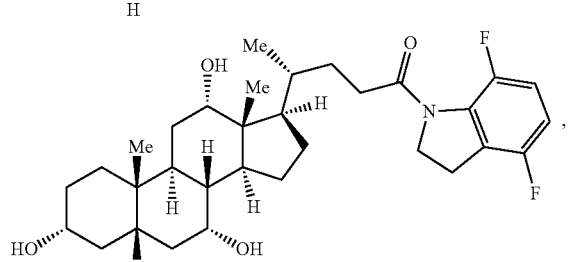
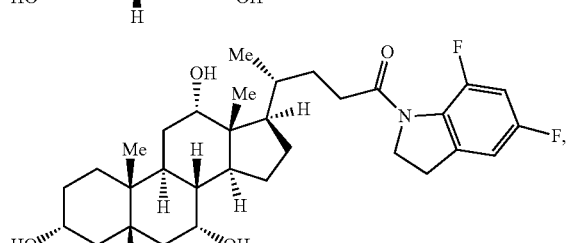
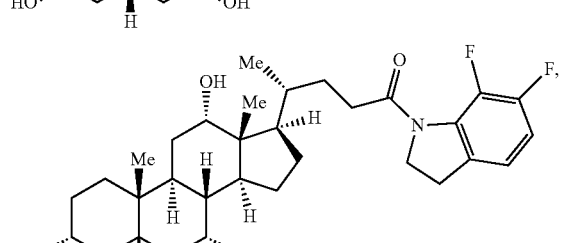
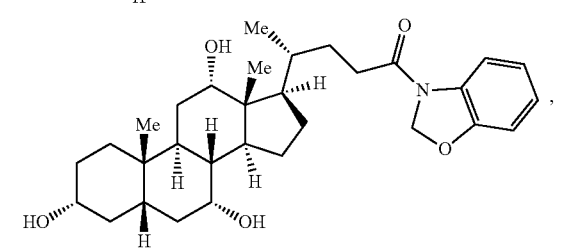
270
-continued
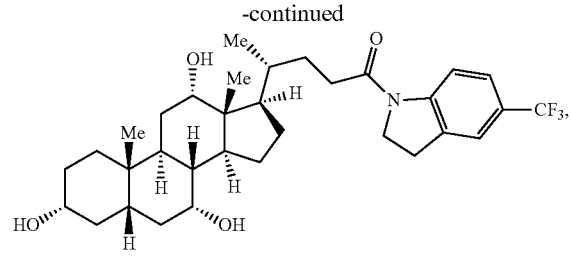
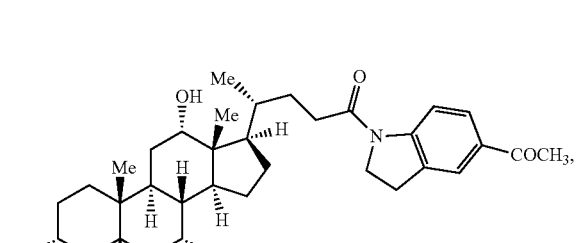
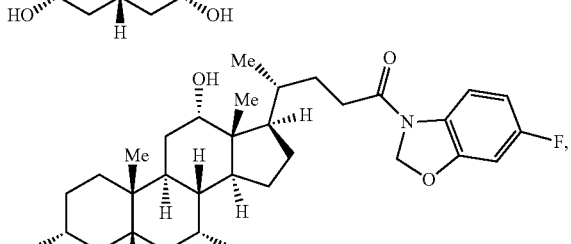
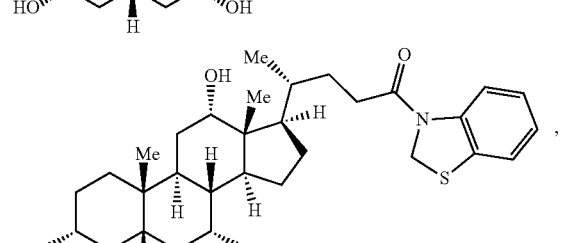
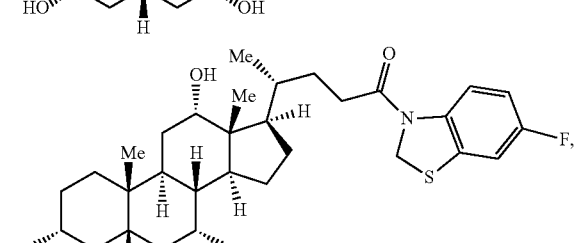
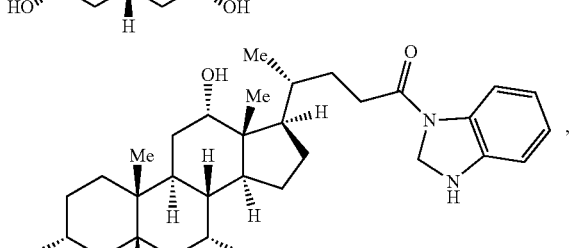
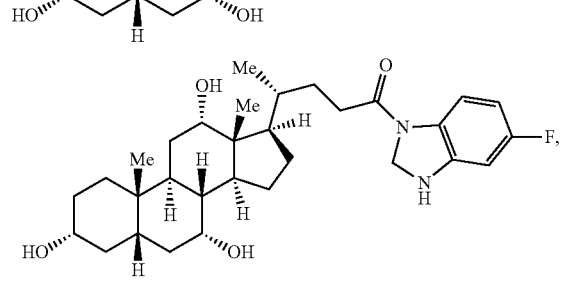
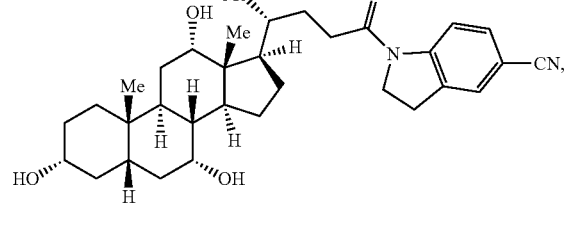

-continued

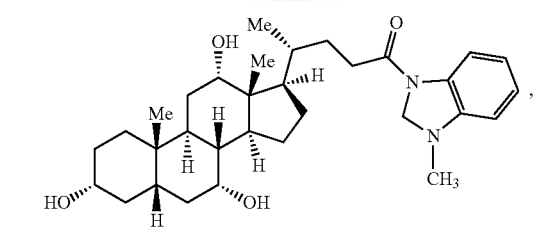

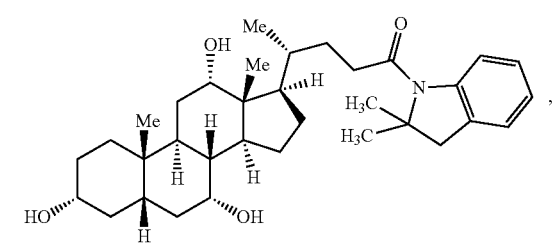

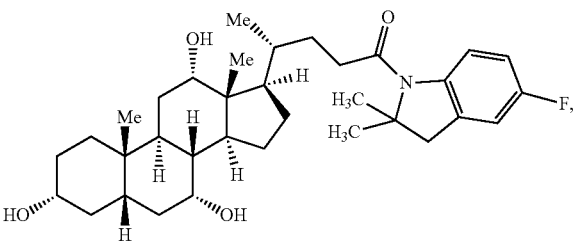

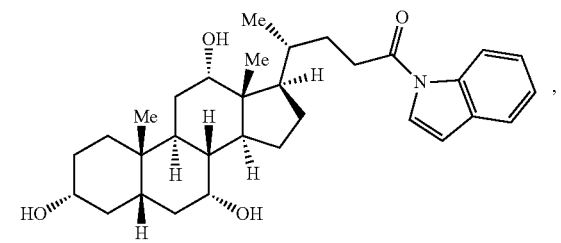

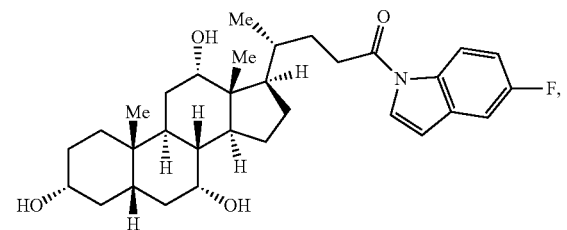

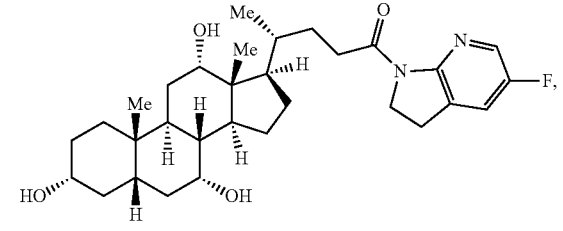

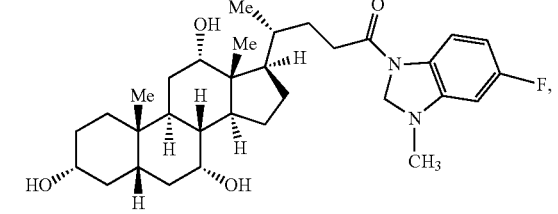

-continued

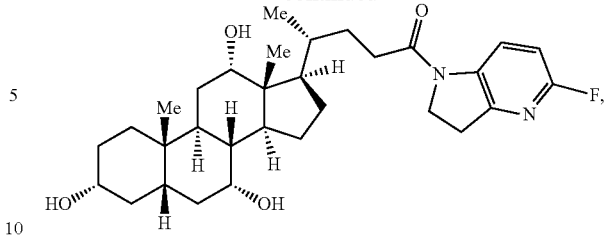

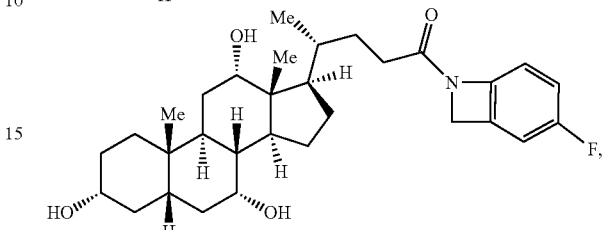

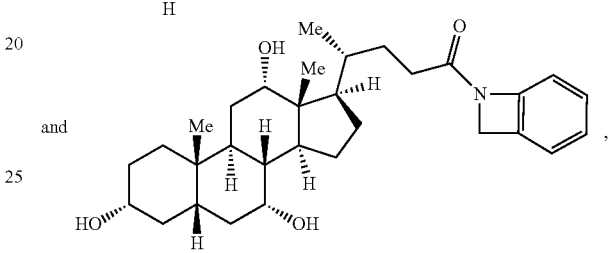

and or a pharmaceutically acceptable salt thereof.

In one aspect, a compound can be selected from:

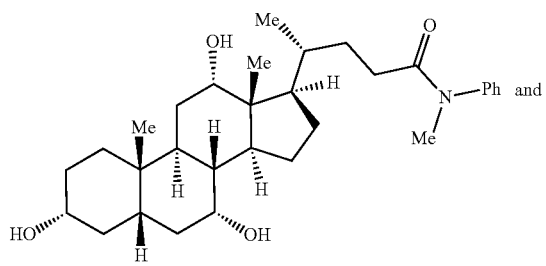

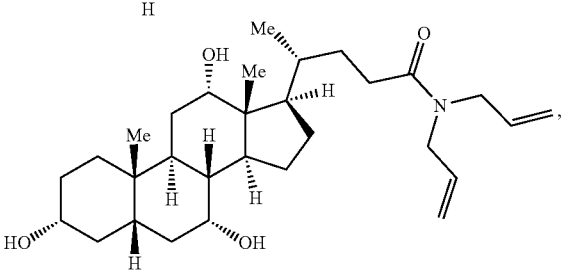

or a pharmaceutically acceptable salt thereof.

C. *C. DIFFICILE*

The first step in *C. difficile* pathogenesis is the germination of ingested spores into replicating bacteria in the gut of hosts. Thus, as described herein, it is possible that compounds able to curtail *C. difficile* spore germination will also prevent diseases or disorders caused by infection of *Clostridium difficile* such as, for example, severe diarrhea or colitis (e.g., pseudomembranous colitis). For example, antigerminants may be added as supplements to the feed of farmed fowl (e.g., chickens, turkeys, geese, and ducks), as well as to the feed of other farm animals such as cattle, sheep, horses, and pigs, for example. Anti-germinants have the advantage that replicating bacteria will not be under selective pressure, thus reducing the possibility of resistance development. Further, since severe diarrhea and colitis are extracellular symptoms of intestinal infections, compounds need only to be optimized for retention in the gastrointestinal tract.

D. COMPOSITIONS

Compounds for use as described herein can be incorporated into compositions for experimental use or for administration to fowl that may experience adverse effects (e.g., severe diarrhea, colitis) from exposure to germinated *C. difficile*. A composition can include, for example, one or more disclosed compounds, or a pharmaceutically acceptable salt thereof, as described herein, in combination with a carrier.

Thus, disclosed are compositions comprising an effective amount of a disclosed compound and a feed component.

Also disclosed are compositions comprising an effective amount of a compound having a structure represented by a formula:

wherein each of $R^1$, $R^{2a}$, and $R^{2b}$ is independently selected from hydrogen and —OH; and wherein $Ar^1$ is a bicyclic heteroaryl having a structure represented by a formula selected from:

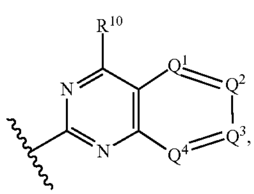

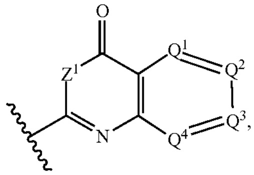

and 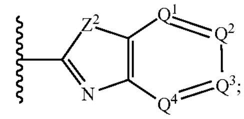 wherein $Z^1$ is selected from —O— and —$NR^{18}$—; wherein $R^{18}$, when present, is selected from hydrogen and C1-C4 alkyl; wherein $Z^2$ is selected from —O—, —S—, and —$NR^{19}$—; wherein $R^{19}$, when present, is selected from hydrogen and C1-C4 alkyl; wherein each of $Q^1$, $Q^2$, $Q^3$, and $Q^4$ is independently selected from —N= and —$CR^{20}$=; wherein each occurrence of $R^{20}$ is independently selected from hydrogen, halogen, C1-C4 alkyl, C1-C4 alkoxy, and phenyl; and wherein $R^{10}$ is selected from hydrogen, halogen, C1-C4 alkyl, C1-C4 alkoxy, C1-C4 haloalkyl, C1-C4 thioalkyl, and phenyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4) (C1-C4) dialkylamino, and C1-C4 aminoalkyl; provided that when Art is:

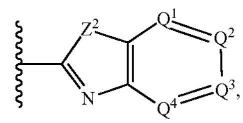

then: (a) at least one of $Q^1$, $Q^2$, $Q^3$, and $Q^4$ is —N= and at least one of $Q^1$, $Q^2$, $Q^3$, and $Q^4$ is —$CR^{20}$=, wherein $R^{20}$ is not hydrogen; or (b) at least two of $Q^1$, $Q^2$, $Q^3$, and $Q^4$ is —$CR^{20}$=, wherein at least two occurrences of $R^{20}$ are not hydrogen, or a pharmaceutically acceptable salt thereof.

Also disclosed are compositions comprising an effective amount of a compound selected from:

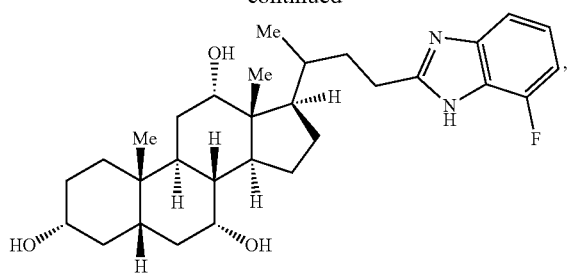,
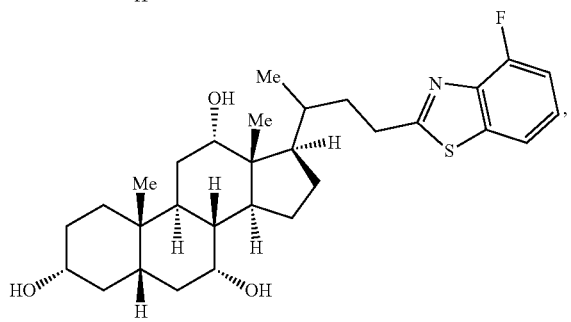,
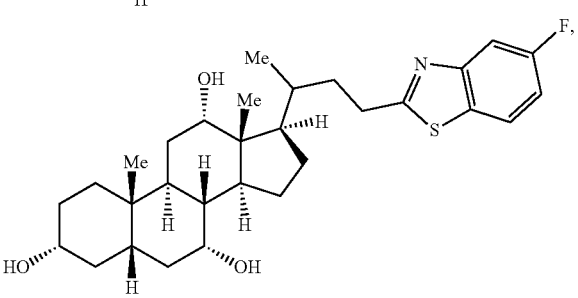,
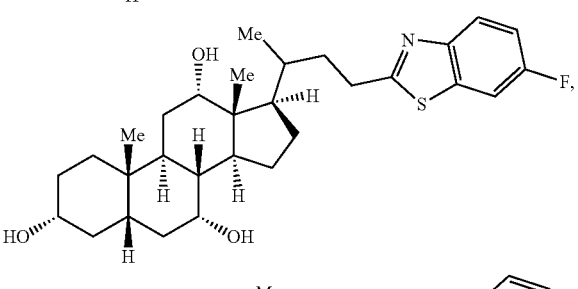,
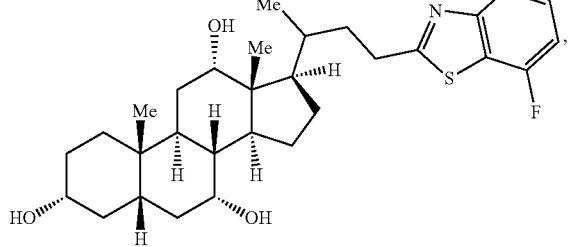,
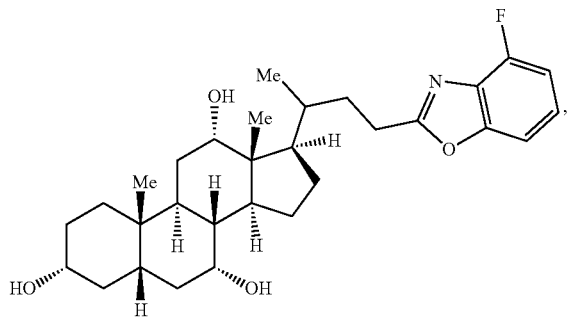,
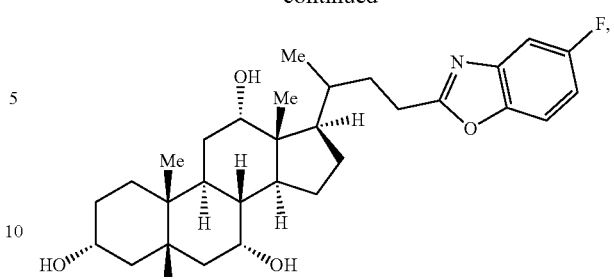,
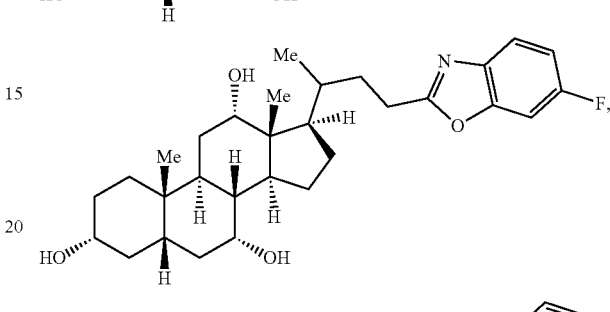,
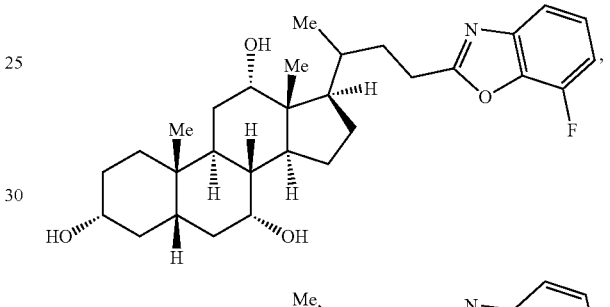,
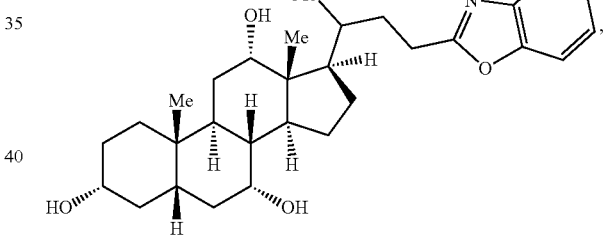,
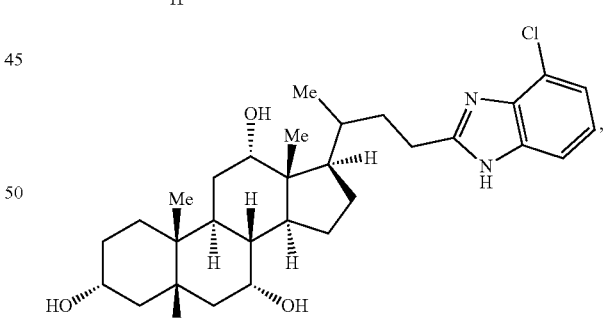,
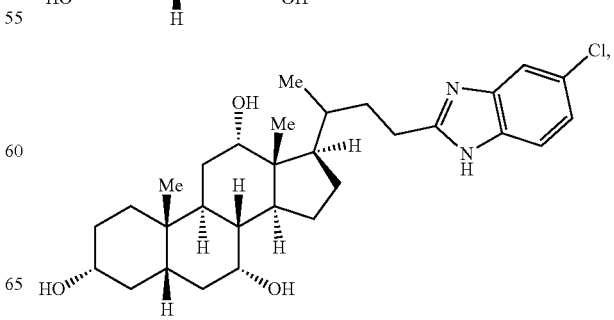, 277
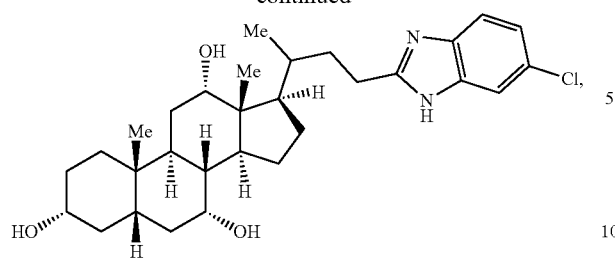
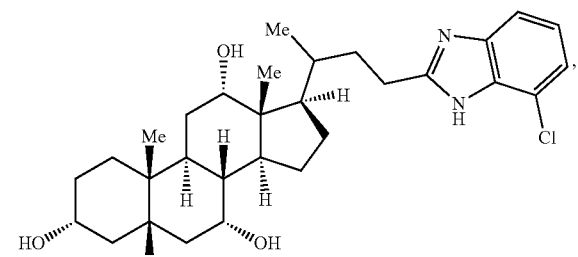
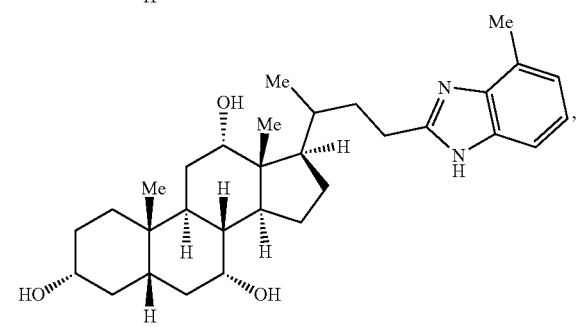
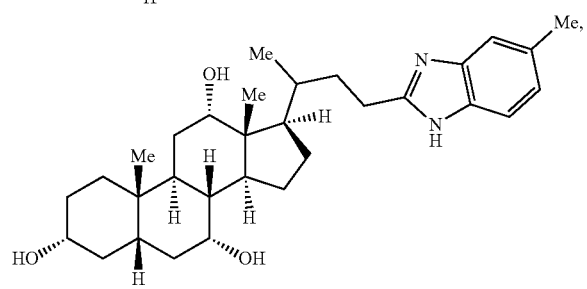
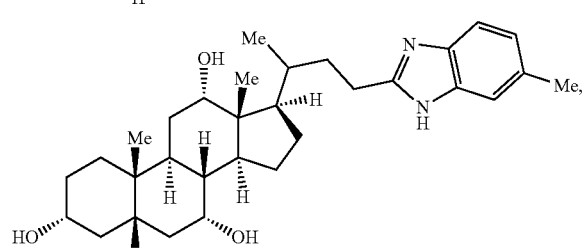
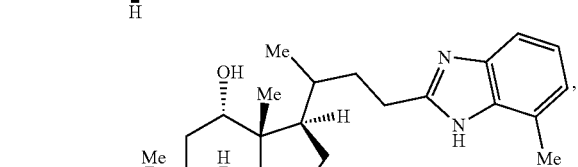
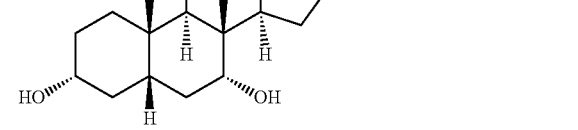
278
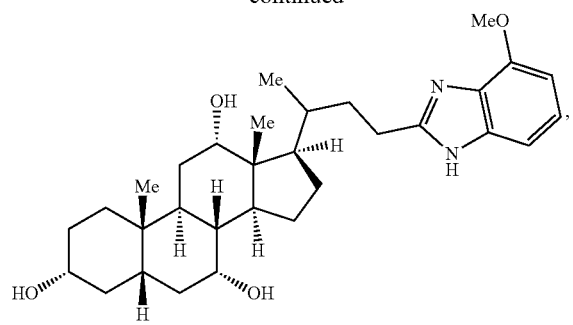
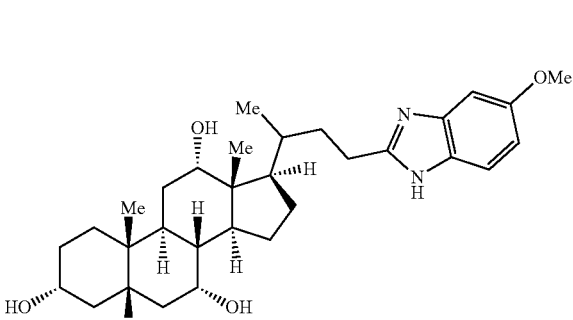
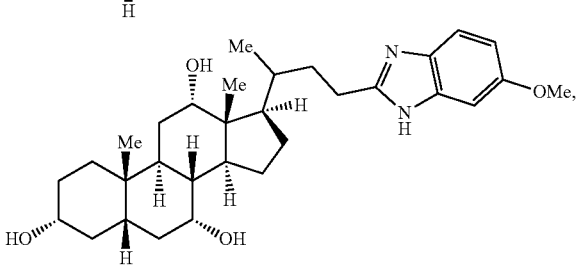
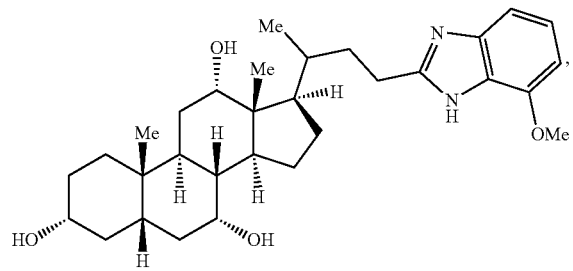
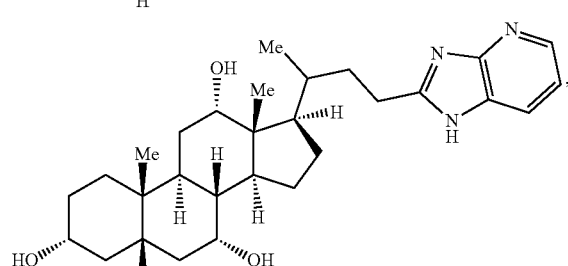
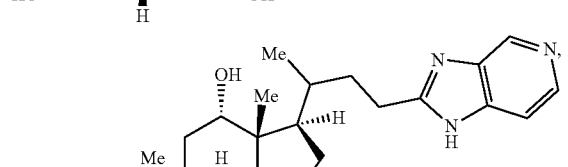
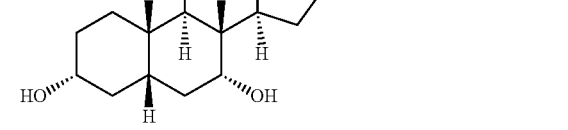

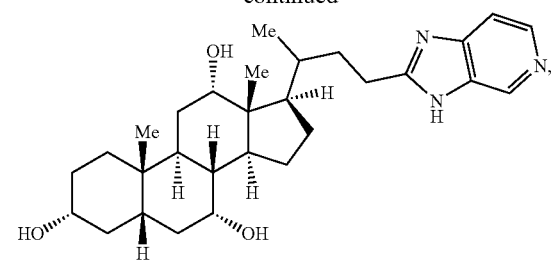
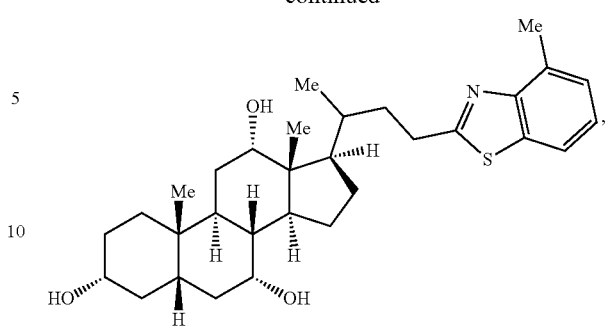
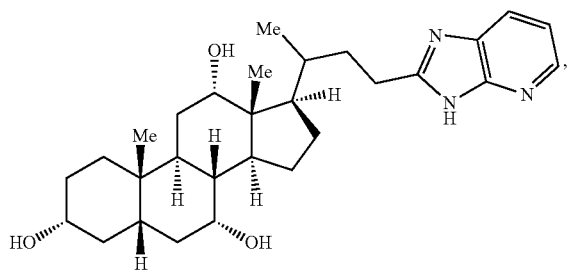
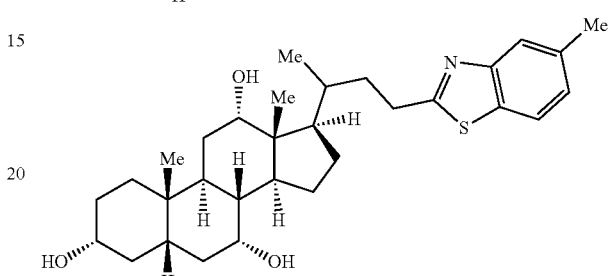
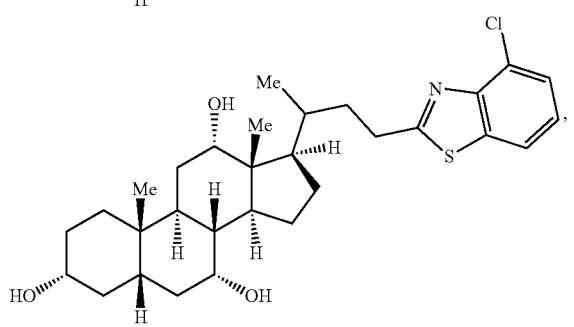
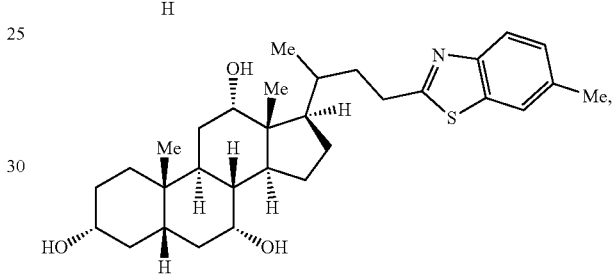
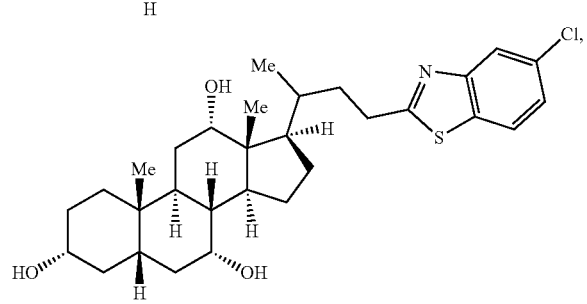
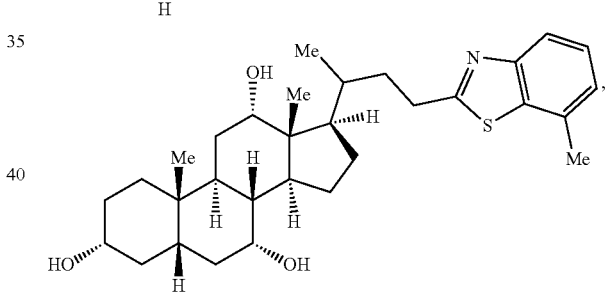
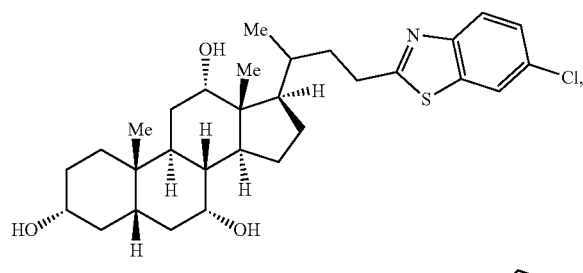
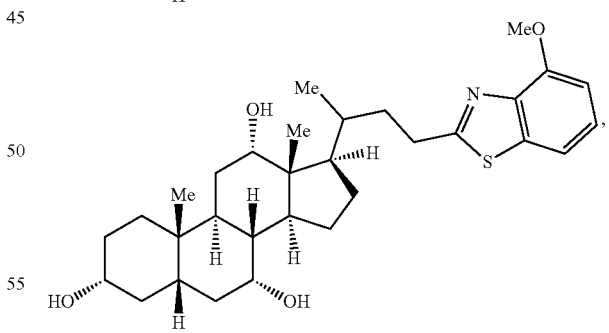
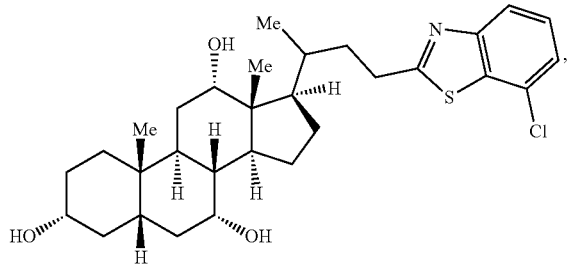
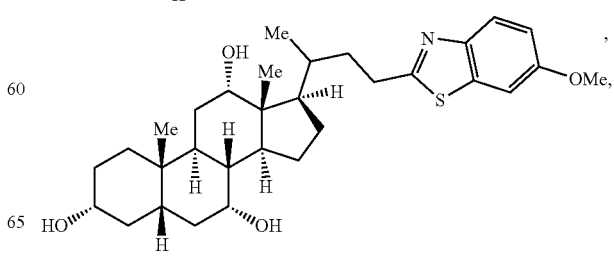

281
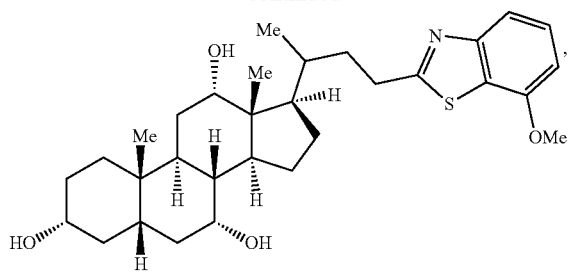
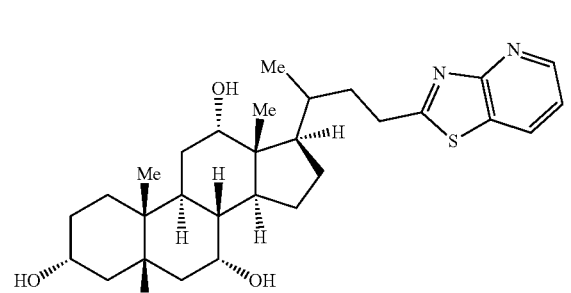
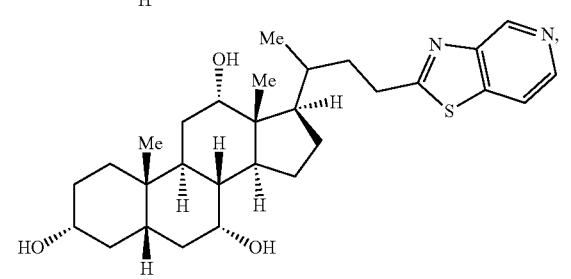
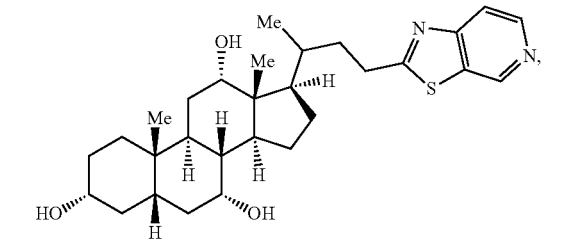
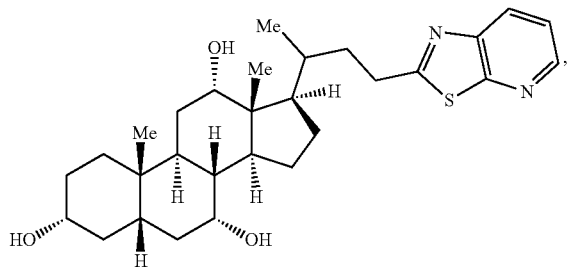
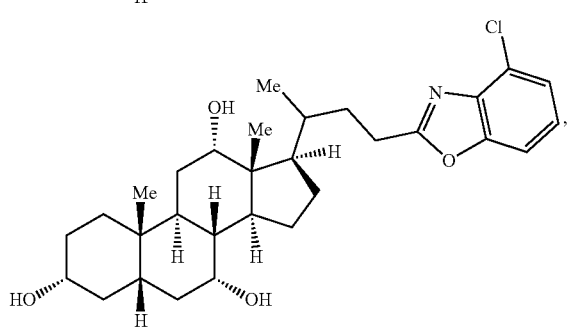
282
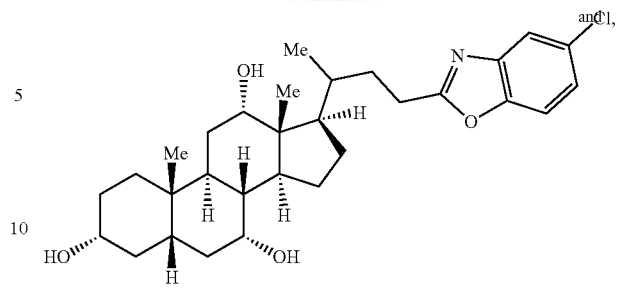
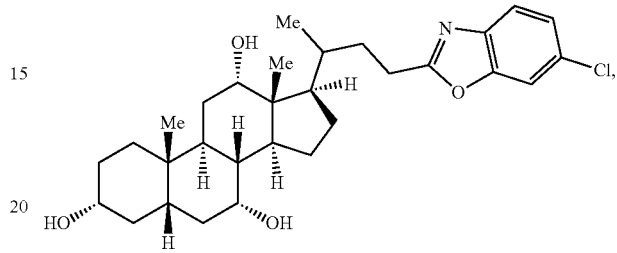
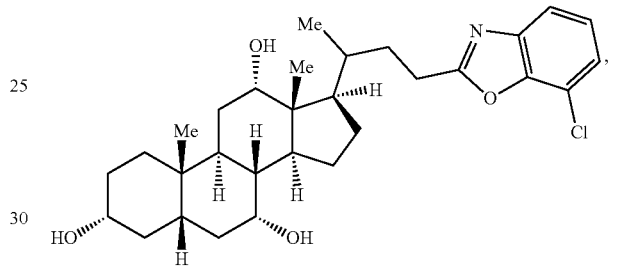
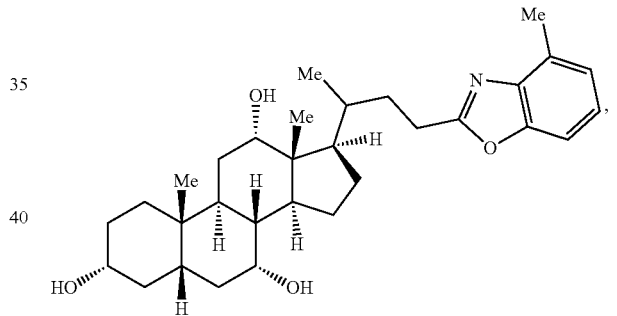
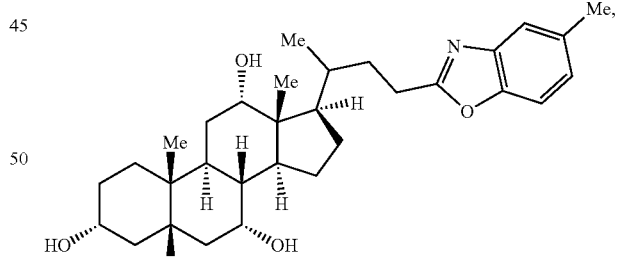
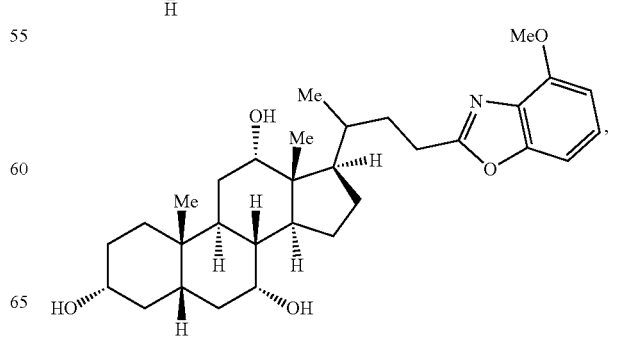

283
-continued

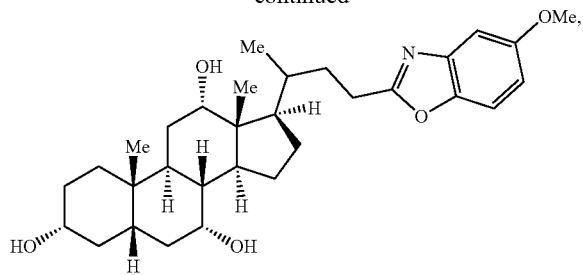

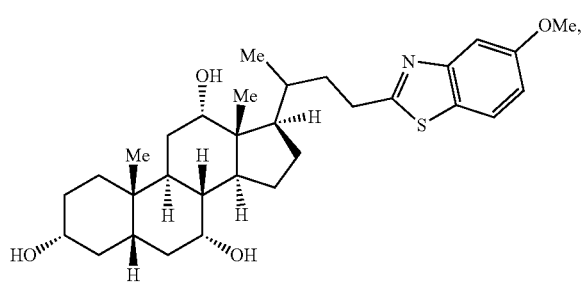

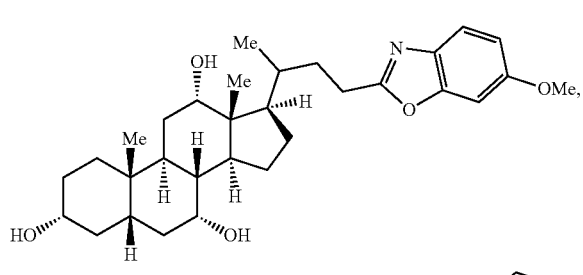

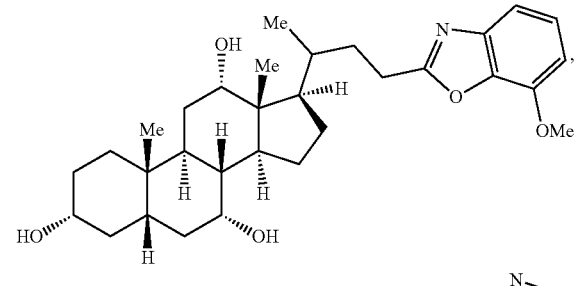

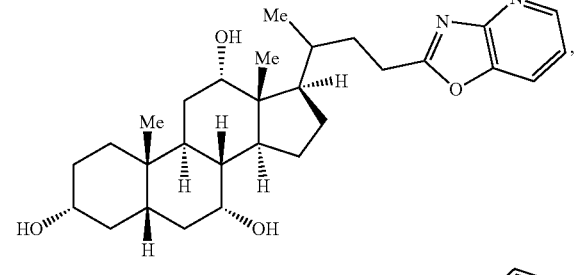

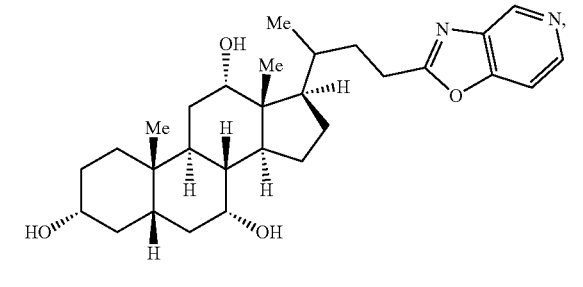

284
-continued

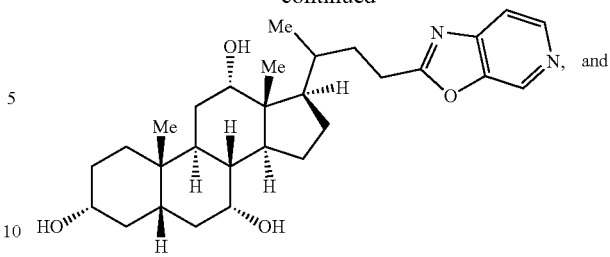

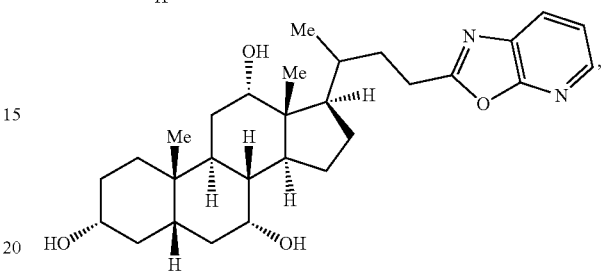

or a pharmaceutically acceptable salt thereof.

Also disclosed are compositions comprising an effective amount of a compound having a structure represented by a formula:

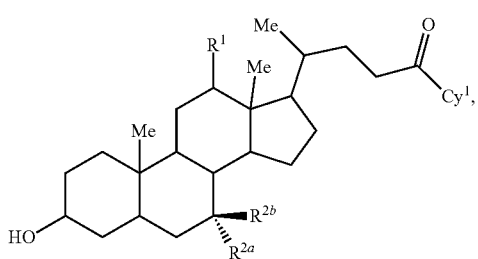

wherein each of $R^1$, $R^{2a}$, and $R^{2b}$ is independently selected from hydrogen and —OH; and wherein $Cy^1$ is a bicycle having a formula selected from:

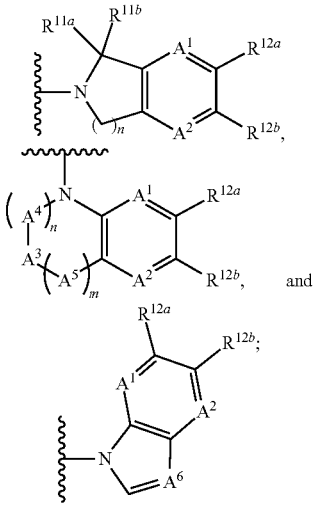

wherein each of n and m, when present, is independently 0, 1, or 2; wherein each of $A^1$ and $A^2$ is independently selected from —N= and —$CR^{21}$=; wherein each occurrence of $R^{21}$ is independently selected from hydrogen, halogen, —$NO_2$, —CN, C1-C4 alkyl, C1-C4 alkoxy, C1-C4 haloalkyl, and —C(O)(C1-C4 alkyl); wherein $A^3$, when present, is selected from —O—, —S—, —$NR^{22}$—, and —$C(R^{23a})(R^{23b})$—; wherein $R^{22}$ is selected from hydrogen and C1-C4 alkyl; wherein each of $R^{23a}$ and $R^{23b}$ is independently selected from hydrogen and C1-C4 alkyl; wherein each of $A^4$ and $A^5$, when present, is independently —$C(R^{23c})(R^{23d})$—; wherein each of $R^{23c}$ and $R^{23d}$ is independently selected from hydrogen and C1-C4 alkyl; wherein $A^6$, when present, is selected from =$C(R^{24})$— and =N—; wherein $R^{24}$, when present, is selected from hydrogen and C1-C4 alkyl; wherein each of $R^{11a}$ and $R^{11B}$, when present, is independently selected from hydrogen and C1-C4 alkyl; and wherein each of $R^{12a}$ and $R^{12b}$ is independently selected from hydrogen, halogen, —$NO_2$, —CN, C1-C4 alkyl, C1-C4 alkoxy, C1-C4 haloalkyl, and —C(O)(C1-C4 alkyl), or a pharmaceutically acceptable salt thereof, and a feed component.

Also disclosed are compositions comprising an effective amount of a compound selected from:

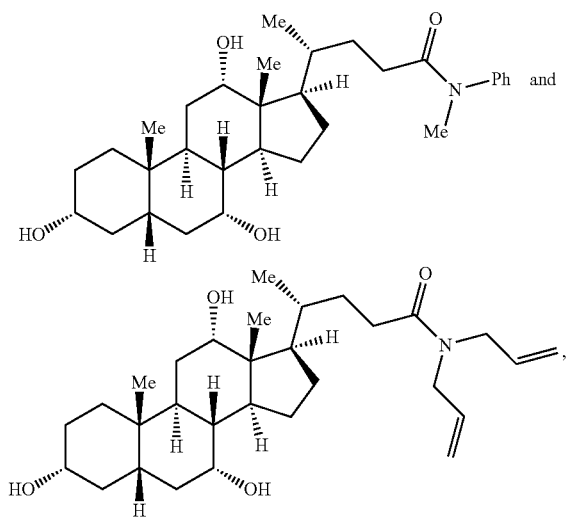

or a pharmaceutically acceptable salt thereof, and a feed component.

Suitable concentrations of a compound within a composition can range from, for example, about 0.1 nM to about 100 mM (e.g., about 0.1 nM to about 1 nM, about 1 nM to about 10 nM, about 10 nM to about 0.1 mM, about 0.1 mM to about 0.5 mM, about 0.5 mM to about 1 mM, about 1 mM to about 5 mM, about 5 mM to about 10 mM, about 10 mM to about 25 mM, about 25 mM to about 50 mM, about 50 mM to about 75 mM, or about 75 mM to about 100 mM).

Suitable carriers can include, without limitation, solvents, suspending agents, stabilizing agents, or any other vehicle for delivering one or more compounds to a recipient. Suitable carriers typically are nontoxic to the organism being exposed thereto at the dosages and concentrations employed. Carriers can be liquid or solid, and can be selected with the planned manner of administration in mind so as to provide for the desired bulk, consistency, and other pertinent transport and chemical properties, when combined with one or more compounds and any other components of a given composition. Suitable carriers can include, by way of example and not limitation, water, saline solution, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Useful carriers also can include aqueous pH buffered solutions or liposomes, as well as buffers such as phosphate, citrate, and other organic acids, antioxidants such as ascorbic acid, low molecular weight (less than about 10 residues) polypeptides, proteins such as serum albumin, gelatin, or immunoglobulins, hydrophilic polymers such as polyvinylpyrrolidone, amino acids such as glycine, glutamine, asparagine, arginine or lysine, monosaccharides, disaccharides, and other carbohydrates including glucose, mannose or dextrins, chelating agents such as EDTA, sugar alcohols such as mannitol or sorbitol, salt-forming counterions such as sodium, and/or nonionic surfactants such as TWEEN™, polyethylene glycol (PEG), and PLURONICS™.

Compositions can be formulated by mixing one or more compounds as described herein with one or more carriers, diluents, and/or adjuvants, and optionally other agents that can be incorporated into formulations to provide improved transfer, delivery, tolerance, and the like. Compositions can be formulated, e.g., in lyophilized formulations, aqueous solutions, dispersions, or solid preparations, such as tablets, dragees, or capsules.

Pharmaceutical compositions can include, without limitation, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Since *C. difficile* is an extracellular organism found in the gut, the compounds and compositions provided herein can be optimized for retention in the gastrointestinal tract.

Such optimization can include, for example, adding hydrophobic groups to the structure, or encapsulating the compound in gelatin or other appropriate media.

In various aspects, the feed component is a vegetable protein, a fat-soluble vitamin, a water-soluble vitamin, a trace mineral, a macro mineral, or a combination thereof.

In various aspects, the compositions is a granule, a pellet, a capsule, a tablet, an emulsion, or a solution. In a further aspect, the composition is a granule. In a still further aspect, the composition is a pellet. In yet a further aspect, the composition is a capsule, a tablet, an emulsion, or a solution.

In various aspects, a compound as described herein can be combined with feed (e.g., poultry feed), such that the compound is ingested as the birds eat. Thus, this document provides feed containing (e.g., mixed with or coated with) a compound that reduces or prevents germination of *C. difficile*, where the compound is as disclosed elsewhere herein. Suitable varieties of feed include those that are commercially available, for example.

In various aspects, the composition further comprises an antibiotic, an arsenical, an antioxidant, an antifungal, a probiotic, a flavoring agent, a binder, a pigment, a preservative, an emulsifier, and a sweetener.

In various aspects, the composition is a feed composition.

In various aspects, the composition is formulated for oral administration.

E. METHODS OF MAKING THE COMPOUNDS

In various aspects, the inventions relates to methods of making compounds useful to prevent diseases associated with infections caused by *C. difficile*. Thus, in one aspect, disclosed are methods of making compounds having a structure represented by a formula:

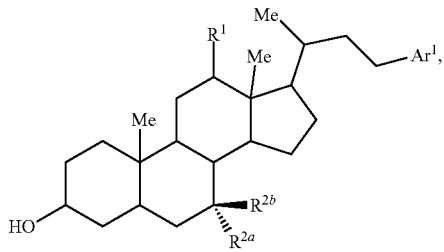

wherein each of $R^1$, $R^{2a}$, and $R^{2b}$ is independently selected from hydrogen and —OH; and wherein $Ar^1$ is a bicyclic heteroaryl having a structure represented by a formula selected from:

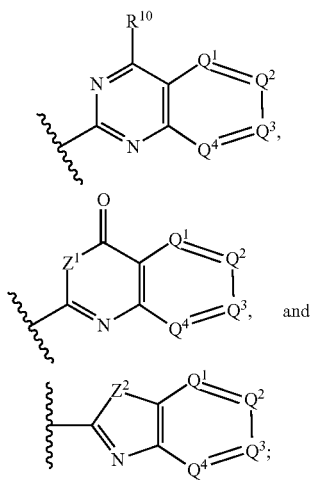

wherein $Z^1$ is selected from —O— and —$NR^{18}$—; wherein $R^{18}$, when present, is selected from hydrogen and C1-C4 alkyl; wherein $Z^2$ is selected from —O—, —S—, and —$NR^{19}$—; wherein $R^{19}$, when present, is selected from hydrogen and C1-C4 alkyl; wherein each of $Q^1$, $Q^2$, $Q^3$, and $Q^4$ is independently selected from —N= and —$CR^{20}$=; wherein each occurrence of $R^{20}$ is independently selected from hydrogen, halogen, C1-C4 alkyl, C1-C4 alkoxy, and phenyl; and wherein $R^{10}$ is selected from hydrogen, halogen, C1-C4 alkyl, C1-C4 alkoxy, C1-C4 haloalkyl, C1-C4 thioalkyl, and phenyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4) (C1-C4) dialkylamino, and C1-C4 aminoalkyl; provided that when $Ar^1$ is:

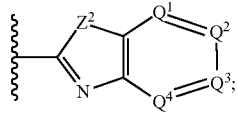

then: (a) at least one of $Q^1$, $Q^2$, $Q^3$, and $Q^4$ is —N= and at least one of $Q^1$, $Q^2$, $Q^3$, and $Q^4$ is —$CR^{20}$=, wherein $R^{20}$ is not hydrogen; or (b) at least two of $Q^1$, $Q^2$, $Q^3$, and $Q^4$ is —$CR^{20}$=, wherein at least two occurrences of $R^{20}$ are not hydrogen, or a pharmaceutically acceptable salt thereof.

Also disclosed are methods of making compounds selected from:

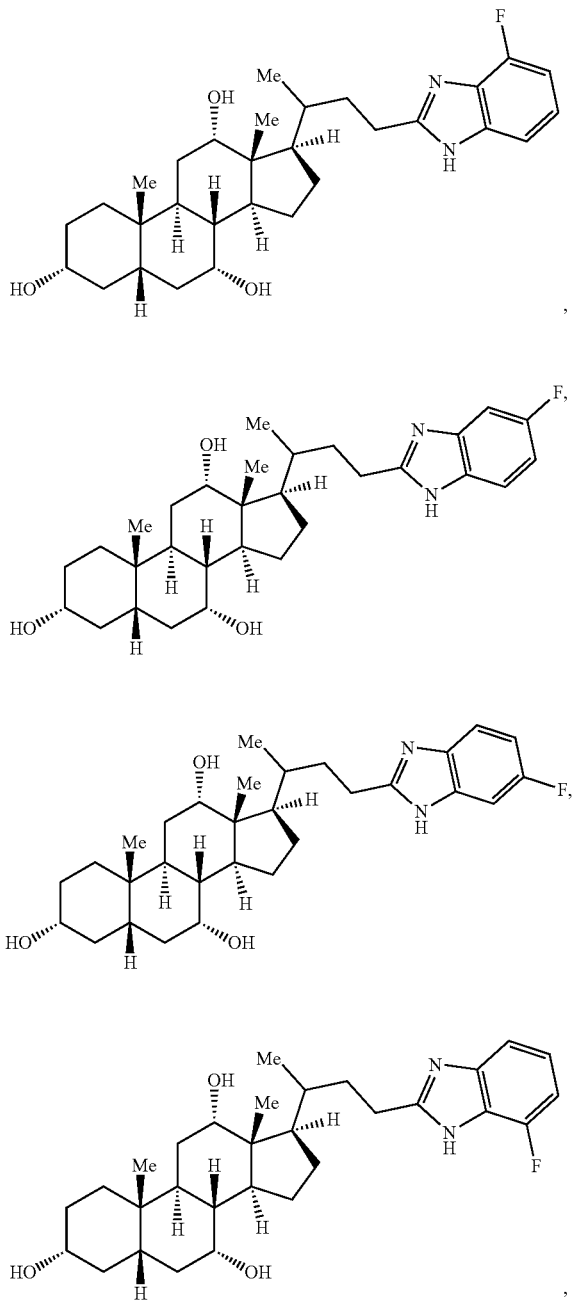

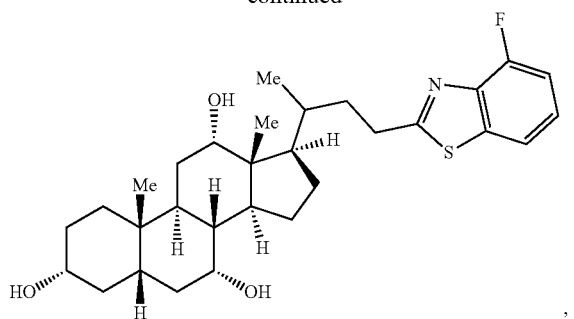
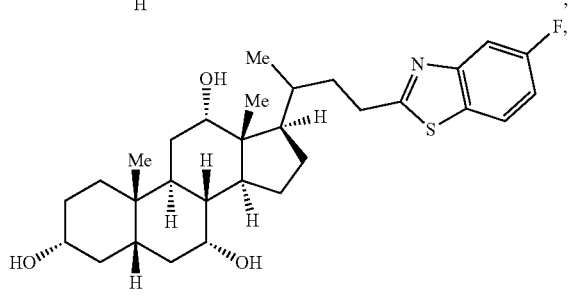
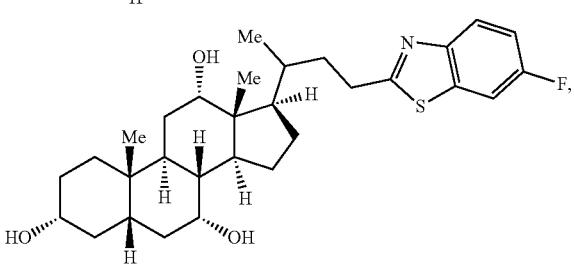
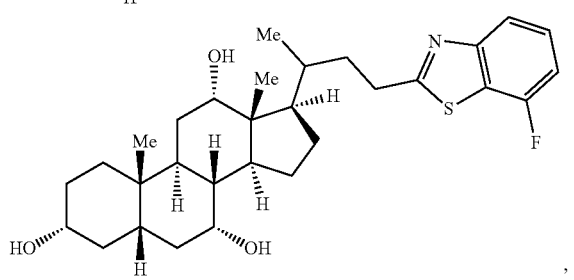
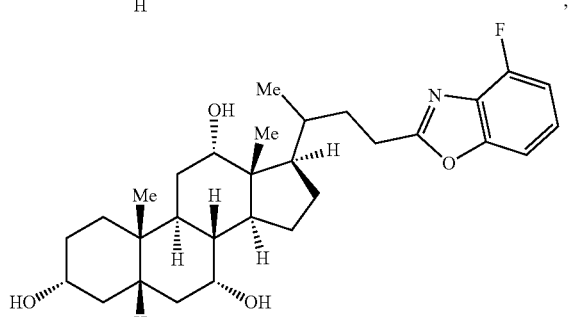
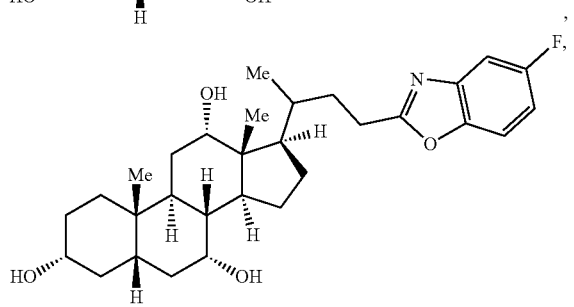
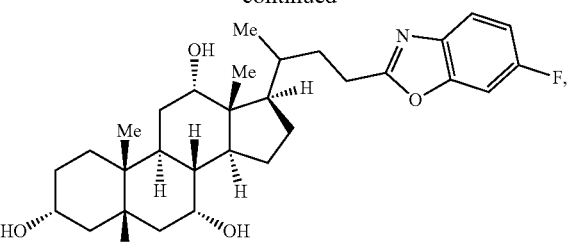
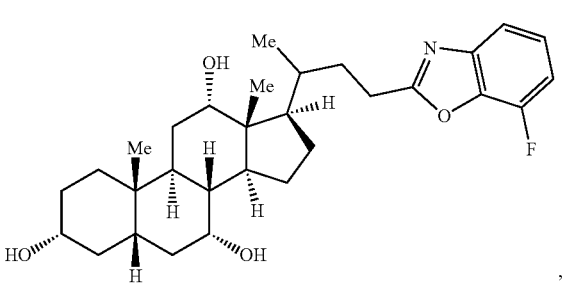
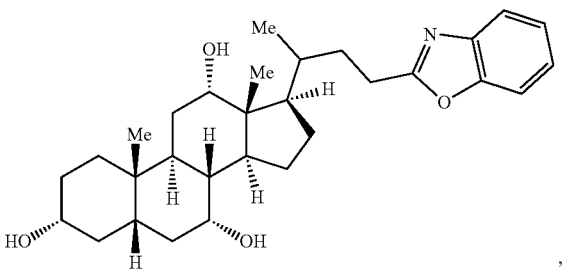
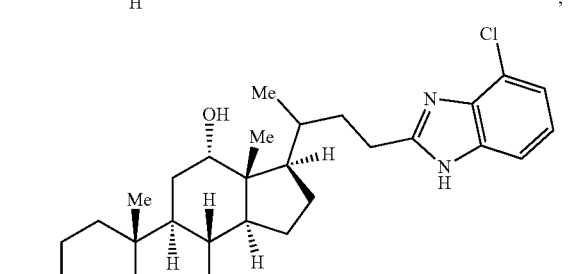
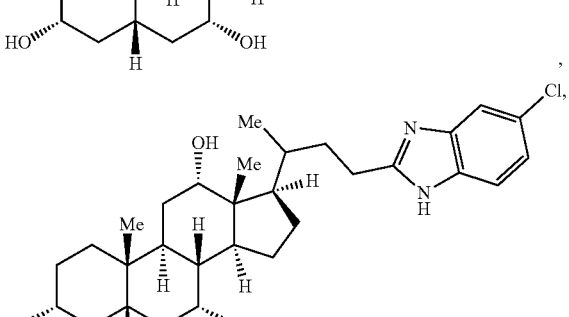
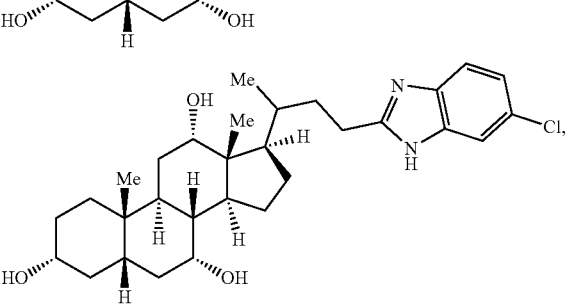

291
-continued
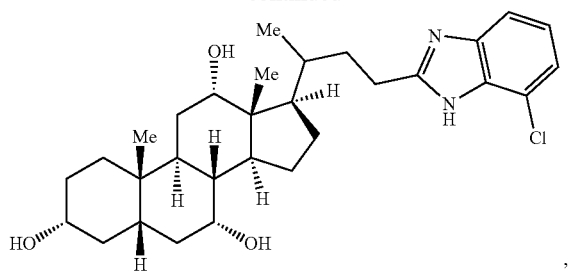
,
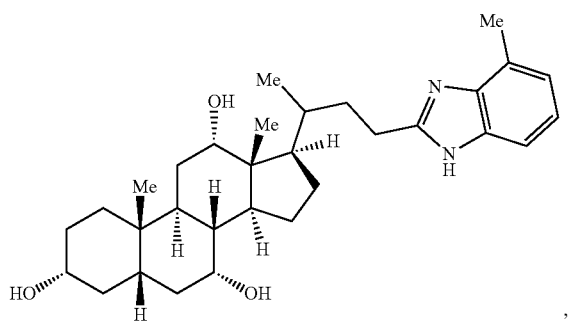
,
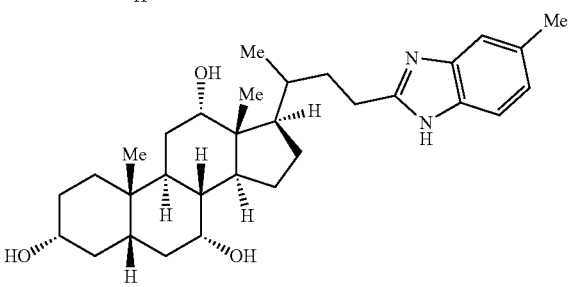
,
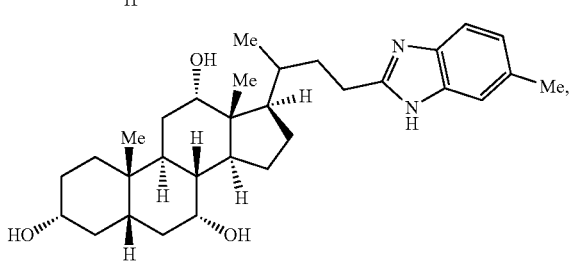
,
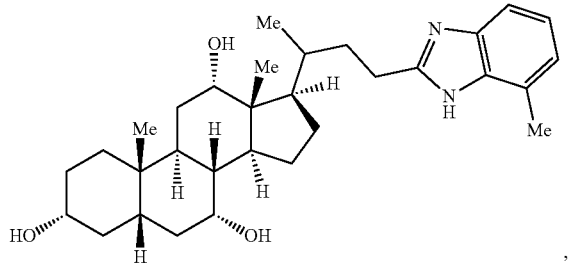
,
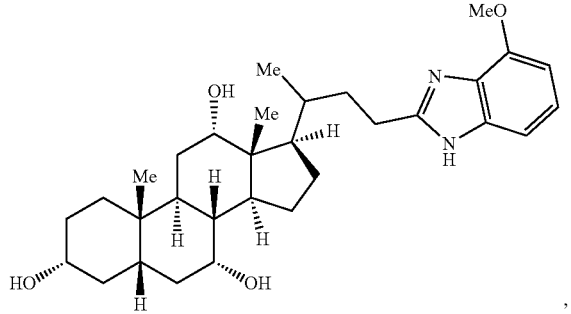
,
292
-continued
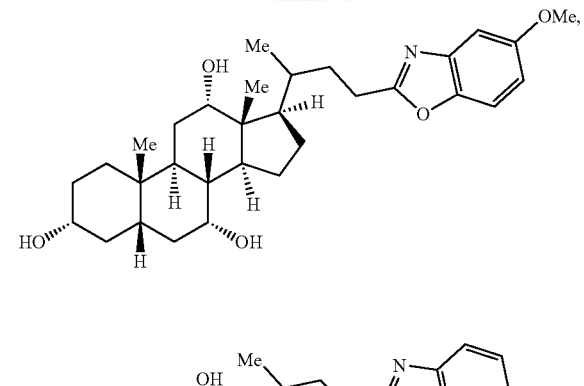
,
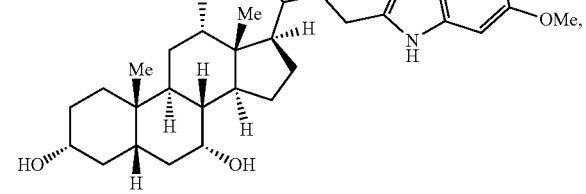
,
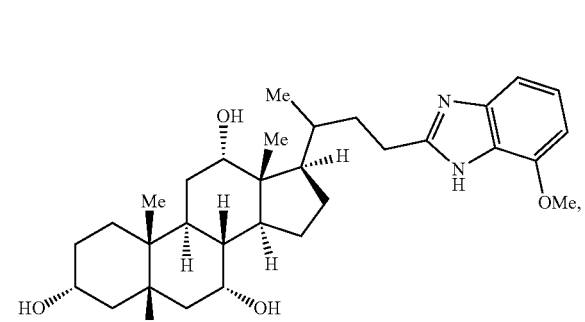
,
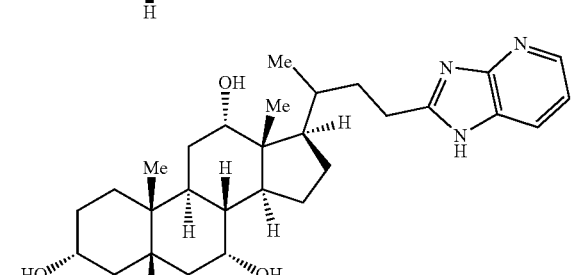
,
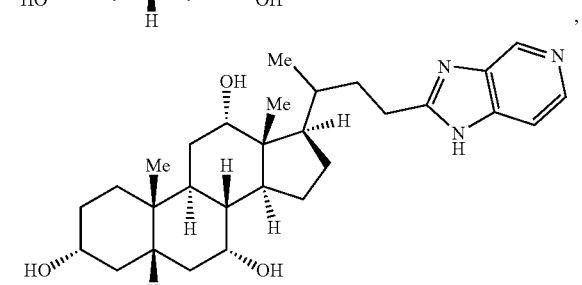
,
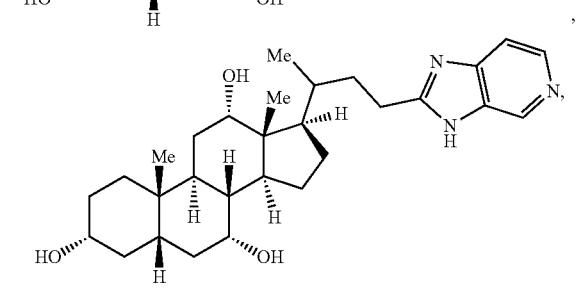
, 293
-continued
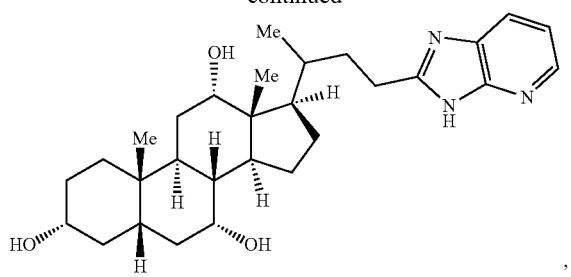
,
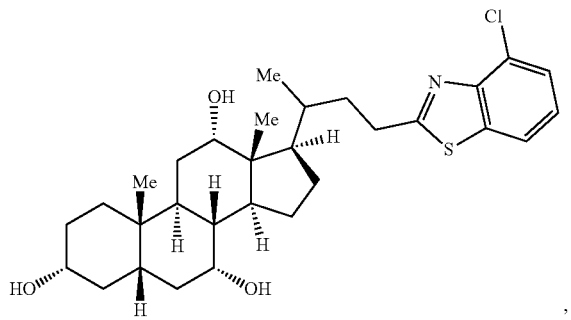
,
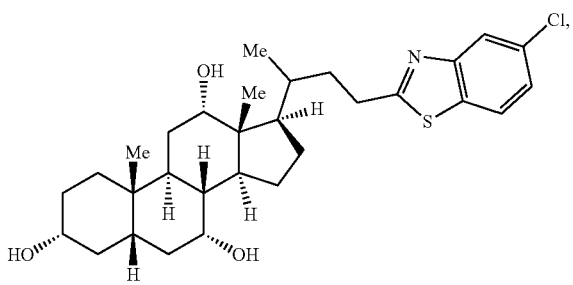
,
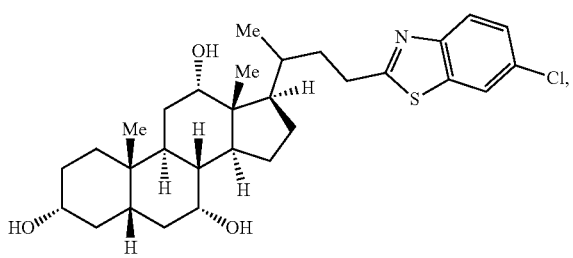
,
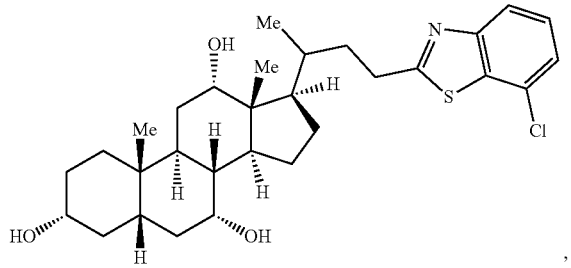
,
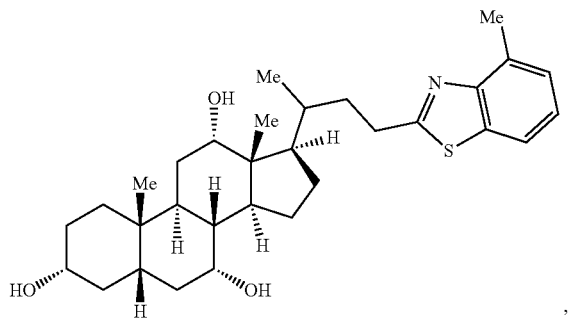
,
294
-continued
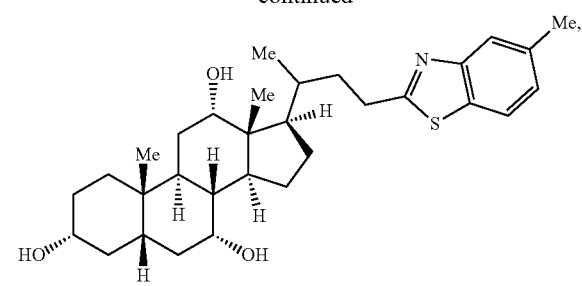
,
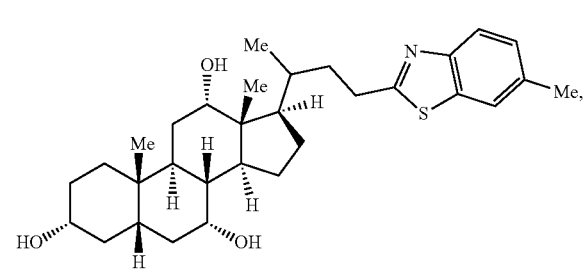
,
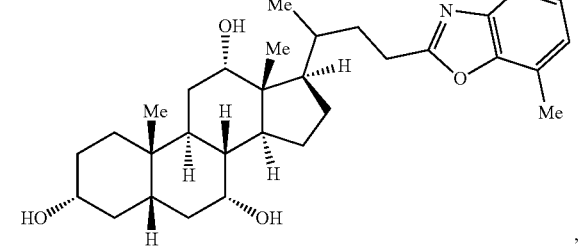
,
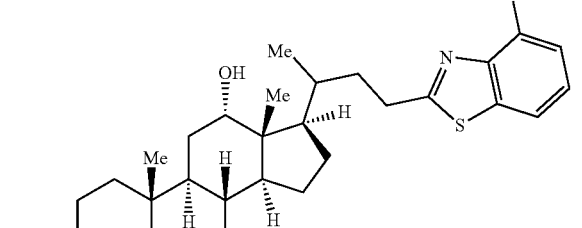
,
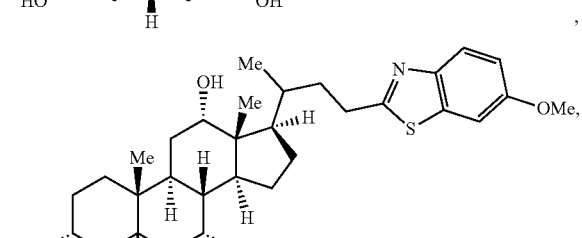
,
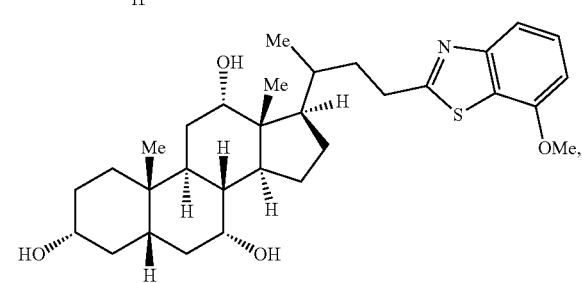
, 295
-continued
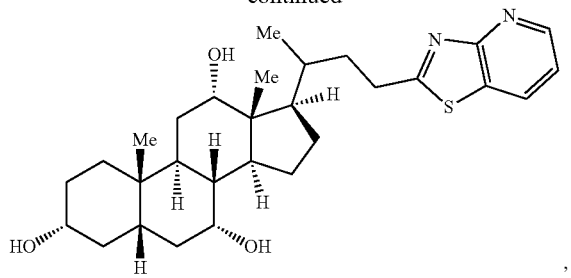
,
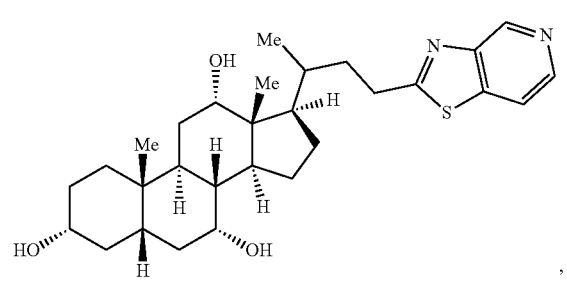
,
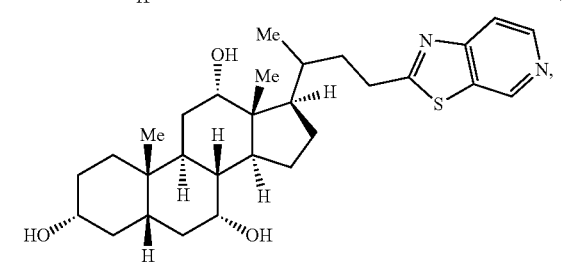
,
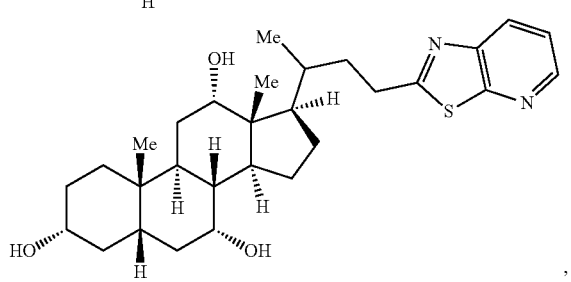
,
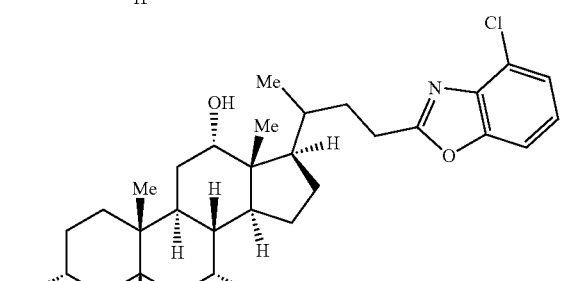
,
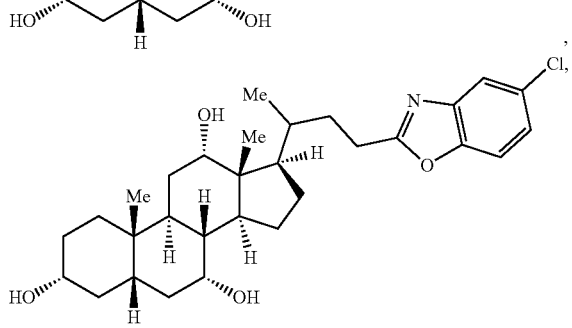
,
296
-continued
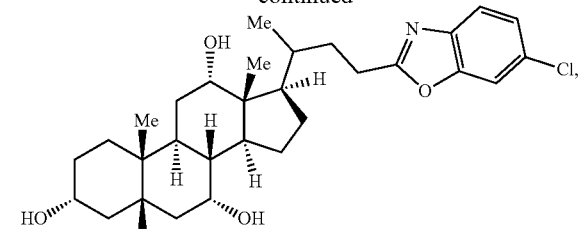
,
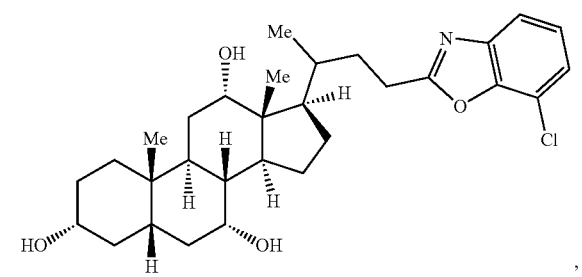
,
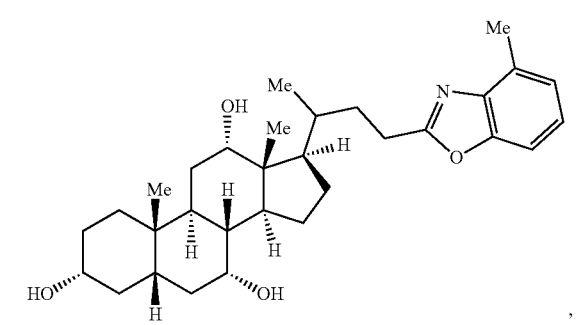
,
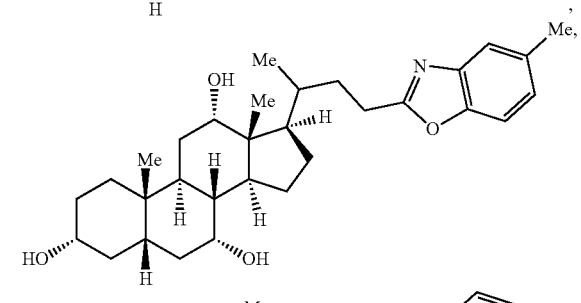
,
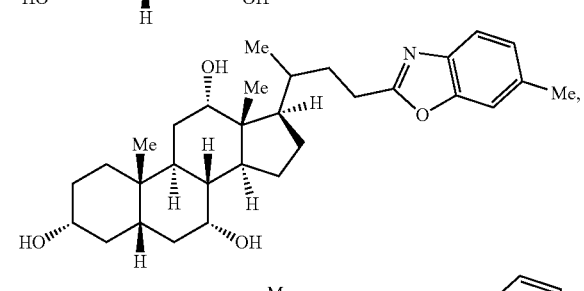
,
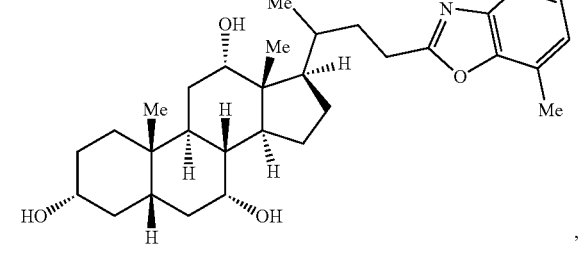
,

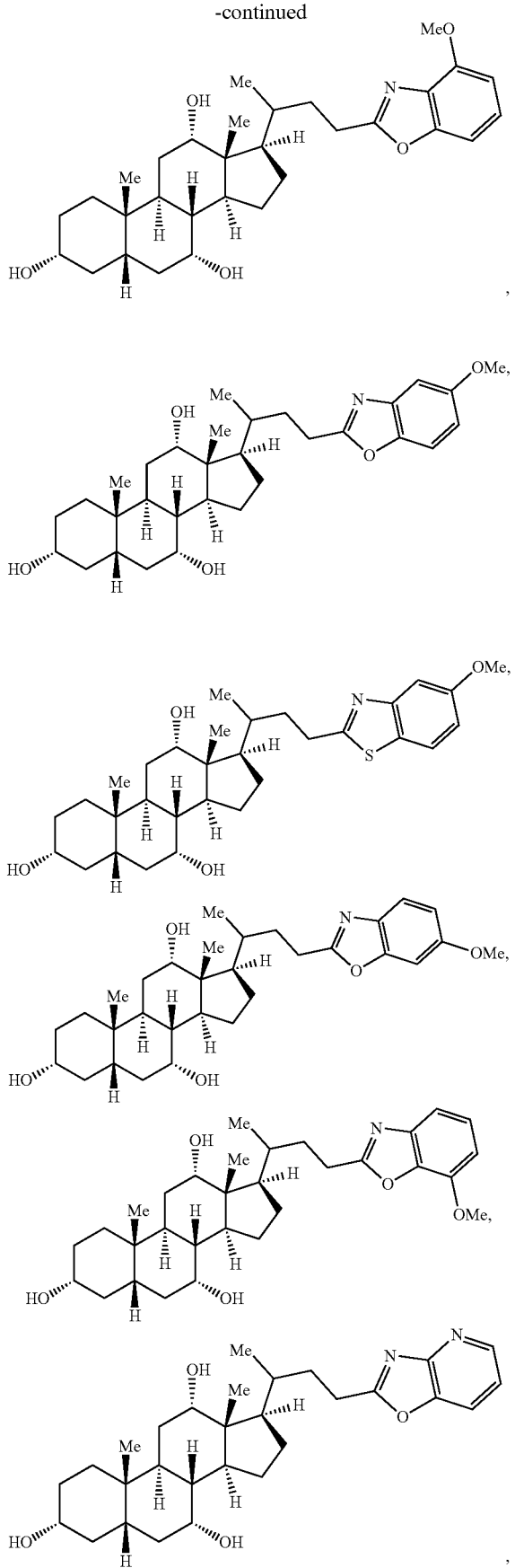

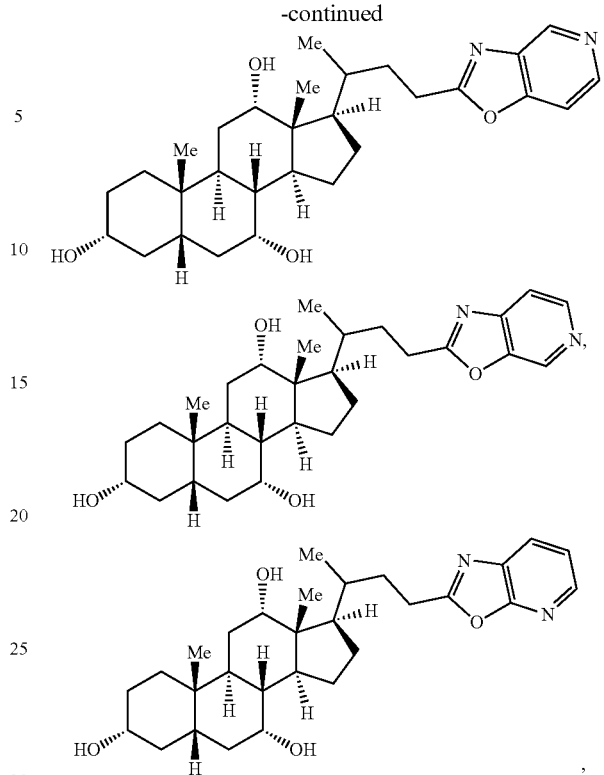

or a pharmaceutically acceptable salt thereof.

In various aspects, procedures known in the art (e.g., methods described by Seijas et al. in, for example, *Synlett,* 2007, 313-316) can be used to synthesize benzoazole analogs. For example, various alkyl and aryl carboxylic acids can be individually aliquoted into multi-well plates, and each well can be supplemented with o-aminophenol and Lawesson's reagent. The mixture can be irradiated in a microwave oven, and crude mixtures can be purified in parallel by recrystallization and/or flash chromatography. A similar procedure can be used to obtain 2-substituted benzothiazole derivatives from o-aminothiophenol and the same set of carboxylic acids.

In various aspects, 2-substituted benzimidazoles can be prepared using the procedure of Ryabukhin et al. (e.g., a procedure as described in *J Org Chem,* 2007, 72(19):7417-7419) can be used. Briefly, different aldehydes can be individually aliquoted into multi-well plates. Each well can be supplemented with 1,2-diaminobenzene and DMF. TMSCl can be added dropwise to the solution, and each well can be sealed and the mixtures heated for 4 hours. After cooling, each reaction mixture can be precipitated with water and recrystallized from an appropriate solvent.

Compounds according to the present disclosure can, for example, be prepared by the several methods outlined below. A practitioner skilled in the art will understand the appropriate use of protecting groups [see: Greene and Wuts, Protective Groups in Organic Synthesis] and the preparation of known compounds found in the literature using the standard methods of organic synthesis. There may come from time to time the need to rearrange the order of the recommended synthetic steps, however this will be apparent to the judgment of a chemist skilled in the art of organic synthesis. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a feed composition comprising an effective amount of the product of the disclosed methods and a feed component. In an even further aspect, the feed component is selected from a vegetable protein, a fat-soluble vitamin, a water-soluble vitamin, a trace mineral, and a macro mineral. In a still further aspect, the feed component is water.

1. Route I

In one aspect, the substituted bile acid analogs can be prepared as shown below.

SCHEME 1A.

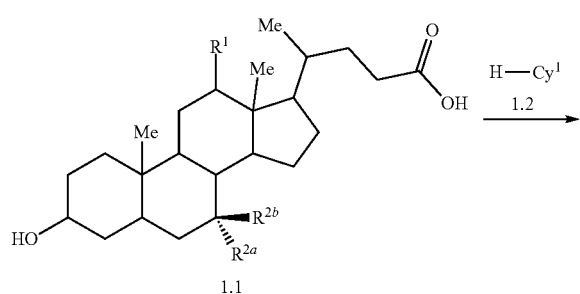

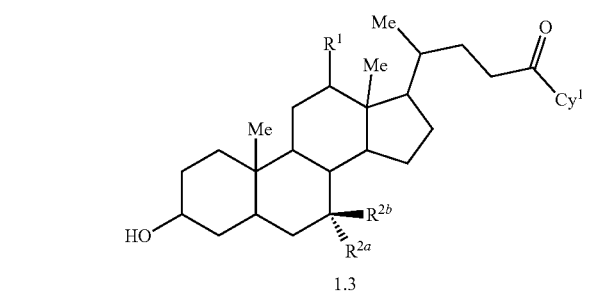

Compounds are represented in generic form, with substituents as noted in compound descriptions elsewhere herein. A more specific example is set forth below.

SCHEME 1B.

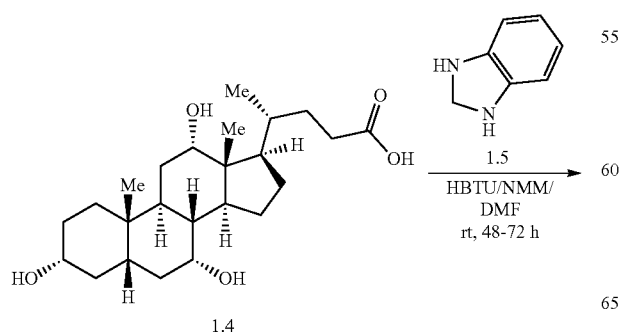

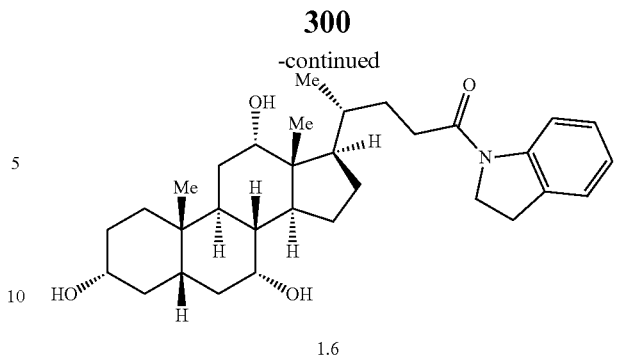

1.6

In one aspect, compounds of type 1.6, and similar compounds, can be prepared according to reaction Scheme 1B above. Thus, compounds of type 1.6 can be prepared by a coupling reaction between an appropriate bile acid, e.g., 1.4 as shown above, and an appropriate amine heterocycle, e.g., 1.5 as shown above. Appropriate bile acids and appropriate amine heterocycles are commercially available or prepared by methods known to one skilled in the art. The coupling reaction is carried out in the presence of an appropriate coupling agent, e.g., 2-(1H-benzotriazol-1-yl)-1,1,3,3-tetramethyluronium hexafluorophosphate (HBTU), an appropriate base, e.g., N-methylmorpholine (NMM), in an appropriate solvent, e.g., dimethylformamide (DMF), for an appropriate period of time, e.g., 48 to 72 hours. As can be appreciated by one skilled in the art, the above reaction provides an example of a generalized approach wherein compounds similar in structure to the specific reactants above (compounds similar to compounds of type 1.1 and 1.2), can be substituted in the reaction to provide substituted bile acid analogs similar to Formula 1.3.

2. Route II

In one aspect, the substituted bile acid analogs can be prepared as shown below.

SCHEME 2A.

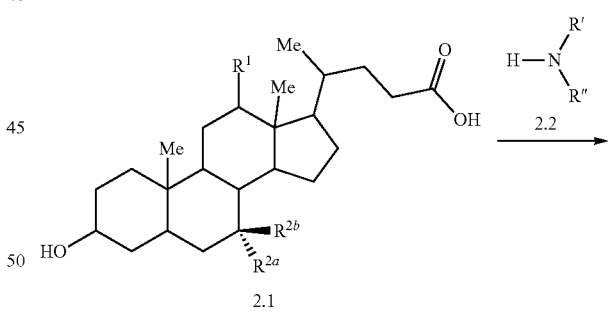

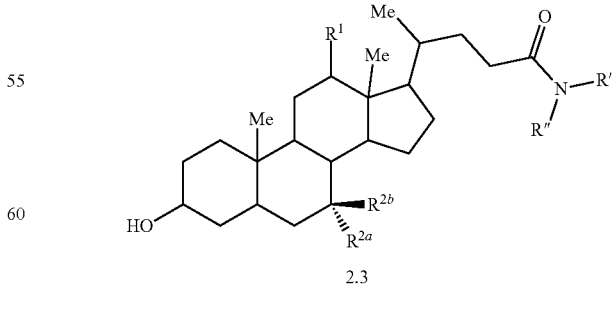

Compounds are represented in generic form, with substituents as noted in compound descriptions elsewhere herein. A more specific example is set forth below.

SCHEME 2B.

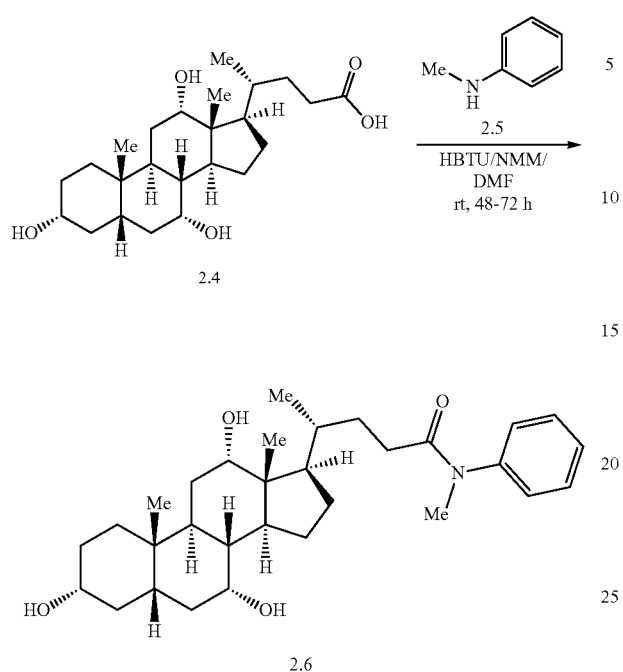

In one aspect, compounds of type 2.6, and similar compounds, can be prepared according to reaction Scheme 2B above. Thus, compounds of type 2.6 can be prepared by a coupling reaction between an appropriate bile acid, e.g., 2.4 as shown above, and an appropriate secondary amine derivative, e.g., 2.5 as shown above. Appropriate bile acids and appropriate secondary amine derivatives are commercially available or prepared by methods known to one skilled in the art. The coupling reaction is carried out in the presence of an appropriate coupling agent, e.g., 2-(1H-benzotriazol-1-yl)-1,1,3,3-tetramethyluronium hexafluorophosphate (HBTU), an appropriate base, e.g., N-methylmorpholine (NMM), in an appropriate solvent, e.g., dimethylformamide (DMF), for an appropriate period of time, e.g., 48 to 72 hours. As can be appreciated by one skilled in the art, the above reaction provides an example of a generalized approach wherein compounds similar in structure to the specific reactants above (compounds similar to compounds of type 2.1 and 2.2), can be substituted in the reaction to provide substituted bile acid analogs similar to Formula 2.3.

3. Route III

In one aspect, the substituted bile acid analogs can be prepared as shown below.

SCHEME 3A.

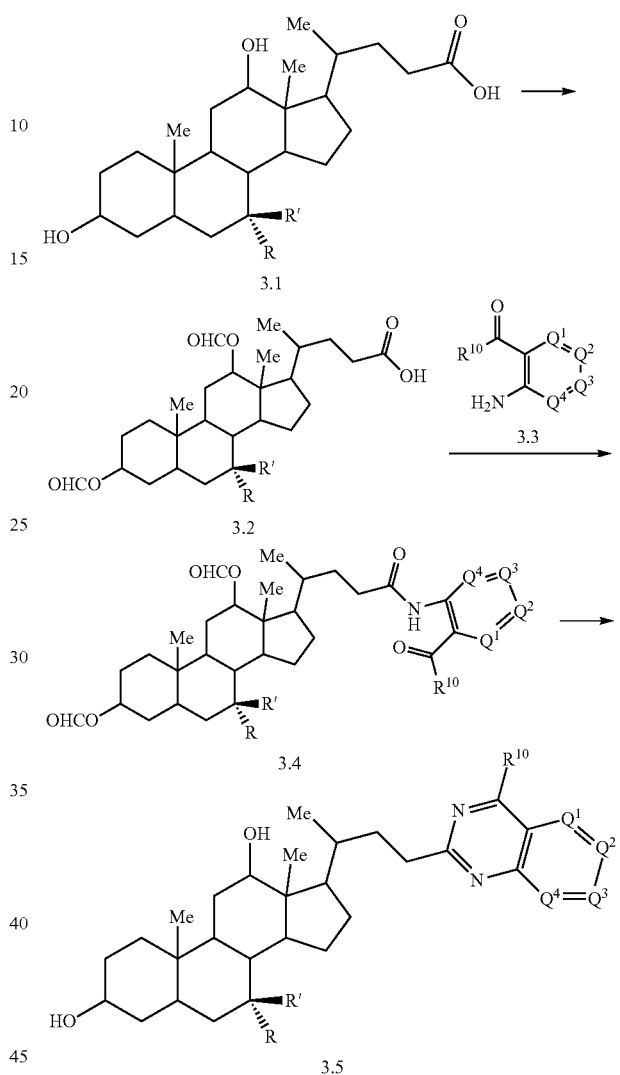

Compounds are represented in generic form, wherein R and R' are independently selected form hydrogen and —CHO, and with other substituents as noted in compound descriptions elsewhere herein. A more specific example is set forth below.

SCHEME 3B.

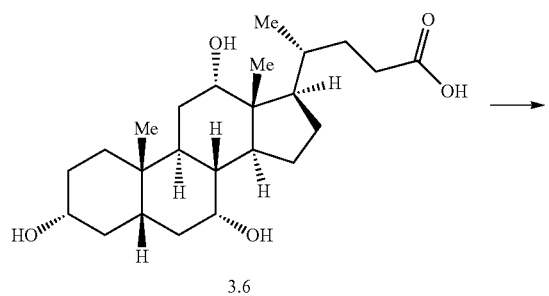

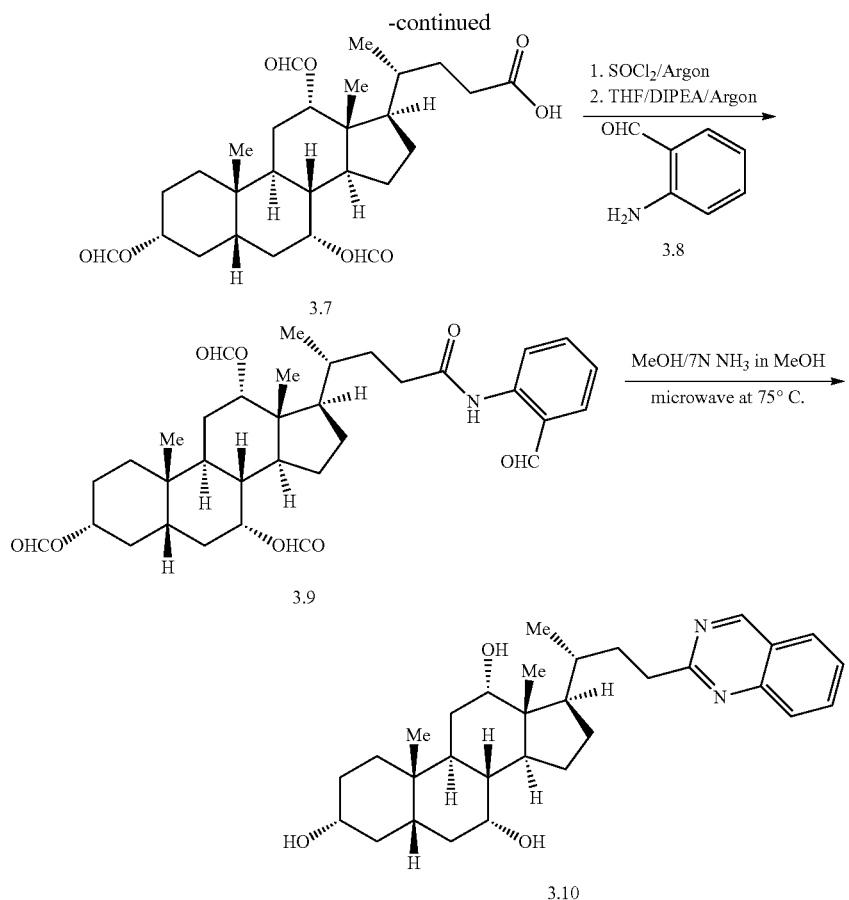

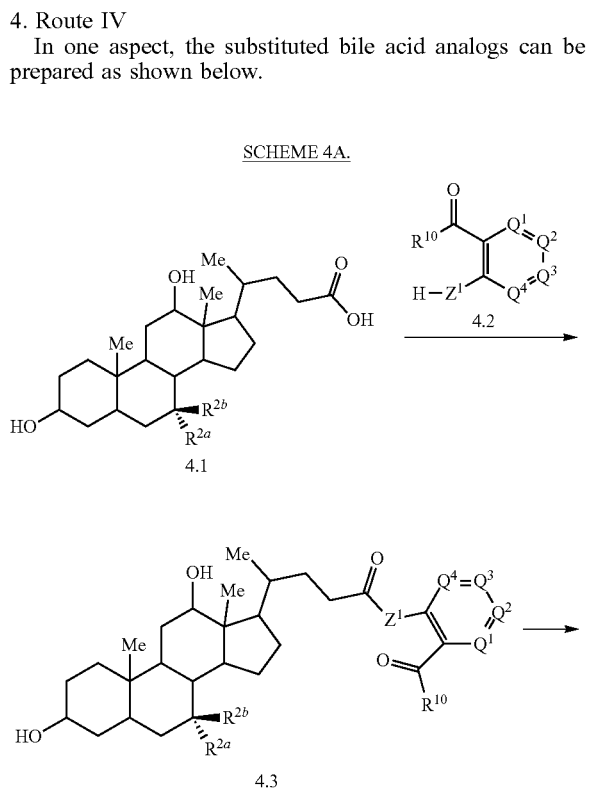

In one aspect, compounds of type 3.10, and similar compounds, can be prepared according to reaction Scheme 3B above. Thus, compounds of type 3.7 can be prepared by oxidation of an appropriate bile acid, e.g., 3.6 as shown above. Appropriate bile acids are commercially available or prepared by methods known to one skilled in the art. The oxidation is carried out in the presence of an appropriate oxidant, e.g., perchloric acid, in an appropriate solvent system, e.g., formic acid and acetic anhydride. Compounds of type 3.9 can be prepared by activation of an appropriate carboxylic acid, e.g., 3.7 as shown above, followed by coupling with an appropriate amine, e.g., 3.8 as shown above. Appropriate amines are commercially available or prepared by methods known to one skilled in the art. The reaction is carried out in the presence of an appropriate activating agent, e.g., thionyl chloride, followed by addition of the amine in the presence of an appropriate base, e.g., diisopropylethylamine, in an appropriate solvent, e.g., tetrahydrofuran. Compounds of type 3.10 can be prepared by reduction and cyclization of an appropriate amide, e.g., 3.9 as shown above. The reduction/cyclization is carried out in the presence of an appropriate base, e.g., 7N ammonia, in an appropriate protic solvent, e.g., methanol, at an appropriate temperature, e.g., 75° C. under microwave irradiation. As can be appreciated by one skilled in the art, the above reaction provides an example of a generalized approach wherein compounds similar in structure to the specific reactants above (compounds similar to compounds of type 3.1, 3.2, 3.3, and 3.4), can be substituted in the reaction to provide substituted bile acid analogs similar to Formula 3.5.

4. Route IV

In one aspect, the substituted bile acid analogs can be prepared as shown below.

SCHEME 4A.

-continued

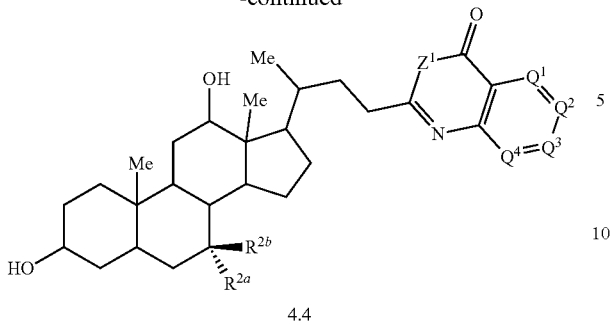

4.4

Compounds are represented in generic form, with other substituents as noted in compound descriptions elsewhere herein. A more specific example is set forth below.

SCHEME 4B.

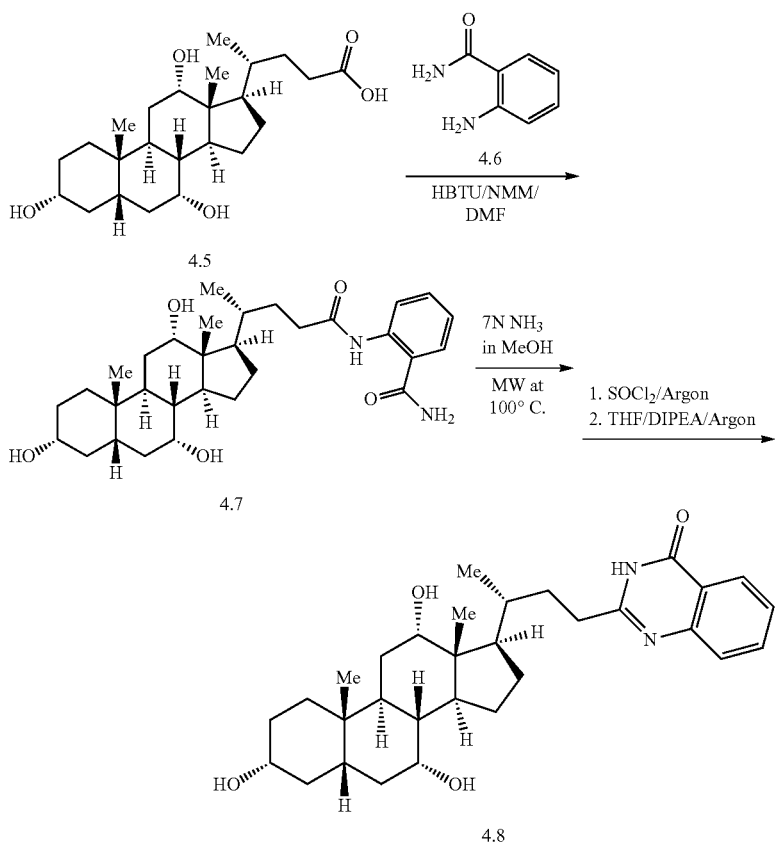

In one aspect, compounds of type 4.8, and similar compounds, can be prepared according to reaction Scheme 4B above. Thus, compounds of type 4.7 can be prepared by a coupling reaction between an appropriate bile acid, e.g., 4.5 as shown above, and an appropriate amine, e.g., 4.6 as shown above. Appropriate bile acids and appropriate amines are commercially available or prepared by methods known to one skilled in the art. The coupling reaction is carried out in the presence of an appropriate coupling agent, e.g., N,N,N',N'-tetramethyl-O-(1H-benzotriazol-1-yl)uronium hexafluorophosphate (HBTU), and an appropriate base, e.g., N-methylmorpholine (NMM), in an appropriate solvent, e.g., dimethylformamide (DMF). Compounds of type 4.8 can be prepared by reduction and cyclization of an appropriate amide, e.g., 4.7 as shown above. The reduction/ cyclization is carried out in the presence of an appropriate base, e.g., 7N ammonia, in an appropriate protic solvent, e.g., methanol, at an appropriate temperature, e.g., 100° C. under microwave irradiation. As can be appreciated by one skilled in the art, the above reaction provides an example of a generalized approach wherein compounds similar in structure to the specific reactants above (compounds similar to compounds of type 4.1, 4.2, and 4.3), can be substituted in the reaction to provide substituted bile acid analogs similar to Formula 4.4.

5. Route V

In one aspect, the substituted bile acid analogs can be prepared as shown below.

SCHEME 5A.

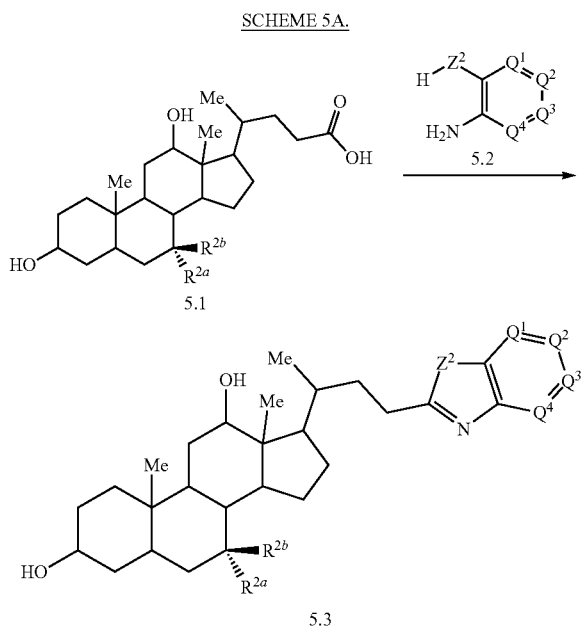

5.1

5.3

Compounds are represented in generic form, with other substituents as noted in compound descriptions elsewhere herein. A more specific example is set forth below.

SCHEME 5B.

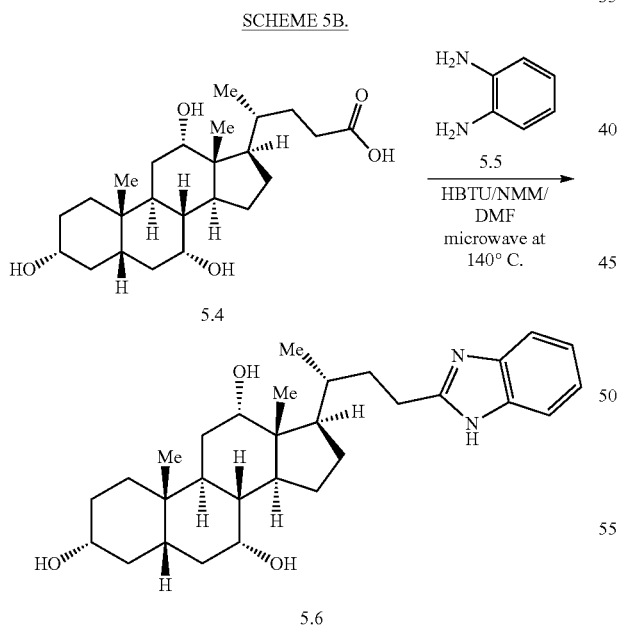

5.4

5.6

In one aspect, compounds of type 5.6, and similar compounds, can be prepared according to reaction Scheme 5B above. Thus, compounds of type 5.6 can be prepared by a coupling reaction between an appropriate bile acid, e.g., 5.4 as shown above, and an appropriate amine, e.g., 5.5, followed by cyclization using microwave irradiation at 140° C. as shown above. Appropriate bile acids and appropriate amines are commercially available or prepared by methods known to one skilled in the art. The coupling reaction is carried out in the presence of an appropriate coupling agent, e.g., N,N,N',N'-tetramethyl-O-(1H-benzotriazol-1-yl)uronium hexafluorophosphate (HBTU), and an appropriate base, e.g., N-methylmorpholine (NMM), in an appropriate solvent, e.g., dimethylformamide (DMF). As can be appreciated by one skilled in the art, the above reaction provides an example of a generalized approach wherein compounds similar in structure to the specific reactants above (compounds similar to compounds of type 5.4 and 5.5), can be substituted in the reaction to provide substituted bile acid analogs similar to Formula 5.6.

F. METHODS FOR PREVENTING OR TREATING A DISEASE OR DISORDER CAUSED BY INFECTION BY *C. DIFFICILE* IN A SUBJECT

In one aspect, disclosed are methods for preventing or treating a disease or disorder caused by infection of *Clostridium difficile* in a subject in need thereof, the method comprising administering to the subject an effective amount of a compound having a structure represented by a formula:

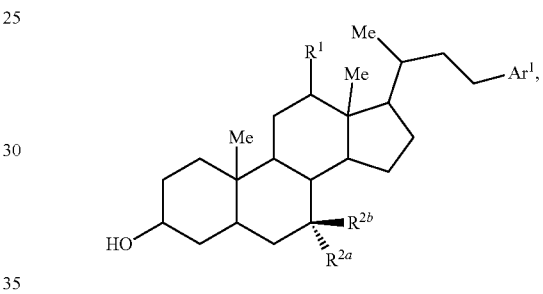

wherein each of $R^1$, $R^{2a}$, and $R^{2b}$ is independently selected from hydrogen and —OH; and wherein $Ar^1$ is a bicyclic heteroaryl having a structure represented by a formula selected from:

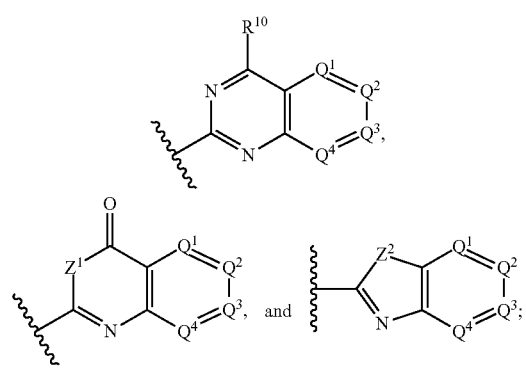

wherein $Z^1$ is selected from —O— and —$NR^{18}$—; wherein $R^{18}$, when present, is selected from hydrogen and C1-C4 alkyl; wherein $Z^2$ is selected from —O—, —S—, and —$NR^{19}$—; wherein $R^{19}$, when present, is selected from hydrogen and C1-C4 alkyl; wherein each of $Q^1$, $Q^2$, $Q^3$, and $Q^4$ is independently selected from —N= and —$CR^{20}$=; wherein each occurrence of $R^{20}$ is independently selected from hydrogen, halogen, C1-C4 alkyl, C1-C4 alkoxy, and phenyl; and wherein $R^{10}$ is selected from hydrogen, halogen, C1-C4 alkyl, C1-C4 alkoxy, and phenyl, or a pharmaceutically acceptable salt thereof.

In various aspects, the compound is selected from:

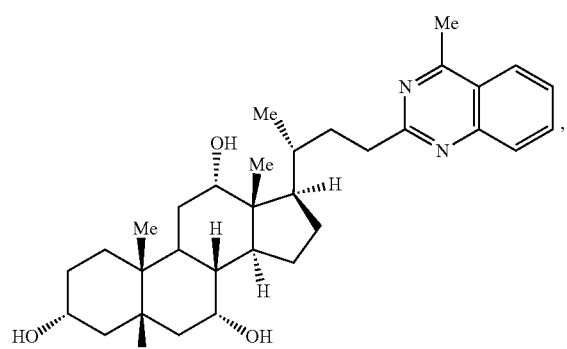

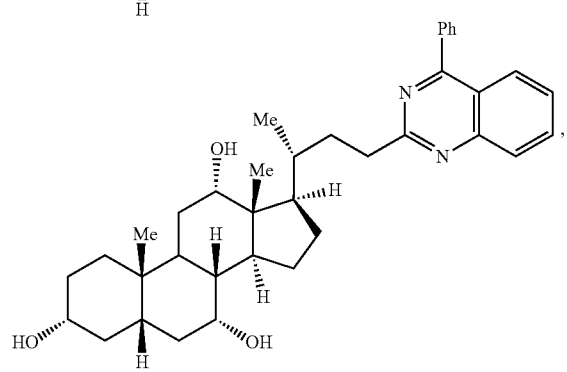

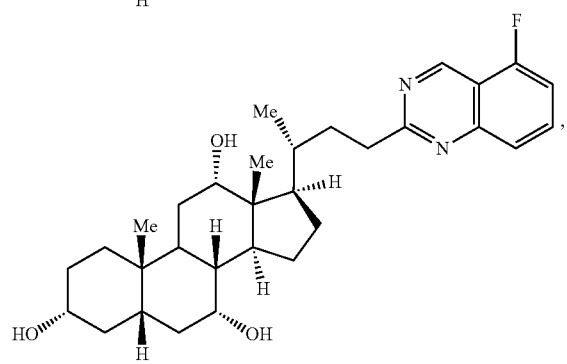

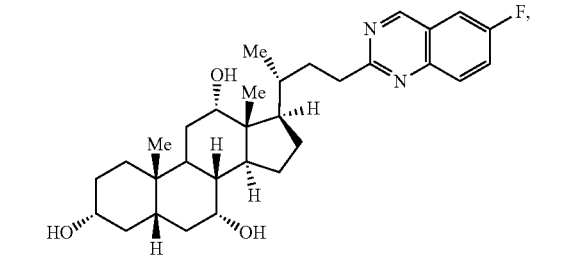

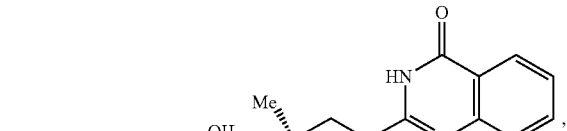

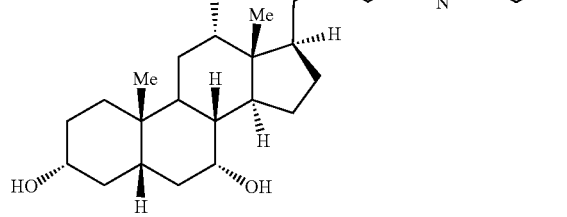

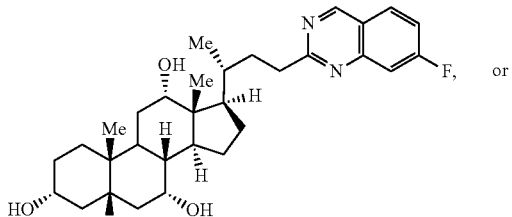

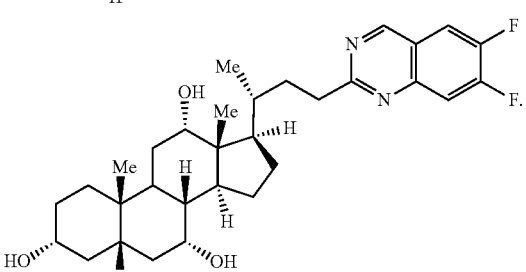

In various aspects, the compound is:

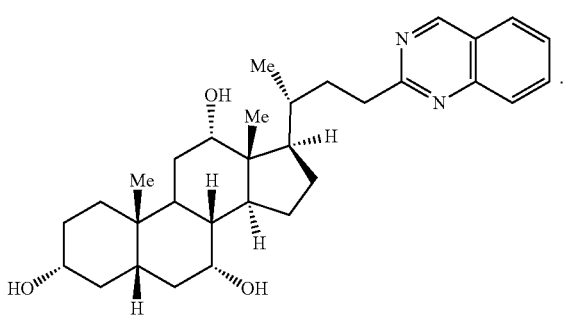

In one aspect, disclosed are methods for preventing or treating a disease caused by infection of *Clostridium difficile* in a subject in need thereof, the method comprising administering to the subject an effective amount of a compound having a structure represented by a formula:

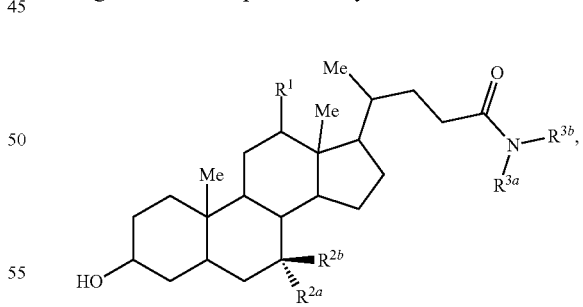

wherein each of $R^1$, $R^{2a}$, and $R^{2b}$ is independently selected from hydrogen and —OH; wherein each of $R^{3a}$ and $R^{3b}$ are independently selected from C1-C4 alkyl, C2-C4 alkenyl, and phenyl substituted with 0, 1, 2, or 3 groups independently selected from halogen, —NO$_2$, —CN, C1-C4 alkyl, C1-C4 haloalkyl, and —C(O)(C1-C4 alkyl), or wherein each of $R^{3a}$ and $R^{3b}$ together comprise a heterocycle having a structure represented by a formula selected from:

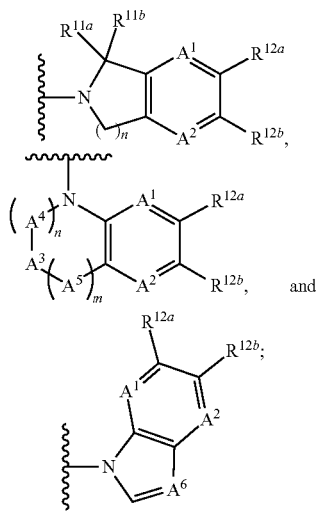

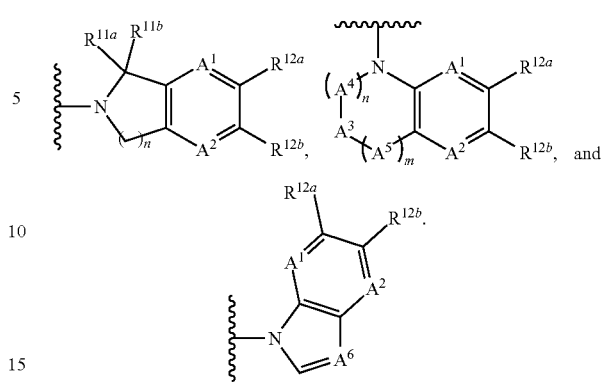

wherein each of n and m, when present, is independently 0, 1, or 2; wherein each of $A^1$ and $A^2$ is independently selected from —N= and —$CR^{21}$=; wherein each occurrence of $R^{21}$ is independently selected from hydrogen, halogen, —$NO_2$, —CN, C1-C4 alkyl, C1-C4 alkoxy, C1-C4 haloalkyl, and —C(O)(C1-C4 alkyl); wherein $A^3$, when present, is selected from —O—, —S—, —$NR^{22}$—, and —$C(R^{23a})(R^{23b})$—; wherein $R^{22}$ is selected from hydrogen and C1-C4 alkyl;

wherein each of $R^{23a}$ and $R^{23b}$ is independently selected from hydrogen and C1-C4 alkyl; wherein each of $A^4$ and $A^5$, when present, is independently —$C(R^{23c})(R^{23d})$—; wherein each of $R^{23c}$ and $R^{23d}$ is independently selected from hydrogen and C1-C4 alkyl; wherein $A^6$, when present, is selected from =$C(R^{24})$— and =N—; wherein $R^{24}$, when present, is selected from hydrogen and C1-C4 alkyl; wherein each of $R^{11a}$ and $R^{11b}$, when present, is independently selected from hydrogen and C1-C4 alkyl; and wherein each of $R^{12a}$ and $R^{12b}$ is independently selected from hydrogen, halogen, —$NO_2$, —CN, C1-C4 alkyl, C1-C4 haloalkyl, and —C(O)(C1-C4 alkyl), or a pharmaceutically acceptable salt thereof.

In various aspects, each of $R^{3a}$ and $R^{3b}$ are independently selected from C1-C4 alkyl, C2-C4 alkenyl, and phenyl substituted with 0, 1, 2, or 3 groups independently selected from halogen, —$NO_2$, —CN, C1-C4 alkyl, C1-C4 haloalkyl, and —C(O)(C1-C4 alkyl). In a further aspect, each of $R^{3a}$ and $R^{3b}$ are independently selected from C1-C4 alkyl. In a still further aspect, each of $R^{3a}$ and $R^{3b}$ are ethyl. In yet a further aspect, each of $R^{3a}$ and $R^{3b}$ are independently selected from C2-C4 alkenyl. In an even further aspect, each of $R^{3a}$ and $R^{3b}$ are —$CH_2CH=CH_2$. In a still further aspect, each of $R^{3a}$ and $R^{3b}$ are independently selected from C1-C4 alkyl and phenyl substituted with 0, 1, 2, or 3 groups independently selected from halogen, —$NO_2$, —CN, C1-C4 alkyl, C1-C4 haloalkyl, and —C(O)(C1-C4 alkyl). In yet a further aspect, each of $R^{3a}$ and $R^{3b}$ are independently selected from C1-C4 alkyl and unsubstituted phenyl. In an even further aspect, one of $R^{3a}$ and $R^{3b}$ is methyl and the other is unsubstituted phenyl. In a still further aspect, each of $R^{3a}$ and $R^{3b}$ together comprise a heterocycle having a structure represented by a formula selected from:

In various aspects, the compound is selected from:

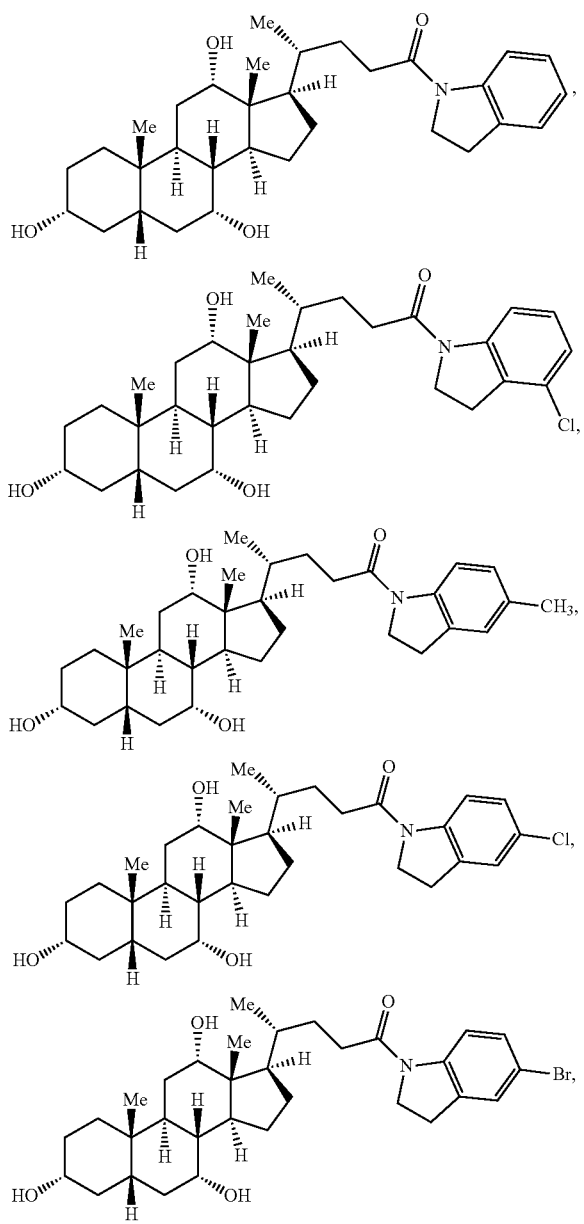

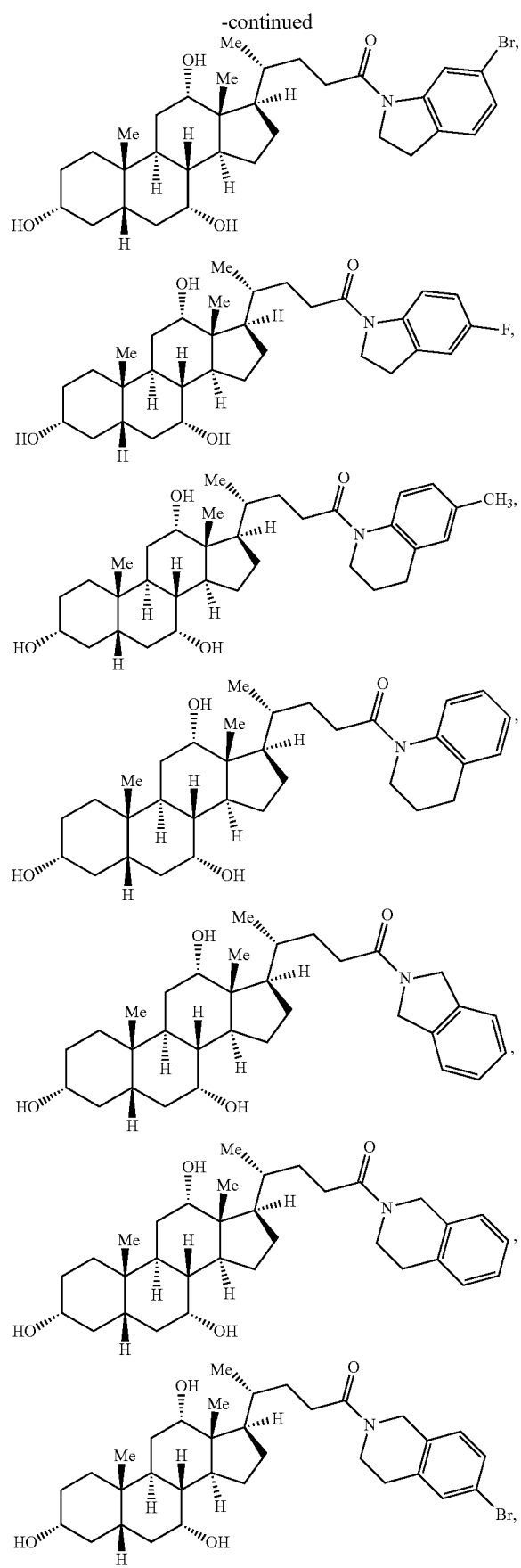
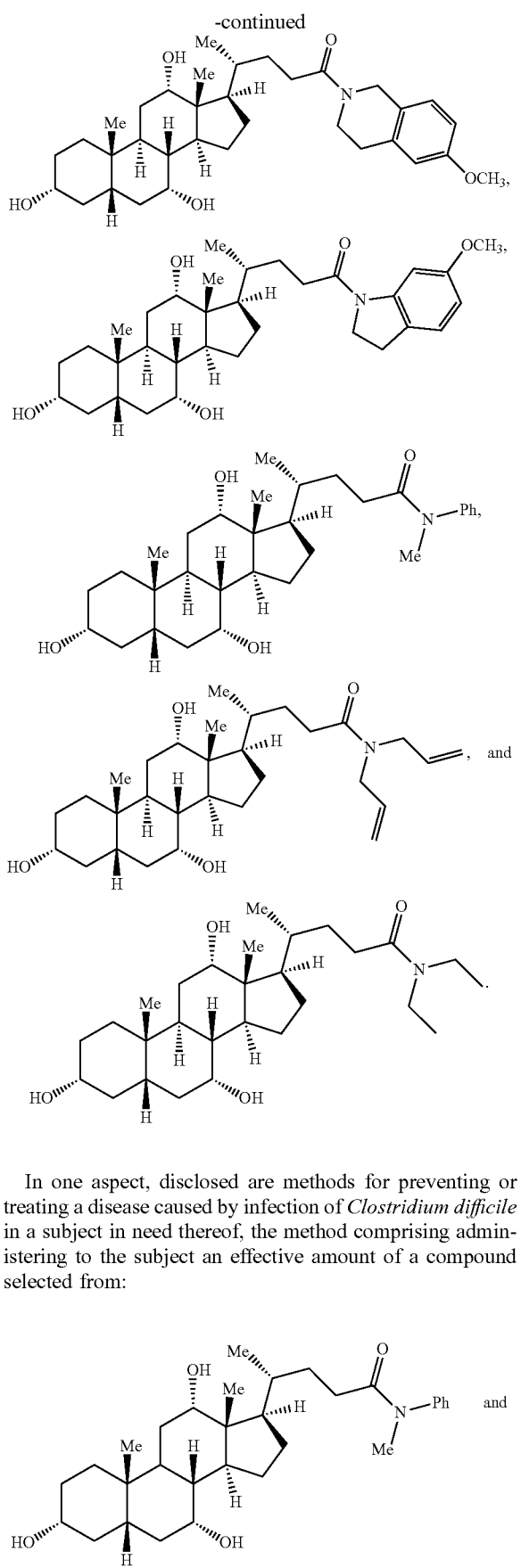
In one aspect, disclosed are methods for preventing or treating a disease caused by infection of *Clostridium difficile* in a subject in need thereof, the method comprising administering to the subject an effective amount of a compound selected from:

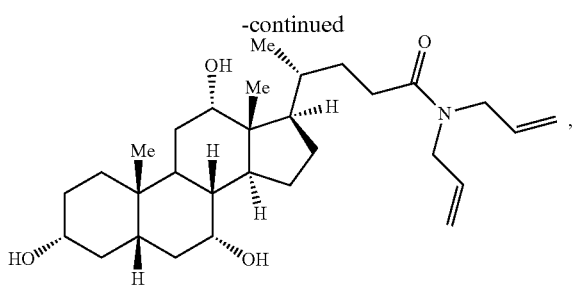

or a pharmaceutically acceptable salt thereof.

In one aspect, disclosed are methods for preventing or treating a disease caused by infection of *Clostridium difficile* in a subject in need thereof, the method comprising administering to the subject an effective amount of a compound selected from:

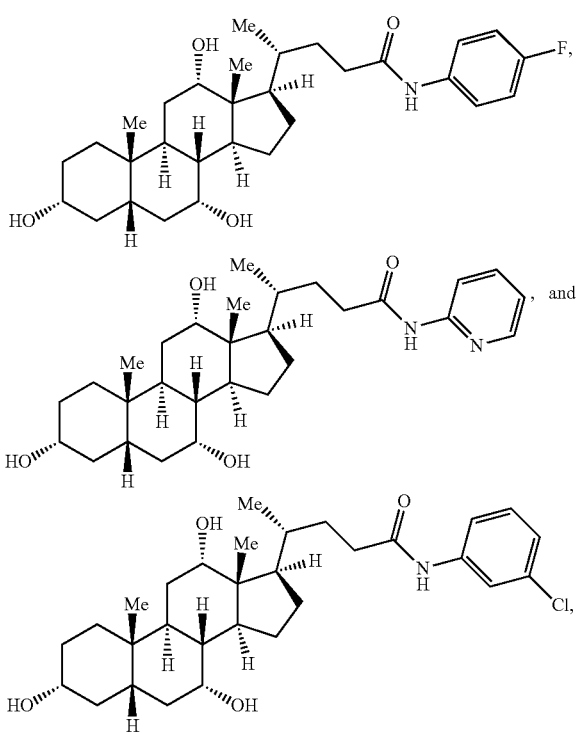

or a pharmaceutically acceptable salt thereof.

In various aspects, the subject is a mammal (e.g., a human, a farm animal). In a further aspect, the subject is a human. In a still further aspect, the subject is a farm animal.

In various aspects, the method further comprises administering to the subject an antibiotic. Examples of antibiotics include, but are not limited to, metronidazole, amoxicillin, levofloxacin, clarithromycin, vancomycin, fusidic acid, rifamycin, teicoplanin, fidaxomicin, and bacitracin.

In various aspects, the compound and the antibiotic are administered simultaneously. In a further aspect, the compound and the antibiotic are administered sequentially.

In various aspects, the compound and the antibiotic are co-formulated. In a further aspect, the compound and the antibiotic are not co-formulated.

In various aspects, the effective amount is a prophylactically effective amount. In a further aspect, the effective amount is a therapeutically effective amount.

In various aspects, the subject is not concurrently receiving antibiotic therapy. In a further aspect, the subject is concurrently receiving antibiotic therapy.

In various aspects, the subject has been diagnosed with an increased risk of the *Clostridium difficile*-associated disease or disorder prior to the administering step. In a further aspect, the subject has been diagnosed with the *Clostridium-difficile*-associated disease or disorder prior to the administering step. Examples of *Clostridium-difficile*-associated diseases or disorder include, but are not limited to, severe diarrhea or colitis (e.g., pseudomembranous colitis).

In various aspects, administering is via oral administration. In a further aspect, administering is via oral gavage.

In various aspects, the method comprises administering a composition comprising the compound and a feed component.

G. METHODS FOR INHIBITING GERMINATION OF A *C. DIFFICILE* SPORE IN A SUBJECT

In one aspect, disclosed are methods for inhibiting germination of *C. difficile* spores in the gut of humans or animals (e.g., domesticated or farmed fowl such as, without limitation, chickens, turkeys, ducks, and geese). The administration of such compounds and compositions can prevent or reduce the likelihood of occurrence of diseases or disorders such as severe diarrhea and colitis in a subject containing intestinal *C. difficile* spores, reduce the occurrence of such diseases or disorders in a population of animals in which at least some of the animals contain intestinal *C. difficile* spores, and treat the occurrence of such diseases or disorders in an animal in which *C. difficile* spores have germinated (e.g., to reduce or prevent transmission of the disease to other animals).

Thus, in one aspect, disclosed are methods for inhibiting germination of a *Clostridium difficile* spore in a subject in need thereof, the method comprising administering to the subject an effective amount of a compound having a structure represented by a formula:

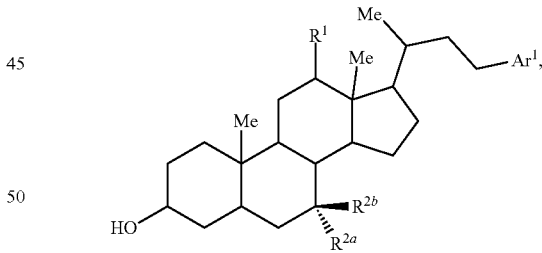

wherein each of $R^1$, $R^{2a}$, and $R^{2b}$ is independently selected from hydrogen and —OH; and wherein $Ar^1$ is a bicyclic heteroaryl having a structure represented by a formula selected from:

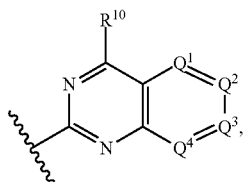

-continued

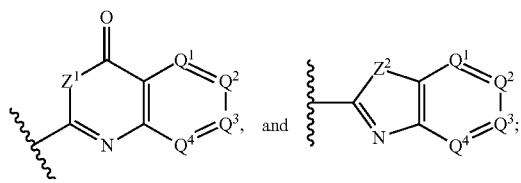
and

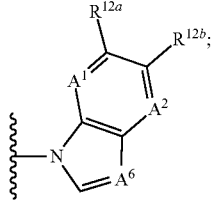

wherein $Z^1$ is selected from —O— and —NR$^{18}$—; wherein $R^{18}$, when present, is selected from hydrogen and C1-C4 alkyl; wherein $Z^2$ is selected from —O—, —S—, and —NR$^{19}$—; wherein $R^{19}$, when present, is selected from hydrogen and C1-C4 alkyl; wherein each of $Q^1$, $Q^2$, $Q^3$, and $Q^4$ is independently selected from —N= and —CR$^{20}$=; wherein each occurrence of $R^{20}$ is independently selected from hydrogen, halogen, C1-C4 alkyl, C1-C4 alkoxy, and phenyl; and wherein $R^{10}$ is selected from hydrogen, halogen, C1-C4 alkyl, C1-C4 alkoxy, and phenyl, or a pharmaceutically acceptable salt thereof.

In one aspect, disclosed are methods for inhibiting germination of a *Clostridium difficile* spore in a subject in need thereof, the method comprising administering to the subject an effective amount of a compound having a structure represented by a formula:

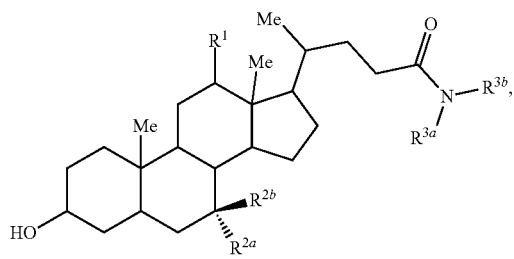

wherein each of $R^1$, $R^{2a}$, and $R^{2b}$ is independently selected from hydrogen and —OH; wherein each of $R^{3a}$ and $R^{3b}$ are independently selected from C1-C4 alkyl, C2-C4 alkenyl, and phenyl substituted with 0, 1, 2, or 3 groups independently selected from halogen, —NO$_2$, —CN, C1-C4 alkyl, C1-C4 haloalkyl, and —C(O)(C1-C4 alkyl), or wherein each of $R^{3a}$ and $R^{3b}$ together comprise a heterocycle having a structure represented by a formula selected from:

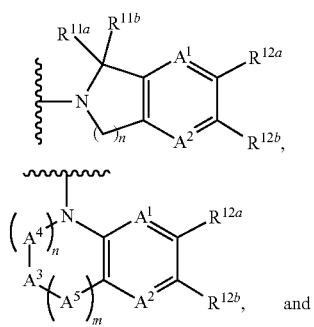
and wherein each of n and m, when present, is independently 0, 1, or 2; wherein each of $A^1$ and $A^2$ is independently selected from —N= and —CR$^{21}$=; wherein each occurrence of $R^{21}$ is independently selected from hydrogen, halogen, —NO$_2$, —CN, C1-C4 alkyl, C1-C4 alkoxy, C1-C4 haloalkyl, and —C(O)(C1-C4 alkyl); wherein $A^3$, when present, is selected from —O—, —S—, —NR$^{22}$—, and —C(R$^{23a}$)(R$^{23b}$)—; wherein $R^{22}$ is selected from hydrogen and C1-C4 alkyl; wherein each of $R^{23a}$ and $R^{23b}$ is independently selected from hydrogen and C1-C4 alkyl; wherein each of $A^4$ and $A^5$, when present, is independently —C(R$^{23c}$)(R$^{23d}$)—; wherein each of $R^{23c}$ and $R^{23d}$ is independently selected from hydrogen and C1-C4 alkyl; wherein $A^6$, when present, is selected from =C(R$^{24}$)— and =N—; wherein $R^{24}$, when present, is selected from hydrogen and C1-C4 alkyl; wherein each of $R^{11a}$ and $R^{11b}$, when present, is independently selected from hydrogen and C1-C4 alkyl; and wherein each of $R^{12a}$ and $R^{12b}$ is independently selected from hydrogen, halogen, —NO$_2$, —CN, C1-C4 alkyl, C1-C4 haloalkyl, and —C(O)(C1-C4 alkyl), or a pharmaceutically acceptable salt thereof.

In one aspect, disclosed are methods for inhibiting germination of a *Clostridium difficile* in a subject in need thereof, the method comprising administering to the subject an effective amount of a compound selected from:

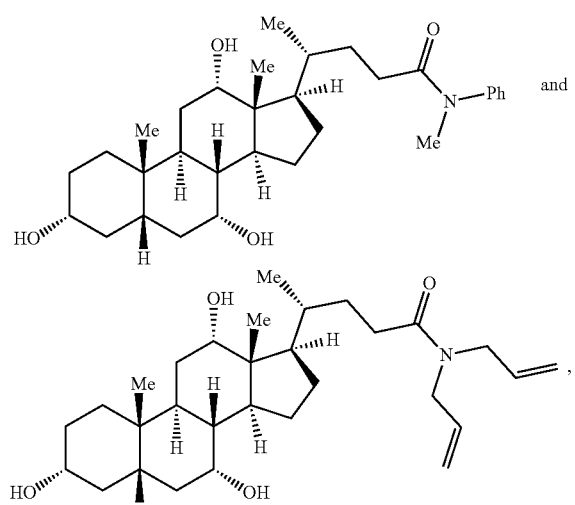

or a pharmaceutically acceptable salt thereof.

In one aspect, disclosed are methods for inhibiting germination of a *Clostridium difficile* in a subject in need thereof, the method comprising administering to the subject an effective amount of a compound selected from:

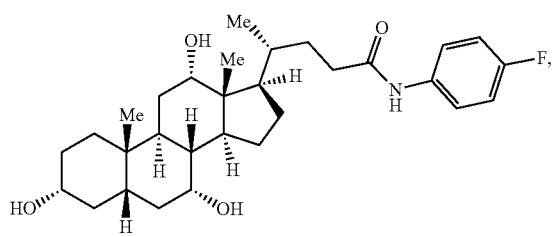

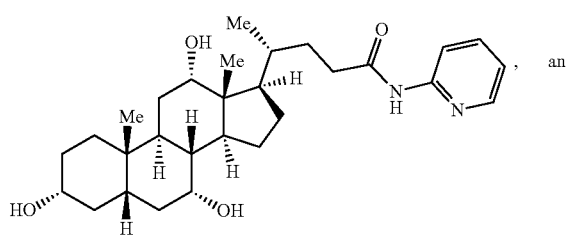, and

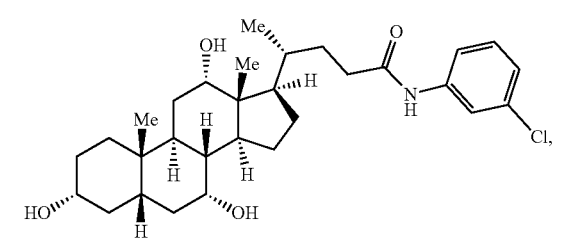

or a pharmaceutically acceptable salt thereof.

The methods can include administering to one or more subject a compound or composition in an amount effective to reduce or prevent germination of *C. difficile*, as described herein. In various aspects, an effective amount can be from about 0.1 nmol to about 100 mmol (e.g., about 0.1 nmol to about 1 nmol, about 1 nmol to about 10 nmol, about 10 nmol to about 0.1 mmol, about 0.1 mmol to about 1 mmol, about 1 mmol to about 5 mmol, about 5 mmol to about 10 mmol, about 10 mmol to about 50 mmol, or about 50 mM to about 100 mmol). In the methods provided herein, the compound(s), composition(s), and/or feed can be administered any number of times during the life of the subject, although it is noted that administration throughout the life of the subject can be useful. Thus, using feed containing one or more compounds as described herein may be particularly useful, as the recipient subject would essentially self-administer the compound(s) simply by eating.

In various aspects, the subject has previously been treated for a *Clostridium difficile*-associated disease or disorder.

In various aspects, administering is via oral administration. In a further aspect, administering is via oral gavage.

In various aspects, the method comprises administering a composition comprising the compound and a feed component.

H. KITS

In one aspect, disclosed are kits comprising a compound having a structure represented by a formula:

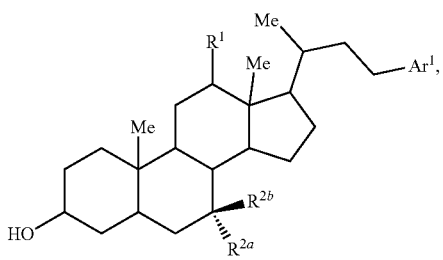

wherein each of $R^1$, $R^{2a}$, and $R^{2b}$ is independently selected from hydrogen and —OH; and wherein $Ar^1$ is a bicyclic heteroaryl having a structure represented by a formula selected from:

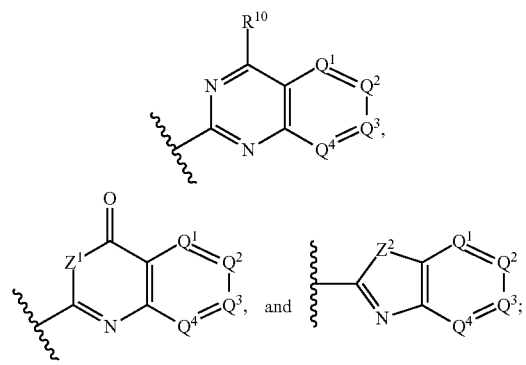

wherein $Z^1$ is selected from —O— and —$NR^{18}$—; wherein $R^{18}$, when present, is selected from hydrogen and C1-C4 alkyl; wherein $Z^2$ is selected from —O—, —S—, and —$NR^{19}$—; wherein $R^{19}$, when present, is selected from hydrogen and C1-C4 alkyl; wherein each of $Q^1$, $Q^2$, $Q^3$, and $Q^4$ is independently selected from —N= and —$CR^{20}$=; wherein each occurrence of $R^{20}$ is independently selected from hydrogen, halogen, C1-C4 alkyl, C1-C4 alkoxy, and phenyl; and wherein $R^{10}$ is selected from hydrogen, halogen, C1-C4 alkyl, C1-C4 alkoxy, and phenyl, or a pharmaceutically acceptable salt thereof, and one or more of: (a) an agent known for use in feed compositions; (b) an antibiotic; (c) instructions for administering the compound for preventing or treating a disease or disorder caused by infection of *Clostridium difficile*; and (d) instructions for preventing or treating a disease or disorder caused by infection of *Clostridium difficile*.

In one aspect, disclosed are kits comprising a compound having a structure represented by a formula:

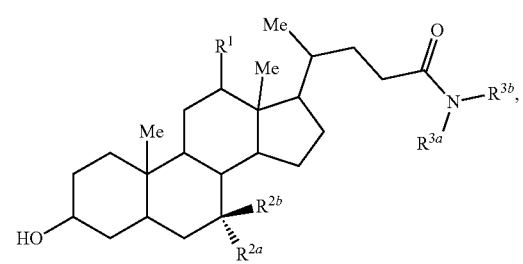

wherein each of $R^1$, $R^{2a}$, and $R^{2b}$ is independently selected from hydrogen and —OH; wherein each of $R^{3a}$ and $R^{3b}$ are independently selected from C1-C4 alkyl, C2-C4 alkenyl, and phenyl substituted with 0, 1, 2, or 3 groups independently selected from halogen, —NO$_2$, —CN, C1-C4 alkyl, C1-C4 haloalkyl, and —C(O)(C1-C4 alkyl), or wherein each of $R^{3a}$ and $R^{3b}$ together comprise a heterocycle having a structure represented by a formula selected from:

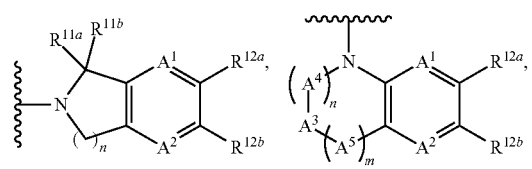

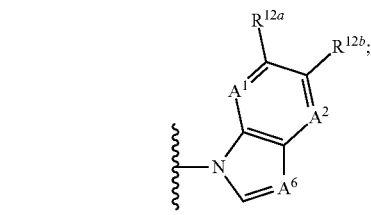

wherein each of n and m, when present, is independently 0, 1, or 2; wherein each of $A^1$ and $A^2$ is independently selected from —N= and —CR$^{21}$=; wherein each occurrence of $R^{21}$ is independently selected from hydrogen, halogen, —NO$_2$, —CN, C1-C4 alkyl, C1-C4 alkoxy, C1-C4 haloalkyl, and —C(O)(C1-C4 alkyl); wherein $A^3$, when present, is selected from —O—, —S—, —NR$^{22}$—, and —C(R$^{23a}$)(R$^{23b}$)—; wherein $R^{22}$ is selected from hydrogen and C1-C4 alkyl; wherein each of $R^{23a}$ and $R^{23b}$ is independently selected from hydrogen and C1-C4 alkyl; wherein each of $A^4$ and $A^5$, when present, is independently —C(R$^{23c}$)(R$^{23d}$)—; wherein each of $R^{23c}$ and $R^{23d}$ is independently selected from hydrogen and C1-C4 alkyl; wherein $A^6$, when present, is selected from =C(R$^{24}$)— and =N—; wherein $R^{24}$, when present, is selected from hydrogen and C1-C4 alkyl; wherein each of $R^{11a}$ and $R^{11b}$, when present, is independently selected from hydrogen and C1-C4 alkyl; and wherein each of $R^{12a}$ and $R^{12b}$ is independently selected from hydrogen, halogen, —NO$_2$, —CN, C1-C4 alkyl, C1-C4 haloalkyl, and —C(O)(C1-C4 alkyl), or a pharmaceutically acceptable salt thereof, and one or more of: (a) an agent known for use in feed compositions; (b) an antibiotic; (c) instructions for administering the compound for preventing or treating a disease or disorder caused by infection of *Clostridium difficile*; and (d) instructions for preventing or treating a disease or disorder caused by infection of *Clostridium difficile*.

In one aspect, disclosed are kits comprising a compound selected from:

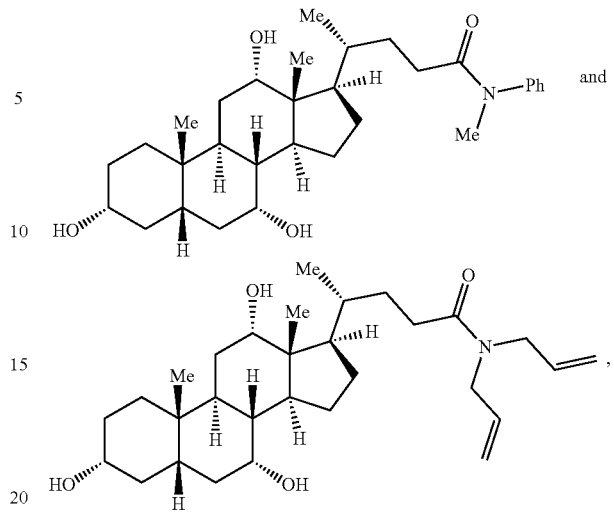

or a pharmaceutically acceptable salt thereof, and one or more of: (a) an agent known for use in feed compositions; (b) an antibiotic; (c) instructions for administering the compound for preventing or treating a disease or disorder caused by infection of *Clostridium difficile*; and (d) instructions for preventing or treating a disease or disorder caused by infection of *Clostridium difficile*.

In one aspect, disclosed are kits comprising a compound selected from:

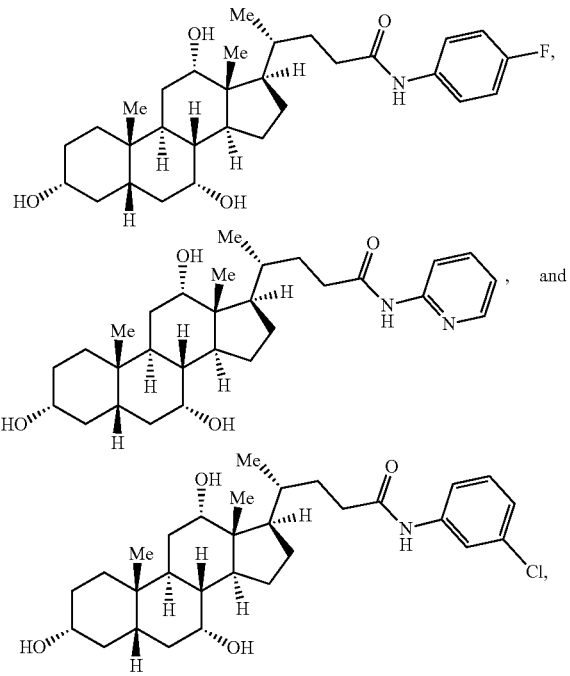

or a pharmaceutically acceptable salt thereof, and one or more of: (a) an agent known for use in feed compositions; (b) an antibiotic; (c) instructions for administering the compound for preventing or treating a disease or disorder caused by infection of *Clostridium difficile*; and (d) instructions for preventing or treating a disease or disorder caused by infection of *Clostridium difficile*.

In various aspects, the kit comprises an antibiotic. Examples of antibiotics include, but are not limited to, metronidazole, amoxicillin, levofloxacin, clarithromycin, vancomycin, fusidic acid, rifamycin, teicoplanin, fidaxomicin, and bacitracin.

In various aspects, the compound and the agent are co-formulated. In a further aspect, the compound and the agent are not co-formulated.

In various aspects, the compound and the antibiotic are co-formulated. In a further aspect, the compound and the antibiotic are not co-formulated.

The invention will be further described in the following examples, which do not limit the scope of the invention described in the claims.

I. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for.

Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. General Chemistry Experimental

Cholic acid (3α,7α,12α-trihydroxy-5β-cholan-24-oic acid), Chenodeoxycholic acid (3α,7α-Dihydroxy-5β-cholan-24-oic acid), Deoxycholic acid (3α,12α-Dihydroxy-5β-cholan-24-oic acid) Lithocholic acid (3α-Hydroxy-5β-cholan-24-oic acid), and Ursodeoxycholic acid (3α,7β-Dihydroxy-5β-cholan-24-oic acid) were purchased from MP Biomedical, Pfaltz and Bauer, and Chem-Impex International. All other reactants, reagents and solvents were purchased from Sigma-Aldrich, Acros Organics, TCI Chemicals, Alfa Aesar, Matrix Scientifics or Chem-Impex International and were used without further purification. Thin layer chromatography (TLC) was performed on pre-coated (0.25 mm) silica gel plate (Sorbtech, 60 F-254), and visualization was done either by UV (254 nm), or iodine staining. Column chromatographic purifications of compounds were performed on silica-gel (Sorbtech, 60-230 mesh, 0.063-0.20 mm). $^1$H and $^{13}$C NMR spectra were recorded on a Varian VNMRS 600 MHz or Bruker 400 MHz spectrometer by dissolving the compounds in deuterated solvents as chloroform-d (CDCl$_3$), methanol-d$_4$ (CD$_3$OD) or dimethyl sulfoxide-d$_6$ (DMSO-d$_6$) and all peaks were referenced with TMS as an internal standard or to the residual solvents. Some of the compound's spectra were recorded in multiple solvents for clarity of the aliphatic region. Chemical shifts are expressed in ppm (δ) whereas coupling constants (J) are listed in hertz (Hz) and the multiplicities are recorded by following abbreviations: s (singlet), d (doublet), t (triplet), q (quartet), m (multiplet), and br (broad signal). High-resolution mass spectra (HRMS) were recorded on a Kratos MS 80 RFA (ESI and CI) spectrometer. The purities of all the testing compounds were determined by $^1$H-NMR.

Melting points were determined using Mel-temp II apparatus by Laboratory Device, in open capillaries and are uncorrected.

2. Cyclic and Acyclic Tertiary Amide Analogs of Cholic Acid

Example compounds 1-13 were synthesized using Scheme 6 whereas compounds 14-15 were obtained by following Scheme 7.

SCHEME 6.

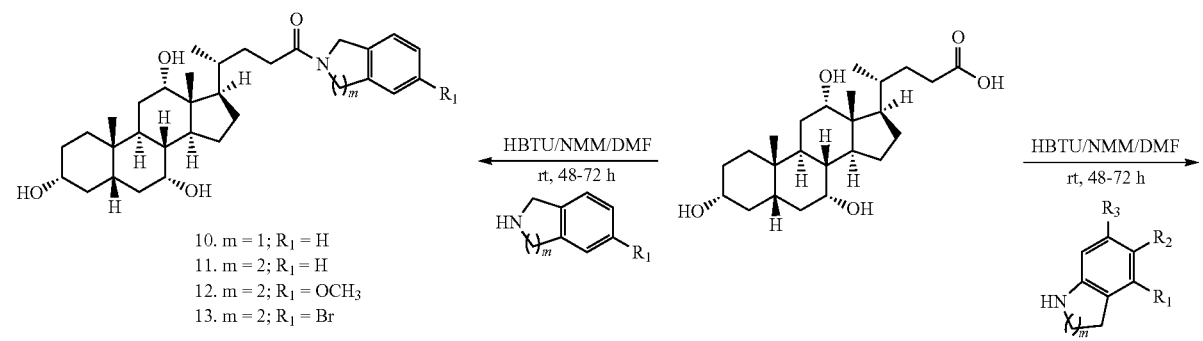

-continued

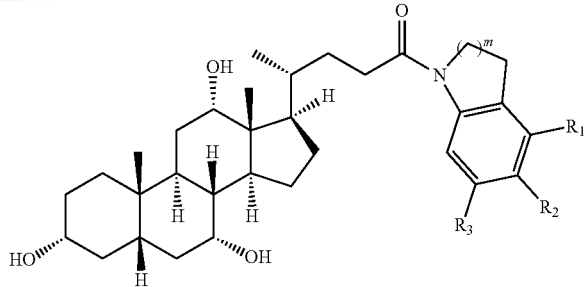

1. m = 1; R₁ = R₂ = R₃ = H
2. m = 1; R₁ = Cl; R₂ = R₃ = H
3. m = 1; R₁ = R₃ = H; R₂ = CH₃
4. m = 1; R₁ = R₃ = H; R₂ = F
5. m = 1; R₁ = R₃ = H; R₂ = Cl
6. m = 1; R₁ = R₃ = H; R₂ = Br
7. m = 1; R₁ = R₂ = H; R₃ = OCH₃
8. m = 2; R₁ = R₂ = R₃ = H
9. m = 2; R₁ = R₃ = H; R₂ = CH₃

SCHEME 7.

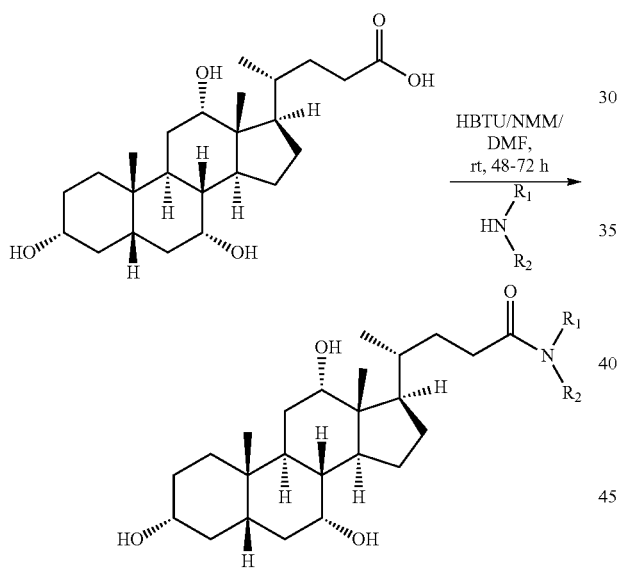

14. R₁ = CH₃; R₂ = Ph
15. R₁ = R₂ = CH₂CH = CH₂

General Procedure. Cholic acid (1 equiv., 0.50-2.50 mmol scale) and HBTU (1.2-1.6 equiv.) were dissolved in anhydrous DMF at room temperature. NMM (1.1-1.8 equiv.) was added into above reaction mixture, and the reaction content allowed to stir for 15-30 min to generate an activated ester. Secondary cyclic or acyclic amines (1.0-1.8 equiv.) either alone or in small quantity of DMF and NMM (0.9-2.7 equiv.) were added into above reaction mixture, and stirred for 0.5-2 hours and left to at room temperature for 48-72 h. The solvent was removed by using high vacuum rotary evaporation at 70-75° C. which produced a viscous light-yellow to dark brown material. A cold dilute HCl (2-5%) solution (50 ml-150 mL) was added into above reaction flask, and subjected to sonication, and stirring which produced a white precipitate; the product was filtered off and water-soluble portion was discarded. The resulting white precipitate was stirred and sonicated again two-three additional times with ice cold 2% HCl solution, the product was filtered off, washed with cold water, and dried under vacuum which produced cyclic or acyclic cholic-24-amides 1-15. Wherever purity of the compound was found not appropriate, the products were further purified by column chromatography over silica gel.

A. Synthesis of Compound 1

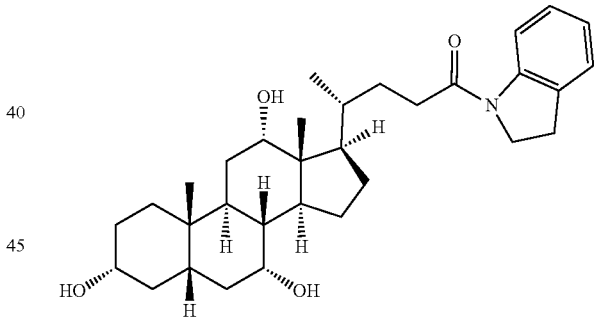

This compound was prepared using the general method described above. Cholic acid (821 mg, 2.01 mmol), HBTU (2.50 mmol), indoline (3.56 mmol), and NMM (5.46 mmol) were reacted to give the desired molecule in 88% yield (903 mg). mp. 280-283° C.; $^1$H NMR (DMSO-$d_6$, 600 MHz): δ 8.07 (d, 1H, J=6.0 Hz), 7.21 (s, 1H), 7.12 (s, 1H), 6.96 (s, 1H), 4.34 (s, 1H), 4.14-4.03 (m, 4H), 3.81 (s, 1H), 3.62 (s, 1H), 3.19 and 3.13 (2 s, 3H), 2.45 (br s, 1H), 2.32 (br s, 1H), 2.25-2.16 (m, 2H), 2.01 and 2.00 (2 peaks, 1H), 1.86-1.66 (m, 6H), 1.45-1.23 (m, 11H), 0.98 (br s, 4H), 0.86-0.81 (m, 4H), 0.61 (s, 3H); $^{13}$C NMR (DMSO-$d_6$, 150 MHz): δ 171.34, 143.11, 131.57, 126.84, 124.66, 122.88, 115.90, 71.08, 70.48, 66.28, 47.39, 46.21, 45.79, 41.55, 41.38, 35.33, 35.19, 34.88, 34.37, 32.16, 30.43, 30.33, 28.54, 27.41, 27.34, 26.21, 22.85, 22.59, 17.22, 12.35. HRMS (ESI, m/z): calcd for $C_{32}H_{47}NO_4Cl$ [M+Cl]$^-$ 544.3188, found 544.3194.

b. Synthesis of Compound 2

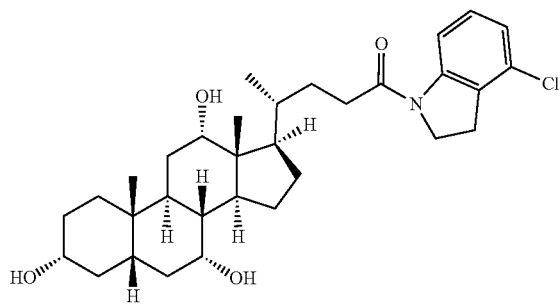

This compound was prepared using the general method described above. Cholic acid (205 mg, 0.50 mmol), HBTU (0.60 mmol), and 4-chloroindoline (0.50 mmol), and NMM (2.27 mmol) were reacted to give the desired molecule. The product was further purified by column chromatography eluted from $CH_2Cl_2$-MeOH—$NH_4OH$ (89:10:1) to furnish 2 in 58% yield (153 mg). mp. 224-227° C.; $^1H$ NMR ($CD_3OD$, 400 MHz): δ 8.04 (d, 1H, J=8.0 Hz), 7.15 (t, 1H, J=7.6 Hz), 7.019 (d, 1H, J=7.6 Hz), 4.20 (t, 2H, J=8.4 Hz), 3.97 (s, 1H), 3.80 (s, 1H), 3.35 (m, peak under solvent), 3.22 (t, 3H, J=8.4 Hz), 2.60-2.54 (m, 1H), 2.42-2.39 (m, 1H), 2.33-2.24 (m, 2H), 2.05-1.75 (m, 9H), 1.67-1.29 (m, 15H), 1.17-1.07 (m, 4H), 1.02-0.92 (m, 5H), 0.74 (s, 3H); $^1H$ NMR (DMSO-$d_6$, 400 MHz): δ 8.02 (d, 1H, J=8.0 Hz), 7.19 (t, 1H, J=8.0 Hz), 7.04 (d, 1H, J=8.0 Hz), 4.33 (s, 1H), 4.18-4.11 (m, 3H), 4.03 (s, 1H), 3.81 (s, 1H), 3.62 (s, 1H), 3.18-3.12 (m, peak under solvent), 2.47-2.44 (m, 1H), 2.36-2.14 (m, 3H), 2.04-1.97 (m, 1H), 1.88-1.78 (m, 4H), 1.67-1.64 (m, 2H), 1.43-1.24 (m, 11H), 0.99-0.93 (m, 4H), 0.88-0.82 (m, 4H), 0.61 (s, 3H); $^{13}C$ NMR ($CD_3OD$, 100 MHz): δ 174.95, 145.73, 131.74, 131.58, 130.70, 124.70, 116.43, 74.20, 73.03, 69.19, 48.11, 47.65, 43.34, 43.16, 40.60, 36.99, 36.63, 36.05, 36.00, 33.77, 31.98, 31.32, 29.72, 28.87, 28.46, 28.03, 24.40, 23.30, 18.03, 13.14.

c. Synthesis of Compound 3

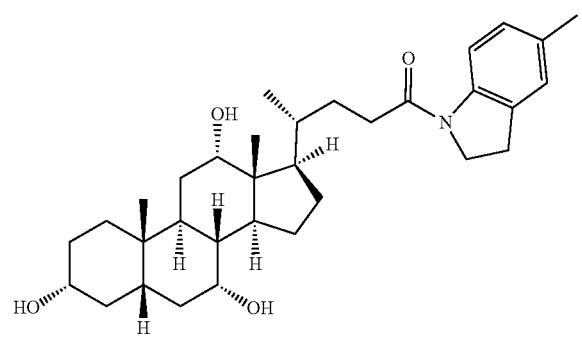

This compound was prepared using the general method described above. Cholic acid (205 mg, 0.50 mmol), HBTU (0.60 mmol), and 5-methyl-2,3-dihydro-1H-indole (0.50 mmol), and NMM (2.27 mmol) were reacted to give the desired molecule. The product was further purified by column chromatography eluted from $CH_2Cl_2$-MeOH—$NH_4OH$ (89:10:1) to furnish 3 in 84% yield (221 mg). mp. 215-218° C.; $^1H$ NMR ($CD_3OD$, 400 MHz): δ 7.98 (d, 1H, J=7.6 Hz), 7.03 (s, 1H), 6.96 (d, 1H, J=7.6 Hz), 4.11 (t, 2H, J=7.6 Hz), 3.97 (s, 1H), 3.80 (s, 1H), 3.16 (t, 2H, J=7.6 Hz), 2.54-2.51 (m, 1H), 2.39-2.29 (m, 6H), 2.03-1.80 (m, 7H), 1.68-1.30 (m, 13H), 1.14-1.08 (m, 4H), 1.02-0.92 (m, 4H), 0.73 (s, 3H); $^{13}C$ NMR ($CD_3OD$, 100 MHz): δ 174.26, 141.89, 134.87, 133.54, 128.68, 126.49, 117.86, 74.17, 73.00, 69.17, 49.98, 48.09, 47.63, 43.32, 43.13, 41.15, 40.59, 37.04, 36.62, 36.03, 35.99, 33.73, 32.18, 31.31, 29.71, 28.91, 28.87, 28.00, 24.39, 23.30, 21.18, 18.03, 13.15.

d. Synthesis of Compound 4

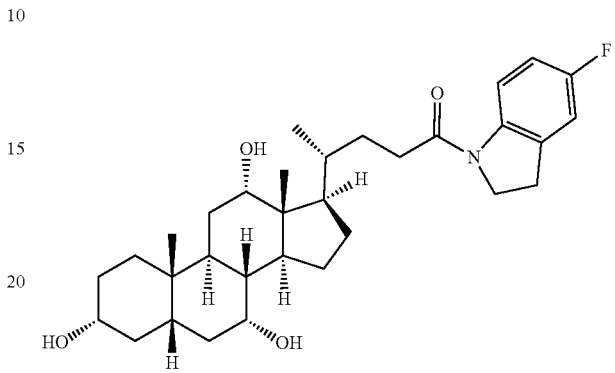

This compound was prepared using the general method described above. Cholic acid (205 mg, 0.50 mmol), HBTU (0.60 mmol), and 5-fluoroindoline (0.50 mmol), and NMM (2.27 mmol) were reacted to give the desired molecule. The product was further purified by column chromatography eluted from $CH_2Cl_2$-MeOH—$NH_4OH$ (89:10:1) to furnish 4 in 93% yield (246 mg). mp. >250° C.; $^1H$ NMR (DMSO-$d_6$, 400 MHz): δ 8.06 (dd, 1H, J=8.8, 5.2 Hz), 7.08 (d, 1H, J=8.4 Hz), 6.94 (td, 1H, J=9.2, 2.4 Hz), 4.32 (d, 1H, J=4.0 Hz), 4.15-4.10 (m, 3H), 4.00 (d, 1H, J=3.2 Hz), 3.81 (d, 1H, J=2.4 Hz), 3.63 (s, 1H), 3.20-3.12 (m, 3H), 2.51-2.45 (m, 1H), 2.36-2.13 (m, 3H), 2.05-1.97 (m, 1H), 1.89-1.64 (m, 7H), 1.43-1.24 (m, 12H), 0.99-0.98 (m, 4H), 0.88-0.82 (m, 4H), 0.61 (s, 3H); $^{13}C$ NMR (DMSO-$d_6$, 100 MHz): δ 171.22, 139.60, 134.27, 116.54, 113.02, 112.80, 112.14, 111.90, 71.02, 70.43, 66.24, 47.73, 46.20, 45.78, 41.51, 41.38, 35.31, 35.15, 34.87, 34.39, 31.92, 30.41, 30.32, 28.55, 27.42, 27.30, 26.20, 22.85, 22.63, 17.22, 12.38.

e. Synthesis of Compound 5

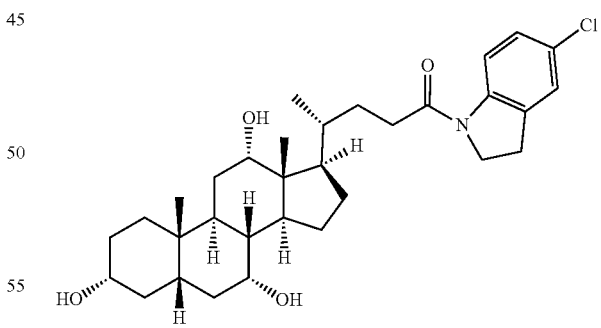

This compound was prepared using the general method described above. Cholic acid (208 mg, 0.50 mmol), HBTU (0.60 mmol), and 5-chloro-2,3-dihydro-(1H)-indole (0.50 mmol), and NMM (2.27 mmol) were reacted to give the desired molecule. The product was further purified by column chromatography eluted from $CH_2Cl_2$-MeOH—$NH_4OH$ (89:10:1) to furnish 5 in 88% yield (243 mg). mp. 231-234° C.; $^1H$ NMR ($CD_3OD$, 400 MHz): δ 8.07 (d, 1H, J=8.8 Hz), 7.21 (s, 1H), 7.13 (d, 1H, J=8.4), 4.17 (t, 2H, J=8.4 Hz), 3.97 (s, 1H), 3.80 (s, 1H), 3.20 (t, 2H, J=8 Hz), 2.58-2.53 (m, 1H), 2.45-2.38 (m, 1H), 2.33-2.24 (m, 2H), 2.05-1.75 (m, 7H), 1.67-1.29 (m, 11H), 1.17-1.06 (m, 4H), 1.02-0.92 (m, 4H), 0.73 (s, 3H); $^{13}$C NMR (CD$_3$OD, 100 MHz): δ 174.74, 143.14, 135.82, 129.79, 128.12, 126.05, 118.96, 74.20, 73.02, 69.19, 48.09, 47.64, 43.33, 43.15, 41.16, 40.60, 37.00 36.62, 36.04, 35.99, 33.66, 32.04, 31.31, 29.71, 28.86, 28.77, 28.02, 24.39, 23.30, 18.02, 13.13.

f. Synthesis of Compound 6

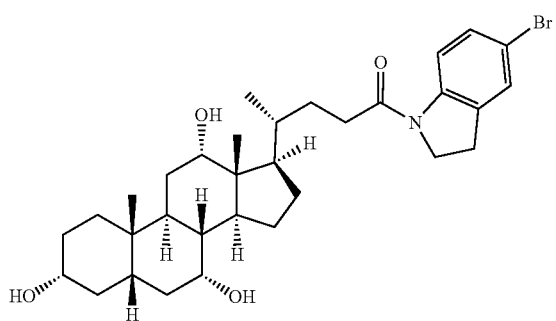

This compound was prepared using the general method described above. Cholic acid (206 mg, 0.50 mmol), HBTU (0.60 mmol), and 5-bromoindoline (0.50 mmol), and NMM (2.27 mmol) were reacted to give the desired molecule. The product was purified by column chromatography eluted from CH$_2$Cl$_2$-MeOH—NH$_4$OH (89:10:1) to furnish 6 in 83% yield (246 mg). mp. 230-233° C.; $^1$H NMR (CD$_3$OD, 400 MHz): δ 8.02 (d, 1H, J=8.4 Hz), 7.36 (s, 1H), 7.27 (d, 1H, J=8.4 Hz), 4.16 (t, 2H, J=8 Hz), 3.96 (s, 1H), 3.80 (s, 1H), 3.20 (t, 2H, J=8.4 Hz), 2.59-2.52 (m, 1H), 2.44-2.34 (m, 1H), 2.30-2.23 (m, 2H), 2.05-1.83 (m, 7H), 1.80-1.75 (m, 2H), 1.67-1.45 (m, 10H), 1.41-1.29 (m, 4H), 1.17-1.06 (m, 4H), 1.01-0.92 (m, 5H), 0.73 (s, 3H); $^{13}$C NMR (CD$_3$OD, 100 MHz): δ 174.79, 143.62, 136.19, 131.13, 129.01, 119.41, 117.18, 74.20, 73.03, 69.18, 48.10, 47.65, 43.35, 43.16, 41.17, 40.61, 37.01, 36.64, 36.05, 36.01, 33.70, 32.03, 31.33, 29.73, 28.88, 28.73, 28.03, 24.40, 23.31, 18.02, 13.14.

g. Synthesis of Compound 7

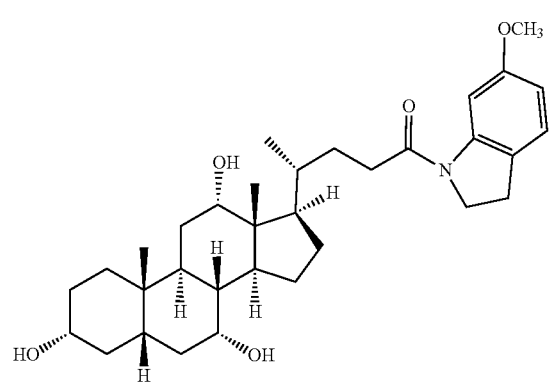

This compound was prepared using the general method described above. Cholic acid (206 mg, 0.50 mmol), HBTU (0.60 mmol), and 6-methoxyindoline (0.50 mmol), and NMM (2.27 mmol) were reacted to give the desired molecule. The product was further purified by column chromatography eluted from CH$_2$Cl2-MeOH—NH$_4$OH (89:10:1) to furnish 7 in 91% yield (248 mg). mp. 234-236° C.; $^1$H NMR (CD$_3$OD, 400 MHz): δ 7.69 (s, 1H), 6.95 (d, 1H, J=6.4 Hz), 6.47 (d, 1H, J=7.2 Hz), 3.98 (s, 2H), 3.85 (s, 1H), 3.25 and 3.21 (2 peaks, 2H), 2.98 (s, 1H), 2.41 (m, 1H), 2.25-2.17 (m, 3H), 1.91-1.68 (m, 7H), 1.56-1.18 (m, 12H), 0.97-0.96 (m, 4H), 0.90-0.80 (m, 4H), 0.61 (s, 3H); $^{13}$C NMR (CD$_3$OD, 100 MHz): δ 174.56, 160.72, 145.23, 125.96, 125.14, 110.42, 104.72, 74.12, 72.97, 69.13, 56.01, 50.25, 48.08, 47.61, 43.27, 43.09, 41.12, 40.55, 36.97, 36.61, 36.00, 33.83, 32.03, 31.28, 29.69, 28.87, 28.15, 27.96, 24.38, 23.31, 18.05, 13.17.

h. Synthesis of Compound 8

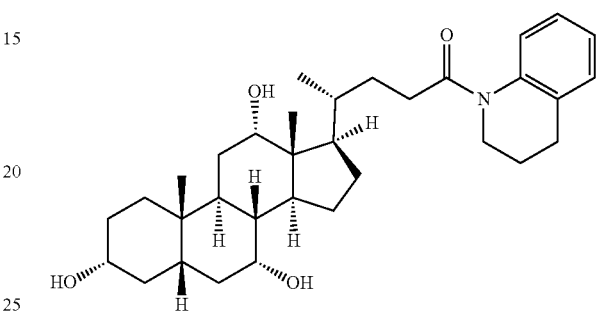

This compound was prepared using the general method described above. Cholic acid (822 mg, 2.01 mmol), HBTU (2.50 mmol), 1,2,3,4-tetrahydroquinoline (2.55 mmol), and NMM (5.46 mmol) were reacted to give the desired molecule in 86% yield (912 mg). mp. 104-106° C.; $^1$H NMR (CDCl$_3$, 600 MHz): δ 7.19-7.12 (m, 4H), 3.94 (s, 1H), 3.84 (s, 2H), 3.75-3.71 (m, 1H), 3.45 (s, 1H), 2.71 (s, 2H), 2.57-2.54 (m, 1H), 2.43 and 2.42 (2 peaks, 1H), 2.25-2.16 (m, 2H), 1.95-1.57 (m, 17H), 1.52 (s, 2H), 1.40-1.37 (m, 3H), 1.27 and 1.26 (2 peaks, 1H), 1.11 (br s 1H), 0.99-0.88 (m, 7H), 0.66 (s, 3H); $^1$H NMR (CD$_3$OD, 400 MHz): δ 7.19 and 7.16 (2 peaks, 4H), 3.89 (s, 1H), 3.78 (s, 2H), 3.71 and 3.69 (2 peaks, 1H), 3.36 (br, 1H), 2.72 (br s, 2H), 2.58 and 2.56 (2 peaks, 1H), 2.50 (br s, 1H), 2.28-2.23 (m, 2H), 1.96 and 1.95 (2 peaks, 4H), 1.77-1.50 (m, 11H), 1.45-1.19 (m, 5H), 1.09-0.90 (m, 8H), 0.67 (s, 3H); $^{13}$C NMR (CD$_3$OD, 100 MHz): δ 176.08, 140.28, 129.59, 127.24, 126.92, 126.01, 73.98, 72.90, 69.05, 48.00, 47.50, 43.22, 42.97, 41.03, 40.49, 36.92, 36.52, 35.91, 35.89, 33.33, 32.38, 31.21, 29.59, 28.62, 27.88, 27.56, 25.29, 24.22, 23.18, 17.70, 12.99.

i. Synthesis of Compound 9

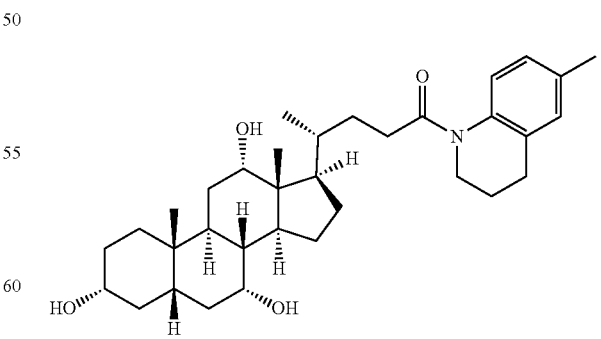

This compound was prepared using the general method described above. Cholic acid (207 mg, 0.50 mmol), HBTU (0.60 mmol), and 6-methyl-1,2,3,4-tetrahydroquinoline (0.50 mmol), and NMM (2.27 mmol) were reacted to give the desired molecule. The product was further purified by column chromatography eluted from CH₂Cl₂-MeOH—NH₄OH (89:10:1) to furnish 9 in 86% yield (234 mg). mp. 163-167° C.; ¹H NMR (CD₃OD, 400 MHz): δ 7.03 (s, 2H), 3.89 (s, 1H), 3.78 (br s, 2H), 3.68-3.65 (m, 1H), 2.67 (br s, 2H), 2.60-2.55 (m, 1H), 2.50-2.45 (m, 1H), 2.28-2.20 (m, 3H), 1.95-1.93 (m, 5H), 1.81-1.46 (m, 14H), 1.43-0.97 (m, 11H), 0.90-0.87 (m, 4H), 0.66 (s, 3H); ¹³C NMR (CD₃OD, 100 MHz): δ 176.17, 137.77, 130.15, 127.96, 125.83, 74.06, 72.97, 69.14, 48.04, 47.56, 43.28, 43.05, 41.08, 40.55, 37.02, 36.60, 35.99, 35.96, 31.27, 29.65, 28.71, 27.95, 27.61, 25.36, 24.32, 23.28, 21.13, 17.79, 13.09.

j. Synthesis of Compound 10

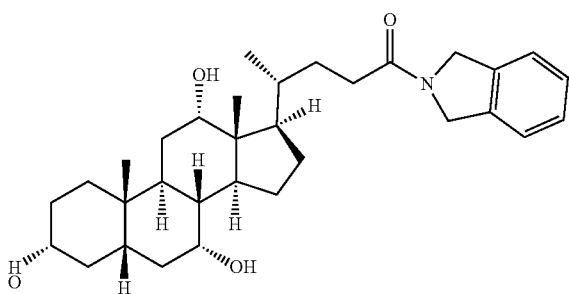

This compound was prepared using the general method described above. Cholic acid (205 mg, 0.50 mmol), HBTU (0.60 mmol), and isoindoline (0.50 mmol), and NMM (2.27 mmol) were reacted to give the desired molecule. The product was further purified by column chromatography eluted from CH₂Cl₂-MeOH—NH₄OH (89:10:1) to furnish 10 in 71% yield (181 mg). mp. >250° C.; ¹H NMR (DMSO-d₆, 400 MHz): δ 7.35 (s, 2H), 7.31 (s, 2H), 4.84 (s, 2H), 4.62 (s, 2H), 4.34 (d, 1H, J=4.0 Hz), 4.13 (d, 1H, J=2.8 Hz), 4.04 (d, 1H, J=2.8 Hz), 3.81 (s, 1H), 3.63 (s, 1H), 3.20-3.17 (m, 1H), 2.43-2.35 (m, 1H), 2.29-2.13 (m, 3H), 2.05-1.97 (m, 1H), 1.89-1.64 (m, 7H), 1.43-1.18 (m, 12H), 0.99-0.94 (m, 4H), 0.88-0.82 (m, 4H), 0.61 (s, 3H); ¹³C NMR (DMSO-d₆, 100 MHz): δ 171.43, 136.97, 136.33, 127.36, 127.27, 122.99, 122.86, 71.03, 70.43, 66.24, 51.82, 51.58, 46.15, 45.76, 41.51, 41.38, 35.31, 35.20, 34.87, 34.39, 30.48, 28.55, 27.29, 26.20, 22.85, 22.63, 17.23, 12.38.

k. Synthesis of Compound 11

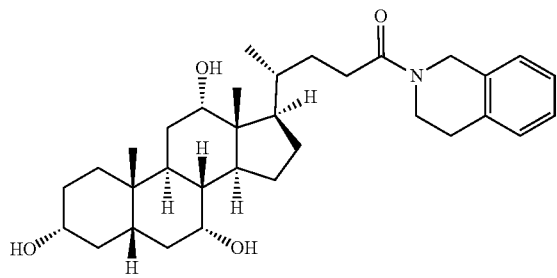

This compound was prepared using the general method described above. Cholic acid (824 mg, 2.01 mmol), HBTU (2.50 mmol), 1,2,3,4-tetrahydroisoquinoline (2.50 mmol), and NMM (5.46 mmol) were reacted to give the desired molecule in 91% yield (961 mg). mp. 225-228° C.; ¹H NMR (CDCl₃, 600 MHz): δ 7.20-7.12 (m, 4H), 4.72 (s, 1H), 4.63 (s, 1H), 3.98 (a, 1H), 3.84 and 3.82 (2 peaks, 2H), 3.68 (m, 1H), 3.45 (s, 1H), 2.91 (s, 1H), 2.84 (s, 1H), 2.48 and 2.46 (2 peaks, 1H), 2.36-2.30 (m, 1H), 2.26-2.00 (m, 4H), 1.95-1.59 (m, 11H), 1.53-1.25 (m, 8H), 1.11 (br, 1H), 1.03-0.95 (m, 4H), 0.88 (s, 3H), 0.69 and 0.67 (2 peaks, 3H); ¹H NMR (CD₃OD, 400 MHz): δ 7.16 (s, 4H), 4.70 and 4.66 (2 s, 2H), 3.94 (d, 1H, J=6.0 Hz), 3.77 (br s, 3H), 3.36 (s, 1H), 2.92 (s, 1H), 2.83 (s, 1H), 2.54 and 2.51 (2 peaks, 1H), 2.41 and 2.40 (2 peaks, 1H), 2.29 and 2.26 (2 peaks, 2H), 1.97-1.78 (m, 7H), 1.66-1.30 (m, 11H), 1.06-0.91 (m, 8H), 0.71 and 0.66 (2 peaks, 3H); ¹³C NMR (CDCl₃, 150 MHz): δ 172.90, 172.72, 135.13, 134.05, 133.59, 132.70, 128.94, 128.29, 126.88, 126.55, 126.47, 126.32, 126.05, 73.05, 71.88, 68.44, 47.49, 46.91, 46.45, 44.25, 43.34, 41.63, 41.48, 39.72, 39.46, 39.40, 35.72, 35.61, 35.26, 34.78, 34.71, 31.33, 31.18, 30.84, 30.71, 30.53, 29.60, 28.50, 28.20, 27.63, 26.60, 26.32, 23.30, 22.46, 17.64, 17.60, 12.51; ¹³C NMR (CD₃OD, 100 MHz): δ 175.34, 175.21, 136.15, 135.66, 134.49, 134.29, 129.79, 129.45, 128.05, 127.76, 127.62, 127.52, 127.22, 74.05, 72.91, 69.05, 47.94, 47.54, 47.52, 45.41, 44.84, 43.23, 43.03, 41.46, 41.06, 40.50, 37.04, 36.89, 36.53, 35.93, 35.90, 32.78, 31.61, 31.38, 31.22, 30.46, 29.61, 29.36, 28.79, 28.74, 27.91, 24.28, 23.21, 17.88, 13.03, 12.98.

l. Synthesis of Compound 12

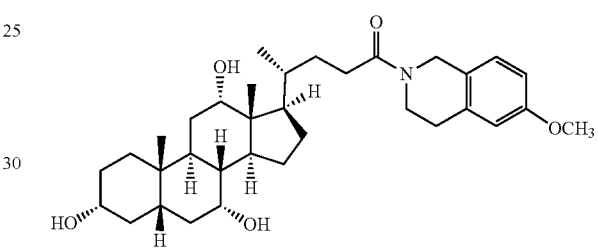

This compound was prepared using the general method described above. Cholic acid (208 mg, 0.50 mmol), HBTU (0.60 mmol), and 6-methoxy-1,2,3,4-tetrahydroisoquinoline (0.50 mmol), and NMM (2.27 mmol) were reacted to give the desired molecule. The product was further purified by column chromatography eluted from CH₂Cl₂-MeOH—NH₄OH (89:10:1) to furnish 12 in 78% yield (219 mg). mp. 164-166° C.; ¹H NMR (CD₃OD, 400 MHz): δ 6.95 (t, 1H, J=9.6 Hz), 6.65 (d, 1H, J=8.4 Hz), 6.62 (s, 1H), 4.49 (d, 2H, J=10.8 Hz), 3.83 (d, 1H, J=8 Hz), 3.67-3.61 (m, peak under solvent), 3.25-3.21 (m, 2H), 2.78 (br s, 1H), 2.69 (br s, 1H), 2.44-2.39 (m, 1H), 2.30-2.13 (m, 3H), 1.94-1.63 (m, 8H), 1.56-1.18 (m, 12H), 1.01-0.95 (m, 4H), 0.90-0.80 (m, 4H), 0.60 and 0.55 (2 peaks, 3H); ¹³C NMR (CD₃OD, 100 MHz): δ 175.43, 175.34, 160.26, 160.03, 137.55, 137.01, 128.64, 128.33, 126.64, 126.48, 114.56, 114.31, 113.93, 113.86, 74.17, 73.02, 69.19, 55.83, 48.05, 47.65, 45.04, 44.88, 43.34, 43.14, 41.54, 41.16, 40.61, 37.14, 36.99, 36.63, 36.04, 35.99, 32.90, 31.73, 31.51, 31.32, 30.81, 29.71, 28.89, 28.83, 28.02, 24.36, 23.29, 17.98, 13.12, 13.08.

m. Synthesis of Compound 13

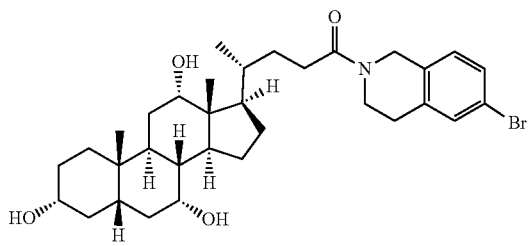

This compound was prepared using the general method described above. Cholic acid (206 mg, 0.50 mmol), HBTU (0.60 mmol), and 6-bromo-1,2,3,4-tetrahydroisoquinoline (0.50 mmol), and NMM (2.27 mmol) were reacted to give the desired molecule. The product was further purified by column chromatography eluted from CH$_2$Cl$_2$-MeOH—NH$_4$OH (89:10:1) to furnish 13 in 87% yield (265 mg). mp. 162-164° C.; $^1$H NMR (CD$_3$OD, 400 MHz): δ 7.24-7.21 (m, 2H), 6.98 (t, 1H, J=8.4 Hz), 4.56 (s, 1H), 4.52 (s, 1H), 3.84 (d, 1H, J=8.8 Hz), 3.68-3.62 (m, 3H), 3.21 (s, 1H), 2.81 (m, 1H), 2.72 (t, 1H, J=4.8 Hz), 2.46-2.40 (m, 1H), 2.34-2.23 (m, 1H), 2.19-2.13 (m, 2H), 1.94-1.63 (m, 7H), 1.56-1.18 (m, 11H), 1.01-0.93 (m, 4H), 0.90-0.80 (m, 4H), 0.60 and 0.55 (2 peaks, 3H); $^{13}$C NMR (CD$_3$OD, 100 MHz): δ 175.34, 175.21, 138.83, 138.31, 133.90, 133.70, 132.73, 132.40, 130.75, 130.63, 129.58, 129.27, 121.58, 121.26, 74.10, 72.96, 69.11, 49.98, 47.98, 47.59, 47.57, 45.03, 44.42, 43.28, 43.08, 43.07, 41.10, 41.02, 40.54, 37.10, 36.94, 36.61, 36.00, 32.79, 31.63, 31.39, 31.28, 30.30, 29.67, 29.23, 28.89, 28.83, 27.95, 24.38, 24.35, 23.32, 23.19, 17.97, 13.15, 13.09.

n. Synthesis of Compound 14

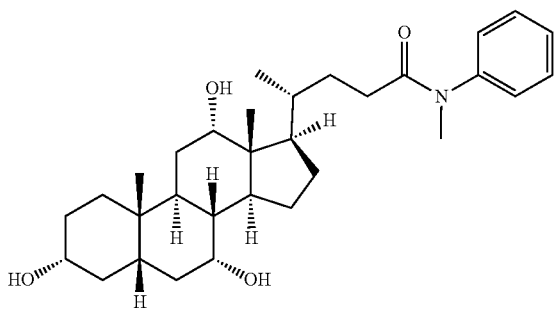

This compound was prepared using the general method described above. Cholic acid (1.022 g, 2.50 mmol), HBTU (3.0 mmol), N-methylaniline (2.96 mmol), and NMM (5.46 mmol) were reacted to give the desired molecule. The product was further purified by column chromatography eluted from CH$_2$Cl$_2$-MeOH (95:5; 90:10; 80:20; 70:30; and 50:50) to give 927 mg (75% yield). mp. 206-207° C.; $^1$H NMR (CDCl$_3$, 400 MHz): δ 7.42 (t, 2H, J=7.6 Hz), 7.33 (t, 1H, J=7.2 Hz), 7.18 (d, 2H, J=7.6 Hz), 3.90 (s, 1H), 3.83 (s, 1H), 3.46-3.41 (m, 1H), 3.25 (s, 3H), 2.23-2.14 (m, 3H), 2.02-1.91 (m, 7H), 1.85-1.74 (m, 5H), 1.64-1.60 (m, 3H), 1.51-1.46 (m, 2H), 1.39 and 1.36 (2 peaks, 2H), 1.26 (br, 3H), 1.13-1.05 (m, 1H), 1.00-0.93 (m, 1H), 0.87 (s, 3H), 0.77 (s, 3H), 0.63 (s, 3H); $^1$H NMR (CD$_3$OD, 400 MHz): δ 7.47 (t, 2H, J=7.2 Hz), 7.39 (t, 1H, J=7.2 Hz), 7.28 (d, 2H, J=7.6 Hz), 3.85 (s, H), 3.77 (d, 1H, J=2.4 Hz), 3.39-3.33 (m, 1H), 3.23 (s, 3H), 2.31-2.14 (m, 3H), 2.04-1.91 (m, 3H), 1.80-1.62 (m, 6H), 1.59-1.51 (m, 5H), 1.45-1.35 (m, 2H), 1.28-1.16 (m, 3H), 1.09-1.05 (m, 1H), 1.00-0.89 (m, 4H), 0.76 (d, 3H, J=5.2 Hz), 0.64 (s, 3H); $^{13}$C NMR (CDCl$_3$, 150 MHz): δ 173.92, 144.20, 129.71, 127.73, 127.28, 72.99, 71.87, 68.41, 47.16, 46.39, 41.55, 41.48, 39.45, 39.40, 37.38, 35.62, 35.27, 34.76, 34.67, 31.73, 31.50, 30.47, 28.12, 27.47, 26.29, 23.24, 22.46, 17.30, 12.47; $^{13}$C NMR (CD$_3$OD, 100 MHz): δ 176.27, 145.35, 131.02, 129.25, 128.46, 73.93, 72.89, 69.05, 47.84, 47.43, 42.21, 42.93, 41.01, 40.48, 37.84, 36.83, 36.51, 35.90, 35.88, 33.22, 32.04, 31.19, 29.57, 28.55, 27.86, 24.19, 23.17, 17.64, 12.95.

o. Synthesis of Compound 15

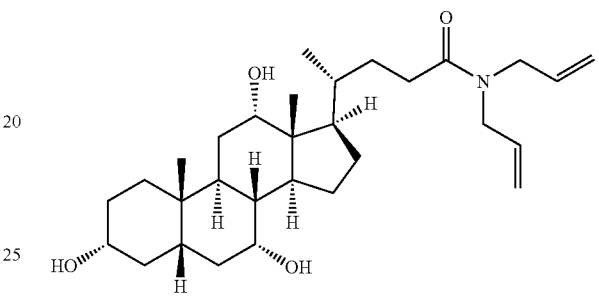

This compound was prepared using the general method described above. Cholic acid (819 mg, 2.0 mmol) HBTU (2.50 mmol), diallyl amine (2.40 mmol), and NMM (5.46 mmol) were reacted to give the desired molecule in 86% yield (843 mg). mp. 171-173° C.; $^1$H NMR (CDCl$_3$, 400 MHz): δ 5.81-5.71 (m, 2H), 5.22-5.09 (m, 4H), 4.05-3.85 (m, 6H), 3.48-3.43 (m, 1H), 2.41-2.34 (m, 1H), 2.28-2.16 (m, 3H), 1.98-1.58 (m, 13H), 1.51-1.30 (m, 8H), 1.19-1.11 (m, 1H), 1.02-0.95 (m, 4H), 0.89 (s, 3H), 0.69 (s, 3H); $^1$H NMR (CD$_3$OD, 400 MHz): δ 5.87-5.72 (m, 2H), 5.24-5.11 (m, 4H), 3.97 and 3.94 (2 peaks, 5H), 3.79 (d, 1H, J=2.4 Hz), 3.39-3.35 (m, 1H), 2.46-2.39 (m, 1H), 2.33-2.22 (m, 3H), 2.03-1.73 (m, 7H), 1.66-1.51 (m, 6H), 1.47-1.29 (m, 5H), 1.17-1.06 (m, 1H), 1.03-0.91 (m, 7H), 0.71 (s, 3H); $^{13}$C NMR (CDCl$_3$, 150 MHz): δ 173.83, 133.36, 132.97, 117.08, 116.62, 73.04, 71.86, 68.42, 49.22, 47.78, 47.06, 46.40, 41.52, 41.50, 39.44, 39.27, 35.71, 35.29, 34.80, 34.73, 31.46, 30.46, 30.24, 27.59, 26.23, 23.28, 22.43, 17.55, 12.49; $^{13}$C NMR (CD$_3$OD, 150 MHz): δ 176.27, 134.45, 134.21, 117.51, 116.97, 73.95, 72.83, 68.97, 50.78, 49.18, 47.45, 43.16, 42.94, 40.99, 40.41, 36.87, 36.49, 35.87, 35.84, 32.85, 31.15, 30.78, 29.56, 28.70, 27.82, 24.22, 23.20, 17.84, 13.01

3. Bicyclic Quinazolin Analogs of Cholic Acid

Example compounds 29-39 and 41 were synthesized using Scheme 8. The intermediate compounds 16-28, and 40 formed during the synthetic route are also described Some of the substituted 2-aminobenzaldehydes as 2-amino-6-fluorobenzaldehyde, 2-amino-4-chlorobenzaldehyde, 2-amino-4-methoxybenzaldehyde, 2-amino-3-fluorobenzaldehyde, 2-amino-4,5-methoxy-benzaldehyde, and 2-amino-4,5-difluorobenzaldehyde were synthesized from corresponding substituted 2-aminobenzoic acids by following reported procedure (Ida, Y.; Matsubara, A.; Nemoto, T.; Saito, M.; Hirayama, S.; Fujii, H.; and Nagase, H. *Bioorg. Med. Chem.*, 2012, 20, 5810-5831).

SCHEME 8.
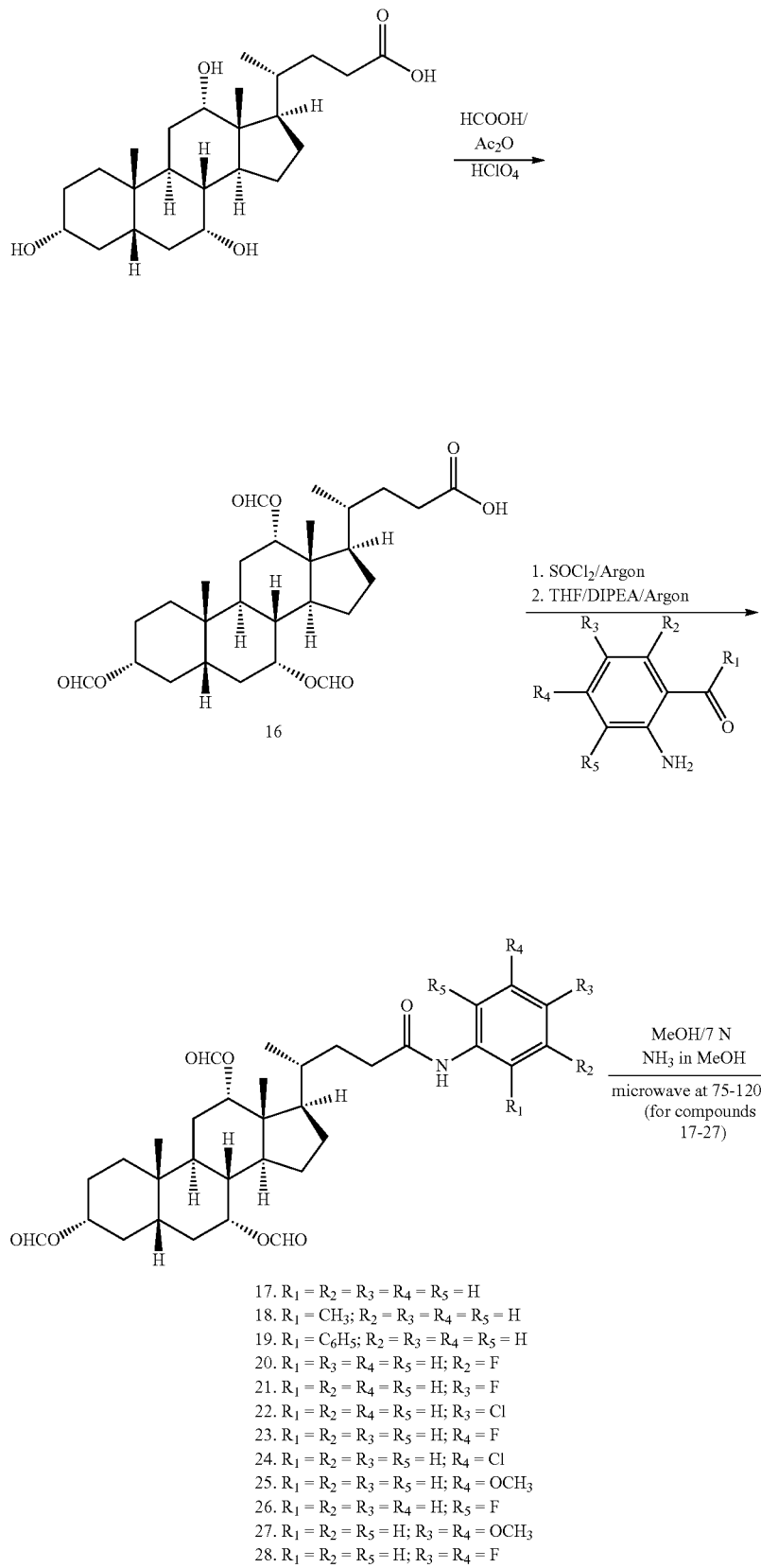
17. $R_1 = R_2 = R_3 = R_4 = R_5 = H$
18. $R_1 = CH_3; R_2 = R_3 = R_4 = R_5 = H$
19. $R_1 = C_6H_5; R_2 = R_3 = R_4 = R_5 = H$
20. $R_1 = R_3 = R_4 = R_5 = H; R_2 = F$
21. $R_1 = R_2 = R_4 = R_5 = H; R_3 = F$
22. $R_1 = R_2 = R_4 = R_5 = H; R_3 = Cl$
23. $R_1 = R_2 = R_3 = R_5 = H; R_4 = F$
24. $R_1 = R_2 = R_3 = R_5 = H; R_4 = Cl$
25. $R_1 = R_2 = R_3 = R_5 = H; R_4 = OCH_3$
26. $R_1 = R_2 = R_3 = R_4 = H; R_5 = F$
27. $R_1 = R_2 = R_5 = H; R_3 = R_4 = OCH_3$
28. $R_1 = R_2 = R_5 = H; R_3 = R_4 = F$ -continued
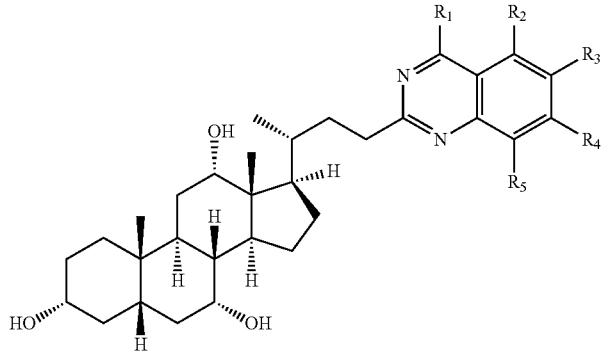
29. $R_1 = R_2 = R_3 = R_4 = R_5 = H$
30. $R_1 = CH_3$; $R_2 = R_3 = R_4 = R_5 = H$
31. $R_1 = C_6H_5$; $R_2 = R_3 = R_4 = R_5 = H$
32. $R_1 = R_3 = R_4 = R_5 = H$; $R_2 = F$
33. $R_1 = R_2 = R_4 = R_5 = H$; $R_3 = F$
34. $R_1 = R_2 = R_4 = R_5 = H$; $R_3 = Cl$
35. $R_1 = R_2 = R_3 = R_5 = H$; $R_4 = F$
36. $R_1 = R_2 = R_3 = R_5 = H$; $R_4 = Cl$
37. $R_1 = R_2 = R_3 = R_5 = H$; $R_4 = OCH_3$
38. $R_1 = R_2 = R_3 = R_4 = H$; $R_5 = F$
39. $R_1 = R_2 = R_5 = H$; $R_3 = R_4 = OCH_3$
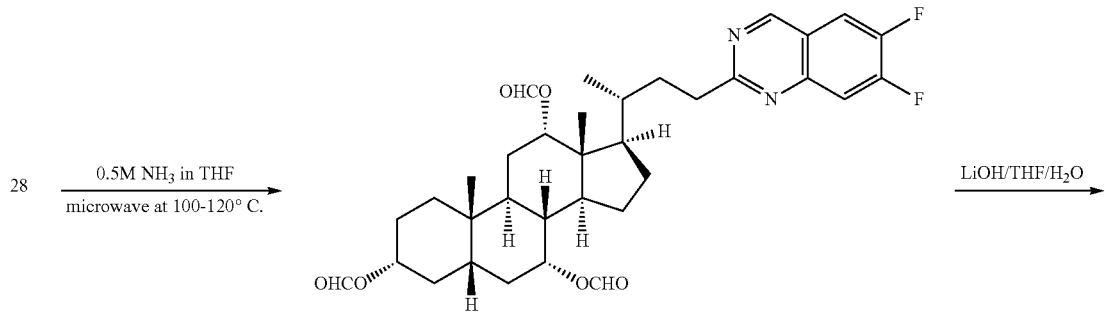
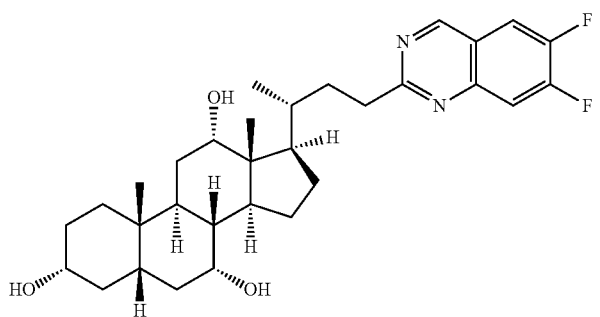

A. Synthesis of Compound 16

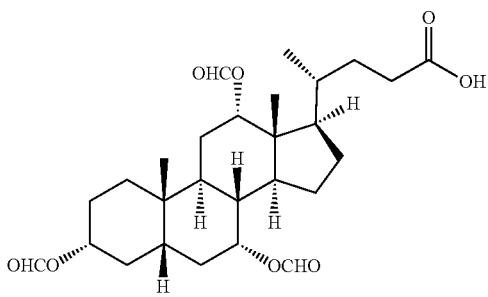

This compound was prepared by following previously reported procedure (Schteingart, C. D.; and Hofmann, A. F. *J. Lipid Res.* 1988, 29, 1387-1395; Coleman, J. P.; Kirby, L. C.; and Klein, R. A. *J. Lipid Res.* 1995, 36, 901-910).

b. Synthesis of Compound 17

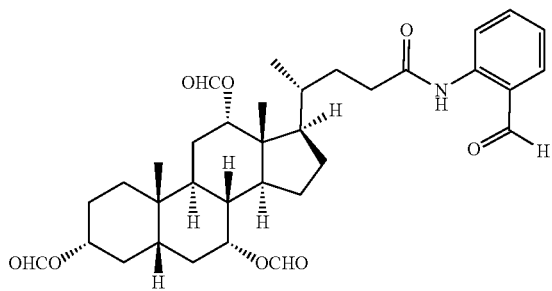

In a 250 mL round bottom flask containing compound 16 (2.955 g, 6.0 mmol) was placed in ice bath added into it $SOCl_2$, (7 mL) stirred for 10 min. The reaction flask was brought to room temperature and was stirred further under argon environment. After the completion of reaction (confirmed by $^1H$ NMR), $SOCl_2$ was removed on rotavapor, and the product was finally dried (placing the flask in hot water at 50-55° C.) on high vacuum. The crude product so obtained was used in the next step without further purification. The crude product was dissolved in anhydrous THF (20 mL) and a solution of 2-aminobenzaldehyde (801 mg, 6.61 mmol) in THE (8.0 mL), and DIPEA (1.70 g, 13.15 mmol) were added simultaneously under cold condition and reaction flask was protected with argon atmosphere. The formation of product was monitored by TLC and $^1H$-NMR, and after 18 h of the reaction, it indicates the presence of some starting materials, it was further allowed to stir and react at room temperature. After the reaction, the solvent was removed using rotavapor and the product so obtained was dried on vacuum to give a brownish solid which was subjected to repeated column chromatography over silica gel eluted with a mixture of n-hexane-AcOEt (3:1; 2:1; 1:1 and 1:2) followed by 100% AcOEt to yield 17 in 1.689 g (47% yield). mp. 92-94° C.; $^1H$ NMR (CDCl$_3$, 600 MHz): δ 11.13 (s, 1H), 9.92 (s, 1H), 8.74 (d, 1H, J=8.4 Hz), 8.17 (s, 1H), 8.11 (s, 1H), 8.02 (s, 1H), 7.67 (d, 1H, J=7.2 Hz), 7.61 (t, 1H, J=7.8 Hz), 7.22 (t, 1H, J=7.2 Hz), 5.28 (s, 1H), 5.07 (s, 1H), 4.74-4.70 (m, 1H), 2.52-2.47 (m, 1H), 2.37-2.31 (m, 1H), 2.17-2.10 (m, 2H), 2.03-1.98 (m, 1H), 1.96-1.90 (m, 3H), 1.81-1.78 (m, 4H), 1.74-1.65 (m, 5H), 1.59-1.52 (m, 2H), 1.47-1.39 (m, 3H), 1.37-1.24 (m, 2H), 1.15-1.06 (m, 2H), 0.94 (s, 3H), 0.90 (d, 3H, J=6.6 Hz), 0.77 (s, 3H); $^{13}C$ NMR (CDCl$_3$, 150 MHz): δ 195.63, 172.91, 160.59, 160.54, 140.98, 136.24, 136.07, 122.78, 121.48, 119.82, 75.26, 73.73, 70.64, 47.25, 45.01, 42.94, 40.78, 37.70, 35.17, 34.79, 34.49, 34.41, 34.26, 31.30, 31.03, 28.53, 27.16, 26.55, 25.51, 22.78, 22.32, 17.59, 12.17.

c. Synthesis of Compound 18

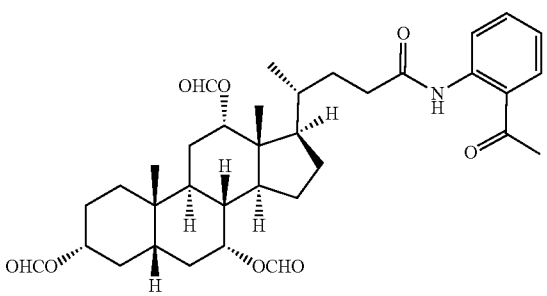

This compound was prepared using the method described above for 17. Compound 16 (616 mg, 1.25 mmol), $SOCl_2$ (1.0 mL), 2-aminoacetophenone (203 mg, 1.50 mmol) and DIPEA (0.40 mL) were reacted in a similar manner. The product was purified by repeated column chromatography over silica gel eluted with a mixture of n-hexane-AcOEt (2:1; 1:1 and 1:2) followed by 100% AcOEt to give 18 in 40% yield (308 mg). mp. 83-85° C. (softening) 93-95° C.; $^1H$ NMR (CDCl$_3$, 400 MHz): δ 11.70 (s, 1H), 8.75 (s, 1H), 8.18 (s, 1H), 8.11 (s, 1H), 8.02 (s, 1H), 7.90 (s, 2H), 7.54 (br, 1H), 7.11 (br, 1H), 5.28 (s, 1H), 5.07 (s, 1H), 4.72 (br s, 1H), 2.67 (s, 3H), 2.47 (br, 1H), 2.33 (br, 1H), 2.15-2.10 (m, 2H), 2.01-1.90 (m, 4H), 1.81-1.60 (m, 8H), 1.47 (br, 3H), 1.38 and 1.35 (2 peaks, 2H), 1.25 (s, 1H), 1.13-1.05 (m, 2H), 0.95 (s, 3H), 0.90 (s, 3H), 0.77 (s, 3H); $^{13}C$ NMR (CDCl$_3$, 100 MHz): δ 202.89, 172.78, 160.58, 160.53, 141.13, 135.19, 131.64, 122.21, 121.67, 120.74, 75.31, 73.76, 70.68, 47.27, 45.05, 42.97, 40.83, 37.76, 35.40, 34.83, 34.54, 34.47, 34.30, 31.35, 31.16, 28.60, 28.57, 27.18, 26.60, 25.55, 22.81, 22.35, 17.62, 12.19.

d. Synthesis of Compound 19

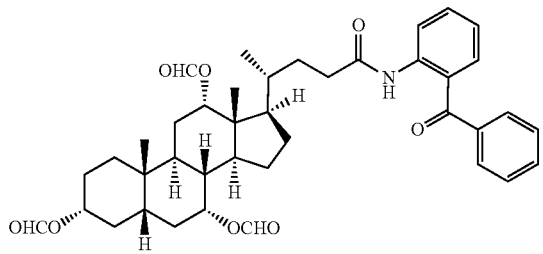

This compound was prepared using the method described above for 17. Compound 16 (616 mg, 1.25 mmol), $SOCl_2$ (1.0 mL), 2-aminobenzophenone (296 mg, 1.50 mmol) and DIPEA (0.40 mL) were reacted in a similar manner. The product was purified by repeated column chromatography over silica gel eluted with a mixture of n-hexane-AcOEt (2:1; 1:1 and 1:2) followed by 100% AcOEt to give 19 in 34% yield (288 mg). mp. 79-82° C. (softening) 95-96° C.; $^1H$ NMR (CDCl$_3$, 400 MHz): δ 10.85 (s, 1H), 8.64 (d, 1H, J=8.0 Hz), 8.16 (s, 1H), 8.10 (s, 1H), 8.02 (s, 1H), 7.69 (d, 2H, J=7.6 Hz), 7.62-7.55 (m, 3H), 7.49 (t, 1H, J=7.6 Hz), 7.07 (t, 1H, J=7.6 Hz), 5.26 (s, 1H), 5.06 (s, 1H), 4.74-4.69 (m, 1H), 2.51-2.44 (m, 1H), 2.36-2.28 (m, 1H), 2.18-2.07 (m, 2H), 2.01-1.88 (m, 4H), 1.81-1.59 (m, 8H), 1.52-1.31 (m, 6H), 1.12-1.05 (m, 2H), 0.94 (s, 3H), 0.89 (d, 3H, J=6.0

Hz), 0.75 (s, 3H); $^{13}$C NMR (CDCl$_3$, 100 MHz): δ 199.86, 172.45, 160.57, 160.52, 140.67, 138.73, 134.36, 133.66, 132.48, 129.85, 128.35, 123.10, 121.95, 121.48, 75.30, 73.76, 70.67, 47.23, 45.03, 42.96, 40.84, 37.76, 35.07, 34.81, 34.54, 34.47, 34.30, 31.35, 31.11, 28.56, 27.19, 26.60, 25.53, 22.79, 22.35, 17.62, 12.16.

e. Synthesis of Compound 20

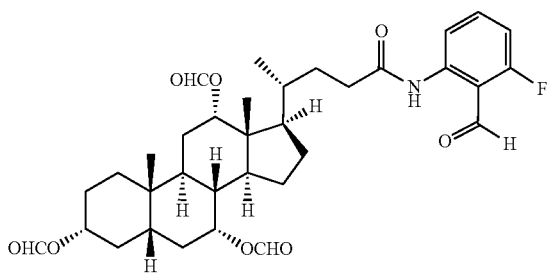

This compound was prepared using the method described above for 17. Compound 16 (616 mg, 1.25 mmol), SOCl$_2$ (1.25 mL), 2-amino-6-fluorobenzaldehyde (320 mg, 2.30 mmol) and DIPEA (0.60 mL) were reacted in a similar manner. The product was purified by repeated column chromatography over silica gel eluted with a mixture of n-hexane-AcOEt (3:1; 2:1; 1:1 and 1:2) to give 20 in 32% yield (246 mg). mp. 92-96° C.; $^1$H NMR (CDCl$_3$, 400 MHz): δ 11.34 (s, 1H), 10.38 (s, 1H), 8.52 (d, 1H, J=8.8 Hz), 8.18 (s, 1H), 8.11 (s, 1H), 8.02 (s, 1H), 7.59-7.53 (m, 1H), 6.85-6.80 (m, 1H), 5.28 (s, 1H), 5.08 (d, 1H, J=2.0 Hz), 4.75-4.69 (m, 1H), 2.52-2.46 (m, 1H), 2.38-2.30 (m, 1H), 2.19-2.09 (m, 2H), 2.02-1.88 (m, 4H), 1.82 (br s, 1H), 1.78 (br s, 1H), 1.76-1.60 (m, 6H), 1.56-1.43 (m, 4H), 1.41-1.32 (m, 2H), 1.18-1.06 (m, 2H), 0.95 (s, 3H), 0.91 (d, 3H, J=6.4 Hz), 0.77 (s, 3H); $^{13}$C NMR (CDCl$_3$, 100 MHz): δ 190.95, 190.82, 172.98, 167.32, 164.75, 160.57, 160.32, 142.23, 138.26, 138.14, 115.70, 115.66, 110.54, 110.46, 109.40, 109.19, 75.29, 73.75, 70.67, 47.29, 45.07, 42.99, 40.84, 37.77, 35.27, 34.82, 34.54, 34.47, 34.31, 31.35, 31.00, 28.58, 27.18, 26.60, 25.56, 22.81, 22.35, 17.62, 12.19.

f. Synthesis of Compound 21

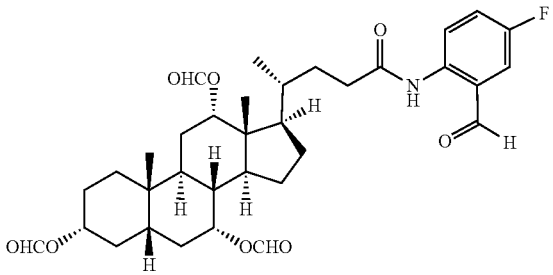

This compound was prepared using the method described above for 17. Compound 16 (616 mg, 1.25 mmol), SOCl$_2$ (1.0 mL), 2-amino-5-fluorobenzaldehyde (348 mg, 2.50 mmol) and DIPEA (0.40 mL) were reacted in a similar manner. The product was purified by repeated column chromatography over silica gel eluted with a mixture of n-hexane-AcOEt (2:1; 1:1 and 1:2) followed by 100% AcOEt to give 21 in 31% yield (241 mg). mp. 91-93° C.; $^1$H NMR (CDCl$_3$, 400 MHz): δ 10.95 (s, 1H), 9.87 (s, 1H), 8.77 (br, 1H), 8.18 (s, 1H), 8.11 (s, 1H), 8.02 (s, 1H), 7.36-7.27 (m, 2H), 5.28 (s, 1H), 5.08 (s, 1H), 4.72 (br s, 1H), 2.48 (br s, 1H), 2.34 (br s, 1H), 2.13 (br, 2H), 2.00-1.94 (br, 4H), 1.85-1.61 (m, 8H), 1.53-1.30 (m, 6H), 1.19-1.04 (m, 2H), 0.95 and 0.91 (2 peaks, 6H), 0.77 (s, 3H); $^{13}$C NMR (CDCl$_3$, 100 MHz): δ 194.28, 194.26, 172.69, 160.57, 160.52, 158.88, 156.45, 137.41, 137.39, 123.41, 123.19, 122.38, 122.33, 122.07, 122.00, 121.12, 120.90, 75.29, 73.75, 70.67, 47.30, 45.07, 42.99, 40.84, 37.77, 35.12, 34.83, 34.55, 34.48, 34.31, 31.36, 31.06, 28.58, 27.19, 26.60, 25.57, 22.81, 22.35, 17.63, 12.19.

g. Synthesis of Compound 22

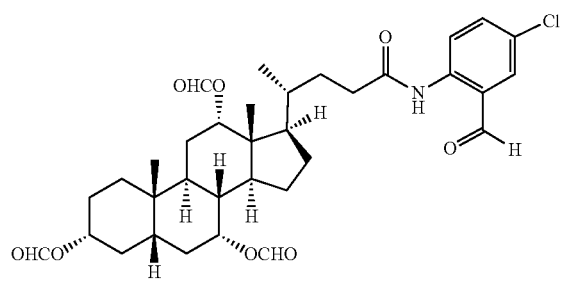

This compound was prepared using the method described above for 17. Compound 16 (616 mg, 1.25 mmol), SOCl$_2$ (1.25 mL), 2-amino-5-chlorobenzaldehyde (292 mg, 1.88 mmol) and DIPEA (0.60 mL) were reacted in a similar manner. The product was purified by column chromatography over silica gel eluted with a mixture of n-hexane-AcOEt (3:1; 2:1; 1:1 and 1:2) to give 22 in 34% yield (266 mg). mp. 104-106° C.; $^1$H NMR (CDCl$_3$, 400 MHz): δ 11.01 (s, 1H), 9.87 (s, 1H), 8.73 (d, 1H, J=9.2 Hz), 8.18 (s, 1H), 8.11 (s, 1H), 8.02 (s, 1H), 7.63 (s, 1H), 7.55 (d, 1H, J=9.2 Hz), 5.28 (s, 1H), 5.08 (s, 1H), 4.72 (t, 1H, J=4.4 Hz), 2.54-2.46 (m, 1H), 2.37-2.31 (m, 1H), 2.19-2.09 (m, 2H), 2.01-1.87 (m, 3H), 1.82 (br s, 1H), 1.78 (br s, 1H), 1.75-1.61 (m, 6H), 1.53-1.46 (m, 4H), 1.42-1.31 (m, 2H), 1.18-1.06 (m, 2H), 0.95 (s, 3H), 0.90 (d, 3H, J=5.6 Hz), 0.77 (s, 3H); $^{13}$C NMR (CDCl$_3$, 100 MHz): δ 194.39, 172.83, 160.57, 160.52, 139.53, 136.04, 135.02, 127.84, 122.52, 121.58, 75.29, 73.76, 70.68, 47.31, 45.08, 43.00, 40.84, 37.78, 35.8, 34.83, 34.55, 34.48, 34.32, 31.37, 31.00, 28.59, 27.20, 26.61, 25.57, 22.82, 22.36, 17.63, 12.21.

h. Synthesis of Compound 23

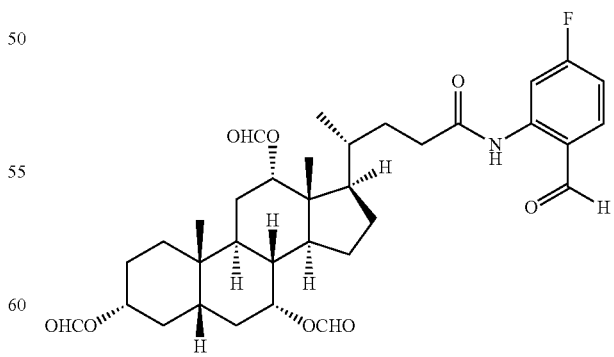

This compound was prepared using the method described above for 17. Compound 16 (616 mg, 1.25 mmol), SOCl$_2$ (1.25 mL), 2-amino-4-fluorobenzaldehyde (223 mg, 1.60 mmol), and DIPEA (0.60 mL) were reacted in a similar manner. The product was purified by repeated column chromatography over silica gel eluted with a mixture of n-hexane-AcOEt (2:1; 1:1 and 1:2) followed by 100% AcOEt to give 23 in 28% yield (218 mg). mp. 96-98° C. (softening) 117-110° C.; $^1$H NMR (CDCl$_3$, 400 MHz): δ 11.31 (s, 1H), 9.86 (s, 1H), 8.53 (dd, 1H, J=12.0 and 2.4 Hz), 8.18 (s, 1H), 8.11 (s, 1H), 8.02 (s, 1H), 7.66 (dd, 1H, J=8.4 and 6.0 Hz), 6.92-6.87 (m, 1H), 5.28 (s, 1H), 5.08 (d, 1H, J=2.4 Hz), 4.75-4.69 (m, 1H), 2.50-2.46 (m, 1H), 2.38-2.30 (m, 1H), 2.19-2.11 (m, 2H), 2.02-1.88 (m, 4H), 1.83-1.56 (m, 10H), 1.52-1.31 (m, 7H), 1.18-1.05 (m, 2H), 0.95 (s, 3H), 0.90 (d, 3H, J=6.4 Hz), 0.77 (s, 3H); $^{13}$C NMR (CDCl$_3$, 100 MHz): δ 194.07, 173.06, 168.64, 166.08, 160.56, 160.51, 143.42, 143.29, 138.58, 138.46, 118.42, 118.40, 110.39, 110.16, 107.48, 107.20, 75.27, 73.74, 70.66, 47.28, 45.06, 42.97, 40.82, 37.75, 35.15, 34.79, 34.53, 34.46, 34.29, 31.34, 30.92, 28.56, 27.17, 26.59, 25.55, 22.79, 22.34, 17.60, 12.18.

i. Synthesis of Compound 24

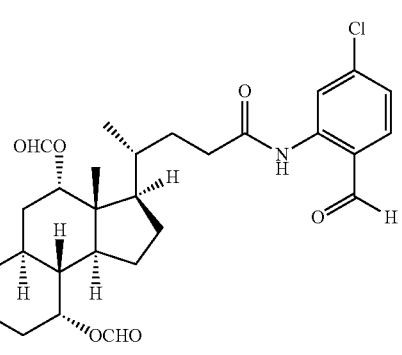

This compound was prepared using the method described above for 17. Compound 16 (616 mg, 1.25 mmol), SOCl$_2$ (1.25 mL), 2-amino-4-chlorobenzaldehyde (293 mg, 1.88 mmol) and DIPEA (0.60 mL) were reacted in a similar manner. The product was purified by column chromatography over silica gel eluted with a mixture of n-hexane-AcOEt (3:1; 2:1; 1:1 and 1:2) to give 24 in 19% yield (148 mg). mp. 107-108° C.; $^1$H NMR (CDCl$_3$, 400 MHz): δ 11.18 (s, 1H), 9.88 (s, 1H), 8.83 (s, 1H), 8.18 (s, 1H), 8.11 (s, 1H), 8.02 (s, 1H), 7.59 (d, 1H, J=8.4 Hz), 7.19 (d, 1H, J=8.0 Hz), 5.28 (s, 1H), 5.08 (s, 1H), 4.75-4.69 (m, 1H), 2.53-2.46 (m, 1H), 2.38-2.30 (m, 1H), 2.19-2.10 (m, 2H), 2.00-1.88 (m, 4H), 1.82 (s, 1H), 1.78 (s, 1H), 1.75-1.61 (m, 6H), 1.54-1.32 (m, 6H), 1.18-1.06 (m, 2H), 0.95 (s, 3H), 0.90 (d, 3H, J=6.0 Hz), 0.77 (s, 3H); $^{13}$C NMR (CDCl$_3$, 100 MHz): δ 194.45, 172.96, 160.58, 160.53, 143.06, 141.79, 136.92, 123.15, 120.02, 119.86, 75.30, 73.76, 70.68, 47.33, 45.08, 43.00, 40.85, 37.78, 35.16, 34.81, 34.55, 34.48, 34.32, 31.36, 30.95, 28.59, 27.19, 26.61, 25.57, 22.82, 22.36, 17.62, 12.21.

j. Synthesis of Compound 25

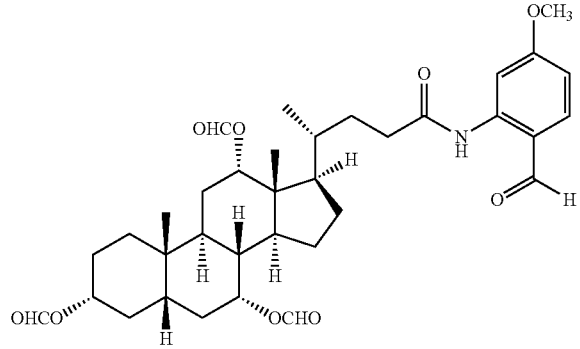

This compound was prepared using the method described above for 17. Compound 16 (616 mg, 1.25 mmol), SOCl$_2$ (1.25 mL), 2-amino-4-methoxybenzaldehyde (303 mg, 2.00 mmol) and DIPEA (0.60 mL) were reacted in a similar manner. The product was purified by repeated column chromatography over silica gel eluted with a mixture of n-hexane-AcOEt (3:1; 2:1; 1:1 and 1:2) to give 25 in 46% yield (359 mg). mp. 87-90° C.; $^1$H NMR (CDCl$_3$, 400 MHz): δ 11.41 (s, 1H), 9.74 (s, 1H), 8.36 (s, 1H), 8.18 (s, 1H), 8.11 (s, 1H), 8.03 (s, 1H), 7.54 (d, 1H, J=8.8 Hz), 6.70 (d, 1H, J=8.8 Hz), 5.28 (s, 1H), 5.07 (s, 1H), 4.71 (t, 1H, J=10.8 Hz), 2.53-2.47 (m, 1H), 2.38-2.30 (m, 1H), 2.19-2.08 (m, 2H), 2.01-1.87 (m, 4H), 1.81 (s, 1H), 1.78 (s, 1H), 1.74-1.61 (m, 5H), 1.54-1.46 (m, 4H), 1.41-1.32 (m, 3H), 1.17-1.06 (m, 2H), 0.95-0.85 (m, 6H), 0.90 (d, 3H), 0.77 (s, 3H); $^{13}$C NMR (CDCl$_3$, 100 MHz): δ 193.58, 173.28, 166.03, 160.60, 160.55, 160.54, 143.54, 137.93, 115.66, 110.24, 103.64, 75.31, 73.77, 70.68, 55.80, 47.28, 45.07, 42.99, 40.85, 37.78, 34.84, 34.55, 34.48, 34.31, 31.36, 31.01, 28.59, 27.19, 26.61, 25.57, 22.82, 22.36, 17.65, 12.21.

k. Synthesis of Compound 26

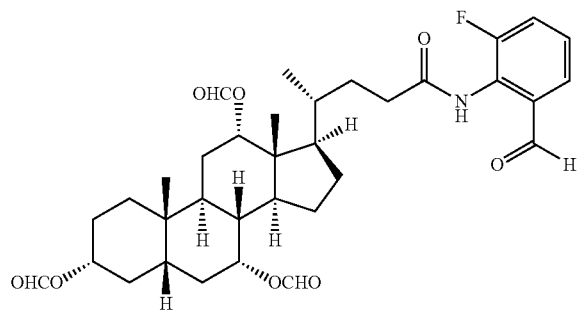

This compound was prepared using the method described above for 17. Compound 16 (1.25 mmol), SOCl$_2$ (1.20 mL), 2-amino-3-fluorobenzaldehyde (2.17 mmol), and DIPEA (0.60 mL) were reacted in a similar manner. The crude product so obtained was subjected to multiple column chromatography purification over silica gel eluted with n-hexane-AcOEt (4:1; 2:1; 1:1; and 1:2) to give a mixture of products 178 mg (26 and 16 in ca. 1:1.25 ratio). This mixture of products was used in the next cyclization step without further purification.

l. Synthesis of Compound 27

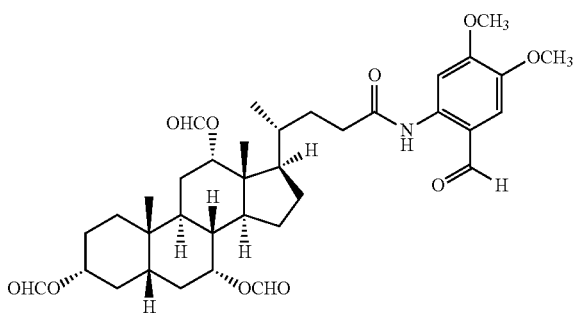

This compound was prepared using the method described above for 17. Compound 16 (616 mg, 1.25 mmol), SOCl$_2$ (1.10 mL), 2-amino-4,5-dimethoxylbenzaldehyde (317 mg, 1.75 mmol), and DIPEA (0.60 mL) were reacted in a similar manner. The product was purified by repeated column chromatography over silica gel eluted with a mixture of n-hexane-AcOEt (2:1; 1:1 and 1:2) followed by 100% AcOEt to give 27 in 41% yield (334 mg). mp. 100-102° C.; $^1$H NMR (CDCl$_3$, 400 MHz): δ 11.34 (s, 1H), 9.76 (s, 1H), 8.49 (s, 1H), 8.18 (s, 1H), 8.11 (s, 1H), 8.02 (s, 1H), 7.04 (d, 1H), 5.28 (s, 1H), 5.07 (d, 1H, J=2.4 Hz), 4.75-4.69 (m, 1H), 3.99 (s, 3H), 3.92 (s, 3H), 2.53-2.45 (m, 1H), 2.37-2.29 (m, 1H), 2.16-2.10 (m, 2H), 2.01-1.87 (m, 4H), 1.82-1.61 (m, 9H), 1.54-1.32 (m, 8H), 1.14-1.05 (m, 2H), 0.95 (s, 3H), 0.90 (d, 3H, J=6.0 Hz), 0.77 (s, 3H); $^{13}$C NMR (CDCl$_3$, 100 MHz): δ 193.28, 173.04, 160.58, 160.54, 155.67, 144.543, 137.76, 116.50, 114.44, 103.03, 75.31, 73.76, 70.67, 56.44, 56.29, 47.27, 45.07, 43.00, 40.85, 37.78, 35.21, 34.85, 34.56, 34.49, 34.32, 31.37, 31.05, 28.59, 27.20, 26.61, 25.57, 22.82, 22.36, 17.67, 12.22.

m. Synthesis of Compound 28

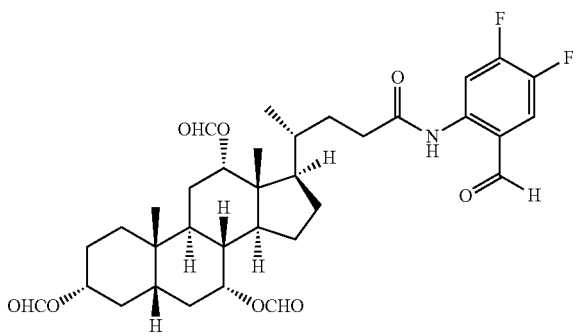

This compound was prepared using the method described above for 17. Compound 16 (616 mg, 1.25 mmol), SOCl$_2$ (1.25 mL), 2-amino-4,5-difluorobenzaldehyde (315 mg, 2.00 mmol), and DIPEA (0.60 mL) were reacted in a similar manner. The product was purified by repeated column chromatography over silica gel eluted with a mixture of n-hexane-AcOEt (3:1; 2:1; 1:1 and 1:2) to give 28 in 37% yield (295 mg). mp. 94-97° C.; $^1$H NMR (CDCl$_3$, 400 MHz): δ 11.15 (s, 1H), 9.80 (s, 1H), 8.72 (dd, 1H, J=13.2 and 7.2 Hz), 8.18 (s, 1H), 8.11 (s, 1H), 8.02 (s, 1H), 7.47 (t, 1H, J=9.2 Hz), 5.28 (s, 1H), 5.08 (s, 1H), 4.76-4.68 (m, 1H), 2.53-2.45 (m, 1H), 2.37-2.29 (m, 1H), 2.19-2.10 (m, 2H), 2.02-1.89 (m, 4H), 1.82 (br s, 1H), 1.78 (br s, 1H), 1.75-1.57 (m, 6H), 1.52-1.32 (m, 6H), 1.15-1.06 (m, 2H), 0.95 (s, 3H), 0.90 (d, 3H, J=6.0 Hz), 0.77 (s, 3H); $^{13}$C NMR (CDCl$_3$, 400 MHz): δ 193.10, 172.91, 160.61, 160.55, 156.40, 156.27, 153.83, 153.70, 146.85, 146.71, 144.38, 144.25, 138.82, 138.80, 138.71, 138.68, 123.42, 123.39, 123.25, 123.21, 118.05, 118.02, 117.99, 109.81, 109.57, 75.29, 73.77, 70.69, 47.29, 45.08, 42.99, 40.83, 37.76, 35.09, 34.80, 34.54, 34.47, 34.31, 31.36, 30.92, 28.58, 27.19, 26.60, 25.57, 22.81, 22.34, 17.61, 12.19.

n. Synthesis of Compound 29

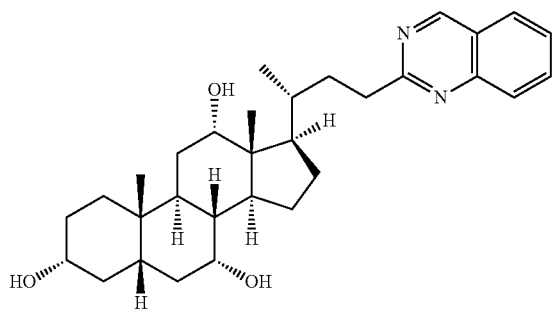

Compound 17 (120 mg, 0.20 mmol) was dissolved in 7N NH$_3$ in MeOH (5 mL) using sonication. The solution was transferred into microwave vial, sealed it, and heated to 75° C. for 30 min under microwave irradiations keeping the absorption level at high (repeated three times). An additional amount of 7N NH$_3$ in MeCOH (3 mL) was added again into above reaction solution, and then subjected it further to microwave heating under the same conditions (repeated three times). The formation of the product was monitored by TLC and $^1$H-NMR. After completion of the reaction, the solution was transferred into round bottom flask, and MeOH was removed using rotavapor to give a solid. The product was dried on high vacuum by placing the flask in hot water (50-60° C.) until all formamide (a byproduct formed during the reaction by cleavage of protecting hydroxyl functionality) disappeared, and thus furnished product 29 in 94% yield (93 mg). mp. 69-71° C. (softening), 83-85° C.; $^1$H NMR (CDCl$_3$, 400 MHz): δ 9.34 (s, 1H), 7.98 (d, 1H, J=8.8 Hz), 7.90-7.86 (m, 2H), 7.59 (t, 1H, J=8.0 Hz), 4.02 (s, 1H), 3.84 (d, 1H, J=2.4 Hz), 3.46-3.41 (m, 1H), 3.25-3.17 (m, 1H), 3.06-2.98 (m, 1H), 2.29-2.18 (m, 3H), 2.11-2.03 (m, 2H), 1.99-1.84 (m, 4H), 1.80-1.49 (m, 11H), 1.46-1.26 (m, 3H), 1.17-1.06 (m, 4H), 1.01-0.94 (m, 1H), 0.89 (s, 3H), 0.69 (s, 3H); $^{13}$C NMR (CDCl$_3$, 100 MHz): δ 168.38, 160.40, 150.38, 134.03, 127.85, 127.11, 126.92, 123.05, 73.02, 71.98, 68.39, 47.29, 46.60, 41.92, 41.53, 39.74, 39.65, 36.90, 35.79, 35.28, 35.12, 34.72, 34.58, 30.57, 28.23, 27.56, 26.65, 23.23, 22.54, 17.80, 12.59; HRMS (ESI, m/z): calcd. for C$_{31}$H$_{44}$N$_2$O$_3$ [M+H]$^+$ 493.3425 found 493.3431.

o. Synthesis of Compound 30

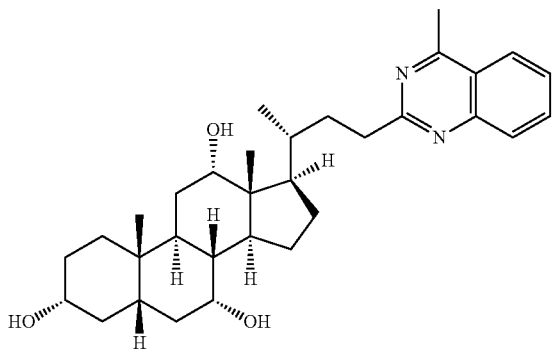

This compound was prepared using the method described above for 29. Compound 18 (123 mg, 0.20 mmol) was dissolved and 7N NH₃ in MeOH (10 mL) by sonication and heated to 75° C. for 30 min under microwave irradiation keeping the absorption level at high (repeated 4 times), followed by at 100° C. (repeated 7 times). The product was purified by stirring with n-hexane, insoluble material was collected and dried on high vacuum to give 30 in 81% yield (83 mg). mp. 110-112° C.; ¹H NMR (CDCl₃, 400 MHz): δ 8.05 (d, 1H, J=8.4 Hz), 7.95 (d, 1H, J=8.4 Hz), 7.83 (t, 1H, J=8.0 Hz), 7.55 (t, 1H, J=7.2 Hz), 4.02 (s, 1H), 3.85 (s, 1H), 3.48-3.43 (m, 1H), 3.19-3.11 (m, 1H), 2.99-2.92 (m, 4H), 2.28-2.18 (m, 2H), 2.08-2.02 (m, 2H), 1.96-1.75 (m, 10H), 1.70-1.57 (m, 6H), 1.52 (s, 1H), 1.41-1.33 (m, 3H), 1.15-1.10 (m, 4H), 0.98 (t, 1H, J=11.6 Hz), 0.89 (s, 3H), 0.70 (s, 3H); ¹³C NMR (CDCl₃, 100 MHz): δ 168.08, 167.52, 149.90, 133.44, 128.36, 126.49, 124.90, 122.39, 73.09, 71.89, 68.38, 47.27, 46.54, 41.79, 41.54, 39.61, 39.92, 35.90, 35.33, 34.99, 34.77, 34.65, 30.49, 28.18, 27.56, 26.52, 23.26, 22.50, 21.69, 17.79, 12.57.

p. Synthesis of Compound 31

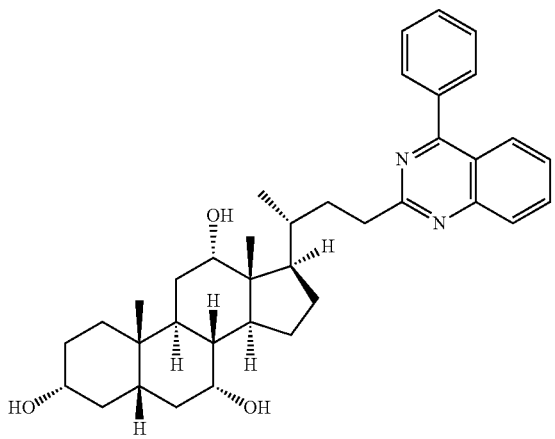

This compound was prepared using the method described above for 29. Compound 19 (137 mg, 0.20 mmol) was dissolved and 7N NH₃ in MeOH (12 mL) by sonication and subjected to microwave heating, performed at 100° C. for 30 min under microwave irradiation keeping the absorption level at high (repeated 4 times). An additional amount of 7N NH₃ in MeOH (6 mL) was added and performed microwave heating at 120° C. (repeated 6 times) and the product was purified by column chromatography over silica gel eluted with a mixture of AcOEt-MeOH (95:5; 90:10; 80:20 and 50:50) to give 31 in 64% yield (74 mg). mp. 119-120° C.; ¹H NMR (CDCl₃, 400 MHz): δ 8.04 (t, 2H, J=7.6 Hz), 7.85 (t, 1H, J=7.6 Hz), 7.77-7.75 (m, 2H), 7.57-7.50 (m, 4H), 4.02 (s, 1H), 3.84 (br s, 1H), 3.46-3.42 (m, 1H), 3.30-3.22 (m, 1H), 3.11-3.04 (m, 1H), 2.29-2.10 (m, 3H), 2.03-1.80 (m, 7H), 1.76-1.57 (m, 8H), 1.54-1.34 (m, 5H), 1.17-1.07 (m, 4H), 0.99 (td, 1H, J=14.0 and 2.8 Hz), 0.89 (s, 3H), 0.70 (s, 3H); ¹³C NMR (CDCl₃, 100 MHz): δ 168.48, 167.73, 151.42, 137.41, 133.49, 139.95, 129.82, 128.56, 128.27, 127.00, 126.64, 121.19, 73.07, 71.97, 68.43, 47.29, 46.60, 41.83, 41.54, 39.67, 39.62, 36.98, 35.84, 35.31, 34.98, 34.75, 34.61, 30.53, 28.18, 27.55, 26.55, 23.25, 22.51, 17.81, 12.62.

q. Synthesis of Compound 32

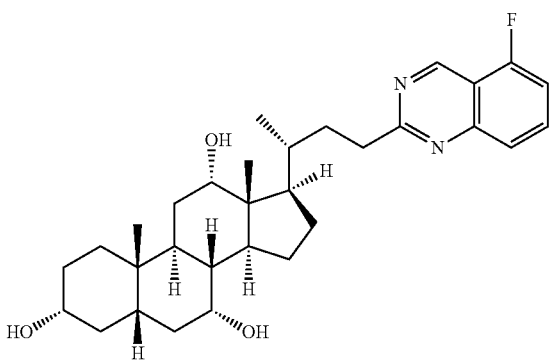

This compound was prepared using the method described above for 29. Compound 20 (184 mg, 0.30 mmol) was dissolved in MeOH (8 mL) and 7N NH₃ in MeOH (8 mL) and subjected to microwave heating, performed at 80° C. for 1 h under microwave irradiation keeping the absorption level at high (repeated 4 times). The product was purified by column chromatography over silica gel eluted with a mixture of CH₂Cl₂-MeOH (90:10; 80:20, 70:30 and 50:50) to give 32 in 67% yield (102 mg). mp. 94-96° C. (softening), 102-105° C.; ¹H NMR (CDCl₃, 400 MHz): δ 9.61 (s, 1H), 7.82-7.76 (m, 2H), 7.21 (t, 1H, J=8.0 Hz), 4.02 (s, 1H), 3.85 (s, 1H), 3.49-3.43 (m, 1H), 3.25-3.18 (m, 1H), 3.07-2.99 (m, 1H), 2.29-2.18 (m, 2H), 2.06-1.77 (m, 11H), 1.71-1.61 (m, 5H), 1.52-1.30 (m, 5H), 1.18-1.11 (m, 4H), 0.96 (t, 1H, J=12.0 Hz), 0.89 (s, 3H), 0.70 (s, 3H); ¹³C NMR (CDCl₃, 100 MHz): δ 169.37, 159.49, 156.91, 154.68, 154.65, 151.08, 134.10, 134.01, 123.85, 123.81, 114.07, 113.92, 110.78, 110.60, 73.08, 71.92, 68.41, 47.16, 46.54, 41.74, 41.54, 39.62, 39.59, 36.93, 35.84, 35.33, 34.99, 34.77, 34.67, 30.53, 28.19, 27.60, 26.47, 23.26, 22.49, 17.76, 12.54.

r. Synthesis of Compound 33

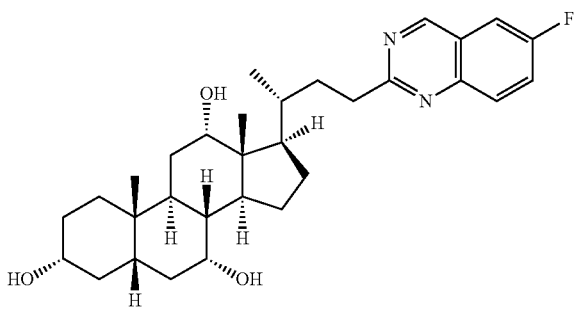

This compound was prepared using the method described above for 29. Compound 21 (154 mg, 0.25 mmol) was dissolved in MeOH (4 mL) and 7N NH$_3$ in MeOH (8 mL) by sonication and subjected to microwave heating, performed at 80° C. for 30 min under microwave irradiation keeping the absorption level at high (repeated 4 times). An additional amount of 7N NH$_3$ in MeOH (4 mL) was added and microwave heating was performed again at 80° C. for 30 min (repeated 4 times). The product was purified by column chromatography over silica gel when eluted from a mixture of CH$_2$Cl$_2$-MeOH (90:10; 85:15; 80:20; and 70:30) to give 33 in 62% yield (79 mg). mp. 102-104° C. (softening), 185-187° C.; $^1$H NMR (CDCl$_3$, 400 MHz): δ 9.31 (s, 1H), 7.98 (dd, 1H, J=9.2 and 5.2 Hz), 7.64 (td, 1H, J=9.2 and 2.8 Hz), 7.49 (dd, 1H, J=8.0 and 2.8 Hz), 4.02 (s, 1H), 3.85 (d, 1H, J=2.4 Hz), 3.50-3.42 (m, 1H), 3.24-3.16 (m, 1H), 3.05-2.97 (m, 1H), 2.28-2.17 (m, 2H), 2.11-1.57 (m, 15H), 1.53-1.49 (m, 2H), 1.43-1.32 (m, 4H), 1.20-1.11 (m, 4H), 0.99 (td, 1H, J=14.0 and 3.2 Hz), 0.90 (s, 3H), 0.70 (s, 3H); $^{13}$C NMR (CDCl$_3$, 100 MHz): δ 167.99, 167.97, 161.39, 159.72, 159.67, 158.90, 147.52, 130.63, 130.55, 124.48, 124.22, 123.37, 123.28, 110.15, 109.94, 73.09, 71.93, 68.40, 47.20, 46.55, 41.77, 41.54, 39.61, 36.72, 35.83, 35.31, 35.07, 34.77, 34.70, 30.57, 28.22, 27.60, 26.50, 23.26, 22.51, 17.79, 12.55.

s. Synthesis of Compound 34

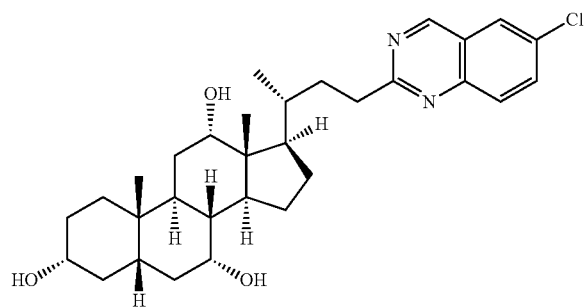

This compound was prepared using the method described above for 29. Compound 22 (233 mg, 0.37 mmol) was dissolved in 7N NH$_3$ in MeOH (12 mL) by sonication and subjected to microwave heating performed at 100° C. for 30 min under microwave irradiation keeping the absorption level at high (repeated 8 times). The product was purified by column chromatography over silica gel eluted with a mixture of CH$_2$Cl$_2$-MeOH (95:5; 90:10; 85:15; 80:20 and 70:30) to give 34 in 63% yield (122 mg). mp. 119-122° C. (softening), 130-132° C.; $^1$H NMR (CDCl$_3$, 400 MHz): δ 9.28 (s, 1H), 7.92 (d, 1H, J=9.2 Hz), 7.87 (s, 1H), 7.80 (d, 1H, J=8.8 Hz), 4.02 (s, 1H), 3.85 (s, 1H), 3.47-3.43 (m, 1H), 3.23-3.16 (m, 1H), 3.05-2.97 (m, 1H), 2.28-2.17 (m, 2H), 2.09-1.58 (m, 15H), 1.55-1.52 (m, 2H), 1.43-1.31 (m, 4H), 1.17-1.10 (m, 4H), 0.99 (t, 1H, J=13.2 Hz), 0.90 (s, 3H), 0.70 (s, 3H); $^{13}$C NMR (CDCl$_3$, 100 MHz): δ 168.81, 159.39, 148.81, 134.96, 132.44, 129.64, 125.76, 123.44, 73.08, 71.91, 68.40, 47.15, 46.54, 41.72, 41.55, 39.60, 36.81, 35.85, 35.33, 35.01, 34.78, 34.71, 30.56, 28.20, 27.62, 26.45, 23.27, 22.50, 17.78, 12.53.

t. Synthesis of Compound 35

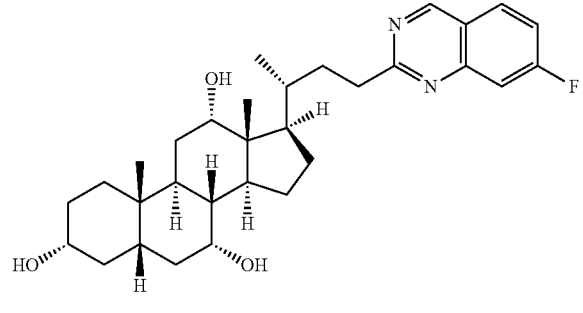

This compound was prepared using the method described above for 29. Compound 23 (154 mg, 0.25 mmol) was dissolved in MeOH (8 mL) and 7N NH$_3$ in MeOH (8 mL) by sonication and subjected to microwave heating, performed at 80° C. for 30 min under microwave irradiation keeping the absorption level at high (repeated 8 times). An additional 4.0 mL of 7N NH$_3$ in MeOH was added and subjected further for microwave heating at 80° C. for 1 h (repeated 4 times). The product was purified by column chromatography over silica gel eluted with a mixture of CH$_2$Cl$_2$-MeOH (90:10; 80:20; 70:30 and 50:50) to give 35 in 71% yield (91 mg). mp. 190-193° C.; $^1$H NMR (CDCl$_3$, 400 MHz): δ 9.30 (s, 1H), 7.90 (dd, 1H, J=9.2 and 6.0 Hz), 7.59 (dd, 1H, J=9.6 and 2.0 Hz), 7.36 (td, 1H, J=8.8 and 2.4 Hz), 4.02 (s, 1H), 3.85 (d, 1H, J=2.4 Hz), 3.49-3.42 (m, 1H), 3.23-3.15 (m, 1H), 3.04-2.97 (m, 1H), 2.29-2.18 (m, 2H), 2.10-1.74 (m, 10H), 1.71-1.58 (m, 6H), 1.53-1.30 (m, 5H), 1.19-1.08 (m, 4H), 0.99 (td, 1H, J=14.0 and 2.8 Hz), 0.90 (s, 3H), 0.70 (s, 3H); $^{13}$C NMR (CDCl$_3$, 100 MHz): δ 169.46, 167.15, 164.60, 159.77, 152.07, 151.94, 129.80, 129.69, 120.30, 117.72, 117.47, 111.93, 111.72, 73.08, 71.92, 68.40, 47.18, 46.55, 41.76, 41.55, 39.64, 39.61, 36.87, 35.85, 35.32, 35.03, 34.78, 34.69, 30.55, 28.21, 27.60, 26.49, 23.26, 22.50, 17.77, 12.55.

u. Synthesis of Compound 36

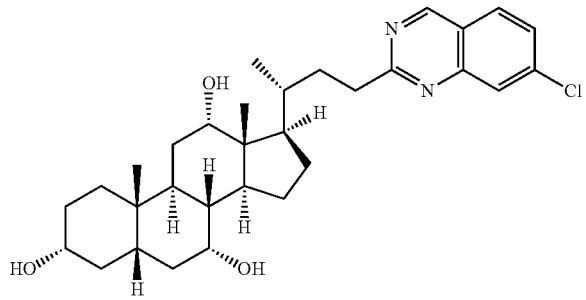

This compound was prepared using the method described above for 29. Compound 24 (126 mg, 0.20 mmol) was dissolved in 7N NH$_3$ in MeOH (12 mL) by sonication and subjected to microwave heating performed at 100° C. for 30 min under microwave irradiation keeping the absorption level at high (repeated 8 times). The product was purified by column chromatography over silica gel eluted with a mixture of CH$_2$Cl$_2$-MeOH (95:5; 90:10; 85:15; 80:20 and 70:30) to give 36 in 61% yield (64 mg). mp. 188-190° C.; $^1$H NMR (CDCl$_3$, 400 MHz): δ 9.30 (s, 1H), 7.97 (s, 1H), 7.82 (d, 1H, J=8.8 Hz), 7.53 (d, 1H, J=8.8 Hz), 4.01 (s, 1H), 3.85 (s, 1H), 3.45 (br s, 1H), 3.21-3.16 (m, 1H), 3.04-2.97 (m, 1H), 2.29-2.20 (m, 2H), 2.05-1.84 (m, 9H), 1.80-1.61

(m, 7H), 1.52-1.26 (m, 5H), 1.10 (d, 3H, J=6.0 Hz), 0.98 (t, 1H, J=13.6 Hz), 0.89 (s, 3H), 0.69 (s, 3H); $^{13}$C NMR (CDCl$_3$, 100 MHz): δ 169.55, 160.05, 150.95, 140.29, 128.41, 128.20, 127.17, 121.42, 73.07, 72.02, 68.45, 47.30, 46.63, 41.94, 41.56, 39.79, 39.68, 36.89, 35.77, 35.32, 35.00, 34.77, 34.65, 30.62, 28.29, 27.61, 26.67, 23.27, 22.58, 17.81, 12.62.

v. Synthesis of Compound 37

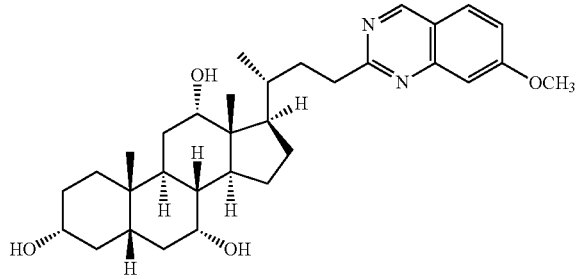

This compound was prepared using the method described above for 29. Compound 25 (219 mg, 0.35 mmol) was dissolved in MeOH (8 mL) and 7N NH$_3$ in MeOH (8 mL) by sonication and subjected to microwave heating performed at 80° C. for 1 h under microwave irradiation keeping the absorption level at high (repeated 4 times). The product was purified by column chromatography over silica gel eluted from a mixture of CH$_2$Cl$_2$-MeOH (90:10; 80:20; 70:30 and 50:50) to yield 37 in 62% yield (114 mg). mp. 110-112° C. (softening) 120-122° C.; $^1$H NMR (CDCl$_3$, 400 MHz): δ 9.16 (s, 1H), 7.75 (d, 1H, J=8.8 Hz), 7.26 (s, 2H, AR and residual CHCl$_3$ peak), 7.20 (d, 1H, J=8.8 Hz), 4.02 (s, 1H), 3.97 (s, 3H), 3.85 (s, 1H), 3.46-3.42 (m, 1H), 3.19-3.12 (m, 1H), 3.00-2.93 (m, 1H), 2.29-2.18 (m, 2H), 2.04-1.81 (m, 9H), 1.77-1.61 (m, 7H), 1.52-1.30 (m, 5H), 1.17-0.93 (m, 5H), 0.89 (s, 3H), 0.70 (s, 3H); $^1$H NMR (CD$_3$OD, 400 MHz): δ 9.24 (s, 1H), 7.95 (d, 1H, J=8.8 Hz), 7.30 and 7.28 (2 peaks, 2H), 4.00 (s, 3H), 3.97 (s, 1H), 3.78 (d, 1H, J=2.0 Hz), 3.40-3.36 (m, 1H), 3.15-3.08 (m, 1H), 2.96-2.89 (m, 1H), 2.33-2.22 (m, 2H), 2.07-1.94 (m, 5H), 1.82-1.73 (m, 2H), 1.66-1.50 (m, 8H), 1.47-1.35 (m, 2H), 1.30-1.27 (m, 1H), 1.15 (d, 3H, J=6.4 Hz), 1.12-0.93 (m, 2H), 0.91 (s, 3H), 0.70 (s, 3H); $^{13}$C NMR (CDCl$_3$, 100 MHz): δ 168.85, 164.34, 158.80, 152.78, 128.38, 120.34, 118.57, 105.51, 73.07, 71.90, 68.38, 55.79, 47.13, 46.54, 41.70, 41.56, 39.61, 36.88, 35.95, 35.34, 35.27, 34.78, 34.79, 30.51, 28.18, 27.61, 26.44, 23.27, 22.50, 17.79, 12.54.

w. Synthesis of Compound 38

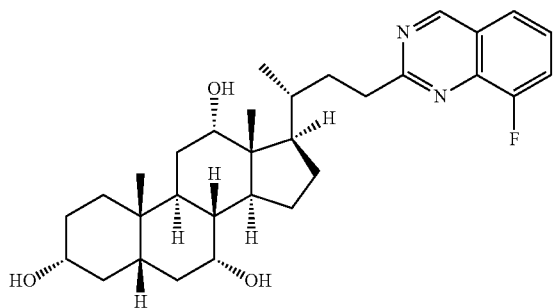

This compound was prepared using the method described above for 29. The mixture of products (26 and 16, 178 mg) was dissolved in MeOH (8 mL) and 7N NH$_3$ in MeOH (8.0 mL), and subjected to microwave heating, performed at 80° C. for 1 h under microwave irradiation keeping the absorption level at high (repeated 6 times). The product was purified by column chromatography over silica gel eluted with a mixture of CH$_2$Cl$_2$-MeOH (90:10; 85:15; 80:20 and 70:30) to give 38 in 8% yield (the yield is based on two steps combined starting from 16). mp. 128-131° C.; 1H NMR (CDCl$_3$, 400 MHz): δ 9.38 (s, 1H), 7.70 (d, 1H, J=7.6 Hz), 7.60-7.50 (m, 2H), 4.02 (s, 1H), 3.85 (s, 1H), 3.48-3.43 (m, 1H), 3.30-3.23 (m, 1H), 3.11-3.05 (m, 1H), 2.29-2.18 (m, 2H), 2.12-2.06 (m, 1H), 2.00-1.81 (m, 5H), 1.77-1.55 (m, 11H), 1.52 (br, 1H), 1.45-1.33 (m, 3H), 1.19-1.11 (m, 4H), 1.02-0.95 (m, 1H), 0.90 (s, 3H), 0.70 (s, 3H); $^{13}$C NMR (CDCl$_3$, 100 MHz): δ 168.93, 160.12, 160.09, 158.13, 155.56, 140.81, 140.69, 126.68, 126.61, 124.35, 124.33, 122.79, 122.74, 118.08, 117.89, 73.06, 71.98, 68.43, 47.33, 46.59, 41.83, 41.54, 39.68, 39.63, 37.03, 35.82, 35.30, 35.04, 34.75, 34.62, 30.56, 28.22, 27.55, 26.56, 23.24, 22.52, 17.76, 12.57.

x. Synthesis of Compound 39

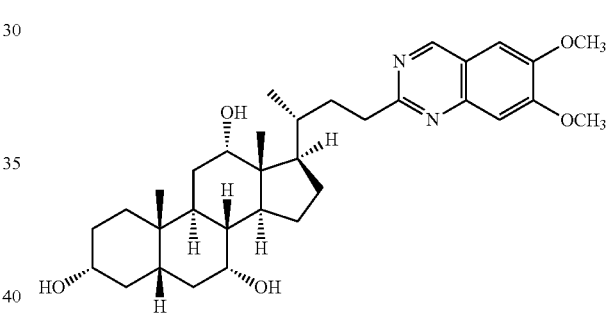

This compound was prepared using the method described above for 29. Compound 27 (164 mg, 0.25 mmol) was dissolved in MeOH (7 mL) and 7N NH$_3$ in MeOH (8 mL) by sonication and subjected to microwave heating performed at 80° C. for 1 h under microwave irradiation keeping the absorption level at high (repeated 4 times). An additional 4.0 mL of 7N NH$_3$ in MeOH was added and subjected further for microwave heating at 80° C. for 1 h (repeated 4 times). The product was purified by column chromatography over silica gel eluted with a mixture of CH$_2$Cl$_2$-MeOH (90:10; 80:20 and 70:30) to give 39 in 73% yield (101 mg). mp. 112-115° C.; $^1$H NMR (CDCl$_3$, 400 MHz): δ 9.10 (s, 1H), 7.28 (s, 1H), 7.08 (s, 1H), 4.05 (s, 3H), 4.02 (s, 4H), 3.85 (s, 1H), 3.48-3.43 (m, 1H), 3.18-3.11 (m, 1H), 2.99-2.91 (m, 1H), 2.29-2.18 (m, 2H), 2.05-1.75 (m, 10H), 1.70-1.55 (m, 6H), 1.52-1.30 (m, 5H), 1.15-1.10 (m, 4H), 1.01-0.95 (m, 1H), 0.89 (s, 3H), 0.70 (s, 3H); $^{13}$C NMR (CDCl$_3$, 100 MHz): δ 166.97, 157.01, 156.20, 150.00, 149.29, 118.70, 106.22, 103.94, 73.06, 71.91, 68.37, 56.43, 56.19, 47.13, 46.54, 41.74, 41.56, 39.61, 36.72, 35.93, 35.34, 34.77, 34.68, 30.57, 28.18, 27.63, 26.48, 23.27, 22.49, 17.82, 12.55.

y. Synthesis of Compound 40

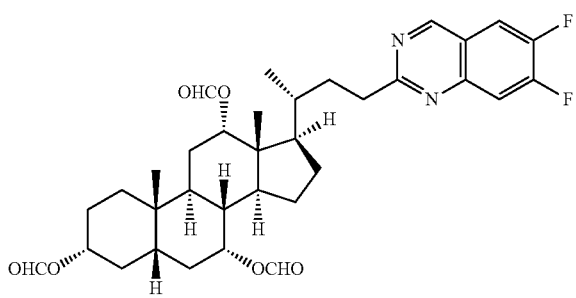

Compound 28 (157 mg, 0.25 mmol) was placed in a microwave vial and added 0.5M NH$_3$ in THF (10 mL), and it was sealed and stirred at room temperature for few minutes. The microwave heating was performed at 100° C. for 1 h under microwave irradiation keeping the absorption level at high (repeated 2 times), and the progress of the reaction was monitored by $^1$H NMR. An additional amount of 7.0 mL (0.5M NH$_3$ in THF) was added into above reaction vial and subjected it further for microwave heating at 120° C. for 1 h (repeated 4 times). After completion of the reaction as revealed by $^1$H NMR, the solution was transferred into a round bottom flask and concentrated to give viscous material. The product was purified by column chromatography over silica gel eluted with a mixture of n-hexane: AcOEt (2:1; 1:1; 1:2, followed by 100% AcOEt) to give 40 in 79% yield (121 mg). mp. 94-97° C.; $^1$H NMR (CDCl$_3$, 400 MHz): δ 9.25 (s, 1H), 8.17 (s, 1H), 8.10 (s, 1H), 8.02 (s, 1H), 7.71 (dd, 1H, J=10.8 and 7.2 Hz), 7.62 (t, 1H, J=8.4 Hz), 5.30 (s, 1H), 5.07 (d, 1H, J=2.4 Hz), 4.75-4.68 (m, 1H), 3.18-3.10 (m, 1H), 3.00-2.92 (m, 1H), 2.19-1.90 (m, 7H), 1.82-1.56 (m, 11H), 1.52-1.24 (m, 5H), 1.14-1.05 (m, 2H), 0.98 (d, 1H, J=6.4 Hz), 0.95 (s, 3H), 0.76 (s, 3H); $^{13}$C NMR (CDCl$_3$, 100 MHz): δ 168.74, 168.71, 160.60, 160.56, 159.16, 159.11, 151.55, 151.40, 149.02, 148.86, 148.32, 148.20, 119.98, 119.90, 114.73, 114.56, 112.68, 112.71, 112.68, 112.51, 75.41, 73.79, 70.74, 47.38, 45.09, 43.05, 40.87, 37.80, 36.52, 35.27, 34.66, 34.58, 34.51, 34.34, 31.40, 28.64, 27.32, 26.64, 25.61, 22.85, 22.39, 17.86, 12.20.

z. Synthesis of Compound 41

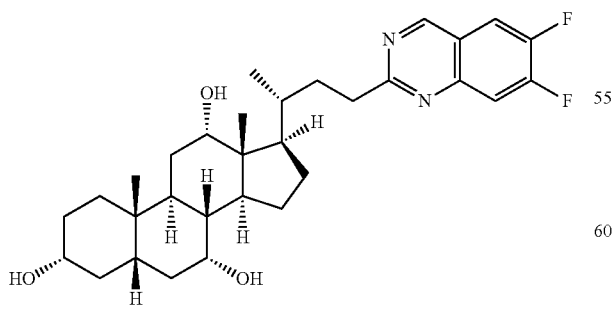

Compound 40 (49 mg, 0.08 mmol) was dissolved in THF (4.0 mL) and added a solution of LiOH (12 mg, 0.50 mmol) in H$_2$O (1.2 mL). The reaction mixture allowed to stir at room temperature for 30 min, and then heated at 50-55° C. for 1.5 h using water bath and the progress was monitored by TLC. After completion of the reaction, THF was removed, and the remaining content was diluted further with water (25 mL) and product was extracted with CHCl$_3$ (25 mL×3 times). The organic layer was separated, combined, and concentrated on rotavapor and further dried on high vacuum to yield a white solid 41 in 36 mg (85% yield). mp. 211-214° C.; $^1$H NMR (CDCl$_3$, 400 MHz): δ 9.26 (s, 1H), 7.72 (t, 1H, J=7.6 Hz), 7.63 (t, 1H, J=8.0 Hz), 4.01 (s, 1H), 3.85 (s, 1H), 3.45 (s, 1H), 3.18 (br, 1H), 2.99 (br, 1H), 2.26-2.20 (m, 2H), 2.04-1.86 (m, 8H), 1.80-1.60 (m, 6H), 1.52-1.25 (m, 7H), 1.11 and 1.10 (2 broad peaks, 4H), 0.98 (t, 1H, J=13.6 Hz), 0.89 (s, 3H), 0.69 (s, 3H); $^{13}$C NMR (CDCl$_3$, 100 MHz): δ 168.97, 168.94, 159.05, 159.01, 156.85, 156.70, 154.27, 154.11, 151.44, 151.28, 148.90, 148.75, 148.24, 148.12, 119.86, 119.79, 114.64, 114.47, 112.59, 112.44, 73.00, 71.91, 68.37, 47.17, 46.52, 41.80, 41.47, 39.65, 39.57, 36.67, 35.69, 35.24, 34.90, 34.70, 34.60, 30.51, 28.19, 27.53, 26.52, 23.19, 22.47, 17.71, 12.51.

4. Bicyclic 4-Quinazolinone Analogs of Cholic Acid

Example compound 43 was synthesized using Scheme 9. The intermediate product (42) formed during the synthetic route are also described here.

SCHEME 9.

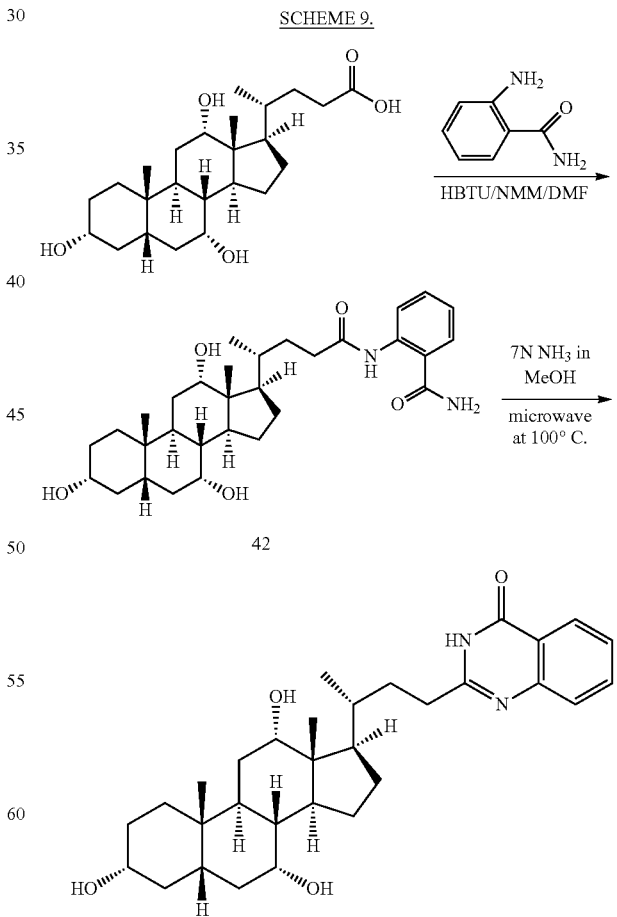

42

43

A. Synthesis of Compound 42

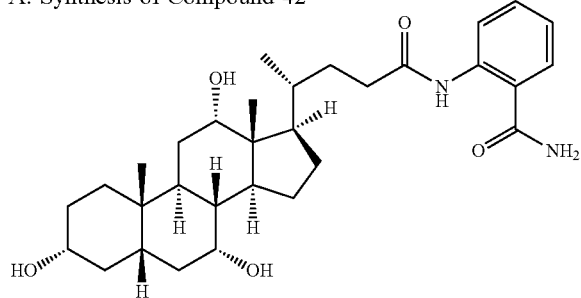

Cholic acid (823 mg, 2.0 mmol) and HBTU (951 mg, 2.5 mmol) were dissolved in anhydrous DMF (7 mL) at room temperature. NMM (0.30 mL) was added into above reaction flask and the reaction content allowed stirring for 30 min to generate an activated ester. 2-Aminobenzamide (355 mg, 2.60 mmol) and NMM (0.30 mL) were added into above reaction mixture, and it was allowed to react for 48 h at room temperature. The reaction mixture was transferred into round bottom flask and solvent was removed on high vacuum rotavapor at 75-80° C. which produced a viscous material; it was subjected to high vacuum dryness. The post-reaction mixture was treated with 2% ice cold HCl (200 mL), and subjected to sonication, which produced a precipitate; the product was filtered off (this step was repeated). The product was finally filtered off and washed with cold water to give product 42 in 91% yield (964 mg) on high vacuum drying. $^1$H NMR (CDCl$_3$, 400 MHz): δ 11.15 (s, 1H), 8.58 (d, 1H, J=8.4 Hz), 7.55 (d, 1H, J=8.0 Hz), 7.48 (t, 1H, J=7.6 Hz), 7.06 (t, 1H, J=7.6 Hz), 6.60 (br, 1H), 6.26 (br, 1H), 3.97 (s, 1H), 3.83 (s, 1H), 3.58-3.42 (m, 1H), 2.49-2.43 (m, 1H), 2.33-2.17 (m, 5H), 1.93-1.63 (m, 11H), 1.55-1.25 (m, 8H), 1.11-0.93 (m, 5H), 0.88 (s, 3H), 0.67 (s, 3H); $^1$H NMR (CD$_3$OD, 600 MHz): δ 8.43 (s, 1H), 7.74 (s, 1H), 7.48 (s, 1H), 7.13 (s, 1H), 3.95 (s, 1H), 3.78 (s, 1H), 3.36 (s, 1H), 2.47 (s, 1H), 2.29 and 2.27 (2 broad peaks, 3H), 1.99-1.86 (m, 5H), 1.80-1.75 (m, 1H), 1.64-1.40 (m, 9H), 1.40-1.26 (br, 2H), 1.06 (br s, 4H), 0.97 (br s, 1H), 0.97 (s, 3H), 0.70 (s, 3H); $^{13}$C NMR (CD$_3$OD, 150 MHz): δ 174.81, 173.49, 140.47, 133.45, 129.45, 124.20, 122.34, 121.72, 73.96, 72.85, 69.02, 47.96, 47.50, 43.15, 42.93, 40.99, 40.42, 36.80, 36.47, 36.15, 35.87, 35.82, 33.00, 31.16, 29.54, 28.67, 27.83, 24.23, 23.19, 17.77, 13.03.

b. Synthesis of Compound 43

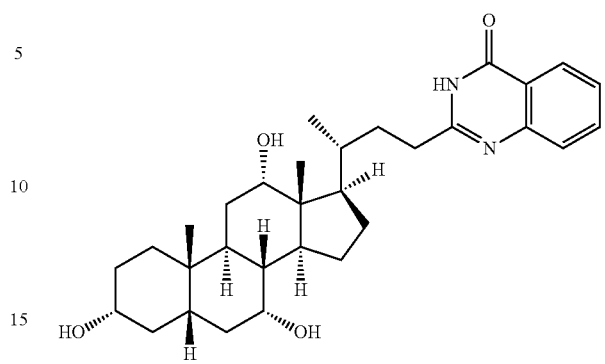

The compound 42 (132 mg, 0.25 mmol) was dissolved in MeOH (8.0 mL) in a microwave vial using sonication. A solution of 7N NH$_3$ in MeOH (8.0 mL) was added into above vial, it was sealed and subjected to microwave heating at 100° C. for 30 min under microwave irradiation keeping the absorption level at high (repeated 4 times). The formation of the product was monitored by $^1$H NMR. After completion of the reaction, the content was transferred in round bottom flask and MeOH was removed using rotavapor to give a solid. The product was dried on high vacuum, which furnished 43 in 90% yield (115 mg). $^1$H NMR (CDCl$_3$, 400 MHz): δ 10.98 (s, 1H), 8.26 (d, 1H, J=8.0 Hz), 7.73-7.65 (m, 2H), 7.43 (t, 1H, J=7.6 Hz), 4.01 (s, 1H), 3.85 (s, 1H), 3.48 (m, 1H), 2.82-2.76 (m, 1H), 2.70-2.63 (m, 1H), 2.29-2.19 (m, 2H), 1.95-1.90 (m, 8H), 1.78-1.58 (m, 8H), 1.52-1.38 (m, 4H), 1.31-1.26 (m, 1H), 1.10 and 1.08 (2 peaks, 4H), 0.98 (t, 1H, J=13.6 Hz), 0.88 (s, 3H), 0.69 (s, 3H); $^{13}$C NMR (CDCl$_3$, 100 MHz): δ 163.94, 157.95, 149.38, 134.63, 126.99, 126.27, 120.56, 73.11, 71.87, 68.4, 46.50, 41.73, 41.51, 39.51, 35.75, 35.34, 34.78, 33.92, 32.54, 30.45, 28.19, 27.62, 26.41, 23.29, 22.46, 17.62, 12.51. HRMS (ESI, m/z): calcd for C$_{31}$H$_{45}$N$_2$O$_4$ [M+H]$^+$ 509.3374, found 509.3377.

5. Bicyclic Benzimidazole, Benzothiazole, and Benzoxazole Analogs of Cholic, Chenodeoxycholic, and Deoxycholic Acids Example compounds 44-52 were synthesized by following Scheme 10.

SCHEME 10.

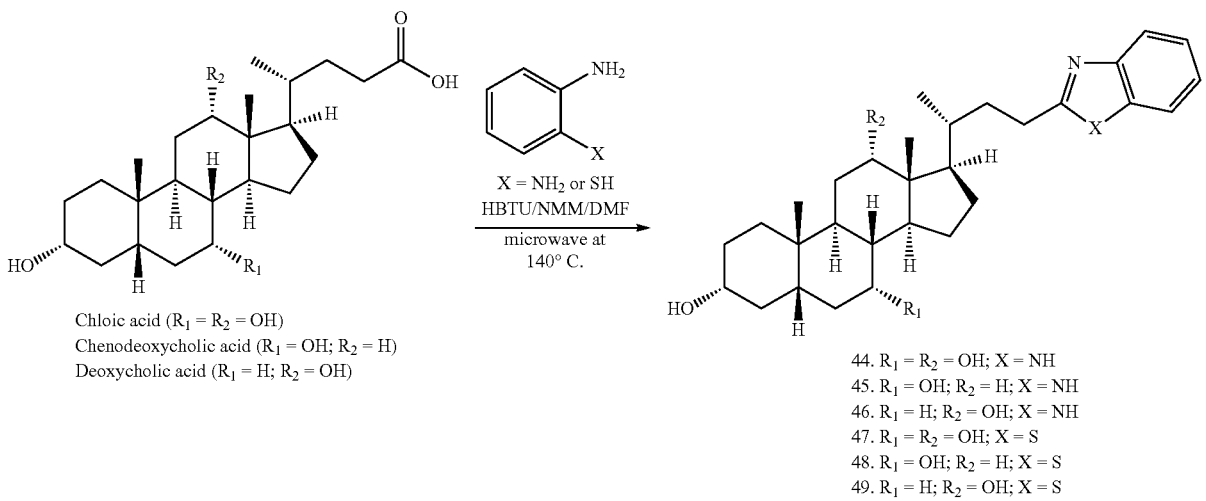

Chloic acid (R$_1$ = R$_2$ = OH)
Chenodeoxycholic acid (R$_1$ = OH; R$_2$ = H)
Deoxycholic acid (R$_1$ = H; R$_2$ = OH)

44. R$_1$ = R$_2$ = OH; X = NH
45. R$_1$ = OH; R$_2$ = H; X = NH
46. R$_1$ = H; R$_2$ = OH; X = NH
47. R$_1$ = R$_2$ = OH; X = S
48. R$_1$ = OH; R$_2$ = H; X = S
49. R$_1$ = H; R$_2$ = OH; X = S

-continued

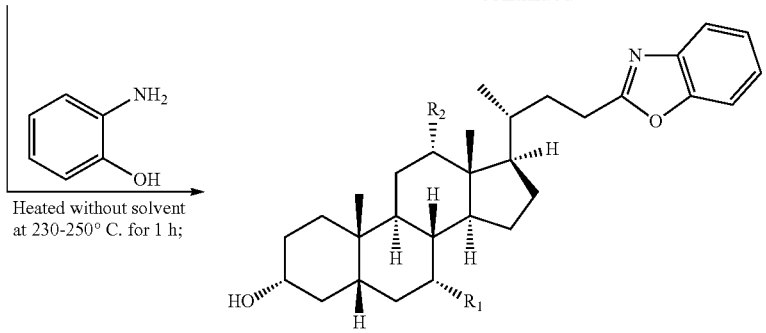

50. R₁ = R₂ = OH
51. R₁ = OH; R₂ = H
52. R₁ = H; R₂ = OH

Cholic acid (818 mg, 2.0 mmol) and HBTU (793 mg, 2.1 mmol) were dissolved in anhydrous DMF (5.0 mL) at room temperature. NMM (0.30 mL) was added, and the reaction content allowed stirring for 30 min to generate an activated ester. In a microwave vial, 1,2-phenylenediamine (217 mg, 2.0 mmol) was dissolved in DMF (8.0 mL) and added NMM (0.30 mL) and it allowed to stir for few min at room temperature. The above activated ester then was added into amino compound containing microwave vial slowly with stirring at room temperature. An additional amount of DMF (3.0 mL) and NMM (0.30 mL) were added into vial, and it was sealed and subjected to microwave heating at 140° C. for 30 min under microwave irradiation keeping the absorption level at very high (repeated 4 times). The reaction content was left at room temperature for overnight. The reaction mixture was transferred into 250 mL round bottom flask and solvent was removed on high vacuum rotavapor to produce a viscous material. Ice cold water (150 mL) was added into above reaction flask, and subjected to sonication for 15 min, which produced a white precipitate; the soluble portion was decanted (this step was repeated 3 additional times). The product was purified by repeated column chromatography over silica gel to elute from $CH_2Cl_2$-MeOH—$NH_4OH$ (89:10:1; 78:20:2) to yield white solid which was stirred and sonicated with 100 mL of $CHCl_3$, and insoluble product was filtered out and vacuum dried to give 44 in 54% yield (528 mg). mp. 287-290° C.; $^1H$ NMR (DMSO-$d_6$, 400 MHz): δ 12.22 (br, 1H), 7.45 (dd, 1H, J=5.2 and 3.2 Hz), 7.10 (dd, 1H, J=5.6 and 3.2 Hz), 4.31 (s, H), 4.14 (d, 1H, J=2.4 Hz), 4.00 (d, 1H, J=2.0 Hz), 3.82 (s, 1H), 3.62 (s, 1H), 3.20 (br s, 1H), 2.88-2.80 (m, 1H), 2.74-2.67 (m, 1H), 2.22-2.14 (m, 2H), 2.05-1.98 (m, 1H), 1.91-1.79 (m, 4H), 1.67 and 1.64 (2 peaks, 2H), 1.44-1.14 (m, 1H), 1.05-0.96 (m, 4H), 0.88-0.82 (m, 4H), 0.60 (s, 3H); $^{13}C$ NMR (DMSO-$d_6$, 100 MHz): δ 155.64, 138.64, 121.03, 114.26, 70.99, 70.41, 66.22, 46.04, 45.75, 41.50, 41.38, 35.28, 34.85, 34.36, 34.19, 30.39, 28.55, 27.33, 26.21, 25.49, 22.78, 22.60, 17.12, 12.33.

b. Synthesis of Compound 45

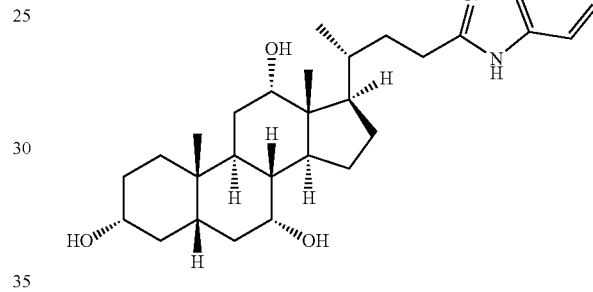

This compound was prepared using the method described above for 44. Chenodeoxycholic acid (786 mg, 2.0 mmol), HBTU (795 mg, 2.1 mmol), 1,2-phenylenediamine (219 mg, 2.0 mmol), and NMM (0.90 mL) were reacted in a similar manner. The isolated product was dissolved in a mixture of $CH_2Cl_2$ (75 mL) and MeOH (10 mL) and treated with half spoon of activated charcoal and stirred for 30 min at room temperature to remove colored material impurities. The product was then subjected to column chromatographic purification over silica gel and eluted from a mixture of $CH_2Cl_2$-MeOH—$NH_4OH$ (89:10:1; 78:20:2) followed by $CH_2Cl_2$-MeOH (50:50) to give a white powder. This product was allowed to stir with $CHCl_3$ (50 mL), and insoluble solid was collected, and vacuum dried to furnish 45 in 53% yield (491 mg). mp. 160-163° C. (softening), 166-168° C.; $^1H$ NMR (CD$_3$OD, 400 MHz): δ 7.89 (s, NH proton), 7.48-7.46 (m, 2H), 7.18-7.16 (m, 2H), 3.78 (s, 1H), 3.39-3.34 (m, 1H), 2.98-2.91 (m, 1H), 2.82-2.75 (m, 1H), 2.27 (q, 1H, J=12.4 Hz), 2.03-1.66 (m, 6H), 1.74 (m, 1H), 1.66-1.56 (m, 2H), 1.53-1.50 (m, 5H), 1.38-1.22 (m, 6H), 1.12-1.06 (m, 4H), 1.02-0.92 (m, 4H), 0.68 (s, 3H); $^1H$ NMR (DMSO-$d_6$, 400 MHz): δ 12.15 (br, NH proton), 7.45-7.44 (m, 2H), 7.11-7.09 (m, 2H), 4.32 (br s, 1H), 4.11 (s, 1H), 3.64 (s, 1H), 3.20 (br s, 1H), 2.88-2.83 (m, 1H), 2.72-2.66 (m, 1H), 2.21 (q, 1H, J=12.4 Hz), 1.95-1.69 (m, 7H), 1.46-1.33 (m, 8H), 1.26-1.14 (m, 6H), 1.01 and 0.99 (2 peaks, 4H), 0.91-0.84 (m, 4H), 0.61 (s, 3H); $^{13}C$ NMR (CD$_3$OD, 100 MHz): δ 157.36, 139.66 (br), 123.04, 115.24 (br), 72.83, 68.99, 57.24, 51.50, 43.68, 43.14, 41.03, 40.74, 40.46, 36.99, 36.54, 36.19, 35.89, 35.80, 34.02, 31.36, 29.30, 26.75, 24.61, 23.39, 21.77, 18.98, 12.17; $^{13}C$ NMR (DMSO-$d_6$, 100 MHz): δ 155.52, 120.94, 70.29, 66.13, 55.50, 49.98, 41.92, 41.39, 35.28, 35.16, 34.78, 34.69, 34.10, 32.26, 30.53, 27.83, 25.44, 23.12, 22.67, 20.23, 18.31, 11.63.

c. Synthesis of Compound 46

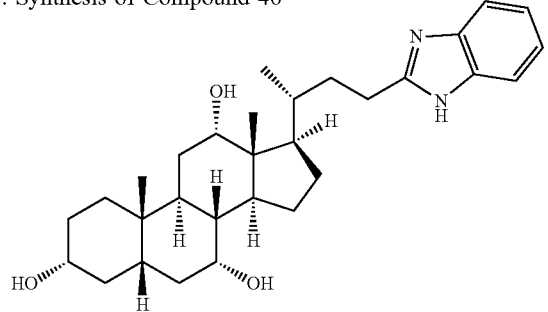

This compound was prepared using the method described above for 44. Deoxycholic acid (786 mg, 2.0 mmol), HBTU (795 mg, 2.1 mmol), 1,2-phenylenediamine (219 mg, 2.0 mmol), and NMM (0.90 mL) were reacted in a similar manner. The product was dissolved in a mixture of CH$_2$Cl$_2$ (75 mL) and MeOH (10 mL) and treated with half spoon of activated charcoal to remove colored material impurities. The product was subjected to column chromatographic purification over silica gel and eluted from a mixture of CH$_2$Cl$_2$-MeOH—NH$_4$OH (89:10:1; 78:20:2) followed by CH$_2$Cl$_2$-MeOH (50:50) to give a white powder. The material was allowed to stir with CHCl$_3$ (50 mL), and insoluble white solid was collected, and vacuum dried to furnish 46 in 59% yield (547 mg). mp. 298-301° C.; $^1$H NMR (CD$_3$OD, 400 MHz): δ 7.89 (s, NH proton), 7.47 (br s, 2H), 7.18-7.16 (m, 2H), 3.77 (s, 1H), 3.55-3.48 (m, 1H), 2.99-2.92 (m, 1H), 2.83-2.76 (m, 1H), 1.98-1.85 (m, 5H), 1.83-1.75 (m, 2H), 1.65-1.59 (m, 3H), 1.53-1.37 (m, 8H), 1.28-1.06 (m, 7H), 1.01-0.92 (m, 4H), 0.69 (s, 3H); $^1$H NMR (DMSO-d$_6$, 400 MHz): δ 12.16 (br, NH proton), 7.46-7.44 (m, 2H), 7.11-7.09 (m, 2H), 4.45 (s, 1H), 4.23 (d, 1H, J=3.2 Hz), 3.82 (s, 1H), 3.37 and 3.18 (2 broad peaks, 1H), 2.88-2.81 (m, 1H), 2.73-2.66 (m, 1H), 1.89-1.82 (m, 5H), 1.66-1.60 (m, 3H), 1.56-1.46 (m, 3H), 1.39-1.30 (m, 8H), 1.23-1.17 (m, 2H), 1.11-0.98 (m, 5H), 0.91-0.85 (m, 4H), 0.60 (s, 3H); $^{13}$C NMR (CD$_3$OD, 100 MHz): δ 157.46, 123.04, 74.03, 72.54, 49.28, 48.08, 47.59, 43.62, 37.45, 37.21, 36.93, 36.43, 35.81, 35.30, 34.83, 31.08, 29.91, 28.70, 28.39, 27.45, 26.75, 24.86, 23.69, 17.72, 13.17; $^{13}$C NMR (DMSO-d$_6$, 100 MHz): δ 155.59, 120.96, 70.98, 69.90, 47.46, 46.12, 45.98, 41.57, 36.27, 35.62, 35.16, 34.13, 33.78, 32.91, 30.21, 28.59, 27.21, 26.94, 26.06, 25.49, 23.47, 23.06, 17.08, 12.43.

d. Synthesis of Compound 47

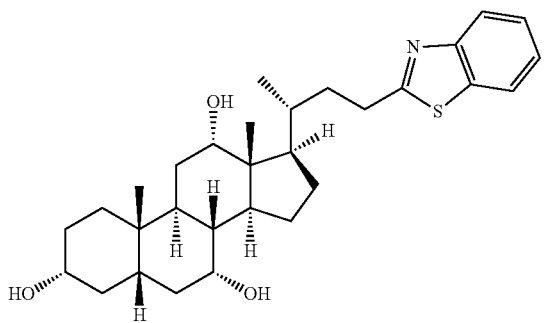

This compound was prepared using the method described above for 44. Cholic acid (819 mg, 2.0 mmol), HBTU (793 mg, 2.1 mmol), 2-aminothiophenol (253 mg, 2.0 mmol), and NMM (0.90 mL) were reacted in a similar manner. The crude product was subjected to column chromatographic purification over silica gel and eluted from a mixture of CH$_2$Cl$_2$-MeOH (90:10; 80:20; 70:30) to give 47 in 72% yield (716 mg). mp. 87-90° C. (softening), 115-117° C.; $^1$H NMR (CDCl$_3$, 400 MHz): δ 7.95 (d, 1H, J=8.0 Hz), 7.83 (d, 1H, J=8.0 Hz), 7.44 (t, 1H, J=7.2 Hz), 7.33 (t, 1H, J=7.6 Hz), 3.99 (s, 1H), 3.85 (s, 1H), 3.48-3.43 (m, 1H), 3.22-3.16 (m, 1H), 3.15-3.07 (m, 1H), 2.93-1.85 (m, 11H), 1.80-1.57 (m, 7H), 1.52-1.49 (m, 2H), 1.45-1.27 (m, 3H), 1.16-1.09 (m, 4H), 1.01-0.94 (m, 1H), 0.89 (s, 3H), 0.68 (s, 3H); $^{13}$C NMR (CDCl$_3$, 100 MHz): δ 173.03, 155.21, 135.16, 125.85, 124.60, 122.47, 121.49, 73.01, 71.96, 68.40, 47.01, 46.56, 41.88, 41.51, 39.71, 39.59, 35.92, 35.47, 35.27, 34.74, 34.69, 31.24, 30.58, 28.33, 27.60, 26.57, 23.24, 22.52, 17.60, 12.55.

e. Synthesis of Compound 48

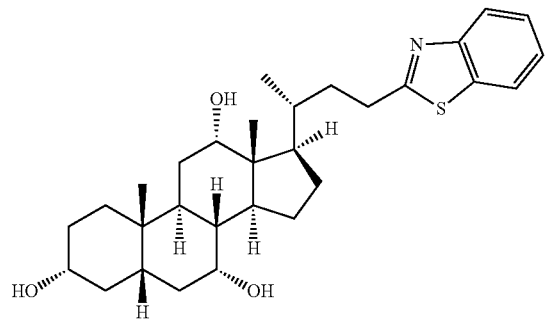

This compound was prepared using the method described above for 44. Chenodeoxycholic acid (786 mg, 2.0 mmol), HBTU (795 mg, 2.1 mmol), 2-aminothiophenol (252 mg, 2.0 mmol), and NMM (0.90 mL) were reacted in a similar manner. The crude product was subjected to column chromatographic purification over silica gel and eluted from a mixture of CH$_2$Cl$_2$-MeOH (95:5; 90:10; 80:20; 70:30) to give 48 in 71% yield ((688 mg). mp. 93-95° C.; $^1$H NMR (CDCl$_3$, 400 MHz): δ 7.96 (d, 1H, J=8.0 Hz), 7.84 (d, 1H, J=8.0 Hz), 7.44 (t, 1H, J=7.6 Hz), 7.34 (t, 1H, J=7.6 Hz), 3.85 (s, 1 h), 3.46 (br s, 1H), 3.21-3.14 (m, 1H), 3.07-2.99 (m, 1H), 2.21 (q, 1H, J=12.8 Hz), 2.05-1.91 (m, 4H), 1.85-1.82 (m, 2H), 1.73-1.61 (m, 4H), 1.53-1.08 (m, 14H), 1.06 (d, 3H, J=6.0 Hz), 0.99 (m, 1H), 0.91 (s, 3H), 0.70 (s, 3H); $^{13}$C NMR (CDCl$_3$, 100 MHz): δ 172.91, 153.26, 135.16, 125.84, 124.59, 122.49, 121.48, 73.01, 68.51, 55.83, 50.49, 42.77, 41.51, 39.93, 39.67, 39.46, 36.03, 35.62, 35.35, 35.06, 34.65, 32.87, 31.28, 30.71, 28.26, 23.73, 22.79, 20.60, 18.50, 11.82.

f. Synthesis of Compound 49

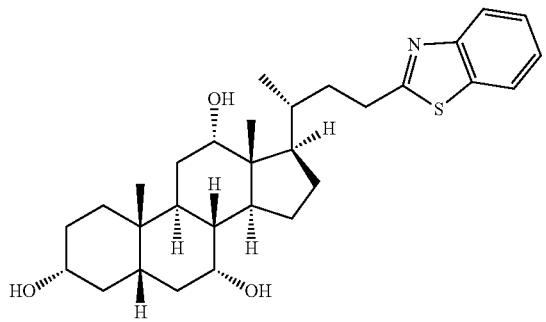

This compound was prepared using the method described above for 44. Deoxycholic acid (786 mg, 2.0 mmol), HBTU (795 mg, 2.1 mmol), 2-aminothiophenol (253 mg, 2.0 mmol), and NMM (0.90 mL) were reacted in a similar manner. The crude product was subjected to column chromatographic purification over silica gel and eluted from a mixture of $CH_2Cl_2$-MeOH (95:5; 90:10; 80:20; 70:30) to give 49 in 73% yield (701 mg). mp. 84-86° C. (softening), 93-95° C.; $^1$H NMR ($CDCl_3$, 400 MHz): δ 7.96 (d, 1H, J=8.0 Hz), 7.84 (d, 1H, J=8.0 Hz), 7.44 (t, 1H, J=7.6 Hz), 7.34 (t, 1H, J=7.6 Hz), 4.00 (s, 1 h), 3.61 (t, 1H, J=10.8 Hz), 3.23-3.15 (m, 1H), 3.08-3.00 (m, 1H), 2.06-1.99 (m, 1H), 1.95-1.73 (m, 6H), 1.69-1.55 (m, 6H), 1.51 (br, 2H), 1.43-1.25 (m, 8H), 1.19-1.04 (m, 5H), 0.99 (td, 1H, J=13.6 and 2.8 Hz), 0.91 (s, 3H), 0.68 (s, 3H); $^{13}$C NMR ($CDCl_3$, 100 MHz): δ 172.89, 153.23, 135.15, 125.85, 124.60, 122.49, 121.48, 73.12, 71.78, 48.28, 47.31, 46.56, 42.10, 36.47, 36.06, 35.92, 35.37, 35.24, 34.13, 33.68, 31.34, 30.52, 28.73, 27.57, 27.14, 26.14, 23.67, 23.16, 17.55, 12.77.

g. Synthesis of Compound 50

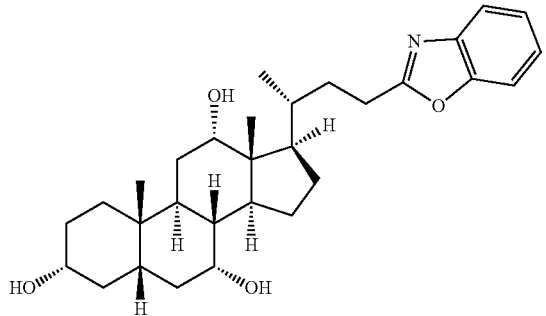

Cholic acid (818 mg, 2.0 mmol) and 2-aminophenol (262 mg, 2.4 mmol) were placed in a microwave vial and mixed well. The microwave vial was sealed and heated conventionally with stirring under argon at 230-250° C. for 1 h. The temperature of the vial was brought at room temperature and 20 mL of cold water was added. The glassy material in the vial was crushed into powder with the help of spatula and sonication. All the material from the vial was transferred into 250-mL round bottom flask and 150 mL additional cold water was added. The reaction mixture was allowed to stir and further sonicated for 15 min when most of the material turned into powder form. The product was filtered off and dried and purified by repeated column chromatography over silica gel to elute from $CH_2Cl_2$-MeOH (95:5; 90:10; 80:20; 70:30) to give 50 in 24% yield (231 mg). mp. 110-112° C.;

$^1$H NMR ($CDCl_3$, 400 MHz): δ 7.67-7.65 (m, 1H), 7.49-7.46 (m, 1H), 7.30-7.28 (m, 2H), 4.00 (s, 1H), 3.86 (d, 1H, J=1.6 Hz), 3.49-3.43 (m, 1H), 3.04-2.96 (m, 1H), 2.90-2.85 (m, 1H), 2.29-2.18 (m, 2H), 2.08-1.86 (m, 5H), 1.84-1.59 (m, 11H), 1.52-1.50 (m, 2H), 1.43-1.29 (m, 3H), 1.20-1.07 (m, 4H), 1.03-0.96 (m, 1H), 0.90 (s, 3H), 0.70 (s, 3H); $^1$H NMR ($CD_3OD$, 400 MHz): δ 7.62-7.59 (m, 1H), 7.57-7.54 (m, 1H), 7.36-7.31 (m, 2H), 3.96 (s, 1H), 3.79 (d, 1H, J=2.4 Hz), 3.48-3.36 (m, 1H), 3.06-2.99 (m, 1H), 2.93-2.87 (m, 1H), 2.33-2.23 (m, 2H), 2.07-1.89 (m, 5H), 1.82-1.73 (m, 2H), 1.67-1.47 (m, 8H), 1.45-1.35 (m, 2H), 1.31-1.28 (m, 1H), 1.17-1.06 (m, 4H), 1.00-0.91 (s, 4H), 0.70 (s, 3H); $^{13}$C NMR ($CDCl_3$, 100 MHz): δ 167.95, 150.77, 141.30, 124.39, 124.05, 119.44, 110.26, 73.05, 71.92, 68.40, 46.79, 46.53, 41.73, 41.54, 39.60, 39.54, 35.51, 35.32, 34.79, 34.75, 32.88, 30.54, 28.25, 27.60, 26.43, 25a54, 23.28, 22.48, 17.48, 12.51.

h. Synthesis of Compound 51

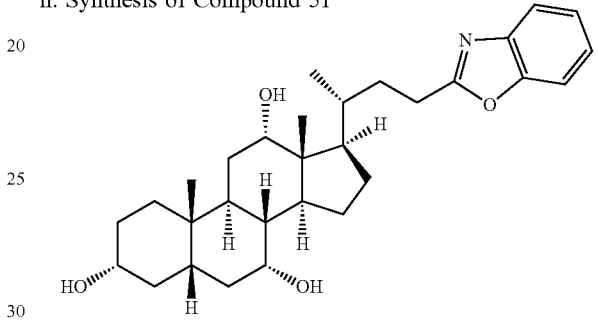

This compound was prepared using the method described above for 50. Chenodeoxycholic acid (786 mg, 2.0 mmol) and 2-aminophenol (655 mg, 6.0 mmol) were reacted in a similar manner. The product was purified by repeated column chromatography when eluted from AcOEt-MeOH (100:0; 95:5; 90:10; 80:20 and 70:30) to give 51 in 36% yield (336 mg). mp. 78-80° C.; $^1$H NMR ($CDCl_3$, 400 MHz): δ 7.68-7.66 (m, 1H), 7.48-7.46 (m, 1H), 7.30-7.28 (m, 2H), 3.86 (s, 1H), 3.49-3.44 (m, 1H), 3.02-2.95 (m, 1H), 2.87-2.81 (m, 1H), 2.25-1.92 (m, 7H), 1.85-1.82 (m, 2H), 1.73-1.58 (m, 5H), 1.50-1.47 (m, 2H), 1.44-1.12 (m, 9H), 1.05-0.94 (m, 4H), 0.91 (s, 3H), 0.67 (s, 3H); $^{13}$C NMR ($CDCl_3$, 100 MHz): δ 167.83, 150.78, 141.33, 124.39, 124.05, 119.49, 110.24, 72.04, 68.55, 55.74, 50.47, 42.76, 41.50, 39.87, 39.65, 39.45, 35.58, 35.33, 35.06, 34.63, 32.98, 32.86, 30.67, 28.21, 25.58, 23.72, 22.78, 20.60, 18.39, 11.81.

i. Synthesis of Compound 52

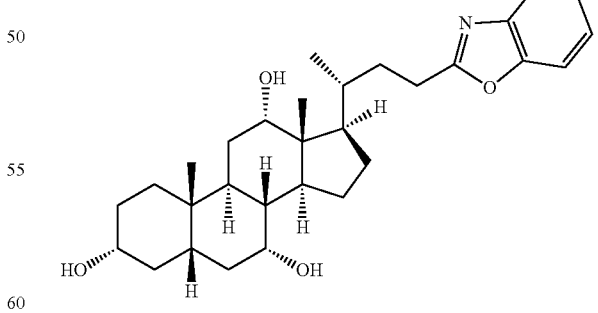

This compound was prepared using the method described above for 50. Deoxycholic acid (786 mg, 2.0 mmol) and 2-aminophenol (655 mg, 2.0 mmol) were reacted in a similar manner. The product was purified by repeated column chromatography when eluted from AcOEt-MeOH (100:0; 95:5; 90:10; and 80:20) to give 52 in 38% yield (352 mg).

mp. 72-74° C.; $^1$H NMR (CDCl$_3$, 400 MHz): δ 7.67-7.65 (m, 1H), 7.48-7.46 (m, 1H), 7.30-7.28 (m, 2H), 4.00 (s, 1H), 3.65-3.58 (m, 1H), 3.04-2.96 (m, 1H), 2.89-2.81 (m, 1H), 2.13-2.03 (m, 2H), 1.95-1.73 (m, 6H), 1.69-1.58 (m, 5H), 1.52-1.50 (m, 3H), 1.44-1.26 (m, 7H), 1.16-1.07 (m, 5H), 1.02-0.95 (m, 1H), 0.91 (s, 3H), 0.69 (s, 3H); $^{13}$C NMR (CDCl$_3$, 100 MHz): δ 167.78, 150.80, 141.37, 124.40, 124.05, 119.51, 110.25, 73.17, 71.84, 48.29, 47.23, 46.56, 42.10, 36.45, 36.06, 35.29, 35.23, 34.13, 33.71, 32.89, 30.51, 28.73, 27.51, 27.13, 26.13, 25.62, 23.66, 23.16, 17.44, 12.78.

6. 24-N-(Aryl) Amide Analogs of Chenodeoxycholic, Deoxycholic, Lithocholic, and Ursodeoxycholic Acids Example compounds 53-68 were synthesized using Scheme 11.

SCHEME 11.

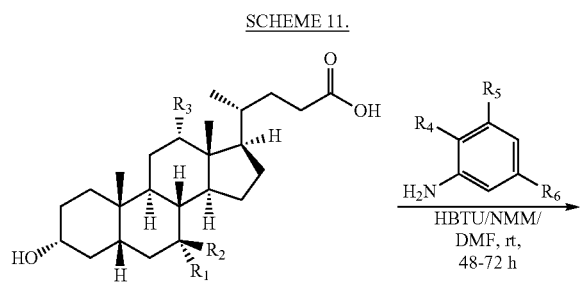

Chenodeoxycholic acid
($R_1$ = OH; $R_2$ = $R_3$ = H)
Deoxycholic acid
($R_1$ = $R_2$ = H; $R_3$ = OH)
Lithocholic acid
($R_1$ = $R_2$ = $R_3$ = H)
Ursodeoxycholic acid
($R_1$ = $R_3$ = H; $R_2$ = OH)

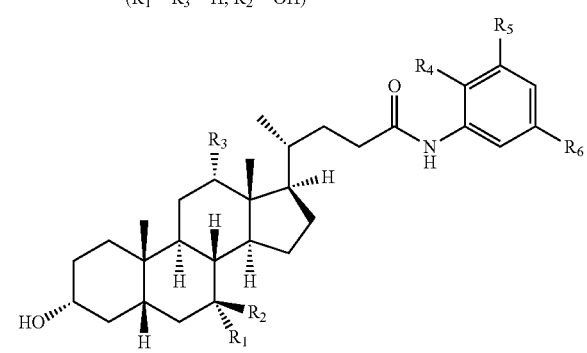

53. $R_1$ = OH; $R_2$ = $R_3$ = $R_4$ = $R_5$ = $R_6$ = H
54. $R_1$ = OH; $R_2$ = $R_3$ = $R_5$ = $R_6$ = H; $R_4$ = OCH$_3$
55. $R_1$ = OH; $R_2$ = $R_3$ = $R_4$ = $R_6$ = H; $R_5$ = F
56. $R_1$ = OH; $R_2$ = $R_3$ = $R_5$ = H; $R_4$ = CH$_3$; $R_6$ = F
57. $R_1$ = $R_2$ = $R_4$ = $R_5$ = $R_6$ = H; $R_3$ = OH
58. $R_1$ = $R_2$ = $R_5$ = $R_6$ = H; $R_3$ = OH; $R_4$ = OCH$_3$
59. $R_1$ = $R_2$ = $R_4$ = $R_6$ = H; $R_3$ = OH; $R_5$ = F
60. $R_1$ = $R_2$ = $R_5$ = H; $R_3$ = OH; $R_4$ = CH$_3$; $R_6$ = F
61. $R_1$ = $R_2$ = $R_3$ = $R_4$ = $R_5$ = $R_6$ = H
62. $R_1$ = $R_2$ = $R_3$ = $R_5$ = $R_6$ = H; $R_4$ = OCH$_3$
63. $R_1$ = $R_2$ = $R_3$ = $R_4$ = $R_6$ = H; $R_5$ = F
64. $R_1$ = $R_2$ = $R_3$ = $R_5$ = H; $R_4$ = CH$_3$; $R_6$ = F
65. $R_1$ = $R_3$ = $R_4$ = $R_5$ = $R_6$ = H; $R_2$ = OH
66. $R_1$ = $R_3$ = $R_5$ = $R_6$ = H; $R_2$ = OH; $R_4$ = OCH$_3$
67. $R_1$ = $R_3$ = $R_4$ = $R_6$ = H; $R_2$ = OH; $R_5$ = F
68. $R_1$ = $R_3$ = $R_5$ = H; $R_2$ = OH; $R_4$ = CH$_3$; $R_6$ = F

A. Synthesis of Compound 53

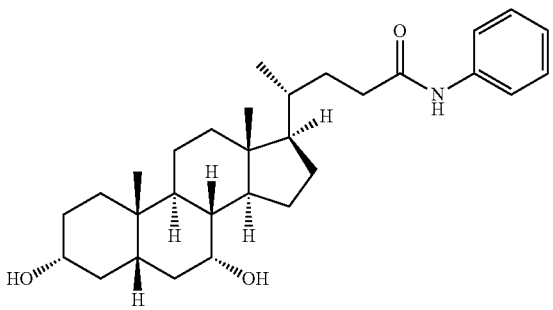

To a round bottom flask, chenodeoxycholic acid (393 mg, 1.0 mmol) and HBTU (476 mg, 1.25 mmol) were placed and dissolved in anhydrous DMF (5.0 mL). NMM (0.14 mL) was added into above reaction flask, and it was sealed with a rubber septum and purged with argon and the resulting solution was stirred for 30 min at room temperature. A solution of aniline (112 mg, 1.20 mmol) in 2 mL of DMF was added to the reaction followed by 0.14 mL of NMM and the reaction was stirred for 30 min and then left at room temperature for overnight. The DMF was removed from the solution using a vacuum rotary evaporator using hot bath, dry further on high vacuum pump, and the residue so obtained, was treated with 150 mL of 2% ice cold HCl and sonicated twice for 10 min each time. A white precipitate formed during the sonication step. The flask was removed from the sonicator bath and allowed the precipitate to settle down on the bottom of flask, the liquid layer (water soluble material) was decanted, and the procedure was repeated two additional times with 100 mL of 2% HCl. The solid was collected by filtration, washed with cold water and dried under high vacuum to give a white solid which was subjected to purification by column chromatography over silica gel when eluted from a mixture of CH$_2$Cl$_2$-MeOH (95:5; 90:10; 85:15; 80:20 and 50:50) to give 383 mg (82% yield) of a white solid. mp: 104-106° C.; TLC R$_f$ 0.53 (CH$_2$Cl$_2$: CH$_3$OH, 9:1); $^1$H NMR (DMSO-d$_6$, 400 MHz): δ 9.82 (s, 1H), 7.57 (d, 2H, J=8.0 Hz), 7.27 (t, 2H, J=7.6 Hz), 7.00 (t, 1H, J=7.2 Hz), 4.29 (d, 1H, J=4.4 Hz), 4.10 (d, 1H, J=3.2 Hz), 3.63 (s, 1H), 3.19-3.16 (m, 1H), 2.37-2.29 (m, 1H), 2.25-2.15 (m, 2H), 1.92 (d, 1H, J=11.6 Hz), 1.88-1.68 (m, 6H), 1.48-1.17 (m, 14H), 1.14-0.84 (m, 8H), 0.61 (s, 3H); $^1$H NMR (CD$_3$, OD, 400 MHz): δ 7.53 (d, 2H, J=8.0 Hz), 7.28 (t, 2H, J=7.6 Hz), 7.06 (t, 1H, J=7.2 Hz), 3.79 (s, 1H), 3.39-3.33 (m, 1H), 2.46-2.38 (m, 1H), 2.31-2.22 (m, 2H), 2.02-1.82 (m, 6H), 1.74 (m, 1H), 1.66-1.53 (m, 2H), 1.50-1.40 (m, 5H), 1.36-1.27 (m, 5H), 1.23-1.17 (m, 3H), 1.14-0.92 (m, 7H), 0.69 (s, 3H); $^{13}$C NMR (DMSO-d$_6$, 100 MHz): δ 171.61, 139.37, 128.57, 122.82, 118.97, 70.30, 66.13, 55.54, 50.00, 41.90, 41.39, 39.39, 35.28, 35.05, 34.81, 34.71, 33.32, 32.26, 31.33, 30.53, 27.77, 23.13, 22.68, 20.23, 18.35, 11.64; $^{13}$C NMR (CD$_3$, OD, 100 MHz): δ 175.16, 139.98, 129.77, 125.09, 121.30, 72.87, 69.05, 57.37, 51.57, 43.72, 43.20, 41.09, 40.80, 40.50, 36.99, 36.59, 36.24, 35.94, 35.02, 34.08, 33.20, 31.39, 29.31, 24.66, 23.43, 21.82, 19.02, 12.23.

b. Synthesis of Compound 54

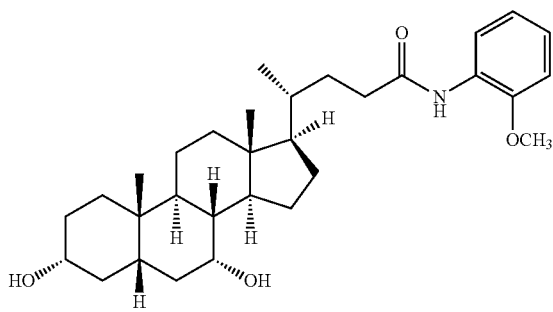

This compound was prepared from chenodeoxycholic acid and 2-methoxyaniline in 81% yield. mp: 85-87° C.; TLC $R_f$ 0.54 (CH$_2$Cl$_2$:CH$_3$OH, 9:1); $^1$H NMR (DMSO-d$_6$, 400 MHz): δ 8.98 (s, 1H), 7.91 (d, 1H, J=7.2 Hz), 7.02 (m, 2H), 6.87 (t, 1H, J=7.2 Hz), 4.30 (d, 1H, J=4.0 Hz), 4.09 (s, 1H), 3.81 (s, 3H), 3.63 (s, 1H), 3.19 (br, 1H), 2.40-2.15 (m, 3H), 1.92 (d, 1H, J=10.8 Hz), 1.82-1.68 (m, 6H), 1.48-1.10 (m, 14H), 1.04-0.83 (m, 8H), 0.61 (s, 3H); $^{13}$C NMR (DMSO-d$_6$, 100 MHz): δ 171.73, 149.52, 127.46, 124.03, 121.94, 120.10, 111.03, 70.31, 66.13, 55.57, 49.99, 41.90, 41.40, 39.40, 35.29, 35.06, 34.81, 34.70, 33.05, 32.26, 31.40, 30.53, 27.77, 23.14, 22.67, 20.24, 18.35, 11.63.

c. Synthesis of Compound 55

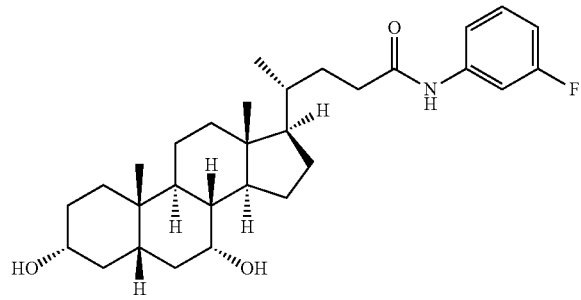

This compound was prepared from chenodeoxycholic acid and 3-fluoroaniline in 65% yield. mp: 106-108 (softening), 189-192° C.; TLC $R_f$ 0.51 (CH$_2$Cl$_2$:CH$_3$OH, 9:1); $^1$H NMR (DMSO-d$_6$, 400 MHz): δ 10.06 (s, 1H), 7.59 (d, 1H, J=12.0 Hz), 7.34-7.26 (m, 2H), 6.83 (t, 1H, J=7.6 Hz), 3.63 (s, 1H), 3.19 (m, 1H), 2.38-2.31 (m, 1H), 2.26-2.15 (m, 2H), 1.92 (d, 1H, J=10.8 Hz), 1.83-1.68 (m, 6H), 1.48-1.37 (m, 7H), 1.32-1.18 (m, 7H), 1.14-0.84 (m, 8H), 0.61 (s, 3H); $^1$H NMR (CD$_3$OD, 400 MHz): δ 7.51 (dt, 1H, J=11.2 and 2.0 Hz), 7.31-7.22 (m, 2H), 6.78 (td, 1H, J=9.6 and 1.6 Hz), 3.79 (s, 1H), 3.38-3.34 (m, 1H), 2.44-2.39 (m, 1H), 2.32-2.22 (m, 2H), 2.03-1.82 (m, 6H), 1.75 (m, 1H), 1.66-1.59 (m, 2H), 1.54-1.48 (m, 5H), 1.45-1.27 (m, 5H), 1.24-1.17 (m, 3H), 1.02-0.92 (m, 7H), 0.70 (s, 3H); $^{13}$C NMR (CD$_3$OD, 100 MHz): δ 175.23, 165.45, 163.04, 141.87, 141.76, 131.13, 131.03, 116.29, 116.26, 111.32, 111.10, 108.08, 107.82, 72.81, 69.00, 57.27, 51.51, 43.66, 43.12, 41.02, 40.72, 40.42, 36.93, 36.52, 36.18, 35.87, 34.96, 34.01, 33.01, 31.32, 29.27, 24.61, 23.39, 21.76, 18.96, 12.18.

d. Synthesis of Compound 56

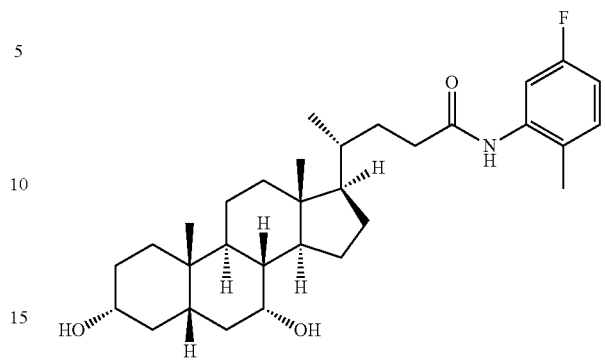

This compound was prepared from chenodeoxycholic acid and 2-methyl-5-fluoroaniline. The product was further purified by column chromatography over silica gel when eluted from a mixture of CH$_2$Cl$_2$-MeOH (95:5, 90:10, 80:20, and 70:30) to yield white solid in 69% yield. mp: 104-106° C.; TLC $R_f$ 0.49 (CH$_2$Cl$_2$:CH$_3$OH, 9:1); $^1$H NMR (CD$_3$OD, 400 MHz): δ 7.22-7.17 (m, 2H), 6.83 (td, 1H, J=8.4 and 2.4 Hz), 3.79 (s, 1H), 3.38-3.31 (m, 1H), 2.47-2.43 (m, 1H), 2.36-2.32 (m, 1H), 2.27 (d, 1H, J=11.6 Hz), 2.22 (s, 3H), 2.03-1.82 (m, 6H), 1.76-1.74 (m, 1H), 1.66-1.59 (m, 2H), 1.54-1.49 (m, 5H), 1.45-1.26 (m, 5H), 1.24-1.18 (m, 2H), 1.13-1.10 (m, 1H), 1.02 (d, 3H, J=6.4 Hz), 0.98-0.94 (m 4H), 0.68 (s, 3H); $^{13}$C NMR (CD$_3$OD, 100 MHz): δ 175.46, 163.45, 161.05, 138.30, 138.20, 132.51, 132.42, 128.95, 128.92, 113.42, 113.28, 113.21, 113.04, 72.81, 68.99, 57.32, 51.52, 43.68, 43.13, 41.04, 40.73, 40.43, 36.92, 36.54, 36.19, 35.89, 34.34, 34.02, 33.21, 31.33, 29.31, 24.62, 23.42, 21.78, 18.97, 17.46, 12.23.

e. Synthesis of Compound 57

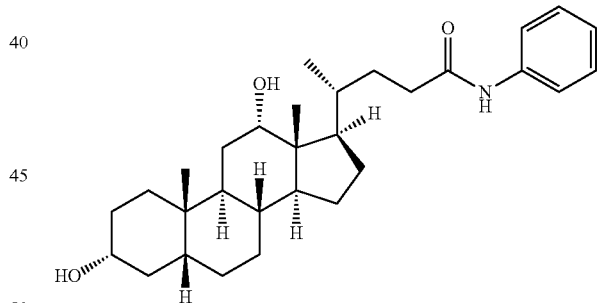

This compound was prepared from deoxycholic acid and aniline. The product was further purified by column chromatography over silica gel when eluted from a mixture of CH$_2$Cl$_2$-MeOH (95:5, 90:10, 80:20, and 70:30) to yield white solid in 70% yield. mp: 102-104 (softening), 185-87° C.; TLC $R_f$ 0.41 (CH$_2$Cl$_2$:CH$_3$OH, 95:5); $^1$H NMR (CD$_3$OD, 400 MHz): δ 7.52 (d, 2H, J=8.0 Hz), 7.28 (t, 2H, J=7.6 Hz), 7.06 (t, 1H, J=7.6 Hz), 3.96 (s, 1H), 3.56-3.47 (m, 1H), 2.43-2.39 (m, 1H), 2.32-2.26 (m, 1H), 1.93-1.75 (m, 7H), 1.65-1.58 (m, 3H), 1.54-1.37 (m, 9H), 1.32-1.25 (m, 2H), 1.18-1.05 (m, 5H), 1.01-0.92 (m, 4H), 0.71 (s, 3H); $^{13}$C NMR (CD$_3$OD, 100 MHz): δ 175.28, 140.01, 129.79, 125.11, 121.30, 74.10, 72.57, 49.34, 48.15, 47.60, 43.66, 37.49, 37.24, 36.95, 36.47, 35.34, 35.02, 34.86, 33.21, 31.11, 29.96, 28.72, 28.44, 27.51, 24.92, 23.75, 17.77, 13.25.

f. Synthesis of Compound 58.

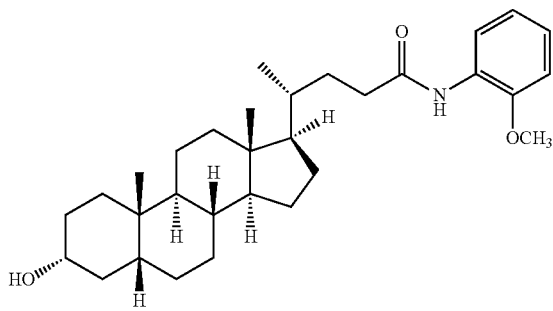

This compound was prepared from deoxycholic acid and 2-methoxyaniline. The product was further purified by column chromatography over silica gel when eluted from a mixture of CH$_2$Cl$_2$-MeOH (95:5, 90:10, 80:20, and 70:30) to yield white solid in 63% yield. mp: 75-78° C.; TLC R$_f$ 0.34 (CH$_2$Cl$_2$:CH$_3$OH, 95:5); $^1$H NMR (CD$_3$OD, 400 MHz): δ 7.88 (dd, 1H, J=8.0 and 1.2 Hz), 7.09 (td, 1H, J=8.0 and 1.2 Hz), 6.99 (d, 1H, J=7.6 Hz), 6.90 (td, 1H, J=8.0 and 1.2 Hz), 3.97 (s, 1H), 3.87 (s, 3H), 3.56-3.48 (m, 1H), 2.52-2.45 (m, 1H), 2.39-2.31 (m, 1H), 1.93-1.75 (m, 7H), 1.65-1.59 (m, 3H), 1.54-1.37 (m, 9H), 1.33-1.25 (m, 2H), 1.85-1.05 (m, 5H), 1.02-0.93 (m, 4H), 0.72 (s, 3H); $^{13}$C NMR (CD$_3$OD, 100 MHz): δ 175.33, 151.76, 128.20, 126.25, 123.79, 121.45, 111.84, 74.11, 72.57, 56.24, 49.34, 48.23, 47.62, 43.66, 37.49, 37.24, 36.90, 36.47, 35.34, 34.89, 34.86, 33.20, 31.11, 29.94, 28.72, 28.44, 27.51, 24.92, 23.74, 17.74, 13.25.

g. Synthesis of Compound 59

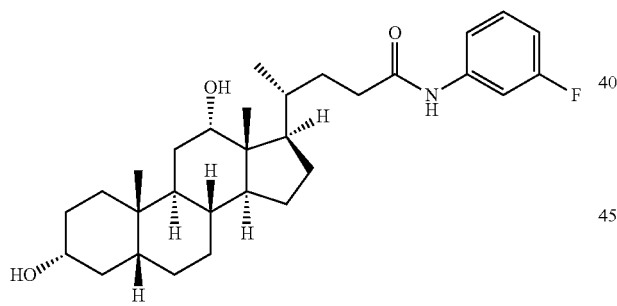

This compound was prepared from deoxycholic acid and 3-fluoroaniline. The product was further purified by column chromatography over silica gel when eluted from a mixture of CH$_2$Cl$_2$-MeOH (95:5, 90:10, 80:20, and 70:30) to yield white solid in 61% yield. mp: 194-196° C.; TLC R$_f$ 0.50 (CH$_2$Cl$_2$:CH$_3$OH, 95:5); $^1$H NMR (CD$_3$OD, 400 MHz): δ 7.51 (dt, 1H, J=11.6 and 1.2 Hz), 7.30-7.22 (m, 2H), 6.81-6.76 (m, 1H), 3.96 (s, 1H), 3.55-3.49 (m, 1H), 2.47-2.39 (m, 1H), 2.32-2.25 (m, 1H), 1.92-1.75 (m, 7H), 1.65-1.58 (m, 3H), 1.54-1.37 (m, 9H), 1.32-1.28 (m, 2H), 1.25-1.05 (m, 5H), 1.02-0.93 (m, 4H), 0.71 (s, 3H); $^{13}$C NMR (CD$_3$OD, 100 MHz): δ 175.34, 165.47, 163.06, 141.89, 141.78, 131.13, 131.04, 116.32, 116.29, 111.32, 111.11, 108.09, 107.83, 74.03, 72.51, 49.29, 48.07, 47.54, 43.60, 37.43, 37.18, 36.87, 36.41, 35.29, 34.97, 34.80, 33.01, 31.05, 29.90, 28.65, 28.38, 27.45, 24.85, 23.69, 17.70, 13.18.

h. Synthesis of Compound 60

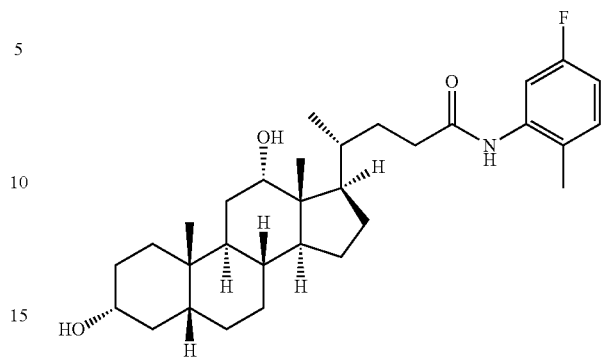

This compound was prepared from deoxycholic acid and 2-methyl-5-fluoroaniline. The product was further purified by column chromatography over silica gel when eluted from a mixture of CH$_2$Cl$_2$-MeOH (95:5, 90:10, 80:20, and 70:30) to yield white solid in 57% yield. mp: 91-93° C.; TLC R$_f$ 0.47 (CH$_2$Cl$_2$:CH$_3$OH, 95:5); $^1$H NMR (CD$_3$OD, 400 MHz): δ 7.21-7.18 (m, 2H), 6.84 (td, 1H, J=8.4 and 2.4 Hz), 3.97 (s, 1H), 3.55-3.49 (m, 1H), 2.51-2.44 (m, 1H), 2.39-2.31 (m, 1H), 2.21 (s, 3H), 1.93-1.85 (m, 5H), 1.81-1.75 (m, 2H), 1.65-1.59 (m, 3H), 1.54-1.37 (m, 9H), 1.33-1.25 (m, 2H), 1.18-1.07 (m, 5H), 1.02-0.95 (m, 4H), 0.71 (s, 3H); $^{13}$C NMR (CD$_3$OD, 100 MHz): δ 175.62, 163.51, 161.11, 138.35, 138.25, 132.55, 132.47, 129.10, 129.07, 113.50, 113.38, 113.29, 113.14, 74.08, 72.55, 49.33, 48.16, 47.60, 43.64, 37.47, 37.22, 36.90, 36.46, 35.33, 34.84, 34.37, 33.24, 31.08, 29.94, 28.73, 28.43, 27.49, 24.90, 23.75, 17.73, 17.46, 13.25.

i. Synthesis of Compound 61

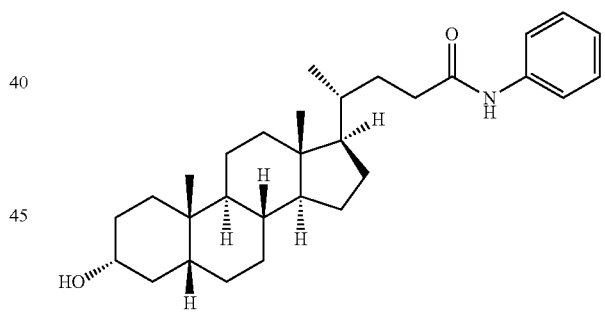

This compound was prepared from lithocholic acid and aniline in 88% yield. mp: 198-200° C.; $^1$H NMR (DMSO-d$_6$, 400 MHz): δ 9.83 (s, 1H), 7.57 (d, 2H, J=8.0 Hz), 7.27 (t, 2H, J=8.0 Hz), 7.00 (t, 1H, J=7.6 Hz), 4.48 (b, 1H), 2.35-2.30 (m, 1H), 2.24-2.17 (m, 1H), 1.94 (d, 1H, J=8.4 Hz), 1.89-1.75 (m, 3H), 1.70-1.63 (m, 2H), 1.60-1.49 (m, 2H), 1.36-1.03 (m, 17H), 0.93-0.87 (m, 7H), 0.62 (s, 3H); $^1$H NMR (CD$_3$OD, 400 MHz): δ 7.52 (d, 2H, J=7.2 Hz), 7.28 (t, 2H, J=7.2 Hz), 7.07 (t, 1H, J=6.8 Hz), 3.53 (br, 1H), 2.42-2.39 (m, 1H), 2.31-2.27 (m, 1H), 2.02 (d, 1H, J=10.8 Hz), 1.89-1.71 (m, 5H), 1.61 (br s, 2H), 1.44-1.10 (m, 17H), 1.01-0.94 (m, 7H), 0.69 (s, 3H); $^{13}$C NMR (DMSO-d$_6$, 100 MHz): δ 171.59, 139.37, 128.57, 122.82, 118.98, 69.83, 56.07, 55.55, 42.25, 41.50, 36.27, 35.36, 35.12, 34.95, 34.18, 33.33, 31.29, 30.35, 27.70, 26.86, 26.13, 23.82, 23.24, 20.38, 18.31, 11.86; $^{13}$C NMR (CD$_3$OD, 100 MHz): δ 175.17, 139.97, 129.75, 125.09, 121.29, 72.43, 57.95, 55.48, 43.94, 43.56, 41.90, 41.56, 37.25, 37.20, 36.93, 36.50, 35.69, 35.01, 33.17, 31.21, 29.29, 28.37, 27.66, 25.28, 23.94, 21.96, 18.94, 12.50.

j. Synthesis of Compound 62

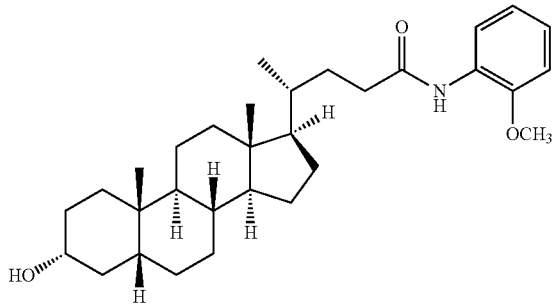

This compound was prepared from lithocholic acid and 2-methoxyaniline in 79% yield. mp: 193-195° C.; $^1$H NMR (DMSO-d$_6$, 600 MHz): δ 9.02 (s, 1H), 7.91 (s, 1H), 7.02 (br s, 2H), 6.88 (s, 1H), 4.46 (s, 1H), 3.81 (s, 3H), 2.40 (s, 1H), 2.30 (s, 1H), 1.94 (d, 1H, J=5.4 Hz), 1.81-1.76 (m, 3H), 1.68 (d, 1H, J=12.6 Hz), 1.62-1.49 (m, 3H), 1.35-1.04 (m, 17H), 0.92-0.87 (2 br peaks, 7H), 0.62 (s, 3H); $^{13}$C NMR (DMSO-d$_6$, 150 MHz): δ 171.79, 149.60, 127.46, 124.13, 122.06, 120.15, 111.06, 69.88, 56.12, 55.61, 42.30, 41.53, 39.99, 39.71, 36.32, 35.40, 35.16, 35.02, 34.23, 33.06, 31.41, 30.40, 27.77, 26.91, 26.20, 23.89, 23.30, 20.43, 18.37, 11.91.

k. Synthesis of Compound 63

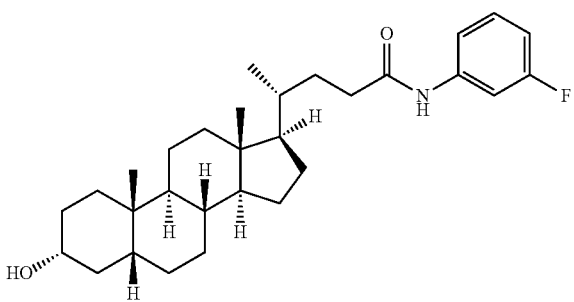

This compound was prepared from lithocholic acid and 3-fluoroaniline in 82% yield. mp: 222-224° C.; $^1$H NMR (DMSO-d$_6$, 600 MHz): δ 10.08 (s, 1H), 7.60 (d, 1H, J=12.0 Hz), 7.33-7.26 (m, 2H), 6.84 (t, 1H, J=8.4 Hz), 4.46 (s, 1H), 3.34 (br, 1H), 2.36-2.32 (m, 1H), 2.24-2.19 (m, 1H), 1.93 (d, 1H, J=9.6 Hz), 1.86-1.76 (m, 3H), 1.67 (d, 1H, J=13.8 Hz), 1.64-1.58 (m, 1H), 1.54-1.49 (m, 2H), 1.36-1.23 (m, 9H), 1.18-1.08 (m, 5H), 1.03 (br, 3H), 0.92-0.87 (m, 7H), 0.62 (s, 3H); 1H NMR (CD$_3$OD, 400 MHz): δ 7.52 (dt, 1H, J=9.2 and 2.0 Hz), 7.31-7.22 (m, 2H), 6.79 (td, 1H, J=7.2 and 1.2 Hz), 3.57-3.50 (m, 1H), 2.46-2.38 (m, 1H), 2.31-2.24 (m, 1H), 2.02 (d, 1H, J=11.6 Hz), 1.97-1.72 (m, 5H), 1.63-1.60 (m, 2H), 1.48-1.05 (m, 17H), 1.01-0.94 (m, 7H), 0.70 (s, 3H); $^{13}$C NMR (DMSO-d$_6$, 150 MHz): δ 172.04, 162.94, 161.34, 141.16, 141.08, 130.30, 130.24, 114.65, 109.38, 109.24, 105.79, 105.62, 69.87, 56.09, 55.55, 42.28, 41.52, 39.97, 36.30, 35.39, 35.15, 34.98, 34.22, 33.37, 31.18, 30.39, 27.75, 26.90, 26.18, 23.87, 23.28, 20.42, 18.32, 11.89.

l. Synthesis of Compound 64

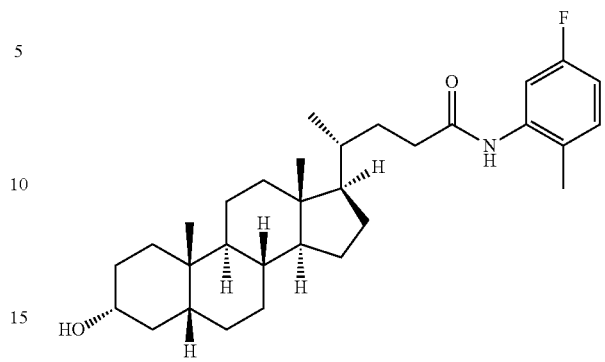

This compound was prepared from lithocholic acid and 2-methyl-5-fluoroaniline in 59% yield. mp: 182-184° C.; $^1$H NMR (DMSO-d$_6$, 400 MHz): δ 9.22 (s, 1H), 7.36 (d, 1H, J=10.0 Hz), 7.20 (s, 1H), 6.88 (s, 1H), 4.42 (s, 1H), 2.44-2.23 (2 br, 2H), 2.17 (s, 3H), 1.94 (d, 1H, J=7.2 Hz), 1.88-1.47 (m, 7H), 1.42-0.99 (m, 17H), 0.94 and 0.87 (2 br, 7H), 0.62 (s, 3H); $^1$H NMR (CD$_3$OD, 400 MHz): δ 7.22-7.18 (m, 2H), 6.85 (td, 1H, J=8.4 and 2.4 Hz), 3.57-3.50 (m, 1H), 2.50-2.43 (m, 1H), 2.38-2.31 (m, 1H), 2.21 (s, 3H), 2.04 (d, 1H, J=11.6 Hz), 1.94-1.87 (m, 3H), 1.83-1.72 (m, 2H), 1.63-1.61 (m, 2H), 1.52-1.40 (m, 7H), 1.37-1.25 (m, 5H), 1.22-1.07 (m, 5H), 1.03-0.93 (m, 7H), 0.71 (s, 3H); $^{13}$C NMR (DMSO-d$_6$, 100 MHz): δ 171.82, 161.24, 158.86, 137.82, 131.72, 131.27, 131.19, 126.33, 111.06, 110.89, 110.65, 69.84, 56.09, 55.57, 42.27, 41.51, 36.28, 35.37, 35.13, 34.93, 34.19, 32.81, 31.38, 30.37, 27.72, 26.87, 26.15, 23.82, 23.24, 20.39, 18.30, 17.11, 11.85.

m. Synthesis of Compound 65

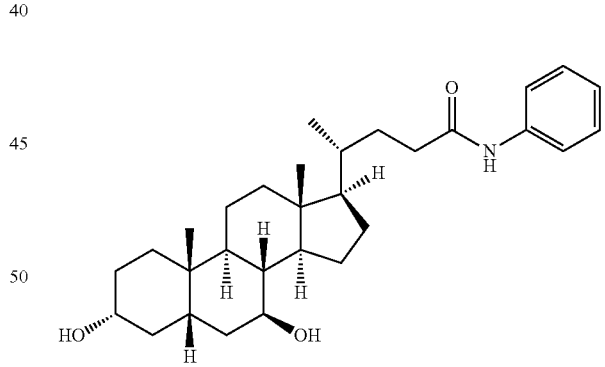

This compound was prepared from ursodeoxycholic acid and aniline in 65% yield. mp: 196-198° C.; TLC R$_f$ 0.58 (CH$_2$Cl$_2$:CH$_3$OH, 9:1); $^1$H NMR (CD$_3$OD, 400 MHz): δ 7.53 (d, 2H, J=7.6 Hz), 7.28 (t, 2H, J=7.6 Hz), 7.07 (t, 1H, J=7.2 Hz), 3.48 (m, 2H), 2.46-2.38 (m, 1H), 2.31-2.24 (m, 1H), 2.05 (d, 1H, J=12.0 Hz), 1.91-1.79 (m, 5H), 1.63-1.37 (m, 10H), 1.34-1.12 (m, 7H), 1.06-0.96 (m, 7H), 0.72 (s, 3H); $^{13}$C NMR (CD$_3$OD, 100 MHz): δ 175.21, 140.00, 129.79, 125.12, 121.34, 72.17, 72.00, 57.57, 56.61, 44.85, 44.57, 44.09, 41.63, 40.78, 38.67, 38.07, 36.95, 36.15, 35.22, 35.09, 33.28, 31.09, 29.73, 28.00, 23.98, 22.44, 19.15, 12.70.

n. Synthesis of Compound 66

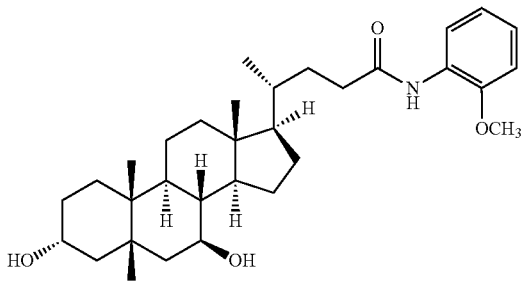

This compound was prepared from ursodeoxycholic acid and 2-methoxyaniline. The product was purified by column chromatography over silica gel when eluted from a mixture of $CH_2Cl_2$-MeOH (95:5, 90:10, 80:20, 70:30 and 50:50) to yield white solid in 74% yield. mp: 87-89° C.; TLC $R_f$ 0.50 ($CH_2Cl_2$:$CH_3OH$, 9:1); $^1H$ NMR ($CD_3OD$, 400 MHz): δ 7.88 (d, 1H, J=8.0 Hz), 7.09 (t, 1H, J=7.6 Hz), 6.99 (d, 1H, J=8.0 Hz), 6.90 (t, H, J=7.6 Hz), 3.87 (s, 3H), 3.50-3.45 (m, 2H), 2.52-2.44 (m, 1H), 2.38-2.31 (m, 1H), 2.05 (d, 1H, J=12.4 Hz), 1.93-1.79 (m, 5H), 1.64-1.10 (m, 17H), 1.07-0.96 (s, 7H), 0.72 (s, 3H); $^{13}C$ NMR ($CD_3OD$, 100 MHz): δ 174.98, 151.43, 128.24, 126.03, 123.44, 121.43, 111.74, 72.07, 71.87, 57.44, 56.53, 56.23, 44.76, 44.46, 43.98, 41.55, 40.67, 38.59, 38.02, 36.81, 36.09, 35.14, 34.95, 33.17, 31.04, 29.68, 27.93, 23.98, 22.38, 19.14, 12.72.

o. Synthesis of Compound 67

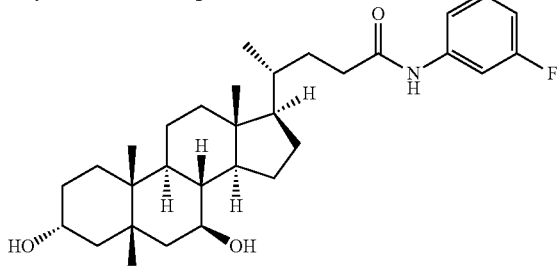

This compound was prepared from ursodeoxycholic acid and 3-fluoroaniline in 72% yield. mp: 120-122 (softening), 201-203° C.; TLC $R_f$ 0.55 ($CH_2Cl_2$:$CH_3OH$, 9:1); $^1H$ NMR ($CD_3OD$, 600 MHz): δ 7.53 (d, 1H, J=11.4 Hz), 7.30-7.23 (m, 2H), 6.79 (t, 1H, J=7.2 Hz), 3.51-3.44 (m, 2H), 2.45-2.40 (m, 1H), 2.30-2.51 (m, 1H), 2.04 (d, 1H, J=12.0 Hz), 1.92-1.80 (m, 4H), 1.62-1.38 (m, 1H), 1.36-1.10 (m, 7H), 1.05-0.96 (m, 7H), 0.71 (s, 3H); $^{13}C$ NMR ($CD_3OD$, 150 MHz): δ 175.23, 165.05, 163.44, 141.85, 131.12, 131.06, 116.31, 111.31, 111.17, 108.08, 107.90, 72.10, 71.91, 57.46, 56.48, 44.77, 44.46, 43.99, 41.55, 40.69, 38.60, 38.00, 36.89, 36.08, 35.15, 35.07, 33.09, 31.03, 29.69, 27.94, 23.96, 22.38, 19.12, 12.68.

p. Synthesis of Compound 68

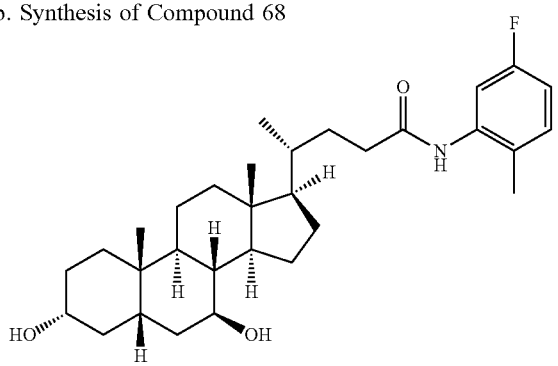

This compound was prepared from ursodeoxycholic acid and 2-methyl-5-fluoroaniline. The product was purified by column chromatography over silica gel when eluted from a mixture of $CH_2Cl_2$-MeOH (95:5, 90:10, 80:20, 70:30 and 50:50) to yield white solid in 49% yield. mp: 93-95° C. (softening), 101-103° C.; TLC $R_f$ 0.52 ($CH_2Cl_2$:$CH_3OH$, 9:1); $^1H$ NMR ($CD_3OD$, 400 MHz): δ 7.22-7.18 (m, 2H), 6.85 (td, 1H, J=8.4 and 2.8 Hz), 3.50-4.46 (m, 2H), 2.51-2.44 (m, 1H), 2.39-2.31 (m, 1H), 2.21 (s, 3H), 2.06 (d, 1H, J=12.4 Hz), 1.93-1.90 (m, 3H), 1.87-1.79 (m, 2H), 1.63-1.57 (m, 3H), 1.54-1.42 (m, 7H), 1.41-1.10 (m, 7H), 1.06-0.94 (m, 7H), 0.71 (s, 3H); $^{13}C$ NMR ($CD_3OD$, 100 MHz): δ 175.48, 163.45, 161.05, 138.30, 138.20, 132.52, 132.43, 128.97, 113.46, 113.31, 113.25, 113.07, 72.09, 71.91, 57.50, 56.55, 44.80, 44.47, 44.00, 41.58, 40.70, 38.60, 37.99, 36.88, 36.08, 35.16, 34.39, 33.28, 31.02, 29.72, 27.95, 23.95, 22.39, 19.09, 17.46, 12.68.

7. Bacterial Strains and Spore Preparation

*C. difficile* R20291 was the kind gift of Prof. Nigel Minton (University of Nottingham). *C. difficile* cells were streaked onto BHIS (Brain heart infusion supplemented with 20 mg/ml yeast extract, 0.1% L-cysteine, and 0.05% sodium taurocholate) agar to yield single colonies. Single *C. difficile* colonies were grown in BHIS (Brain heart infusion supplemented with 5 mg/mL yeast extract) broth overnight and spread onto BHIS agar to obtain bacterial lawns. The plates were incubated for 7 days at 37° C. in an anaerobic environment (10% $CO_2$, 10% $H_2$, and 80% $N_2$). The resulting bacterial lawns were collected by flooding the plates with ice-cold deionized water. The spores were pelleted and washed three times by centrifugation at 8,800×g for five minutes. To remove any contaminating vegetative cells, the spores were purified through a 20% to 50% HistoDenz gradient at 18,200×g for 30 minutes. The resulting spore pellet was washed five times with water, resuspended in a 0.05% sodium thioglycolate solution, and stored at 4° C.

8. *C. difficile* Spore Germination Assays

Purified *C. difficile* spores were pelleted and washed with deionized water three times by centrifugation at 9,400×g to remove the storage buffer. The spores were heat activated at 68° C. for 30 minutes, then washed an additional three times to remove any spores that auto germinated. The spores were diluted to an optical density of 580 nm ($OD_{580}$) to 1.0 with a 100 mM sodium phosphate buffer, pH 6.0, containing 5 mg/ml sodium bicarbonate. To test for antagonists of spore germination, a 96-well plate was prepared by adding compounds to a final concentration of 125 μM into separate wells in triplicate along with 6 mM taurocholate and 12 mM glycine. Upon the addition of spores, the $OD_{580}$ was measured once every minute for 2 hours and normalized using the $OD_{580}$ obtained at time zero [relative $OD_{580}$=$OD_{580}(t)$/$OD_{580}(t_0)$]. Selected compounds were further tested for germination inhibition at increasing concentrations to determine the concentration that reduces spore germination by 50% ($IC_{50}$).

9. Antigerminant Activity of Compounds.

All compounds were analyzed as inhibitors of spore germination using a standard optical density assay, which measures germination as a decrease in absorbance at 580 nm (Sharma et al., The Design, Synthesis, and Characterizations of Spore Germination Inhibitors Effective against an Epidemic Strain of *Clostridium difficile*. J Med Chem 2018, 61, 6759-6778). A two-step process was taken for the analysis of the biological activity of the compounds. Compounds were first analyzed for their ability to inhibit spore germination of *C. difficile* R20291 at a single concentration of 125 μM. Compounds that were able to slow spore germination >40% compared to untreated samples were then reanalyzed at different concentrations to determine their $IC_{50}$ values. The anti-germinant activity of the compounds are shown in Table 2-5.

10. Preliminary Determination of CDI Prophylaxis

To test for murine *C. difficile* infection (CDI) protection, published procedures were followed (Howerton et al. (2013) *Journal of Infectious Diseases* 207(10): 1498-1504; Phan et al. (2022) *Antimicrobial Agents and Chemotherapy* 66(1): e01435-01421). Briefly, antibiotic-treated female mice were challenged by oral gavage with spores from *C. difficile* hypervirulent strain R20291 (Chen et al. (2008) *Gastroenterology* 135(6): 1984-1992). At this point, animals were divided randomly into groups (Table 1). Starting on the day of infection and continuing for the next two days, animals in group C were given daily doses of 50 mg/kg of an individual NHBS analog by oral gavage. Animals in group B were given vancomycin. Animals in group A were given excipient (Howerton et al. (2013) *Journal of Infectious Diseases* 207(10): 1498-1504; Howerton et al. (2018) *Antimicrobial Agents and Chemotherapy* 62(10): e02251-17). For up to 5 days following challenge, animals were scored for signs of CDI, using a published rubric (Howerton et al. (2013) *Journal of Infectious Diseases* 207(10): 1498-1504). Moribund or severely distressed animals were euthanized. Non-diseased animals were observed for 30 additional days to monitor delayed CDI onset.

TABLE 1

| Group | Purpose | *C. difficile* | Vancomycin | NHBS |
|---|---|---|---|---|
| A | CDI Control | + | − | − |
| B | Vancomycin Control | + | + | − |
| C | NHBS analog | + | − | + |

11. Evaluation of *C. difficile* Spore Germination Activity in Tertiary Amide Analogs A list of tertiary amide compounds evaluated for their ability to affect *C. difficile* germination activity is shown in Table 2 below.

TABLE 2

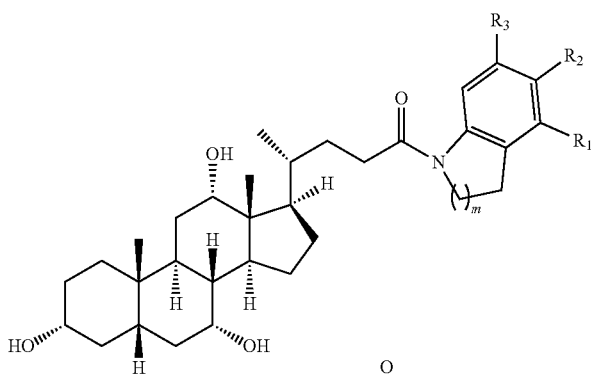

1-9

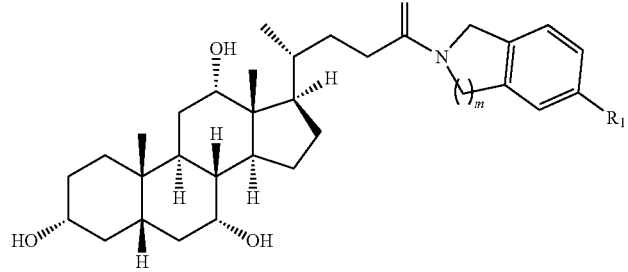

10-13

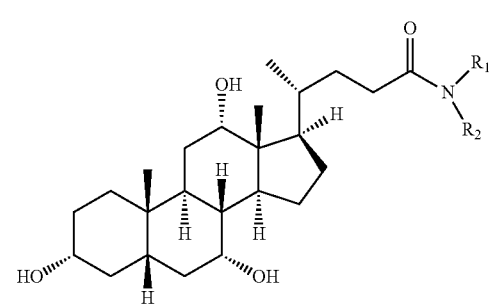

14-15

| Compound[a] | $R_1$ | $R_2$ | $R_3$ | m | % Germination[b] | $IC_{50}$ (μM)[c] |
|---|---|---|---|---|---|---|
| 1 | H | H | H | 1 | 4 ± 1 | 1 ± 0.3 |
| 2 | Cl | H | H | 1 | 95 ± 8 | ND[d] |
| 3 | H | $CH_3$ | H | 1 | 100 | ND[d] |
| 4 | H | F | H | 1 | 5 ± 3 | 0.4 ± 0.04 |
| 5 | H | Cl | H | 1 | 70 ± 3 | ND[d] |

TABLE 2-continued

| | | | | | | |
|---|---|---|---|---|---|---|
| 6 | H | Br | H | 1 | 90 ± 3 | ND[d] |
| 7 | H | H | $OCH_3$ | 1 | 100 | ND[d] |
| 8 | H | H | H | 2 | 17 ± 3 | 22 ± 3 |
| 9 | H | $CH_3$ | H | 2 | 100 | ND[d] |
| 10 | H | — | — | 1 | not tested[e] | ND[d] |
| 11 | H | — | — | 2 | 78 ± 2 | ND[d] |
| 12 | $OCH_3$ | — | — | 2 | 100 | ND[d] |
| 13 | Br | — | — | 2 | 100 | ND |
| 14 | Ph | $CH_3$ | — | — | 31 ± 2 | 32 ± 5 |
| 15 | $CH_2CH{=}CH_2$ | $CH_2CH{=}CH_2$ | — | — | 0.9 ± 0.2 | 8 ± 3 |

[a]Number corresponding to Schemes 6 and 7.
[b]Percent (%) germination of each compound was reported with standard deviations and tested at a final concentration of 125 μM. A 96-well plate was prepared by adding individual CamSA analogs to separate wells in triplicate along with 6 mM taurocholate and 12 mM glycine. Upon the addition of spores, the OD580 was measured once every minute for 2 hours and normalized using the OD580 obtained at time zero [relative OD580 = OD580(t)/OD580(t0)].
[c]*C. difficile* spores were incubated with various concentrations of analogs with 6 mM taurocholate and 12 mM glycine. The $IC_{50}$ was calculated by plotting the extent of germination versus the logarithm of the concentration of the analog.
[d]ND $IC_{50}$ was not determined.
[e]Compound was not tested due to solubility problems with the compound.

Tertiary cholonamide 1 and its analogs (e.g., 6) have been prepared as spore germination inhibitors for *C. difficile* infections and studies have revealed that these compounds possess $IC_{50}$ values of 1 and 0.4 μM, respectively against the R20291 strain. These compounds were prepared as conformationally locked analogs of lead agent N-(Phenyl)-cholan-24-amide (FIG. 1), based upon hypotheses that the conformation of the amide played a critical role in the activity of these germination inhibitors.

12. Evaluation of *C. difficile* Spore Germination Activity in Bicyclic Heteroaryl Analogs A list of bicyclic heteroaryl compounds evaluated for their ability to affect *C. difficile* germination activity is shown in Tables 3 and 4 below.

TABLE 3

29-39 and 41

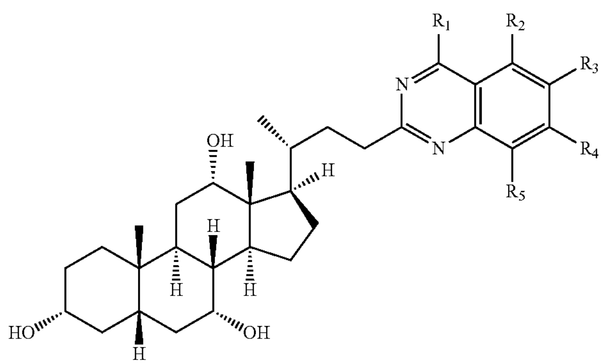

43

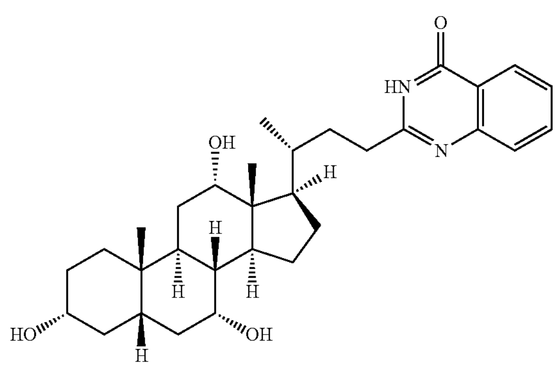

| Compounds[a] | $R_1$ | $R_2$ | $R_3$ | $R_4$ | $R_5$ | % Germination[b] | $IC_{50}$ (μM)[c] |
|---|---|---|---|---|---|---|---|
| 29 | H | H | H | H | H | 17 ± 3 | 22 ± 3 |
| 30 | $CH_3$ | H | H | H | H | 35 ± 5 | 37 ± 4 |
| 31 | $C_6H_5$ | H | H | H | H | 92 ± 4 | ND[d] |

TABLE 3-continued

| | | | | | | | |
|---|---|---|---|---|---|---|---|
| 32 | H | F | H | H | H | 36 ± 6 | ND[d] |
| 33 | H | H | F | H | H | 7 ± 3 | 28 ± 4 |
| 34 | H | H | Cl | H | H | 59 ± 0.2 | ND[d] |
| 35 | H | H | H | F | H | 57 ± 2 | ND[d] |
| 36 | H | H | H | Cl | H | 89 ± 10 | ND[d] |
| 37 | H | H | H | OCH$_3$ | H | 61 ± 5 | ND[d] |
| 38 | H | H | H | H | F | 7 ± 0.7 | 79 ± 23 |
| 39 | H | H | OCH$_3$ | OCH$_3$ | H | 78 ± 3 | ND[d] |
| 41 | H | H | F | F | H | 70 ± 23 | ND[d] |
| 70 | H | H | F/OCH$_3$ | OCH$_3$/F | H | 62 ± 9.9 | ND[d] |
| 43 | — | — | — | — | — | 32 ± 0.6 | 20 ± 11 |

[a]Number corresponding to Schemes 8 and 9.
[b]Percent (%) germination of each compound was reported with standard deviations and tested at a final concentration of 125 μM. A 96-well plate was prepared by adding individual CamSA analogs to separate wells in triplicate along with 6 mM taurocholate and 12 mM glycine. Upon the addition of spores, the OD$_{580}$ was measured once every minute for 2 hours and normalized using the OD$_{580}$ obtained at time zero [relative OD$_{580}$ = OD$_{580}$(t)/OD$_{580}$(t$_0$)].
[c]C. difficile spores were incubated with various concentrations of analogs along with 6 mM taurocholate and 12 mM glycine. The IC$_{50}$ was calculated by plotting the extent of germination versus the logarithm of the concentration of the analog.
[d]ND IC$_{50}$ was not determined.

TABLE 4

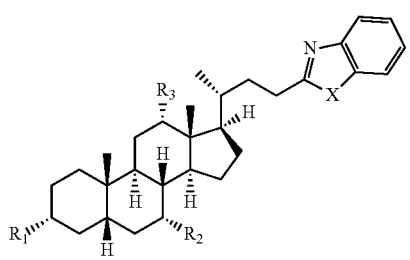

44-52

| Compounds[a] | R$_1$ | R$_2$ | R$_3$ | X | % Germination[b] | IC$_{50}$ (μM)[c] |
|---|---|---|---|---|---|---|
| 44 | OH | OH | OH | NH | −3 ± 0.3 | 4.4 ± 0.3 |
| 45 | OH | OH | H | NH | 18 ± 2 | 12 ± 7 |
| 46 | OH | H | OH | NH | 23 ± 5 | 6 ± 1 |
| 47 | OH | OH | OH | S | −6 ± 0.05 | 6 ± 4 |
| 48 | OH | OH | H | S | 88 ± 5 | ND[d] |
| 49 | OH | H | OH | S | 81 ± 2 | ND[d] |
| 50 | OH | OH | OH | O | −4 ± 0.8 | 6 ± 3 |

TABLE 4-continued

| | | | | | | |
|---|---|---|---|---|---|---|
| 51 | OH | OH | H | O | 80 ± 4 | ND[d] |
| 52 | OH | H | OH | O | 83 ± 8 | ND[d] |
| 71 | OCHO | OCHO | OCHO | NH | 88 ± 8 | ND[d] |
| 72 | OH | OH | OH | — | — | ND[d] |

[a]Number corresponding to Scheme 10.
[b]Percent (%) germination of each compound was reported with standard deviations and tested
at a final concentration of 125 uM. A 96-well plate was prepared by adding individual CamSA analogs to separate wells in triplicate along with 6 mM taurocholate and 12 mM glycine. Upon the addition of spores, the OD$_{580}$ was measured once every minute for 2 hours and normalized using the OD$_{580}$ obtained a time zero [relative OD$_{580}$ = OD$_{580}$(t)/OD$_{580}$(t$_0$)].
[c]C. difficile spores were incubated with various concentrations of analogs along with 6 mM taurocholate and 12 mM glycine. The IC$_{50}$ was calculated by plotting the extent of germination versus the logarithm of the concentration of the analog. Standard deviations are shown in parentheses.
[d]ND IC$_{50}$ was not determined.

13. Evaluation of *C. difficile* Spore Germination Activity in Secondary Amide Analogs A list of secondary amide compounds evaluated for their ability to affect *C. difficile* germination activity is shown in Table 5 below.

TABLE 5

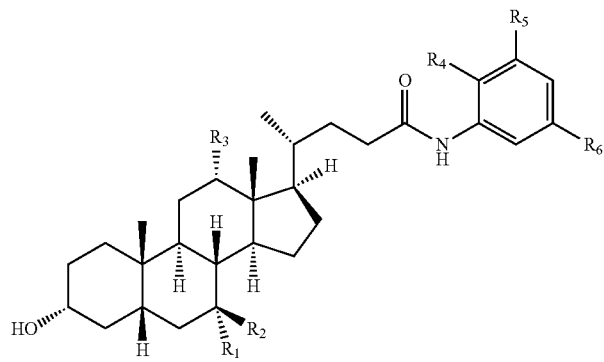

| Base | Compound[a] | R$_1$ | R$_2$ | R$_3$ | R$_4$ | R$_5$ | R$_6$ | % Germination (125 μM)[b] | IC$_{50}$ (μM)[c] |
|---|---|---|---|---|---|---|---|---|---|
| Chenodeoxycholate | 53 | OH | H | H | H | H | H | 14 ± 0.6 | 4 ± 0.5 |
| | 54 | OH | H | H | OCH$_3$ | H | H | 31 ± 2 | 6 ± 1 |
| | 55 | OH | H | H | H | F | H | 100 | ND[d] |
| | 56 | OH | H | H | CH$_3$ | H | F | 66 ± 6 | ND[d] |

TABLE 5-continued

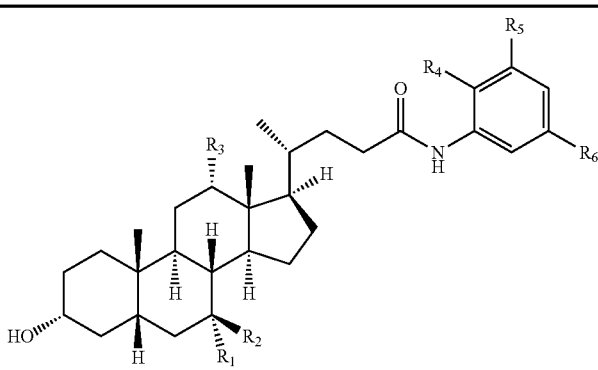

| Base | Compound[a] | $R_1$ | $R_2$ | $R_3$ | $R_4$ | $R_5$ | $R_6$ | % Germination (125 μM)[b] | $IC_{50}$ (μM)[c] |
|---|---|---|---|---|---|---|---|---|---|
| Deoxycholate | 57 | H | H | OH | H | H | H | 3 ± 0.2 | 1.3 ± 0.1 |
|  | 58 | H | H | OH | OCH$_3$ | H | H | 0.4 ± 3 | 2.4 ± 0.3 |
|  | 59 | H | H | OH | H | F | H | 59 ± 5 | ND[d] |
|  | 60 | H | H | OH | CH$_3$ | H | F | 65 ± 0.9 | ND[d] |
| Lithocholate | 61 | H | H | H | H | H | H | 100 | ND[d] |
|  | 62 | H | H | H | OCH$_3$ | H | H | 100 | ND[d] |
|  | 63 | H | H | H | H | F | H | 100 | ND[d] |
|  | 64 | H | H | H | CH$_3$ | H | F | 100 | ND[d] |
| Ursodeloxycholate | 65 | H | OH | H | H | H | H | 57 ± 0.8 | ND[d] |
|  | 66 | H | OH | H | OCH$_3$ | H | H | 100 | ND[d] |
|  | 67 | H | OH | H | H | F | H | 100 | ND[d] |
|  | 68 | H | OH | H | CH$_3$ | H | F | 100 | ND[d] |

[a]Number corresponding to Scheme 11.
[b]Percent (%) germination of each compound was reported with standard deviations and tested at a final concentration of 125 μM. A 96-well plate was prepared by adding individual CamSA analogs to separate wells in triplicate along with 6 mM taurocholate and 12 mM glycine. Upon the addition of spores, the $OD_{580}$ was measured once every minute for 2 hours and normalized using the $OD_{580}$ obtained at time zero [relative $OD_{580}$ = $OD_{580}(t)/OD_{580}(t_0)$]. 100% indicates no inhibition at 125 μM.
[c]C. difficile spores were incubated with various concentrations of analogs along with 6 mM taurocholate and 12 mM glycine. The $IC_{50}$ was calculated by plotting the extent of germination versus the logarithm of the concentration of the analog.
[d]ND $IC_{50}$ was not determined.

14. Murine Protection

The minimum effective dose of non-hydrolysable bile salts (NHBS) as CDI prophylactic is shown in Table 6 below. As shown, compound no. 29 prevented all CDI signs in mice from hypervirulent C. difficile strain R20291. Although compound no. 48 did not completely prevent CDI, it significantly reduced sign severity. Furthermore, whereas cholan-24-amides were hydrolyzed by undisturbed murine microbiota (Yip et al. (2021) Biochemical Pharmacology 183: 114314; Howerton et al. (2013) PLoS One 8(8): e72620-e72620), compound no. 29 was not degraded even after 3 days incubation with feces.

TABLE 6

| Compound No. | Murine CDI prophylaxis at 50 mg/kg |
|---|---|
| 29 | Complete protection |
| 44 | No protection |
| 48 | Partial protection |

15. Discussion

It was previously shown that cholonamides are potent inhibitors of spore germination with the most potent compound, N-(phenyl)-cholan-24-amide, displaying an $IC_{50}$ of 1.8 μM (Sharma et al., The Design, Synthesis, and Characterizations of Spore Germination Inhibitors Effective against an Epidemic Strain of Clostridium difficile. J Med Chem 2018, 61, 6759-6778). Cholic acid, the base bile acid used in these analogs, is an activator of germination whereas chenodeoxycholate, ursodeoxycholate and lithocholate are potent natural bile salt inhibitors (Howerton et al., Mapping interactions between germinants and Clostridium difficile spores. J Bacteriol 2011, 193, 274-82; Sorg and Sonenshein, Bile salts and glycine as cogerminants for Clostridium difficile spores. J Bacteriol 2008, 190, 2505-12; Sorg, J. A.; Sonenshein, A. L., Chenodeoxycholate is an inhibitor of Clostridium difficile spore germination. J Bacteriol 2009, 191, 1115-7; Sorg and Sonenshein, Inhibiting the initiation of Clostridium difficile spore germination using analogs of chenodeoxycholic acid, a bile acid. J Bacteriol 2010, 192, 4983-90). Thus, amide-based analogs derived from chenodeoxycholate, ursodeoxycholate and lithocholate should be more potent inhibitors of spore germination.

Given this, a series of bile salt amides were synthesized and evaluated.

Without wishing to be bound by theory, the results indicate that one of the two hydroxyl groups at the 7 or 12 position is expendable, but removal of both group leads to inactive compounds. Alteration of the stereochemistry at the 7-position also eliminated activity suggesting a specific interaction between the target and the anti-germinant. These results are distinctly different from the natural bile acids in which lithocholate is the most potent inhibitor followed by ursodeoxycholic acid (Sorg and Sonenshein, Bile salts and glycine as cogerminants for *Clostridium difficile* spores. *J Bacteriol* 2008, 190, 2505-12; Sorg and Sonenshein, Chenodeoxycholate is an inhibitor of *Clostridium difficile* spore germination. *J Bacteriol* 2009, 191, 1115-7). Both this work as well as previous research on the effects of bile acids on germination were conducted in a ribotype 027 *C. difficile* strain. Studies on amide-based bile salt anti-germinants have also been conducted against the *C. difficile* 630 strain (Howerton, A. Anti-Germinants as a New Strategy to Prevent *Clostridium difficile* Infections. University of Nevada, Las Vegas, Las Vegas, 2012). N-(Phenyl)-cholan-24-amide, the simple phenyl cholanamide, gave an $IC_{50}$ of 270 µM against 630 while the chenodeoxycholic version (53) was inactive up to the maximum tested concentration.[26] The chenodeoxycholic analog of CamSA had an $IC_{50}$ of 6.5 mM, which is approximately 100-fold less potent than the cholate derivative (CamSA, $IC_{50}$=58 µM) (Howerton, A. Anti-Germinants as a New Strategy to Prevent *Clostridium difficile* Infections. University of Nevada, Las Vegas, Las Vegas, 2012). However, other analogs examined in the study gave greater potency for the chenodeoxycholate versus the cholate derivative. Thus, no definitive conclusions can be reached regarding a strict preference for the steroid nucleus used in bile salt inhibitors for the 630 strain. Comparison of data across strains is also problematic since it is known that there are substantial differences in the effects of amide-based anti-germinants between the 630 and R20291 strains. For example, CamSA is active against the 630 strain, but inactive in the R20291 strain (Sharma et al., The Design, Synthesis, and Characterizations of Spore Germination Inhibitors Effective against an Epidemic Strain of *Clostridium difficile. J Med Chem* 2018, 61, 6759-6778). N-(Phenyl)-cholan-24-amide inhibits the 630 strain with an $IC_{50}$ of 270 µM, but inhibits the R20291 strain with an $IC_{50}$ of 1.8 µM (Howerton, A. Anti-Germinants as a New Strategy to Prevent *Clostridium difficile* Infections. University of Nevada, Las Vegas, Las Vegas, 2012).

The observation that one of the hydroxyl groups can be removed, but not more than one, is interesting. It is believed that germinants bind to the CspC protein to regulate germination (Setlow et al., Germination of Spores of the Orders Bacillales and Clostridiales. *Annu Rev Microbiol* 2017, 71, 459-477; Lawler et al., A Revised Understanding of *Clostridioides difficile* Spore Germination. *Trends Microbiol* 2020, 28, 744-752; Sorg and Sonenshein, Bile salts and glycine as cogerminants for *Clostridium difficile* spores. *J Bacteriol* 2008, 190, 2505-12; Bhattacharjee et al., Reexamining the Germination Phenotypes of Several *Clostridium difficile* Strains Suggests Another Role for the CspC Germinant Receptor. *J Bacteriol* 2015, 198, 777-86; Francis et al., Bile acid recognition by the *Clostridium difficile* germinant receptor, CspC, is important for establishing infection. *PLoS Pathog* 2013, 9, e1003356; Kevorkian and Shen, Revisiting the Role of Csp Family Proteins in Regulating *Clostridium difficile* Spore Germination. *J Bacteriol* 2017, 199, e00266-17; Rohlfing et al., The CspC pseudoprotease regulates germination of *Clostridioides difficile* spores in response to multiple environmental signals. *PLoS Genet* 2019, 15, e1008224). While the crystal structure of CspC has been solved, there is no structural or biophysical information on the binding of any bile salt to the protein (Rohlfing et al., The CspC pseudoprotease regulates germination of *Clostridioides difficile* spores in response to multiple environmental signals. *PLoS Genet* 2019, 15, e1008224). Thus, the bile acid binding site and protein-ligand interactions are unknown. An examination of cholate and chenodeoxycholate binding sites in other lipid and bile salt binding proteins (PDB codes: 2QO5, 1TW4, 3EM0, 3EL7, 2FT9, 5L8O, 2QO6, 2QO4, 4QE6, 6HL1) reveals that often only 2 of the 3 hydroxyl groups interact with the protein and in many instances a bridging water molecule is part of the interaction. The presence of the water molecule provides flexibility in the interaction between the protein and the hydroxyl groups, all of which occur on the same face of the molecule and near each other is space. However, it should be noted that the spore germination assay utilizes the intact spore and thus does not directly measure binding to a target protein. The variances observed in this assay could also be the result of differences in compound transport through the spore (Lawler et al., A Revised Understanding of *Clostridioides difficile* Spore Germination. *Trends Microbiol* 2020, 28, 744-752). Ultimately, the rationale for the structure-activity data observed here will have to await structural data on the binding of anti-germinates to their target(s).

J. REFERENCES

Ryan, K. J., *Clostridium, Bacteroides*, and Other Anaerobes. In *Sherris Medical Microbiology, 7e*, McGraw-Hill Education: New York, NY, 2017 Chapter 29, sectionid=176086328

Czepiel, J.; Drozdz, M.; Pituch, H.; Kuijper, E. J.; Perucki, W.; Mielimonka, A.; Goldman, S.; Wultanska, D.; Garlicki, A.; Biesiada, G., *Clostridium difficile* infection: review. *Eur J Clin Microbiol Infect Dis* 2019, 38, 1211-1221.

Di Bella, S.; Ascenzi, P.; Siarakas, S.; Petrosillo, N.; di Masi, A., *Clostridium difficile* Toxins A and B: Insights into Pathogenic Properties and Extraintestinal Effects. *Toxins (Basel)* 2016, 8, E134.

Antibiotic Resistance Threats in the United States. CDC, Ed. CDC: Atlanta, GA, 2019.

Durre, P., Physiology and Sporulation in *Clostridium*. In *The Bacterial Spore: From Molecules to Systems*, Eichenberger, P.; Driks, A., Eds. American Society for Microbiology: Washington D.C., 2016; Vol. IV, pp 315-329.

Setlow, P.; Wang, S.; Li, Y. Q., Germination of Spores of the Orders Bacillales and Clostridiales. *Annu Rev Microbiol* 2017, 71, 459-477.

Doll, M.; Marra, A. R.; Apisarnthanarak, A.; Al-Maani, A. S.; Abbas, S.; Rosenthal, V. D., Prevention of *Clostridioides difficile* in hospitals: A position paper of the International Society for Infectious Diseases. *Int J Infect Dis* 2021, 102, 188-195.

Lawler, A. J.; Lambert, P. A.; Worthington, T., A Revised Understanding of *Clostridioides difficile* Spore Germination. *Trends Microbiol* 2020, 28, 744-752.

Shen, A.; Edwards, A. N.; Sarker, M. R.; Paredes-Sabja, D., Sporulation and Germination in Clostridial Pathogens. *Microbiol Spectr* 2019, 7, GPP3-0017-2018.

Howerton, A.; Ramirez, N.; Abel-Santos, E., Mapping interactions between germinants and *Clostridium difficile* spores. *J Bacteriol* 2011, 193, 274-82.

Sorg, J. A.; Sonenshein, A. L., Bile salts and glycine as cogerminants for *Clostridium difficile* spores. *J Bacteriol* 2008, 190, 2505-12.

Ramirez, N.; Liggins, M.; Abel-Santos, E., Kinetic evidence for the presence of putative germination receptors in *Clostridium difficile* spores. *J Bacteriol* 2010, 192, 4215-22.

Sorg, J. A.; Sonenshein, A. L., Chenodeoxycholate is an inhibitor of *Clostridium difficile* spore germination. *J Bacteriol* 2009, 191, 1115-7.

Sorg, J. A.; Sonenshein, A. L., Inhibiting the initiation of *Clostridium difficile* spore germination using analogs of chenodeoxycholic acid, a bile acid. *J Bacteriol* 2010, 192, 4983-90.

Winston, J. A.; Theriot, C. M., Diversification of host bile acids by members of the gut microbiota. *Gut Microbes* 2020, 11, 158-171.

Weingarden, A. R.; Chen, C.; Zhang, N.; Graiziger, C. T.; Dosa, P. I.; Steer, C. J.; Shaughnessy, M. K.; Johnson, J. R.; Sadowsky, M. J.; Khoruts, A., Ursodeoxycholic Acid Inhibits *Clostridium difficile* Spore Germination and Vegetative Growth, and Prevents the Recurrence of Ileal Pouchitis Associated With the Infection. *J Clin Gastroenterol* 2016, 50, 624-30.

Winston, J. A.; Rivera, A. J.; Cai, J.; Thanissery, R.; Montgomery, S. A.; Patterson, A. D.; Theriot, C. M., Ursodeoxycholic Acid (UDCA) Mitigates the Host Inflammatory Response during *Clostridioides difficile* Infection by Altering Gut Bile Acids. *Infect Immun* 2020, 88, e00045-20.

Palmieri, L. J.; Rainteau, D.; Sokol, H.; Beaugerie, L.; Dior, M.; Coffin, B.; Humbert, L.; Eguether, T.; Bado, A.; Hoys, S.; Janoir, C.; Duboc, H., Inhibitory Effect of Ursodeoxycholic Acid on *Clostridium difficile* Germination Is Insufficient to Prevent Colitis: A Study in Hamsters and Humans. *Front Microbiol* 2018, 9, 2849.

Stoltz, K. L.; Erickson, R.; Staley, C.; Weingarden, A. R.; Romens, E.; Steer, C. J.; Khoruts, A.; Sadowsky, M. J.; Dosa, P. I., Synthesis and Biological Evaluation of Bile Acid Analogues Inhibitory to *Clostridium difficile* Spore Germination. *J Med Chem* 2017, 60, 3451-3471.

Howerton, A.; Patra, M.; Abel-Santos, E., A new strategy for the prevention of *Clostridium difficile* infection. *J Infect Dis* 2013, 207, 1498-504.

Howerton, A.; Patra, M.; Abel-Santos, E., Fate of ingested *Clostridium difficile* spores in mice. *PLoS One* 2013, 8, e72620.

Howerton, A.; Seymour, C. O.; Murugapiran, S. K.; Liao, Z.; Phan, J. R.; Estrada, A.; Wagner, A. J.; Mefferd, C. C.; Hedlund, B. P.; Abel-Santos, E., Effect of the Synthetic Bile Salt Analog CamSA on the Hamster Model of *Clostridium difficile* Infection. *Antimicrob Agents Chemother* 2018, 62, e02251-17.

Yip, C.; Okada, N. C.; Howerton, A.; Amei, A.; Abel-Santos, E., Pharmacokinetics of CamSA, a potential prophylactic compound against *Clostridioides difficile* infections. *Biochem Pharmacol* 2021, 183, 114314.

Sharma, S. K.; Yip, C.; Esposito, E. X.; Sharma, P. V.; Simon, M. P.; Abel-Santos, E.; Firestine, S. M., The Design, Synthesis, and Characterizations of Spore Germination Inhibitors Effective against an Epidemic Strain of *Clostridium difficile*. *J Med Chem* 2018, 61, 6759-6778.

Adam, S. HBTU—a Mild Activating Agent of Muramic Acid. *Bioorg Med Chem Lett* 1992, 2, 571-574.

Howerton, A. Anti-Germinants as a New Strategy to Prevent *Clostridium difficile* Infections. University of Nevada, Las Vegas, Las Vegas, 2012.

Bhattacharjee, D.; Francis, M. B.; Ding, X.; McAllister, K. N.; Shrestha, R.; Sorg, J. A., Reexamining the Germination Phenotypes of Several *Clostridium difficile* Strains Suggests Another Role for the CspC Germinant Receptor. *J Bacteriol* 2015, 198, 777-86.

Francis, M. B.; Allen, C. A.; Shrestha, R.; Sorg, J. A., Bile acid recognition by the *Clostridium difficile* germinant receptor, CspC, is important for establishing infection. *PLoS Pathog* 2013, 9, e1003356.

Kevorkian, Y.; Shen, A., Revisiting the Role of Csp Family Proteins in Regulating *Clostridium difficile* Spore Germination. *J Bacteriol* 2017, 199, e00266-17.

Rohlfing, A. E.; Eckenroth, B. E.; Forster, E. R.; Kevorkian, Y.; Donnelly, M. L.; Benito de la Puebla, H.; Doublie, S.; Shen, A., The CspC pseudoprotease regulates germination of *Clostridioides difficile* spores in response to multiple environmental signals. *PLoS Genet* 2019, 15, e1008224.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

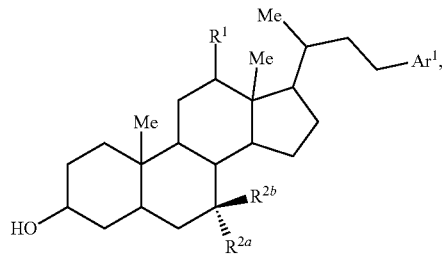

wherein each of $R^1$, $R^{2a}$, and $R^{2b}$ is independently selected from hydrogen and —OH; and wherein $Ar^1$ is a bicyclic heteroaryl having a structure represented by a formula selected from:

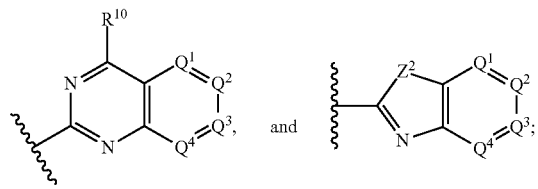

wherein $Z^1$ is selected from —O— and —$NR^{18}$—;
wherein $R^{18}$, when present, is selected from hydrogen and C1-C4 alkyl;
wherein each of $Q^1$, $Q^2$, $Q^3$, and $Q^4$ is independently selected from —N= and —$CR^{20}$=;
wherein each occurrence of $R^{20}$ is independently selected from hydrogen, halogen, C1-C4 alkyl, C1-C4 alkoxy, and phenyl; and
wherein $R^{10}$ is selected from hydrogen, halogen, C1-C4 alkyl, C1-C4 alkoxy, C1-C4 haloalkyl, C1-C4 thioalkyl, and phenyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

2. The compound of claim 1, wherein one of $R^1$, $R^{2a}$, and $R^{2b}$ is —OH, and two of $R^1$, $R^{2a}$, and $R^{2b}$ are hydrogen.

3. The compound of claim 1, wherein two of $R^1$, $R^{2a}$, and $R^{2b}$ are —OH, and one of $R^1$, $R^{2a}$, and $R^{2b}$ is hydrogen.

4. The compound of claim 1, wherein the compound has a structure represented by a formula:

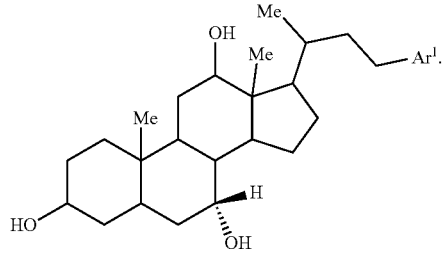

5. The compound of claim 1, wherein the compound has a structure represented by a formula:

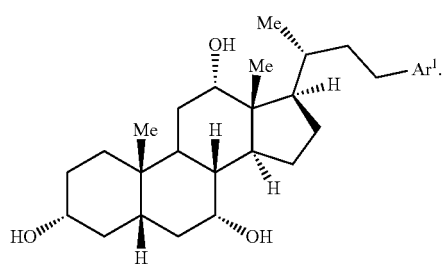

6. The compound of claim 5, wherein the compound is selected from:

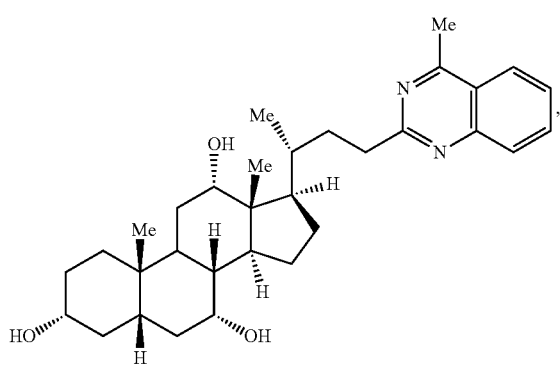

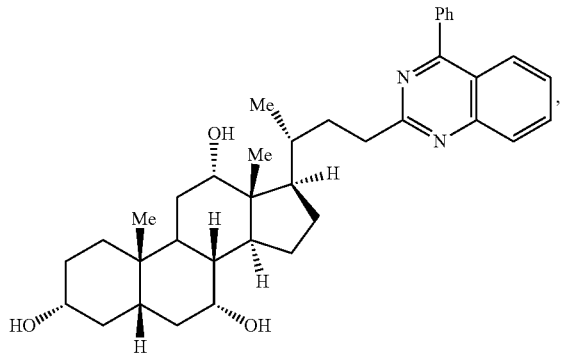

-continued

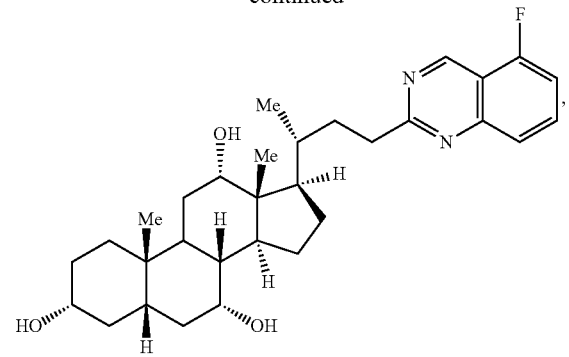

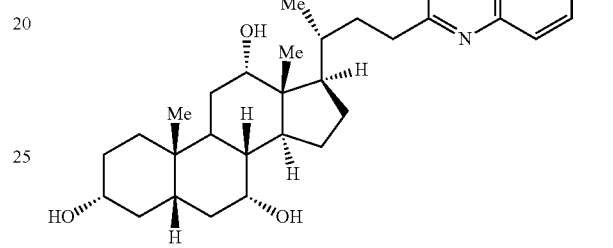

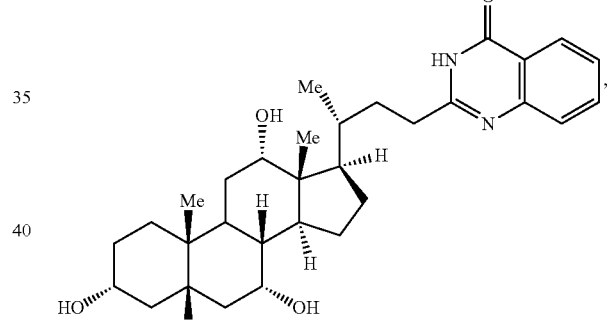

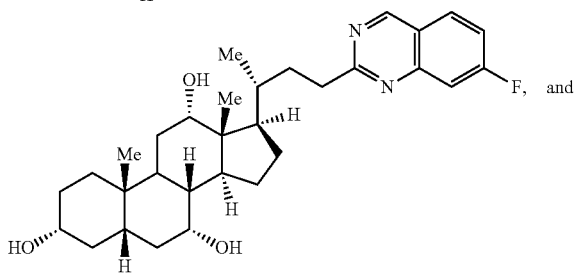

, and

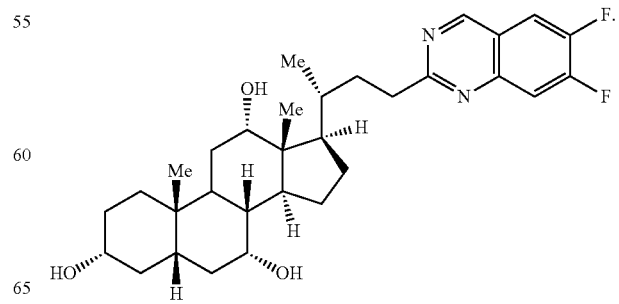

7. The compound of claim 5, wherein the compound is:

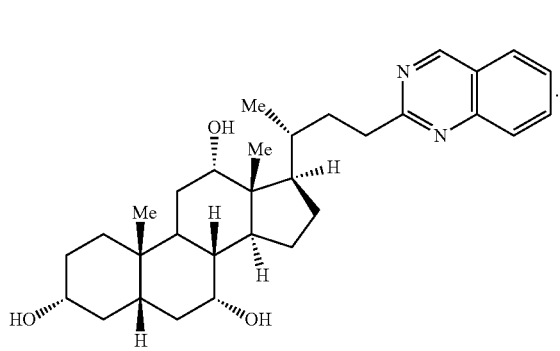

8. The compound of claim 1, wherein the compound has a structure represented by a formula:

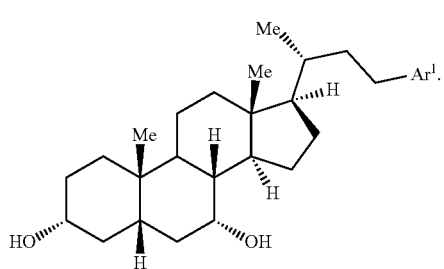

9. The compound of claim 1, wherein the compound has a structure represented by a formula:

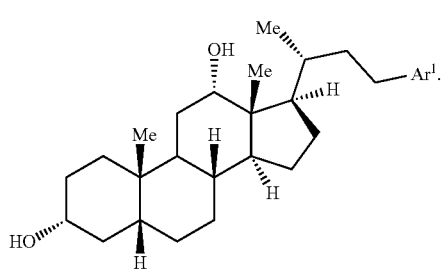

10. The compound of claim 1, wherein the compound has a structure represented by a formula:

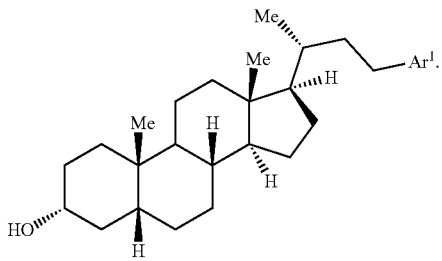

11. The compound of claim 1, wherein the compound has a structure represented by a formula:

12. A composition comprising an effective amount of the compound of claim 1, and a feed component.

13. The composition of claim 12, wherein the feed component is a vegetable protein, a fat-soluble vitamin, a water-soluble vitamin, a trace mineral, a macro mineral, or a combination thereof.

14. The composition of claim 12, wherein the composition is a granule or a pellet.

15. A method for preventing or treating a disease or disorder caused by infection of *Clostridium difficile* in a subject in need thereof, the method comprising administering to the subject an effective amount of the compound of claim 1 or a pharmaceutically acceptable salt thereof.

16. The method of claim 15, further comprising administering to the subject an antibiotic.

17. The method of claim 15, wherein the disease or disorder is severe diarrhea or colitis.

18. The method of claim 15, wherein the method comprises administering a composition comprising the compound and a feed component.

* * * * *